US 11,498,930 B2

(12) United States Patent
Zou et al.

(10) Patent No.: US 11,498,930 B2
(45) Date of Patent: Nov. 15, 2022

(54) PYRIMIDINE-FUSED CYCLIC COMPOUND, PREPARATION METHOD THEREFOR AND APPLICATION THEREOF

(71) Applicant: BLUERAY THERAPEUTICS (SHANGHAI) CO., LTD., Shanghai (CN)

(72) Inventors: Bin Zou, Shanghai (CN); Xianlei Fu, Shanghai (CN); Rui Zhang, Shanghai (CN); Shichao Ma, Shanghai (CN); Shuaijie Xu, Shanghai (CN); Wencheng Fu, Shanghai (CN); Lanzhen Liu, Shanghai (CN)

(73) Assignee: BLUERAY THERAPEUTICS (SHANGHAI) CO., LTD, Shanghai (CN)

( * ) Notice: Subject to any disclaimer, the term of this patent is extended or adjusted under 35 U.S.C. 154(b) by 11 days.

(21) Appl. No.: 16/969,392

(22) PCT Filed: Feb. 3, 2019

(86) PCT No.: PCT/CN2019/074685
§ 371 (c)(1),
(2) Date: Aug. 12, 2020

(87) PCT Pub. No.: WO2019/158019
PCT Pub. Date: Aug. 22, 2019

(65) Prior Publication Data
US 2021/0053989 A1    Feb. 25, 2021

(30) Foreign Application Priority Data

Feb. 13, 2018 (CN) .......................... 201810144135.3
Jun. 29, 2018 (CN) .......................... 201810692211.4

(51) Int. Cl.
*C07D 519/00* (2006.01)
*C07D 401/14* (2006.01)
*C07D 405/14* (2006.01)
*C07D 413/14* (2006.01)
*C07D 417/00* (2006.01)

(52) U.S. Cl.
CPC ......... *C07D 519/00* (2013.01); *C07D 401/14* (2013.01); *C07D 405/14* (2013.01); *C07D 413/14* (2013.01); *C07D 417/00* (2013.01)

(58) Field of Classification Search
CPC .. C07D 519/00; C07D 401/14; C07D 405/14; C07D 413/14; C07D 417/00
USPC ...................................................... 514/257
See application file for complete search history.

(56) References Cited

U.S. PATENT DOCUMENTS

2011/0237565 A1  9/2011 Borchardt et al.
2014/0371199 A1  12/2014 Nacro et al.
2017/0015680 A1  1/2017 Chen et al.
2017/0204080 A1  7/2017 Chen et al.
2020/0317695 A1  10/2020 Zheng et al.
2020/0407372 A1* 12/2020 Koltun ................. C07D 519/00

FOREIGN PATENT DOCUMENTS

| AU | 2019386036 A1 | 5/2021 |
|---|---|---|
| CN | 102869666 A | 1/2013 |
| CN | 104350055 A | 2/2015 |
| CN | 105899491 A | 8/2016 |
| CN | 105916845 A | 8/2016 |
| CN | 111433205 A | 7/2020 |
| EP | 3094627 A1 | 11/2016 |
| JP | 2013522222 A | 6/2013 |
| JP | 2021506776 A | 2/2021 |
| WO | WO-2010114881 A1 | 10/2010 |
| WO | WO-2011112766 A2 | 9/2011 |
| WO | WO-2015107493 A1 | 7/2015 |
| WO | WO-2015107494 A1 | 7/2015 |
| WO | WO-2015107495 A1 | 7/2015 |
| WO | WO-2016203404 A1 | 12/2016 |
| WO | WO-2016203405 A1 | 12/2016 |

(Continued)

OTHER PUBLICATIONS

First Office Action regarding Australian Patent Application No. 2019222026, dated May 5, 2021.
First Office Action regarding Chinese Patent Application No. 201810144135.3, dated Mar. 24, 2021.
Extended European Search Report dated Aug. 3, 2021 issued in counterpart European application No. 19754599.9.
Apr. 29, 2019 International Search Report issued in International Patent Application No. PCT/CN2019/074685.
Apr. 29, 2019 Written Opinion of the International Searching Authority issued in International Patent Application No. PCT/CN2019/074685.
Huang, Ying et al., "Discovery of First-in-Class, Potent, and Orally Bioavailable Embryonic Ectoderm Development (EED) Inhibitor with Robust Anticancer Efficacy", Journal of Medicinal Chemistry, 2017, vol. 60, Issue 6.

(Continued)

*Primary Examiner* — Kahsay Habte
(74) *Attorney, Agent, or Firm* — Harness, Dickey & Pierce, P.L.C.

(57) ABSTRACT

Disclosed in the present disclosure are a pyrimidine-fused cyclic compound or a pharmaceutically acceptable salt, hydrate, prodrug, stereoisomer, solvate or isotope labeled compound thereof. Also provided in the present disclosure are a preparation method for the compound, a composition comprising the compound and a use of the compound for the preparation of a medicament for the prevention and/or treatment of a disease or condition associated with abnormal SHP2 activity.

12 Claims, No Drawings

(56) References Cited

FOREIGN PATENT DOCUMENTS

| WO | WO-2016203406 A1 | 12/2016 |
|----|------------------|---------|
| WO | WO-2017210134 A1 | 12/2017 |
| WO | WO-2017211303 A1 | 12/2017 |
| WO | WO-2017216706 A1 | 12/2017 |
| WO | WO-2018013597 A1 | 1/2018 |
| WO | WO-2019118909 A1 | 6/2019 |
| WO | WO-2020072656 A1 | 4/2020 |
| WO | WO-2020094018 A1 | 5/2020 |

OTHER PUBLICATIONS

Chen et al., "Allosteric inhibition of SHP2 phosphatase inhibits cancers driven by receptor tyrosine kinases", Nature, 2016, vol. 535, pp. 148-152.

Carey and Sundberg "Advanced Organic Chemistry Part A: Structure and Mechanisms." 2000, 4th Edition, Plenum Publishers, New York.

Carey and Sundberg "Advanced Organic Chemistry Part B: Reactions and Synthesis." 2001, 4th Edition, Plenum Publishers, New York.

Gerald Gübitz and Martin G. Schmid (Eds.), Chiral Separations, Methods and Protocols, Methods in Molecular Biology, vol. 243, 375-386, 2004.

A.M. Stalcup, "Chiral Separations", Annual Review of Analytical Chemistry. 2010, vol. 3, pp. 341-363.

Furniss et al. (eds.), Vogel's Encyclopedia of Practical Organic Chemistry 5.sup.TH ED., Longman Scientific and Technical Ltd., Essex, 1991, 809-816.

Heller, "Electrical Wiring of Redox Enzymes", Acc. Chem. Res. 1990, vol. 23, pp. 128-134.

Brunton et al., "The Pharmacological Basis of Therapeutics", Goodman and Gilman's, 13th Edition.; Pergamon; and Remington's, Pharmaceutical Sciences (current edition), Mack Publishing Co., Easton, Pa.

Wuts and Greene, Greene's Protective Groups in Organic Synthesis, (1999), 4th Ed., John Wiley & Sons, Inc.

The First Examination Report issued in the counterpart Indian Application No. 202047039337, dated Dec. 14, 2020.

Second Office Action regarding Australian Patent Application No. 2019222026, dated May 5, 2022.

First office action regarding European Patent Application No. 19754599.9, dated May 10, 2022.

Jun. 28, 2022 1st OA issued in Japanese counterpart application.

* cited by examiner

PYRIMIDINE-FUSED CYCLIC COMPOUND, PREPARATION METHOD THEREFOR AND APPLICATION THEREOF

The present application is a U.S. National Phase Application under 35 U.S.C. 371 of International Application No. PCT/CN2019/074685 filed on Feb. 3, 2019, which claims the priority of Chinese Patent Application CN201810144135.3 filed on Feb. 13, 2018 and the priority of Chinese Patent Application CN201810692211.4 filed on Jun. 29, 2018. The entire disclosures of the above applications are incorporated herein by reference in their entireties.

TECHNICAL FIELD

The present disclosure discloses a pyrimidine-fused compound, a pharmaceutically acceptable salt thereof, a hydrate thereof, a prodrug thereof, a stereoisomer thereof, a solvate thereof or an isotope-labeled compound thereof. The present disclosure also provides a method for preparing the compound and an intermediate compound thereof, a composition comprising the compound, and a use of the compound in the manufacture of a medicament for the prevention and/or treatment of a disease or condition associated with abnormal activity of SHP2.

BACKGROUND ART

Tyrosine phosphatase SHP2 is composed of two N-terminal Src homology 2 domains (N—SH2 and C—SH2) and a protein tyrosine phosphatase catalytic domain (PTP). In the basic state, N—SH2 can bind to PTP to form a ring structure, thereby hindering the binding of PTP to the substrate, so that the catalytic activity of the enzyme is inhibited. When the tyrosine of the upstream receptor protein is phosphorylated, N—SH2 binds to it and the PTP catalytic domain is released to exert phosphatase activity.

At the cellular level, SHP2 participates in diverse tumor cell signaling pathways, e.g., RTK/Ras/MAPK, JAK/STAT, and PI3K/Akt, through its functional role in the cytoplasmic downstream of many receptor tyrosine kinases. Through the regulation of these kinases and signaling pathways, SHP2 is closely related to many important cell life activities, e.g., cell proliferation, migration, differentiation, death, cytokine regulation, and tumorigenesis.

In addition, SHP2 is also involved in the immune system suppression mediated by programmed death receptor 1 (PD1). After PD-1 binds to PD-L1 of T cells, a large amount of SHP2 can be recruited in the cells. SHP2 can dephosphorylate antigen receptor pathway proteins in T cells, thereby inhibiting T cell activation. Therefore, the inhibition of the SHP2 activity can reverse immunosuppression in the tumor microenvironment.

SHP2 is an important member of the protein tyrosine phosphatase family and is associated with various human diseases, e.g., Noonan syndrome, Leopard syndrome, juvenile myelomonocytic leukemia, neuroblastoma, melanoma, acute myeloid leukemia, breast cancer, esophageal cancer, lung cancer, colon cancer, head cancer, neuroblastoma, squamous cell carcinoma of the head and neck, gastric cancer, anaplastic large cell lymphoma, and glioblastoma.

A series of patents have been published recently, e.g., WO2018/013597A1, WO2017/210134A1, WO2017/211303A1, WO2017/216706A1, WO2016/203406A1, WO2016/203405A1, WO2016/203404A1, WO2015/107495A1, WO2015/107494A1, and WO2015/107493A1, indicating that SHP2 as a novel druggable target has attracted more and more attention. There are two main strategies in the development of SHP2 inhibitors, one of which aims at developing inhibitors for the PTP catalytic domain of SHP2 and the other aims at developing allosteric inhibitors for the non-catalytic domain of SHP2. Due to poor selectivity and druggability of PTP catalytic region inhibitors, more research currently focuses on the development of allosteric inhibitors. All of the above patents relate to allosteric inhibitors, but most of which have low inhibitory activity on tumor cells, e.g., the compound SHP099 (6-(4-amino-4-methylpiperidin-1-yl)-3-(2,3-dichlorophenyl)pyrazine-2-amine) disclosed in WO2015/107493A1. There is a need to further develop a SHP2 inhibitor with novel structure, good biological activity and high druggability.

Content of the Disclosure

The pyrimidine-fused compound of the present disclosure is a novel class of SHP2 inhibitor, which exhibits good inhibitory activity on tumor cells and good druggability, and has broad prospects in drug development. Moreover, the preparation method of such compound is simple, which is beneficial to industrial production.

In a first aspect, the present disclosure provides a pyrimidine-fused compound represented by formula (I), a pharmaceutically acceptable salt thereof, a hydrate thereof, a prodrug thereof, a stereoisomer thereof or a solvate thereof,

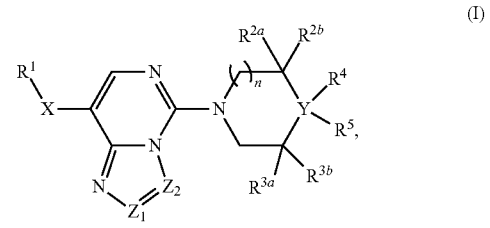

wherein, $Z_1$ and $Z_2$ are both CH; or, one of $Z_1$ and $Z_2$ is N, and the other is CH;

X is independently S or absent;

Y is independently C or N;

n is independently 0, 1 or 2;

$R^1$ is independently phenyl substituted by zero to four $R^{1a}$, heteroaryl containing one to four nitrogen atoms and substituted by zero to four $R^{1a}$, naphthyl substituted by zero to four $R^{1a}$, heteronaphthyl containing one to four nitrogen atoms and substituted by zero to four $R^{1a}$, benzoheterocyclyl unsubstituted or substituted by zero to four $R^{1a}$, fused heteroaryl containing one to four nitrogen atoms and unsubstituted or substituted by zero to four $R^{1a}$, heteroaryl containing one to four heteroatoms selected from N, $NR^{1b}$, O and $S(O)_m$ and substituted by zero to four $R^{1a}$, $C_{1-8}$ alkyl unsubstituted or substituted by $R^{1c}$, or $C_{1-8}$ haloalkyl unsubstituted or substituted by $R^{1c}$; wherein m is 0, 1 or 2;

$R^{2a}$, $R^{2b}$, $R^{3a}$ and $R^{3b}$ are independently hydrogen, or $C_{1-4}$ alkyl unsubstituted or substituted by $R^{1a1}$;

when Y is N, then $R^4$ is independently hydrogen, or $C_{1-4}$ alkyl unsubstituted or substituted by $R^{1a1}$; and $R_5$ is absent;

when Y is C, then $R^4$ and $R^5$ are independently hydrogen, aryl, $C_{1-4}$ alkyl, $C_{1-4}$ alkoxy, —O—$C_{1-4}$ alkyl, amino, amino substituted by $C_{1-4}$ alkyl or amino substituted by —O—$C_{1-4}$ alkyl, or $R^4$ and $R^5$ together with Y form 3- to 7-membered saturated or partially unsaturated spiro ring substituted by zero to three $R^{4a}$, wherein the ring optionally contains one to three heteroatoms or groups independently selected from N, C(=O) and/or O; or, $R^4$ and $R^5$ together with Y form 3- to 7-membered cycloalkyl substituted by zero to three $R^{4a}$ or 3- to 7-membered heterocycloalkyl substituted by zero to three $R^{4a}$; in the 3- to 7-membered heterocycloalkyl, the heteroatom is selected from one or more of N, O and S, and the number of the heteroatom is 1-3;

or, any two adjacent groups of $R^{2a}$, $R^{2b}$, $R^{3a}$, $R^{3b}$, $R^4$ and $R^5$, together with the carbon atom and Y to which they are attached, form 3- to 7-membered cycloalkyl substituted by zero to three $R^{4a}$, or 3- to 7-membered heterocycloalkyl substituted by zero to three $R^{4a}$; in the 3- to 7-membered heterocycloalkyl, the heteroatom is selected from one or more of N, O and S, and the number of the heteroatom is 1-3;

$R^{1a}$ is independently halogen, $C_{1-4}$ alkoxy unsubstituted or substituted by $R^{1a1}$, $C_{1-4}$ alkyl unsubstituted or substituted by $R^{1a1}$, trifluoromethyl, —C(=O)OR$^{1a2}$, —NR$^{1a2}$R$^{1a3}$, —NHC(=O)R$^{1a4}$, or $C_{3-8}$ cycloalkyl unsubstituted or substituted by $R^{1a1}$;

$R^{1b}$ is independently hydrogen, or $C_{1-4}$ alkyl unsubstituted or substituted by $R^{1a1}$;

$R^{1c}$ is independently hydrogen, —C(=O)OR$^{1a2}$, or $C_{1-4}$ alkyl unsubstituted or substituted by $R^{1a1}$;

$R^{4a}$ is independently hydrogen, halogen, $C_{1-4}$ alkoxy unsubstituted or substituted by $R^{1a1}$, $C_{1-4}$ alkyl unsubstituted or substituted by $R^{1a1}$, hydroxyl, amino or $C_{1-4}$ alkylamino;

$R^{1a1}$ is independently halogen or $C_{1-4}$ alkyl;

$R^{1a2}$ and $R^{1a3}$ are independently hydrogen or $C_{1-4}$ alkyl;

$R^{1a4}$ is independently $C_{1-4}$ alkyl, substituted or unsubstituted alkenyl, —NHC(=O)H substituted by one or two $R^{1a1}$, —C(=O)NH$_2$ substituted by one or two $R^{1a1}$, amide, $C_{3-12}$ monocyclic or polycyclic heterocyclyl, or, substituted $C_{3-12}$ monocyclic or polycyclic heterocyclyl; the substituent in the substituted $C_{3-12}$ monocyclic or polycyclic heterocyclyl is independently one or more substituents selected from $R^{1a1}$, —OH and =O; when there are multiple substituents, then the substituents are the same or different.

In the present disclosure, some substituents in the pyrimidine-fused compound represented by formula (I) can be defined as follows, and the definitions of unmentioned substituents are as defined in any of the embodiments.

In an embodiment of the present disclosure, in the pyrimidine-fused compound represented by formula (I) according to the present disclosure, $Z_1$ and $Z_2$ are both C, or one of them is N;

X is independently S or absent;

Y is independently C or N;

n is independently 0, 1 or 2;

$R^1$ is independently phenyl substituted by zero to four $R^{1a}$, heteroaryl containing one to four nitrogen atoms and substituted by zero to four $R^{1a}$, naphthyl substituted by zero to four $R^{1a}$, heteronaphthyl containing one to four nitrogen atoms and substituted by zero to four $R^{1a}$, benzoheterocyclyl unsubstituted or substituted by zero to four $R^{1a}$, fused heteroaryl containing one to four nitrogen atoms and unsubstituted or substituted by zero to four $R^{1a}$, heteroaryl containing one to four heteroatoms selected from N, NR$^{1b}$, O and S(O)$_m$ etc., and substituted by zero to four $R^{1a}$, $C_{1-8}$ alkyl unsubstituted or substituted by $R^{1c}$, or $C_{1-8}$ haloalkyl unsubstituted or substituted by $R^{1c}$; wherein m is 0, 1 or 2;

$R^{1a}$ is independently halogen, $C_{1-4}$ alkoxy unsubstituted or substituted by $R^{1a1}$, $C_{1-4}$ alkyl unsubstituted or substituted by $R^{1a1}$, trifluoromethyl, C(=O)OR$^{1a2}$, NR$^{1a2}$R$^{1a3}$, NHC(=O)R$^{1a4}$, or $C_{3-8}$ cycloalkyl unsubstituted or substituted by $R^{1a1}$; $R^{1a1}$ is independently halogen or $C_{1-4}$ alkyl; $R^{1a2}$ and $R^{1a3}$ are independently hydrogen or $C_{1-4}$ alkyl; $R^{1a4}$ is independently $C_{1-4}$ alkyl, substituted or unsubstituted alkenyl, amide, or $C_{3-12}$ monocyclic or polycyclic heterocyclyl;

$R^{1b}$ is independently hydrogen, or $C_{1-4}$ alkyl unsubstituted or substituted by $R^{1a1}$.

$R^{1c}$ is independently hydrogen, —C(=O)OR$^{1a2}$, or $C_{1-4}$ alkyl unsubstituted or substituted by $R^{1a1}$;

$R^{2a}$, $R^{2b}$, $R^{3a}$ and $R^{3b}$ are independently hydrogen, or $C_{1-4}$ alkyl unsubstituted or substituted by $R^{1a1}$;

when Y is N, then $R^4$ is independently hydrogen, or $C_{1-4}$ alkyl unsubstituted or substituted by $R^{1a1}$; and $R_5$ is absent;

when Y is C, then $R^4$ and $R^5$ are independently hydrogen, aryl, $C_{1-4}$ alkyl, $C_{1-4}$ alkoxy, —O—$C_{1-4}$ alkyl, amino, amino substituted by $C_{1-4}$ alkyl or amino substituted by —O—$C_{1-4}$ alkyl, or $R^4$ and $R^5$ together with Y form 3- to 7-membered saturated or partially unsaturated spiro ring substituted by zero to three $R^{4a}$, wherein the ring optionally contains one to three heteroatoms or groups independently selected from N, C(=O) and/or O;

$R^{4a}$ is independently hydrogen, halogen, $C_{1-4}$ alkoxy unsubstituted or substituted by $R^{1a1}$, $C_{1-4}$ alkyl unsubstituted or substituted by $R^{1a1}$, hydroxyl, amino or $C_{1-4}$ alkylamino.

In an embodiment of the present disclosure, in the pyrimidine-fused compound represented by formula (I) according to the present disclosure, $Z_1$ is C, $Z_2$ is N; or, $Z_1$ is N, $Z_2$ is C;

X is independently S or absent;

Y is independently C or N;

n is independently 0, 1 or 2;

$R^1$ is independently phenyl substituted by zero to four $R^{1a}$, heteroaryl containing one to four nitrogen atoms and substituted by zero to four $R^{1a}$, naphthyl substituted by zero to four $R^{1a}$, heteronaphthyl containing one to four nitrogen atoms and substituted by zero to four $R^{1a}$, benzoheterocyclyl unsubstituted or substituted by zero to four $R^{1a}$, fused heteroaryl containing one to four nitrogen atoms and unsubstituted or substituted by zero to four $R^{1a}$, heteroaryl containing one to four heteroatoms selected from N, NR$^{1b}$, O and S(O)$_m$ and substituted by zero to four $R^{1a}$, $C_{1-8}$ alkyl unsubstituted or substituted by $R^{1c}$, or $C_{1-8}$ haloalkyl unsubstituted or substituted by $R^{1c}$; wherein m is 0, 1 or 2;

$R^{1a}$ is independently halogen, $C_{1-4}$ alkoxy unsubstituted or substituted by $R^{1a1}$, $C_{1-4}$ alkyl unsubstituted or substituted by $R^{1a1}$, trifluoromethyl, C(=O)OR$^{1a2}$, NR$^{1a2}$R$^{1a3}$, NHC(=O)R$^{1a4}$, or $C_{3-8}$ cycloalkyl unsubstituted or substituted by $R^{1a1}$; $R^{1a1}$ is independently halogen or $C_{1-4}$ alkyl; $R^{1a2}$ and $R^{1a3}$ are independently hydrogen or $C_{1-4}$ alkyl; $R^{1a4}$ is independently $C_{1-4}$ alkyl, substituted or unsubstituted alkenyl, amide, or $C_{3-12}$ monocyclic or polycyclic heterocyclyl;

$R^{1b}$ is independently hydrogen, or $C_{1-4}$ alkyl unsubstituted or substituted by $R^{1a1}$;

$R^{1c}$ is independently hydrogen, —C(=O)OR$^{1a2}$, or $C_{1-4}$ alkyl unsubstituted or substituted by $R^{1a1}$;

$R^{2a}$, $R^{2b}$, $R^{3a}$ and $R^{3b}$ are independently hydrogen, or $C_{1-4}$ alkyl unsubstituted or substituted by $R^{1a1}$;

when Y is N, then $R^4$ is independently hydrogen, or $C_{1-4}$ alkyl unsubstituted or substituted by $R^{1a1}$; and $R_5$ is absent;

when Y is C, then $R^4$ and $R^5$ are independently hydrogen, aryl, $C_{1-4}$ alkyl, $C_{1-4}$ alkoxy, —O—$C_{1-4}$ alkyl, amino, amino substituted by $C_{1-4}$ alkyl or amino substituted by —O—$C_{1-4}$ alkyl; or $R^4$ and $R^5$ together with Y form 3- to 7-membered saturated or partially unsaturated spiro ring substituted by zero to three $R^{4a}$, wherein the ring optionally contains one to three heteroatoms or groups independently selected from N, C(=O) and/or O;

$R^{4a}$ is independently hydrogen, halogen, $C_{1-4}$ alkoxy unsubstituted or substituted by $R^{1a1}$, $C_{1-4}$ alkyl unsubstituted or substituted by $R^{1a1}$, hydroxyl, amino or $C_{1-4}$ alkylamino.

In a preferable embodiment, the pyrimidine-fused compound represented by formula (I) is represent by formula (II),

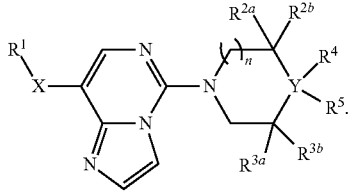

(II)

In a preferable embodiment of the present disclosure, in the pyrimidine-fused compound represented by formula (I) according to the present disclosure, $Z_1$ is C, $Z_2$ is N; or $Z_1$ is N, $Z_2$ is C.

In a preferable embodiment of the present disclosure, the pyrimidine-fused compound represented by formula (I) is represent by formula (III),

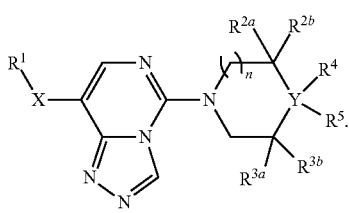

(III)

In a preferable embodiment of the present disclosure, the pyrimidine-fused compound represented by formula (I) is represent by formula (I-A),

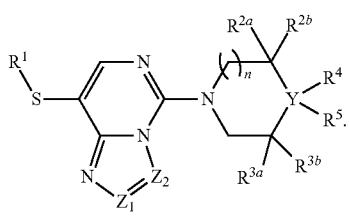

I-A

In a preferable embodiment of the present disclosure, the pyrimidine-fused compound represented by formula (I) is represent by formula (II-A),

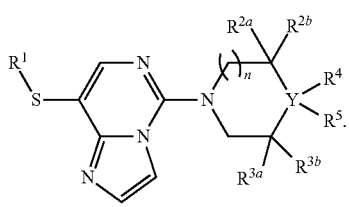

II-A

In a preferable embodiment of the present disclosure, when Y is C, then the pyrimidine-fused compound represented by formula (I) is represent by formula (I-B),

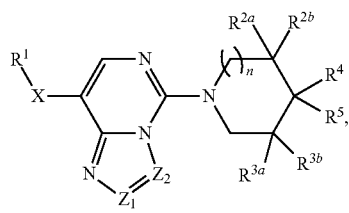

I-B wherein $R^4$ and $R^5$ together with the carbon atom to which they are attached form

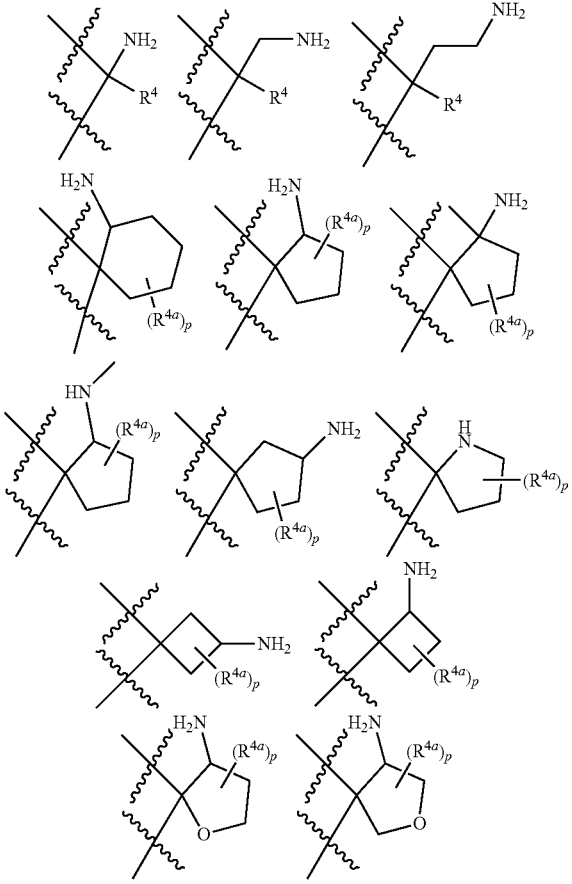

wherein p is 0, 1, 2 or 3.

In a preferable embodiment of the present disclosure, when Y is C, then the pyrimidine-fused compound represented by formula (I) is represent by formula (I-B),

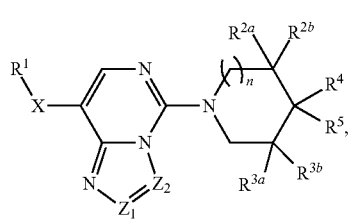

I-B wherein R⁴ and R⁵ together with the carbon atom to which they are attached form

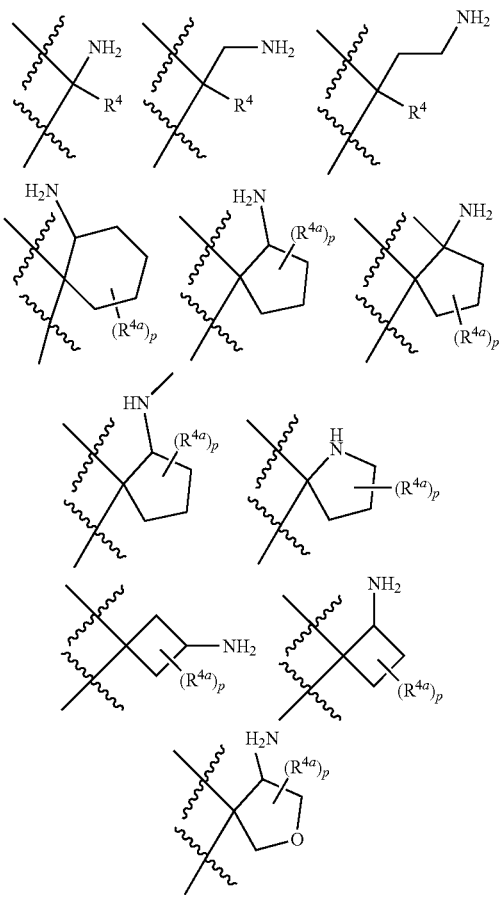

wherein p is 0, 1, 2 or 3.

In a preferable embodiment of the present disclosure, when Y is C, then the pyrimidine-fused compound represented by formula (I) is represent by formula (II-B),

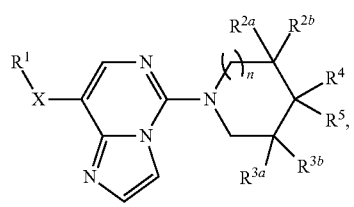

II-B wherein R⁴ and R⁵ together with the carbon atom to which they are attached form

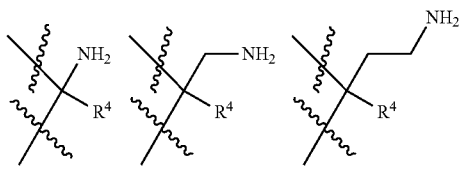

In a preferable embodiment, the pyrimidine-fused compound represented by formula (I) is represent by formula (I-C),

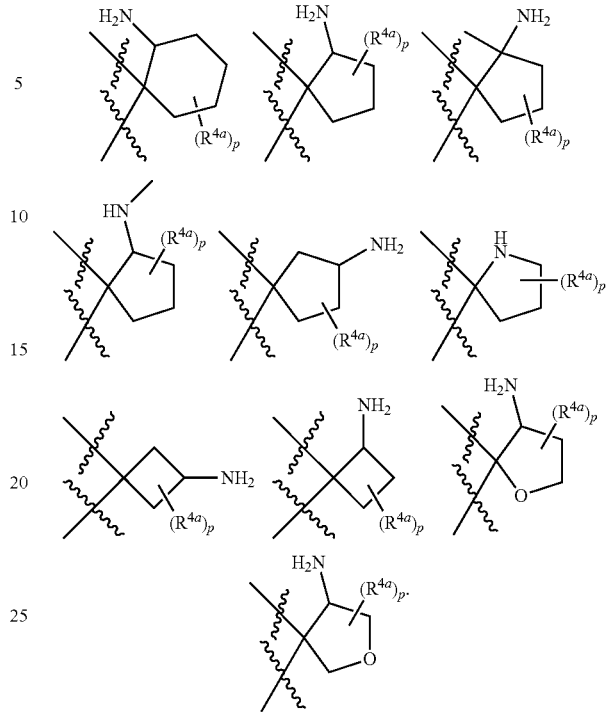

I-C

In a preferable embodiment, the pyrimidine-fused compound represented by formula (I) is represent by formula (III-C),

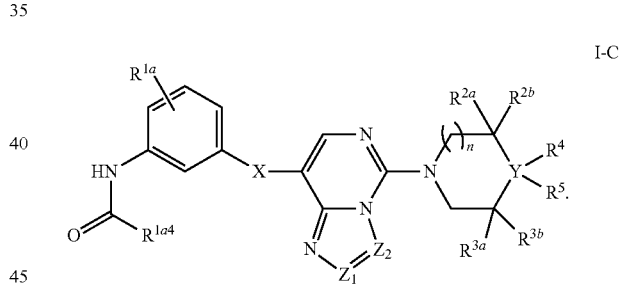

III-C

In a preferable embodiment, the pyrimidine-fused compound represented by formula (I) is represent by formula (II-C),

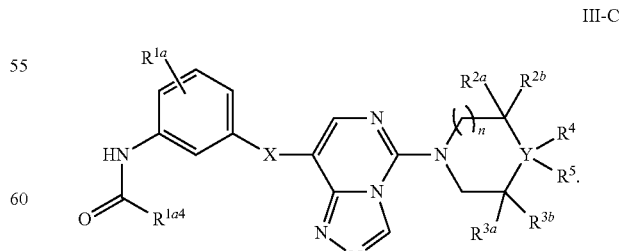

II-C

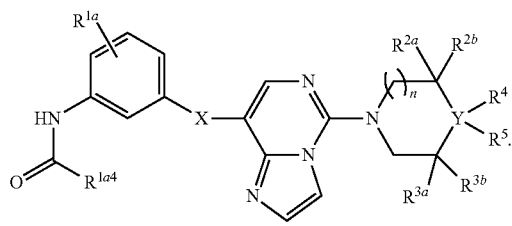

In an embodiment of the present disclosure, the phenyl substituted by zero to four $R^{1a}$ is

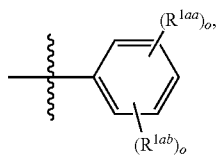

wherein o is independently 0, 1, 2, 3 or 4, and the total number of $R^{1aa}$ and $R^{1ab}$ is 0-4, the definitions of $R^{1aa}$ and $R^{1ab}$ are the same as $R^{1a}$.

In an embodiment of the present disclosure, the naphthyl substituted by zero to four $R^{1a}$ is

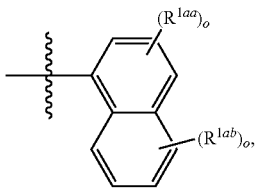

wherein o is independently 0, 1, 2, 3 or 4, and the total number of $R^{1aa}$ and $R^{1ab}$ is 0-4, the definitions of $R^{1aa}$ and $R^{1ab}$ are the same as $R^{1a}$; the naphthyl is preferably

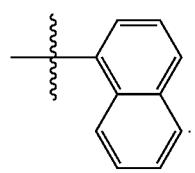 [SMILES: *c1cccc2ccccc12]

In an embodiment of the present disclosure, the heteroaryl containing one to four nitrogen atoms and substituted by zero to four $R^{1a}$ is

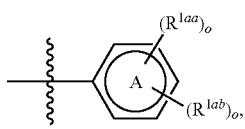

wherein o is independently 0, 1, 2, 3 or 4, and the total number of $R^{1aa}$ and $R^{1ab}$ is 0-4, the definitions of $R^{1aa}$ and $R^{1ab}$ are the same as $R^{1a}$;

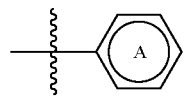

is the heteroaryl containing one to four nitrogen atoms; the heteroaryl containing one to four nitrogen atoms is preferably pyridinyl

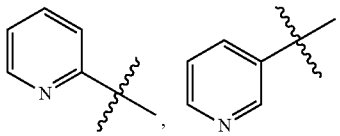 or 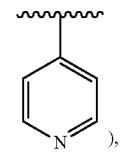, (e.g., ), pyrimidinyl

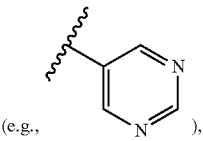

(e.g., ), pyrazinyl

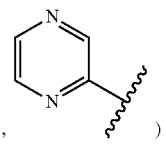

(e.g., )

or pyridazinyl

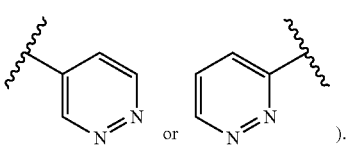

(e.g., or ).

In an embodiment of the present disclosure, the heteronaphthyl containing one to four nitrogen atoms and substituted by zero to four $R^{1a}$ is

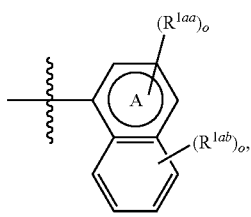

wherein o is 0, 1, 2, 3 or 4, and the total number of $R^{1aa}$ and $R^{1ab}$ is 0-4, the definitions of $R^{1aa}$ and $R^{1ab}$ are the same as $R^{1a}$;

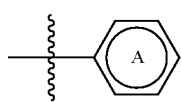

is heteroaryl containing one to four nitrogen atoms; the heteronaphthyl containing one to four nitrogen atoms is preferably quinolinyl (e.g., 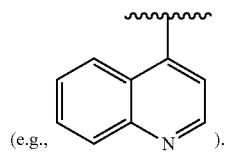 ).

In an embodiment of the present disclosure, the benzoheterocyclyl unsubstituted or substituted by zero to four $R^{1a}$ is

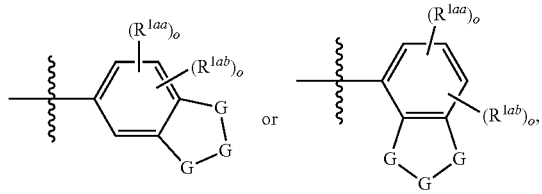

wherein G is independently selected from C, C(=O), N, S and O; o is 0, 1, 2, 3 or 4, and the total number of $R^{1aa}$ and $R^{1ab}$ is 0-4, the definitions of $R^{1aa}$ and $R^{1b}$ are the same as $R^{1a}$;

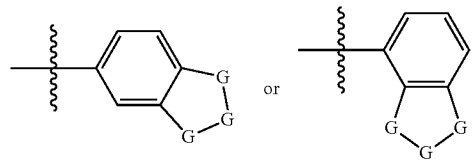

is the benzoheterocyclyl; the benzoheterocyclyl is preferably 2,3-dihydrobenzofuranyl (e.g., 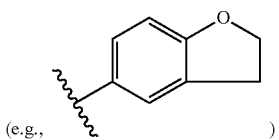 [SMILES: *c1ccc2c(c1)CCO2] )

or indolinyl (e.g., 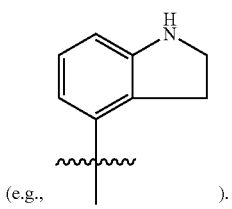 [SMILES: *c1cccc2c1CCN2] ).

In an embodiment of the present disclosure, the fused heteroaryl containing one to four nitrogen atoms and unsubstituted or substituted by zero to four $R^{1a}$ is

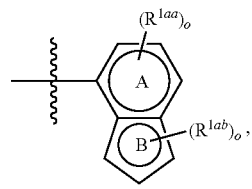

wherein o is 0, 1, 2, 3 or 4, and the total number of $R^{1aa}$ and $R^{1ab}$ 0-4, the definitions of $R^{1aa}$ and $R^{1ab}$ are the same as $R^{1a}$;

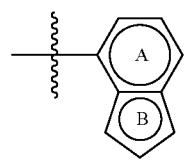

is the fused heteroaryl containing one to four nitrogen atoms, wherein

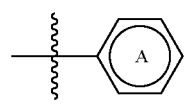

is heteroaryl containing one to four nitrogen atoms, and

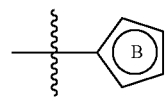

is heteroaryl containing one to four heteroatoms selected from N, $NR^{1b}$, O and $S(O)_m$; the fused heteroaryl containing one to four nitrogen atoms is preferably 1H-pyrrolo[2,3-b]pyridine (e.g., 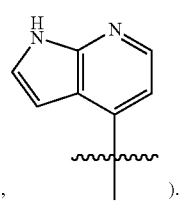 ).

In an embodiment of the present disclosure, the heteroaryl containing one to four heteroatoms selected from N, $NR^{1b}$, O and $S(O)_m$ and substituted by zero to four $R^{1a}$ is

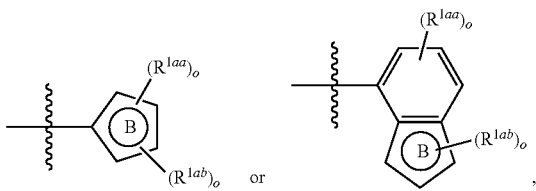

wherein o is 0, 1, 2, 3 or 4, and the total number of $R^{1aa}$ and $R^{1ab}$ is 0-4, the definitions of $R^{1aa}$ and $R^{1ab}$ are the same as $R^{1a}$;

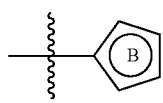

is heteroaryl containing one to four heteroatoms selected from N, $NR^{1b}$, O and $S(O)_m$; the heteroaryl containing one to four heteroatoms selected from N, NRb, O and $S(O)_m$ is preferably a heteroaryl containing one to three heteroatoms selected from N, $NR^{1b}$, O and $S(O)_m$, more preferably imidazolyl

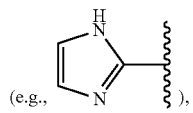

thiazolyl

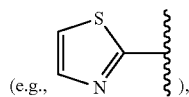

oxazolyl

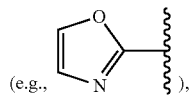

thiadiazolyl

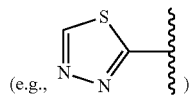

or benzothiazolyl

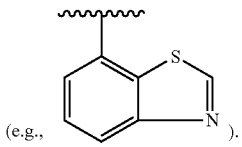

In an embodiment of the present disclosure, in the $C_{1-8}$ alkyl unsubstituted or substituted by $R^{1c}$ and $C_{1-8}$ haloalkyl unsubstituted or substituted by $R^{1c}$, the $C_{1-8}$ alkyl in the $C_{1-8}$ alkyl and $C_{1-8}$ haloalkyl (e.g., methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl or octyl) can be independently $C_{1-6}$ alkyl (e.g., methyl, ethyl, n-propyl, isopropyl, n-butyl, tert-butyl, sec-butyl, isobutyl, n-pentyl, 1-ethylpropyl, 1-methylbutyl, 2-methyl-1-butyl, 3-methyl-1-butyl, neopentyl, 3-methyl-2-butyl, tert-amyl, n-hexyl or isohexyl), preferably ethyl.

In an embodiment of the present disclosure, in the $C_{1-8}$ haloalkyl unsubstituted or substituted by $R^{1c}$, the halogen can be fluorine, chlorine, bromine or iodine.

In an embodiment of the present disclosure, in the $C_{1-8}$ haloalkyl unsubstituted or substituted by $R^{1c}$, the number of the halogen can be 1, 2, 3, 4, 5 or 6.

In an embodiment of the present disclosure, in the $C_{1-4}$ alkyl unsubstituted or substituted by $R^{1a1}$, the $C_{1-4}$ alkyl can be methyl, ethyl, n-propyl, isopropyl, n-butyl, isobutyl, sec-butyl or tert-butyl; preferably methyl.

In an embodiment of the present disclosure, when $R^4$ and/or $R^5$ are aryl, then the aryl is $C_6$-$C_{10}$ aryl, preferably phenyl or naphthyl.

In an embodiment of the present disclosure, when $R^4$ and/or $R^5$ are $C_{1-4}$ alkyl, —O—$C_{1-4}$ alkyl, amino substituted by $C_{1-4}$ alkyl or amino substituted by —O—$C_{1-4}$ alkyl, then the $C_{1-4}$ alkyl can be methyl, ethyl, n-propyl, isopropyl, n-butyl, isobutyl, sec-butyl or tert-butyl.

In an embodiment of the present disclosure, when $R^4$ and/or $R^5$ are $C_{1-4}$ alkoxy, then the $C_{1-4}$ alkoxy can be methyloxy, ethyloxy, n-propyloxy, isopropyloxy, n-butyloxy, isobutyloxy, sec-butyloxy or tert-butyloxy.

In an embodiment of the present disclosure, when $R^4$ and $R^5$ together with Y form 3- to 7-membered cycloalkyl substituted by zero to three $R^{4a}$, then the 3- to 7-membered cycloalkyl (e.g., cyclopropyl, cyclobutyl, cyclopentyl, cyclohexyl or cycloheptyl) can be cyclobutyl

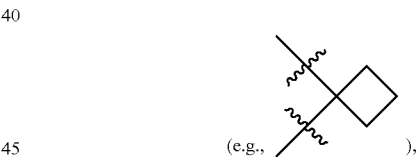

cyclopentyl

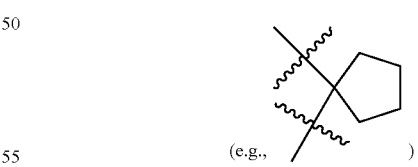

or cyclohexyl

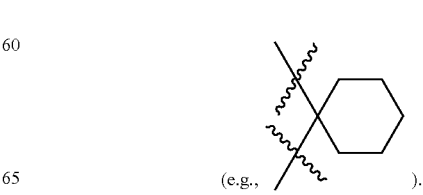

In an embodiment of the present disclosure, when $R^4$ and $R^5$ together with Y form 3- to 7-membered heterocycloalkyl substituted by zero to three $R^{4a}$, then the 3- to 7-membered heterocycloalkyl can be 5- to 6-membered heterocycloalkyl; in the 5- to 6-membered heterocycloalkyl, the heteroatom is selected from one or more of N, O and S, and the number of the heteroatom is 1-2; preferably tetrahydrofuranyl (e.g., 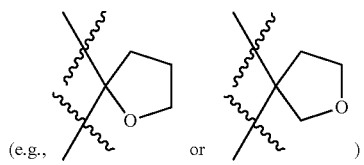 [SMILES: *C1(*)CCCO1 ; *C1(*)CCOC1] )

or pyrrolidinyl (e.g., 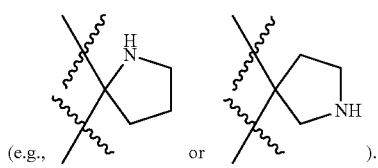 [SMILES: *C1(*)CCCN1 ; *C1(*)CCNC1] ).

In an embodiment of the present disclosure, when any two adjacent groups of $R^{2a}$, $R^{2b}$, $R^{3a}$, $R^{3b}$, $R^4$ and $R^5$, together with the carbon atom and Y to which they are attached, form 3- to 7-membered cycloalkyl substituted by zero to three $R^{4a}$, then the 3- to 7-membered cycloalkyl (e.g., cyclopropyl, cyclobutyl, cyclopentyl, cyclohexyl or cycloheptyl) can be cyclopentyl (e.g., 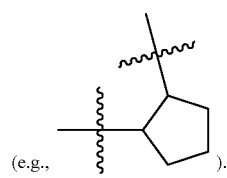 ).

In an embodiment of the present disclosure, when one or more of $R^{1a}$, $R^{4a}$ and $R^{1a1}$ is independently halogen, then the halogen is fluorine, chlorine, bromine or iodine, preferably fluorine or chlorine.

In an embodiment of the present disclosure, in the $C_{1-4}$ alkoxy unsubstituted or substituted by $R^{1a1}$, the $C_{1-4}$ alkoxy can be methyloxy, ethyloxy, n-propyloxy, isopropyloxy, n-butyloxy, isobutyloxy, sec-butyloxy or tert-butyloxy, preferably methyloxy.

In an embodiment of the present disclosure, in the $C_{3-8}$ cycloalkyl unsubstituted or substituted by $R^{1a1}$, the $C_{3-8}$ cycloalkyl can be cyclopropyl, cyclobutyl, cyclopentyl, cyclohexyl, cycloheptyl or cyclooctyl, preferably cyclopropyl.

In an embodiment of the present disclosure, when one or more of $R^{1a1}$, $R^{1a2}$, $R^{1a3}$ and $R^{1a4}$ is independently $C_{1-4}$ alkyl, then the $C_{1-4}$ alkyl can be methyl, ethyl, n-propyl, isopropyl, n-butyl, isobutyl, sec-butyl or tert-butyl, preferably methyl.

In an embodiment of the present disclosure, when $R^{4a}$ is $C_{1-4}$ alkylamino, then the $C_{1-4}$ alkyl can be methyl, ethyl, n-propyl, isopropyl, n-butyl, isobutyl, sec-butyl or tert-butyl.

In an embodiment of the present disclosure, in the substituted or unsubstituted alkenyl, the alkenyl can be $C_2$-$C_{10}$ alkenyl, preferably $C_2$-$C_6$ alkenyl; e.g., ethenyl, 1-propenyl, allyl, but-1-enyl, but-2-enyl, pent-1-enyl or pent-1,4-dienyl, preferably ethenyl.

In an embodiment of the present disclosure, the amide can be —C(=O)NH$_2$ or —NHC(=O)H.

In an embodiment of the present disclosure, in the $C_{3-12}$ monocyclic or polycyclic heterocyclyl, or substituted $C_{3-12}$ monocyclic or polycyclic heterocyclyl, the heteroatom is selected from one or more of N, O and S, and the number of the heteroatom is 1-4; preferably monocyclic or bicyclic heterocyclyl, wherein the heteroatom is selected from one or more of N, O and S, and the number of the heteroatom is 1-2;

e.g., 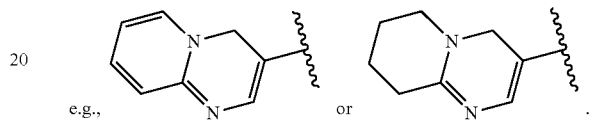

In an embodiment of the present disclosure, in $R^4$ and $R^5$, or, in $R^{4a}$, the amino substituted by $C_{1-4}$ alkyl is NH(CH$_3$).

In an embodiment of the present disclosure, the —C(=O)OR$^{1a2}$ is —C(=O)OCH$_3$.

In an embodiment of the present disclosure, the NR$^{1a2}$R$^{1a3}$ is —NH$_2$ or N(CH$_3$).

In an embodiment of the present disclosure, the —C(=O)NH$_2$ substituted by two R$^{1a1}$ is —C(=O)N(CH$_3$)$_2$.

In an embodiment of the present disclosure, the substituted $C_{3-12}$ monocyclic or polycyclic heterocyclyl is

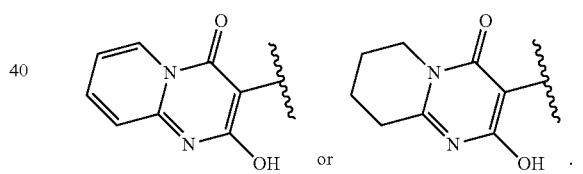

In an embodiment of the present disclosure, the NHC(=O)R$^{1a4}$ is —NHC(=O)CH$_3$ or

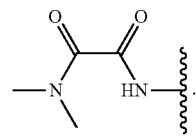 [SMILES: *NC(=O)C(=O)N(C)C]

In an embodiment of the present disclosure, the phenyl substituted by zero to four R$^{1a}$ is

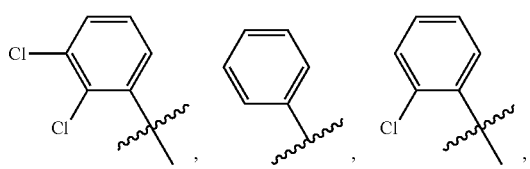

-continued
In an embodiment of the present disclosure, the heteroaryl containing one to four nitrogen atoms and substituted by zero to four $R^{1a}$ is
In an embodiment of the present disclosure, the fused heteroaryl containing one to four nitrogen atoms and unsubstituted or substituted by zero to four $R^{1a}$ is
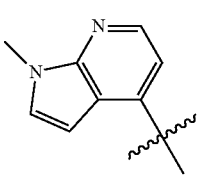
.

In an embodiment of the present disclosure, the heteroaryl containing one to four heteroatoms selected from N, NR$^{1b}$, and S(O)$_m$ and substituted by zero to four R$^{1a}$ is

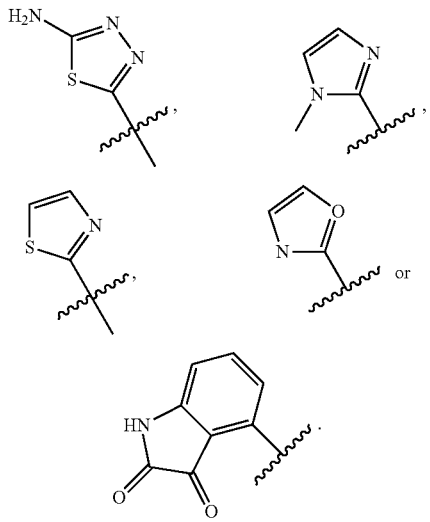

In an embodiment of the present disclosure, the C$_{1-8}$ alkyl substituted by R$^{1c}$ is

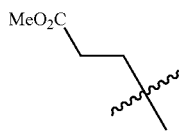

In an embodiment of the present disclosure, R$^{2a}$, R$^{2b}$, R$^{3a}$ and R$^{3b}$ are independently hydrogen or methyl.

In an embodiment of the present disclosure, when Y is N, then R$^4$ is independently hydrogen or methyl; and R$_5$ is absent;

In an embodiment of the present disclosure, when Y is C, then R$^4$ and R$^5$ are independently hydrogen, methyl, ethyl, phenyl, amino, methylamino or ethylamino.

In a preferable embodiment R$^1$ is selected from

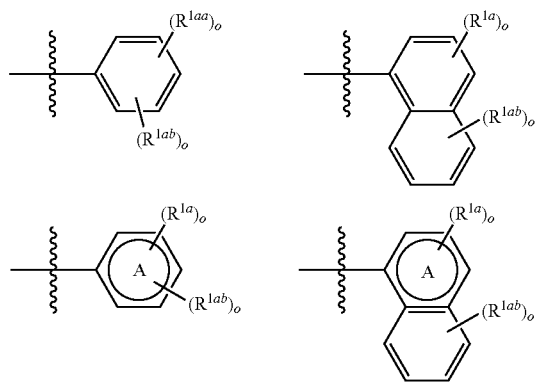

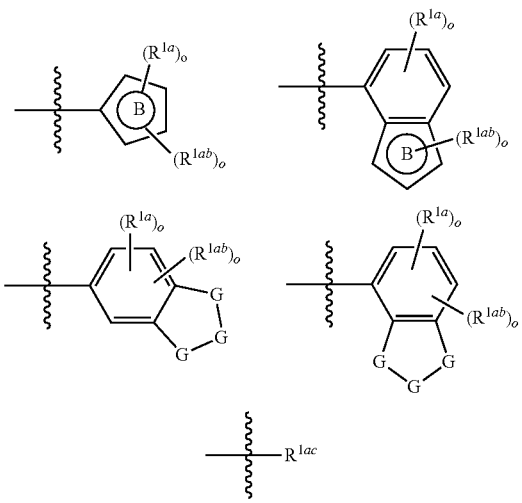

wherein, o is 0, 1, 2, 3 or 4; ring A is heteroaryl containing one to four nitrogen atoms; ring B is heteroaryl containing one to four heteroatoms selected from N, S and O; G is independently selected from C, C(=O), N, S and O; R$^{1aa}$ and R$^{1ab}$ are independently R$^{1a}$; R$^{1ac}$ is independently C$_{1-8}$ alkyl unsubstituted or substituted by R or C$_{1-8}$ haloalkyl unsubstituted or substituted by R$^{1c}$.

In an embodiment of the present disclosure,

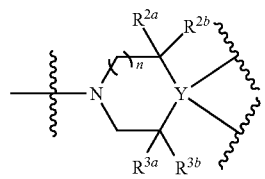

can be

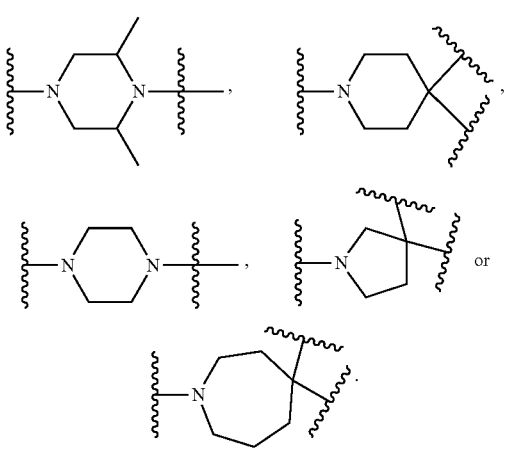

In an embodiment of the present disclosure, when Y is C, and R$^4$ and R$^5$ together with Y form 3- to 7-membered cycloalkyl substituted by zero to three R$^{4a}$, then the 3- to 7-membered cycloalkyl substituted by zero to three R$^{4a}$ is heterocycloalkyl substituted by zero to three $R^{4a}$, then the 3- to 7-membered heterocycloalkyl substituted by zero to three $R^{4a}$ is

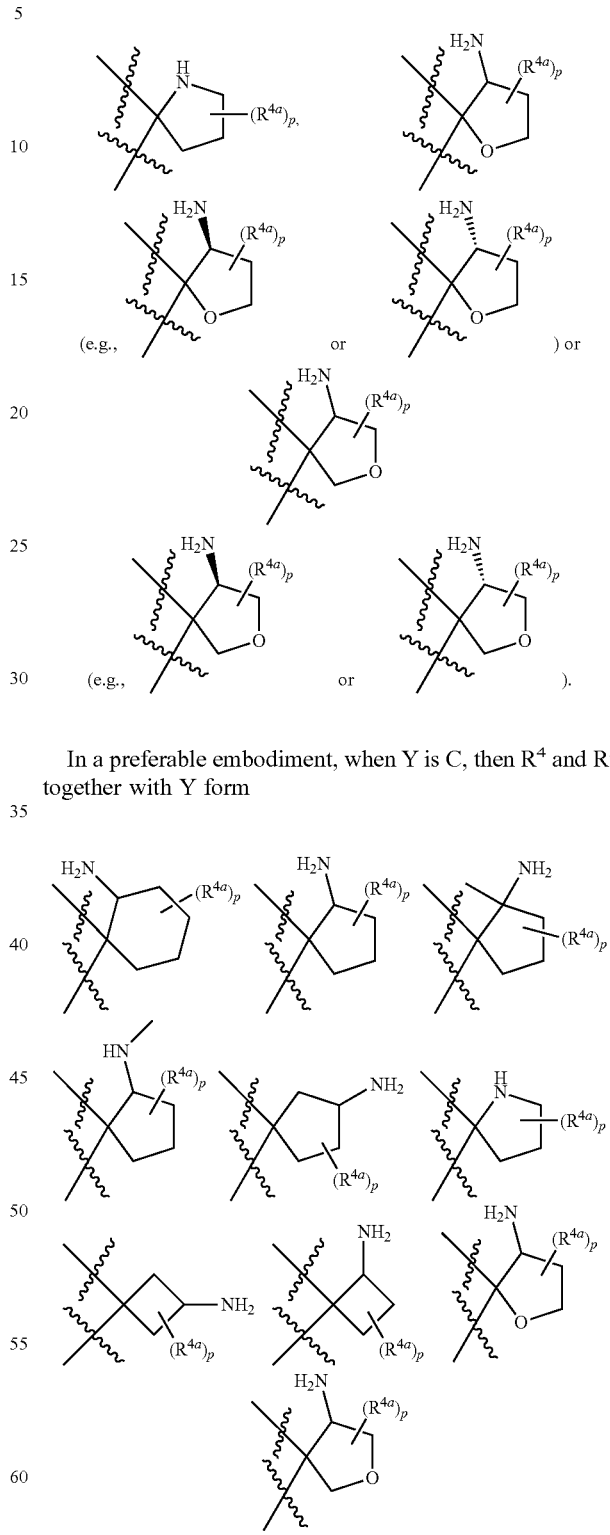

In a preferable embodiment, when Y is C, then $R^4$ and $R^5$ together with Y form wherein, p is 0, 1, 2 or 3; $R^{4a}$ is as defined above.

In a preferable embodiment, when Y is C, then $R^4$ and $R^5$ together with Y form

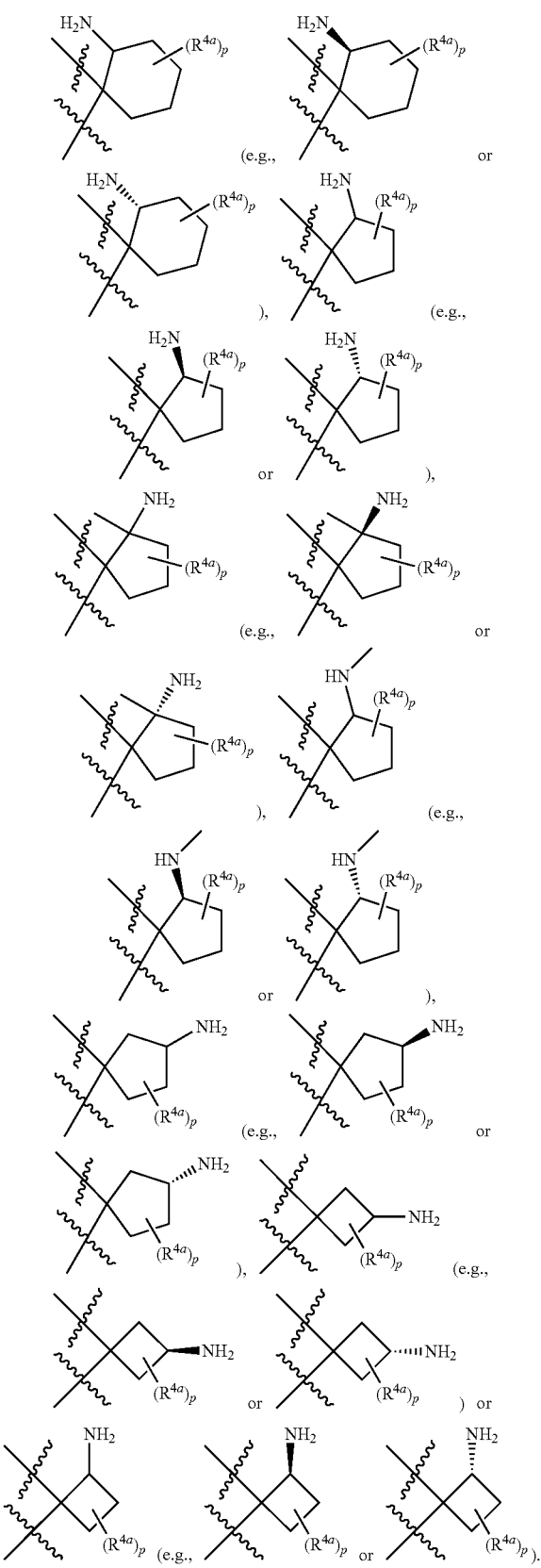

In an embodiment of the present disclosure, when Y is C, and $R^4$ and $R^5$ together with Y form 3- to 7-membered

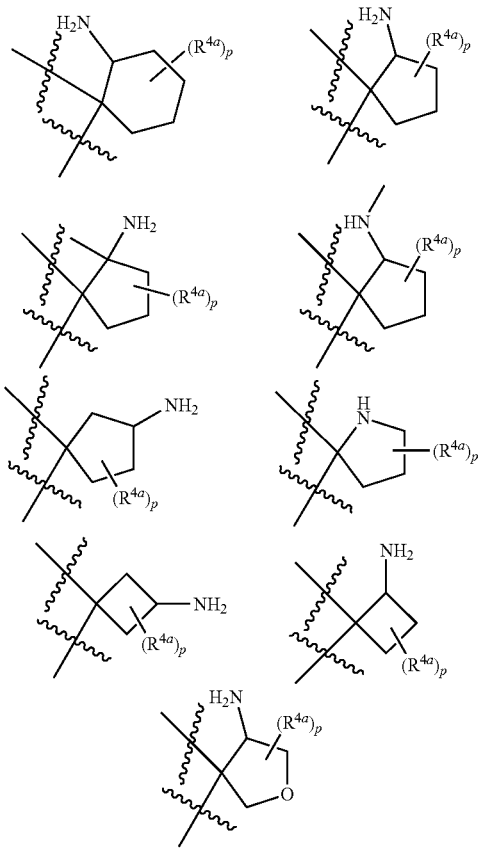
In a preferable embodiment, when Y is C, then R⁴ and R⁵ together with Y form
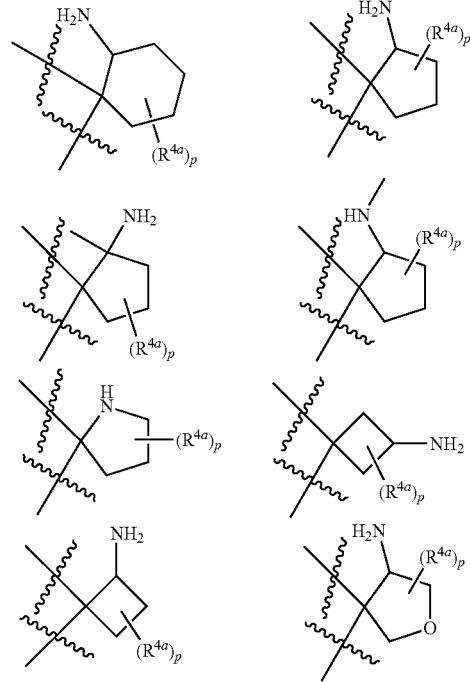
wherein, p and $R^{4a}$ are as defined above.
In a preferable embodiment, when Y is C, then $R^4$ and $R^5$ together with Y form
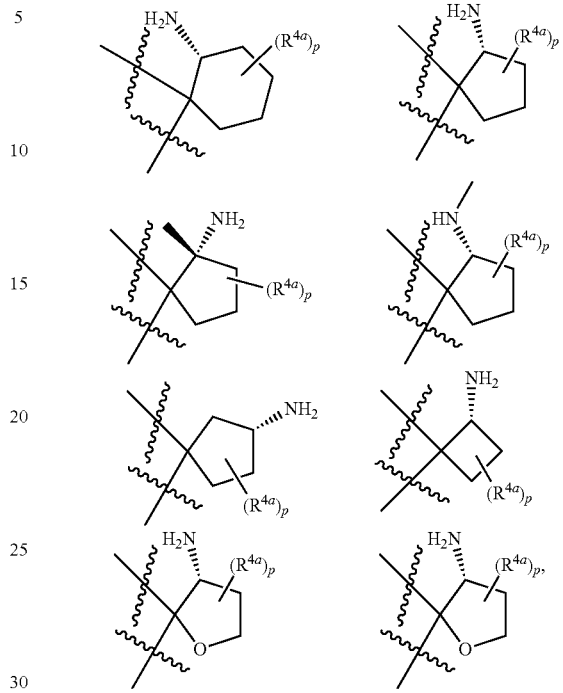
wherein, p and $R^{4a}$ are as defined above.
In an embodiment of the present disclosure, when Y is C, then $R^4$ and $R^5$ together with Y form
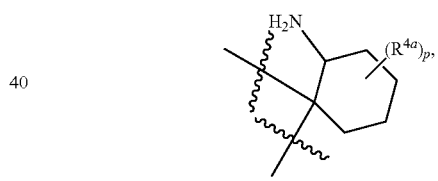
wherein the
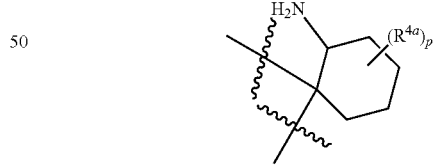
is preferably
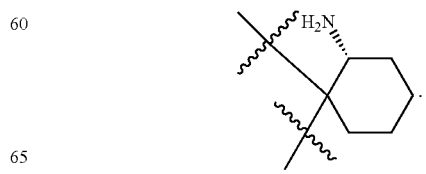

In an embodiment of the present disclosure, when Y is C, then R⁴ and R⁵ together with Y form

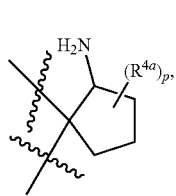

wherein the

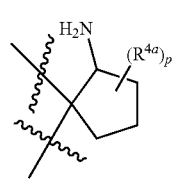

is preferably

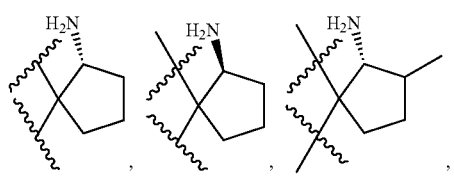

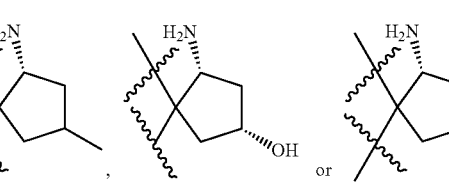

In an embodiment of the present disclosure, when Y is C, then R⁴ and R⁵ together with Y form

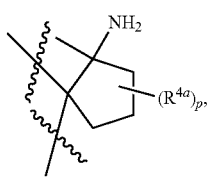

wherein the

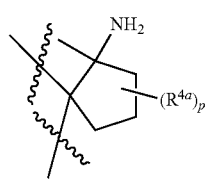

is preferably

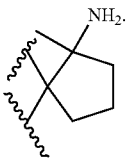

In an embodiment of the present disclosure, when Y is C, then R⁴ and R⁵ together with Y form

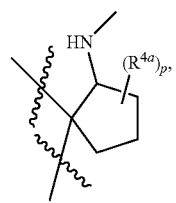

wherein the

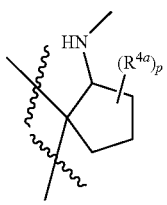

is preferably

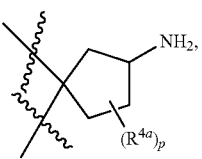

In an embodiment of the present disclosure, when Y is C, then R⁴ and R⁵ together with Y form

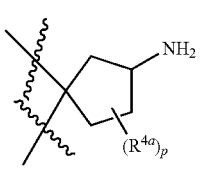

wherein the is preferably

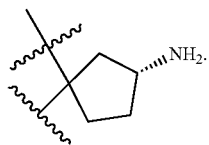 [SMILES: *C1(*)CC[C@@H](N)C1]

In an embodiment of the present disclosure, when Y is C, then R⁴ and R⁵ together with Y form

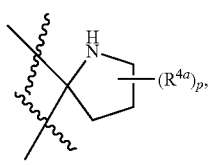

wherein the

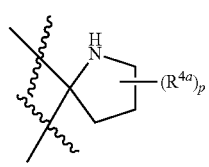

is preferably

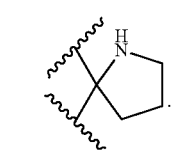 [SMILES: *C1(*)CCCN1]

In an embodiment of the present disclosure, when Y is C, then R⁴ and R⁵ together with Y form

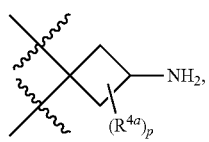

wherein the

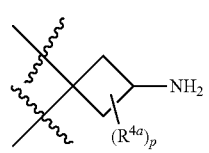

is preferably

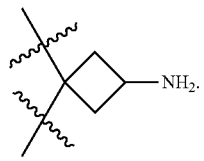 [SMILES: *C1(*)CC(N)C1]

In an embodiment of the present disclosure, when Y is C, then R⁴ and R⁵ together with Y form

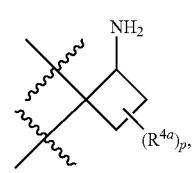

wherein the

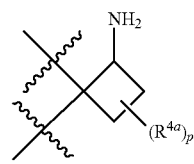

is preferably

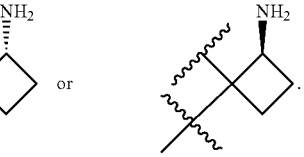

In an embodiment of the present disclosure, when Y is C, then R⁴ and R⁵ together with Y form

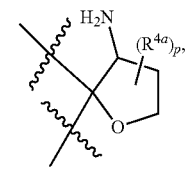

wherein the

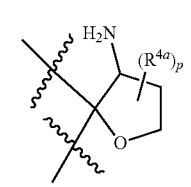

is preferably

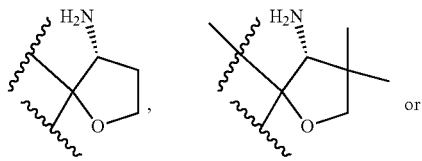,

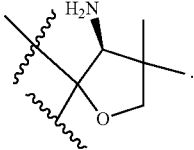.

In an embodiment of the present disclosure, when Y is C, then $R^4$ and $R^5$ together with Y form

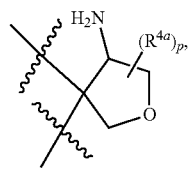

wherein the

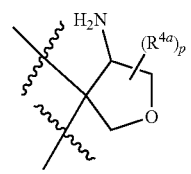

is preferably

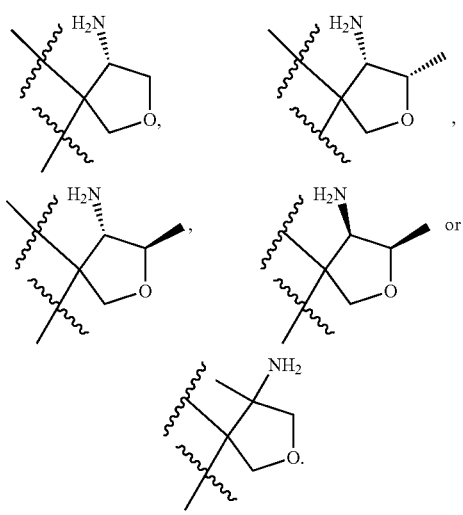

In an embodiment of the present disclosure, when Y is N, then

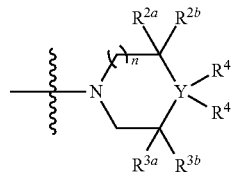

can be or

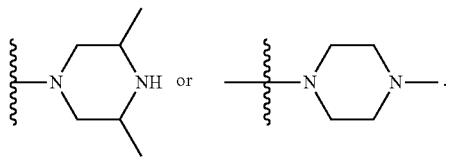

In an embodiment of the present disclosure, when any two adjacent groups of $R^{2a}$, $R^{2b}$, $R^{3a}$, $R^{3b}$, $R^4$ and $R^5$, together with the carbon atom and Y to which they are attached, form 3- to 7-membered cycloalkyl substituted by zero to three $R^{4a}$, then the 3- to 7-membered cycloalkyl substituted by zero to three $R^4$ is

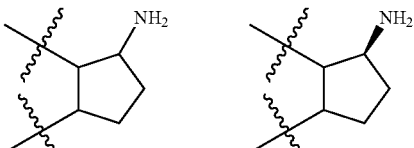 (e.g., 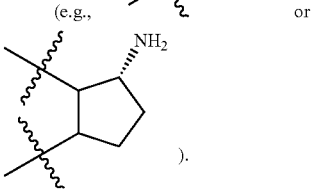).

In an embodiment of the present disclosure, when any two adjacent groups of $R^{2a}$, $R^{2b}$, $R^{3a}$, $R^{3b}$, $R^4$ and $R^5$, together with the carbon atom and Y to which they are attached, form 3- to 7-membered cycloalkyl substituted by zero to three $R^{4a}$, then

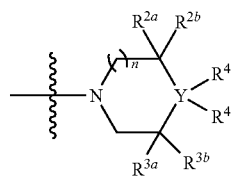

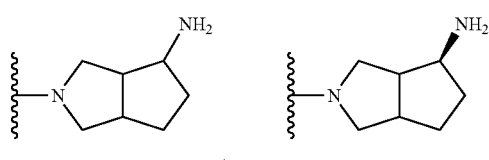 (e.g., or

-continued

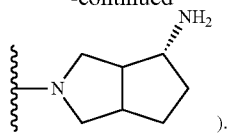

).

In an embodiment of the present disclosure, when Y is C, then

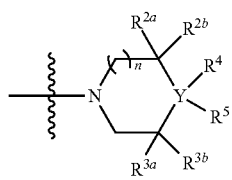

can be

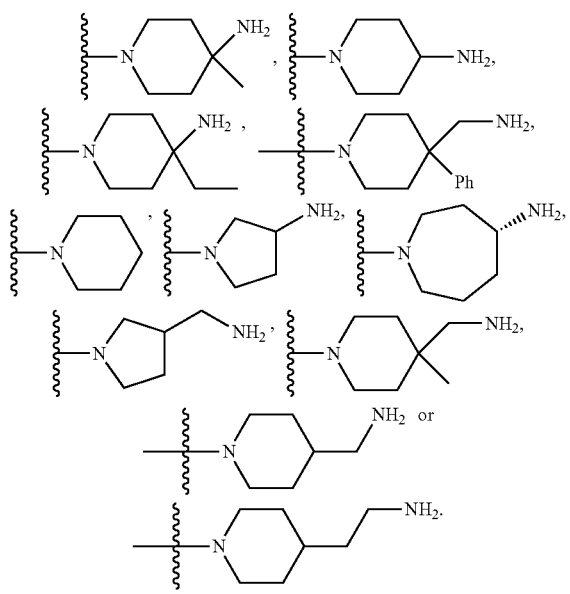

In an embodiment of the present disclosure, when Y is C, and $R^4$ and $R^5$ together with Y form 3 to 7-membered cycloalkyl substituted by zero to three $R^{4a}$ then

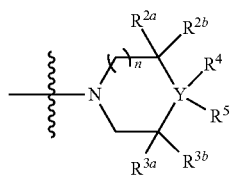

can be

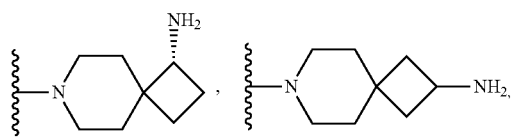

-continued

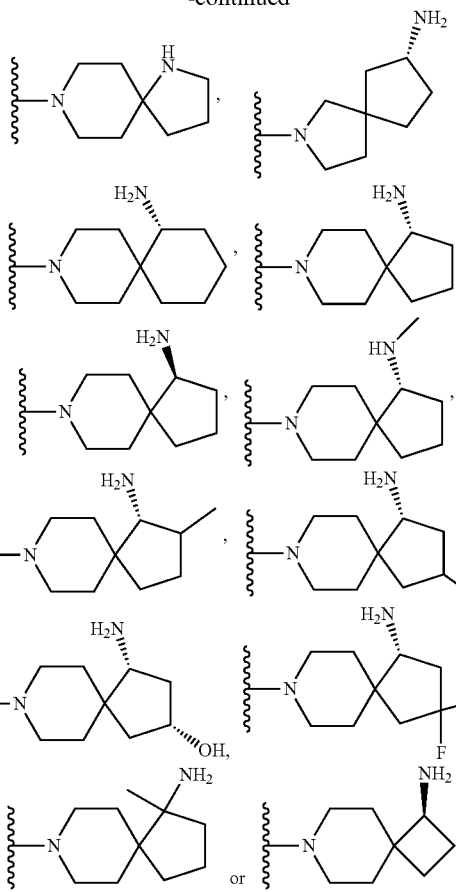

In an embodiment of the present disclosure, when Y is C, and $R^4$ and $R^5$ together with Y form 3- to 7-membered heterocycloalkyl substituted by zero to three $R^{4a}$, then

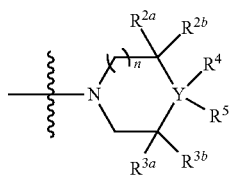

can be

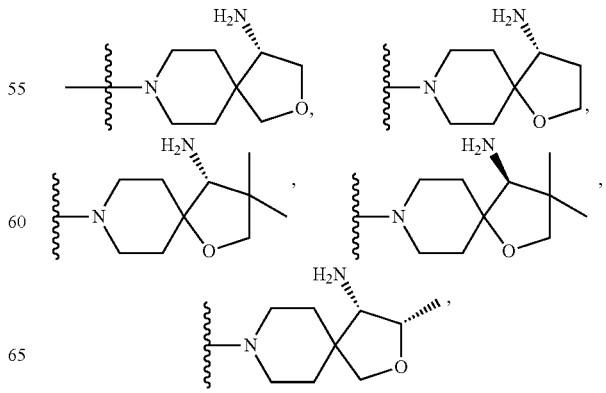

33
-continued

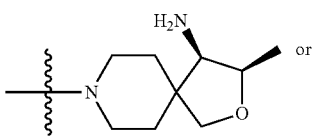 or

34
-continued

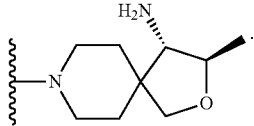

In a preferred embodiment, the compound is selected from any of the following compounds:

| No. | Compound structure | Compound name |
|---|---|---|
| 1 | 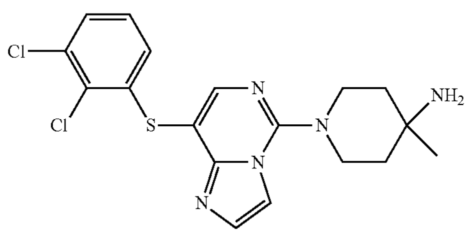 [SMILES: CC1(N)CCN(c2ncc(Sc3cccc(Cl)c3Cl)c3nccn23)CC1] | 1-(8-((2,3-dichlorophenyl)thio)imidazo[1,2-c]pyrimidin-5-yl)-4-methylpiperidin-4-amine |
| 2 | 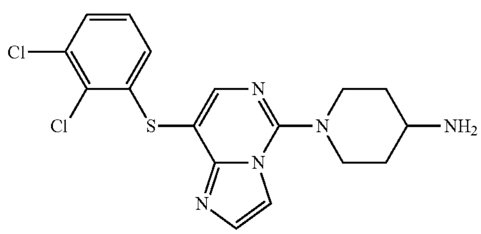 [SMILES: NC1CCN(c2ncc(Sc3cccc(Cl)c3Cl)c3nccn23)CC1] | 1-(8-((2,3-dichlorophenyl)thio)imidazo[1,2-c]pyrimidin-5-yl)piperidin-4-amine |
| 3 | 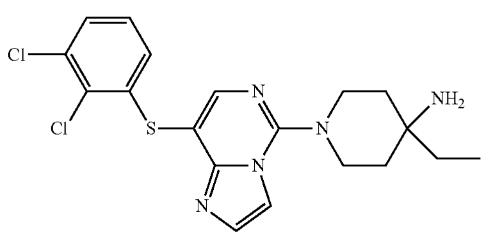 [SMILES: CCC1(N)CCN(c2ncc(Sc3cccc(Cl)c3Cl)c3nccn23)CC1] | 1-(8-((2,3-dichlorophenyl)thio)imidazo[1,2-c]pyrimidin-5-yl)-4-ethylpiperidin-4-amine |
| 4 | 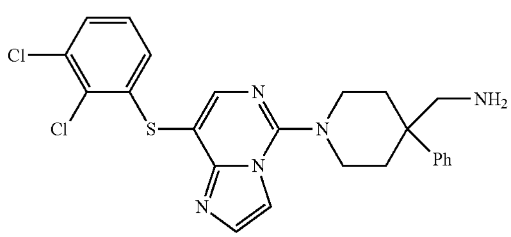 [SMILES: NCC1(c2ccccc2)CCN(c2ncc(Sc3cccc(Cl)c3Cl)c3nccn23)CC1] | (1-(8-((2,3-dichlorophenyl)thio)imidazo[1,2-c]pyrimidin-5-yl)-4-phenylpiperidin-4-yl)methanamine |
| 5 | 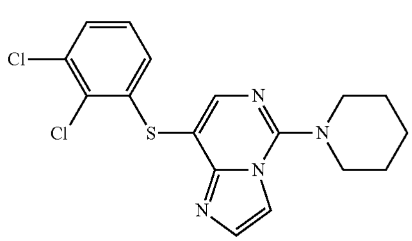 [SMILES: Clc1cccc(Sc2cnc(N3CCCCC3)n3ccnc23)c1Cl] | 8-((2,3-dichlorophenyl)thio)-5-(piperidin-1-yl)imidazo[1,2-c]pyrimidine |

-continued

| No. | Compound structure | Compound name |
|---|---|---|
| 6 | 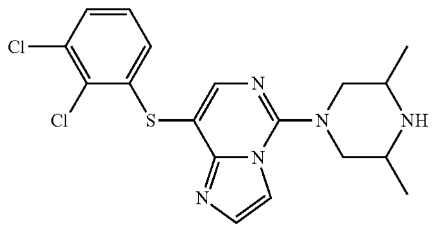 [SMILES: CC1CN(c2ncc(Sc3cccc(Cl)c3Cl)c3nccn23)CC(C)N1] | 8-((2,3-dichlorophenyl)thio)-5-(3,5-dimethylpiperazin-1-yl)imidazo[1,2-c]pyrimidine |
| 7 | 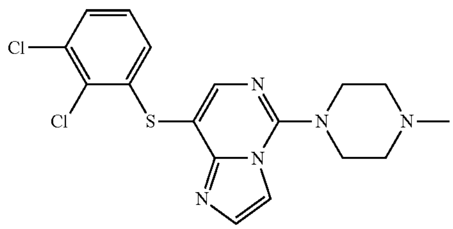 [SMILES: CN1CCN(c2ncc(Sc3cccc(Cl)c3Cl)c3nccn23)CC1] | 8-((2,3-dichlorophenyl)thio)-5-(4-methylpiperazin-1-yl)imidazo[1,2-c]pyrimidine |
| 8 | 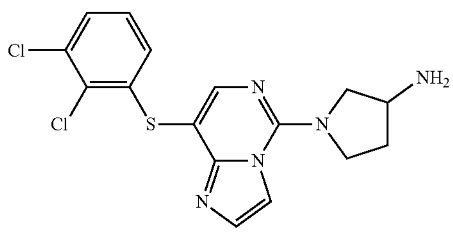 [SMILES: NC1CCN(c2ncc(Sc3cccc(Cl)c3Cl)c3nccn23)C1] | 1-(8-((2,3-dichlorophenyl)thio)imidazo[1,2-c]pyrimidin-5-yl)pyrrolidin-3-amine |
| 9 | 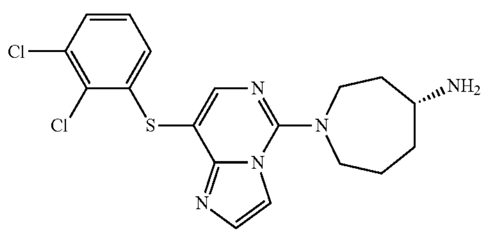 [SMILES: N[C@@H]1CCCN(c2ncc(Sc3cccc(Cl)c3Cl)c3nccn23)CC1] | (R)-1-(8-((2,3-dichlorophenyl)thio)imidazo[1,2-c]pyrimidin-5-yl)azepan-4-amine |
| 10 | 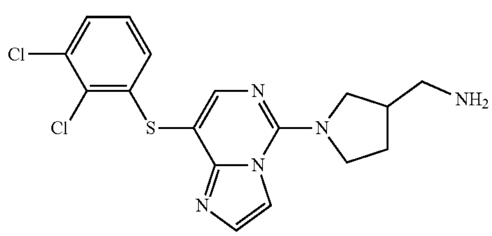 [SMILES: NCC1CCN(c2ncc(Sc3cccc(Cl)c3Cl)c3nccn23)C1] | (1-(8-((2,3-dichlorophenyl)thio)imidazo[1,2-c]pyrimidin-5-yl)pyrrolidin-3-yl)methanamine |
| 11 | 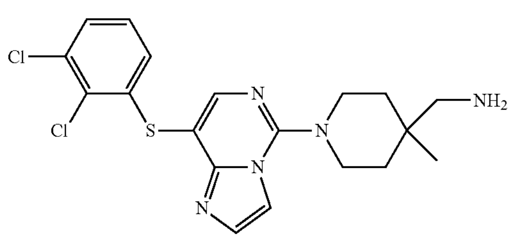 [SMILES: CC1(CN)CCN(c2ncc(Sc3cccc(Cl)c3Cl)c3nccn23)CC1] | (1-(8-((2,3-dichlorophenyl)thio)imidazo[1,2-c]pyrimidin-5-yl)-4-methylpiperidin-4-yl)methanamine |

| No. | Compound structure | Compound name |
|---|---|---|
| 12 | 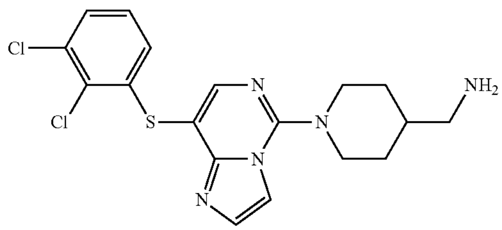 [SMILES: NCC1CCN(c2ncc(Sc3cccc(Cl)c3Cl)c3nccn23)CC1] | (1-(8-((2,3-dichlorophenyl)thio)imidazo[1,2-c]pyrimidin-5-yl)piperidin-4-yl)methanamine |
| 13 | 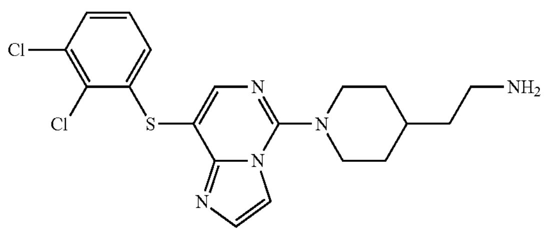 [SMILES: NCCC1CCN(c2ncc(Sc3cccc(Cl)c3Cl)c3nccn23)CC1] | 2-(1-(8-((2,3-dichlorophenyl)thio)imidazo[1,2-c]pyrimidin-5-yl)piperidin-4-yl)ethan-1-amine |
| 14 | 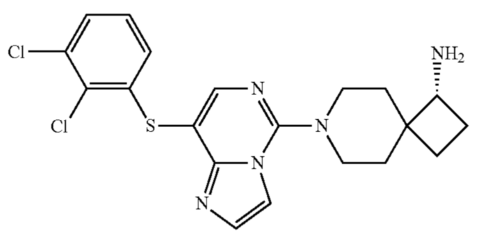 [SMILES: N[C@@H]1CCC12CCN(c1ncc(Sc3cccc(Cl)c3Cl)c3nccn13)CC2] | (R)-7-(8-((2,3-dichlorophenyl)thio)imidazo[1,2-c]pyrimidin-5-yl)-7-azaspiro[3.5]nonan-1-amine |
| 15 | 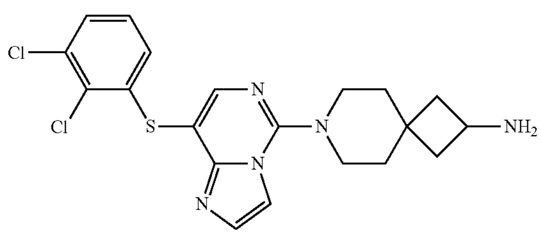 [SMILES: NC1CC2(CCN(c3ncc(Sc4cccc(Cl)c4Cl)c4nccn34)CC2)C1] | 7-(8-((2,3-dichlorophenyl)thio)imidazo[1,2-c]pyrimidin-5-yl)-7-azaspiro[3.5]nonan-2-amine |
| 16 | 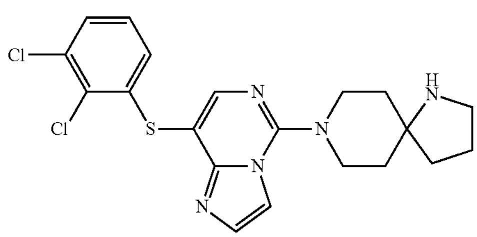 [SMILES: Clc1cccc(Sc2cnc(N3CCC4(CCCN4)CC3)n3ccnc23)c1Cl] | 8-((2,3-dichlorophenyl)thio)-5-(1,8-diazaspiro[4.5]decan-8-yl)imidazo[1,2-c]pyrimidine |
| 17 | 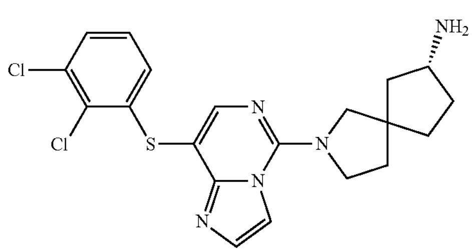 [SMILES: N[C@@H]1CCC2(CCN(c3ncc(Sc4cccc(Cl)c4Cl)c4nccn34)C2)C1] | (7R)-2-(8-((2,3-dichlorophenyl)thio)imidazo[1,2-c]pyrimidin-5-yl)-2-azaspiro[4.4]nonan-7-amine |

| No. | Compound structure | Compound name |
| --- | --- | --- |
| 18 | 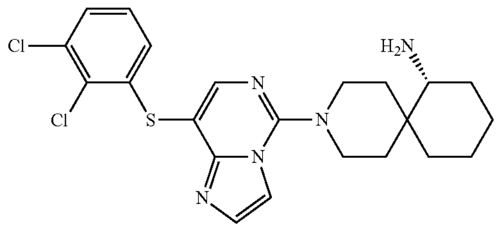 | (R)-3-(8-((2,3-dichlorophenyl)thio)imidazo[1,2-c]pyrimidin-5-yl)-3-azaspiro[5.5]undecan-7-amine |
| 19 | 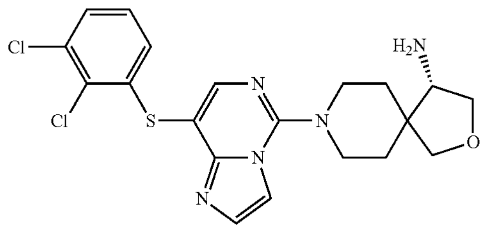 [SMILES: N[C@@H]1COCC12CCN(c1ncc(Sc3cccc(Cl)c3Cl)c3nccn13)CC2] | (S)-8-(8-((2,3-dichlorophenyl)thio)imidazo[1,2-c]pyrimidin-5-yl)-2-oxa-8-azaspiro[4.5]decan-4-amine |
| 20 | 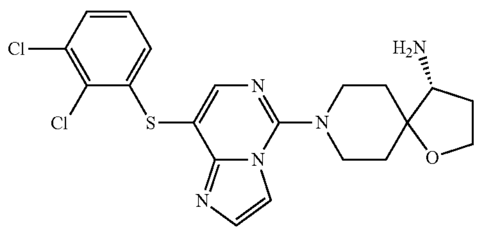 [SMILES: N[C@@H]1CCOC12CCN(c1ncc(Sc3cccc(Cl)c3Cl)c3nccn13)CC2] | (R)-8-(8-((2,3-dichlorophenyl)thio)imidazo[1,2-c]pyrimidin-5-yl)-1-oxa-8-azaspiro[4.5]decan-4-amine |
| 21 | 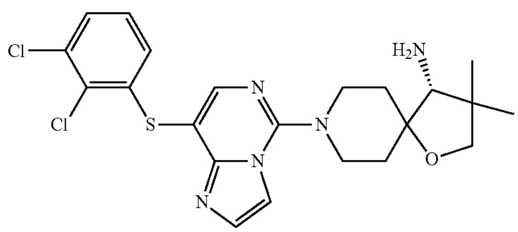 [SMILES: CC1(C)COC2(CCN(c3ncc(Sc4cccc(Cl)c4Cl)c4nccn34)CC2)[C@@H]1N] | (R)-8-(8-((2,3-dichlorophenyl)thio)imidazo[1,2-c]pyrimidin-5-yl)-3,3-dimethyl-1-oxa-8-azaspiro[4.5]decan-4-amine |
| 22 | 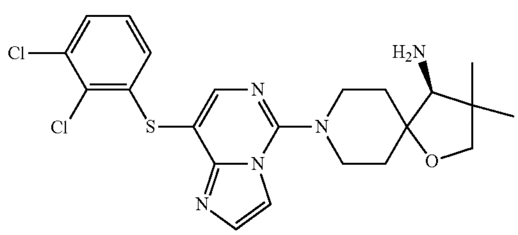 [SMILES: CC1(C)COC2(CCN(c3ncc(Sc4cccc(Cl)c4Cl)c4nccn34)CC2)[C@H]1N] | (S)-8-(8-((2,3-dichlorophenyl)thio)imidazo[1,2-c]pyrimidin-5-yl)-3,3-dimethyl-1-oxa-8-azaspiro[4.5]decan-4-amine |
| 23 | 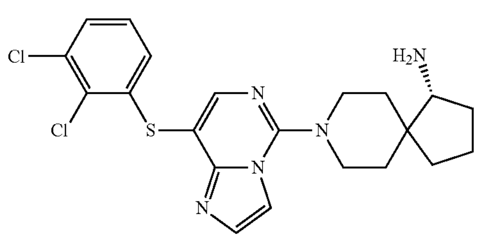 [SMILES: N[C@@H]1CCCC12CCN(c1ncc(Sc3cccc(Cl)c3Cl)c3nccn13)CC2] | (R)-8-(8-((2,3-dichlorophenyl)thio)imidazo[1,2-c]pyrimidin-5-yl)-8-azaspiro[4.5]decan-1-amine |

| No. | Compound structure | Compound name |
| --- | --- | --- |
| 24 | 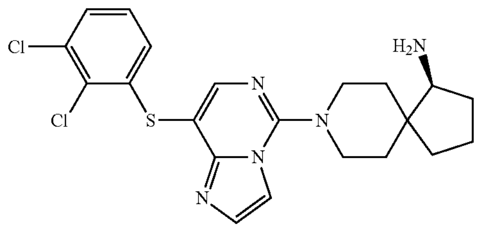 | (S)-8-(8-((2,3-dichlorophenyl)thio)imidazo[1,2-c]pyrimidin-5-yl)-8-azaspiro[4.5]decan-1-amine |
| 25 | 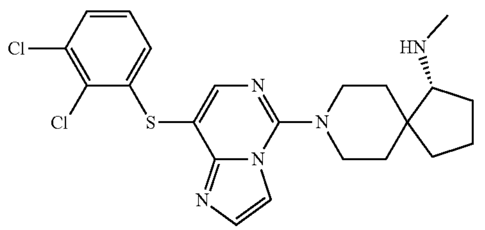 [SMILES: CN[C@@H]1CCCC12CCN(c1ncc(Sc3cccc(Cl)c3Cl)c3nccn13)CC2] | (R)-8-(8-((2,3-dichlorophenyl)thio)imidazo[1,2-c]pyrimidin-5-yl)-N-methyl-8-azaspiro[4.5]decan-1-amine |
| 26 | 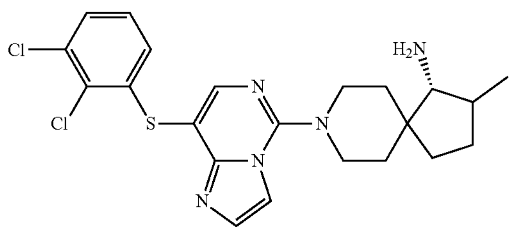 [SMILES: CC1CCC2(CCN(c3ncc(Sc4cccc(Cl)c4Cl)c4nccn34)CC2)[C@@H]1N] | (1R)-8-(8-((2,3-dichlorophenyl)thio)imidazo[1,2-c]pyrimidin-5-yl)-2-methyl-8-azaspiro[4.5]decan-1-amine |
| 27 | 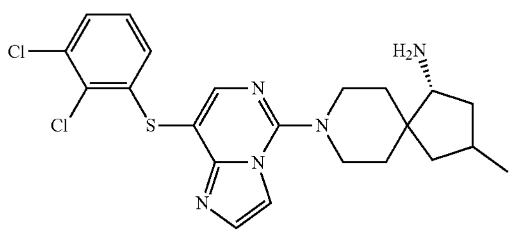 [SMILES: CC1C[C@@H](N)C2(CCN(c3ncc(Sc4cccc(Cl)c4Cl)c4nccn34)CC2)C1] | (1R)-8-(8-((2,3-dichlorophenyl)thio)imidazo[1,2-c]pyrimidin-5-yl)-3-methyl-8-azaspiro[4.5]decan-1-amine |
| 28 | 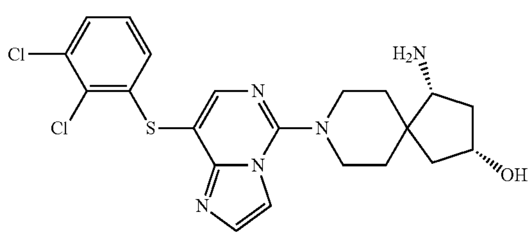 [SMILES: N[C@@H]1C[C@H](O)CC12CCN(c1ncc(Sc3cccc(Cl)c3Cl)c3nccn13)CC2] | (2R,4R)-4-amino-8-(8-((2,3-dichlorophenyl)thio)imidazo[1,2-c]pyrimidin-5-yl)-8-azaspiro[4.5]decan-2-ol |
| 29 | 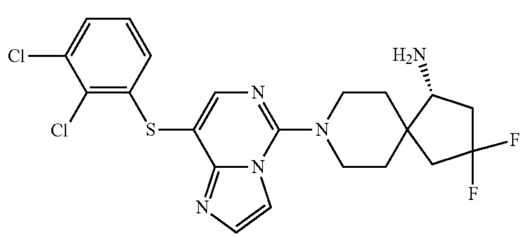 [SMILES: N[C@@H]1CC(F)(F)CC12CCN(c1ncc(Sc3cccc(Cl)c3Cl)c3nccn13)CC2] | (R)-8-(8-((2,3-dichlorophenyl)thio)imidazo[1,2-c]pyrimidin-5-yl)-3,3-difluoro-8-azaspiro[4.5]decan-1-amine |

| No. | Compound structure | Compound name |
|---|---|---|
| 30 | 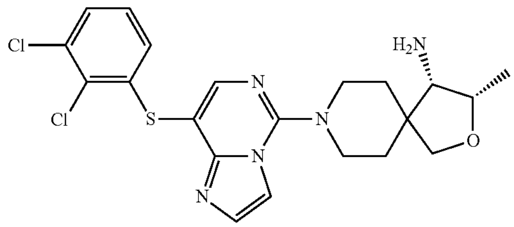 [SMILES: C[C@@H]1OCC2(CCN(c3ncc(Sc4cccc(Cl)c4Cl)c4nccn34)CC2)[C@@H]1N] | (3S,4S)-8-(8-((2,3-dichlorophenyl)thio)imidazo[1,2-c]pyrimidin-5-yl)-3-methyl-2-oxa-8-azaspiro[4.5]decan-4-amine |
| 31 | 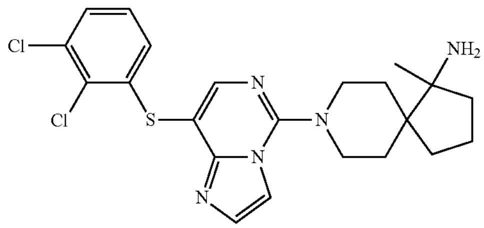 [SMILES: CC1(N)CCCC12CCN(c1ncc(Sc3cccc(Cl)c3Cl)c3nccn13)CC2] | 8-(8-((2,3-dichlorophenyl)thio)imidazo[1,2-c]pyrimidin-5-yl)-1-methyl-8-azaspiro[4.5]decan-1-amine |
| 32 | 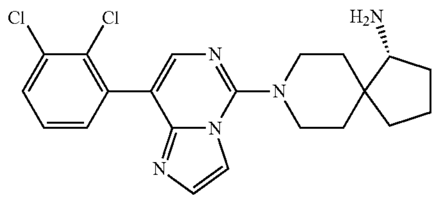 [SMILES: N[C@@H]1CCCC12CCN(c1ncc(-c3cccc(Cl)c3Cl)c3nccn13)CC2] | (R)-8-(8-(2,3-dichlorophenyl)imidazo[1,2-c]pyrimidin-5-yl)-8-azaspiro[4.5]decan-1-amine |
| 33 | 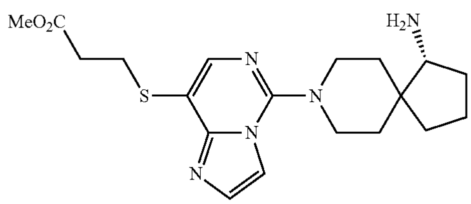 [SMILES: COC(=O)CCSc1cnc(N2CCC3(CCC[C@H]3N)CC2)n2ccnc12] | methyl (R)-3-((5-(1-amino-8-azaspiro[4.5]decan-8-yl)imidazo[1,2-c]pyrimidin-8-yl)thio)propionate |
| 34 | 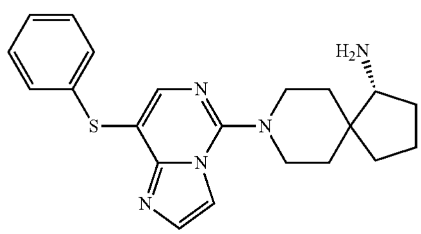 | (R)-8-(8-(phenylthio)imidazo[1,2-c]pyrimidin-5-yl)-8-azaspiro[4.5]decan-1-amine |
| 35 | 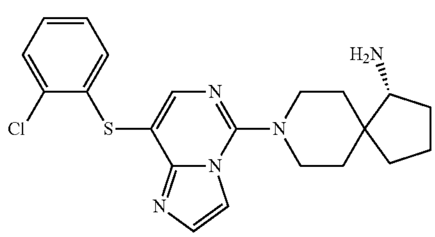 [SMILES: N[C@@H]1CCCC12CCN(c1ncc(Sc3ccccc3Cl)c3nccn13)CC2] | (R)-8-(8-((2-chlorophenyl)thio)imidazo[1,2-c]pyrimidin-5-yl)-8-azaspiro[4.5]decan-1-amine |
| 36 | 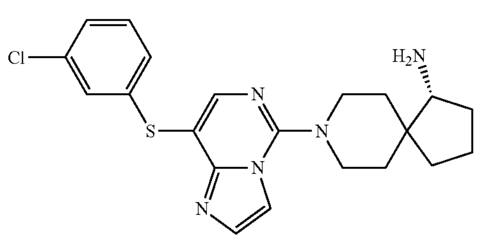 [SMILES: N[C@@H]1CCCC12CCN(c1ncc(Sc3cccc(Cl)c3)c3nccn13)CC2] | (R)-8-(8-((3-chlorophenyl)thio)imidazo[1,2-c]pyrimidin-5-yl)-8-azaspiro[4.5]decan-1-amine |

| No. | Compound structure | Compound name |
|---|---|---|
| 37 | 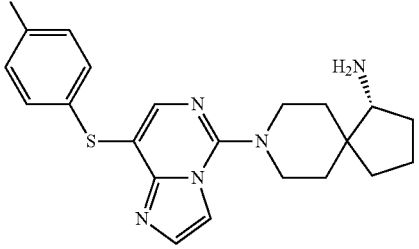 | (R)-8-(8-((4-chlorophenyl)thio)imidazo[1,2-c]pyrimidin-5-yl)-8-azaspiro[4.5]decan-1-amine |
| 38 | 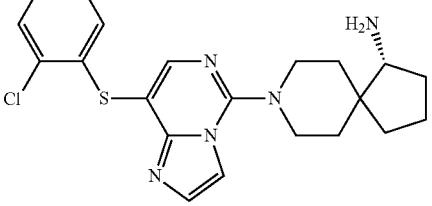 | (R)-8-(8-((2,4-dichlorophenyl)thio)imidazo[1,2-c]pyrimidin-5-yl)-8-azaspiro[4.5]decan-1-amine |
| 39 | 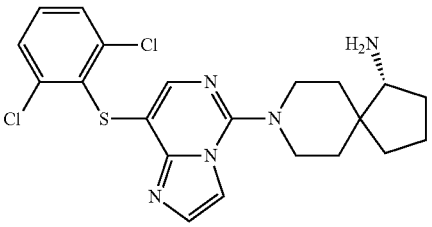 [SMILES: N[C@@H]1CCCC12CCN(c1ncc(Sc3c(Cl)cccc3Cl)c3nccn13)CC2] | (R)-8-(8-((2,6-dichlorophenyl)thio)imidazo[1,2-c]pyrimidin-5-yl)-8-azaspiro[4.5]decan-1-amine |
| 40 | 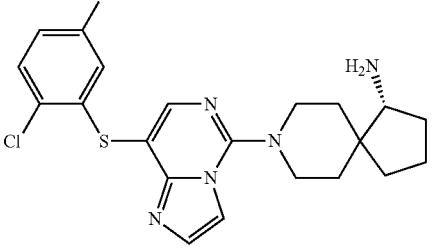 | (R)-8-(8-((2,5-dichlorophenyl)thio)imidazo[1,2-c]pyrimidin-5-yl)-8-azaspiro[4.5]decan-1-amine |
| 41 | 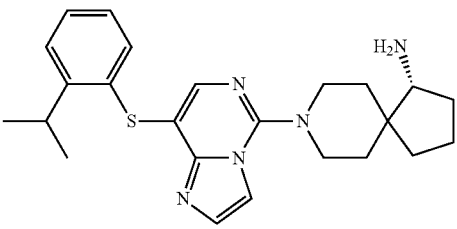 [SMILES: CC(C)c1ccccc1Sc1cnc(N2CCC3(CCC[C@H]3N)CC2)n2ccnc12] | (R)-8-(8-((2-isopropylphenyl)thio)imidazo[1,2-c]pyrimidin-5-yl)-8-azaspiro[4.5]decan-1-amine |
| 42 | 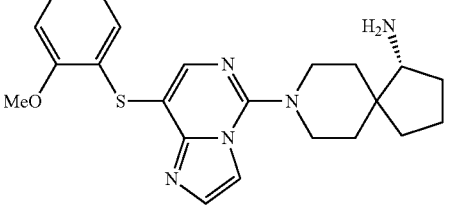 | (R)-8-(8-((2-methoxyphenyl)thio)imidazo[1,2-c]pyrimidin-5-yl)-8-azaspiro[4.5]decan-1-amine |

| No. | Compound structure | Compound name |
|---|---|---|
| 43 | 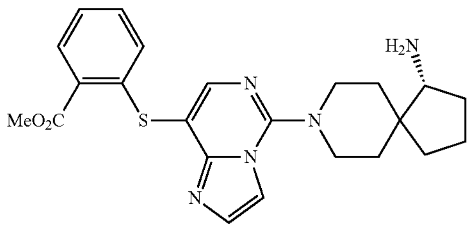 [SMILES: COC(=O)c1ccccc1Sc1cnc(N2CCC3(CCC[C@H]3N)CC2)n2ccnc12] | methyl (R)-2-((5-(1-amino-8-azaspiro[4.5]decan-8-yl)imidazo[1,2-c]pyrimidin-8-yl)thio)benzoate |
| 44 | 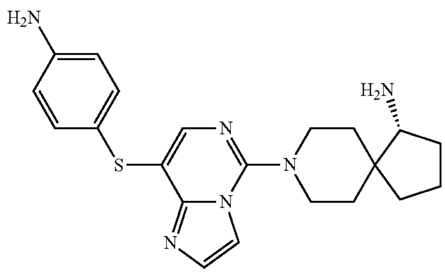 [SMILES: Nc1ccc(Sc2cnc(N3CCC4(CCC[C@H]4N)CC3)n3ccnc23)cc1] | (R)-8-(8-((4-aminophenyl)thio)imidazo[1,2-c]pyrimidin-5-yl)-8-azaspiro[4.5]decan-1-amine |
| 45 | 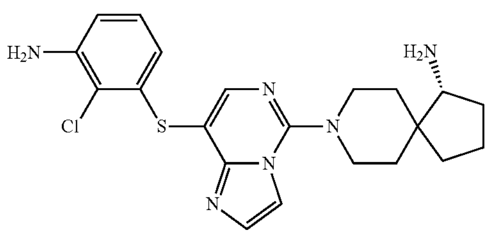 [SMILES: Nc1cccc(Sc2cnc(N3CCC4(CCC[C@H]4N)CC3)n3ccnc23)c1Cl] | (R)-8-(8-((3-amino-2-chlorophenyl)thio)imidazo[1,2-c]pyrimidin-5-yl)-8-azaspiro[4.5]decan-1-amine |
| 46 | 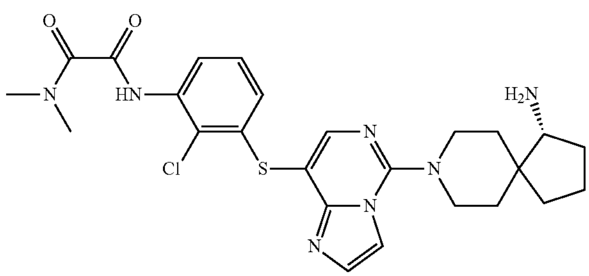 [SMILES: CN(C)C(=O)C(=O)Nc1cccc(Sc2cnc(N3CCC4(CCC[C@H]4N)CC3)n3ccnc23)c1Cl] | (R)-N$^1$-(3-((5-(1-amino-8-azaspiro[4.5]decan-8-yl)imidazo[1,2-c]pyrimidin-8-yl)thio)-2-chlorophenyl)-N$^2$,N$^2$-dimethyloxalamide |
| 47 | 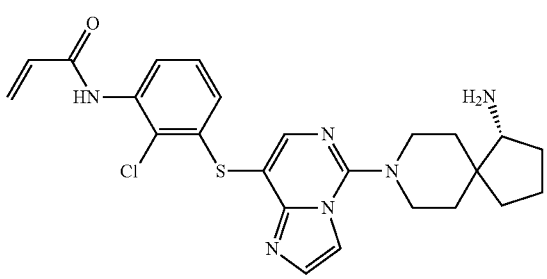 [SMILES: C=CC(=O)Nc1cccc(Sc2cnc(N3CCC4(CCC[C@H]4N)CC3)n3ccnc23)c1Cl] | (R)-N-(3-((5-(1-amino-8-azaspiro[4.5]decan-8-yl)imidazo[1,2-c]pyrimidin-8-yl)thio)-2-chlorophenyl)acrylamide |
| 48 | 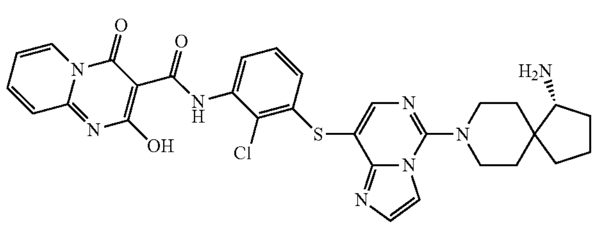 [SMILES: N[C@@H]1CCCC12CCN(c1ncc(Sc3cccc(NC(=O)c4c(O)nc5ccccn5c4=O)c3Cl)c3nccn13)CC2] | (R)-N-(3-((5-(1-amino-8-azaspiro[4.5]decan-8-yl)imidazo[1,2-c]pyrimidin-8-yl)thio)-2-chlorophenyl)-2-hydroxy-4-oxo-4H-pyrido[1,2-a]pyrimidin-3-carboxamide |

| No. | Compound structure | Compound name |
|---|---|---|
| 49 | 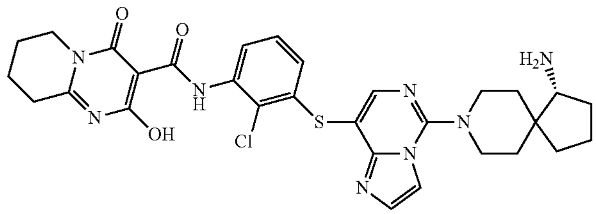 [SMILES: N[C@@H]1CCCC12CCN(c1ncc(Sc3cccc(NC(=O)c4c(O)nc5n(c4=O)CCCC5)c3Cl)c3nccn13)CC2] | (R)-N-(3-((5-(1-amino-8-azaspiro[4.5]decan-8-yl)imidazo[1,2-c]pyrimidin-8-yl)thio)-2-chlorophenyl)-2-hydroxy-4-oxo-6,7,8,9-tetrahydro-4H-pyrido[1,2-a]pyrimidin-3-carboxamide |
| 50 | 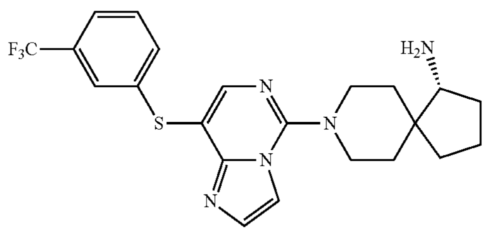 [SMILES: N[C@@H]1CCCC12CCN(c1ncc(Sc3cccc(C(F)(F)F)c3)c3nccn13)CC2] | (R)-8-(8-((3-(trifluoromethyl)phenyl)thio)imidazo[1,2-c]pyrimidin-5-yl)-8-azaspiro[4.5]decan-1-amine |
| 51 | 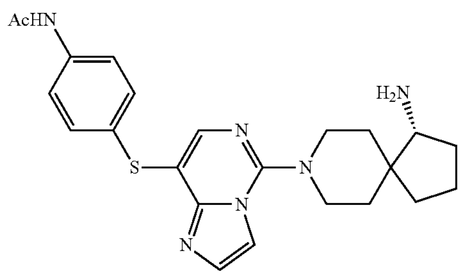 [SMILES: CC(=O)Nc1ccc(Sc2cnc(N3CCC4(CCC[C@H]4N)CC3)n3ccnc23)cc1] | (R)-N-(4-((5-(1-amino-8-azaspiro[4.5]decan-8-yl)imidazo[1,2-c]pyrimidin-8-yl)thio)phenyl)acetamide |
| 52 | 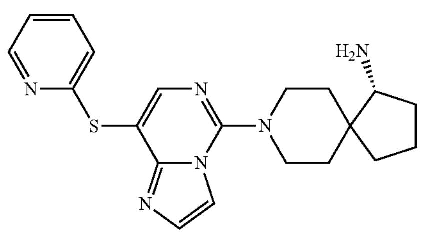 | (R)-8-(8-(pyridin-2-ylthio)imidazo[1,2-c]pyrimidin-5-yl)-8-azaspiro[4.5]decan-1-amine |
| 53 | 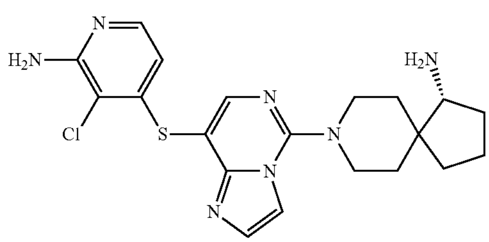 [SMILES: Nc1nccc(Sc2cnc(N3CCC4(CCC[C@H]4N)CC3)n3ccnc23)c1Cl] | (R)-8-(8-((2-amino-3-chloropyridin-4-yl)thio)imidazo[1,2-c]pyrimidin-5-yl)-8-azaspiro[4.5]decan-1-amine |
| 54 | 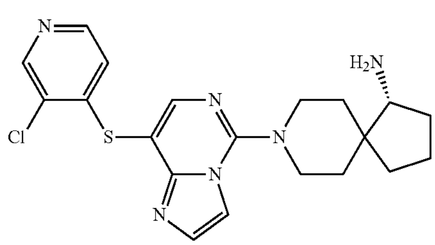 [SMILES: N[C@@H]1CCCC12CCN(c1ncc(Sc3ccncc3Cl)c3nccn13)CC2] | (R)-8-(8-((3-chloropyridin-4-yl)thio)imidazo[1,2-c]pyrimidin-5-yl)-8-azaspiro[4.5]decan-1-amine |

| No. | Compound structure | Compound name |
|---|---|---|
| 55 | 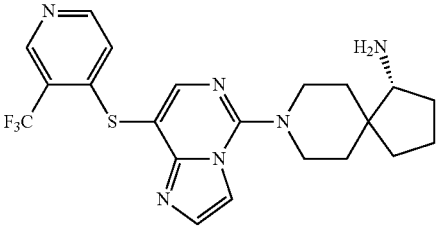 [SMILES: N[C@@H]1CCCC12CCN(c1ncc(Sc3ccncc3C(F)(F)F)c3nccn13)CC2] | (R)-8-(8-((3-(trifluoromethyl)pyridin-4-yl)thio)imidazo[1,2-c]pyrimidin-5-yl)-8-azaspiro[4.5]decan-1-amine |
| 56 | 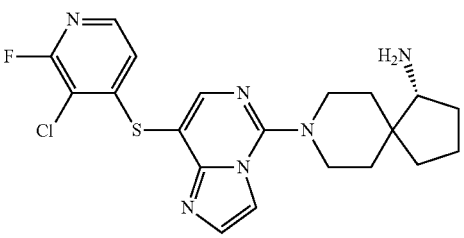 [SMILES: N[C@@H]1CCCC12CCN(c1ncc(Sc3ccnc(F)c3Cl)c3nccn13)CC2] | (R)-8-(8-((3-chloro-2-fluoropyridin-4-yl)thio)imidazo[1,2-c]pyrimidin-5-yl)-8-azaspiro[4.5]decan-1-amine |
| 57 | 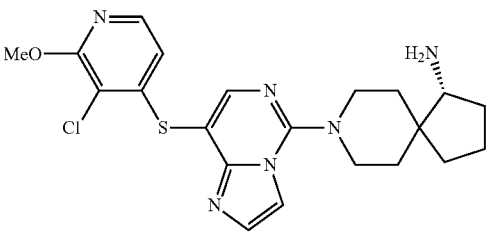 [SMILES: COc1nccc(Sc2cnc(N3CCC4(CCC[C@H]4N)CC3)n3ccnc23)c1Cl] | (R)-8-(8-((3-chloro-2-methoxypyridin-4-yl)thio)imidazo[1,2-c]pyrimidin-5-yl)-8-azaspiro[4.5]decan-1-amine |
| 58 | 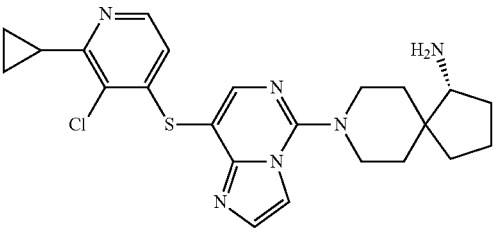 [SMILES: N[C@@H]1CCCC12CCN(c1ncc(Sc3ccnc(C4CC4)c3Cl)c3nccn13)CC2] | (R)-8-(8-((3-chloro-2-cyclopropylpyridin-4-yl)thio)imidazo[1,2-c]pyrimidin-5-yl)-8-azaspiro[4.5]decan-1-amine |
| 59 | 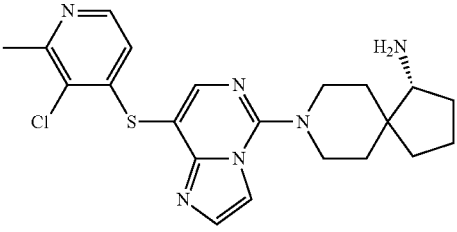 [SMILES: Cc1nccc(Sc2cnc(N3CCC4(CCC[C@H]4N)CC3)n3ccnc23)c1Cl] | (R)-8-(8-((3-chloro-2-methyl-pyridin-4-yl)thio)imidazo[1,2-c]pyrimidin-5-yl)-8-azaspiro[4.5]decan-1-amine |
| 60 | 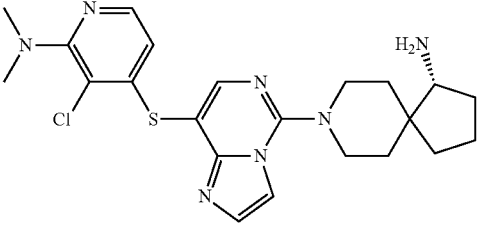 [SMILES: CN(C)c1nccc(Sc2cnc(N3CCC4(CCC[C@H]4N)CC3)n3ccnc23)c1Cl] | (R)-8-(8-((3-chloro-2-(dimethylamino)pyridin-4-yl)thio)imidazo[1,2-c]pyrimidin-5-yl)-8-azaspiro[4.5]decan-1-amine |

-continued

| No. | Compound structure | Compound name |
|---|---|---|
| 61 | 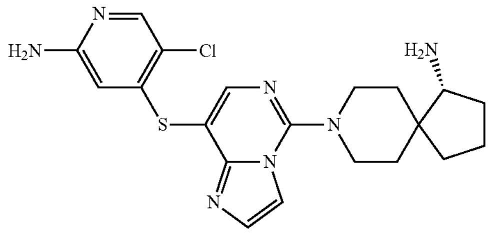 [SMILES: Nc1cc(Sc2cnc(N3CCC4(CCC[C@H]4N)CC3)n3ccnc23)c(Cl)cn1] | (R)-8-(8-((2-amino-5-chloropyridin-4-yl)thio)imidazo[1,2-c]pyrimidin-5-yl)-8-azaspiro[4.5]decan-1-amine |
| 62 | 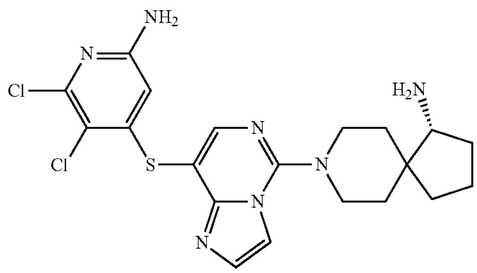 [SMILES: Nc1cc(Sc2cnc(N3CCC4(CCC[C@H]4N)CC3)n3ccnc23)c(Cl)c(Cl)n1] | (R)-8-(8-((6-amino-2,3-dichloropyridin-4-yl)thio)imidazo[1,2-c]pyrimidin-5-yl)-8-azaspiro[4.5]decan-1-amine |
| 63 | 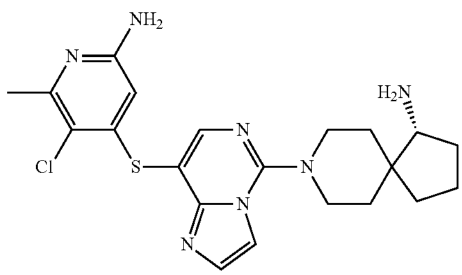 [SMILES: Cc1nc(N)cc(Sc2cnc(N3CCC4(CCC[C@H]4N)CC3)n3ccnc23)c1Cl] | (R)-8-(8-((6-amino-3-chloro-2-methyl-pyridin-4-yl)thio)imidazo[1,2-c]pyrimidin-5-yl)-8-azaspiro[4.5]decan-1-amine |
| 64 | 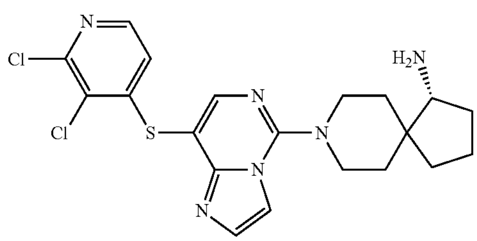 [SMILES: N[C@@H]1CCCC12CCN(c1ncc(Sc3ccnc(Cl)c3Cl)c3nccn13)CC2] | (R)-8-(8-((2,3-dichloropyridin-4-yl)thio)imidazo[1,2-c]pyrimidin-5-yl)-8-azaspiro[4.5]decan-1-amine |
| 65 | 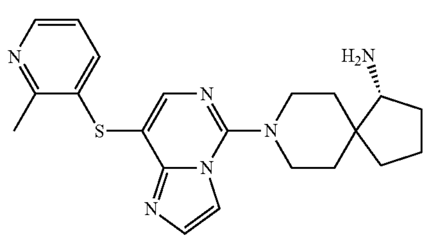 [SMILES: Cc1ncccc1Sc1cnc(N2CCC3(CCC[C@H]3N)CC2)n2ccnc12] | (R)-8-(8-((2-methylpyridin-3-yl)thio)imidazo[1,2-c]pyrimidin-5-yl)-8-azaspiro[4.5]decan-1-amine |
| 66 | 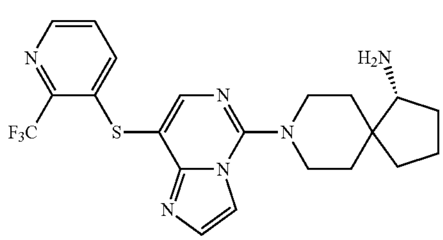 [SMILES: N[C@@H]1CCCC12CCN(c1ncc(Sc3cccnc3C(F)(F)F)c3nccn13)CC2] | (R)-8-(8-((2-(trifluoromethyl)pyridin-3-yl)thio)imidazo[1,2-c]pyrimidin-5-yl)-8-azaspiro[4.5]decan-1-amine |

-continued

| No. | Compound structure | Compound name |
|---|---|---|
| 67 | 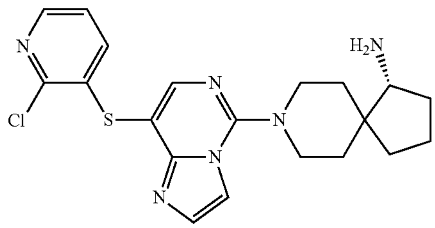 | (R)-8-(8-((2-chloropyridin-3-yl)thio)imidazo[1,2-c]pyrimidin-5-yl)-8-azaspiro[4.5]decan-1-amine |
| 68 | 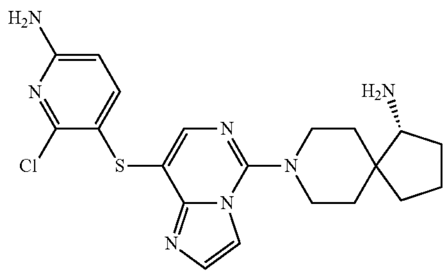 [SMILES: Nc1ccc(Sc2cnc(N3CCC4(CCC[C@H]4N)CC3)n3ccnc23)c(Cl)n1] | (R)-8-(8-((6-amino-2-chloropyridin-3-yl)thio)imidazo[1,2-c]pyrimidin-5-yl)-8-azaspiro[4.5]decan-1-amine |
| 69 | 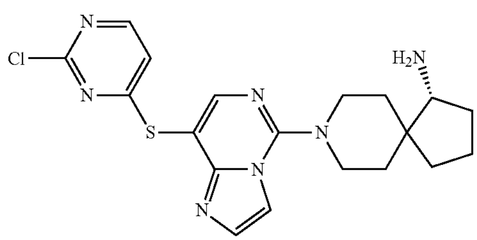 [SMILES: N[C@@H]1CCCC12CCN(c1ncc(Sc3ccnc(Cl)n3)c3nccn13)CC2] | (R)-8-(8-((2-chloropyrimidin-4-yl)thio)imidazo[1,2-c]pyrimidin-5-yl)-8-azaspiro[4.5]decan-1-amine |
| 70 | 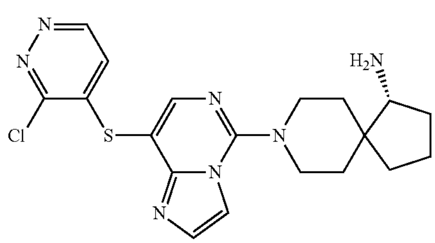 [SMILES: N[C@@H]1CCCC12CCN(c1ncc(Sc3ccnnc3Cl)c3nccn13)CC2] | (R)-8-(8-((3-chloropyridazin-4-yl)thio)imidazo[1,2-c]pyrimidin-5-yl)-8-azaspiro[4.5]decan-1-amine |
| 71 | 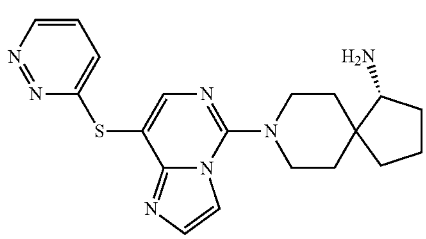 [SMILES: N[C@@H]1CCCC12CCN(c1ncc(Sc3cccnn3)c3nccn13)CC2] | (R)-8-(8-(pyridazin-3-ylthio)imidazo[1,2-c]pyrimidin-5-yl)-8-azaspiro[4.5]decan-1-amine |
| 72 | 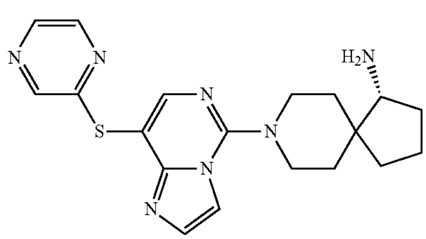 [SMILES: N[C@@H]1CCCC12CCN(c1ncc(Sc3cnccn3)c3nccn13)CC2] | (R)-8-(8-(pyrazin-2-ylthio)imidazo[1,2-c]pyrimidin-5-yl)-8-azaspiro[4.5]decan-1-amine |

-continued

| No. | Compound structure | Compound name |
|---|---|---|
| 73 | 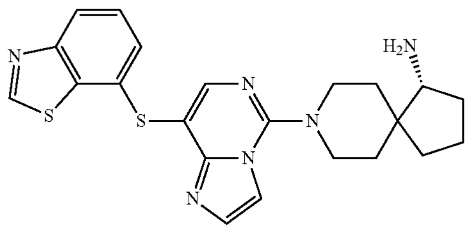 [SMILES: N[C@@H]1CCCC12CCN(c1ncc(Sc3cccc4ncsc34)c3nccn13)CC2] | (R)-8-(8-(benzo[d]thiazol-7-ylthio)imidazo[1,2-c]pyrimidin-5-yl)-8-azaspiro[4.5]decan-1-amine |
| 74 | 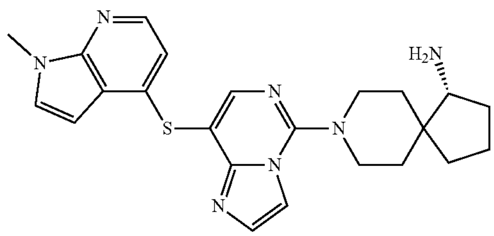 [SMILES: Cn1ccc2c(Sc3cnc(N4CCC5(CCC[C@H]5N)CC4)n4ccnc34)ccnc21] | (R)-8-(8-((1-methyl-1H-pyrrolo[2,3-I]]pyridin-4-yl)thio)imidazo[1,2-c]pyrimidin-5-yl)-8-azaspiro[4.5]decan-1-amine |
| 75 | 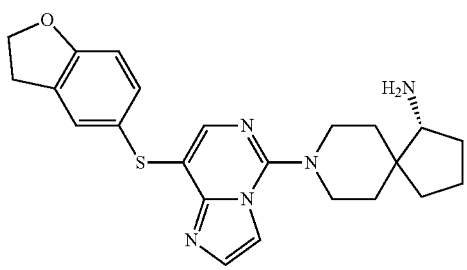 [SMILES: N[C@@H]1CCCC12CCN(c1ncc(Sc3ccc4c(c3)CCO4)c3nccn13)CC2] | (R)-8-(8-((2,3-dihydrobenzofuran-5-yl)thio)imidazo[1,2-c]pyrimidin-5-yl)-8-azaspiro[4.5]decan-1-amine |
| 76 | 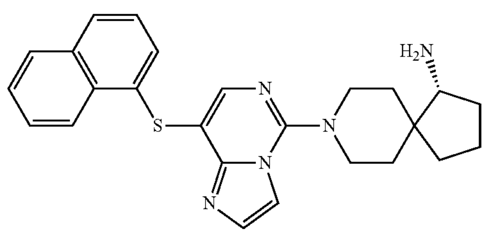 [SMILES: N[C@@H]1CCCC12CCN(c1ncc(Sc3cccc4ccccc34)c3nccn13)CC2] | (R)-8-(8-(naphthalen-1-ylthio)imidazo[1,2-c]pyrimidin-5-yl)-8-azaspiro[4.5]decan-1-amine |
| 77 | 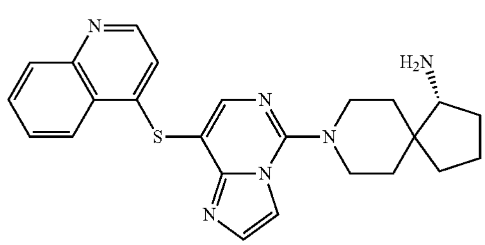 [SMILES: N[C@@H]1CCCC12CCN(c1ncc(Sc3ccnc4ccccc34)c3nccn13)CC2] | (R)-8-(8-(quinolin-4-ylthio)imidazo[1,2-c]pyrimidin-5-yl)-8-azaspiro[4.5]decan-1-amine |
| 78 | 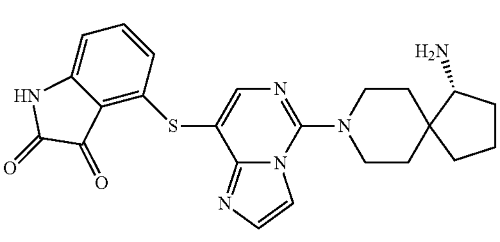 [SMILES: N[C@@H]1CCCC12CCN(c1ncc(Sc3cccc4c3C(=O)C(=O)N4)c3nccn13)CC2] | (R)-4-((5-(1-amino-8-azaspiro[4.5]decan-8-yl)imidazo[1,2-c]pyrimidin-8-yl)thio)indoline-2,3-dione |

| No. | Compound structure | Compound name |
|---|---|---|
| 79 | 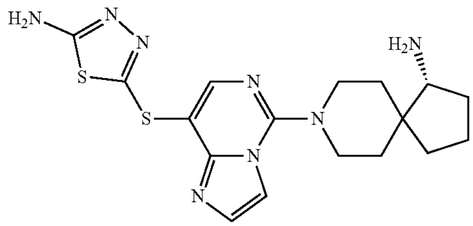 [SMILES: Nc1nnc(Sc2cnc(N3CCC4(CCC[C@H]4N)CC3)n3ccnc23)s1] | (R)-5-((5-(1-amino-8-azaspiro[4.5]decan-8-yl)imidazo[1,2-c]pyrimidin-8-yl)thio)-1,3,4-thiadiazol-2-amine |
| 80 | 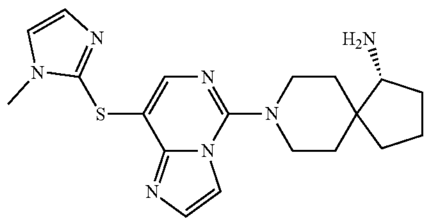 [SMILES: Cn1ccnc1Sc1cnc(N2CCC3(CCC[C@H]3N)CC2)n2ccnc12] | (R)-8-(8-((1-methyl-1H-imidazol-2-yl)thio)imidazo[1,2-c]pyrimidin-5-yl)-8-azaspiro[4.5]decan-1-amine |
| 81 | 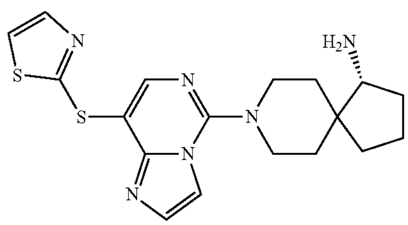 [SMILES: N[C@@H]1CCCC12CCN(c1ncc(Sc3nccs3)c3nccn13)CC2] | (R)-8-(8-(thiazol-2-ylthio)imidazo[1,2-c]pyrimidin-5-yl)-8-azaspiro[4.5]decan-1-amine |
| 82 | 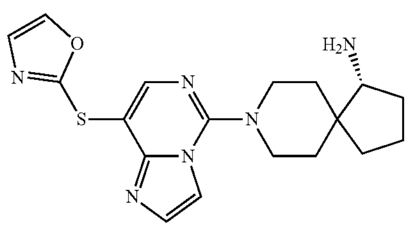 [SMILES: N[C@@H]1CCCC12CCN(c1ncc(Sc3ncco3)c3nccn13)CC2] | (R)-8-(8-(oxazol-2-ylthio)imidazo[1,2-c]pyrimidin-5-yl)-8-azaspiro[4.5]decan-1-amine |
| 83 | 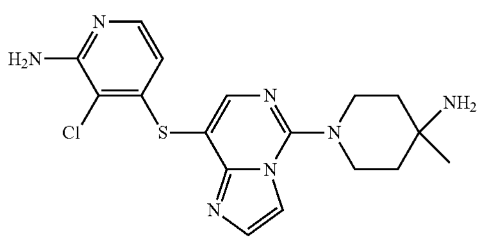 [SMILES: CC1(N)CCN(c2ncc(Sc3ccnc(N)c3Cl)c3nccn23)CC1] | 4-((5-(4-amino-4-methylpiperidin-1-yl)imidazo[1,2-c]pyrimidin-8-yl)thio)-3-chloropyridin-2-amine |
| 84 | 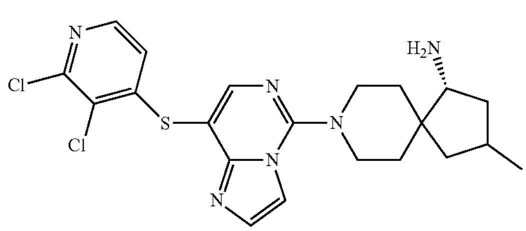 [SMILES: CC1C[C@@H](N)C2(CCN(c3ncc(Sc4ccnc(Cl)c4Cl)c4nccn34)CC2)C1] | (1R)-8-(8-((2,3-dichloropyridin-4-yl)thio)imidazo[1,2-c]pyrimidin-5-yl)-3-methyl-8-azaspiro[4.5]decan-1-amine |

-continued

| No. | Compound structure | Compound name |
|---|---|---|
| 85 | 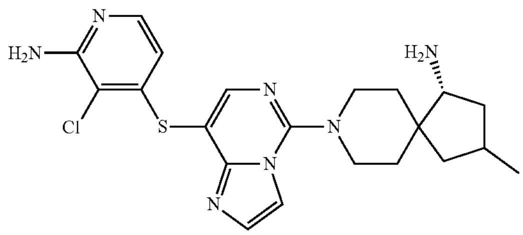 [SMILES: CC1C[C@@H](N)C2(CCN(c3ncc(Sc4ccnc(N)c4Cl)c4nccn34)CC2)C1] | (1R)-8-(8-((2-amino-3-chloropyridin-4-yl)thio)imidazo[1,2-c]pyrimidin-5-yl)-3-methyl-8-azaspiro[4.5]decan-1-amine |
| 86 | 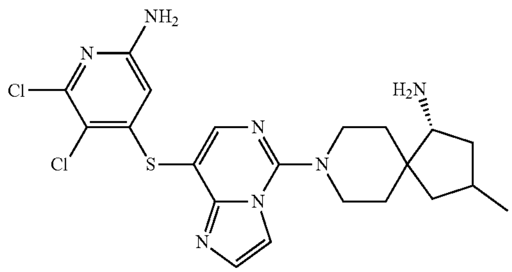 [SMILES: CC1C[C@@H](N)C2(CCN(c3ncc(Sc4cc(N)nc(Cl)c4Cl)c4nccn34)CC2)C1] | (1R)-8-(8-((6-amino-2,3-dichloropyridin-4-yl)thio)imidazo[1,2-c]pyrimidin-5-yl)-3-methyl-8-azaspiro[4.5]decan-1-amine |
| 87 | 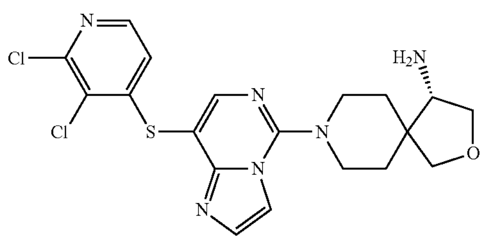 [SMILES: N[C@@H]1COCC12CCN(c1ncc(Sc3ccnc(Cl)c3Cl)c3nccn13)CC2] | (S)-8-(8-((2,3-dichloropyridin-4-yl)thio)imidazo[1,2-c]pyrimidin-5-yl)-2-oxa-8-azaspiro[4.5]decan-4-amine |
| 88 | 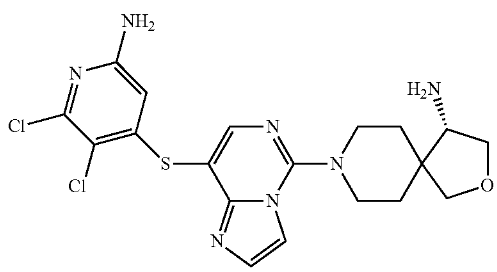 [SMILES: Nc1cc(Sc2cnc(N3CCC4(CC3)COC[C@H]4N)n3ccnc23)c(Cl)c(Cl)n1] | (S)-8-(8-((6-amino-2,3-dichloropyridin-4-yl)thio)imidazo[1,2-c]pyrimidin-5-yl)-2-oxa-8-azaspiro[4.5]decan-4-amine |
| 89 | 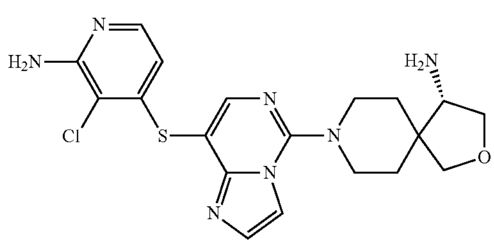 [SMILES: Nc1nccc(Sc2cnc(N3CCC4(CC3)COC[C@H]4N)n3ccnc23)c1Cl] | (S)-8-(8-((2-amino-3-chloropyridin-4-yl)thio)imidazo[1,2-c]pyrimidin-5-yl)-2-oxa-8-azaspiro[4.5]decan-4-amine |
| 90 | 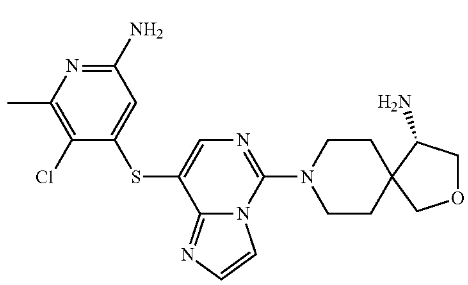 [SMILES: Cc1nc(N)cc(Sc2cnc(N3CCC4(CC3)COC[C@H]4N)n3ccnc23)c1Cl] | (S)-8-(8-((6-amino-3-chloro-2-methyl-pyridin-4-yl)thio)imidazo[1,2-c]pyrimidin-5-yl)-2-oxa-8-azaspiro[4.5]decan-4-amine |

| No. | Compound structure | Compound name |
|---|---|---|
| 91 | 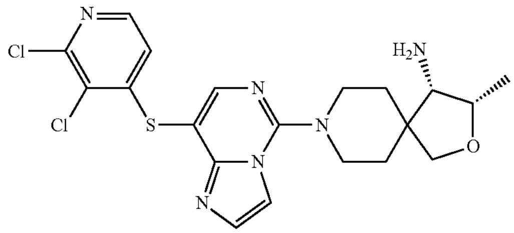 [SMILES: C[C@@H]1OCC2(CCN(c3ncc(Sc4ccnc(Cl)c4Cl)c4nccn34)CC2)[C@@H]1N] | (3S,4S)-8-(8-((2,3-dichloropyridin-4-yl)thio)imidazo[1,2-c]pyrimidin-5-yl)-3-methyl-2-oxa-8-azaspiro[4.5]decan-4-amine |
| 92 | 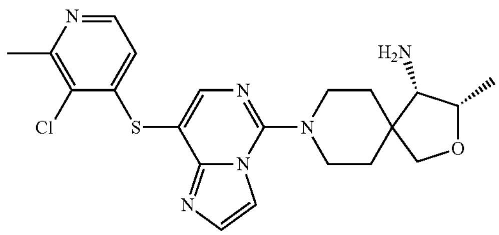 | (3S,4S)-8-(8-((3-chloro-2-methylpyridin-4-yl)thio)imidazo[1,2-c]pyrimidin-5-yl)-3-methyl-2-oxa-8-azaspiro[4.5]decan-4-amine |
| 93 | 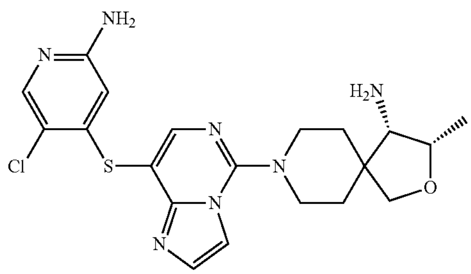 [SMILES: C[C@@H]1OCC2(CCN(c3ncc(Sc4cc(N)ncc4Cl)c4nccn34)CC2)[C@@H]1N] | (3S,4S)-8-(8-((2-amino-5-chloro-pyridin-4-yl)thio)imidazo[1,2-c]pyrimidin-5-yl)-3-methyl-2-oxa-8-azaspiro[4.5]decan-4-amine |
| 94 | 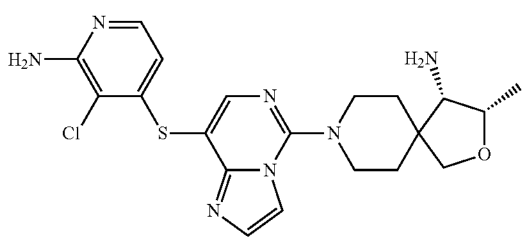 [SMILES: C[C@@H]1OCC2(CCN(c3ncc(Sc4ccnc(N)c4Cl)c4nccn34)CC2)[C@@H]1N] | (3S,4S)-8-(8-((2-amino-3-chloropyridin-4-yl)thio)imidazo[1,2-c]pyrimidin-5-yl)-3-methyl-2-oxa-8-azaspiro[4.5]decan-4-amine |
| 95 | 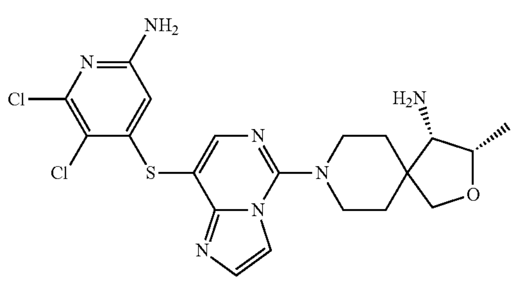 [SMILES: C[C@@H]1OCC2(CCN(c3ncc(Sc4cc(N)nc(Cl)c4Cl)c4nccn34)CC2)[C@@H]1N] | (3S,4S)-8-(8-((6-amino-2,3-dichloropyridin-4-yl)thio)imidazo[1,2-c]pyrimidin-5-yl)-3-methyl-2-oxa-8-azaspiro[4.5]decan-4-amine |
| 96 | 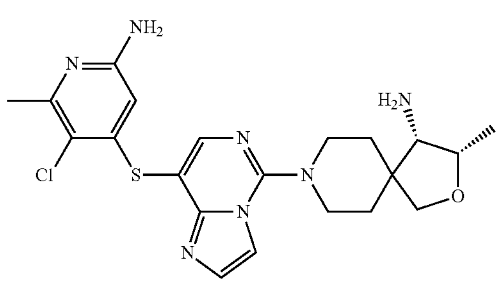 | (3S,4S)-8-(8-((6-amino-3-chloro-2-methyl-pyridin-4-yl)thio)imidazo[1,2-c]pyrimidin-5-yl)-3-methyl-2-oxa-8-azaspiro[4.5]decan-4-amine |

| No. | Compound structure | Compound name |
|---|---|---|
| 97 | 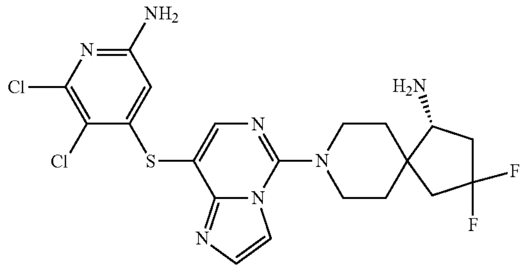 [SMILES: Nc1cc(Sc2cnc(N3CCC4(CC3)CC(F)(F)C[C@H]4N)n3ccnc23)c(Cl)c(Cl)n1] | (R)-8-(8-((6-amino-2,3-dichloropyridin-4-yl)thio)imidazo[1,2-c]pyrimidin-5-yl)-3,3-difluoro-8-azaspiro[4.5]decan-1-amine |
| 98 | 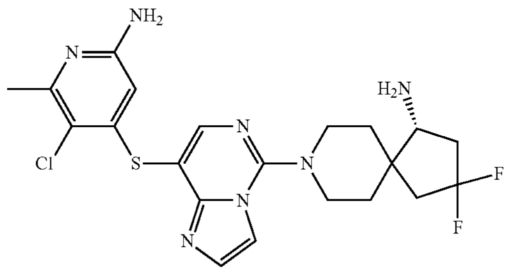 [SMILES: Cc1nc(N)cc(Sc2cnc(N3CCC4(CC3)CC(F)(F)C[C@H]4N)n3ccnc23)c1Cl] | (R)-8-(8-((6-amino-3-chloro-2-methyl-pyridin-4-yl)thio)imidazo[1,2-c]pyrimidin-5-yl)-3,3-difluoro-8-azaspiro[4.5]decan-1-amine |
| 99 | 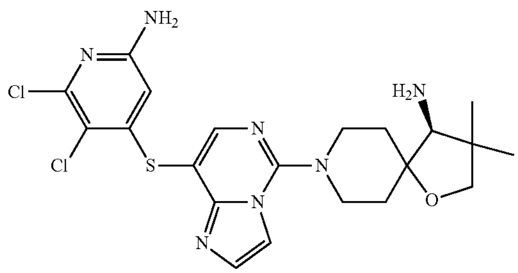 [SMILES: CC1(C)COC2(CCN(c3ncc(Sc4cc(N)nc(Cl)c4Cl)c4nccn34)CC2)[C@H]1N] | (S)-8-(8-((6-amino-2,3-dichloropyridin-4-yl)thio)imidazo[1,2-c]pyrimidin-5-yl)-3,3-dimethyl-1-oxa-8-azaspiro[4.5]decan-4-amine |
| 100 | 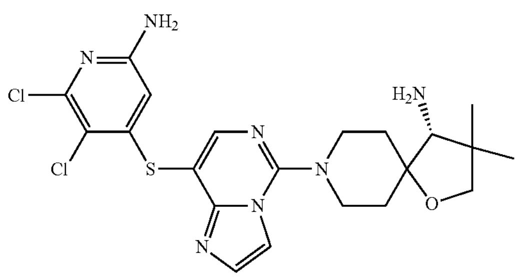 [SMILES: CC1(C)COC2(CCN(c3ncc(Sc4cc(N)nc(Cl)c4Cl)c4nccn34)CC2)[C@@H]1N] | (R)-8-(8-((6-amino-2,3-dichloropyridin-4-yl)thio)imidazo[1,2-c]pyrimidin-5-yl)-3,3-dimethyl-1-oxa-8-azaspiro[4.5]decan-4-amine |
| 101 | 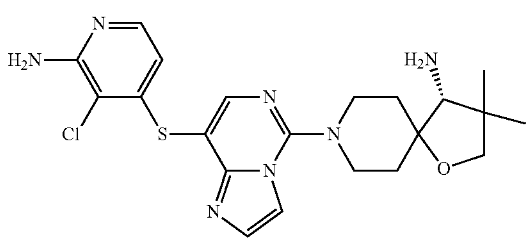 [SMILES: CC1(C)COC2(CCN(c3ncc(Sc4ccnc(N)c4Cl)c4nccn34)CC2)[C@@H]1N] | (R)-8-(8-((2-amino-3-chloropyridin-4-yl)thio)imidazo[1,2-c]pyrimidin-5-yl)-3,3-dimethyl-1-oxa-8-azaspiro[4.5]decan-4-amine |
| 102 | 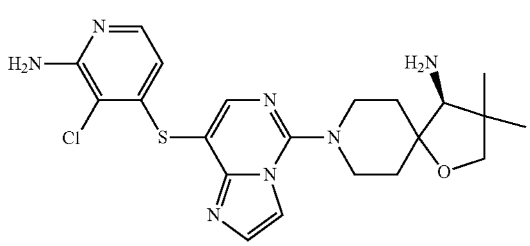 [SMILES: CC1(C)COC2(CCN(c3ncc(Sc4ccnc(N)c4Cl)c4nccn34)CC2)[C@H]1N] | (S)-8-(8-((2-amino-3-chloropyridin-4-yl)thio)imidazo[1,2-c]pyrimidin-5-yl)-3,3-dimethyl-1-oxa-8-azaspiro[4.5]decan-4-amine |

-continued

| No. | Compound structure | Compound name |
|---|---|---|
| 103 | 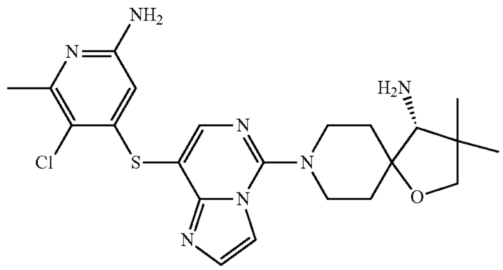 | (R)-8-(8-((6-amino-3-chloro-2-methyl-pyridin-4-yl)thio)imidazo[1,2-c]pyrimidin-5-yl)-3,3-dimethyl-1-oxa-8-azaspiro[4.5]decan-4-amine |
| 104 | 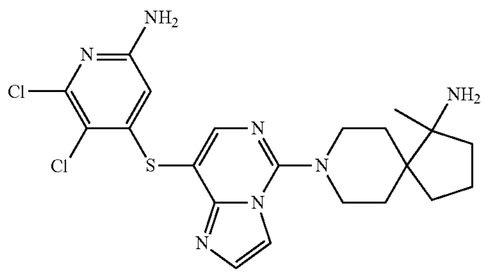 [SMILES: CC1(N)CCCC12CCN(c1ncc(Sc3cc(N)nc(Cl)c3Cl)c3nccn13)CC2] | 8-(8-((6-amino-2,3-dichloropyridin-4-yl)thio)imidazo[1,2-c]pyrimidin-5-yl)-1-methyl-8-azaspiro[4.5]decan-1-amine |

In another preferred embodiment, the compound is selected from any of the following compounds:

| No. | Compound structure | Compound name |
|---|---|---|
| 1 | 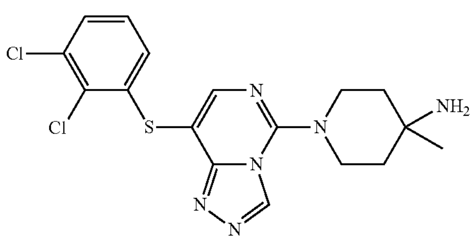 [SMILES: CC1(N)CCN(c2ncc(Sc3cccc(Cl)c3Cl)c3nncn23)CC1] | 1-(8-((2,3-dichlorophenyl)thio)-[1,2,4]triazolo[4,3-c]pyrimidin-5-yl)-4-methylpiperidin-4-amine |
| 2 | 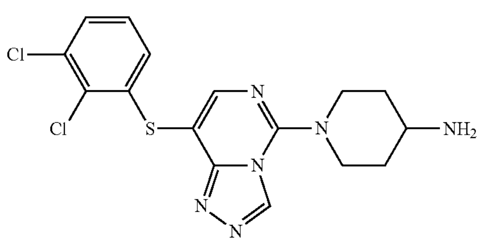 [SMILES: NC1CCN(c2ncc(Sc3cccc(Cl)c3Cl)c3nncn23)CC1] | 1-(8-((2,3-dichlorophenyl)thio)-[1,2,4]triazolo[4,3-c]pyrimidin-5-yl)piperidin-4-amine |
| 3 | 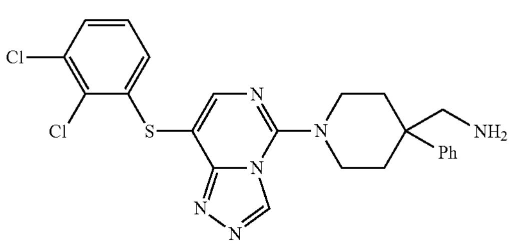 [SMILES: NCC1(c2ccccc2)CCN(c2ncc(Sc3cccc(Cl)c3Cl)c3nncn23)CC1] | (1-(8-((2,3-dichlorophenyl)thio)-[1,2,4]triazolo[4,3-c]pyrimidin-5-yl)-4-phenylpiperidin-4-yl)methanamine |

-continued

| No. | Compound structure | Compound name |
| --- | --- | --- |
| 4 | 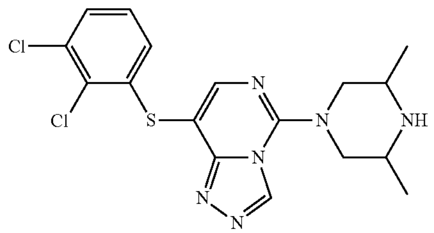 [SMILES: CC1CN(c2ncc(Sc3cccc(Cl)c3Cl)c3nncn23)CC(C)N1] | 8-((2,3-dichlorophenyl)thio)-5-(3,5-dimethylpiperazin-1-yl)-[1,2,4]triazolo[4,3-c]pyrimidine |
| 5 | 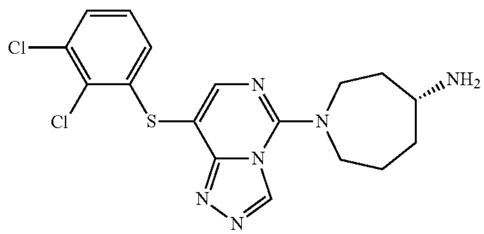 [SMILES: N[C@@H]1CCCN(c2ncc(Sc3cccc(Cl)c3Cl)c3nncn23)CC1] | (R)-1-(8-((2,3-dichlorophenyl)thio)-[1,2,4]triazolo[4,3-c]pyrimidin-5-yl)azepan-4-amine |
| 6 | 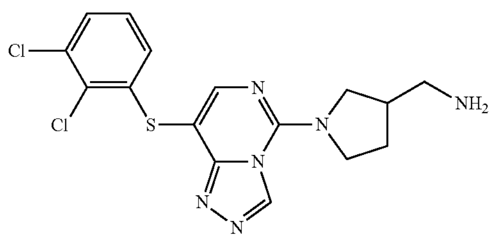 [SMILES: NCC1CCN(c2ncc(Sc3cccc(Cl)c3Cl)c3nncn23)C1] | (1-(8-((2,3-dichlorophenyl)thio)-[1,2,4]triazolo[4,3-c]pyrimidin-5-yl)pyrrolidin-3-yl)methanamine |
| 7 | 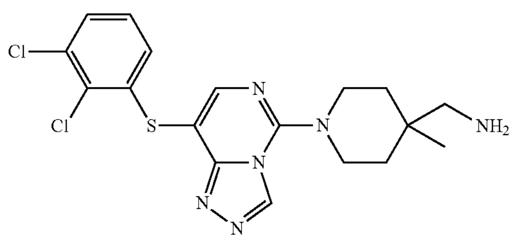 [SMILES: CC1(CN)CCN(c2ncc(Sc3cccc(Cl)c3Cl)c3nncn23)CC1] | (1-(8-((2,3-dichlorophenyl)thio)-[1,2,4]triazolo[4,3-c]pyrimidin-5-yl)-4-methylpiperidin-4-yl)methanamine |
| 8 | 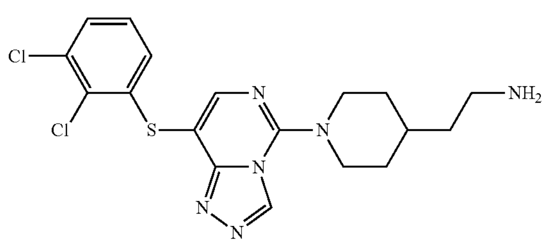 [SMILES: NCCC1CCN(c2ncc(Sc3cccc(Cl)c3Cl)c3nncn23)CC1] | 2-(1-(8-((2,3-dichlorophenyl)thio)-[1,2,4]triazolo[4,3-c]pyrimidin-5-yl)piperidin-4-yl)ethan-1-amine |
| 9 | 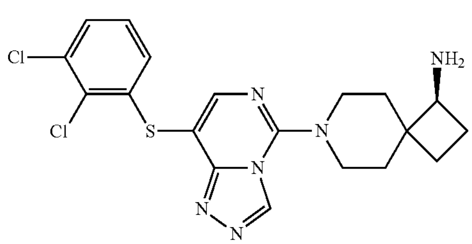 [SMILES: N[C@H]1CCC12CCN(c1ncc(Sc3cccc(Cl)c3Cl)c3nncn13)CC2] | (S)-7-(8-((2,3-dichlorophenyl)thio)-[1,2,4]triazolo[4,3-c]pyrimidin-5-yl)-7-azaspiro[3,5]nonan-1-amine |

-continued

| No. | Compound structure | Compound name |
|---|---|---|
| 10 | 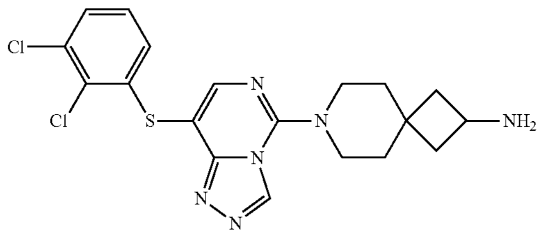 [SMILES: NC1CC2(CCN(c3ncc(Sc4cccc(Cl)c4Cl)c4nncn34)CC2)C1] | 7-(8-((2,3-dichlorophenyl)thio)-[1,2,4]triazolo[4,3-c]pyrimidin-5-yl)-7-azaspiro[3.5]nonan-2-amine |
| 11 | 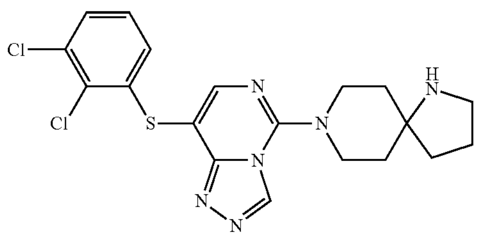 [SMILES: Clc1cccc(Sc2cnc(N3CCC4(CCCN4)CC3)n3cnnc23)c1Cl] | 8-(8-((2,3-dichlorophenyl)thio)-[1,2,4]triazolo[4,3-c]pyrimidin-5-yl)-1,8-diazaspiro[4.5]decane |
| 12 | 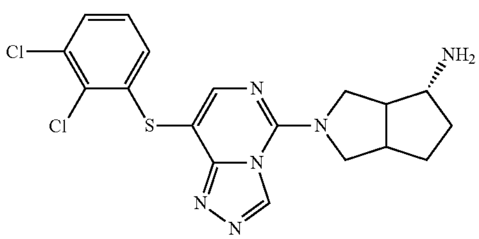 [SMILES: N[C@@H]1CCC2CN(c3ncc(Sc4cccc(Cl)c4Cl)c4nncn34)CC21] | (4R)-2-(8-((2,3-dichlorophenyl)thio)-[1,2,4]triazolo[4,3-c]pyrimidin-5-yl)octahydrocyclopenta[c]pyrrol-4-amine |
| 13 | 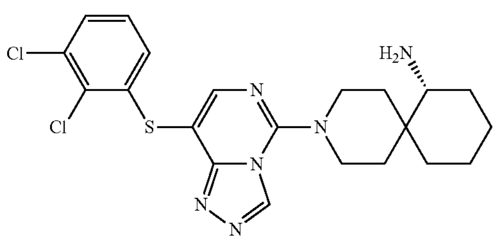 [SMILES: N[C@@H]1CCCCC12CCN(c1ncc(Sc3cccc(Cl)c3Cl)c3nncn13)CC2] | (R)-3-(8-((2,3-dichlorophenyl)thio)-[1,2,4]triazolo[4,3-c]pyrimidin-5-yl)-3-azaspiro[5.5]undecan-7-amine |
| 14 | 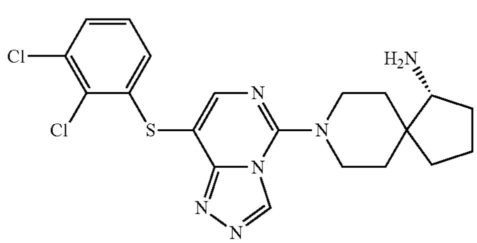 [SMILES: N[C@@H]1CCCC12CCN(c1ncc(Sc3cccc(Cl)c3Cl)c3nncn13)CC2] | (R)-8-(8-((2,3-dichlorophenyl)thio)-[1,2,4]triazolo[4,3-c]pyrimidin-5-yl)-8-azaspiro[4.5]decan-1-amine |
| 15 | 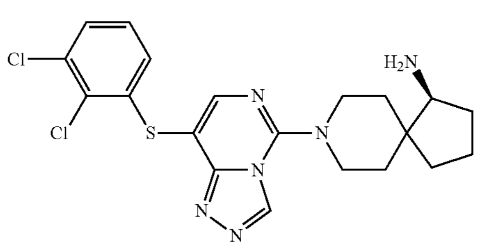 [SMILES: N[C@H]1CCCC12CCN(c1ncc(Sc3cccc(Cl)c3Cl)c3nncn13)CC2] | (S)-8-(8-((2,3-dichlorophenyl)thio)-[1,2,4]triazolo[4,3-c]pyrimidin-5-yl)-8-azaspiro[4.5]decan-1-amine |

-continued

| No. | Compound structure | Compound name |
|---|---|---|
| 16 | 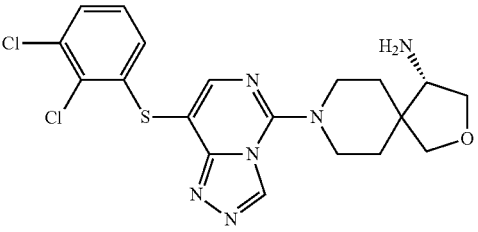 [SMILES: N[C@@H]1COCC12CCN(c1ncc(Sc3cccc(Cl)c3Cl)c3nncn13)CC2] | (S)-8-(8-((2,3-dichlorophenyl)thio)-[1,2,4]triazolo[4,3-c]pyrimidin-5-yl)-2-oxa-8-azaspiro[4.5]decan-4-amine |
| 17 | 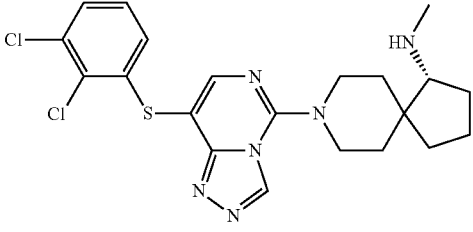 [SMILES: CN[C@@H]1CCCC12CCN(c1ncc(Sc3cccc(Cl)c3Cl)c3nncn13)CC2] | (R)-8-(8-((2,3-dichlorophenyl)thio)-[1,2,4]triazolo[4,3-c]pyrimidin-5-yl)-N-methyl-8-azaspiro[4.5]decan-1-amine |
| 18 | 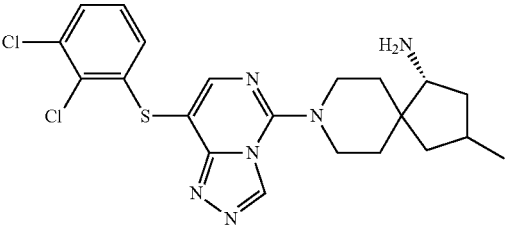 [SMILES: CC1C[C@@H](N)C2(CCN(c3ncc(Sc4cccc(Cl)c4Cl)c4nncn34)CC2)C1] | (1R)-8-(8-((2,3-dichlorophenyl)thio)-[1,2,4]triazolo[4,3-c]pyrimidin-5-yl)-3-methyl-8-azaspiro[4.5]decan-1-amine |
| 19 | 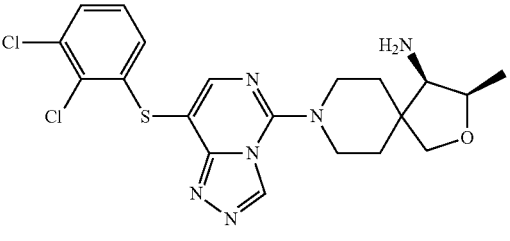 [SMILES: C[C@H]1OCC2(CCN(c3ncc(Sc4cccc(Cl)c4Cl)c4nncn34)CC2)[C@H]1N] | (3R,4R)-8-(8-((2,3-dichlorophenyl)thio)-[1,2,4]triazolo[4,3-c]pyrimidin-5-yl)-3-methyl-2-oxa-8-azaspiro[4.5]decan-4-amine |
| 20 | 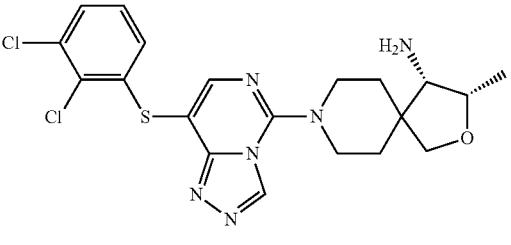 [SMILES: C[C@@H]1OCC2(CCN(c3ncc(Sc4cccc(Cl)c4Cl)c4nncn34)CC2)[C@@H]1N] | (3S,4S)-8-(8-((2,3-dichlorophenyl)thio)-[1,2,4]triazolo[4,3-c]pyrimidin-5-yl)-3-methyl-2-oxa-8-azaspiro[4.5]decan-4-amine |
| 21 | 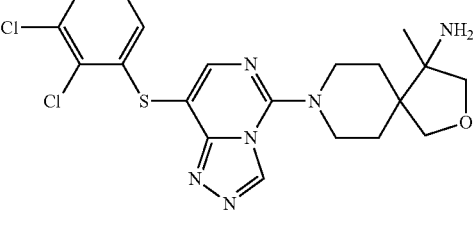 | 8-(8-((2,3-dichlorophenyl)thio)-[1,2,4]triazolo[4,3-c]pyrimidin-5-yl)-4-methyl-2-oxa-8-azaspiro[4.5]decan-4-amine |

-continued

| No. | Compound structure | Compound name |
|---|---|---|
| 22 | 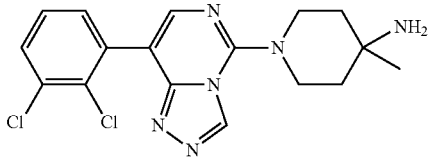 [SMILES: CC1(N)CCN(c2ncc(-c3cccc(Cl)c3Cl)c3nncn23)CC1] | 1-(8-(2,3-dichlorophenyl)-[1,2,4]triazolo[4,3-c]pyrimidin-5-yl)-4-methylpiperidin-4-amine |
| 23 | 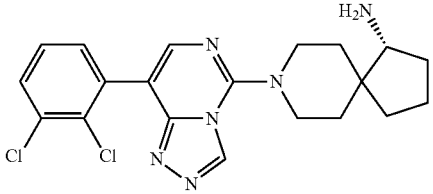 [SMILES: N[C@@H]1CCCC12CCN(c1ncc(-c3cccc(Cl)c3Cl)c3nncn13)CC2] | (R)-8-(8-(2,3-dichlorophenyl)-[1,2,4]triazolo[4,3-c]pyrimidin-5-yl)-8-azaspiro[4.5]decan-1-amine |
| 24 | 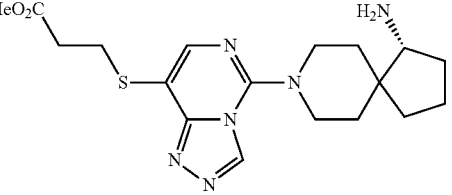 | methyl (R)-3-((5-(1-amino-8-azaspiro[4.5]decan-8-yl)-[1,2,4]triazolo[4,3-c]pyrimidin-8-yl)thio)propionate |
| 25 | 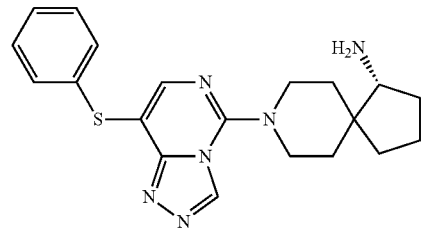 [SMILES: N[C@@H]1CCCC12CCN(c1ncc(Sc3ccccc3)c3nncn13)CC2] | (R)-8-(8-(phenylthio)-[1,2,4]triazolo[4,3-c]pyrimidin-5-yl)-8-azaspiro[4.5]decan-1-amine |
| 26 | 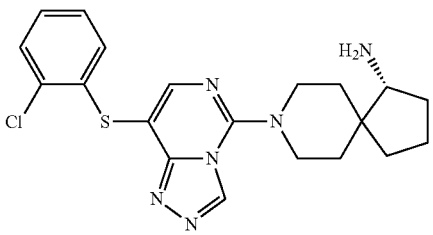 [SMILES: N[C@@H]1CCCC12CCN(c1ncc(Sc3ccccc3Cl)c3nncn13)CC2] | (R)-8-(8-((2-chlorophenyl)thio)-[1,2,4]triazolo[4,3-c]pyrimidin-5-yl)-8-azaspiro[4.5]decan-1-amine |
| 27 | 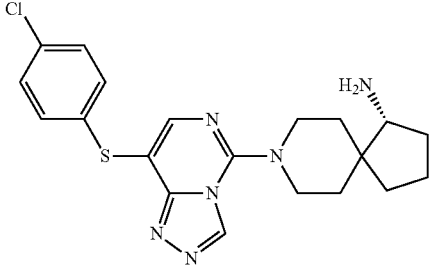 [SMILES: N[C@@H]1CCCC12CCN(c1ncc(Sc3ccc(Cl)cc3)c3nncn13)CC2] | (R)-8-(8-((4-chlorophenyl)thio)-[1,2,4]triazolo[4,3-c]pyrimidin-5-yl)-8-azaspiro[4.5]decan-1-amine |

-continued

| No. | Compound structure | Compound name |
|---|---|---|
| 28 | 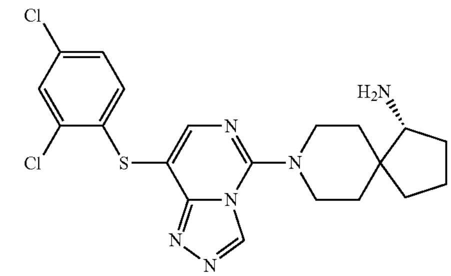 [SMILES: N[C@@H]1CCCC12CCN(c1ncc(Sc3ccc(Cl)cc3Cl)c3nncn13)CC2] | (R)-8-(8-((2,4-dichlorophenyl)thio)-[1,2,4]triazolo[4,3-c]pyrimidin-5-yl)-8-azaspiro[4.5]decan-1-amine |
| 29 | 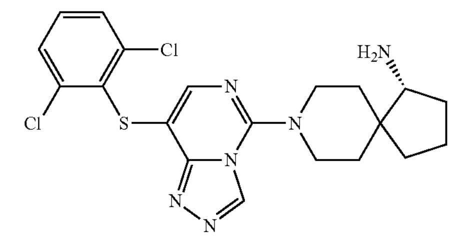 [SMILES: N[C@@H]1CCCC12CCN(c1ncc(Sc3c(Cl)cccc3Cl)c3nncn13)CC2] | (R)-8-(8-((2,6-dichlorophenyl)thio)-[1,2,4]triazolo[4,3-c]pyrimidin-5-yl)-8-azaspiro[4.5]decan-1-amine |
| 30 | 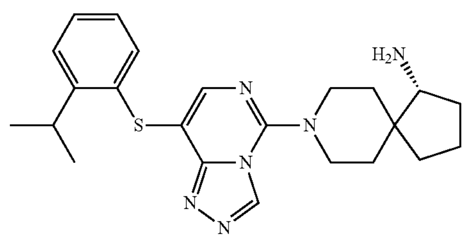 [SMILES: CC(C)c1ccccc1Sc1cnc(N2CCC3(CCC[C@H]3N)CC2)n2cnnc12] | (R)-8-(8-((2-isopropylphenyl)thio)-[1,2,4]triazolo[4,3-c]pyrimidin-5-yl)-8-azaspiro[4.5]decan-1-amine |
| 31 | 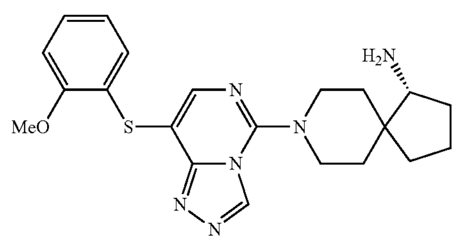 [SMILES: COc1ccccc1Sc1cnc(N2CCC3(CCC[C@H]3N)CC2)n2cnnc12] | (R)-8-(8-((2-methoxyphenyl)thio)-[1,2,4]triazolo[4,3-c]pyrimidin-5-yl)-8-azaspiro[4.5]decan-1-amine |
| 32 | 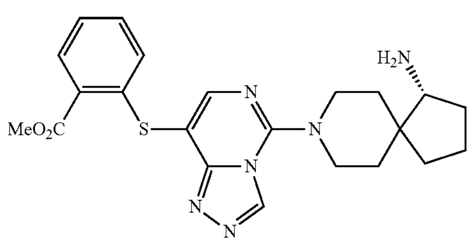 [SMILES: COC(=O)c1ccccc1Sc1cnc(N2CCC3(CCC[C@H]3N)CC2)n2cnnc12] | methyl (R)-2-((5-(1-amino-8-azaspiro[4.5]decan-8-yl)-[1,2,4]triazolo[4,3-c]pyrimidin-8-yl)thio)benzoate |
| 33 | 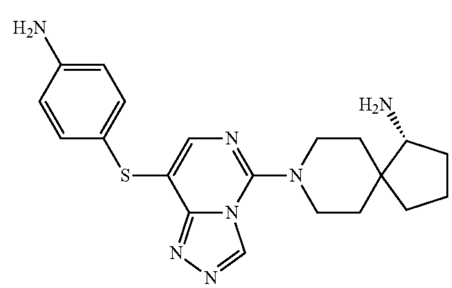 [SMILES: Nc1ccc(Sc2cnc(N3CCC4(CCC[C@H]4N)CC3)n3cnnc23)cc1] | (R)-8-(8-((4-aminophenyl)thio)-[1,2,4]triazolo[4,3-c]pyrimidin-5-yl)-8-azaspiro[4.5]decan-1-amine |

| No. | Compound structure | Compound name |
|---|---|---|
| 34 | 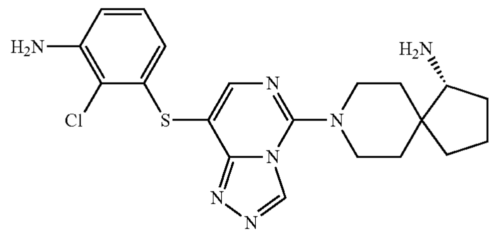 [SMILES: Nc1cccc(Sc2cnc(N3CCC4(CCC[C@H]4N)CC3)n3cnnc23)c1Cl] | (R)-8-(8-((3-amino-2-chlorophenyl)thio)-[1,2,4]triazolo[4,3-c]pyrimidin-5-yl)-8-azaspiro[4.5]decan-1-amine |
| 35 | 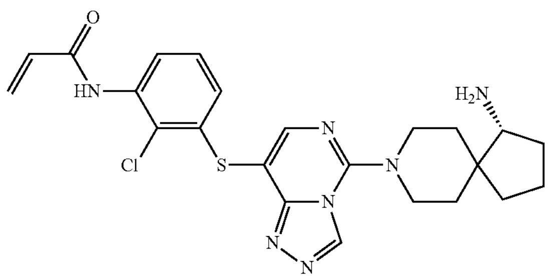 [SMILES: C=CC(=O)Nc1cccc(Sc2cnc(N3CCC4(CCC[C@H]4N)CC3)n3cnnc23)c1Cl] | (R)-N-(3-((5-(1-amino-8-azaspiro[4.5]decan-8-yl)-[1,2,4]triazolo[4,3-c]pyrimidin-8-yl)thio)-2-chlorophenyl)acrylamide |
| 36 | 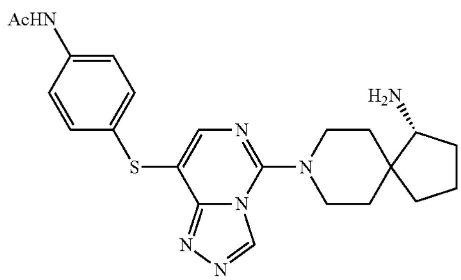 [SMILES: CC(=O)Nc1ccc(Sc2cnc(N3CCC4(CCC[C@H]4N)CC3)n3cnnc23)cc1] | (R)-N-(4-((5-(1-amino-8-azaspiro[4.5]decan-8-yl)-[1,2,4]triazolo[4,3-c]pyrimidin-8-yl)thio)phenyl)acetamide |
| 37 | 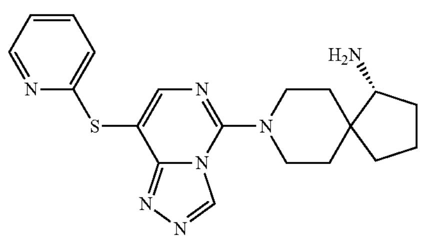 [SMILES: N[C@@H]1CCCC12CCN(c1ncc(Sc3ccccn3)c3nncn13)CC2] | (R)-8-(8-(pyridin-2-ylthio)-[1,2,4]triazolo[4,3-c]pyrimidin-5-yl)-8-azaspiro[4.5]decan-1-amine |
| 38 | 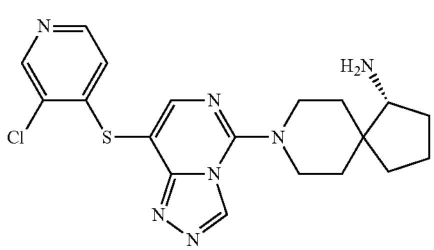 [SMILES: N[C@@H]1CCCC12CCN(c1ncc(Sc3ccncc3Cl)c3nncn13)CC2] | (R)-8-(8-((3-chloropyridin-4-yl)thio)-[1,2,4]triazolo[4,3-c]pyrimidin-5-yl)-8-azaspiro[4.5]decan-1-amine |
| 39 | 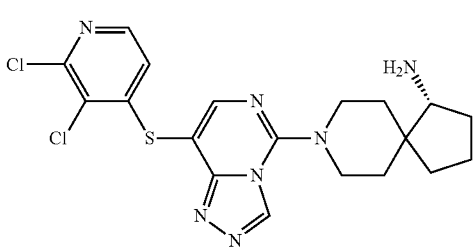 [SMILES: N[C@@H]1CCCC12CCN(c1ncc(Sc3ccnc(Cl)c3Cl)c3nncn13)CC2] | (R)-8-(8-((2,3-dichloropyridin-4-yl)thio)-[1,2,4]triazolo[4,3-c]pyrimidin-5-yl)-8-azaspiro[4.5]decan-1-amine |

| No. | Compound structure | Compound name |
|---|---|---|
| 40 | 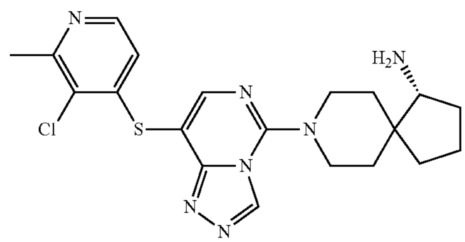 [SMILES: Cc1nccc(Sc2cnc(N3CCC4(CCC[C@H]4N)CC3)n3cnnc23)c1Cl] | (R)-8-(8-((3-chloro-2-methylpyridin-4-yl)thio)-[1,2,4]triazolo[4,3-c]pyrimidin-5-yl)-8-azaspiro[4.5]decan-1-amine |
| 41 | 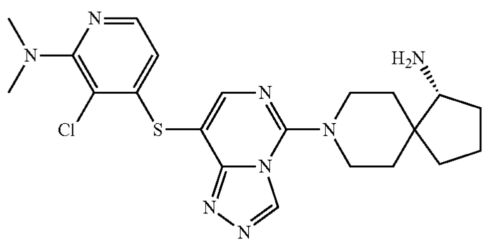 [SMILES: CN(C)c1nccc(Sc2cnc(N3CCC4(CCC[C@H]4N)CC3)n3cnnc23)c1Cl] | (R)-8-(8-((3-chloro-2-(dimethylamino)pyridin-4-yl)thio)-[1,2,4]triazolo[4,3-c]pyrimidin-5-yl)-8-azaspiro[4.5]decan-1-amine |
| 42 | 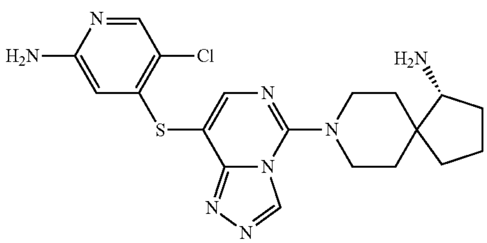 [SMILES: Nc1cc(Sc2cnc(N3CCC4(CCC[C@H]4N)CC3)n3cnnc23)c(Cl)cn1] | (R)-8-(8-((2-amino-5-chloropyridin-4-yl)thio)-[1,2,4]triazolo[4,3-c]pyrimidin-5-yl)-8-azaspiro[4.5]decan-1-amine |
| 43 | 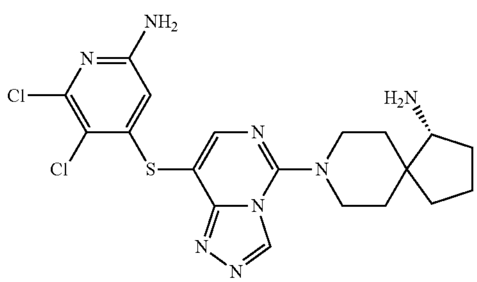 [SMILES: Nc1cc(Sc2cnc(N3CCC4(CCC[C@H]4N)CC3)n3cnnc23)c(Cl)c(Cl)n1] | (R)-8-(8-((6-amino-2,3-dichloropyridin-4-yl)thio)-[1,2,4]triazolo[4,3-c]pyrimidin-5-yl)-8-azaspiro[4.5]decan-1-amine |
| 44 | 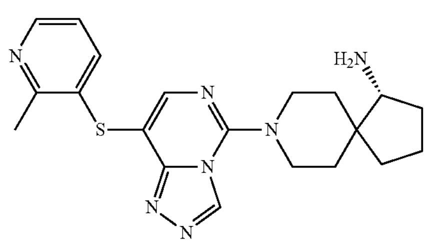 [SMILES: Cc1ncccc1Sc1cnc(N2CCC3(CCC[C@H]3N)CC2)n2cnnc12] | (R)-8-(8-((2-methylpyridin-3-yl)thio)-[1,2,4]triazolo[4,3-c]pyrimidin-5-yl)-8-azaspiro[4.5]decan-1-amine |
| 45 | 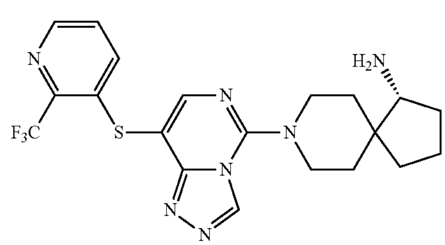 [SMILES: N[C@@H]1CCCC12CCN(c1ncc(Sc3cccnc3C(F)(F)F)c3nncn13)CC2] | (R)-8-(8-((2-(trifluoromethyl)pyridin-3-yl)thio)-[1,2,4]triazolo[4,3-c]pyrimidin-5-yl)-8-azaspiro[4.5]decan-1-amine |

| No. | Compound structure | Compound name |
|---|---|---|
| 46 | 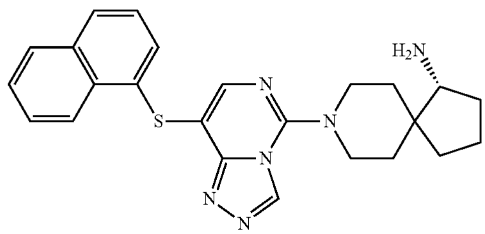 [SMILES: N[C@@H]1CCCC12CCN(c1ncc(Sc3cccc4ccccc34)c3nncn13)CC2] | (R)-8-(8-(naphthalen-1-ylthio)-[1,2,4]triazolo[4,3-c]pyrimidin-5-yl)-8-azaspiro[4.5]decan-1-amine |
| 47 | 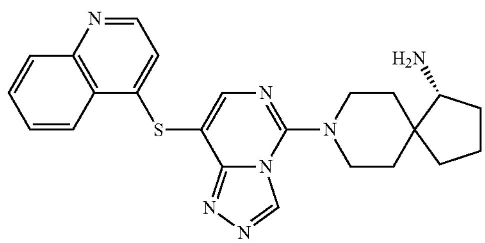 [SMILES: N[C@@H]1CCCC12CCN(c1ncc(Sc3ccnc4ccccc34)c3nncn13)CC2] | (R)-8-(8-(quinolin-4-ylthio)-[1,2,4]triazolo[4,3-c]pyrimidin-5-yl)-8-azaspiro[4.5]decan-1-amine |
| 48 | 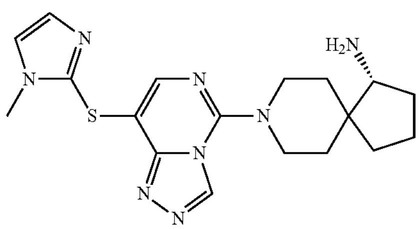 [SMILES: Cn1ccnc1Sc1cnc(N2CCC3(CCC[C@H]3N)CC2)n2cnnc12] | (R)-8-(8-((1-methyl-1H-imidazol-2-yl)thio)-[1,2,4]triazolo[4,3-c]pyrimidin-5-yl)-8-azaspiro[4.5]decan-1-amine |
| 49 | 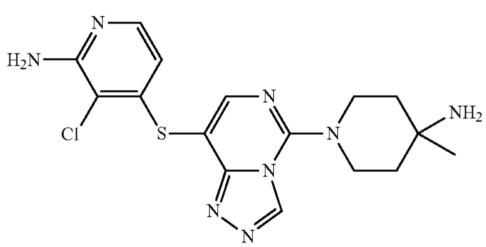 [SMILES: CC1(N)CCN(c2ncc(Sc3ccnc(N)c3Cl)c3nncn23)CC1] | 4-((5-(4-amino-4-methylpiperidin-1-yl)-[1,2,4]triazolo[4,3-c]pyrimidin-8-yl)thio)-3-chloropyridin-2-amine |
| 50 | 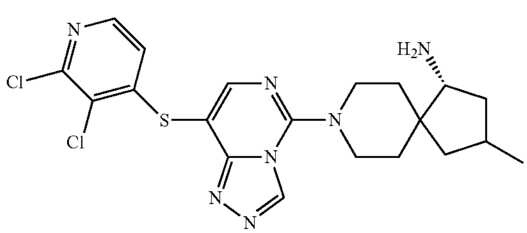 [SMILES: CC1C[C@@H](N)C2(CCN(c3ncc(Sc4ccnc(Cl)c4Cl)c4nncn34)CC2)C1] | (1R)-8-(8-((2,3-dichloropyridin-4-yl)thio)-[1,2,4]triazolo[4,3-c]pyrimidin-5-yl)-3-methyl-8-azaspiro[4.5]decan-1-amine |
| 51 | 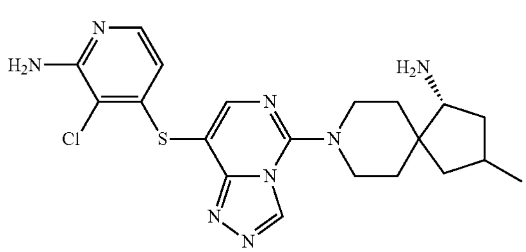 [SMILES: CC1C[C@@H](N)C2(CCN(c3ncc(Sc4ccnc(N)c4Cl)c4nncn34)CC2)C1] | (1R)-8-(8-((2-amino-3-chloropyridin-4-yl)thio)-[1,2,4]triazolo[4,3-c]pyrimidin-5-yl)-3-methyl-8-azaspiro[4.5]decan-1-amine |

-continued

| No. | Compound structure | Compound name |
| --- | --- | --- |
| 52 | 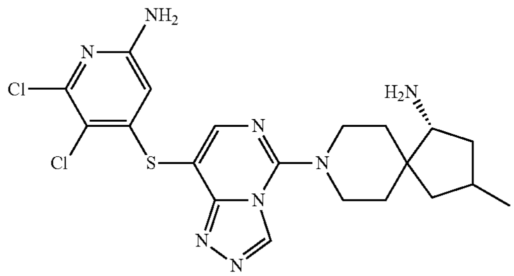 [SMILES: CC1C[C@@H](N)C2(CCN(c3ncc(Sc4cc(N)nc(Cl)c4Cl)c4nncn34)CC2)C1] | (1R)-8-(8-((6-amino-2,3-dichloropyridin-4-yl)thio)-[1,2,4]triazolo[4,3-c]pyrimidin-5-yl)-3-methyl-8-azaspiro[4.5]decan-1-amine |
| 53 | 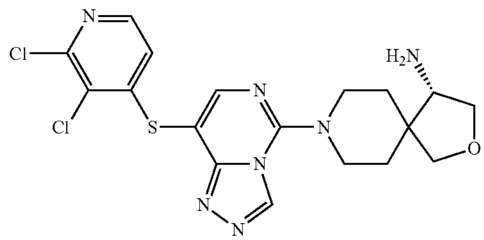 [SMILES: N[C@@H]1COCC12CCN(c1ncc(Sc3ccnc(Cl)c3Cl)c3nncn13)CC2] | (S)-8-(8-((2,3-dichloropyridin-4-yl)thio)-[1,2,4]triazolo[4,3-c]pyrimidin-5-yl)-2-oxa-8-azaspiro[4.5]decan-4-amine |
| 54 | 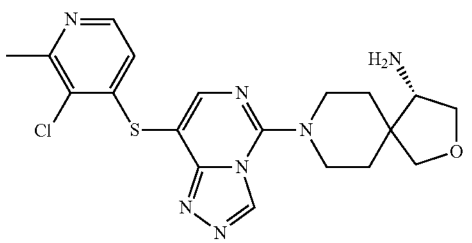 [SMILES: Cc1nccc(Sc2cnc(N3CCC4(CC3)COC[C@H]4N)n3cnnc23)c1Cl] | (S)-8-(8-((3-chloro-2-methylpyridin-4-yl)thio)-[1,2,4]triazolo[4,3-c]pyrimidin-5-yl)-2-oxa-8-azaspiro[4.5]decan-4-amine |
| 55 | 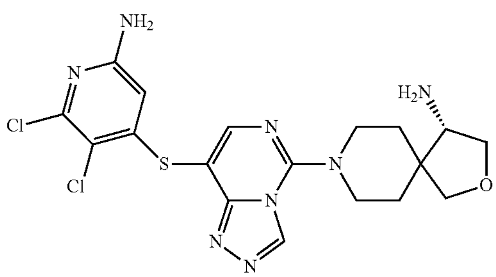 [SMILES: Nc1cc(Sc2cnc(N3CCC4(CC3)COC[C@H]4N)n3cnnc23)c(Cl)c(Cl)n1] | (S)-8-(8-((6-amino-2,3-dichloropyridin-4-yl)thio)-[1,2,4]triazolo[4,3-c]pyrimidin-5-yl)-2-oxa-8-azaspiro[4.5]decan-4-amine |
| 56 | 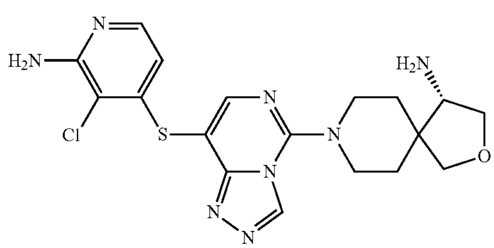 [SMILES: Nc1nccc(Sc2cnc(N3CCC4(CC3)COC[C@H]4N)n3cnnc23)c1Cl] | (S)-8-(8-((2-amino-3-chloropyridin-4-yl)thio)-[1,2,4]triazolo[4,3-c]pyrimidin-5-yl)-2-oxa-8-azaspiro[4.5]decan-4-amine |
| 57 | 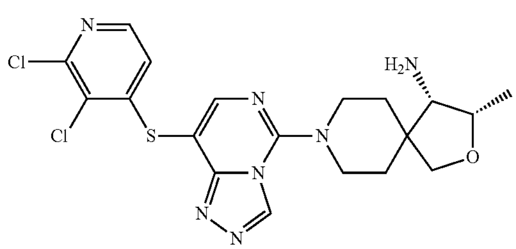 [SMILES: C[C@@H]1OCC2(CCN(c3ncc(Sc4ccnc(Cl)c4Cl)c4nncn34)CC2)[C@@H]1N] | (3S,4S)-8-(8-((2,3-dichloropyridin-4-yl)thio)-[1,2,4]triazolo[4,3-c]pyrimidin-5-yl)-3-methyl-2-oxa-8-azaspiro[4.5]decan-4-amine |

-continued

| No. | Compound structure | Compound name |
|---|---|---|
| 58 | 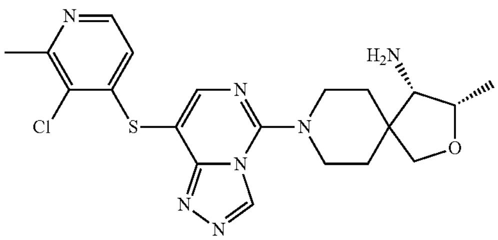 | (3S,4S)-8-(8-((3-chloro-2-methylpyridin-4-yl)thio)-[1,2,4]triazolo[4,3-c]pyrimidin-5-yl)-3-methyl-2-oxa-8-azaspiro[4.5]decan-4-amine |
| 59 | 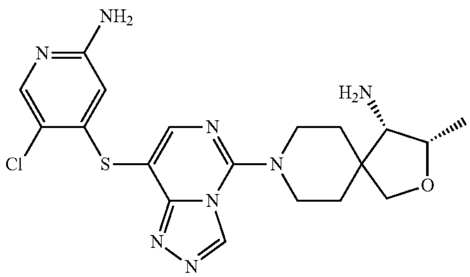 [SMILES: C[C@@H]1OCC2(CCN(c3ncc(Sc4cc(N)ncc4Cl)c4nncn34)CC2)[C@@H]1N] | (3S,4S)-8-(8-((2-amino-5-chloropyridin-4-yl)thio)-[1,2,4]triazolo[4,3-c]pyrimidin-5-yl)-3-methyl-2-oxa-8-azaspiro[4.5]decan-4-amine |
| 60 | 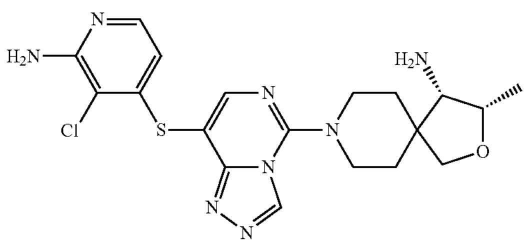 [SMILES: C[C@@H]1OCC2(CCN(c3ncc(Sc4ccnc(N)c4Cl)c4nncn34)CC2)[C@@H]1N] | (3S,4S)-8-(8-((2-amino-3-chloropyridin-4-yl)thio)-[1,2,4]triazolo[4,3-c]pyrimidin-5-yl)-3-methyl-2-oxa-8-azaspiro[4.5]decan-4-amine |
| 61 | 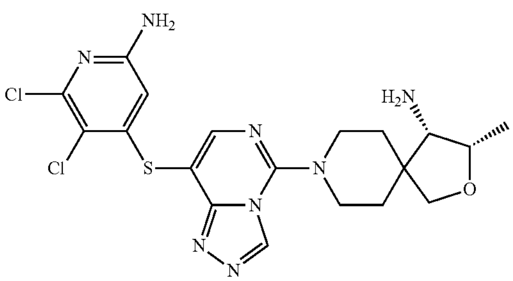 [SMILES: C[C@@H]1OCC2(CCN(c3ncc(Sc4cc(N)nc(Cl)c4Cl)c4nncn34)CC2)[C@@H]1N] | (3S,4S)-8-(8-((6-amino-2,3-dichloropyridin-4-yl)thio)-[1,2,4]triazolo[4,3-c]pyrimidin-5-yl)-3-methyl-2-oxa-8-azaspiro[4.5]decan-4-amine |
| 62 | 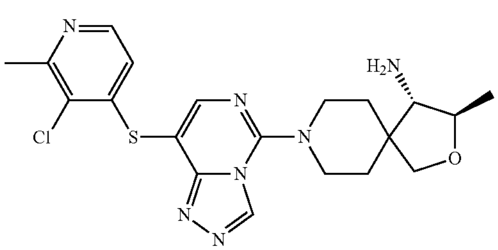 | (3R,4S)-8-(8-((3-chloro-2-methylpyridin-4-yl)thio)-[1,2,4]triazolo[4,3-c]pyrimidin-5-yl)-3-methyl-2-oxa-8-azaspiro[4.5]decan-4-amine |
| 63 | 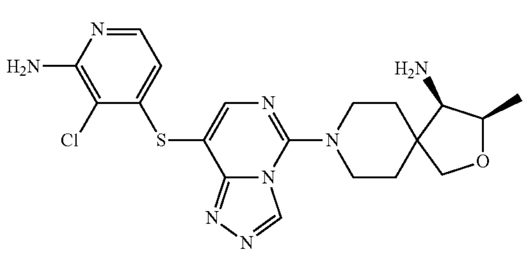 [SMILES: C[C@H]1OCC2(CCN(c3ncc(Sc4ccnc(N)c4Cl)c4nncn34)CC2)[C@H]1N] | (3R,4R)-8-(8-((2-amino-3-chloropyridin-4-yl)thio)-[1,2,4]triazolo[4,3-c]pyrimidin-5-yl)-3-methyl-2-oxa-8-azaspiro[4.5]decan-4-amine |

-continued

| No. | Compound structure | Compound name |
| --- | --- | --- |
| 64 | 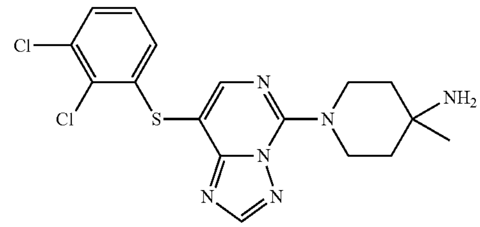 [SMILES: CC1(N)CCN(c2ncc(Sc3cccc(Cl)c3Cl)c3ncnn23)CC1] | 1-(8-((2,3-dichlorophenyl)thio)-[1,2,4]triazolo[1,5-c]pyrimidin-5-yl)-4-methylpiperidin-4-amine |
| 65 | 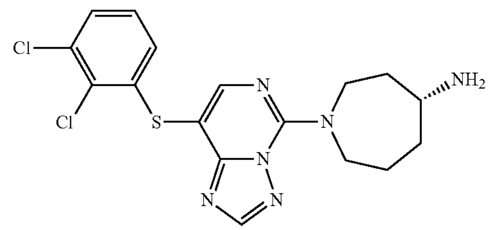 | 1-(8-((2,3-dichlorophenyl)thio)-[1,2,4]triazolo[1,5-c]pyrimidin-5-yl)azepan-4-amine |
| 66 | 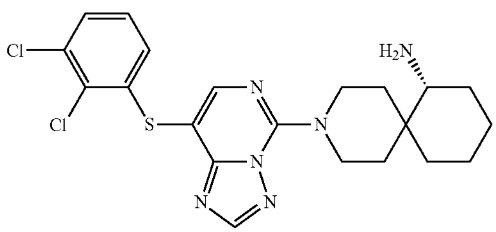 | 3-(8-((2,3-dichlorophenyl)thio)-[1,2,4]triazolo[1,5-c]pyrimidin-5-yl)-3-azaspiro[5.5]undecan-7-amine |
| 67 | 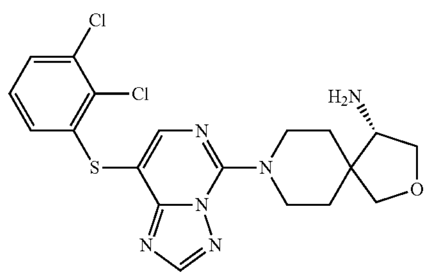 [SMILES: N[C@@H]1COCC12CCN(c1ncc(Sc3cccc(Cl)c3Cl)c3ncnn13)CC2] | (S)-8-(8-((2,3-dichlorophenyl)thio)-[1,2,4]triazolo[1,5-c]pyrimidin-5-yl)-2-oxa-8-azaspiro[4.5]decan-4-amine |
| 68 | 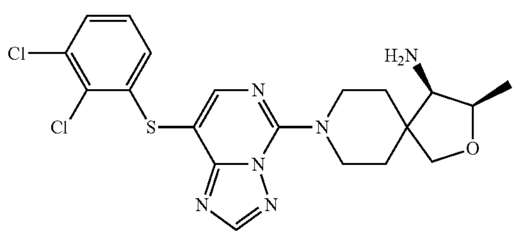 [SMILES: C[C@H]1OCC2(CCN(c3ncc(Sc4cccc(Cl)c4Cl)c4ncnn34)CC2)[C@H]1N] | (3R,4R)-8-(8-((2,3-dichlorophenyl)thio)-[1,2,4]triazolo[1,5-c]pyrimidin-5-yl)-3-methyl-2-oxa-8-azaspiro[4.5]decan-4-amine |
| 69 | 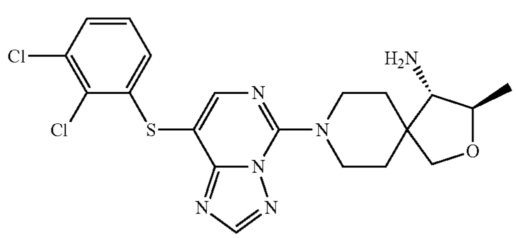 [SMILES: C[C@H]1OCC2(CCN(c3ncc(Sc4cccc(Cl)c4Cl)c4ncnn34)CC2)[C@@H]1N] | (3R,4S)-8-(8-((2,3-dichlorophenyl)thio)-[1,2,4]triazolo[1,5-c]pyrimidn-5-yl)-3-methyl-2-oxa-8-azaspiro[4.5]decan-4-amine |

| No. | Compound structure | Compound name |
|---|---|---|
| 70 | 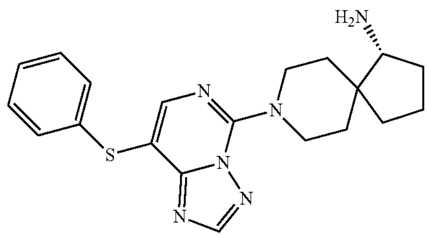 [SMILES: N[C@@H]1CCCC12CCN(c1ncc(Sc3ccccc3)c3ncnn13)CC2] | (R)-8-(8-(phenylthio)-[1,2,4]triazolo[1,5-c]pyrimidin-5-yl)-8-azaspiro[4.5]decan-1-amine |
| 71 | 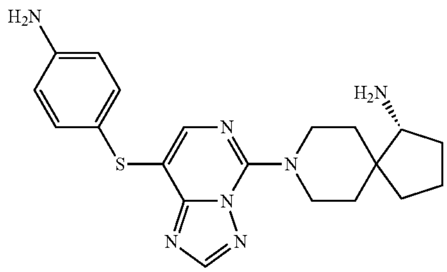 [SMILES: Nc1ccc(Sc2cnc(N3CCC4(CCC[C@H]4N)CC3)n3ncnc23)cc1] | (R)-8-(8-((4-aminophenyl)thio)-[1,2,4]triazolo[1,5-c]pyrimidin-5-yl)-8-azaspiro[4.5]decan-1-amine |
| 72 | 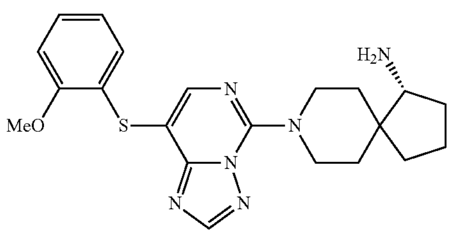 [SMILES: COc1ccccc1Sc1cnc(N2CCC3(CCC[C@H]3N)CC2)n2ncnc12] | (R)-8-(8-((2-methoxyphenyl)thio)-[1,2,4]triazolo[1,5-c]pyrimidin-5-yl)-8-azaspiro[4.5]decan-1-amine |
| 73 | 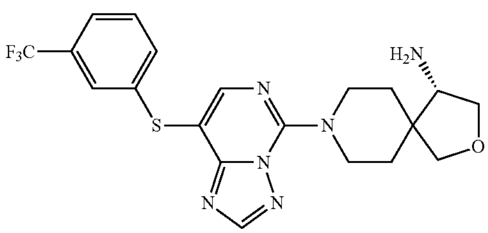 [SMILES: N[C@@H]1COCC12CCN(c1ncc(Sc3cccc(C(F)(F)F)c3)c3ncnn13)CC2] | (R)-8-(8-((3-(trifluoromethyl)phenyl)thio)-[1,2,4]triazolo[1,5-c]pyrimidin-5-yl)-8-azaspiro[4.5]decan-1-amine |
| 74 | 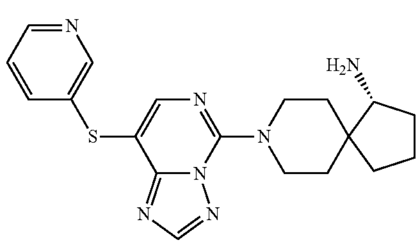 [SMILES: N[C@@H]1CCCC12CCN(c1ncc(Sc3cccnc3)c3ncnn13)CC2] | (R)-8-(8-(pyridin-3-ylthio)-[1,2,4]triazolo[1,5-c]pyrimidin-5-yl)-8-azaspiro[4.5]decan-1-amine |
| 75 | 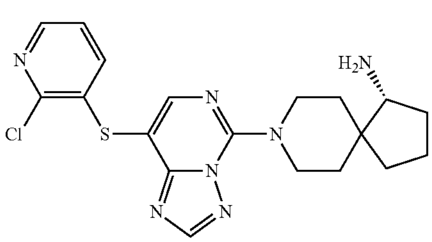 [SMILES: N[C@@H]1CCCC12CCN(c1ncc(Sc3cccnc3Cl)c3ncnn13)CC2] | (R)-8-(8-((2-chloropyridin-3-yl)thio)-[1,2,4]triazolo[1,5-c]pyrimidin-5-yl)-8-azaspiro[4.5]decan-1-amine |

| No. | Compound structure | Compound name |
|---|---|---|
| 76 | 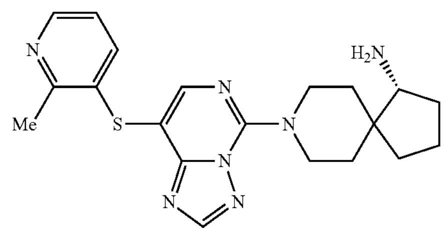 [SMILES: Cc1ncccc1Sc1cnc(N2CCC3(CCC[C@H]3N)CC2)n2ncnc12] | (R)-8-(8-((2-methylpyridin-3-yl)thio)-[1,2,4]triazolo[1,5-c]pyrimidin-5-yl)-8-azaspiro[4.5]decan-1-amine |
| 77 | 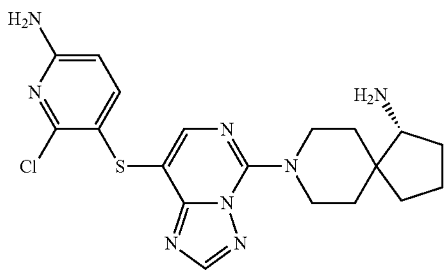 [SMILES: Nc1ccc(Sc2cnc(N3CCC4(CCC[C@H]4N)CC3)n3ncnc23)c(Cl)n1] | (R)-8-(8-((6-amino-2-chloropyridin-3-yl)thio)-[1,2,4]triazolo[1,5-c]pyrimdin-5-yl)-8-azaspiro[4.5]decan-1-amine |
| 78 | 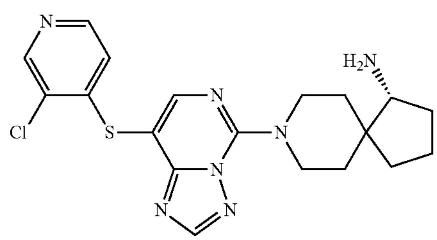 [SMILES: N[C@@H]1CCCC12CCN(c1ncc(Sc3ccncc3Cl)c3ncnn13)CC2] | (R)-8-(8-((3-chloropyridin-4-yl)thio)-[1,2,4]triazolo[1,5-c]pyrimidin-5-yl)-8-azaspiro[4.5]decan-1-amine |
| 79 | 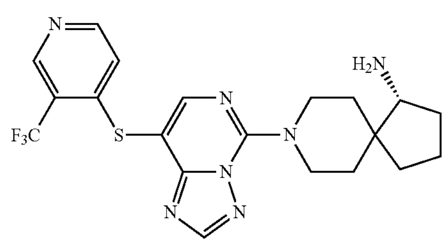 [SMILES: N[C@@H]1CCCC12CCN(c1ncc(Sc3ccncc3C(F)(F)F)c3ncnn13)CC2] | (R)-8-(8-((3-(trifluoromethyl)pyridin-4-yl)thio)-[1,2,4]triazolo[1,5-c]pyrimidin-5-yl)-8-azaspiro[4.5]decan-1-amine |
| 80 | 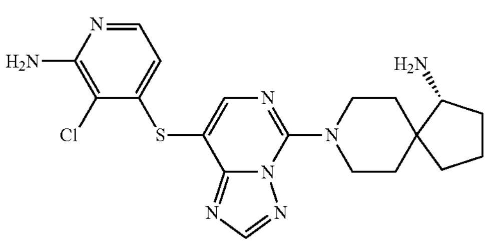 [SMILES: Nc1nccc(Sc2cnc(N3CCC4(CCC[C@H]4N)CC3)n3ncnc23)c1Cl] | (R)-8-(8-((2-amino-3-chloropyridin-4-yl)thio)-[1,2,4]triazolo[1,5-c]pyrimidin-5-yl)-8-azaspiro[4.5]decan-1-amine |
| 81 | 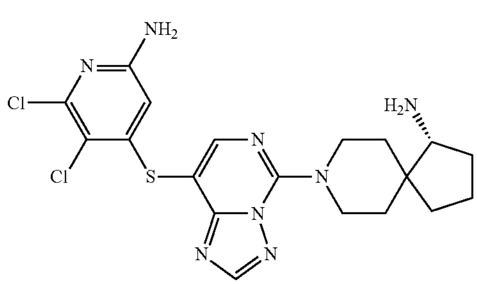 [SMILES: Nc1cc(Sc2cnc(N3CCC4(CCC[C@H]4N)CC3)n3ncnc23)c(Cl)c(Cl)n1] | (R)-8-(8-((6-amino-2,3-dichloropyridin-4-yl)thio)-[1,2,4]triazolo[1,5-c]pyrimidin-5-yl)-8-azaspiro[4.5]decan-1-amine |

| No. | Compound structure | Compound name |
|---|---|---|
| 82 | 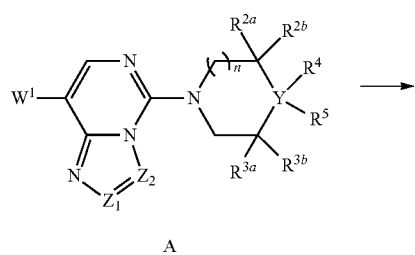 | (S)-8-(8-((3-chloro-2-methylpyridin-4-yl)thio)-[1,2,4]triazolo[1,5-c]pyrimidin-5-yl)-2-oxa-8-azaspiro[4.5]decan-4-amine |
| 83 | 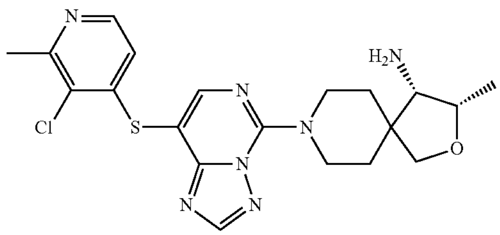 | (3S,4S)-8-(8-((3-chloro-2-methylpyridin-4-yl)thio)-[1,2,4]triazolo[1,5-c]pyrimidin-5-yl)-3-methyl-2-oxa-8-azaspiro[4.5]decan-4-amine |

In a second aspect, the present disclosure provides an isotope-labeled compound of the pyrimidine-fused compound represented by formula (I), the pharmaceutically acceptable salt thereof, the hydrate thereof, the prodrug thereof, the stereoisomer thereof, or the solvate thereof. The atoms that can be labeled with isotopes in the compound represented by formula (I) include, but are not limited to, hydrogen, carbon, nitrogen, oxygen, phosphorus, fluorine, chlorine, and iodine. They can be replaced by isotopes $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ and the like.

The present disclosure also provides a preparation method of the pyrimidine-fused compound represented by formula (I) and an intermediate compound thereof, mainly including the following aspects.

The present disclosure provides a preparation method of a pyrimidine-fused compound represented by formula (I), which comprises any of the following schemes: scheme 1, which comprises a step of:

conducting a coupling reaction of halogenated intermediate compound represented by formula A with compound F to obtain the pyrimidine-fused compound represented by formula (I), and the reaction equation is shown below:

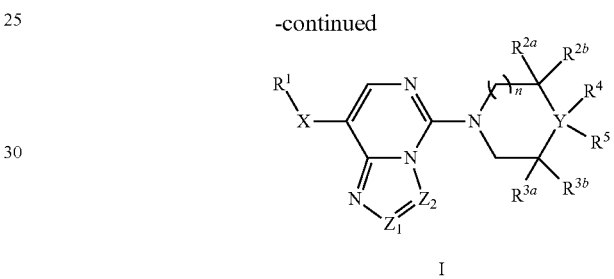

wherein, when X is absent, then compound F is boronic acid, thiol or sodium thiolate of $R^1$; when X is S, then compound F is thiol or sodium thiolate;

$W^1$ is halogen; preferably, Br or I; X, Y, $Z_1$, $Z_2$, n, $R^1$, $R^{2a}$, $R^{2b}$, $R^{3a}$, $R^{3b}$, $R^4$ and $R^5$ are as defined above;

scheme 2, which comprises a step of:

conducting a substitution reaction of an intermediate represented by formula B with an amine represented by formula C to obtain the pyrimidine-fused compound represented by formula (I), and the reaction equation is as shown below:

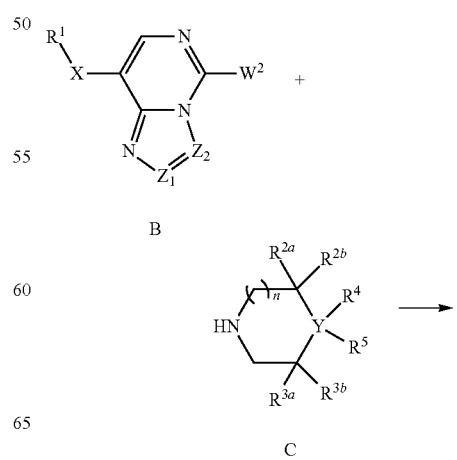

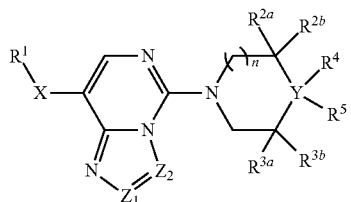

I wherein, $W^2$ is halogen, preferably, Cl, Br or I; $Z_1$, $Z_2$, X, Y, n, $R^1$, $R^{2a}$, $R^{2b}$, $R^{3a}$, $R^{3b}$, $R^4$ and $R^5$ are as defined above;

scheme 3 in the case the pyrimidine-fused compound represented by formula (I) is a pyrimidine-fused compound represented by formula (I-B), which comprises a step of removing the amino protecting group Pg from an intermediate represented by formula I-B1 to obtain the pyrimidine-fused compound represented by formula (I-B) under acidic or basic condition, and the reaction equation is as shown below:

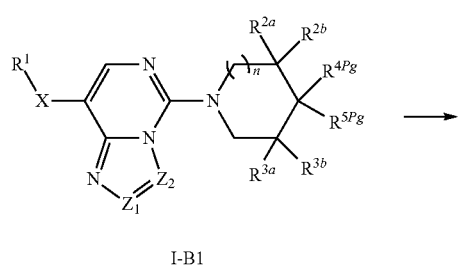

I-B1

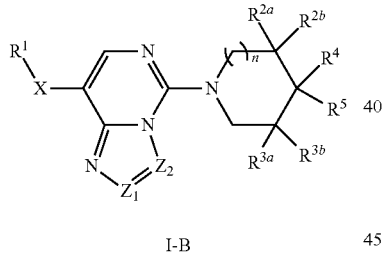

I-B wherein, X, $Z_1$, $Z_2$, n, p, $R^1$, $R^{2a}$, $R^{2b}$, $R^{3a}$, $R^{3b}$, $R^4$, $R^5$ and $R^{4a}$ are as defined above; $R^{4Pg}$ and $R^{5Pg}$, together with the carbon atom to which they are attached, form

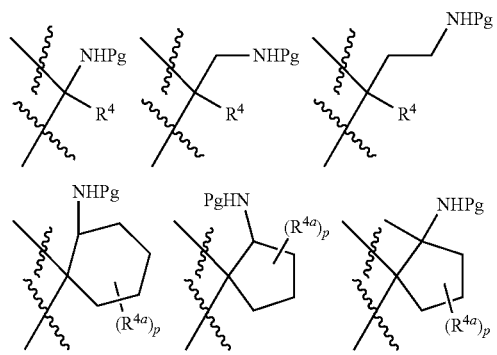

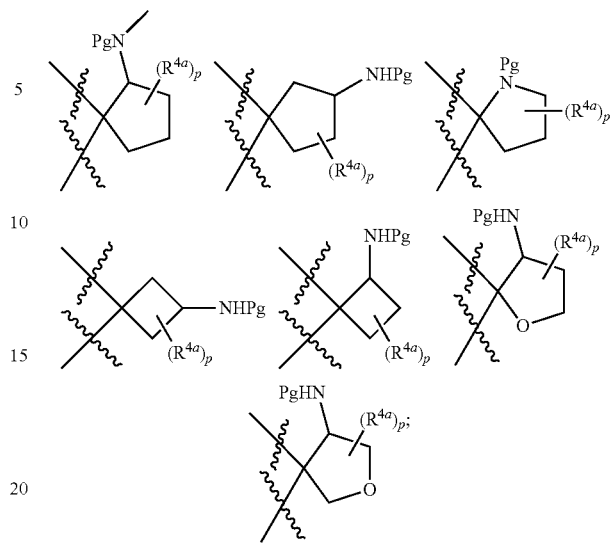

$R^4$ and $R^5$ together with the carbon atom to which they are attached, form

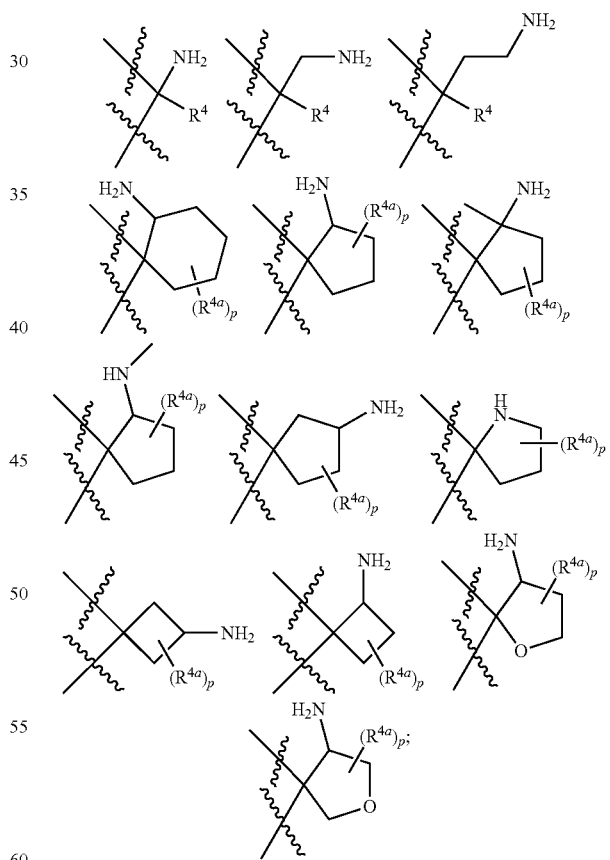

Pg is a protecting group selected from Boc, Ac and S(=O)$^t$Bu; p is 0, 1, 2 or 3;

scheme 4 in the case the pyrimidine-fused compound represented by formula (I) is a pyrimidine-fused compound represented by formula (I-C), which comprises a step of:

conducting an amidation reaction of an intermediate represented by formula I-C1 to obtain the pyrimidine-fused compound represented by formula (I-C), and the reaction equation is as shown below:

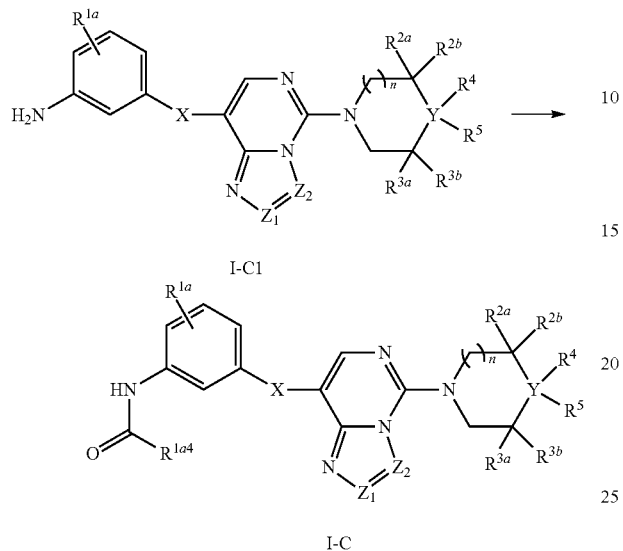

I-C1

I-C wherein, X, Y, n, $R^{2a}$, $R^{2b}$, $R^{3a}$, $R^{3b}$, $R^4$, $R^5$, $R^{1a}$ and $R^{1a4}$ are as defined above;

scheme 5 in the case the pyrimidine-fused compound represented by formula (I) is a pyrimidine-fused compound represented by formula (I-A), which comprises a step of:

conducting a coupling reaction of sodium thiolate intermediate compound represented by formula D with a halogenated compound $R^1$—$W^1$ to obtain the pyrimidine-fused compound represented by formula (I-A), and the reaction equation is as shown below:

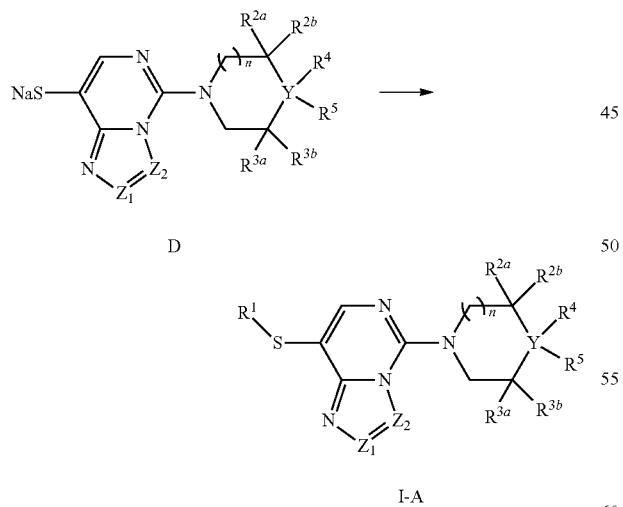

D

I-A wherein, Y, n, $W^1$, $R^1$, $R^{2a}$, $R^{2b}$, $R^{3a}$, $R^{3b}$, $R^4$ and $R^5$ are as defined above.

In a preferable embodiment, when the pyrimidine-fused compound represented by formula (I) is compound I-B, then the preparation method of compound I-B comprises a step of:

removing the amino protecting group from an intermediate I-B1 under acidic or basic condition to obtain the compound I-B, and the reaction equation is as shown below:

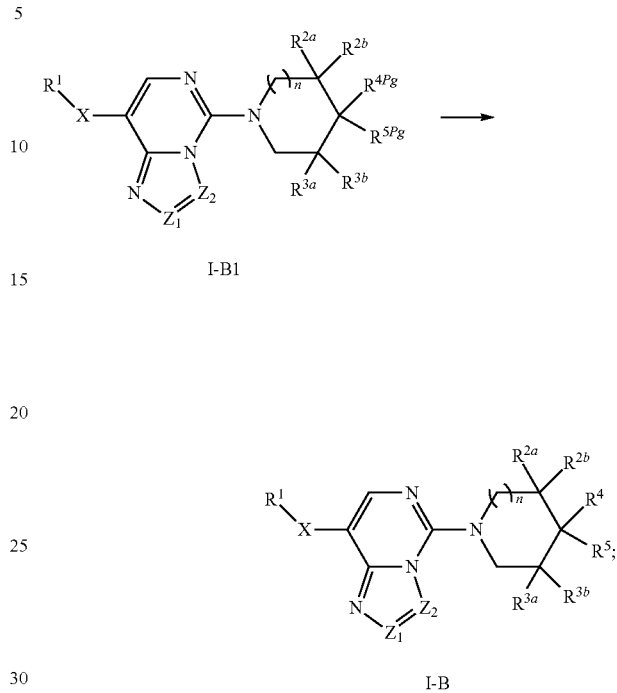

I-B1

I-B wherein, X, $Z_1$, $Z_2$, n, p, $R^1$, $R^{2a}$, $R^{2b}$, $R^{3a}$, $R^{3b}$, $R^4$, $R^5$ and $R^{4a}$ are as defined above; Pg is a protecting group selected from Boc, Ac and S(=O)$^t$Bu; $R^{4Pg}$ and $R^{5Pg}$, together with the carbon atom to which they are attached, form

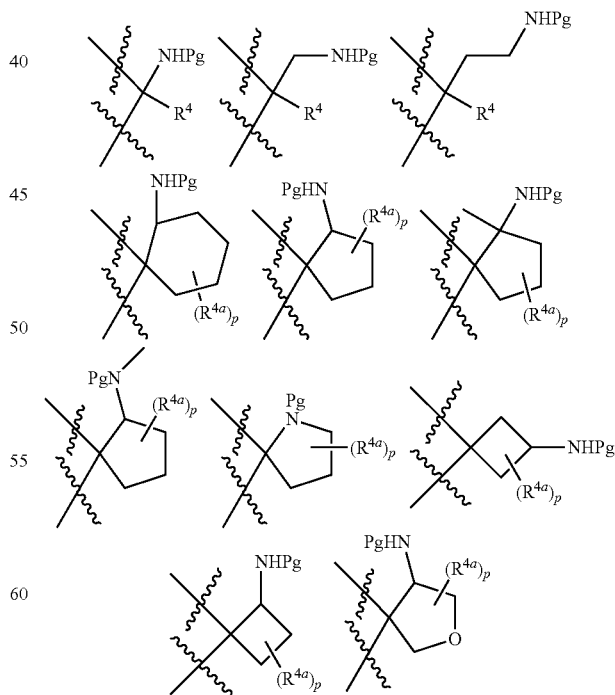

$R^4$ and $R^5$ together with the carbon atom to which they are attached, form

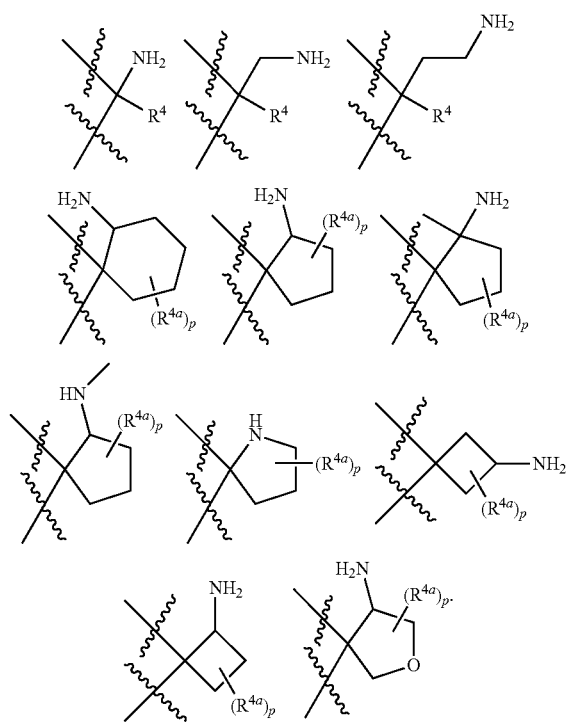

In a preferable embodiment, the preparation method of a pyrimidine-fused compound represented by formula (III) comprises any of the following schemes:

scheme 1, which comprises a step of:

conducting a coupling reaction of a halogenated intermediate compound

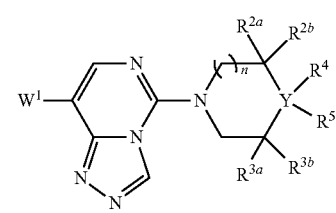

with F to obtain the pyrimidine-fused compound represented by formula (III), and the reaction equation is as shown below:

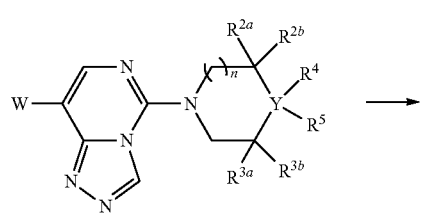

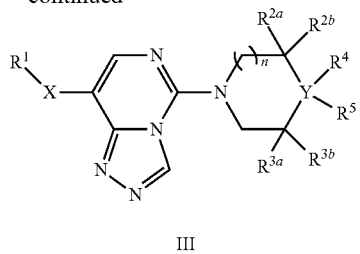

wherein, F can be boronic acid, thiol or sodium thiolate;

scheme 2, which comprises a step of: conducting an amidation reaction of an intermediate III-C1 to obtain a compound III-C, and the reaction equation is as shown below:

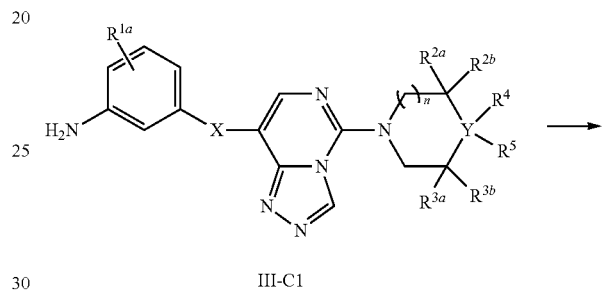

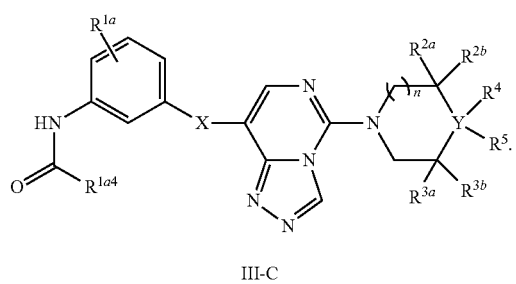

In a preferable embodiment, the preparation method of a pyrimidine-fused compound represented by formula (TI) comprises any of the following schemes:

scheme 1, which comprises a step of:

conducting a coupling reaction of a halogenated intermediate compound A-IT with F to obtain the pyrimidine-fused compound represented by formula (I), and the reaction equation is as shown below:

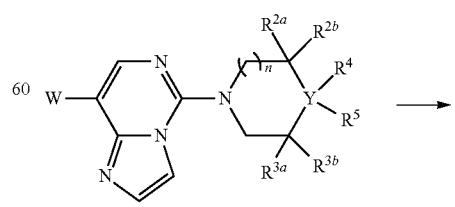

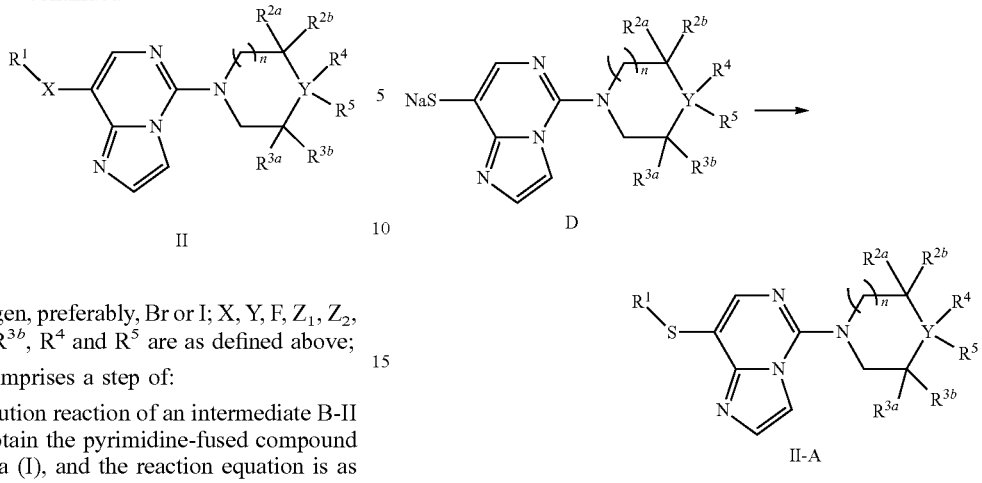

II wherein, $W^1$ is halogen, preferably, Br or I; X, Y, F, $Z_1$, $Z_2$, n, $R^1$, $R^{2a}$, $R^{2b}$, $R^{3a}$, $R^{3b}$, $R^4$ and $R^5$ are as defined above;

scheme 2, which comprises a step of:

conducting a substitution reaction of an intermediate B-II with an amine C to obtain the pyrimidine-fused compound represented by formula (I), and the reaction equation is as shown below:

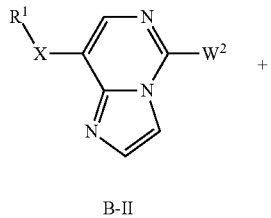

B-II

+

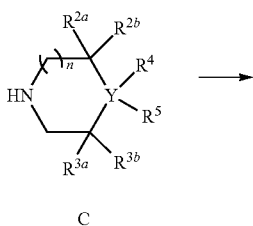

C

→

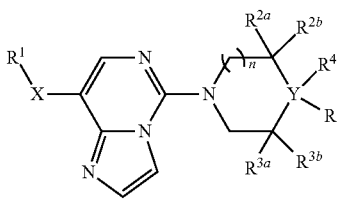

II wherein, $W^2$ is halogen, preferably, Cl, Br or I; X, Y, n, $R^1$, $R^{2a}$, $R^{2b}$, $R^{3a}$, $R^{3b}$, $R^4$ and $R^5$ are as defined above;

scheme 3 in the case the pyrimidine-fused compound represented by formula (II) is a pyrimidine-fused compound represented by formula (II-A), which comprises a step of:

conducting a coupling reaction of the sodium thiolate intermediate compound D with a halogenated compound to obtain the pyrimidine-fused compound represented by formula (II-A), and the reaction equation is as shown below:

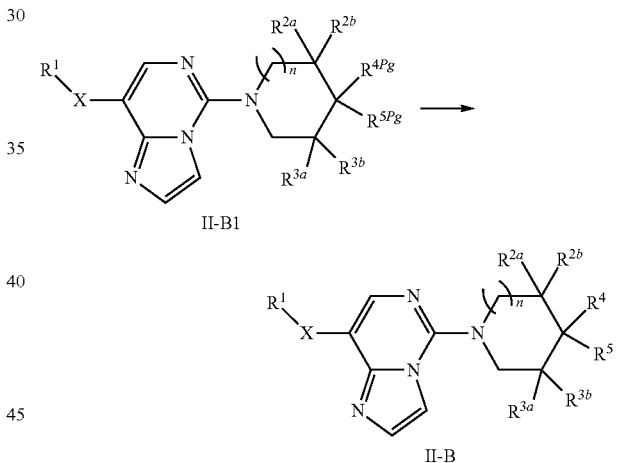

wherein, Y, n, $R^1$, $R^{2a}$, $R^{2b}$, $R^{3a}$, $R^{3b}$, $R^4$ and $R^5$ are as defined above;

scheme 4, which comprises a step of:

removing the amino protecting group form an intermediate II-B1 to obtain a compound II-B under acidic or basic condition, and the reaction equation is as shown wherein, Pg is a protecting group selected from Boc, Ac and S(=O)$^t$Bu; $R^{4Pg}$ and $R^{5Pg}$, together with the carbon atom to which they are attached, form

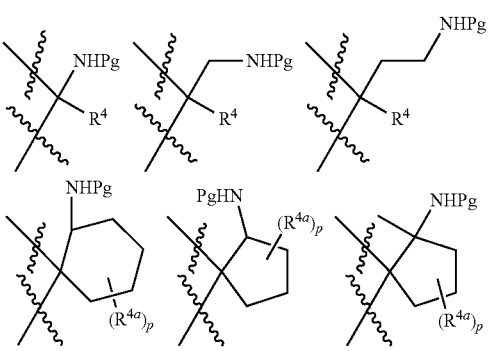

-continued

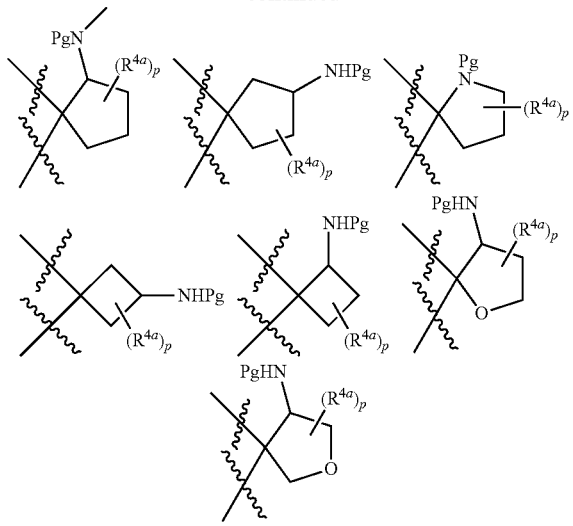

R⁴ and R⁵, together with the carbon atom to which they are attached, form

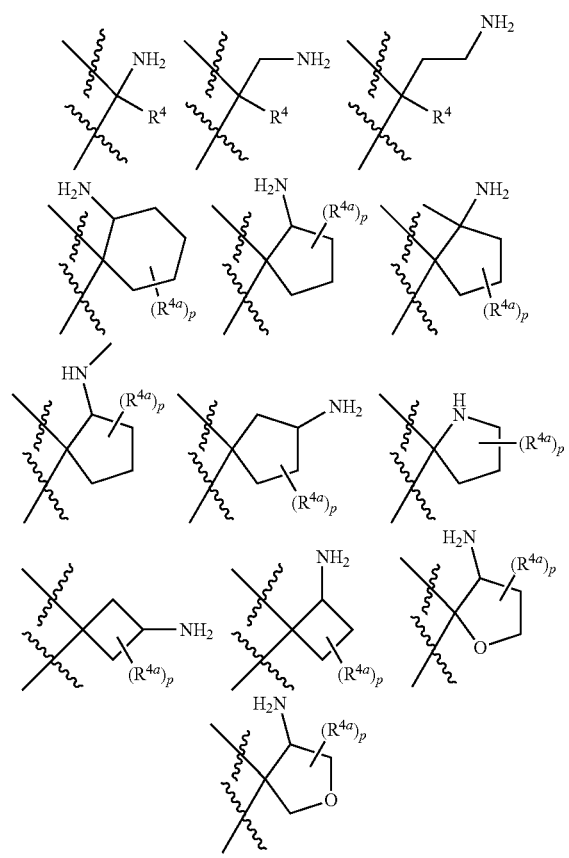

X, n, R¹, R²ᵃ, R²ᵇ, R³ᵃ, R³ᵇ, R⁴, R⁵ and R⁴ᵃ are as defined above; p is 0, 1, 2 or 3;

scheme 5, which comprises a step of:

conducting an amidation reaction of an intermediate I-C1 to obtain a compound II-C, and the reaction equation is as shown below:

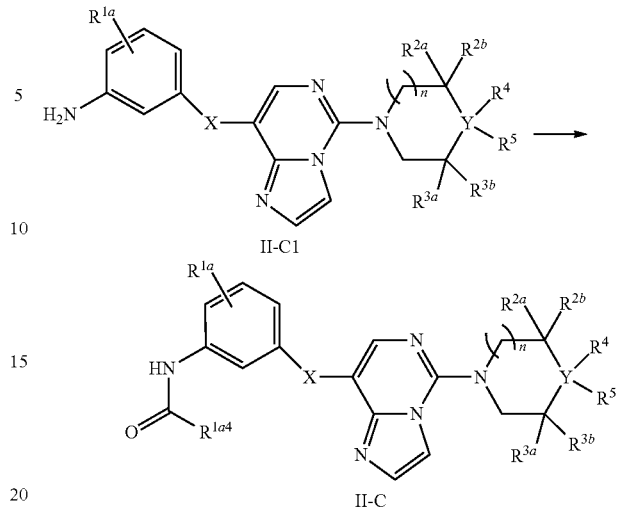

wherein, X, Y, n, R¹, R²ᵃ, R²ᵇ, R³ᵃ, R³ᵇ, R⁴, R⁵, R¹ᵃ and R¹ᵃ⁴ are as defined above.

The present disclosure also provides a compound A,

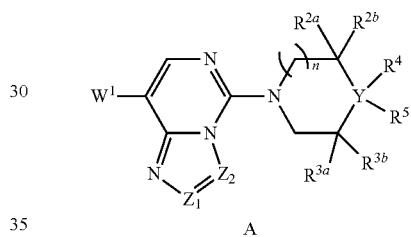

wherein, $W^1$ is halogen, preferably, Br or I; $R^2$, $R^{2b}$, $R^{3a}$, $R^{3b}$, $R^4$, $R^5$, Y and n are as defined above.

In a preferable embodiment, the compound A is represented by compound A-II,

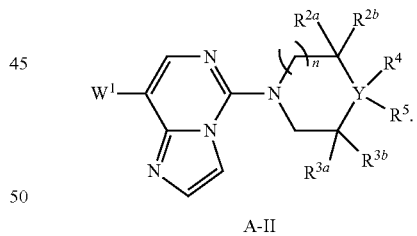

In a preferable embodiment, the compound A is represented by compound A-III,

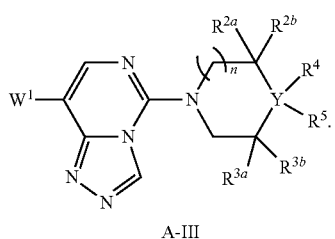

In a preferable embodiment, the compound A-II is selected from
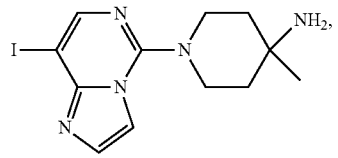
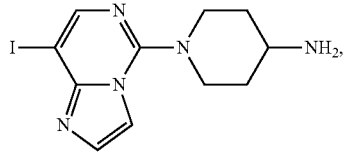
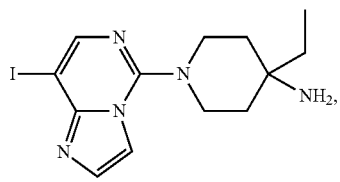
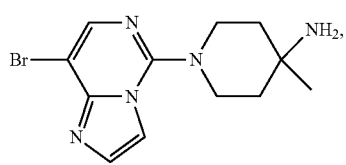
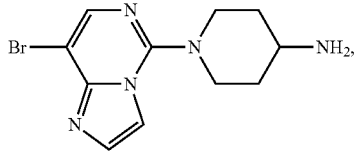
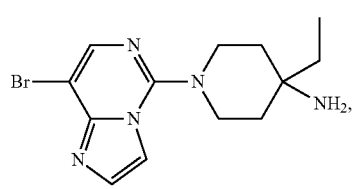
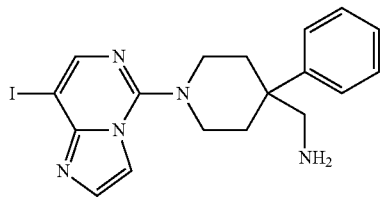
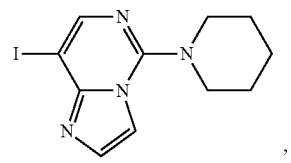
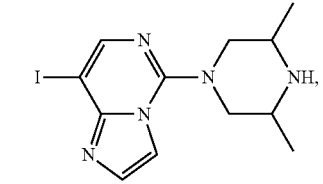
-continued
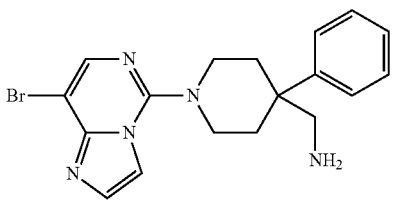
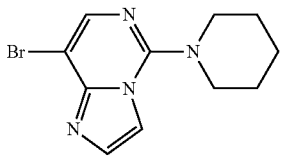
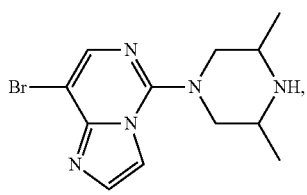
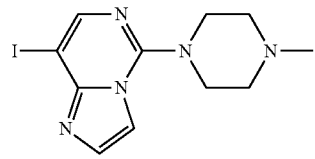
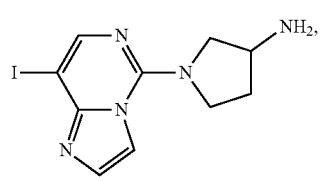
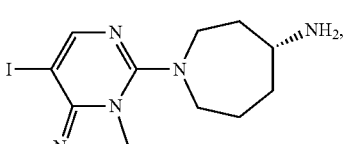
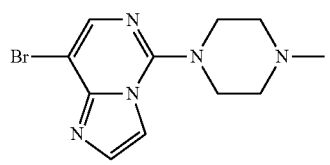
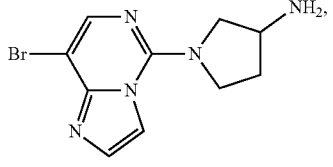
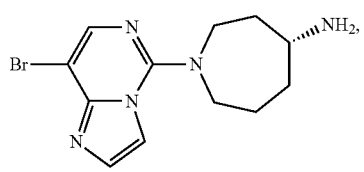

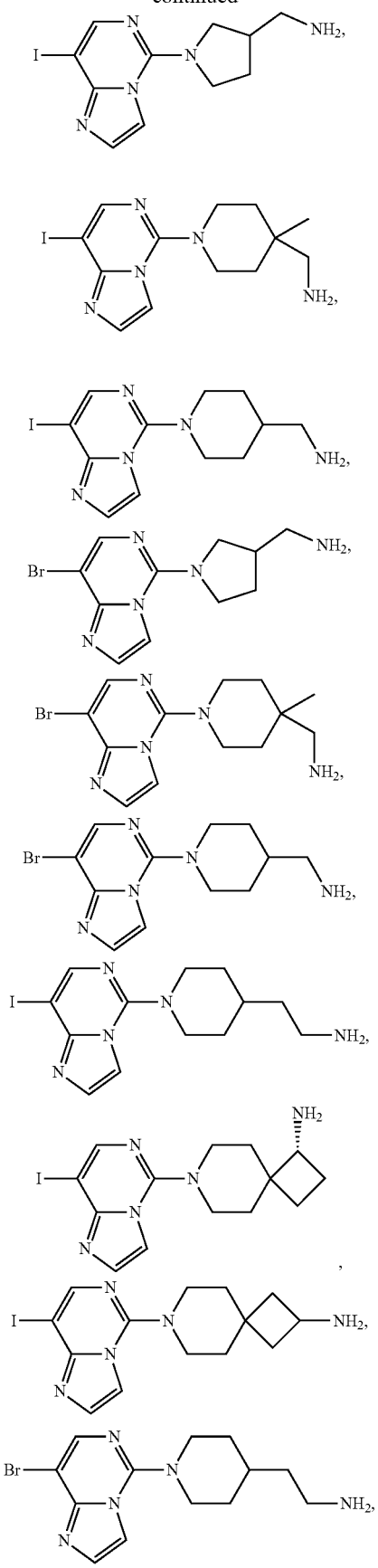
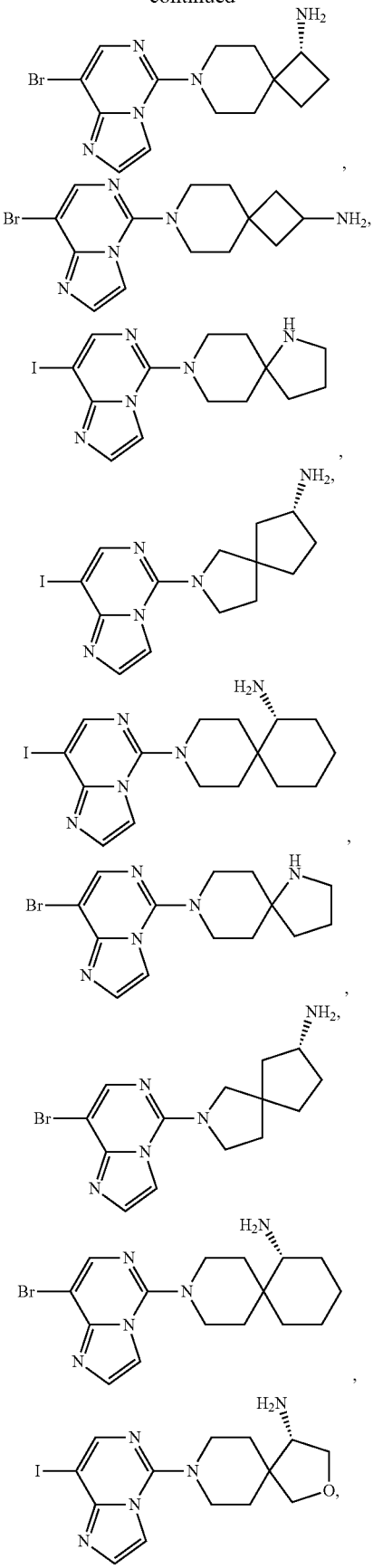

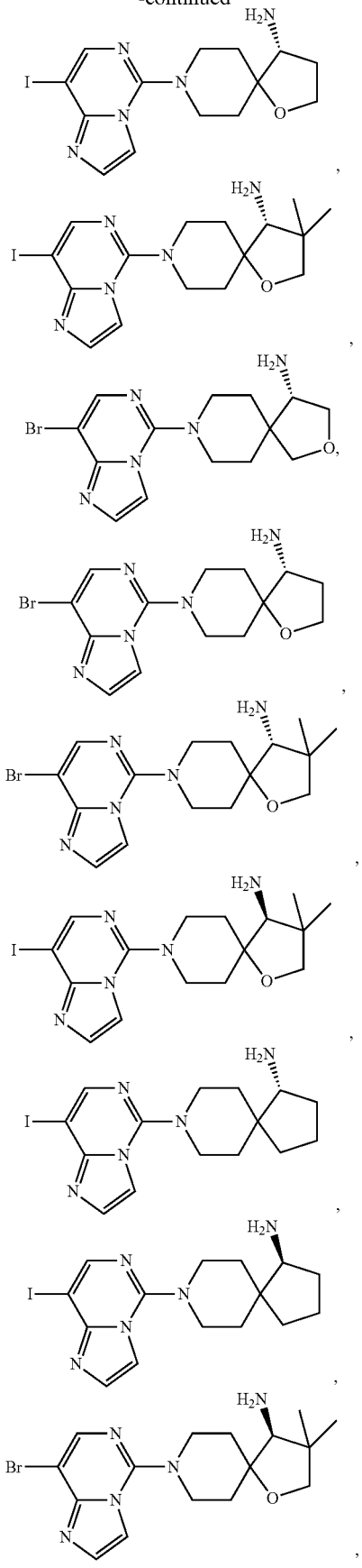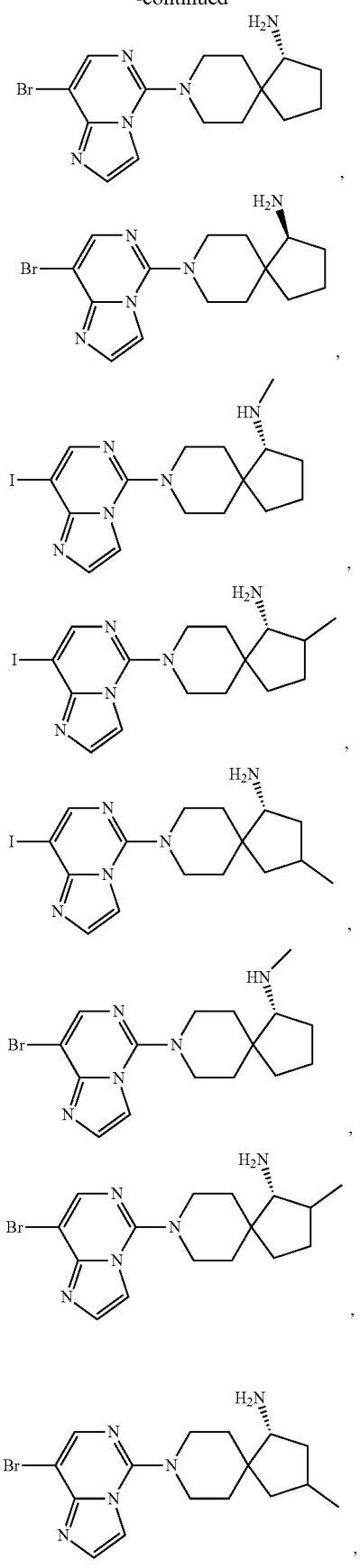

-continued
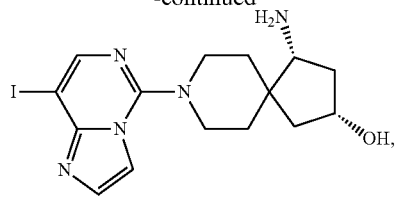
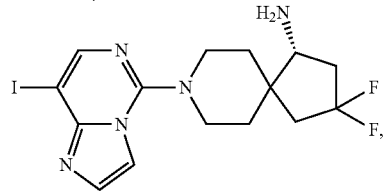
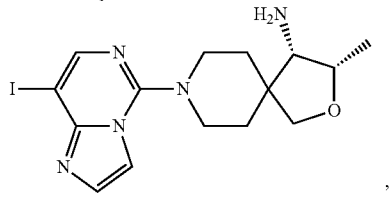
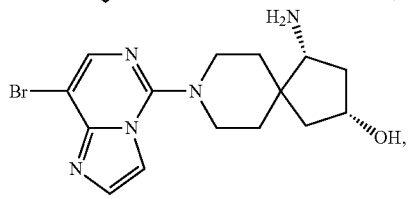
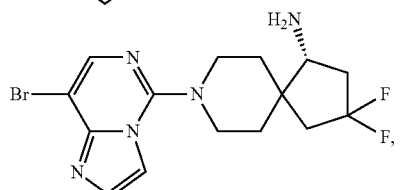
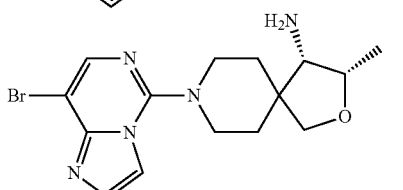
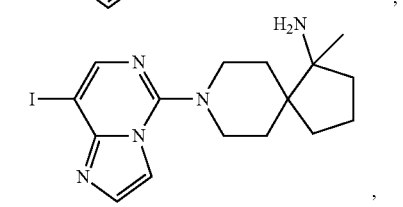
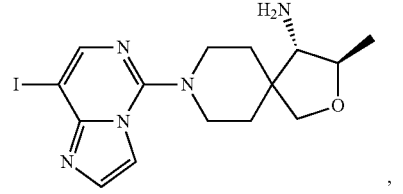
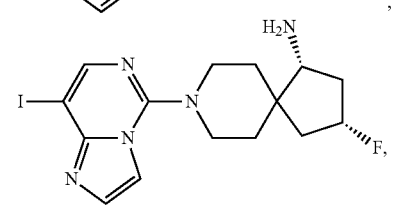
-continued
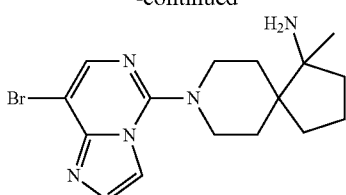
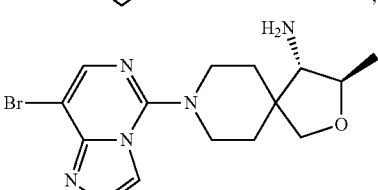
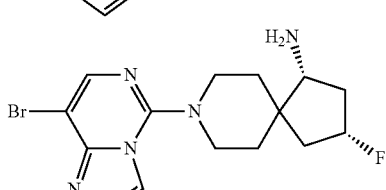
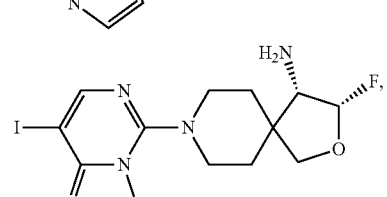
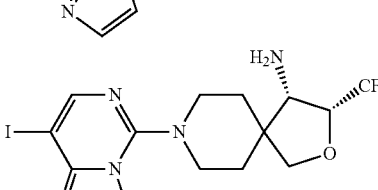
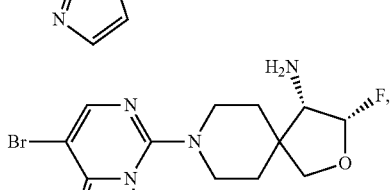
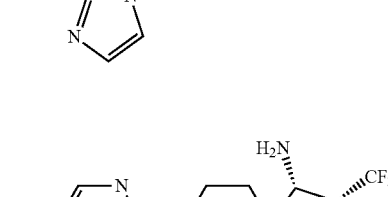
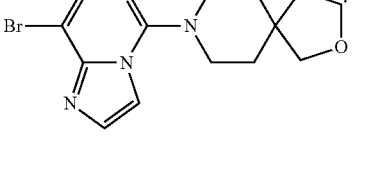
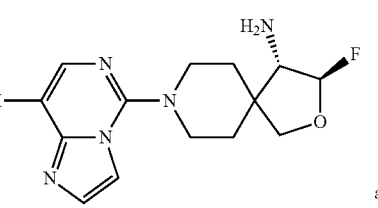
and

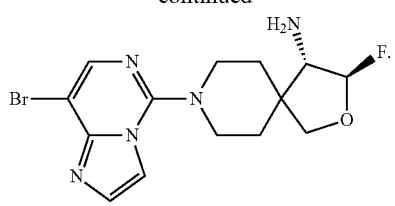
In a preferable embodiment, the compound A-III is selected from
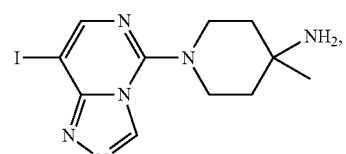
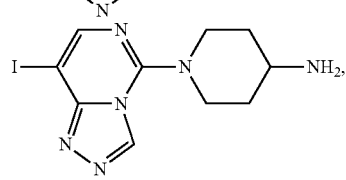
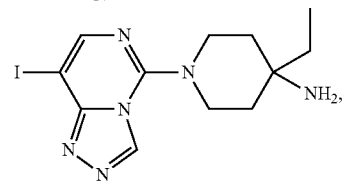
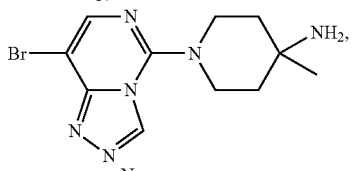
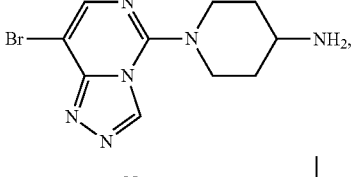
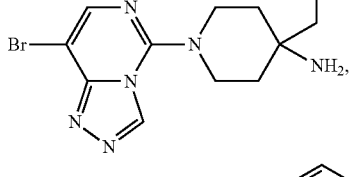
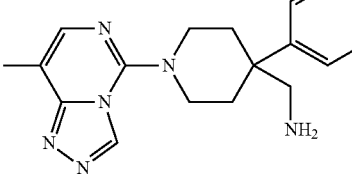
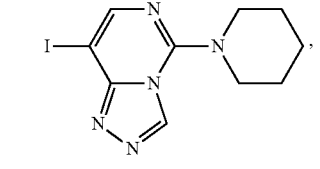
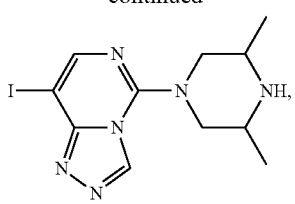
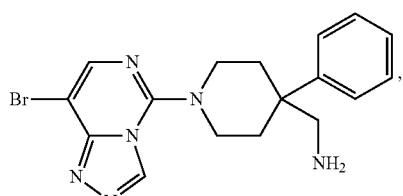
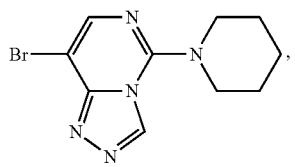
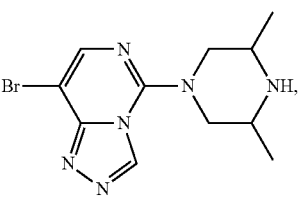
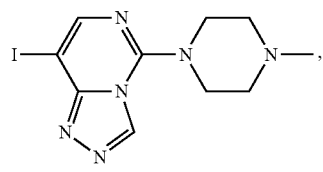
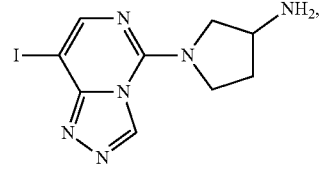
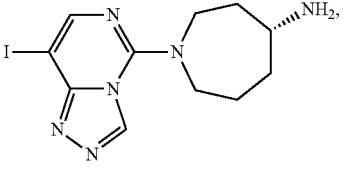
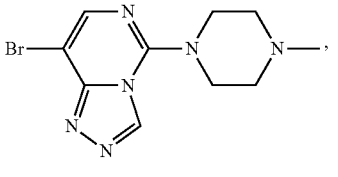
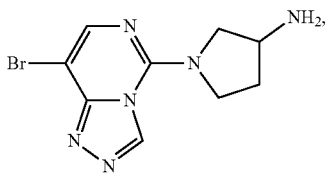

-continued
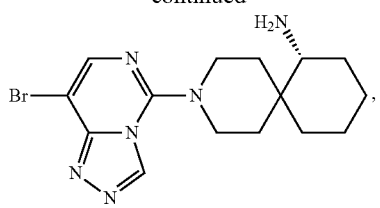
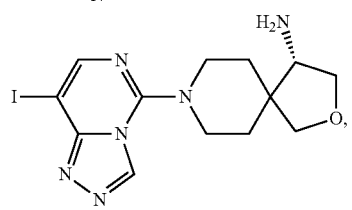
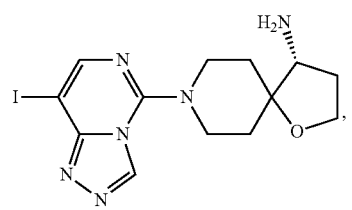
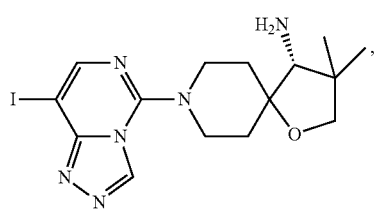
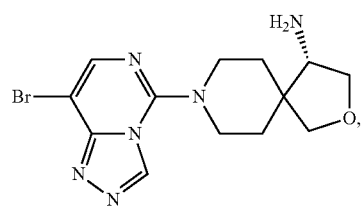
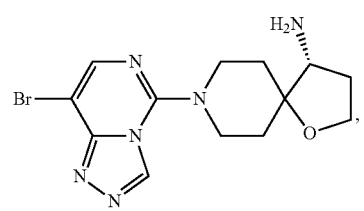
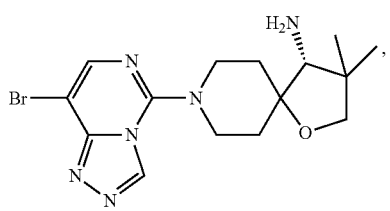
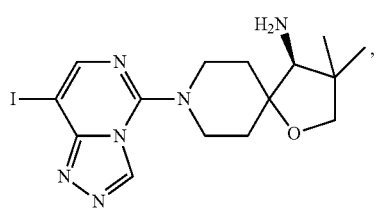
-continued
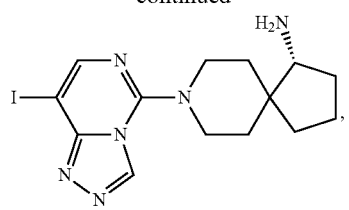
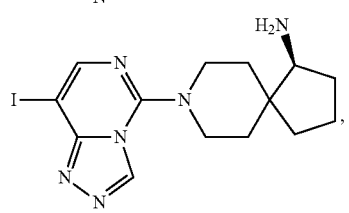
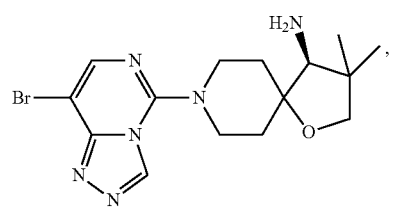
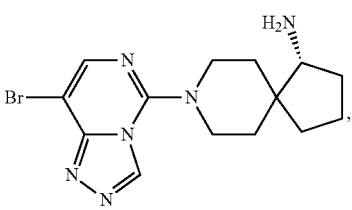
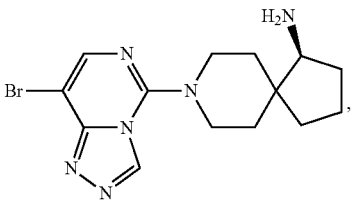
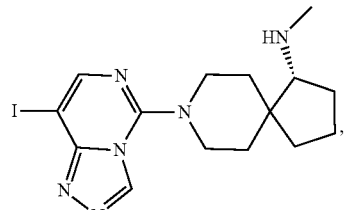
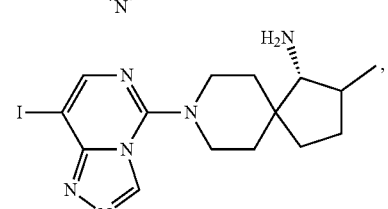
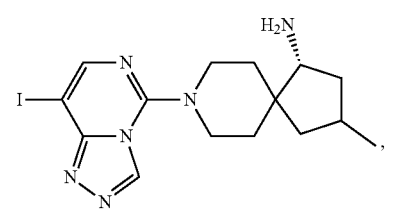

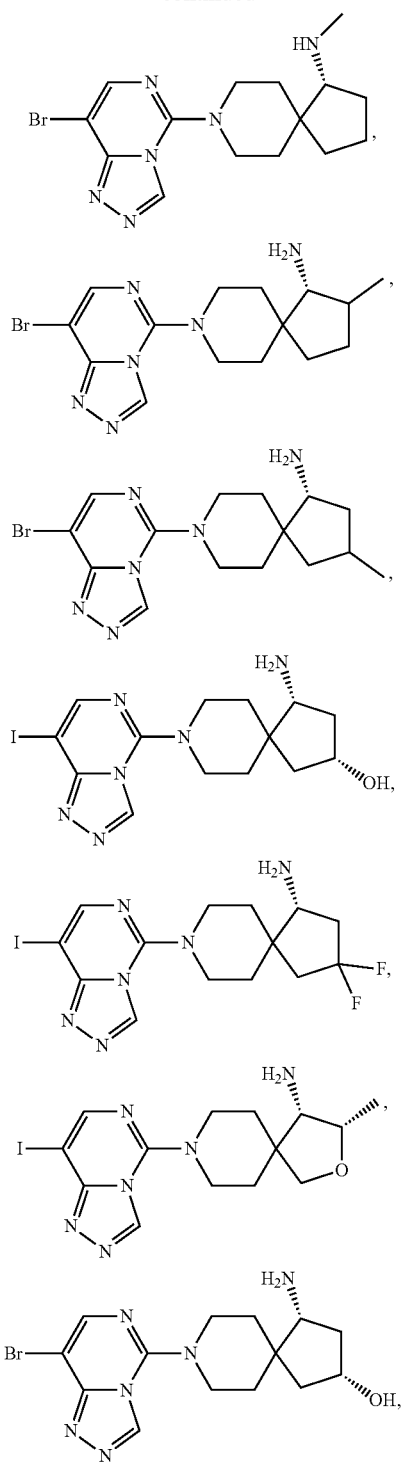
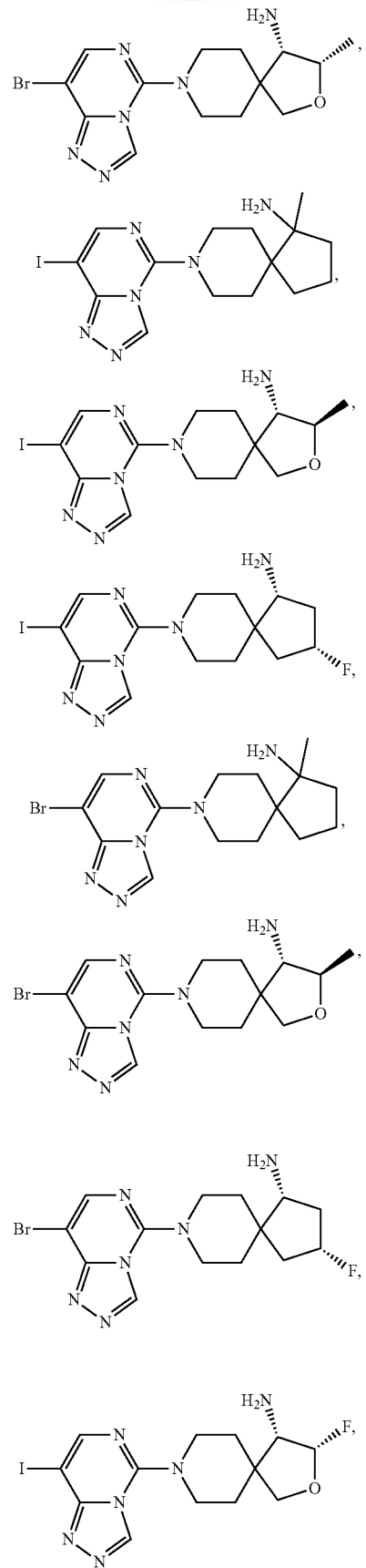

-continued

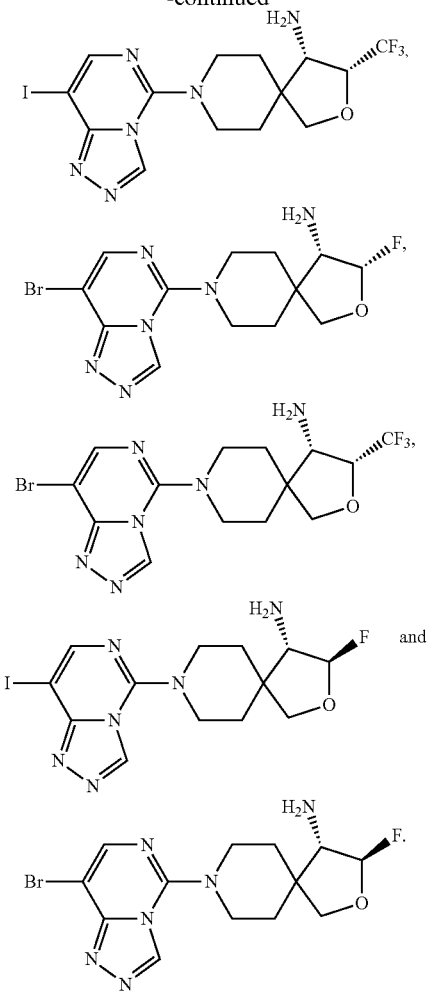

The present disclosure also provides a preparation method of a compound represented by formula A, which comprises a step of:

conducting a substitution reaction of a halogenated intermediate E with an intermediate amine C under basic condition to obtain the compound A, and the reaction equation is as shown below:

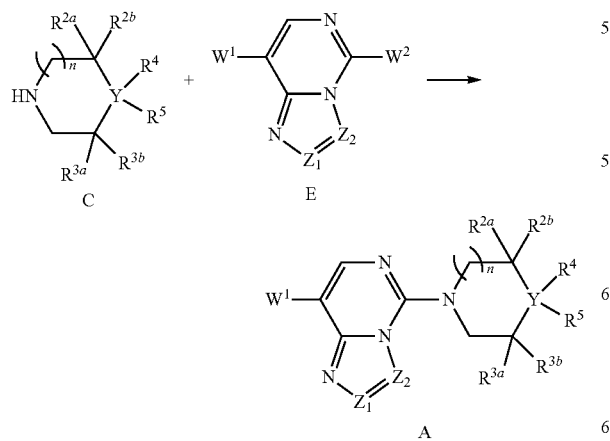

wherein, $W^1$ is halogen, preferably, Br or I; $W^2$ is halogen, preferably, Cl, Br or I; Y, n, $R^{2a}$, $R^{2b}$, $R^{3a}$, $R^{3b}$, $R^4$ and $R^5$ are as defined above.

In a preferable embodiment, the preparation method of compound A-II comprises a step of:

conducting a substitution reaction of a halogenated intermediate E-II with an intermediate amine C under basic condition to obtain the compound A-II, and the reaction equation is as shown below:

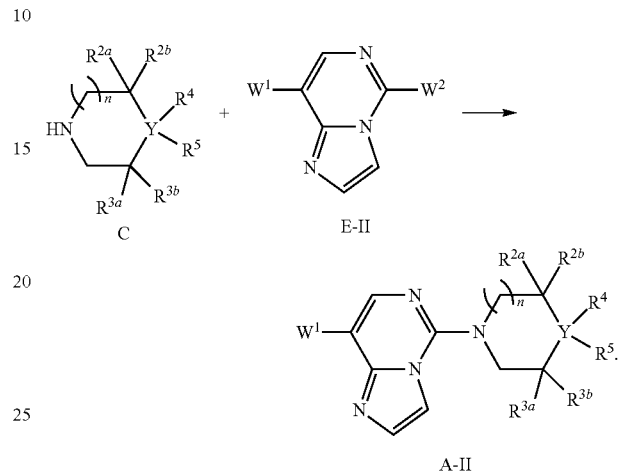

In a preferable embodiment, the preparation method of compound A-III comprises a step of:

conducting a substitution reaction of a halogenated intermediate E-III with an intermediate amine C under basic condition to obtain the compound A-III, and the reaction equation is as shown below:

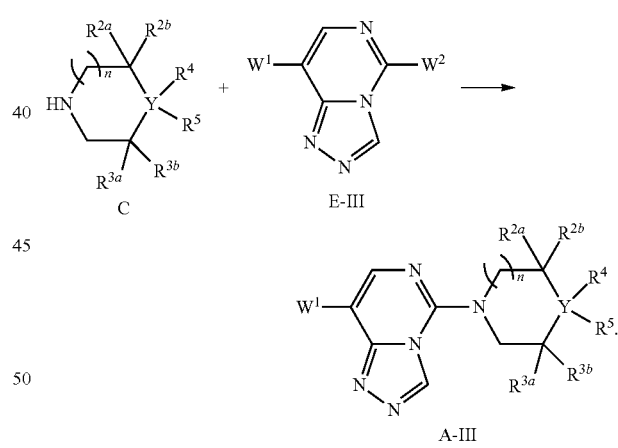

The present disclosure also provides a compound represented by formula C-1,

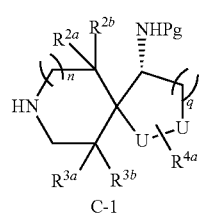

wherein, U is independently C or O; q is 0, 1, or 2; Pg is a protective group selected from Boc, Ac and S(=O)$^t$Bu; n, $R^{2a}$, $R^{2b}$, $R^{3a}$, $R^{3b}$, and $R^{4a}$ are as defined above.
In a preferable embodiment, the compound C-1 is selected from
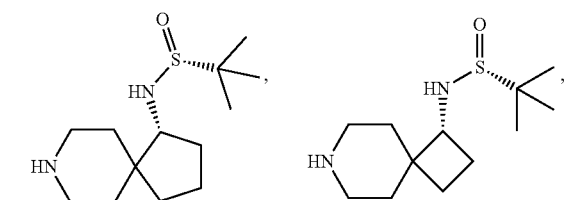
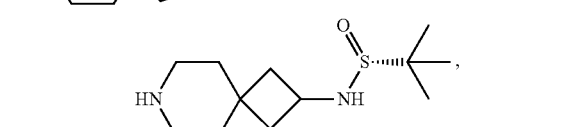
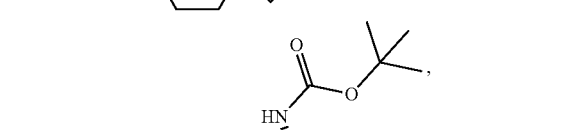
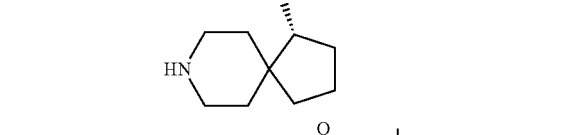
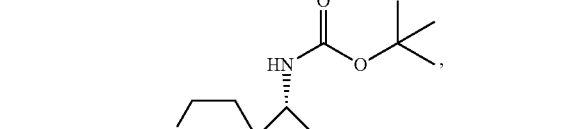
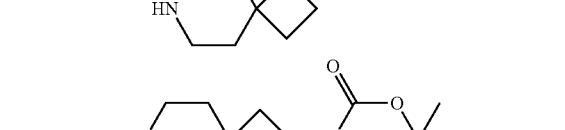
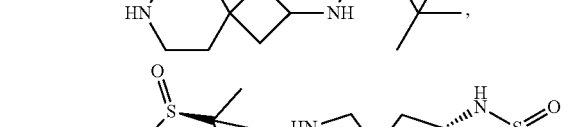
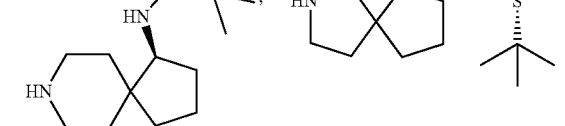
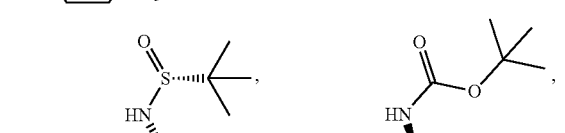
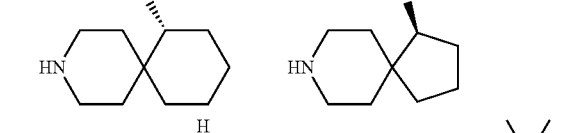
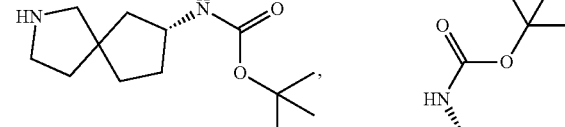
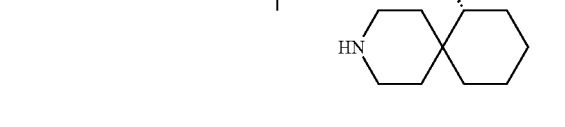
-continued
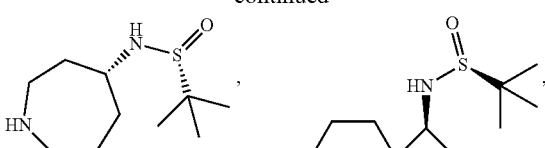
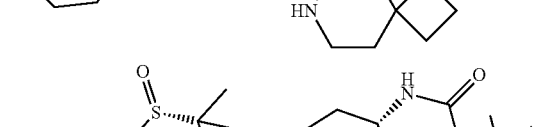
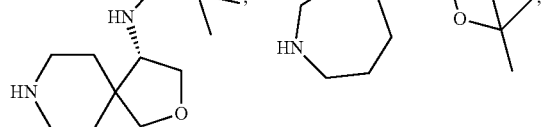
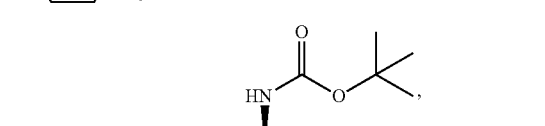
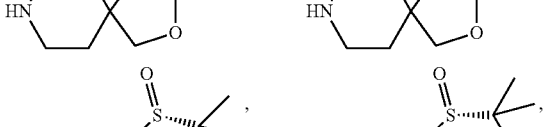
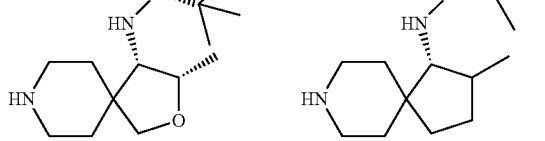
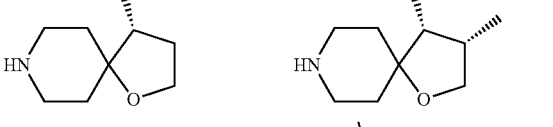
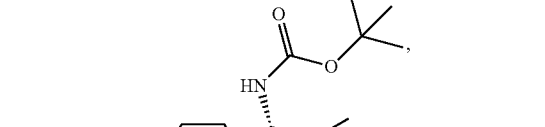
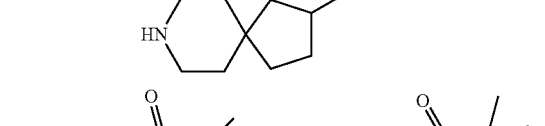
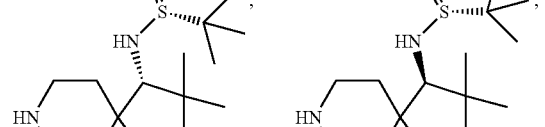

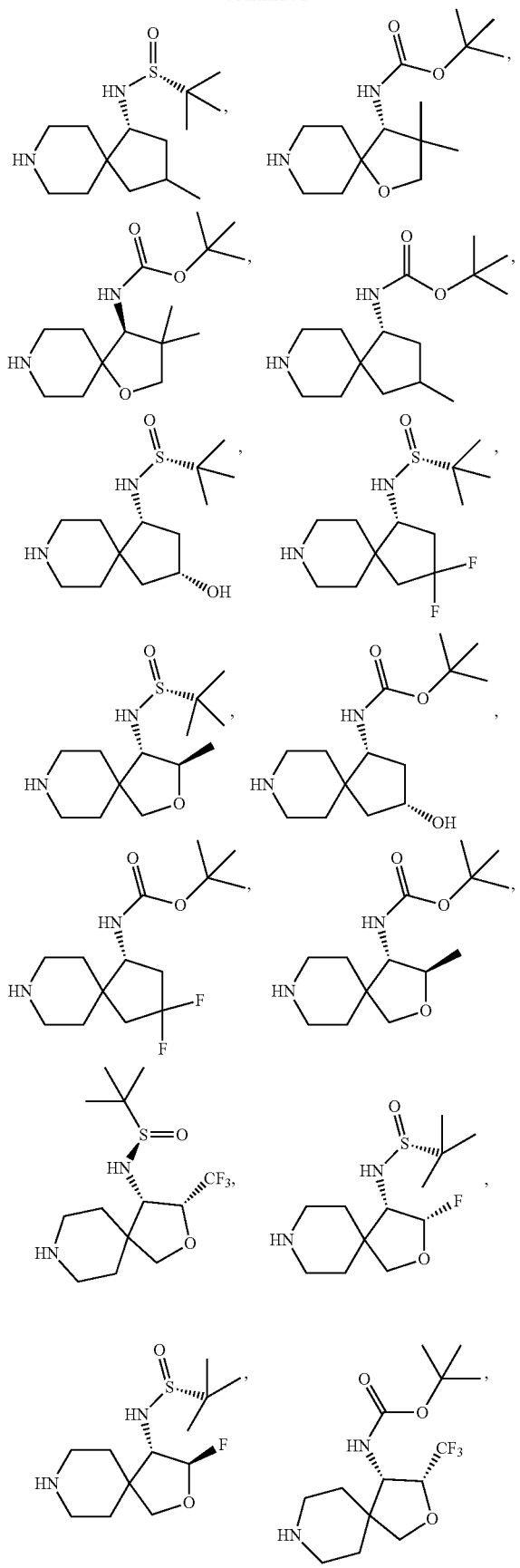

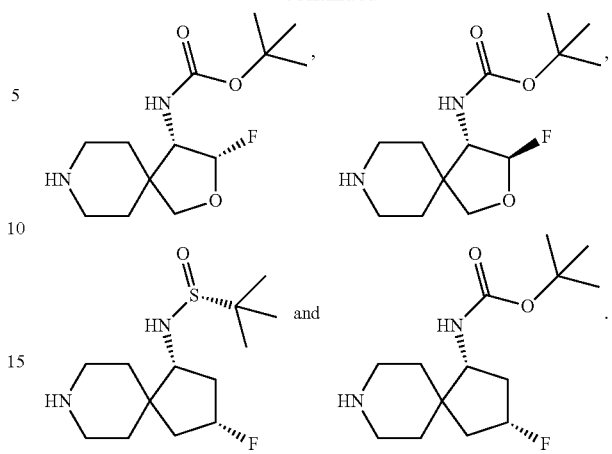

The present disclosure also provides a preparation method of a compound C-1, which comprises the following steps:

conducting a reductive amination reaction of a spirocyclic ketone compound C-1a to obtain an intermediate C-1b, and conducting selective deprotection on C-1b to obtain C-1, and the reaction equation is as shown below:

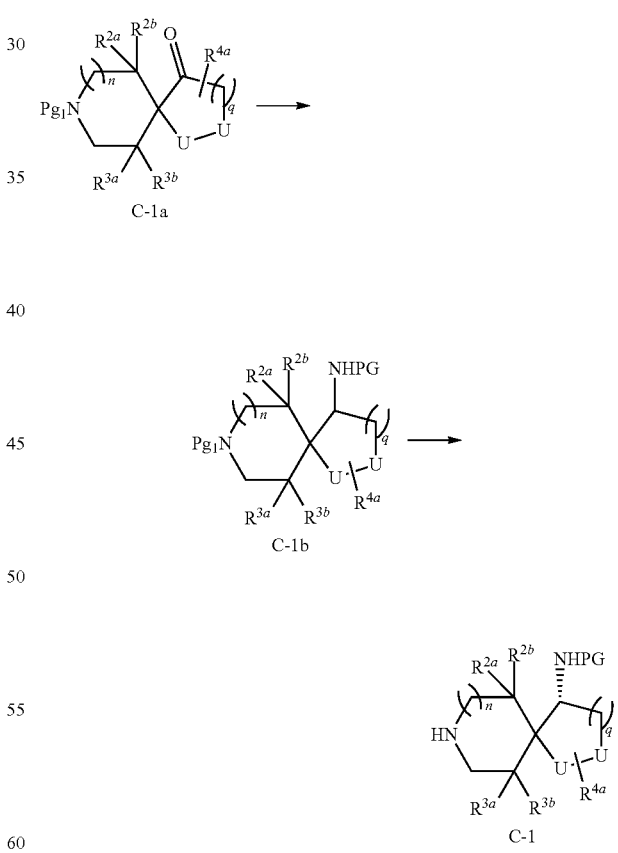

wherein, Pg1 is a protecting group selected from Boc, benzoyl and benzyl; Pg, U, q, n, $R^{2a}$, $R^{2b}$, $R^{3a}$, $R^{3b}$ and $R^{4a}$ are as defined above.

The present disclosure also provides a compound represented by formula C-2,

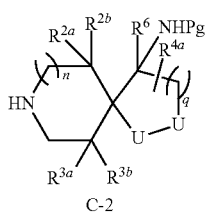

C-2 wherein $R^6$ is independently $C_{1-8}$ alkyl, substituted or unsubstituted aryl, or substituted or unsubstituted alkenyl; U, q, Pg, n, $R^{2a}$, $R^{2b}$, $R^{3a}$, $R^{3b}$ and $R^{4a}$ are as defined above.

In a preferable embodiment, the compound C-2 is selected from

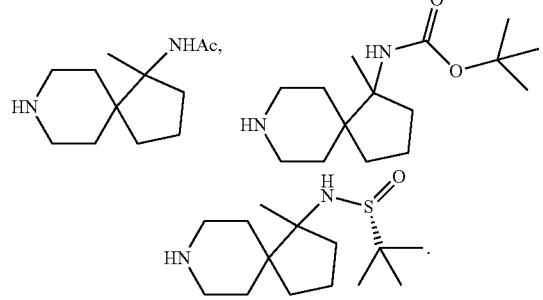

The present disclosure also provides a preparation method of a compound C-2, which comprises the following steps:

conducting an addition reaction of spirocyclic ketone compound C-1a with a nucleophile substituted by $R^6$ to obtain a hydroxy compound C-2a; converting the compound C-2a into an amino compound C-2b via Ritter reaction; and selectively removing the protective group Pg1 to obtain the compound C-2, and the reaction equation is as shown below:

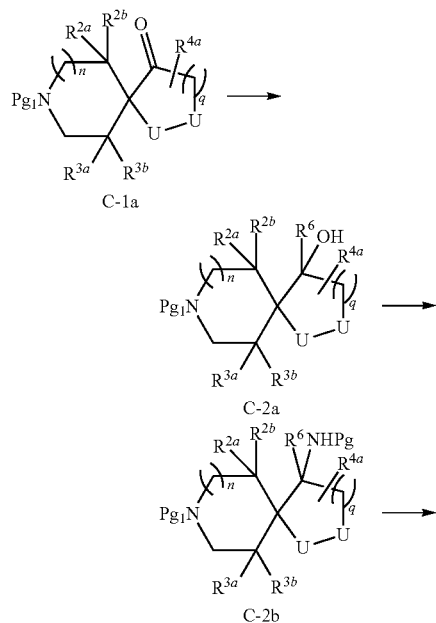

-continued

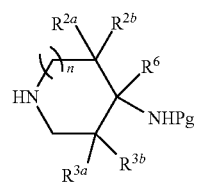

C-2 wherein, $R^6$, U, q, Pg1, Pg, n, $R^{2a}$, $R^{2b}$, $R^{3a}$, $R^{3b}$ and $R^{4a}$ are as defined above.

The present disclosure also provides a compound represented by formula C-3,

C-3

wherein, $R^6$, Pg, n, $R^{2a}$, $R^{2b}$, $R^{3a}$ and $R^{3b}$ are as defined above.

In a preferable embodiment, the compound C-3 is

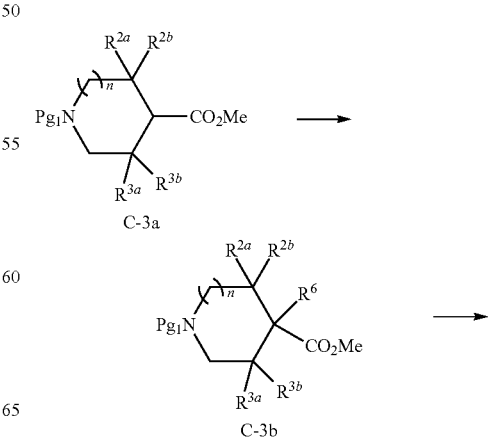

The present disclosure also provides a preparation method of a compound C-3, which comprises the following steps:

substituting the ortho-position of the ester group of compound C-3a with an electrophile substituted by $R^6$ after dehydrogenating the ortho-position of the ester group to obtain a compound C-3b; hydrolyzing the ester group of the compound C-3b to obtain an acid C-3c; subjecting the acid C-3c to molecular rearrangement to obtain an amine C-3d; and then selectively removing the protective group Pg1 to obtain the compound C-3, and the reaction equation is as shown below:

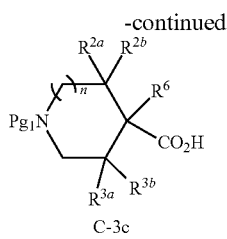

C-3c

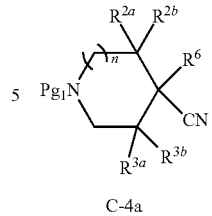

C-4a

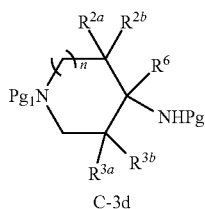

C-3d

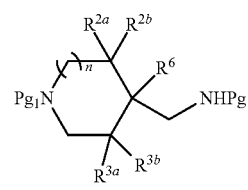

C-4b

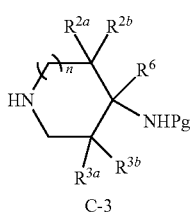

C-3 wherein, $R^6$, Pg1, Pg, n, $R^{2a}$, $R^{2b}$, $R^{3a}$ and $R^{3b}$ are as defined above.

The present disclosure also provides a compound represented by formula C-4,

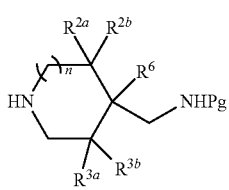

C-4 wherein, $R^6$, Pg, n, $R^{2a}$, $R^{2b}$, $R^{3a}$ and $R^{3b}$ are as defined above.

In a preferable embodiment, the compound C-4 is selected from

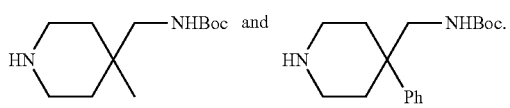 [SMILES: CC1(CNC(=O)OC(C)(C)C)CCNCC1 ; CC(C)(C)OC(=O)NCC1(c2ccccc2)CCNCC1]

The present disclosure also provides a preparation method of a compound C-4, which comprises the following steps:

reducing a cyano compound C-4a and protecting the amino group to obtain an intermediate C-4b; and then selectively removing the protective group Pg1 to obtain the compound C-4, and the reaction equation is as shown below:

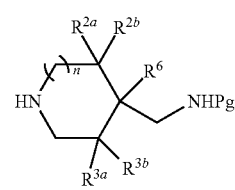

C-4 wherein, Pg1, Pg, $R^6$, n, $R^{2a}$, $R^{2b}$, $R^{3a}$ and $R^{3b}$ are as defined above.

The present disclosure also provides a compound represented by formula E,

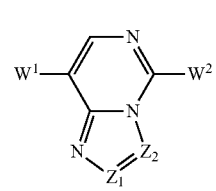

E wherein, $W^1$ is halogen, preferably, Br or I; $W^2$ is halogen, preferably, Cl, Br or I.

In a preferable embodiment, the compound E is represented by formula E-II,

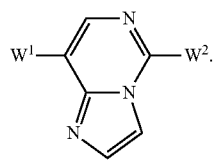

E-II

In a preferable embodiment, the compound E is represented by formula E-III,

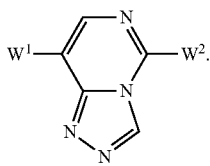
E-III

In a preferable embodiment, the compound E-II is selected from

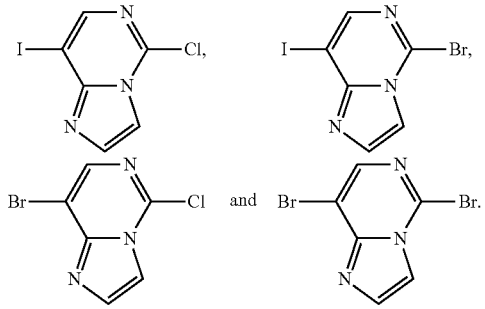

In a preferable embodiment, the compound E-III is selected from

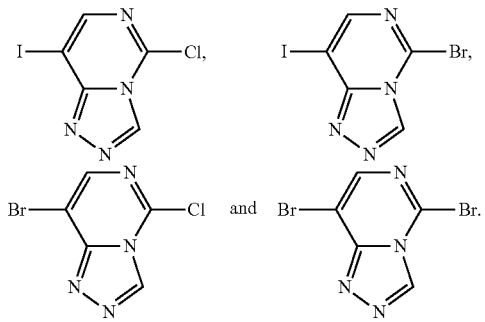

The present disclosure also provides a preparation method of a compound E-II, which comprises a step of halogenating a hydroxy intermediate B-3 to obtain a dihalogenated compound E-II, and the reaction equation is as shown below:

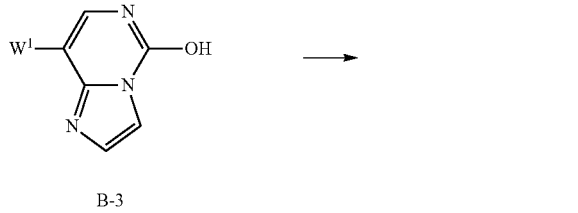

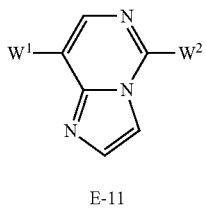
E-II wherein, $W^1$ is halogen, preferably, Br or I; $W^2$ is halogen, preferably, Cl, Br or I.

The present disclosure also provides a preparation method of a compound E-III, which comprises the following steps: conducting a substitution reaction of 4-chloropyrimidine compound E-1-III with hydrazine to obtain an intermediate E-2-III; conducting a condensation cyclization reaction of the intermediate E-2-III to obtain the halogenated intermediate E-III, and the reaction equation is as shown below:

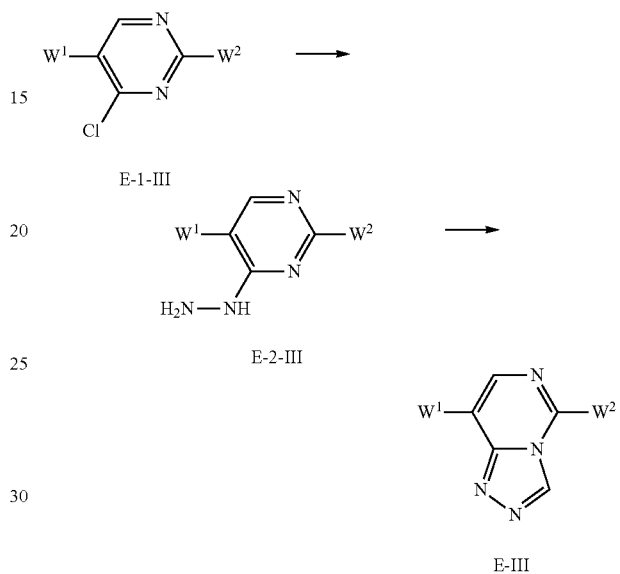

wherein, $W^1$ and $W^2$ are as defined above.

The present disclosure also provides a compound represented by formula F-1, and a compound represented by formula F-1c,

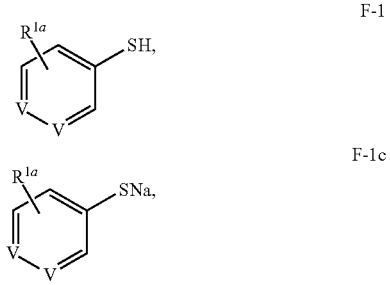

wherein, V is independently C or N; $R^{1a}$ is as defined above.

In a preferable embodiment, the compound F-1 is selected from

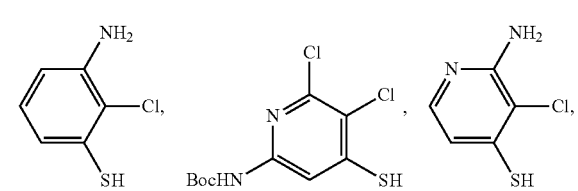

-continued

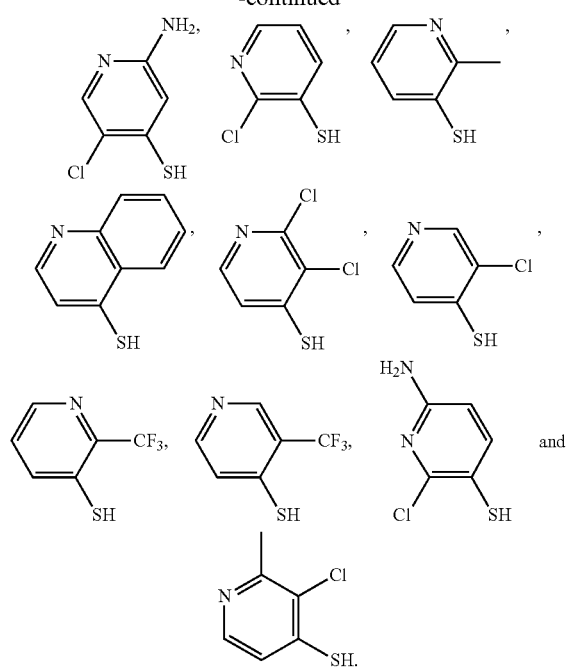

In a preferable embodiment, the compound F-1c is selected from

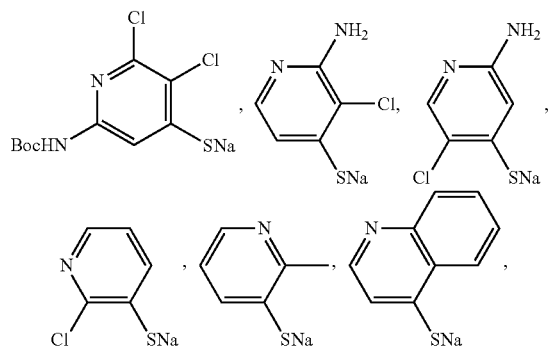

-continued

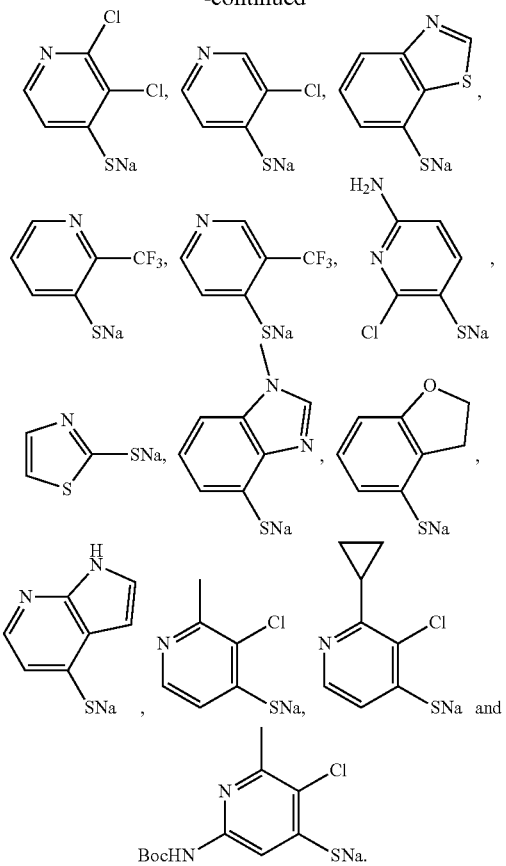

The present disclosure also provides a preparation method of a compound F-1, which comprises the following steps:
coupling a halogenated compound F-1a with methyl mercaptopropionate under catalytic coupling condition to obtain an intermediate F-1b-1, obtaining a corresponding sodium thiolate compound F-1c under basic condition, and then obtaining F-1 under acidic condition; or conducting a substitution reaction of a halogenated compound F-1a with tert-butylthiolate (e.g., sodium tert-butylthiolate) to obtain intermediate F-1b-2, and then obtaining F-1 under acidic condition;

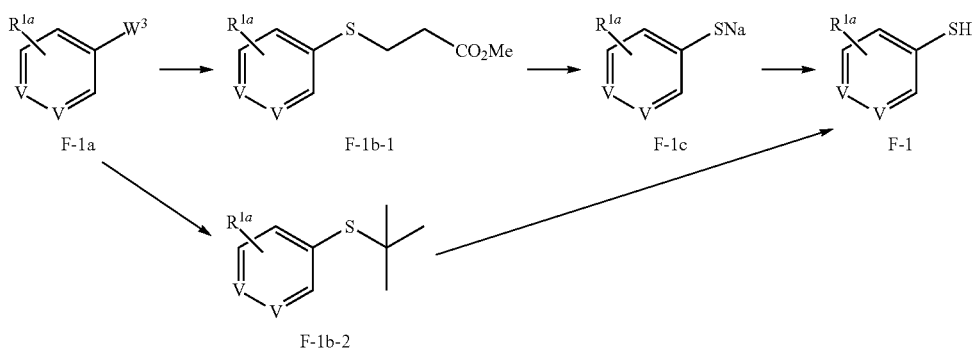

wherein, $W^3$ is halogen, preferably Br or I; V and $R^{1a}$ are as defined above.

The present disclosure also provides a compound represented by formula B,

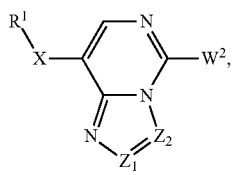

wherein, $W^2$ is halogen, preferably Cl, Br or I; $R^1$ and X are as defined above.

The present disclosure also provides a compound represented by formula B-II,

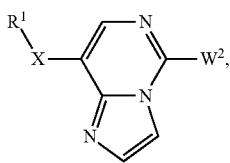

wherein, $W^2$ is halogen, preferably Cl, Br or I; $R^1$ and X are as defined above.

In a preferable embodiment, the compound B-II is selected from

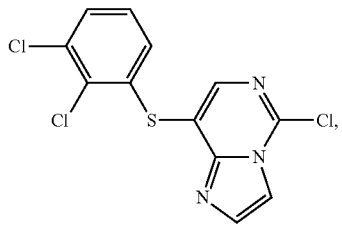

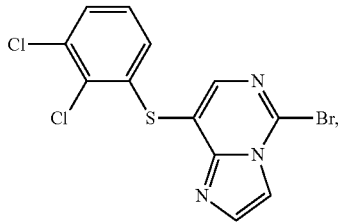

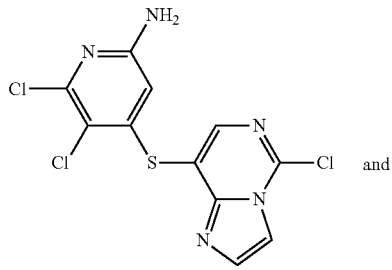
and

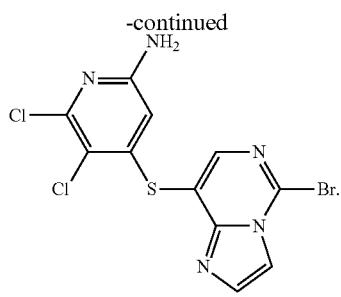

The present disclosure also provides a preparation method of a compound B-II, which comprises the following steps:
conducting a substitution reaction of a dichloropyrimidine compound B-1-II with an amine to obtain an intermediate B-2-II; conducting a condensation cyclization reaction of the intermediate B-2-II under strong acid condition to obtain a halogenated intermediate B-3-II; coupling the halogenated intermediate B-3-II under catalytic coupling condition to obtain an intermediate B-4-II, and then converting the intermediate B-4-II into the intermediate B-II, and the reaction equation is as shown below:

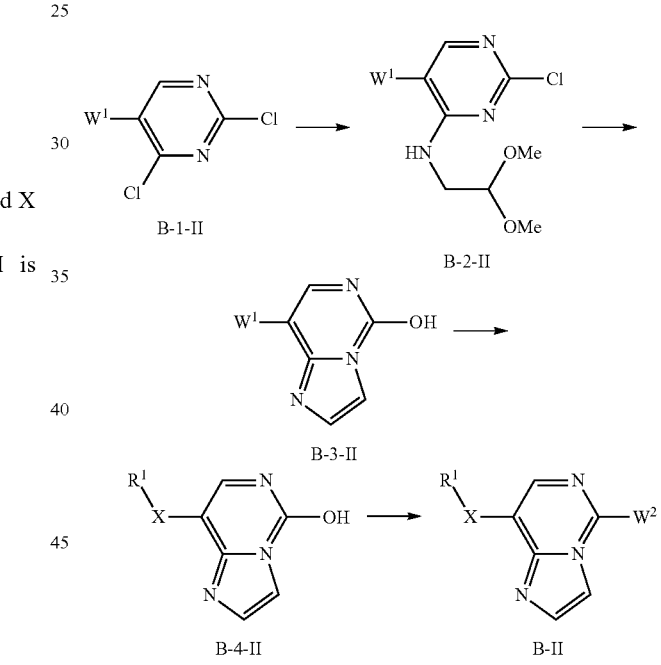

wherein, $W^1$ is halogen, preferably Br or I; $W^2$ is halogen, preferably Cl, Br or I; R and X are as defined above.

The present disclosure also provides a compound represented by formula D,

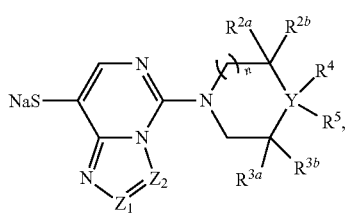

wherein, Y, n, $R^{2a}$, $R^{2b}$, $R^{3a}$, $R^{3b}$, $R^4$ and $R^5$ are as defined above.

The present disclosure also provides a compound represented by formula

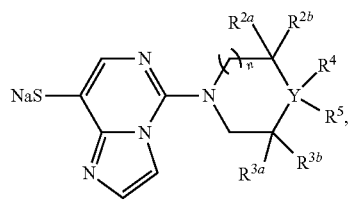

D-II wherein, Y, n, $R^{2a}$, $R^{2b}$, $R^{3a}$, $R^{3b}$, $R^4$ and $R^5$ are as defined above.

In a preferable embodiment, the compound D is

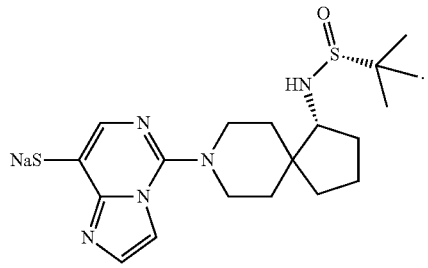

The present disclosure also provides a preparation method of a compound represented by formula D, which comprises the following steps:

coupling an intermediate compound A with methyl mercaptopropionate under catalytic coupling condition to obtain an intermediate D-1, and then obtaining the corresponding sodium thiolate compound D under basic condition, and the reaction equation is as shown below:

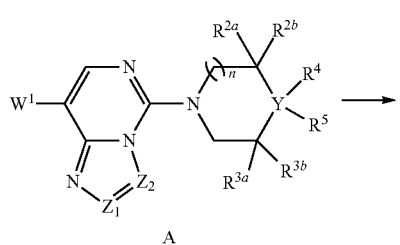

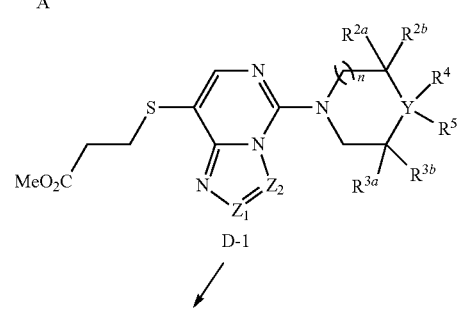

D wherein, $W^1$ is halogen, preferably Br or I; Y, n, $R^{2a}$, $R^{2b}$, $R^{3a}$, $R^{3b}$, $R^4$ and $R^5$ are as defined above.

In a preferable embodiment, the preparation method of the compound represented by formula D-II comprises the following steps:

coupling an intermediate compound A-II with methyl mercaptopropionate under catalytic coupling condition to obtain an intermediate D-1-II, and then obtaining the corresponding sodium thiolate compound D-II under basic condition, and the reaction equation is as shown below:

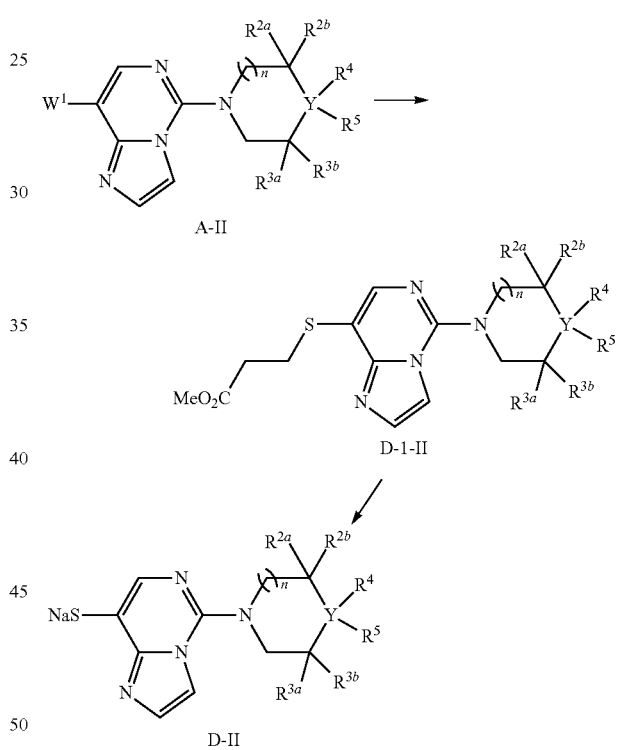

wherein, $W^1$ is halogen, preferably Br or I; Y, n, $R^{2a}$, $R^{2b}$, $R^{3a}$, $R^{3b}$, $R^4$ and $R^5$ are as defined above.

The solvent used in the present disclosure is preferably an inert solvent, e.g., dichloromethane, chloroform, 1,2-dichloroethane, dioxane, DMF, acetonitrile, DMSO, NMP, THF, or a mixture thereof.

The base used in the present disclosure includes organic base and inorganic base.

The organic base used in the present disclosure is preferably TEA, DIPEA or a mixture thereof.

The inorganic base used in the present disclosure is preferably sodium hydride, potassium carbonate, sodium carbonate, cesium carbonate, potassium tert-butoxide, sodium tert-butoxide, LiHMDS, LDA, butyl lithium, or a mixture thereof.

The isotope-labeled compound of the pyrimidine-fused compound represented by formula (I) as defined in the present disclosure can be prepared by a similar synthesis method as that of the unlabeled compound, except that the unlabeled starting materials and/or reagents are replaced by the isotope-labeled starting materials and/or reagents.

The present disclosure also provides a pharmaceutical composition, which comprises the pyrimidine-fused compound represented by formula (I), the pharmaceutically acceptable salt thereof, the hydrate thereof, the prodrug thereof, the stereoisomer thereof or the solvate thereof, or, an isotope-labeled compound of the pyrimidine-fused compound represented by formula (I), the pharmaceutically acceptable salt thereof, the hydrate thereof, the prodrug thereof, the stereoisomer thereof or the solvate thereof, and a pharmaceutically acceptable excipient. The pharmaceutically acceptable excipient is selected from diluent, absorbent, wetting agent, binder, disintegrant and lubricant.

The present disclosure also provides a use of the pyrimidine-fused compound represented by formula (I), the pharmaceutically acceptable salt thereof, the hydrate thereof, the prodrug thereof, the stereoisomer thereof or the solvate thereof, or an isotope-labeled compound of the pyrimidine-fused compound represented by formula (I), the pharmaceutically acceptable salt thereof, the hydrate thereof, the prodrug thereof, the stereoisomer thereof or the solvate thereof in the manufacture of a medicament for the treatment of a disease or condition associated with abnormal activity of SHP2. Preferably, the disease or condition includes, but is not limited to, Noonan syndrome, Leopard syndrome, juvenile myelomonocytic leukemia, neuroblastoma, melanoma, acute myeloid leukemia, breast cancer, esophageal cancer, lung cancer, colon cancer, head cancer, neuroblastoma, head and neck squamous cell carcinoma, gastric cancer, anaplastic large cell lymphoma and glioblastoma.

The present disclosure also provides a pharmaceutical preparation, which comprises the pyrimidine-fused compound represented by formula (I), the pharmaceutically acceptable salt thereof, the hydrate thereof, the prodrug thereof, the stereoisomer thereof or the solvate thereof, or an isotope-labeled compound of the pyrimidine-fused compound represented by formula (I), the pharmaceutically acceptable salt thereof, the hydrate thereof, the prodrug thereof, the stereoisomer thereof or the solvate thereof. It can be administered in a suitable manner, e.g., tablets, capsules (e.g., sustained-release or time-release capsules), pills, powders, granules (e.g., small granules), elixirs, tinctures, suspensions (e.g., nanosuspensions, microsuspensions) and spray-dried dispersions and other forms of suspensions, syrups, emulsions, solutions and other forms, and can be administered via oral administration, sublingual administration, injection including subcutaneous injection, intravenous injection, intramuscular injection, intrasternal injection, infusion and the like, nasal administration (e.g., nasal inhalation), local topical administration (e.g., cream and ointment), rectal administration (e.g., suppositories) and other manners. The compound disclosed in the present disclosure can be administered alone or in combination with an appropriate pharmaceutical carrier.

The present disclosure also provides the pharmaceutical preparation which can be formulated with an appropriate dosage to facilitate the control of the drug dose. The dosage regimen of the compound as defined in the present disclosure differs according to specific factors, e.g., the pharmacodynamics and the administration method, the subjects, and the subjects' sex, age, health status, weight, disease characteristics, other concurrent medication status, administration frequency, liver and kidney function, desired effect and the like. The compound as defined in the present disclosure can be administered in single daily dose or in multiple daily doses (e.g., two to four times per day).

The present disclosure also provides a combination product of the pyrimidine-fused compound represented by formula (I), the pharmaceutically acceptable salt thereof, the hydrate thereof, the prodrug thereof, the stereoisomer thereof or the solvate thereof, or an isotope-labeled compound of the pyrimidine-fused compound represented by formula (I), the pharmaceutically acceptable salt thereof, the hydrate thereof, the prodrug thereof, the stereoisomer thereof or the solvate thereof with another medicament, wherein the another medicament is selected from anticancer medicaments, tumor immune medicaments, antiallergic medicaments, antiemetic medicaments, analgesics, cell protection medicaments and the like, wherein the combination results in better efficacy.

The present disclosure also provides a method of using the pyrimidine-fused compound represented by formula (I), the pharmaceutically acceptable salt thereof, the hydrate thereof, the prodrug thereof, the stereoisomer thereof or the solvate thereof, or an isotope-labeled compound of the pyrimidine-fused compound represented by formula (I), the pharmaceutically acceptable salt thereof, the hydrate thereof, the prodrug thereof, the stereoisomer thereof or the solvate thereof in combination with another medicament, wherein the another medicament is selected from anticancer medicaments, tumor immune medicaments, antiallergic medicaments, antiemetic medicaments, analgesics, cell protection medicaments and the like, wherein the combination results in better efficacy.

It should be understood, within the scope of the present disclosure, the above technical features of the present disclosure and the technical features specifically described in the following (e.g., examples) can be combined with each other, thereby obtaining new or preferred technical solutions. Because of the limitation of length, here is no more tautology.

The present disclosure has the following advantages:

1. The pyrimidine-fused compound disclosed in the present disclosure is a novel type of allosteric inhibitor, which can inhibit the activity of SHP2 by binding to the non-catalytic domain of SHP2 and "locking" the basic state of SHP2 with weak activity. The pyrimidine-fused compound disclosed in the present disclosure overcomes the drawbacks of PTP catalytic domain inhibitors e.g., general poor selectivity and druggability, exhibits good biological activity and druggability, and has good drug development prospects.

2. In the evaluation system of SHP2 enzyme activity inhibition assay, phosphorylated protein kinase (p-ERK) cell assay and MOLM-13 cell proliferation assay under the same conditions, the compound of the present disclosure exhibits superior activity compared with the compound SHP099 (6-(4-amino-4-methylpiperidin-1-yl)-3-(2,3-dichlorophenyl)pyrazine-2-amine) disclosed in WO 2015/107493 A1 and literature (Nature 2016, 535, 148-152).

Terminology

Unless otherwise defined, all technical and scientific terms used herein have the same meaning as commonly understood by those of ordinary skill in the art to which this disclosure pertain. As used herein, when referring to specifically recited values, the term "about" means that the value can vary from the recited value by no more than 1%.

For example, as used herein, the expression "about 100" includes all values between 99 and 101 (e.g., 99.1, 99.2, 99.3, 99.4, etc.).

As used herein, the terms "contain" or "include (comprise)" can be open, semi-closed, and closed. In other words, the term also includes "essentially consist of" or "consist of".

Definitions of Groups

Definitions of standard chemical terms can be found in references (including Carey and Sundberg "ADVANCED ORGANIC CHEMISTRY 4TH ED." Vols. A (2000) and B (2001), Plenum Press, New York). Unless otherwise specified, conventional methods within the technical scope of the art, e.g., mass spectrometry, NMR, IR, and UV/VIS spectroscopy, and pharmacological methods are used. Unless specific definitions are provided, the terms used in the description of analytical chemistry, organic synthetic chemistry, and drugs and medicinal chemistry are known in the art. Standard techniques can be used in chemical synthesis, chemical analysis, drug preparation, formulation and delivery, and treatment of patients. For example, the reaction and purification can be carried out according to the manufacturer's instructions for the kit, or in a manner known in the art or according to the present disclosure. In general, the above-mentioned techniques and methods can be implemented according to conventional methods well known in the art according to the descriptions in a number of summary and more specific documents cited and discussed in this specification. In this specification, groups and their substituents can be selected by those skilled in the art to provide stable moieties and compounds. When a substituent is described by a general chemical formula written from left to right, this substituent also includes chemically equivalent substituents obtained when the structural formula is written from right to left. For example, —CH$_2$O— is equivalent to OCH$_2$—.

The section headings used herein are for the purpose of organizing the article and should not be interpreted as a limitation on the subject. All documents or document parts cited in this application, including but not limited to patents, patent applications, articles, books, operation manuals and papers, are incorporated herein by reference in their entireties.

Some chemical groups defined herein are preceded by simplified symbols to indicate the total number of carbon atoms present in the group. For example, C$_{1-6}$ alkyl refers to an alkyl group having a total of 1, 2, 3, 4, 5 or 6 carbon atoms as defined below. The total number of carbon atoms in the simplified symbol does not include carbons that may be present in the substituents of the group.

As used herein, the numerical ranges as defined in the substituents, e.g., 0-4, 1-4, 1-3, 1-6 and the like, indicate integers within the range, e.g., 0, 1, 2, 3, 4, 5, 6.

In addition to the foregoing, when used in the specification and claims of this application, unless otherwise specified, the following terms have the meanings below.

Those skilled in the art can understand that, according to the conventions used in the art, the "-$\frac{1}{2}$-" used in the structural formula of the group described in this application means that the corresponding group is connected to other fragments and groups in the compound through this site.

In this application, the term "halogen" refers to fluorine, chlorine, bromine or iodine.

"Hydroxy" refers to the —OH group. "Alkoxy" refers to an alkyl group as defined below substituted by hydroxyl (—OH).

"Carbonyl" refers to the —C(=O)— group. "Cyano" refers to —CN.

"Amino" refers to —NH$_2$.

"Substituted amino" refers to an amino group substituted by one or two groups selected from alkyl, alkylcarbonyl, arylalkyl, heteroarylalkyl groups as defined below, e.g., monoalkylamino, dialkylamino, alkylacylamino, arylalkylamino, heteroarylalkylamino.

"Carboxyl" refers to —COOH.

"Amide" refers to —C(=O)NH$_2$ or —NHC(=O)H.

In this application, as a group or a part of other groups (e.g., used in an alkyl substituted by halogen and the like), the term "alkyl" refers to a fully saturated linear or branched chain hydrocarbon group consisting of only carbon atoms and hydrogen atoms, has for example 1-12 (preferably 1-8, more preferably 1-6) carbon atoms, and is connected to the rest of the molecule by a single bond, including but not limited to methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl, octyl, nonyl and decyl and the like. For the purposes of the present disclosure, the term "alkyl" refers to an alkyl containing 1 to 6 carbon atoms.

In this application, as a group or part of other groups, the term "alkenyl" refers to a linear or branched chain hydrocarbon group consisting of only carbon atoms and hydrogen atoms, contains at least one double bond, has for example 2-14 (preferably 2-10, more preferably 2-6) carbon atoms, and is connected to the rest of the molecule by a single bond, e.g., including but not limited to vinyl, propenyl, allyl, but-1-enyl, but-2-enyl, pent-1-enyl, pent-1,4-dienyl and the like.

In the present application, as a group or part of other groups, the term "cyclic hydrocarbon group" means a stable non-aromatic monocyclic or polycyclic hydrocarbon group consisting of only carbon atoms and hydrogen atoms, and can include fused ring system, bridged ring system or spiro ring system, has 3-15 carbon atoms, preferably 3-10 carbon atoms, more preferably 3-8 carbon atoms, and it is saturated or unsaturated and can be connected to the rest of the molecule by a single bond through any suitable carbon atom. Unless otherwise specified in the specification, the carbon atom in the cyclic hydrocarbon group can be optionally oxidized. Examples of the cyclic hydrocarbon group include, but are not limited to, cyclopropyl, cyclobutyl, cyclopentyl, cyclopentenyl, cyclohexyl, cyclohexenyl, cyclohexadienyl, cycloheptyl, cyclooctyl, 1H-indenyl, 2,3-dihydroindenyl, 1,2,3,4-tetrahydro-naphthyl, 5,6,7,8-tetrahydro-naphthyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, 7,7-dimethyl-bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantyl, octahydro-4,7-methylene-1H-indenyl, octahydro-2,5-methylene-pentalenyl and the like.

In this application, as a group or part of other groups, the term "cycloalkyl" refers to a saturated monocyclic or polycyclic hydrocarbon group consisting of only carbon atoms and hydrogen atoms, and it can include bridged ring system or spiro ring system, and has 3-15 carbon atoms, preferably 3-10 carbon atoms, more preferably 3-7 carbon atoms. It can be connected to the rest of the molecule by a single bond through any suitable carbon atom, which can include connection to form a fused ring or a spiro ring. Examples of cycloalkyl include, but are not limited to, cyclopropyl, cyclobutyl, cyclopentyl, cyclohexyl, cycloheptyl, cyclooctyl, adamantyl, and the like.

In the present application, as a group or part of other groups, the term "heterocyclyl" refers to a stable 3- to 20-membered non-aromatic cyclic group consisting of 2-14 carbon atoms and 1-6 heteroatoms selected from nitrogen, phosphorus, oxygen and sulfur. Unless otherwise specified in the specification, the heterocyclyl can be a monocyclic, bicyclic, tricyclic or above-tricyclic system, which can include a fused ring system, a bridged ring system or a spiro ring system. The nitrogen, carbon or sulfur atom in the heterocyclyl can be optionally oxidized, and the nitrogen atom can be optionally quaternized. The heterocyclyl can be partially or fully saturated. The heterocyclyl can be connected to the rest of the molecule by a single bond through a carbon atom or a heteroatom. In a heterocyclyl containing a fused ring, one or more rings can be an aryl group or a heteroaryl group as defined below, provided that the site connected to the rest of the molecule is a non-aromatic ring atom. For the purposes of the present disclosure, the heterocyclyl is preferably a stable 4- to 11-membered non-aromatic monocyclic, bicyclic, bridged cyclic or spiro cyclic group containing 1-3 heteroatoms selected from nitrogen, oxygen and sulfur, more preferably a stable 4- to 8-membered non-aromatic monocyclic, bicyclic, bridged cyclic or spiro cyclic group containing 1-3 heteroatoms selected from nitrogen, oxygen and sulfur. Examples of heterocyclyl groups include, but are not limited to: pyrrolidinyl, morpholinyl, piperazinyl, homopiperazinyl, piperidinyl, thiomorpholinyl, 2,7-diazaspiro[3.5]nonan-7-yl, 2-oxa-6-azaspiro[3.3]heptane-6-yl, 2,5-diaza-bicyclo[2.2.1]heptane-2-yl, azetidinyl, pyranyl, tetrahydropyranyl, thiopyranyl, tetrahydrofuranyl, oxazinyl, dioxolanyl, tetrahydroisoquinolinyl, decahydroisoquinolinyl, imidazolinyl, imidazolidinyl, quinolizinyl, thiazolidinyl, isothiazolidinyl, isoxazolidinyl, indolinyl, octahydroindolyl, octahydroisoindolyl, pyrrolidinyl, pyrazolidinyl, phthalimido and the like.

In this application, as a group or part of other groups, the term "heterocycloalkyl" refers to a stable 3- to 20-membered saturated cyclic group consisting of 2-14 carbon atoms and 1-6 heteroatoms selected from nitrogen, phosphorus, oxygen and sulfur. Unless otherwise specified in this specification, heterocycloalkyl can be a monocyclic, bicyclic, tricyclic or above-tricyclic system, which can include a bridged ring system or a spiro ring system. The nitrogen, carbon or sulfur atom in the heterocycloalkyl can be optionally oxidized, and the nitrogen atoms can be optionally quaternized. The heterocycloalkyl can be connected to the rest of the molecule by a single bond through a carbon atom or a heteroatom, which can include connection to form a fused ring or a spiro ring. For the purposes of the present disclosure, the heterocycloalkyl is preferably a stable 4- to 11-membered saturated monocyclic, bicyclic, bridged cyclic or spiro cyclic group containing 1-3 heteroatoms selected from nitrogen, oxygen and sulfur, more preferably a stable 4- to 7-membered saturated monocyclic, bicyclic, bridged cyclic or spiro cyclic group containing 1-3 heteroatoms selected from nitrogen, oxygen and sulfur. Examples of heterocycloalkyl include, but are not limited to, pyrrolidinyl, morpholinyl, piperazinyl, piperidinyl, thiomorpholinyl, 2,7-diazaspiro[3.5]nonan-7-yl, 2-oxa-6-azaspiro[3.3]heptane-6-yl, 2,5-diaza-bicyclo[2.2.1]heptane-2-yl, azetidinyl, tetrahydropyranyl, tetrahydrofuranyl, dioxolanyl, decahydroisoquinolinyl, imidazolidinyl, thiazolidinyl, isothiazolidinyl, isoxazolidinyl, octahydroindolyl, octahydroisoindolyl, pyrazolidinyl and the like.

In the present application, as a group or part of other groups, the term "aryl" refers to a conjugated cyclic hydrocarbon group having 6 to 18 carbon atoms (preferably having 6 to 10 carbon atoms). For the purposes of the present disclosure, the aryl group can be a monocyclic, bicyclic, tricyclic or above-tricyclic system, or can be fused to a cycloalkyl or heterocyclyl group as defined above, provided that the aryl is connected to the rest of the molecule by a single bond through the atom on the aromatic ring. Examples of aryl include, but are not limited to, phenyl, naphthyl, anthracenyl, phenanthrenyl, fluorenyl, 2,3-dihydro-1H-isoindolyl, 2-benzoxazolinone, 2H-1,4-benzoxazine-3(4H)-one-7-yl and the like.

In the present application, the term "arylalkyl" refers to an alkyl group as defined above substituted by an aryl as defined above.

In this application, as a group or part of other groups, the term "heteroaryl" refers to a 5- to 16-membered conjugated cyclic group having 1-15 carbon atoms (preferably having 1-10 carbon atoms) and 1-6 heteroatoms selected from nitrogen, oxygen and sulfur arranged on the ring. Unless otherwise specified in this specification, the heteroaryl can be a monocyclic, bicyclic, tricyclic or above-tricyclic ring system, and can also be fused to a cycloalkyl or heterocyclyl as defined above, provided that the heteroaryl is connected to the rest of the molecule by a single bond through the atom on the aromatic ring. The nitrogen, carbon or sulfur atom of the heteroaryl can be optionally oxidized, and the nitrogen atom can be optionally quaternized. For the purposes of the present disclosure, the heteroaryl is preferably a stable 5- to 12-membered aromatic group containing 1-5 heteroatoms selected from nitrogen, oxygen, and sulfur, and more preferably a stable 5- to 10-membered aromatic group containing 1-4 heteroatoms from nitrogen, oxygen and sulfur or 5- to 6-membered aromatic group containing 1-3 heteroatoms selected from nitrogen, oxygen and sulfur. Examples of heteroaryl groups include, but are not limited to, thienyl, imidazolyl, pyrazolyl, thiazolyl, oxazolyl, oxadiazolyl, isoxazolyl, pyridinyl, pyrimidinyl, pyrazinyl, pyridazinyl, benzimidazolyl, benzpyrazolyl, indolyl, furyl, pyrrolyl, triazolyl, tetrazolyl, triazinyl, indolizinyl, isoindolyl, indazolyl, isoindazolyl, purinyl, quinolinyl, isoquinolinyl, diazanaphthyl, naphthyridinyl, quinoxalinyl, pteridinyl, carbazolyl, carbolinyl, phenanthridinyl, phenanthrolinyl, acridinyl, phenazinyl, isothiazolyl, benzothiazolyl, benzothienyl, oxtriazolyl, cinnolinyl, quinazolinyl, phenylthio, indolizinyl, o-phenanthrolinyl, isoxazolyl, phenoxazinyl, phenothiazinyl, 4,5,6,7-tetrahydrobenzo[b]thienyl, naphthopyridyl, triazolo[4,3-b]pyridazine, [1,2,4]triazolo[4,3-a]pyrazine, triazolo[4,3-c]pyrimidine, [1,2,4]triazolo[4,3-a]pyridine, imidazo[1,2-a]pyridine, imidazo[1,2-b]pyridazine, imidazo[1,2-a]pyrazine and the like.

In the present application, the term "heteroarylalkyl" refers to an alkyl as defined above substituted by a heteroaryl as defined above. In this application, "optionally" or "optionally" means that the subsequently described event or condition can or cannot occur, and the description includes both the occurrence and non-occurrence of the event or condition. For example, "optionally substituted aryl" means that the aryl is substituted or unsubstituted, and the description includes both substituted aryl and unsubstituted aryl.

As used herein, the terms "moiety", "structural moiety", "chemical moiety", "group", "chemical group" refer to a specific segment or functional group in a molecule. The chemical moiety is usually considered to be a chemical entity embedded or attached to the molecule.

When the compound of the present disclosure contains an olefinic double bond, unless otherwise specified, the compound of the present disclosure is intended to include E- and Z-geometric isomers.

"Tautomer" refers to an isomer formed by the transfer of proton from one atom of a molecule to another atom of the same molecule.

All tautomeric forms of the compounds of the disclosure will also be included within the scope of the disclosure. The compounds of the present disclosure or the pharmaceutically acceptable salts thereof can contain one or more chiral carbon atoms, and thus can produce enantiomers, diastereomers and other stereoisomeric forms. Each chiral carbon atom can be defined as (R)- or (S)-based on stereochemistry. The present disclosure is intended to include all the potential isomers, as well as their racemates and optically pure forms. For the preparation of the compounds of the present disclosure, racemates, diastereomers or enantiomers can be selected as starting materials or intermediates. Optically active isomers can be prepared using chiral synthons or chiral reagents, or resolved using conventional techniques, e.g., crystallization and chiral chromatography.

Conventional techniques for preparing/resolving some isomers include chiral synthesis from suitable optically pure precursors, or resolution of racemates (or salts or derivative racemates) using, e.g., chiral high performance liquid chromatography), e.g., referring to Gerald Gubitz and Martin G. Schmid (Eds.), Chiral Separations, Methods and Protocols, *Methods in Molecular Biology*, Vol. 243, 2004; A. M. Stalcup, Chiral Separations, *Annu. Rev. Anal. Chem.* 3:341-63, 2010; Furniss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; Heller, Acc. Chem. Res. 1990, 23, 128.

In this application, the term "pharmaceutically acceptable salt" includes pharmaceutically acceptable acid addition salts and pharmaceutically acceptable base addition salts.

"Pharmaceutically acceptable acid addition salt" refers to a salt formed with an inorganic acid or an organic acid that can retain the biological activity of the free base without other side effects. Inorganic acid salts include, but are not limited to hydrochloride, hydrobromide, sulfate, nitrate, phosphate, and the like; organic acid salts include, but are not limited to formate, acetate, 2,2-dichloroacetate, trifluoroacetate, propionate, caproate, caprylate, caprate, undecylenate, glycolate, gluconate, lactate, sebacate, adipate, glutarate, malonate, oxalate, maleate, succinate, fumarate, tartrate, citrate, palmitate, stearate, oleate, cinnamate, laurate, malate, glutamate, pyroglutamate, aspartate, benzoate, methanesulfonate, benzenesulfonate, p-toluenesulfonate, alginate, ascorbate, salicylate, 4-aminosalicylate, naphthalene disulfonate and the like. These salts can be prepared by methods known in the art.

"Pharmaceutically acceptable base addition salt" refers to a salt formed with an inorganic base or an organic base that can retain the biological activity of the free acid without other side effects. Salts derived from inorganic bases include, but are not limited to, sodium salts, potassium salts, lithium salts, ammonium salts, calcium salts, magnesium salts, iron salts, zinc salts, copper salts, manganese salts, aluminum salts, and the like. Preferred inorganic salts are ammonium salts, sodium salts, potassium salts, calcium salts and magnesium salt. Salts derived from organic bases include but are not limited to primary amines, secondary amines and tertiary amines, substituted amines, including natural substituted amines, cyclic amines and basic ion exchange resins, e.g., ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, dicyclohexylamine, lysine, arginine, histidine, caffeine, procaine, choline, betaine, ethylenediamine, glucosamine, methylglucosamine, theobromine, purine, piperazine, piperidine, N-ethylpiperidine, polyamine resin and the like. Preferred organic bases include isopropylamine, diethylamine, ethanolamine, trimethylamine, dicyclohexylamine, choline, and caffeine. These salts can be prepared by methods known in the art.

In the present application, "pharmaceutical composition" refers to a preparation of a compound of the present disclosure and a medium generally accepted in the art for delivering a biologically active compound to a mammal (e.g., a human). The medium includes a pharmaceutically acceptable carrier. The purpose of the pharmaceutical composition is to promote the administration to organisms, which facilitates the absorption of active ingredients to exert biological activity.

The term "pharmaceutically acceptable" as used herein refers to a substance (e.g., a carrier or diluent) that does not affect the biological activity or properties of the compound of the present disclosure, and is relatively non-toxic, that is, the substance can be administered to an individual without causing harmful biological reactions or interacting with any components contained in the composition in an undesirable manner. In this application, "pharmaceutically acceptable excipients" include, but are not limited to, any of adjuvants, carriers, excipients, glidants, sweeteners, diluents, preservatives, dyes/colorants, flavoring agents, surfactants, wetting agents, dispersants, suspending agents, stabilizers, isotonic agents, solvents or emulsifiers, which are approved by the relevant government regulatory agency as acceptable for human or domestic animal use.

The "tumor" in the present disclosure includes but is not limited to brain tumors including neuroblastoma, glioma, glioblastoma and astrocytoma, sarcoma, melanoma, articular chondroma, cholangiocarcinoma, leukemia, gastrointestinal stromal tumor, diffuse large B-cell lymphoma, follicular lymphoma, histiocytic lymphoma, non-small cell lung cancer, small cell lung cancer, pancreatic cancer, lung squamous cell carcinoma, lung adenocarcinoma, breast cancer, prostate cancer, liver cancer, skin cancer, epithelial cell carcinoma, cervical cancer, ovarian cancer, intestinal cancer, nasopharyngeal cancer, brain cancer, bone cancer, esophageal cancer, melanoma, kidney cancer, oral cancer, multiple myeloma, mesothelioma, malignant rhabdoid tumor, endometrial cancer, head and neck cancer, thyroid cancer, parathyroid tumor, uterine tumor and soft tissue sarcoma and other diseases.

As used herein, the terms "preventive", "prevention" and "preventing" include reducing the likelihood of the occurrence or worsening of a disease or condition in a patient.

As used herein, the term "treatment" and other similar synonyms include the following meanings:

preventing the occurrence of the disease or condition in mammals, especially when such mammals are susceptible to the disease or condition but have not been diagnosed with the disease or condition;

inhibiting the disease or condition, that is, curbing its development;

alleviating the disease or condition, that is, causing the state of the disease or condition to subside; or relieving the symptoms caused by the disease or condition.

As used herein, the term "effective amount", "therapeutically effective amount" or "pharmaceutically effective amount" refers to the amount of at least one medicament or compound that is sufficient to alleviate one or more symptoms of the disease or condition being treated to some extent after administration. The result can be the reduction and/or remission of signs, symptoms or causes, or any other desired change in the biological system. For example, an "effective amount" for treatment is the amount of a composition containing a compound disclosed herein required to provide a clinically significant disease relief effect. Techniques e.g., dose escalation tests can be used to determine the effective amount suitable for any individual case. As used herein, the terms "administer", "administration" and the like refer to a method capable of delivering a compound or composition to a desired site for biological action. These methods include, but are not limited to, oral administration, transduodenal administration, parenteral injection (including intravenous, subcutaneous, intraperitoneal, intramuscular, intraarterial injection or infusion), topical administration, and transrectal administration. Those skilled in the art are familiar with the application techniques that can be used for the compounds and methods described herein, e.g., those discussed in Goodman and Gilman, The Pharmacological Basis of Therapeutics, current ed.; Pergamon; and Remington's, Pharmaceutical Sciences (current edition), Mack Publishing Co., Easton, Pa. In a preferred embodiment, the compounds and compositions discussed herein are administered orally.

As used herein, the terms "pharmaceutical combination", "drug combination", "combination drug", "administration of other treatments", "administration of other therapeutic agents" and the like refer to medical treatments obtained by mixing or combining more than one active ingredient, which includes fixed and unfixed combinations of active ingredients. The term "fixed combination" refers to the simultaneous administration of at least one compound described herein and at least one synergistic agent to a patient in the form of a single entity or a single dosage. The term "unfixed combination" refers to simultaneous administration, co-administration, or sequential administration of at least one compound described herein and at least one synergistic preparation to a patient in the form of separate entities. These also apply to cocktail therapy, for example the administration of three or more active ingredients. Those skilled in the art should also understand that in the method described below, the functional group of the intermediate compound may need to be protected by an appropriate protecting group. Such functional groups include hydroxyl, amino, mercapto and carboxyl. Suitable hydroxyl protecting groups include trialkylsilyl or diarylalkylsilyl (e.g., tert-butyldimethylsilyl, tert-butyldiphenylsilyl or trimethylsilyl), tetrahydropyranyl, benzyl and the like. Suitable amino, amidino and guanidino protecting groups include tert-butoxycarbonyl, benzyloxycarbonyl and the like. Suitable thiol protecting groups include —C(O)—R" (where R" is alkyl, aryl or arylalkyl), p-methoxybenzyl, trityl and the like. Suitable carboxyl protecting groups include alkyl, aryl or arylalkyl esters. Protecting groups can be introduced and removed according to standard techniques known to those skilled in the art and as described herein. The use of protecting groups is detailed in Greene, TW and PG Wuts, Protective Groups in Organic Synthesis, (1999), 4th Ed., Wiley. The protective group can also be a polymer resin.

DETAILED DESCRIPTION OF THE EMBODIMENT

The present disclosure is further described by way of examples below, but the present disclosure is not limited to the scope of the described examples. The experimental methods without specific conditions in the following examples are selected according to the conventional methods and conditions or according to the product instruction.

The starting materials used in the following examples can be purchased from chemical vendors e.g., Aldrich, TCI, Alfa Aesar, Bide, and Energy Chemical, or can be synthesized by known methods.

In the following examples, the ice bath refers to −5° C. to 0° C., the room temperature refers to 10° C. to 30° C., and the reflux temperature generally refers to the solvent reflux temperature under normal pressure. Overnight reaction refers to a time of 8-15 hours. In the following examples, if the operating temperature is not specified, the operation is carried out at room temperature.

In the following examples, the isolation and purification of the intermediates and final products are performed by normal phase or reversed-phase chromatography column separation or other suitable methods. Normal phase flash chromatography columns use ethyl acetate and n-hexane or methanol and dichloromethane as mobile phases. Reversed-phase preparative high-performance liquid chromatography (HPLC) uses C18 column and uses UV 214 nm and 254 nm for detection, of which the mobile phase is A (water and 0.1% formic acid) and B (acetonitrile), or mobile phase A (water and 0.1% ammonium bicarbonate) and B (acetonitrile).

In each example: LCMS instrument: Pump Agilent 1260 UV detector: Agilent 1260 DAD Mass Spectrometer API 3000.

Chromatography column: Waters sunfire C18, 4.6×50 mm, 5 m.

Mobile phase: A-H$_2$O (0.1% HCOOH); B-acetonitrile NMR.

Instrument: Bruker Ascend 400M (H NMR: 400 MHz; $^{13}$C NMR: 100 MHz).

Example 1

Preparation of Intermediate: 5-chloro-8-((2,3-dichlorophenyl)thio)imidazo[1,2-c]pyrimidine (B1)

Step 1:2-chloro-N-(2,2-dimethoxyethyl)-5-iodopyrimidin-4-amine

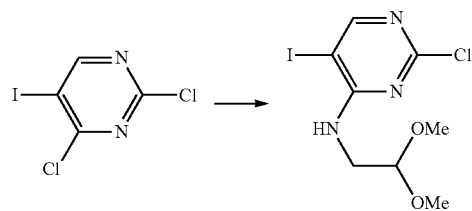 [SMILES: Clc1ncc(I)c(Cl)n1 ; COC(CNc1nc(Cl)ncc1I)OC]

To a dry 2 L flask were successively added 2,4-dichloro-5-iodopyrimidine (110 g, 400 mmol), 2,2-dimethoxyethylamine (84 g, 800 mmol) and anhydrous ethanol (1.2 L). At 0° C. under nitrogen atmosphere, triethylamine (109 mL, 800 mmol) was slowly added dropwise thereto, and the mixture was stirred at room temperature for 10 hours. After the reaction was completed, the mixture was concentrated in vacuum, and the resulting concentrate was added with 1 L of water, and extracted with dichloromethane (3×300 mL). The organic phases were combined, washed with saturated brine, dried over anhydrous sodium sulfate, filtered and concentrated. The resulting brown-black solid was washed with anhydrous ethanol (3×50 mL) to obtain 2-chloro-N-(2,2-dimethoxyethyl)-5-iodopyrimidin-4-amine (110 g, yield: 78%) as a brown solid.

$^1$H NMR (400 MHz, DMSO-d$_6$) δ 8.35 (s, 1H), 4.58 (t, J=5.4 Hz, 1H), 3.47 (t, J=5.6 Hz, 2H), 3.29 (s, 6H) ppm; LC-MS: m/z 344.1 [M+H]$^+$.

Step 2: 8-iodoimidazo[1,2-c]pyrimidin-5-ol

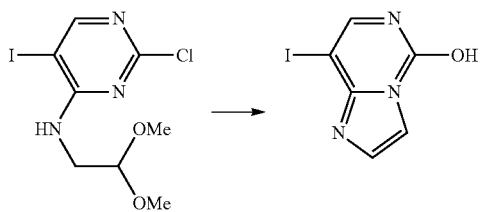

To a dry 2 L flask were successively added 2-chloro-N-(2,2-dimethoxyethyl)-5-iodopyrimidin-4-amine (110 g, 317 mmol) and 800 mL of concentrated sulfuric acid. Under nitrogen atmosphere, the mixture was heated to 65° C. and stirred for 2 hours. After the reaction was completed, the reaction solution was cooled to room temperature and slowly poured into ice water, and then the pH was adjusted to about 6.0 with 4 M NaOH solution, followed by extraction with ethyl acetate (3×300 mL). The organic phases were combined, washed with saturated brine, dried over anhydrous sodium sulfate, filtered and concentrated to obtain 8-iodoimidazo[1,2-c]pyrimidin-5-ol (70 g, yield 84.5%).

$^1$H NMR (400 MHz, DMSO-d$_6$) δ 11.80 (s, 1H), 7.92 (d, J=1.5 Hz, 1H), 7.60 (d, J=3.9 Hz, 1H), 7.40 (d, J=1.5 Hz, 1H); LC-MS: m/z 262.1 [M+H]$^+$

Step 3: 8-((2,3-dichlorophenyl)thio)imidazo[1,2-c]pyrimidin-5-ol

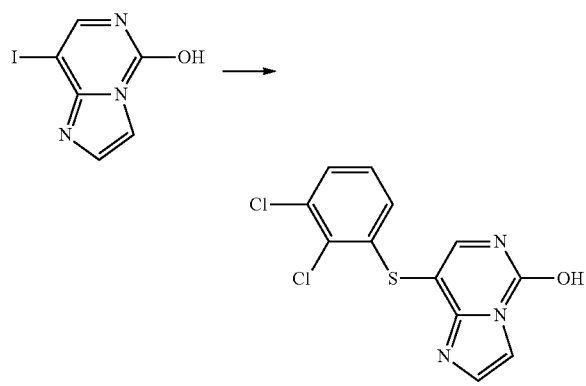

To a dry 250 mL three-neck flask were successively added 8-iodoimidazo[1,2-c]pyrimidin-5-ol (2.61 g, 10 mmol), cuprous iodide (190 mg, 1 mmol), 1,10-phenanthroline (360 mg, 2 mmol), 2,3-dichlorothiophenol (2.15 g, 12 mmol), potassium phosphate (4.2 g, 20 mmol) and 50 mL of dioxane. The mixture was heated for 3 hours under nitrogen atmosphere. After the reaction was completed, saturated NH$_4$Cl solution (200 mL) was added, followed by extraction with ethyl acetate (3×200 mL). The organic phases were combined, dried over Na$_2$SO$_4$, filtered, and the filtrate was concentrated under reduced pressure. The resulting residue was purified by silica gel chromatography (methanol:ethyl acetate with a gradient of 0 to 10%) to obtain 8-((2,3-dichlorophenyl)thio)imidazo[1,2-c]pyrimidin-5-ol (2.3 g, yield: 74%) as pale yellow solid.

LC-MS: m/z 312.1 [M+H]$^+$.

Step 4: 5-chloro-8-((2,3-dichlorophenyl)thio)imidazo[1,2-c]pyrimidine (B1)

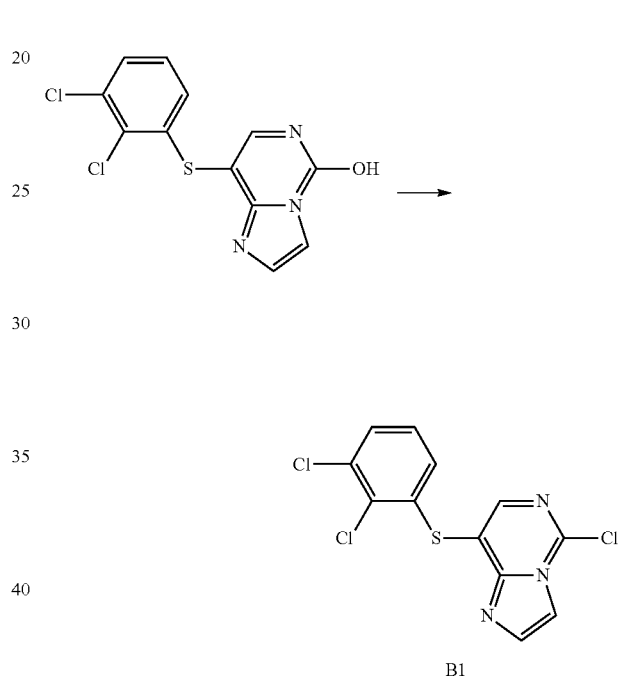

B1

To a dry 100 mL single-necked flask were added 8-((2,3-dichlorophenyl)thio)imidazo[1,2-c]pyrimidin-5-ol (2.3 g, 7.3 mmol) and phosphorus oxychloride (30 mL) sequentially, and N,N-diisopropylethylamine (1 mL) was slowly added dropwise under nitrogen atmosphere. The mixture was then heated to 120° C. and stirred for 4 hours. After the reaction was completed, the mixture was cooled to room temperature and then concentrated in vacuum, and the reaction was quenched with saturated sodium bicarbonate solution. The mixture was extracted with ethyl acetate (3×30 mL), and washed with saturated brine. The organic phases were combined, dried over anhydrous sodium sulfate, filtered and concentrated. The resulting residue was purified by silica gel chromatography (methanol: ethyl acetate with a gradient of 0 to 10%) to obtain 5-chloro-8-((2,3-dichlorophenyl)thio)imidazo[1,2-c]pyrimidine (B1) as a white solid (660 mg, yield: 27.4%).

$^1$H NMR (400 MHz, DMSO-d$_6$) δ 8.18 (d, J=1.4 Hz, 1H), 8.07 (s, 1H), 7.76 (d, J=1.4 Hz, 1H), 7.52 (dd, J=8.0, 1.3 Hz, 1H), 7.17 (t, J=8.0 Hz, 1H), 7.00 (dd, J=8.1, 1.2 Hz, 1H) ppm; LC-MS: m/z 330.1 [M+H]$^+$.

Example 2: Preparation of Intermediate: 5-chloro-8-iodoimidazo[1,2-c]pyrimidine (E1)

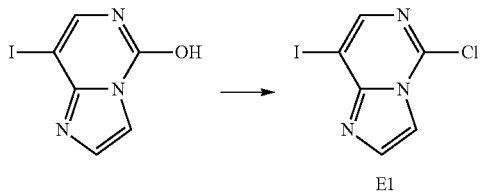 [SMILES: Oc1ncc(I)c2nccn12 ; Clc1ncc(I)c2nccn12]

E1

To a dry 250 mL single-necked flask were sequentially added 8-iodoimidazo[1,2-c]pyrimidin-5-ol (5 g, 19.1 mmol) and phosphorus oxychloride (50 mL), and N,N-diisopropylethylamine (1 mL) was slowly added dropwise under nitrogen atmosphere. The mixture was then heated to 120° C. and stirred for 4 hours. After the reaction was completed, the reaction solution was cooled to room temperature and concentrated in vacuum, quenched with saturated sodium bicarbonate solution, and extracted with ethyl acetate (3×100 mL). The organic phases were combined and washed with saturated brine, dried over anhydrous sodium sulfate, filtered, concentrated and purified by column chromatography to give a residue, which was purified by silica gel chromatography (methanol: ethyl acetate with a gradient of 0 to 10%) to obtain 5-chloro-8-iodoimidazo[1,2-c]pyrimidine E1 (1.6 g, yield: 29.8%).

$^1$H NMR (400 MHz, Methanol-$d_4$) δ 8.28 (s, 1H), 8.16 (d, J=1.6 Hz, 1H), 7.81 (d, J=1.6 Hz, 1H) ppm; LC-MS: m/z 280.1 [M+H]$^+$.

Example 3: Preparation of Intermediate: (R)-2-methyl-N—((R)-8-azaspiro[4.5]decan-1-yl)propane-2-sulfinamide (C-1A)

Step 1: Tert-Butyl (R)-1-((R)-1,1-dimethylethylsulfinamido)-8-azaspiro[4.5]decane-8-carboxylate

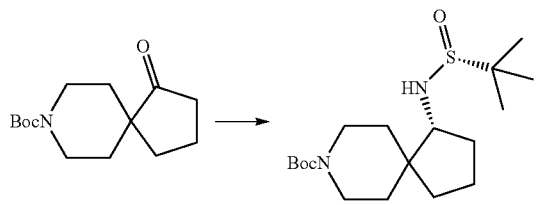 [SMILES: CC(C)(C)OC(=O)N1CCC2(CCCC2=O)CC1 ; CC(C)(C)OC(=O)N1CCC2(CCC[C@H]2N[S@](=O)C(C)(C)C)CC1]

To a dry 100 mL single-necked flask were successively added tert-butyl 1-oxo-8-azaspiro[4.5]decane-8-carboxylate (2.53 g, 10 mmol), (R)-2-methylpropane-2-sulfinamide (1.45 g, 12 mmol), titanium tetraethoxide (6.84 g, 30 mmol) and 50 mL of tetrahydrofuran. The reaction solution was stirred under reflux for 4 hours. After cooling to room temperature, methanol (10 mL) was added followed by lithium borohydride (0.65 g, 30 mmol). The resulting mixture was stirred at room temperature for 3 hours. Methanol was slowly added to quench excess borohydride, followed by addition of brine. The resulting mixture was stirred for 15 minutes and then filtered through diatomite. The aqueous mixture was extracted with ethyl acetate (3×50 mL). The organic phases were combined, dried over MgSO$_4$, filtered, and the volatiles were removed under reduced pressure. The resulting residue was purified by silica gel chromatography (ethyl acetate: petroleum ether with a gradient 0 to 50%) to obtain tert-butyl (R)-1-((R)-1,1-dimethylethylsulfinamido)-8-azaspiro[4.5]decane-8-carboxylate as a white solid (2.86 g, yield: 80%).

LC-MS: m/z 359.1 [M+H]$^+$.

Step 2: (R)-2-methyl-N—((R)-8-azaspiro[4.5]decan-1-yl)propane-2-sulfinamide (C-1A)

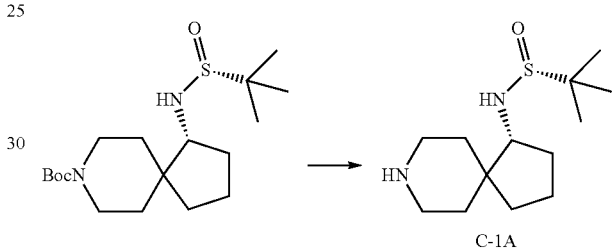

A solution of tert-butyl (R)-1-((R)-1,1-dimethylethylsulfinamido)-8-azaspiro[4.5]decane-8-carboxylate (2.86 g, 8 mmol) and concentrated sulfuric acid (2.0 mL, 32 mmol) in dioxane (50 mL) was stirred at room temperature for 2 hours. A saturated aqueous solution of Na$_2$CO$_3$ was added until pH reached 11, and the aqueous mixture was extracted with DCM (3×50 mL). The organic phases were combined, washed with brine, dried over Na$_2$SO$_4$, filtered, and the volatiles were removed under reduced pressure to obtain (R)-2-methyl-N—((R)-8-azaspiro[4.5]decan-1-yl)propane-2-sulfinamide (C-1A) as a white solid (1.86 g, yield: 90%)

$^1$H NMR (400 MHz, DMSO-$d_6$) δ 4.82 (d, J=7.5 Hz, 1H), 3.04 (d, J=7.6 Hz, 1H), 2.81 (ddd, J=12.1, 8.0, 4.0 Hz, 2H), 2.60-2.51 (m, 2H), 1.92-1.14 (m, 10H), 1.12 (s, 9H) ppm; LC-MS: m/z 259.1 [M+H]$^+$.

According to the synthesis method of Example 3, the following intermediates C-1B, C-1C, C-D, C-1E, C-1F, C-1G and C-1H were obtained by carrying out the reaction with similar raw materials.

| No. | Name | Structure | Analysis data |
|---|---|---|---|
| C-1B | (R)-2-methyl-N-((R)-7-azaspiro[3.5]nonan-1-yl)propane-2-sulfinamide | 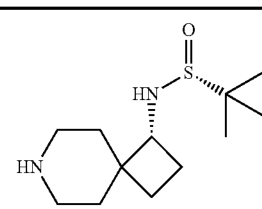 | $^1$H NMR (400 MHz, CDCl$_3$) δ 3.56 (t, J = 8.9 Hz, 1H), 3.51-3.20 (m, 2H), 3.18-2.97 (m, 2H), 2.34 (d, J = 10.1 Hz, 1H), 2.06-1.83 (m, 3H), 1.70 (dt, J = 26.3, 12.0 |

| No. | Name | Structure | Analysis data |
|---|---|---|---|
| | | | Hz, 3H), 1.52 (t, J = 10.0 Hz, 1H), 1.19 (s, 9H) ppm; LC-MS: m/z 244.1 [M + H]⁺. |
| C-1C | (R)-2-methyl-N-(7-azaspiro[3.5]no-nan-2-yl)propan-2-sulfinamide | 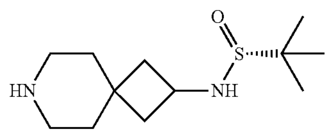 [SMILES: CC(C)(C)[S@@](=O)NC1CC2(CCNCC2)C1] | LC-MS: m/z 244.1 [M + H]⁺ |
| C-1D | (S)-2-methyl-N-((S)-8-azaspiro[4.5]decan-1-yl)propane-2-sulfinamide | 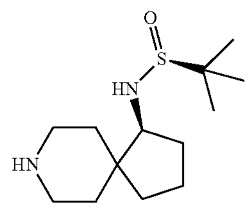 [SMILES: CC(C)(C)[S@](=O)N[C@H]1CCCC12CCNCC2] | LC-MS: m/z 259.1 [M + H]⁺ |
| C-1E | (R)-2-methyl-N-((7R)-2-azaspiro[4.4]nonan-7-yl)propane-2-sulfinamide | 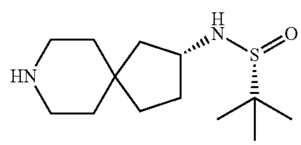 | LC-MS: m/z 245.1 [M + H]⁺ |
| C-1F | (R)-1-methyl-N-((R)-3-azaspiro[5.5]undecan-7-yl)propane-2-sulfinamide | 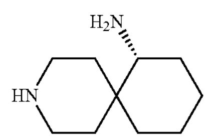 [SMILES: N[C@@H]1CCCCC12CCNCC2] | LC-MS: m/z 169.1 [M + H]⁺ |
| C-1G | (R)-N-((R)-azepan-4-yl)-2-methylpropane-2-sulfinamide | 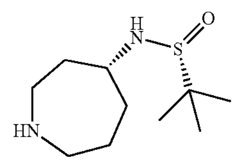 | LC-MS: m/z 219.1 [M + H]⁺ |
| C-1H | (S)-2-methyl-N-((S)-7-azaspiro[3.5]nonan-1-yl)propane-2-sulfinamide | 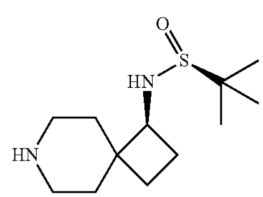 [SMILES: CC(C)(C)[S@](=O)N[C@H]1CCC12CCNCC2] | LC-MS: m/z 245.2 [M + H]⁺ |

Example 4: Preparation of Intermediate: (R)-2-methyl-N—((S)-2-oxa-8-azaspiro[4.5]decan-4-yl)propane-2-sulfinamide (C-1H)

Step 1: 1-(tert-butyl)-4-methyl 4-(2-(benzyloxy)-1-hydroxyethyl)piperidine-1,4-dicarboxylate

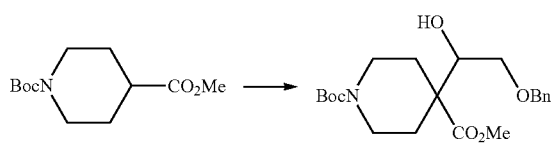

Under the atmosphere of nitrogen, 1-tert-butyl-4-methylpiperidine-1,4-dicarboxylate (45 g, 180 mmol) and tetrahydrofuran (400 mL) were added to a dry 500 mL three-necked flask sequentially. The solution was then cooled to −78° C., and LiHMDS (261 mL, 261 mmol) was added dropwise. After the dropwise addition was completed, the temperature was raised to room temperature and the mixture was stirred at room temperature for 3 hours, and then cooled to −78° C., followed by slow addition of a solution of benzyloxyacetaldehyde (46 g, 300 mmol) in tetrahydrofuran (50 mL). The reaction solution was slowly warmed to room temperature and stirred for 2.5 hours. After the reaction was completed, saturated NH₄Cl solution (200 mL) was added to quench the reaction, followed by extraction with ethyl acetate (3×200 mL). The combined organic phase was dried over Na₂SO₄, filtered, and the filtrate was concentrated under reduced pressure. The resulting residue was purified by silica gel chromatography (ethyl acetate/petroleum ether with a gradient of 0 to 50%) to obtain 1-(tert-butyl)-4- methyl 4-(2-(benzyloxy)-1-hydroxyethyl)piperidine-1,4-dicarboxylate (52 g, yield: 73.3%).

¹H NMR (400 MHz, CDCl₃) δ 7.36-7.30 (m, 5H), 4.50 (s, 2H), 3.97 (s, 2H), 3.73-3.65 (m, 2H), 3.62 (s, 3H), 3.59-3.48 (m, 3H), 2.88 (d, J=6.2 Hz, 1H), 2.23 (dd, J=13.7, 2.7 Hz, 1H), 2.04-1.88 (m, 2H), 1.74 (d, J=14.7 Hz, 1H), 1.56 (d, J=4.2 Hz, 1H), 1.44 (s, 9H) ppm; LC-MS: m/z 294.1 [M+H]⁺.

Step 2: Tert-Butyl 4-(2-(benzyloxy)-1-hydroxyethyl)-4-(hydroxymethyl)piperidine-1-carboxylate

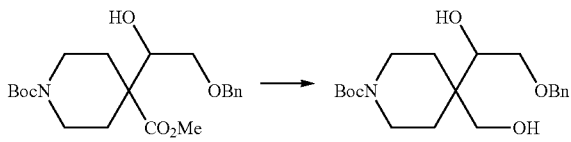 [SMILES: COC(=O)C1(C(O)COCc2ccccc2)CCN(C(=O)OC(C)(C)C)CC1 ; CC(C)(C)OC(=O)N1CCC(CO)(C(O)COCc2ccccc2)CC1]

1-(tert-butyl)-4-methyl 4-(2-(benzyloxy)-1-hydroxyethyl)piperidine-1,4-dicarboxylate (51.4 g, 130 mmol) and tetrahydrofuran (500 mL), then LiBH₄ (11.44 g, 520 mmol) was added to the solution, and the resulting mixture was stirred at room temperature for 6 hours. After the reaction was completed, the reaction was quenched with saturated NaHCO₃ (200 mL). The mixture was extracted with ethyl acetate (3×200 mL). The combined organic phase was dried over Na₂SO₄, filtered, and the filtrate was concentrated under reduced pressure. The resulting residue was purified by silica gel chromatography (ethyl acetate/petroleum ether with a gradient of 0 to 50%) to obtain tert-butyl 4-(2-(benzyloxy)-1-hydroxyethyl)-4-(hydroxymethyl)piperidine-1-carboxylate (27 g, yield: 57%).

LC-MS: m/z 266.1 [M+H]⁺.

Step 3: Tert-Butyl 4-(1,2-dihydroxyethyl)-4-(hydroxymethyl)piperidine-1-carboxylate

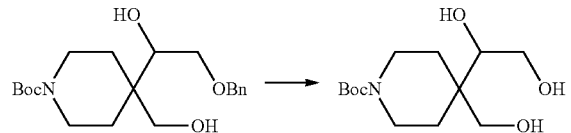 [SMILES: CC(C)(C)OC(=O)N1CCC(CO)(C(O)COCc2ccccc2)CC1 ; CC(C)(C)OC(=O)N1CCC(CO)(C(O)CO)CC1]

To a dry 500 mL single-necked flask were added tert-butyl 4-(2-(benzyloxy)-1-hydroxyethyl)-4-(hydroxymethyl)piperidine-1-carboxylate (27 g, 74 mmol), methanol (270 mL) and Pd/C (20 g) and then the flask was purged with a hydrogen balloon three times. The mixture was stirred at room temperature for 12 hours. The reaction solution was filtered and concentrated to obtain tert-butyl 4-(1,2-dihydroxyethyl)-4-(hydroxymethyl)piperidine-1-carboxylate (18.9 g, yield: 93%).

LC-MS: m/z 176.1 [M+H]⁺.

Step 4: Tert-Butyl 4-hydroxy-2-oxa-8-azaspiro[4.5]decane-8-carboxylate

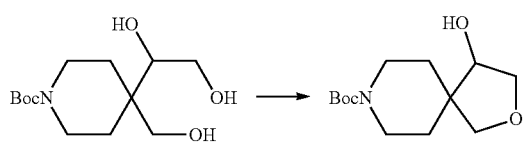

To a dry 500 mL single-necked flask were successively added tert-butyl 4-(1,2-dihydroxyethyl)-4-(hydroxymethyl)piperidine-1-carboxylate (18.9 g, 69 mmol), triphenyl phosphine (25.2 g, 86.25 mmol) and tetrahydrofuran (350 mL). The reaction solution was cooled to 0° C., followed by addition of DEAD (12.46 mL, 86 mmol). The reaction solution was then warmed to room temperature and stirred for 5 hours. After the reaction was completed, saturated water (200 mL) was added to quench the reaction, followed by extraction with ethyl acetate (3×200 mL). The organic phases were combined and dried over Na₂SO₄, filtered, and the filtrate was concentrated under reduced pressure. The resulting residue was purified by silica gel chromatography (methanol/dichloromethane with a gradient of 0 to 2%) to give tert-butyl 4-hydroxy-2-oxa-8-azaspiro[4.5]decane-8-carboxylate (13.2 g, yield: 74%).

¹H NMR (400 MHz, CDCl₃) δ 4.04 (dd, J=10.0, 4.6 Hz, 1H), 3.98-3.90 (m, 1H), 3.71-3.63 (m, 2H), 3.64-3.49 (m, 3H), 3.20 (dt, J=13.4, 6.3 Hz, 1H), 3.07 (ddd, J=13.2, 9.2, 3.5 Hz, 1H), 1.95 (d, J=5.2 Hz, 1H), 1.74-1.66 (m, 1H), 1.53-1.46 (m, 1H), 1.39 (s, 9H), 1.27-1.11 (m, 1H) ppm; LC-MS: m/z 202.1[M-56+H]⁺.

Step 5: Tert-Butyl 4-oxo-2-oxa-8-azaspiro[4.5]decane-8-carboxylate

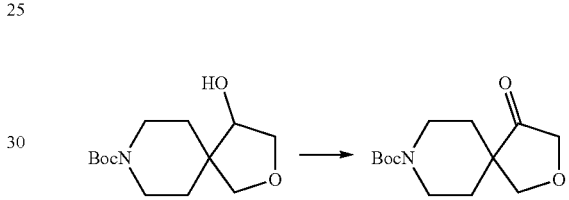

To a dry 500 mL single-necked flask were added tert-butyl 4-hydroxy-2-oxa-8-azaspiro[4.5]decane-8-carboxylate (13.2 g, 51 mmol), dichloromethane (280 mL) and Dess-Martin oxidant (32.2 g, 76.5 mmol), and the mixture was stirred for 5 hours in an ice bath. After the reaction was completed, a saturated solution (200 mL) of NaHCO₃: Na₂S₂O₃ (1:1) was added. The organic phase was separated, and the aqueous phase was extracted with DCM (3×100 mL).

The organic phases were combined, dried over Na₂SO₄ and the filtrate was concentrated under reduced pressure. The resulting residue was purified by silica gel chromatography (ethyl acetate/petroleum ether with a gradient of 0 to 40%) to obtain tert-butyl 4-oxo-2-oxa-8-azaspiro[4.5]decane-8-carboxylate (12 g, yield: 92.1%).

¹H NMR (400 MHz, CDCl₃) δ 4.05 (d, J=13.6 Hz, 4H), 3.87 (d, J=12.9 Hz, 2H), 3.09 (ddd, J=13.5, 9.8, 3.5 Hz, 2H), 1.73 (ddd, J=13.9, 9.8, 4.3 Hz, 2H), 1.53 (d, J=15.1 Hz, 2H), 1.46 (s, 9H) ppm; LC-MS: m/z 200.0 [M-56+H]⁺.

Step 6: Tert-Butyl (S)-4-(((R)-tert-butylsulfinyl) amino)-2-oxa-8-azaspiro[4.5]decane-8-carboxylate

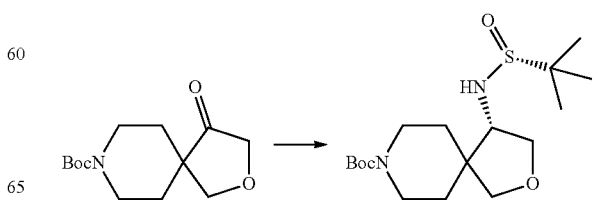

Using the same synthesis method as Step 1 of Example 3 (intermediate C-1A), tert-butyl 4-oxo-2-oxa-8-azaspiro[4.5]decane-8-carboxylate was subjected to reductive amination to obtain (S)-4-(((R)-tert-butylsulfinyl)amino)-2-oxa-8-azaspiro[4.5]decane-8-carboxylate as a white solid.

$^1$H NMR (400 MHz, CDCl$_3$) δ 4.14 (dd, J=9.3, 6.2 Hz, 1H), 3.90 (d, J=13.8 Hz, 2H), 3.77 (s, 2H), 3.70 (dd, J=9.2, 5.3 Hz, 1H), 3.63 (q, J=6.1 Hz, 1H), 3.27 (d, J=6.4 Hz, 1H), 2.90 (t, J=12.4 Hz, 2H), 1.71 (dt, J=16.6, 7.9 Hz, 2H), 1.51 (s, 2H), 1.45 (s, 9H), 1.22 (s, 9H) ppm; LC-MS: m/z 361.1 [M-100]$^+$

Step 7: (R)-2-methyl-N—((S)-2-oxa-8-azaspiro[4.5]decan-4-yl)propane-2-sulfinamide (C-1H)

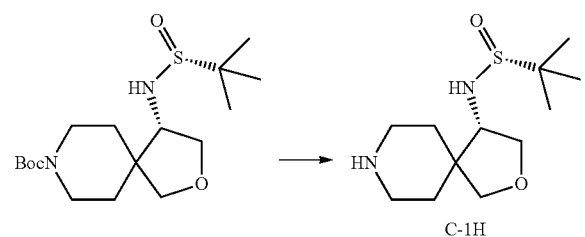

C-1H

Using the same synthesis method as Step 2 of Example 3 (intermediate C-1A), (S)-4-(((R)-tert-butylsulfinyl)amino)-2-oxa-8-azaspiro[4.5]decane-8-carboxylate was subjected to deprotection of the Boc protecting group to obtain (R)-2-methyl-N—((S)-2-oxa-8-azaspiro[4.5]decan-4-yl)propane-2-sulfinamide (C-1H) as a white solid.

$^1$H NMR (400 MHz, DMSO-d$_6$) δ 5.30 (s, 1H), 5.23 (d, J=8.9 Hz, 1H), 3.93 (dd, J=8.6, 7.2 Hz, 1H), 3.69 (d, J=8.6 Hz, 1H), 3.58 (d, J=8.6 Hz, 1H), 3.46 (dd, J=8.5, 7.0 Hz, 2H), 2.89-2.73 (m, 2H), 2.48-2.42 (m, 1H), 1.69-1.50 (m, 2H), 1.39-1.21 (m, 3H), 1.12 (s, 9H) ppm; LC-MS: m/z 261.1 [M+H]$^+$.

Example 5: Preparation of (R)-2-methyl-N—((R)-1-oxa-8-azaspiro[4.5]decan-4-yl)propane-2-sulfinamide (C-1I)

Step 1: 3-methoxyprop-1-yne

To a stirred solution of prop-2-yn-1-ol (50 g, 892.8 mmol) in water (40 mL) was added 50% aqueous NaOH solution (98.2 g), and the reaction mixture was heated to 70° C. Dimethyl sulfate (67.4 g, 535.7 mmol) was slowly added to the reaction mixture below 70° C. The reaction mixture was stirred at 60° C. for 2 hours. The product was distilled from the reaction mixture at 60° C. and collected into a receiving flask cooled at −70° C. The distillate was dried over calcium chloride overnight and further distilled to obtain 3-methoxyprop-1-yne (30 g, yield: 48%) as a colorless liquid.

$^1$H NMR (CDCl$_3$, 400 MHz) δ 4.10 (d, J=2.0 Hz, 2H), 3.39 (s, 3H), 2.43 (t, J=2.0 Hz, 1H) ppm.

Step 2: 1-methoxy-1,2-propadiene

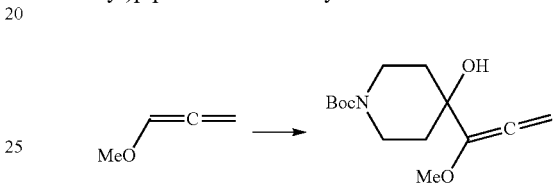

A suspension of potassium tert-butoxide (3.9 g, 35.7 mmol) and 3-methoxyprop-1-yne (50 g, 714.2 mmol) was stirred at 70° C. for 2 hours. The product was distilled from the reaction mixture at 50° C. and collected into a receiving cooled at −70° C. to obtain 1-methoxyprop-1,2-diene (35 g, yield: 70%) as a colorless liquid. The compound was dried over KOH and stored at 0° C.

$^1$H NMR (CDCl$_3$, 400 MHz) δ 6.76 (t, J=8.0 Hz, 1H), 5.48 (d, J=6.0 Hz, 2H), 3.41 (s, 3H) ppm Step 3: Tert-Butyl 4-hydroxy-4-(1-methoxyprop-1,2-dien-1-yl)piperidine-1-carboxylate

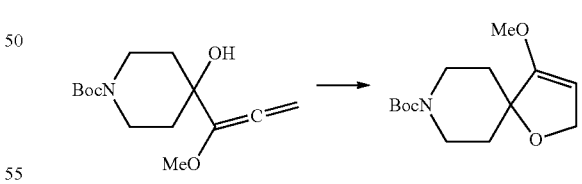

At −78° C., to a stirred solution of 1-methoxyprop-1,2-diene (0.527 g, 7.5 mmol) in THF (10 mL) was slowly added dropwise n-butyllithium (2.5 M in THF) (2.8 mL, 7.0 mmol), and the reaction solution was stirred at this temperature for 30 minutes. Then a solution of tert-butyl 4-carbonylpiperidine-1-carboxylate (1.0 g, 5.0 mmol) in THF (5 mL) was added to the reaction mixture, and further stirred at −78° C. for 4 hours. The reaction mixture was quenched with saturated aqueous NaHCO$_3$ and extracted with ethyl acetate (3×10 mL). The organic phases were combined, washed with brine (50 mL), dried over anhydrous sodium sulfate, filtered and concentrated under reduced pressure to obtain tert-butyl 4-hydroxy-4-(1-methoxyprop-1,2-dien-1-yl)piperidine-1-carboxylate (1.0 g, yield: 90%) as a brown gum.

Step 4: Tert-Butyl 4-methoxy-1-oxa-8-azaspiro[4.5]dec-3-ene-8-carboxylate

To a stirred solution of tert-butyl 4-hydroxy-4-(1-methoxyprop-1,2-dien-1-yl)piperidine-1-carboxylate (6.0 g, 22.3 mmol) in tert-butanol (60 mL) were added potassium tert-butoxide (12.5 g, 111.5 mmol) and dicyclohexyl-18-crown-6 (0.42 g, 1.1 mmol). The reaction mixture was stirred under reflux for 9 hours. The reaction mixture was cooled to 10° C., neutralized with 5% HCl (pH=7.0), and extracted with ethyl acetate (3×150 mL). The organic phases were combined, washed with brine (200 mL), dried over anhydrous sodium sulfate, filtered, and the filtrate was concentrated under reduced pressure to obtain tert-butyl 4-methoxy-1-oxa-8-azaspiro[4.5]dec-3-ene-8-carboxylate, which was used in the next step without purification.

$^1$H NMR (CDCl$_3$, 400 MHz) δ 4.56 (s, 2H), 3.97 (s, 1H), 3.69 (s, 3H), 3.08 (s, 1H), 1.79-1.74 (m, 1H), 1.52 (s, 9H), 1.45-1.26 (m, 1H) ppm; LCMS: m/z 214 [M-55]$^+$

Step 5: Tert-Butyl 4-oxo-1-oxa-8-azaspiro[4.5]decane-8-carboxylate

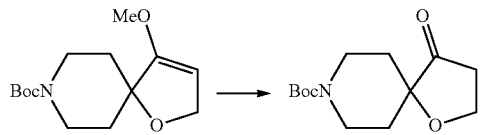 [SMILES: COC1=CCOC12CCN(C(=O)OC(C)(C)C)CC2 ; CC(C)(C)OC(=O)N1CCC2(CC1)OCCC2=O]

A mixture of tert-butyl 4-methoxy-1-oxa-8-azaspiro[4.5]dec-3-ene-8-carboxylate (38.0 g, 141.3 mmol) and p-TSA.H$_2$O (29.6 g, 155.4 mmol) and acetone (400 mL) was stirred at room temperature for 1 hour. The reaction mixture was quenched with saturated aqueous NaHCO$_3$, and extracted with ethyl acetate (3×500 mL). The organic phases were combined, washed with brine (1000 mL), dried over anhydrous sodium sulfate, filtered, and concentrated under reduced pressure to obtain tert-butyl 4-oxo-1-oxa-8-azaspiro[4.5]decane-8-carboxylate (25 g) as a brown gum, which was directly used in the next reaction.

LCMS: m/z 278 [M+Na]$^+$.

Steps 6 and 7: Synthesis of (R)-2-methyl-N—((R)-1-oxa-8-azaspiro[4.5]decan-4-yl)propane-2-sulfinamide (C-1I)

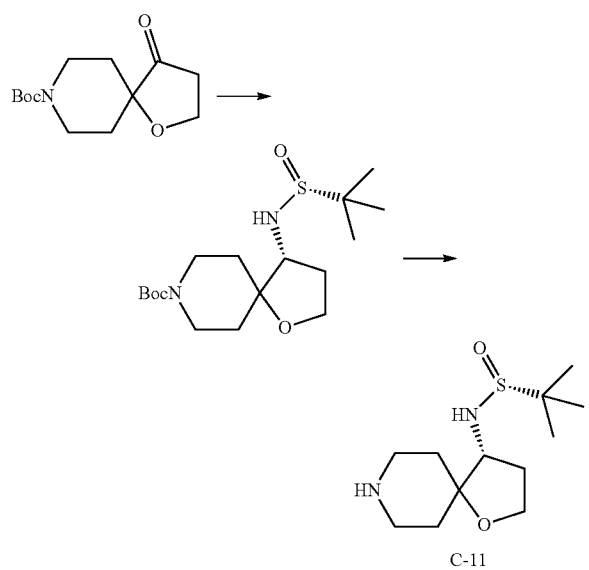

According to the same synthesis method as that of the intermediate C-1A in Example 3, the keto intermediate tert-butyl 4-oxo-1-oxa-8-azaspiro[4.5]decane-8-carboxylate was subjected to reductive amination, followed by deprotection of the Boc protecting group to obtain (R)-2-methyl-N—((R)-1-oxa-8-azaspiro[4.5]decan-4-yl)propane-2-sulfinamide (C-1I).

LCMS: m/z 261 [M+Na]$^+$.

Example 6: Preparation of (R)-2-methyl-N-((3S, 4S)-3-methyl-2-oxa-8-azaspiro[4.5]decan-4-yl)propane-2-sulfinamide (C-1J)

Step 1: ethyl (S)-2-((tert-butyldimethylsilyl)oxy)propionate

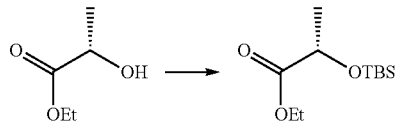

To a solution of ethyl (S)-2-hydroxypropionate (30 g, 254 mmol) in dichloromethane (300 mL) was added imidazole (2.75 g, 304.9 mmol) and the solution was cooled to 0° C., followed by addition of tert-butyldimethylsilyl chloride (46.0 g, 304.9 mmol) in portions. The mixture was stirred at room temperature for 16 hours. After the completion of the reaction was confirmed by TLC analysis, the reaction mixture was quenched with water and extracted with dichloromethane (2×100 mL). The organic phases were combined, dried over anhydrous sodium sulfate, filtered and concentrated under reduced pressure to obtain ethyl (S)-2-((tert-butyldimethylsilyl)oxy)propionate (50 g, yield: 84%) as a colorless liquid.

$^1$H NMR (400 MHz, CDCl$_3$) δ 4.32-4.27 (m, 1H), 4.21-4.12 (m, 2H), 1.37 (d, J=6.8 Hz, 3H), 1.27 (d, J=7.2 Hz, 3H), 0.90 (s, 9H), 0.08 (s, 6H) ppm.

Step 2: (S)-2-((tert-butyldimethylsilyl)oxy)propanal

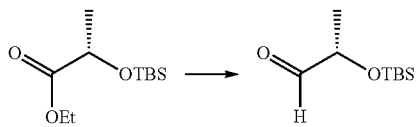

At −78° C., to a solution of ethyl (S)-2-((tert-butyldimethylsilyl)oxy)propionate (25 g, 107.6 mmol) in diethyl ether (500 mL) was slowly added dropwise diisobutylaluminum hydride (1M in hexane) (129 mL, 129.1 mmol), and stirred at −78° C. for 1 hour. After the completion of the reaction was confirmed by TLC analysis, the reaction mixture was warmed to −40° C., and the reaction was quenched with a saturated aqueous solution of Rochelle salt (1 L), followed by addition of diethyl ether (500 mL). The resulting mixture was stirred at room temperature for 2 hours and extracted with diethyl ether (200 mL). The organic phase was washed with saturated brine (250 mL), dried over Na$_2$SO$_4$, filtered and concentrated under reduced pressure to obtain (S)-2-((tert-butyldimethylsilyl)oxy)propanal (19 g, yield: 94%).

$^1$H NMR (400 MHz, CDCl$_3$) δ 9.61 (s, 1H), 4.12-4.06 (m, 1H), 1.27 (d, J=6.8 Hz, 3H), 0.91 (s, 9H), 0.10 (s, 6H) ppm.

Step 3: 1-(tert-butyl) 4-ethyl 4-((2S)-2-((tert-butyldimethylsilyl)oxy)-1-hydroxypropyl)piperidine-1,4-dicarboxylate

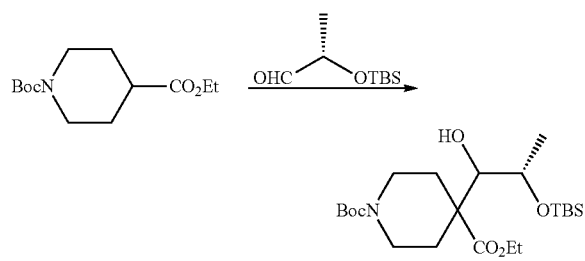

At 0° C., to a stirred solution of 1-(tert-butyl)-4-ethylpiperidine-1,4-dicarboxylate (30 g, 116.6 mmol) in THF (250 mL) was added lithium diisopropylamide (2M in THF) (93.3 mL, 186.6 mmol), and the solution was stirred at 0° C. for 30 minutes, followed by addition of (S)-2-((tert-butyldimethylsilyl)oxy)propanal (22 g, 116.6 mmol) in THF (50 mL). The resulting reaction mixture was stirred at 0° C. for 1 hour, and then kept at room temperature for 1 hour. After the completion of the reaction was confirmed by TLC analysis, the reaction mixture was quenched with saturated NH$_4$Cl solution and extracted with ethyl acetate (2×250 mL). The organic phases were combined, washed with water (150 mL), brine (150 mL), dried over anhydrous sodium sulfate, filtered and concentrated under reduced pressure. The crude product was purified by silica gel column (60-120 mesh) chromatography, using 25% ethyl acetate in petroleum ether as eluent to obtain 1-(tert-butyl) 4-ethyl 4-((2S)-2-((tert-butyldimethylsilyl)oxy)-1-hydroxypropyl)piperidine-1,4-dicarboxylate (17 g, yield: 32%) as a light red oil.

$^1$H NMR (400 MHz, CDCl$_3$) δ 4.29-4.09 (m, 2H), 3.96-3.94 (m, 2H), 3.86-3.80 (m, 1H), 3.56-3.54 (m, 1H), 2.86-2.76 (m, 2H), 2.46 (d, J=5.2 Hz, 1H), 2.16-2.13 (m, 1H), 2.13-2.04 (m, 1H), 1.77-1.60 (m, 2H), 1.46 (s, 9H), 1.29-1.24 (m, 3H), 1.12 (d, J=4 Hz, 3H), 0.89 (s, 9H), 0.05 (s, 6H) ppm; LCMS: m/z 346 [M-100]$^+$.

Step 4: Tert-Butyl 4-((2S)-2-((tert-butyldimethylsilyl)oxy)-1-hydroxypropyl)-4-(hydroxymethyl)piperidine-1-carboxylate

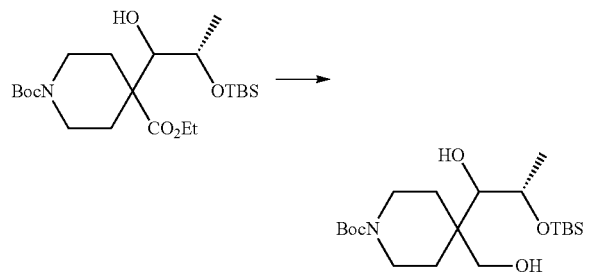

To a stirred solution of 1-tert-butyl 4-ethyl 4-((2S)-2-((tert-butyldimethylsilyl)oxy)-1-hydroxypropyl)piperidine-1,4-dicarboxylate (5 g, 11.21 mmol) in THF (50 mL) was added LiBH$_4$ (0.73 g, 33.65 mmol) in portions, and the mixture was stirred at room temperature for 16 hours. After the reaction was completed, the reaction mixture was quenched with saturated NaHCO$_3$ solution at 0° C. and stirred at room temperature for 15 minutes. The precipitated solid was filtered off, and the aqueous phase was extracted with ethyl acetate (2×50 mL). The organic phases were combined, dried over anhydrous sodium sulfate, filtered and concentrated under reduced pressure to obtain a crude product, which was then purified by silica gel column (100-200 mesh) chromatography using 25% ethyl acetate in petroleum ether as eluent to obtain tert-butyl 4-((2S)-2-((tert-butyldimethylsilyl)oxy)-1-hydroxypropyl)-4-(hydroxymethyl)piperidine-1-carboxylate (3 g, yield: 66%).

$^1$H NMR (400 MHz, CDCl$_3$) δ 4.55 (t, J=4.8 Hz, 1H), 4.43 (d, J=6.4 Hz, 1H), 3.52-3.47 (m, 5H), 3.31-3.28 (m, 1H), 3.05-3.01 (m, 2H), 1.58-1.49 (m, 2H), 1.42-1.38 (m, 11H), 1.11 (d, J=6.4 Hz, 3H), 0.85 (m, 9H), 0.04 (s, 6H) ppm; LC-MS: m/z 404.3 [M+H]$^+$.

Step 5: Tert-Butyl 4-((2S)-1,2-dihydroxypropyl)-4-(hydroxymethyl)piperidine-1-carboxylate

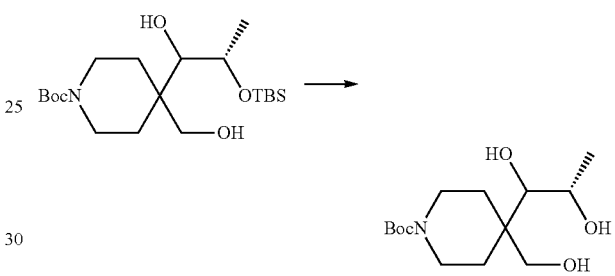

To a solution of tert-butyl 4-((2S)-2-((tert-butyldimethylsilyl)oxy)-1-hydroxypropyl)-4-(hydroxymethyl)piperidine-1-carboxylate (25 g, 61.93 mmol) in THF (500 mL) was added tetrabutylammonium fluoride (1M in THF) (93 mL, 92.89 mmol), and the resulting reaction mixture was stirred at room temperature for 2 hours. After the completion of the reaction was confirmed by TLC analysis, the reaction mixture was quenched with saturated NaHCO$_3$ solution and extracted with ethyl acetate (2×500 mL). The organic phases were combined, dried over anhydrous sodium sulfate, filtered and concentrated under reduced pressure to obtain a crude product, which was then purified by silica gel (60-120 mesh) column chromatography, using ethyl acetate in petroleum ether with a gradient of 70-90% as eluent to obtain tert-butyl 4-((2S)-1,2-dihydroxypropyl)-4-(hydroxymethyl)piperidine-1-carboxylate (12 g, yield: 67%) as a colorless liquid.

$^1$H NMR (400 MHz, DMSO-d$_6$) δ 4.72 (t, J=4.8 Hz, 1H), 4.61 (d, J=5.2 Hz, 1H), 4.50 (d, J=7.2 Hz, 1H), 3.72-3.68 (m, 1H), 3.53-3.44 (m, 4H), 3.11-2.98 (m, 3H), 1.68-1.53 (m, 2H), 1.42-1.35 (m, 11H), 1.10 (d, J=6.4 Hz, 3H) ppm; LC-MS: m/z 290.1 [M+H]$^+$.

Step 6: Tert-Butyl (3S)-4-hydroxy-3-methyl-2-oxa-8-azaspiro[4.5]decane-8-carboxylate

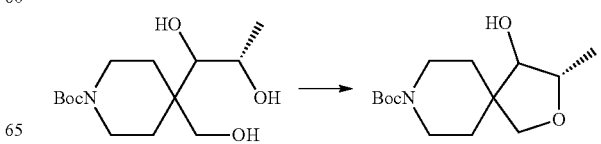

At 0° C., to a stirred suspension of NaH (60% in mineral oil) (1.45 g, 60.5 mmol) in THF (30 mL) was added a solution of tert-butyl 4-((2S)-1,2-dihydroxypropyl)-4-(hydroxymethyl)piperidine-1-carboxylate (5 g, 17.3 mmol) and p-toluenesulfonyl chloride (3.29 g, 17.3 mmol) in THF (20 mL), and the resulting reaction mixture was reacted at 0° C. for 3 hours. After the reaction was completed, the reaction mixture was quenched with saturated NH₄Cl solution (250 mL) at −20° C. and extracted with ethyl acetate (2×50 mL). The organic phases were combined, dried over anhydrous sodium sulfate, filtered and concentered under reduced pressure to obtain a crude product, which was then purified by silica gel (100-200 mesh) column chromatography, using 40% ethyl acetate in petroleum ether as eluent to obtain tert-butyl (3S)-4-hydroxy-3-methyl-2-oxa-8-azaspiro[4.5]decane-8-carboxylate (2.1 g, yield: 44%).

¹H NMR (400 MHz, CDCl₃) δ 3.83-3.62 (m, 5H), 3.43 (d, J=6.0, 1H), 3.07-2.97 (m, 2H), 1.72-1.55 (m, 3H), 1.51-1.42 (m, 11H), 1.33 (d, J=6.4 Hz, 3H) ppm; LC-MS: m/z 172.2 [M-100]⁺.

Step 7: (S)-tert-butyl-3-methyl-4-oxo-2-oxa-8-azaspiro[4.5]decane-8-carboxylate

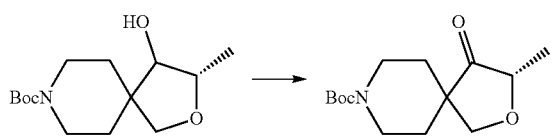 [SMILES: C[C@@H]1OCC2(CCN(C(=O)OC(C)(C)C)CC2)C1O ; C[C@@H]1OCC2(CCN(C(=O)OC(C)(C)C)CC2)C1=O]

Tert-butyl (3S)-4-hydroxy-3-methyl-2-oxa-8-azaspiro[4.5]decane-8-carboxylate (2.1 g, 7.74 mmol) was added to tetrahydrofuran (50 mL), and the solution was stirred for 1 hour. After the reaction was completed, the solvent was evaporated under reduced pressure. The resulting residue was purified by silica gel (100-200 mesh) column chromatography using 30% ethyl acetate in petroleum ether as eluent, followed by flash chromatography using 0.1% formic acid and acetonitrile as eluent to obtain (S)-tert-butyl-3-methyl-4-oxo-2-oxa-8-azaspiro[4.5]decane-8-carboxylate (1.2 g, yield: 57%).

¹H NMR (400 MHz, CDCl₃) δ 4.20 (d, J=9.5 Hz, 1H), 3.94-3.90 (m, 4H), 3.16-3.10 (m, 1H), 3.03-2.97 (m, 1H), 1.81-1.75 (m, 1H), 1.67-1.62 (m, 1H), 1.61-1.57 (m, 1H), 1.42-1.45 (m, 10H), 1.32 (d, J=6.0 Hz, 3H) ppm; LC-MS: m/z 214.1 [M-55]⁺.

Step 8: Tert-Butyl (3S,4S)-4-(((R)-tert-butylsulfinyl)amino)-3-methyl-2-oxa-8-azaspiro[4.5]decane-8-carboxylate

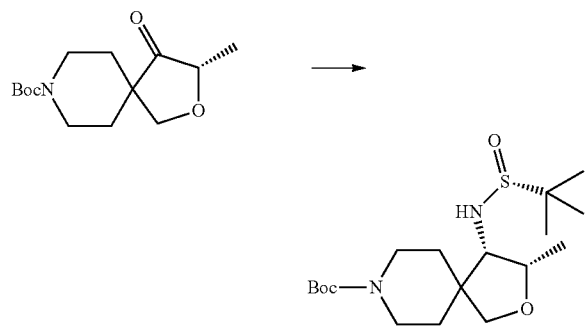

To a solution of tert-butyl (S)-3-methyl-4-oxo-2-oxa-8-azaspiro[4.5]decane-8-carboxylate (1.2 g, 4.46 mmol) in THF (15 mL) were added (R)-2-methylpropane-2-sulfinamide (1.07 g, 8.91 mmol) and titanium tetraethoxide (4.07 g, 17.84 mmol). The resulting reaction mixture was stirred at 90° C. for 20 hours. The reaction mixture was cooled to −4° C., MeOH (2 mL) was added, then LiBH₄ (282 mg, 12.99 mmol) was added in portions and the resulting mixture was stirred at the same temperature for 1 hour. After the reaction was completed, the reaction mixture was quenched with saturated brine at 0° C. and stirred at room temperature for 15 minutes, followed by filtration and extraction with ethyl acetate (2×50 mL). The organic phases were combined, dried over anhydrous sodium sulfate, filtered and concentered under reduced pressure to obtain a crude product, which was then purified by GRACE flash chromatography using 0.1% formic acid and acetonitrile as eluent to obtain tert-butyl (3S,4S)-4-(((R)-tert-butylsulfinyl)amino)-3-methyl-2-oxa-8-azaspiro[4.5]decane-8-carboxylate (1.2 g, yield: 72%).

¹H NMR (400 MHz, CDCl₃) δ 4.20-4.15 (m, 1H), 3.90-3.84 (m, 2H), 3.63-3.59 (m, 1H), 3.49-3.43 (m, 1H), 3.31-3.29 (m, 1H), 2.95-2.81 (m, 2H), 1.90-1.71 (m, 2H), 1.49-1.40 (m, 11H), 1.25 (s, 9H), 1.19 (d, J=6.5 Hz, 3H) ppm; LC-MS: m/z 375.2 [M+H]⁺.

Step 9: (R)-2-methyl-N-((3S,4S)-3-methyl-2-oxa-8-azaspiro[4.5]decan-4-yl)propane-2-sulfinamide (C-1J)

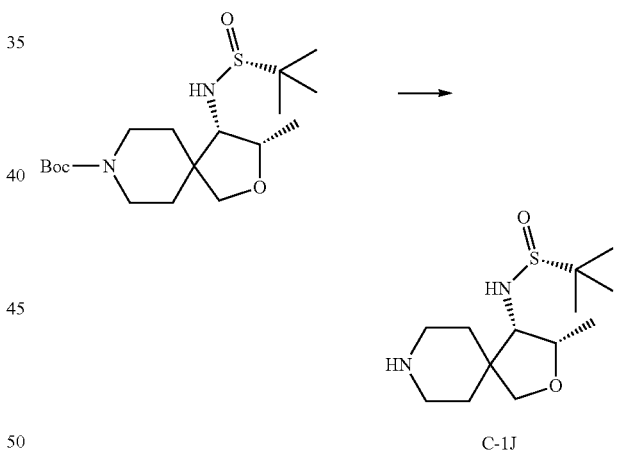

To a solution of tert-butyl (3S,4S)-4-(((R)-tert-butylsulfinyl)amino)-3-methyl-2-oxa-8-azaspiro[4.5]decane-8-carboxylate (1.1 g, 2.936 mmol) in dichloromethane (10 mL) was dropwise added trifluoroacetic acid (1.12 mL, 14.68 mmol) and the mixture was stirred at room temperature for 6 hours. After the reaction was completed, the reaction mixture was concentrated under reduced pressure to obtain a crude product, which was purified by chromatography using 0.1% formic acid and acetonitrile to obtain (R)-2-methyl-N-((3S,4S)-3-methyl-2-oxa-8-azaspiro[4.5]decan-4-yl)propane-2-sulfinamide (C-1J) (850 mg, yield: 72%).

¹H NMR (400 MHz, DMSO-d₆) δ 8.40 (brs, D₂O Exchangeable, 1H), 8.30 (brs, D₂O Exchangeable, 1H), 5.28 (d, J=12.0 Hz, 1H), 4.13-4.09 (m, 1H), 3.77 (d, J=9.0 Hz, 1H), 3.50-3.45 (m, 2H), 3.29-3.26 (m, 1H), 3.19-3.15 (m, 1H), 2.94-2.85 (m, 2H), 1.87-1.80 (m, 2H), 1.69-1.59 (m, 2H), 1.17 (s, 9H), 1.08 (d, J=6.0 Hz, 3H) ppm; LC-MS: m/z 275.2 [M+H]$^+$.

Example 7: Preparation of Intermediate: (R)-2-methyl-N-((1R)-2-methyl-8-azaspiro[4.5]decan-1-yl)propane-2-sulfinamide (C-1K)

Step 1: Tert-Butyl 2-methyl-1-oxo-8-azaspiro[4.5]decane-8-carboxylate

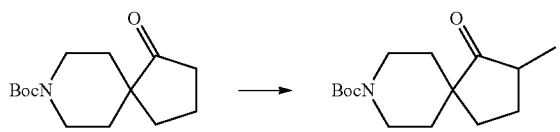 [SMILES: CC(C)(C)OC(=O)N1CCC2(CCCC2=O)CC1 ; CC1CCC2(CCN(C(=O)OC(C)(C)C)CC2)C1=O]

At 0° C. and under nitrogen atmosphere, to a 100 mL dry single-necked flask were added tert-butyl 1-oxo-8-azaspiro[4.5]decane-8-carboxylate (1 g, 3.95 mmol) and anhydrous tetrahydrofuran (15 mL), and LiHMDS (3.95 mL, 3.95 mmol) was then slowly added dropwise thereto. After stirring at 0° C. for 1 hour, iodomethane (0.25 mL, 3.95 mmol) was added thereto, and stirring was continued for 2 hours. After the reaction was completed, the reaction was quenched with saturated sodium bicarbonate solution, and the mixture was extracted with ethyl acetate (3×20 mL). The organic phases were combined, dried over Na$_2$SO$_4$, and the filtrate was concentrated under reduced pressure and purified by silica gel column chromatography (ethyl acetate/petroleum ether with a gradient of 0 to 20%) to obtain tert-butyl 2-methyl-1-oxo-8-azaspiro[4.5]decane-8-carboxylate. LCMS: m/z 368.0 [M+H]$^+$.

Step 2 and Step 3: (R)-2-methyl-N-((1R)-2-methyl-8-azaspiro[4.5]decan-1-yl)propane-2-sulfinamide (C-1K)

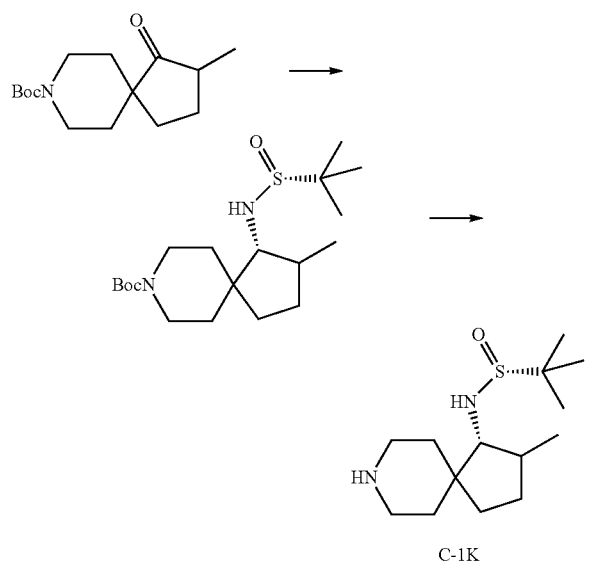

C-1K

According to the same synthesis method as the intermediate C-1A in Example 3, the ketone intermediate tert-butyl 2-methyl-1-oxo-8-azaspiro[4.5]decane-8-carboxylate was subjected to reductive amination, followed by the deprotection of the Boc protecting group to obtain (R)-2-methyl-N-((1R)-2-methyl-8-azaspiro[4.5]decan-1-yl)propane-2-sulfinamide (C-1K).

$^1$H NMR (400 MHz, CDCl$_3$) δ 5.07-4.97 (m, 1H), 3.32-3.20 (m, 1H), 3.01-2.84 (m, 2H), 2.81-2.61 (m, 2H), 2.20-2.11 (m, 1H), 2.02-1.34 (m, 8H), 1.25-1.20 (m, 9H), 1.06-0.99 (m, 3H) ppm; LCMS: m/z 273.0 [M+H]$^+$.

Example 8: Preparation of (R)—N—((R)-3,3-dimethyl-1-oxa-8-azaspiro[4.5]decan-4-yl)-2-methylpropane-2-sulfinamide (C-1L)

Step 1: Tert-Butyl 3,3-dimethyl-4-oxo-1-oxa-8-azaspiro[4.5]decane-8-carboxylate

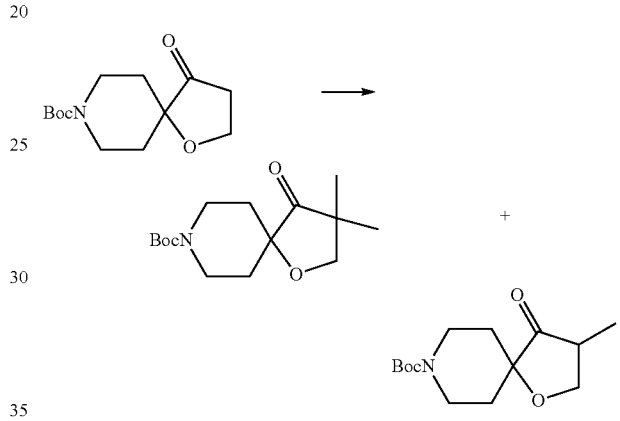

At −78° C. and under nitrogen atmosphere, to a solution of tert-butyl 4-oxo-1-oxa-8-azaspiro[4.5]decane-8-carboxylate (5 g, 19.6 mmol) in THF (50 mL) was slowly added dropwise LiHMDS (1M in THF; 19.6 mL, 19.6 mmol) and the mixture was stirred at −78° C. for 2 hours. After the reaction mixture was warmed to room temperature, iodomethane (1.22 mL, 19.6 mmol) was added thereto in portions. The resulting reaction mixture was further stirred at room temperature for 2 hours. The reaction mixture was diluted with ethyl acetate (150 mL) and quenched with saturated NaHCO$_3$ solution (150 mL), and extracted with ethyl acetate (2×300 mL). The organic phases were combined, dried over anhydrous sodium sulfate, filtered and concentrated under reduced pressure. The resulting residue was purified by silica gel chromatography (ethyl acetate/petroleum ether with a gradient of 0 to 15%) to obtain tert-butyl 3,3-dimethyl-4-oxo-1-oxa-8-azaspiro[4.5]decane-8-carboxylate (1 g, yield: 18%) and tert-butyl 3-methyl-4-oxo-1-oxa-8-azaspiro[4.5]decane-8-carboxylate (0.7 g, yield: 14%)

Tert-butyl 3,3-dimethyl-4-oxo-1-oxa-8-azaspiro[4.5]decane-8-carboxylate:

$^1$HNMR (400 MHz, CDCl$_3$) δ 3.94 (brs, 2H), 3.89 (s, 2H), 3.16-3.10 (m, 2H), 1.70-1.61 (m, 4H), 1.48 (s, 9H), 1.14 (s, 6H) ppm; LCMS: m/z 306 [M+Na]$^+$.

Tert-butyl 3-methyl-4-oxo-1-oxa-8-azaspiro[4.5]decane-8-carboxylate:

$^1$H-NMR (400 MHz, CDCl$_3$) δ 4.38 (t, J=8.8 Hz, 1H), 3.96 (brs, 2H), 3.67 (t, J=9.6 Hz, 1H), 3.14-3.09 (m, 2H), 2.65-2.58 (m, 1H), 1.75-1.46 (m, 13H), 1.15 (d, J=7.2 Hz, 3H) ppm; LCMS: m/z 292 [M+Na]$^+$.

Step 2: Tert-Butyl (S)-4-((tert-butylsulfinyl)imino)-3,3-dimethyl-1-oxa-8-azaspiro[4.5]decane-8-carboxylate

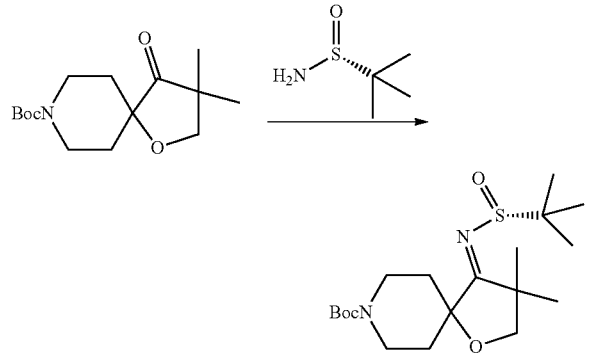

To a stirred solution of tert-butyl 3,3-dimethyl-4-oxo-1-oxa-8-azaspiro[4.5]decane-8-carboxylate (2.0 g, 7.1 mmol) in THF (5.0 mL) were added (R)-2-methylpropane-2-sulfinamide (2.56 g, 21.2 mmol) and titanium tetraethoxide (8.05 g, 35.3 mmol). The resulting reaction mixture was stirred at 90° C. for 48 hours. The reaction mixture was quenched with methanol (10 mL) and diluted with ethyl acetate (50 mL), then filtered through diatomite. The crude product obtained by concentration was separated by reversed-phase flash chromatography using 0.1% formic acid and acetonitrile as eluent to obtain tert-butyl (S)-4-((tert-butylsulfinyl)imino)-3,3-dimethyl-1-oxa-8-azaspiro[4.5]decane-8-carboxy late (1.5 g, yield: 55%).

$^1$HNMR (400 MHz, CDCl$_3$) δ 4.10-3.88 (brs, 2H), 3.80-3.72 (m, 2H), 3.04 (brs, 2H), 1.70-1.59 (m, 5H), 1.46-1.41 (m, 14H), 1.24-1.14 (m, 9H) ppm; LCMS: m/z 331 [M-55]$^+$.

Step 3: Tert-Butyl (R)-4-(((R)-tert-butylsulfinyl)amino)-3,3-dimethyl-1-oxa-8-azaspiro[4.5]decane-8-carboxylate and tert-butyl (S)-4-(((R)-tert-butylsulfinyl)amino)-3,3-dimethyl-1-oxa-8-azaspiro[4.5]decane-8-carboxylate

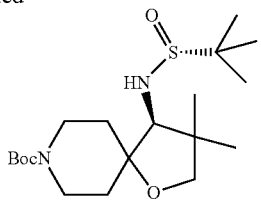

To a solution of tert-butyl (S)-4-((tert-butylsulfinyl)imino)-3,3-dimethyl-1-oxa-8-azaspiro[4.5]decane-8-carboxy late (1.5 g, 3.88 mmol) in a mixed solvent of MeOH and THF (3:1, 30 mL) was added NaBH$_4$ (886 mg, 23.3 mmol) and then the mixture was heated to reflux and stirred for 16 hours. After cooling to room temperature, the reaction mixture was concentrated to 10 mL under reduced pressure, and then poured into ice water (100 mL) and stirred for 10 minutes. The resulting solid precipitate was removed by filtration, followed by extraction with ethyl acetate (3×50 mL). The combined organic phase was dried and concentrated. The crude product obtained was isolated and purified to obtain tert-butyl (R)-4-(((R)-tert-butylsulfinyl)amino)-3,3-dimethyl-1-oxa-8-azaspiro[4.5]decane-8-carboxylate (350 mg, yield: 23%), tert-butyl (S)-4-(((R)-tert-butylsulfinyl)amino)-3,3-dimethyl-1-oxa-8-azaspiro[4.5]decane-8-carboxylate (350 mg, yield: 23%) and a mixture of the two (400 mg, yield: 28%).

Tert-butyl (S)-4-(((R)-tert-butylsulfinyl)amino)-3,3-dimethyl-1-oxa-8-azaspiro[4.5]decane-8-carboxylate: $^1$H NMR (400 MHz, CDCl$_3$) δ 3.94 (brs, 2H), 3.61 (d, J=9.2 Hz, 1H), 3.54 (d, J=9.2 Hz, 1H), 3.22 (d, J=10 Hz, 1H), 3.07-3.00 (m, 3H), 1.54-1.49 (m, 4H), 1.45 (s, 9H), 1.24 (s, 9H), 1.21 (s, 3H), 1.03 (s, 3H) ppm; LCMS: m/z 411 [M+Na]$^+$; [α]$^{25}_D$=+19.62 (c 0.25, MeOH); retention time: 1.835 min Tert-butyl (R)-4-(((R)-tert-butylsulfinyl)amino)-3,3-dimethyl-1-oxa-8-azaspiro[4.5]decane-8-carboxylate: $^1$HNMR (400 MHz, CDCl$_3$) δ 4.03-3.93 (m, 2H), 3.62-3.58 (m, 1H), 3.50-3.47 (m, 1H), 3.30 (brs, 1H), 3.11-2.96 (m, 3H), 1.91-1.76 (m, 2H), 1.54-1.56 (m, merged in DMSO, 2H) 1.43 (s, 9H), 1.25 (s, 9H), 1.03 (s, 3H), 0.99 (s, 3H) ppm; LCMS: m/z 411 [M+Na]; [α]$^{25}_D$=−43.56 (c 0.25, MeOH); retention time: 2.009 min.

Step 4: (R)—N—((R)-3,3-dimethyl-1-oxa-8-azaspiro[4.5]decan-4-yl)-2-methylpropane-2-sulfinamide (C-1L)

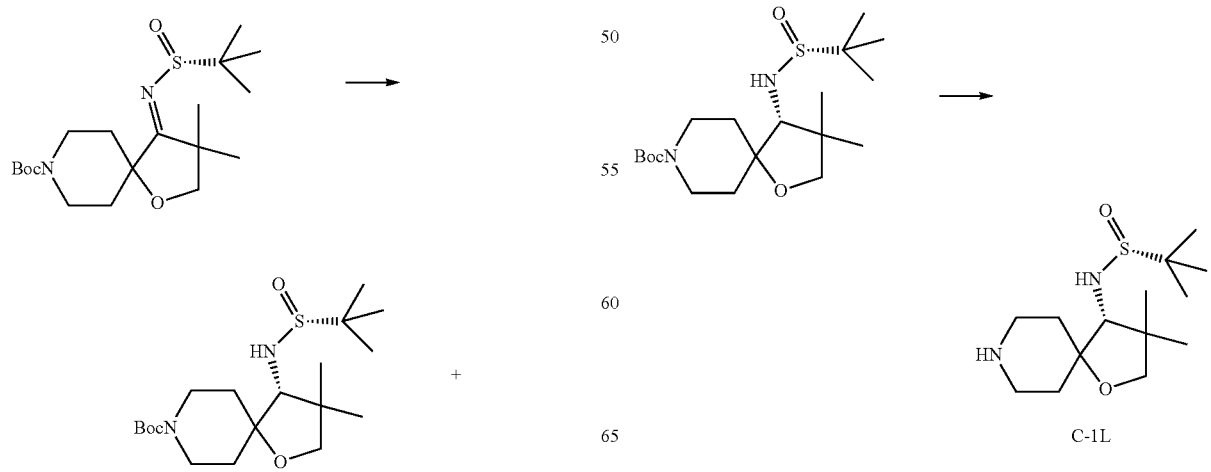

Using the same synthetic method as Step 9 of Example 6 (intermediate C-1J), tert-butyl (R)-4-(((R)-tert-butylsulfinyl)amino)-3,3-dimethyl-1-oxa-8-azaspiro[4.5]decane-8-carboxylate was subjected to deprotection of the Boc protecting group to obtain (R)—N—((R)-3,3-dimethyl-1-oxa-8-azaspiro[4.5]decan-4-yl)-2-methylpropane-2-sulfinamide C-1L.

¹H-NMR (400 MHz, DMSO-d₆) δ 4.92 (d, D₂O Exchangeable, J=11.5 Hz, 1H), 3.50 (d, J=9.0 Hz, 1H), 3.43 (d, J=9.0 Hz, 1H), 3.20-3.14 (m, 2H), 3.09 (d, J=12.0, 1H), 3.00-2.89 (m, 2H), 1.92-1.86 (m, 1H), 1.82-1.80 (m, 2H), 1.73-1.70 (m, 1H), 1.19 (s, 9H), 0.97 (s, 3H), 0.94 (s, 3H) ppm; LCMS: m/z 289 [M+H]⁺.

Example 9: Preparation of (R)—N—((S)-3,3-dimethyl-1-oxa-8-azaspiro[4.5]decan-4-yl)-2-methylpropane-2-sulfinamide (C-1M)

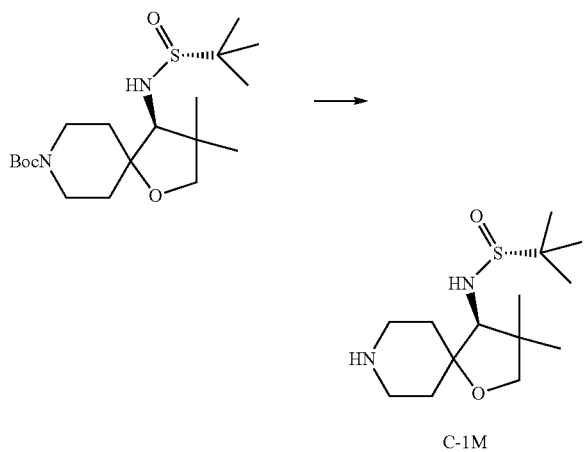

C-1M

Using the same synthetic method as Step 9 of Example 6 (intermediate C-1J), tert-butyl (S)-4-(((R)-tert-butylsulfinyl)amino)-3,3-dimethyl-1-oxa-8-azaspiro[4.5]decane-8-carboxylate was subjected to deprotection of the Boc protecting group to obtain (R)—N—((S)-3,3-dimethyl-1-oxa-8-azaspiro[4.5]decan-4-yl)-2-methylpropane-2-sulfinamide C-1M.

¹H NMR (400 MHz, DMSO-d₆) δ 8.40 (brs, D₂O Exchangeable, 1H), 8.40 (brs, D₂O Exchangeable, 1H), 5.27 (d, J=11.0 Hz, 1H), 4.12-4.10 (m, 1H), 3.77 (d, J=8.5 Hz, 1H), 3.47-3.44 (m, 2H), 3.28-3.24 (m, 1H), 3.17-3.15 (m, 1H), 2.95-2.87 (m, 2H), 1.86-1.82 (m, 2H), 1.69-1.59 (m, 2H), 1.17 (s, 9H), 1.08 (d, J=6.0 Hz, 3H) ppm; LCMS: m/z 289 [M+H]⁺.

Example 10: Preparation of Intermediate: (R)-2-methyl-N-((1R)-3-methyl-8-azaspiro[4.5]decan-1-yl)propane-2-sulfinamide (C-1N)

Step 1: Tert-Butyl 4-allyl-4-formylpiperidine-1-carboxylate

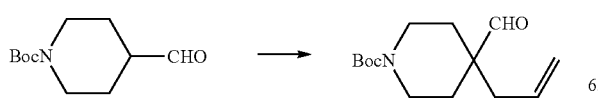

To a dry 1 L flask were added tert-butyl 4-formylpiperidine-1-carboxylate (35.0 g, 164 mmol), lithium tert-butoxide (15.77 g, 197 mmol) and allyl bromide (11.54 mL, 189 mmol) and DMF (328 mL), and the mixture was stirred at 0° C. for 1 hour. After the reaction was completed, the mixture was poured into a separating funnel charged with saturated aqueous NH₄Cl solution and H₂O (1:1, 500 mL), and extracted with Et₂O (5×50 mL). The organic phases were combined, dried over MgSO₄, filtered, and the filtrate was concentrated under reduced pressure. The resulting residue was purified by silica gel chromatography (ethyl acetate/petroleum ether with a gradient of 0 to 25%) to obtain tert-butyl 4-allyl-4-formylpiperidine-1-carboxylate as a colorless oil (24 g, yield: 48%).

¹H NMR (400 MHz, CDCl₃) δ 9.52 (s, 1H), 5.53-5.76 (m, 1H), 4.96-5.19 (m, 2H), 3.80 (br.s., 2H), 2.97 (t, J=11.49 Hz, 2H), 2.26 (d, J=7.33 Hz, 2H), 1.95 (dt, J=13.71, 3.13 Hz, 2H), 1.38-1.58 (m, 11H) ppm.

Step 2: Tert-Butyl 4-allyl-4-(1-hydroxyallyl)piperidine-1-carboxylate

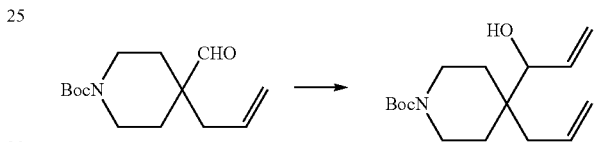

To a dry 1 L three-necked flask were added tert-butyl 4-allyl-4-formylpiperidine-1-carboxylate (24 g, 95 mmol) and THF (300 mL) sequentially, and the solution was cooled to −78° C., and vinylmagnesium bromide (1 M in THF, 118 mL, 118 mmol) was slowly added dropwise under nitrogen atmosphere. The resulting solution was slowly warmed to room temperature within 1 hour. After the reaction was completed, the mixture was poured into a separating funnel charged with saturated aqueous NH₄Cl solution (250 mL), and extracted with EtOAc (4×50 mL). The organic phases were combined, dried over MgSO₄, filtered, and the filtrate was concentrated under reduced pressure to obtain tert-butyl 4-allyl-4-(1-hydroxyallyl)piperidine-1-carboxylate (26.7 g), which was used in the next step without further purification.

¹H NMR (400 MHz, CDCl₃) δ 6.05-5.83 (m, 2H), 5.32-5.21 (m, 2H), 5.12 (s, 1H), 5.08 (d, J=3.5 Hz, 1H), 4.05-3.97 (m, 1H), 3.71 (s, 2H), 3.12 (ddd, J=13.8, 10.4, 3.6 Hz, 2H), 2.33 (dd, J=14.3, 7.8 Hz, 1H), 2.20 (dd, J=14.3, 7.2 Hz, 1H), 1.60 (q, J=4.3 Hz, 2H), 1.57-1.50 (m, 2H), 1.45 (s, 9H) ppm.

Step 3: Tert-Butyl 4-acryloyl-4-allylpiperidine-1-carboxylate

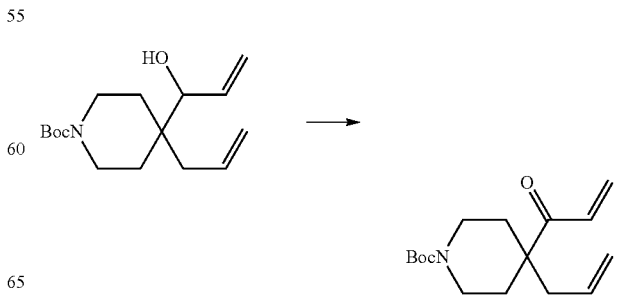

To a dry 1 L three-necked flask were successively added tert-butyl 4-allyl-4-(1-hydroxyallyl)piperidine-1-carboxylate (26.7 g, 95 mmol), and Dess-Martin oxidant (44.3 g, 105 mmol) and anhydrous dichloromethane (380 mL), and the mixture was stirred at room temperature for 1 hour. After the reaction was completed, the mixture was poured into a separating funnel charged with a saturated aqueous solution of NaHCO$_3$:Na$_2$SO$_3$ (1:1, 300 mL), and then extracted with DCM (4×50 mL). The organic phases were combined, dried over MgSO$_4$, filtered, and the filtrate was concentrated under reduced pressure to obtain a white solid. The white solid was suspended in petroleum ether (250 mL) and sonicated for 20 minutes. The white suspension was filtered through a pad of diatomite, and the filtrate was concentrated under reduced pressure to obtain tert-butyl 4-acryloyl-4-allylpiperidine-1-carboxylate (25 g, two-step yield: 94%) as a yellow oil.

$^1$H NMR (400 MHz, CDCl$_3$) δ 6.80 (dd, J=16.8, 10.3 Hz, 1H), 6.39 (dd, J=16.8, 1.9 Hz, 1H), 5.70 (dd, J=10.3, 1.9 Hz, 1H), 5.55 (ddt, J=17.5, 10.2, 7.4 Hz, 1H), 5.09-4.98 (m, 2H), 3.77 (s, 2H), 2.94 (s, 2H), 2.31 (d, J=7.4 Hz, 2H), 2.08 (d, J=13.8 Hz, 2H), 1.47-1.41 (m, 11H) ppm Step 4: Tert-Butyl 1-oxo-8-azaspiro[4.5]dec-2-ene-8-carboxylate

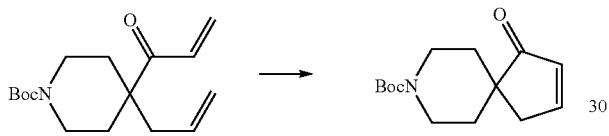

To a dry 1 L three-necked flask were added tert-butyl 4-acryloyl-4-allylpiperidine-1-carboxylate (25 g, 89.6 mmol), toluene (degassed, 850 mL), and a solution of Grubbs' second-generation catalyst (2.02 g, 2.38 mmol) in toluene (degassed, 100 mL). The resulting mixture was stirred at 85° C. for 45 minutes under nitrogen atmosphere. After the reaction was completed, the solvent was removed under reduced pressure, and the obtained residue was purified by silica gel chromatography (ethyl acetate/petroleum ether with a gradient of 0 to 40%) to obtain tert-butyl 1-oxo-8-azaspiro[4.5]dec-2-ene-8-carboxylate (19 g, 83 mmol) as a brown solid. A solution of this compound and DDQ (565 mg, 2.49 mmol) in toluene (540 mL) was stirred at room temperature for 15 minutes. The resulting bright red solution was filtered through a pad of diatomite, followed by addition of charcoal (100 g), and the resulting suspension was stirred at room temperature for 2 hours. The mixture was filtered through a pad of diatomite and the filtrate was concentrated under reduced pressure. The residue obtained was purified by silica gel chromatography (ethyl acetate/petroleum ether with a gradient of 0 to 40%) to obtain tert-butyl 1-oxo-8-azaspiro[4.5]dec-2-ene-8-carboxylate (12 g, yield: 53.3%) as a white solid.

Step 5: Tert-Butyl 3-methyl-1-oxo-8-azaspiro[4.5]decane-8-carboxylate

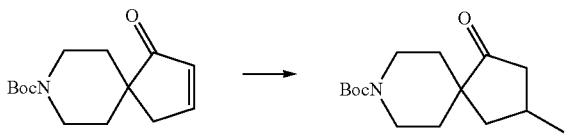 [SMILES: CC(C)(C)OC(=O)N1CCC2(CC=CC2=O)CC1 ; CC1CC(=O)C2(CCN(C(=O)OC(C)(C)C)CC2)C1]

Under nitrogen atmosphere, to a 250 mL dry three-necked flask was added CuI (3.8 g, 20 mmol) and anhydrous tetrahydrofuran (100 mL) sequentially. The solution was cooled to −20° C., and MeLi (1.6 M in THF, 25 mL, 40 mmol) was slowly added dropwise to the solution. After the dropwise addition, the reaction solution was reacted at −20° C. until the solution was clear. At this temperature, a solution of tert-butyl 1-oxo-8-azaspiro[4.5]dec-2-ene-8-carboxylate (2.51 g, 10 mmol) in tetrahydrofuran (20 mL) was slowly added dropwise. After the reaction was completed, the mixture was poured into a separating funnel charged with saturated aqueous NH$_4$Cl solution, and extracted with ethyl acetate (3×15 mL). The organic phases were combined, dried over MgSO$_4$, filtered and the filtrate was concentrated under reduced pressure and purified by silica gel chromatography (ethyl acetate/petroleum ether with a gradient of 0 to 50%) to obtain tert-butyl 3-methyl-1-oxo-8-azaspiro[4.5]decane-8-carboxylate (1.6 g, yield: 60%).

$^1$H NMR (400 MHz, CDCl$_3$) δ 3.92 (s, 1H), 3.81 (s, 1H), 3.55 (d, J=5.0 Hz, 1H), 3.13-3.04 (m, 1H), 2.96 (t, J=10.9 Hz, 1H), 2.56-2.46 (m, 1H), 2.31-2.21 (m, 2H), 1.94-1.75 (m, 2H), 1.62-1.49 (m, 1H), 1.45 (s, 9H), 1.41-1.35 (m, 2H), 1.15 (d, J=6.0 Hz, 3H), 0.90 (t, J=6.9 Hz, 3H) ppm.

Step 6 and Step 7: (R)-2-methyl-N-((1R)-3-methyl-8-azaspiro[4.5]decan-1-yl)propane-2-sulfinamide (C-1N)

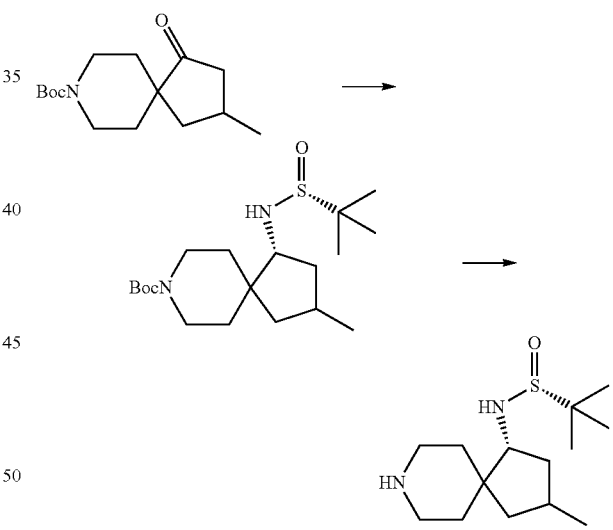

Using the same synthetic method as that of steps 8 and 9 of the intermediate C-1J, the ketone intermediate tert-butyl 3-methyl-1-oxo-8-azaspiro[4.5]decane-8-carboxylate was subjected to reductive amination and deprotection of the Boc protecting group to obtain (R)-2-methyl-N-((1R)-3-methyl-8-azaspiro[4.5]decan-1-yl)propane-2-sulfinamide (C-1N).

$^1$H NMR (400 MHz, CDCl$_3$) δ $^1$H NMR (400 MHz, DMSO-d$_6$) δ 3.04-2.95 (m, 1H), 2.75 (s, 2H), 2.62-2.53 (m, 2H), 1.93-1.57 (m, 5H), 1.52-1.27 (m, 13H), 0.96 (d, J=6.5 Hz, 3H) ppm; LCMS: m/z 273 [M+H]$^+$.

Example 11: Preparation of Intermediate: (R)-2-methyl-N-((1R,3R)-3-hydroxy-8-azaspiro[4.5]decan-1-yl)propane-2-sulfinamide (C-10)

Step 1: Tert-Butyl (R)-3-((tert-butyldimethylsilyl)oxy)-1-oxo-8-azaspiro[4.5]decane-8-carboxylate

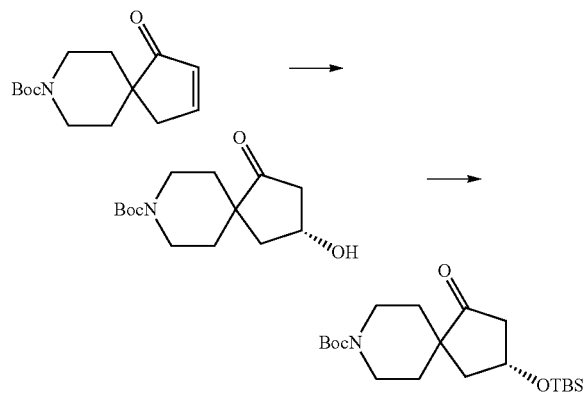

To a dry 100 mL three-necked flask were added CuCl (19 mg, 0.19 mmol), (s)-TolBINAP (129 mg, 0.19 mmol), sodium tert-butoxide (18 mg, 0.19 mmol) and THF (9 mL). The mixture was stirred at room temperature for 30 minutes, followed by addition of a solution of $B_2Pin_2$ (1.78 g, 7.01 mmol) in THF (2.5 mL). The resulting mixture was stirred at room temperature for 10 minutes, followed by addition of a solution of tert-butyl 1-oxo-8-azaspiro[4.5]dec-2-ene-8-carboxylate (1.60 g, 6.37 mmol) in THF (9 mL) and MeOH (0.53 mL, 12.74 mmol). The resulting mixture was stirred at room temperature for 16 hours. After the reaction was completed, $H_2O$ (20 mL) was added, followed by sodium perborate (4.84 g, 32 mmol), and the resulting mixture was vigorously stirred at room temperature for 1 hour. The resulting green suspension was filtered through a pad of diatomite, poured into a separating funnel charged with saturated aqueous $NaHCO_3$ and saturated aqueous $Na_2SO_3$ (40 mL), and extracted with EtOAc (4×40 mL). The organic phases were combined, dried over $MgSO_4$, filtered and the filtrate was concentrated under reduced pressure to obtain crude tert-butyl (R)-3-hydroxy-1-oxo-8-azaspiro[4.5]decane-8-carboxylate.

In a 100 mL single-necked flask were added the crude tert-butyl (R)-3-hydroxy-1-oxo-8-azaspiro[4.5]decane-8-carboxylate (theoretical amount, 6.37 mmol), imidazole (650 mg, 9.56 mmol), TBSCl (1.20 g, 7.96 mmol) and DMF (16 mL) sequentially, and the mixture was stirred at room temperature for 16 hours. After the reaction was completed, the reaction mixture was poured into a separating funnel charged with saturated aqueous $NH_4Cl$ solution (30 mL), and extracted with ethyl acetate (5×50 mL). The organic phases were combined, dried over $MgSO_4$, filtered and concentrated under reduced pressure. The residue obtained was purified by silica gel chromatography (ethyl acetate/petroleum ether with a gradient of 0 to 40%) to obtain tert-butyl (R)-3-((tert-butyldimethylsilyl)oxy)-1-oxo-8-azaspiro[4.5]decane-8-carboxylate (1.26 g, yield: 51.6%) as a colorless oil LCMS: m/z 328 [M-56+H]$^+$.

Step 2: Tert-Butyl (1R,3R)-3-((tert-butyldimethylsilyl)oxy)-1-((R)-1,1-dimethylethylsulfinamido)-8-azaspiro[4.5]decane-8-carboxylate

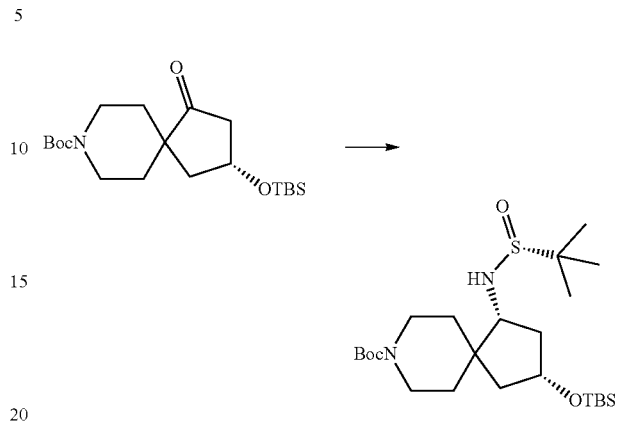

Using the same synthetic method as that of Step 8 of the intermediate C-1J, the ketone intermediate (R)-3-((tert-butyldimethylsilyl)oxy)-1-oxo-8-azaspiro[4.5]decane-8-carboxylate was subjected to reductive amination to obtain tert-butyl (1R,3R)-3-((tert-butyldimethylsilyl)oxy)-1-((R)-1,1-dimethylethylsulfinamido)-8-azaspiro[4.5]decane-8-carboxylate (1.24 g, yield: 77%) as a white solid.

$^1$H NMR (400 MHz, CDCl$_3$) δ 4.23 (s, 1H), 3.84 (d, J=13.6 Hz, 2H), 3.24 (s, 1H), 2.77 (td, J=12.7, 12.0, 3.0 Hz, 2H), 2.27 (d, J=8.8 Hz, 1H), 1.72-1.54 (m, 5H), 1.38 (s, 9H), 1.19 (d, J=2.5 Hz, 3H), 1.14 (s, 9H), 0.80 (s, 9H), −0.03 (s, 6H) ppm; LCMS: m/z 488.9 [M+H]$^+$.

Step 3: (R)—N-((1R,3R)-3-hydroxy-8-azaspiro[4.5]decan-1-yl)-2-methylpropane-2-sulfinamide (C-10)

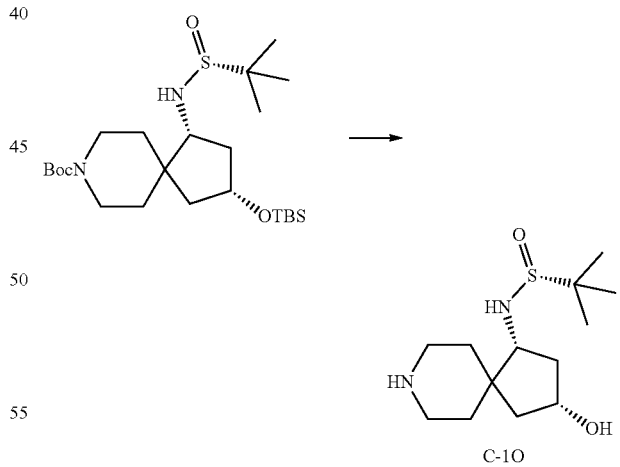

Under an ice bath, to a solution of tert-butyl (1R)-3-((tert-butyldimethylsilyl)oxy)-1-((R)-1,1-dimethylethylsulfinamido)-8-azaspiro[4.5]decane-8-carboxylate (49 mg, 0.1 mmol) in 1,4-dioxane (1 mL) was added concentrated sulfuric acid (0.023 mL, 0.4 mmol). The reaction mixture was stirred at room temperature for 2 hours. The reaction solution was adjusted to pH of 12 with sodium hydroxide solution, and then extracted with DCM (4×10 mL). The organic phases were combined, dried over anhydrous sodium sulfate, filtered, and the volatiles were removed under reduced pressure to obtain (R)—N-((1R,3R)-3-hydroxy-8-azaspiro[4.5]decan-1-yl)-2-methylpropane-2-sulfinamide (C-10) (20 mg, yield: 70%). LC-MS: m/z 275 [M+H]+.

Example 12: Preparation of Intermediate: (R)-3,3-difluoro-8-azaspiro[4.5]decan-1-amine (C-1P)

Step 1: (1R,3R)-1-amino)-3-hydroxy-8-azaspiro[4.5]decane

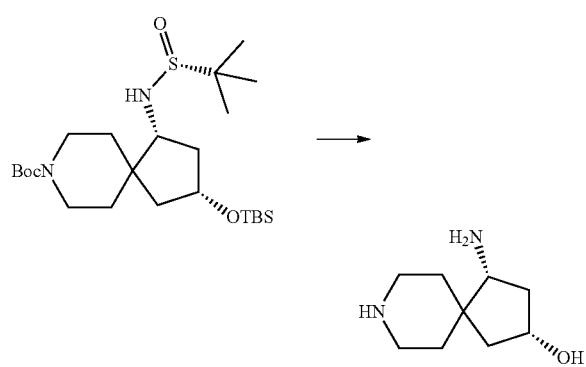

At room temperature, to a solution of tert-butyl (1R,3R)-3-((tert-butyldimethylsilyl)oxy)-1-((R)-1,1-dimethylethylsulfinamido)-8-azaspiro[4.5]decane-8-carboxylate (100 mg, 0.2 mmol) in methanol (5 mL) was slowly added a solution of hydrogen chloride in 1,4-dioxane (4M, 2 mmol, 0.5 mL), and the reaction solution was heated at 40° C. for 1 hour. The mixture was concentrated under reduced pressure to obtain (1R,3R)-1-amino)-3-hydroxy-8-azaspiro[4.5]decane, which was directly used in the next reaction.
LC-MS: m/z 171.0.

Step 2: Tert-Butyl (1R,3R)-1-((tert-butoxycarbonyl)amino)-3-hydroxy-8-azaspiro[4.5]decane-8-carboxylate (C-1P-b)

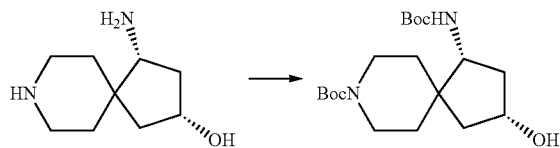 [SMILES: N[C@@H]1C[C@H](O)CC12CCNCC2 ; CC(C)(C)OC(=O)N[C@@H]1C[C@H](O)CC12CCN(C(=O)OC(C)(C)C)CC2]

The above (1R,3R)-1-amino)-3-hydroxy-8-azaspiro[4.5]decane (0.2 mmol) was dissolved in tetrahydrofuran (10 mL), followed by addition of (Boc)₂O (109 mg, 0.5 mmol) and DIPEA (516 mg, 4.0 mmol), and the reaction solution was stirred at room temperature for 16 hours. After the reaction was completed, saturated ammonium chloride was added to quench the reaction, followed by extraction with diethyl ether (5×50 mL). The organic phases were combined, dried over anhydrous sodium sulfate, filtered and concentrated under reduced pressure to obtain a crude product, which was purified by silica gel chromatography (ethyl acetate/petroleum ether with a gradient of 0 to 50%) to obtain tert-butyl (1R,3R)-1-((tert-butoxycarbonyl)amino)-3-hydroxy-8-azaspiro[4.5]decane-8-carboxylate (C-1P-b) (60 mg, two-step yield: 80%).
¹H NMR (400 MHz, CDCl₃) δ 5.11 (s, 1H), 4.36 (s, 1H), 3.86-3.62 (m, 3H), 2.94 (t, J=11.7 Hz, 2H), 2.20-2.08 (m, 1H), 1.81 (d, J=8.5 Hz, 1H), 1.64-1.55 (m, 3H), 1.49-1.42 (m, 3H), 1.37 (d, J=4.9 Hz, 18H) ppm; LC-MS: m/z 393.2 [M+H]+.

Step 3: Tert-Butyl (R)-1-((tert-butoxycarbonyl)amino)-3-oxo-8-azaspiro[4.5]decane-8-carboxylate

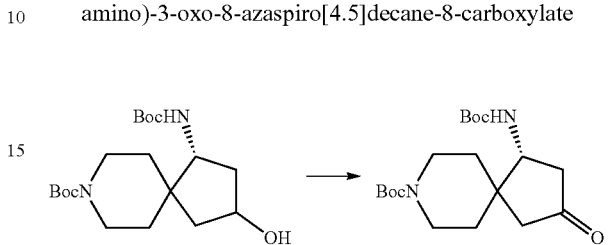

Tert-butyl (1R,3R)-1-((tert-butoxycarbonyl)amino)-3-hydroxy-8-azaspiro[4.5]decane-8-carboxylate (60 mg, 0.16 mmol) was dissolved in dichloromethane (5 mL) at 0° C., then Dess-Martin (76 mg, 0.18 mmol) was slowly added at 0° C., and the reaction solution was kept at 0° C. to further react for 2 hours. After the reaction was completed, water (4 mL) was added to quench the reaction, followed by extraction with dichloromethane (5×50 mL). The organic phases were combined, dried over anhydrous sodium sulfate, filtered and concentrated under reduced pressure to obtain a crude product, which was then purified by silica gel chromatography (ethyl acetate/petroleum ether with a gradient of 0 to 80%) to obtain tert-butyl (R)-1-((tert-butoxycarbonyl)amino)-3-oxo-8-azaspiro[4.5]decane-8-carboxylate (30 mg, yield: 50%).
¹H NMR (400 MHz, CDCl₃) δ 4.46 (d, J=9.4 Hz, 1H), 4.07 (d, J=7.0 Hz, 1H), 3.92 (s, 2H), 2.73 (t, J=12.7 Hz, 2H), 2.63 (dd, J=19.0, 8.1 Hz, 1H), 2.41 (d, J=18.3 Hz, 1H), 2.14-2.01 (m, 2H), 1.68 (td, J=12.9, 4.6 Hz, 1H), 1.59 (d, J=4.8 Hz, 1H), 1.39 (d, J=2.5 Hz, 18H), 1.26 (d, J=2.9 Hz, 1H) ppm; LC-MS: m/z 369.1 [M+H]+.

Step 4: Tert-Butyl (R)-1-((tert-butoxycarbonyl)amino)-3,3-difluoro-8-azaspiro[4.5]decane-8-carboxylate

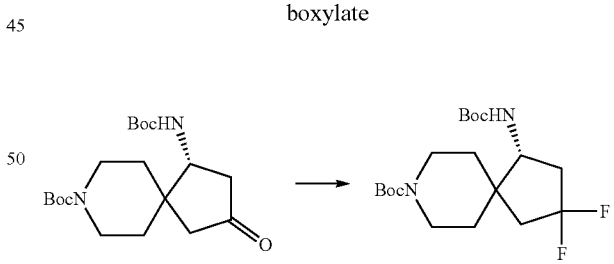

(R)-1-((Tert-butoxycarbonyl)amino)-3-oxo-8-azaspiro[4.5]decane-8-carboxylate (80 mg, 0.22 mmol) was dissolved in dichloromethane (10 mL), then DeoxoFluor (162 µL, 0.88 mmol) was added, and the reaction solution was stirred at 50° C. for 48 hours. After the reaction was completed, the reaction solution was quenched with saturated sodium bicarbonate solution at 0° C., extracted with ethyl acetate (3×20 mL). The organic phases were combined, dried over anhydrous sodium sulfate, filtered, and concentrated under reduced pressure to obtain (R)-1-((tert-butoxycarbonyl)amino)-3,3-difluoro-8-azaspiro[4.5]decane-8-carboxylate (46 mg, yield: 54%).

$^1$H NMR (400 MHz, CDCl$_3$) δ 4.49 (d, J=9.9 Hz, 1H), 3.92 (dd, J=24.5, 15.9 Hz, 3H), 2.87-2.68 (m, 2H), 2.58-2.42 (m, 1H), 2.21 (td, J=17.7, 16.8, 9.6 Hz, 1H), 2.06-1.86 (m, 2H), 1.60 (t, J=6.6 Hz, 1H), 1.38 (d, J=4.0 Hz, 21H) ppm; LC-MS: m/z 391.1 [M+H]$^+$ Step 5: (R)-3,3-difluoro-8-azaspiro[4.5]decan-1-amine (C-1P)

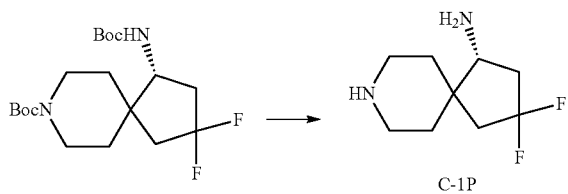

To a solution of (R)-1-((tert-butoxycarbonyl)amino)-3,3-difluoro-8-azaspiro[4.5]decane-8-carboxylate (46 mg, 0.12 mmol) in methanol (5 mL) was slowly added a solution of hydrogen chloride in 1,4-dioxane (4 M, 1.2 mmol, 0.3 mL), and the reaction solution was reacted at room temperature for 1 hour. The mixture was concentrated under reduced pressure to obtain (R)-3,3-difluoro-8-azaspiro[4.5]decan-1-amine (C-1P). LC-MS: m/z 191.1 [M+H]$^+$.

Example 13: Preparation of Intermediate: 1-methyl-8-azaspiro[4.5]decan-1-amine (C-2A)

Step 1: tert-butyl 1-hydroxy-1-methyl-8-azaspiro[4.5]decane-8-carboxylate

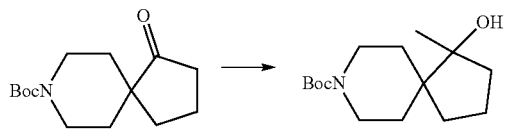 [SMILES: CC(C)(C)OC(=O)N1CCC2(CCCC2=O)CC1 ; CC(C)(C)OC(=O)N1CCC2(CCCC2(C)O)CC1]

To a solution of tert-butyl 1-oxo-8-azaspiro[4.5]decane-8-carboxylate (500 mg, 2.0 mmol) in toluene (20 mL) was slowly added a solution of methyl magnesium bromide in tetrahydrofuran (1 M, 2.2 mmol, 2.2 mL) at 0° C., and the reaction solution was stirred at 0° C. for 1 hour. After the reaction was completed, the reaction solution was quenched with saturated aqueous ammonium chloride solution, and then extracted with ethyl acetate (3×20 mL). The organic phases were combined, dried over anhydrous sodium sulfate, filtered and concentrated under reduced pressure to obtain a crude product, which was purified by silica gel chromatography (ethyl acetate/petroleum ether with a gradient of 0 to 50%) to obtain tert-butyl 1-hydroxy-1-methyl-8-azaspiro[4.5]decane-8-carboxylate (410 mg, yield: 77%).

$^1$H NMR (400 MHz, CDCl$_3$) δ 4.16-4.04 (m, 2H), 3.12-2.56 (m, 2H), 1.98-1.49 (m, 8H), 1.49 (s, 9H), 1.42-1.29 (m, 2H), 1.16 (s, 3H) ppm; LC-MS: m/z 270.2 [M+H]$^+$.

Step 2: N-(1-methyl-8-azaspiro[4.5]decan-1-yl)acetamide

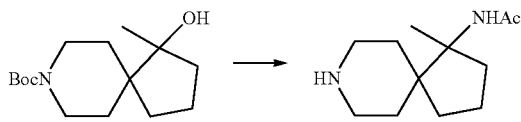 [SMILES: CC(C)(C)OC(=O)N1CCC2(CCCC2(C)O)CC1 ; CC(=O)NC1(C)CCCC12CCNCC2]

Tert-butyl 1-hydroxy-1-methyl-8-azaspiro[4.5]decane-8-carboxylate (410 mg, 1.52 mmol) was dissolved in acetonitrile (1.82 mL), followed by addition of concentrated sulfuric acid (1.56 mL) at 0° C., and then the reaction solution was stirred at room temperature for 16 hours. After the reaction was completed, the reaction solution was poured into ice water, and then basified with aqueous NaOH (50%) solution to pH of 12, followed by extraction with ethyl acetate (3×20 mL). The organic phases were combined, dried over anhydrous sodium sulfate, filtered and concentrated under reduced pressure to obtain a crude product of N-(1-methyl-8-azaspiro[4.5]decan-1-yl)acetamide (260 mg, yield: 81%), which was directly used in the next step.

LC-MS: m/z 211.0 [M+H]$^+$.

Step 3: 1-methyl-8-azaspiro[4.5]decan-1-amine (C-2A)

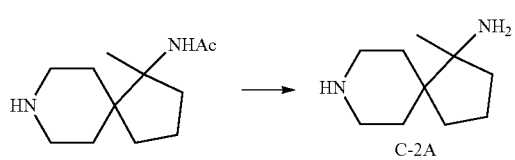

The crude product of N-(1-methyl-8-azaspiro[4.5]decan-1-yl)acetamide (260 mg, 1.23 mmol) was dissolved in 6 M hydrochloric acid (5 mL) at room temperature and the reaction solution was reacted under microwave heating at 120° C. for 4 hours. After the reaction was completed, the reaction solution was concentrated under reduced pressure and then lyophilized to obtain a crude product of 1-methyl-8-azaspiro[4.5]decan-1-amine C-2A (200 mg, yield: 97%), which was used in the next reaction without purification.

LC-MS: m/z 169.1 [M+H]$^+$.

Example 14: Preparation of intermediate: 4-ethylpiperidin-4-amine (C-3A)

Step 1: methyl 1-benzyl-4-ethylpiperidine-4-carboxylate

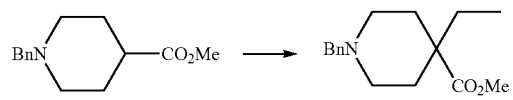

At −78° C. under nitrogen atmosphere, to a solution of methyl 1-benzylpiperidine-4-carboxylate (1 g, 4.3 mmol) in tetrahydrofuran (10 mL) was slowly added dropwise a solution of LDA in tetrahydrofuran (1 M, 5.1 mmol, 5.1 mL), and the reaction solution was stirred at −78° C. for 1 hour. Then iodoethane (795 mg, 5.1 mmol) in tetrahydrofuran (1 mL) was slowly added, and the reaction solution was further reacted at −78° C. for 4 hours. After the reaction was completed, the reaction solution was quenched with saturated aqueous ammonium chloride solution, and then extracted with ethyl acetate (3×30 mL). The organic phases were combined, dried over anhydrous sodium sulfate, filtered and concentrated under reduced pressure to obtain a crude product, which was purified by silica gel chromatography (ethyl acetate/petroleum ether with a gradient of 0 to 50%) to obtain methyl 1-benzyl-4-ethylpiperidine-4-carboxylate (800 mg, yield: 71%).

LC-MS: m/z 262.2 [M+H]⁺.

Step 2: 1-benzyl-4-ethylpiperidine-4-carboxylic Acid

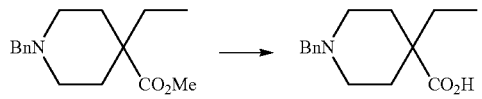

Methyl 1-benzyl-4-ethylpiperidine-4-carboxylate (800 mg, 3.23 mmol) was dissolved in an aqueous solution of ethanol (ethanol:water=4:1, 20 mL), followed by addition of NaOH (517 mg, 12.9 mmol), and then the reaction solution was stirred at room temperature for 16 hours. After the reaction was completed, the reaction solution was concentrated under reduced pressure, then acidified with 1 N hydrochloric acid to pH of 3, and then extracted with ethyl acetate (3×30 mL). The organic phases were combined, dried over anhydrous sodium sulfate, filtered and concentrated under reduced pressure to obtain the product 1-benzyl-4-ethylpiperidine-4-carboxylic acid (720 mg, yield: 90%), which was directly used in the next reaction.

LC-MS: m/z 248.2 [M+H]⁺.

Step 3: 1-methyl-8-azaspiro[4.5]decan-1-amine

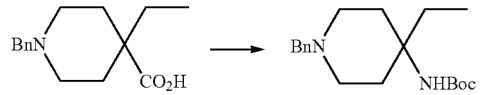

1-Benzyl-4-ethylpiperidine-4-carboxylic acid (250 mg, 1.0 mmol) was dissolved in tert-butanol (5 mL) at room temperature, followed by addition of triethylamine (306 mg, 3.0 mmol) and diphenyl azidophosphate (330 mg, 2.0 mmol), and then the reaction solution was refluxed for 8 hours. After the reaction was completed, water was added to quench the reaction, and the resulting mixture was extracted with ethyl acetate (3×30 mL). The organic phases were combined, dried over anhydrous sodium sulfate, filtered and concentrated under reduced pressure to obtain a crude product, which was purified by silica gel chromatography (ethyl acetate/petroleum ether with a gradient of 0 to 70%) to obtain 1-methyl-8-azaspiro[4.5]decan-1-amine (160 mg, yield: 50%).

LC-MS: m/z 319.2 [M+H]⁺.

Step 4: Tert-Butyl (4-ethylpiperidin-4-yl)carbamate

1-Methyl-8-azaspiro[4.5]decan-1-amine (160 mg, 0.5 mmol) was dissolved in 10 mL of methanol at room temperature, followed by addition of Pd/C (16 mg, 10%). The reaction solution was reacted under hydrogen atmosphere for 16 hours, and then filtered through diatomite, washed with ethyl acetate, and concentrated under reduced pressure to obtain tert-butyl (4-ethylpiperidin-4-yl)carbamate (110 mg, yield: 95%), which was directly used in the next reaction.

LC-MS: m/z 229.2 [M+H]⁺.

Step 5: 4-ethylpiperidin-4-amine (C-3A)

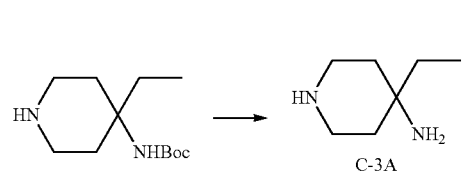

Tert-butyl (4-ethylpiperidin-4-yl)carbamate (110 mg, 0.5 mmol) was dissolved in methanol (3 mL) at room temperature, followed by addition of a solution of hydrogen chloride in 1,4-dioxane (4 N, 5 mmol, 1.1 mL). The reaction solution was stirred at room temperature for 2 hours, and concentrated under reduced pressure to obtain the product 4-ethylpiperidin-4-amine (C-3A) (50 mg, yield: 95%), which was directly used in the next reaction.

LC-MS: m/z 128.2 [M+H]⁺.

Example 15: Preparation of Intermediate: tert-butyl ((4-methylpiperidin-4-yl)methyl)carbamate (C-4A)

Step 1: 1-benzoyl-4-methylpiperidine-4-carbonitrile

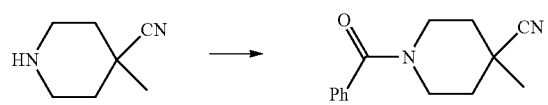

Under nitrogen atmosphere, to a 100 mL dry single-necked flask were added 4-methylpiperidine-4-carbonitrile (496 mg, 4 mmol), DCM (10 mL) and triethylamine (611 mg, 6 mmol), and benzoyl chloride (670 mg, 4.8 mmol) was slowly added dropwise at room temperature. The mixture was stirred at room temperature for 1 hour, and the reaction was monitored by TLC until the raw material was consumed. The reaction solution was quenched with 1N HCl solution, and then extracted with dichloromethane (3×20 mL). The organic phases were combined, dried over Na₂SO₄, and the filtrate was concentrated under reduced pressure and purified by silica gel column chromatography (ethyl acetate/petroleum ether with a gradient of 0 to 40%) to obtain 1-benzoyl-4-methylpiperidine-4-carbonitrile (650 mg, yield: 70.72%).

LC-MS: m/z 229 [M+H]⁺.

Step 2: Tert-Butyl 1-benzoyl-((4-methylpiperidin-4-yl)methyl)carbamate

At 0° C. and under nitrogen atmosphere, to a 100 mL dry flask were added 1-benzoyl-4-methylpiperidine-4-carbonitrile (650 mg, 2.85 mmol), nickel chloride hexahydrate (135 mg, 0.67 mmol), di-tert-butyl dicarbonate (1.86 g, 8.54 mmol) and methanol (12 mL), and sodium borohydride (754 mg, 20 mmol). The reaction solution was stirred at room temperature for 12 hours, and the reaction was monitored by TLC until the raw material was consumed. After the reaction was completed, the reaction solution was concentrated and extracted with dichloromethane (3×20 mL). The organic phases were combined, and dried over $Na_2SO_4$. The filtrate was concentrated under reduced pressure and purified by silica gel column chromatography (ethyl acetate/petroleum ether with a gradient of 0 to 40%) to obtain tert-butyl 1-benzoyl-((4-methylpiperidin-4-yl)methyl)carbamate (620 mg, yield: 65.50%).

LC-MS: m/z 333 [M+H]$^+$.

Step 3: Tert-Butyl ((4-methylpiperidin-4-yl)methyl)carbamate (C-4A)

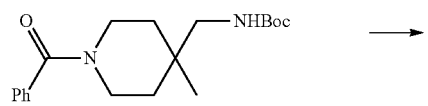

To a 100 mL single-necked flask were added tert-butyl 1-benzoyl-((4-methylpiperidin-4-yl)methyl)carbamate (620 mg, 1.87 mmol), ethanol (8 mL) and 7N NaOH (2 mL), and then the mixture was heated to 90° C. under nitrogen atmosphere and stirred for 8 hours. After the mixture was cooled to room temperature, the mixture was filtered, diluted with water and extracted with ethyl acetate (3×20 mL). The organic phases were combined, and dried over $Na_2SO_4$. The filtrate was concentrated under reduced pressure and purified by silica gel column chromatography (ethyl acetate/petroleum ether with a gradient of 0 to 80%) to obtain tert-butyl ((4-methylpiperidin-4-yl)methyl)carbamate (C-4A) (300 mg, yield: 70.5%).

$^1$H NMR (400 MHz, DMSO-$d_6$) δ 3.97 (q, J=7.0 Hz, 2H), 2.80 (d, J=6.4 Hz, 2H), 2.65 (d, J=30.3 Hz, 2H), 1.38 (s, 9H), 1.27 (dd, J=16.2, 7.0 Hz, 2H), 1.10 (d, J=12.8 Hz, 2H), 0.81 (s, 3H) ppm; LC-MS: m/z 229 [M+H]$^+$.

Example 16: Preparation of Intermediate: tert-butyl ((4-phenylpiperidin-4-yl)methyl)carbamate (C-4B)

Step 1: Tert-Butyl 4-cyano-4-phenylpiperidine-1-carboxylate

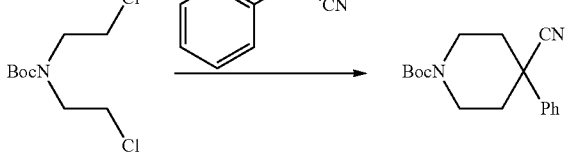

At 0° C., to a solution of tert-butyl (2-chloroethyl)carbamate (2 g, 8.26 mmol) and 2-phenylacetonitrile (968 mg, 8.26 mmol) in anhydrous DMF (20 mL) was added NaH (60% dispersed in mineral oil, 1.6 g, 41.3 mmol) in portions. The reaction mixture was heated at 60° C. for 16 hours. After the reaction was completed, the reaction solution was quenched with ice water (30 mL), and then extracted (3×50 mL). The organic phases were combined, washed with saturated brine (2×50 mL), dried over sodium sulfate, filtered and concentrated under reduced pressure. The crude product was purified by silica gel column chromatography (ethyl acetate/petroleum ether with a gradient of 0 to 40%) to obtain tert-butyl 4-cyano-4-phenylpiperidine-1-carboxylate (500 mg, yield: 21%).

LCMS: m/z 187.2 [M-100]$^+$.

Step 2: Tert-Butyl 4-(aminomethyl)-4-phenylpiperidine-1-carboxylate

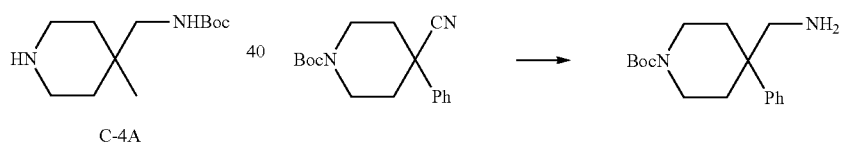

Tert-butyl 4-cyano-4-phenylpiperidine-1-carboxylate (0.5 g, 1.75 mmol) was dissolved in 20 mL of methanol, followed by addition of palladium on carbon (50 mg), and the reaction solution was reacted under hydrogen atmosphere for 16 hours. After the reaction was completed, the mixture was filtered and concentrated under reduced pressure to obtain tert-butyl 4-(aminomethyl)-4-phenylpiperidine-1-carboxylate (0.4 g, yield: 80%).

$^1$H NMR (400 MHz, CDCl$_3$) δ 7.38 (t, J=7.6 Hz, 2H), 7.30 (d, J=7.5 Hz, 2H), 7.24 (d, J=7.2 Hz, 1H), 3.75 (d, J=7.8 Hz, 2H), 3.04 (t, J=11.2 Hz, 2H), 2.58 (brs, 2H), 2.21 (d, J=13.9 Hz, 2H), 1.76-1.61 (m, 2H), 1.44 (s, 9H) ppm; LC-MS: m/z 191.0 [M-100]$^+$.

Step 3: (4-phenylpiperidin-4-yl)methanamine (C-4B)

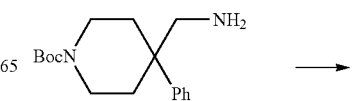

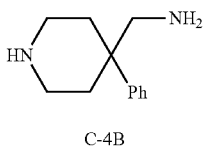

C-4B

Tert-butyl 4-(aminomethyl)-4-phenylpiperidine-1-carboxylate (0.4 g, 1.37 mmol) was dissolved in 10 mL of methanol, followed by addition of a solution of hydrogen chloride in 1,4-dioxane (4 M, 13.7 mmol) at room temperature. The reaction solution was reacted at room temperature for 2 hours. After the reaction was completed, the mixture was concentrated under reduced pressure to obtain (4-phenylpiperidin-4-yl)methanamine (C-4B) (0.25 g, yield: 95%), which was directly used in the next reaction.
LC-MS: m/z 191.2 [M+H]$^+$.

Example 17: Preparation of Intermediate Sodium 6-((tert-butoxycarbonyl)amino)-2,3-dichloropyridine-4-thiolate (F-1A)

Step 1: Tert-Butyl (6-chloropyridin-2-yl)carbamate

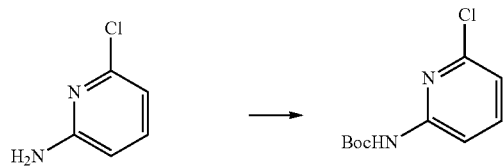 [SMILES: Nc1cccc(Cl)n1 ; CC(C)(C)OC(=O)Nc1cccc(Cl)n1]

Under nitrogen atmosphere, to a dry 250 mL three-necked flask were added 6-chloropyridin-2-amine (8 g, 62.2 mmol) and THF (80 mL). The mixture was stirred at 0° C. for 10 minutes, followed by addition of NaHDMS (124.4 mL, 1.0 M in THF). The mixture was kept at 0° C., and a solution of di-tert-butyl dicarbonate (16.3 g, 74.7 mmol) in tetrahydrofuran (50 mL) was slowly added, and the reaction was continued at 0° C. for 4 hours. After the reaction was completed, H$_2$O (40 mL) was added, followed by extraction with EtOAc (3×100 mL). The organic phases were combined, dried over MgSO$_4$, filtered and concentrated under reduced pressure. The resulting residue was purified by silica gel chromatography (ethyl acetate/petroleum ether with a gradient of 0 to 10%) to obtain tert-butyl (6-chloropyridin-2-yl)carbamate (7 g, yield: 49%).
$^1$H NMR (400 MHz, DMSO-d$_6$) δ 10.04 (s, 1H), 7.79-7.58 (m, 2H), 7.02 (dd, J=5.5, 2.9 Hz, 1H), 1.38 (s, 9H) ppm; LCMS: m/z 288.1 [M+H]$^+$.

Step 2: Tert-Butyl (5,6-dichloropyridin-2-yl)carbamate

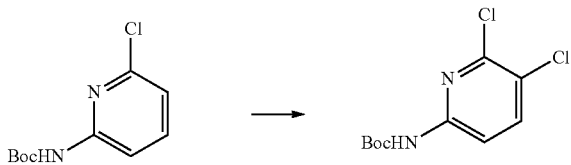 [SMILES: CC(C)(C)OC(=O)Nc1cccc(Cl)n1 ; CC(C)(C)OC(=O)Nc1ccc(Cl)c(Cl)n1]

To a dry 100 mL round bottom flask were added tert-butyl (6-chloropyridin-2-yl)carbamate (7 g, 30.6 mmol) and N,N-dimethylformamide (50 mL), and the mixture was stirred at room temperature for 10 minutes, followed by addition of N-chlorosuccinimide (4.50 g, 33.67 mmol). The mixture was reacted at 100° C. for 4 hours. After the reaction was completed, the reaction solution was cooled to room temperature, followed by addition of H$_2$O (50 mL) and extraction with ethyl acetate (3×80 mL). The organic phase was washed with saturated aqueous lithium chloride solution (2×40 mL), dried over MgSO$_4$, filtered and concentrated under reduced pressure, and the resulting residue was purified by silica gel chromatography (ethyl acetate/petroleum ether with a gradient of 0 to 5%) to obtain tert-butyl (5,6-dichloropyridin-2-yl)carbamate (5.3 g, yield: 65.8%).
$^1$H NMR (400 MHz, CDCl$_3$) δ 7.86 (d, J=8.7 Hz, 1H), 7.69 (d, J=8.7 Hz, 1H), 7.24 (s, 1H), 1.51 (s, 9H); LCMS: m/z 207.1 [M-55]$^+$.

Step 3: Tert-Butyl (5,6-dichloro-4-iodopyridin-2-yl)carbamate

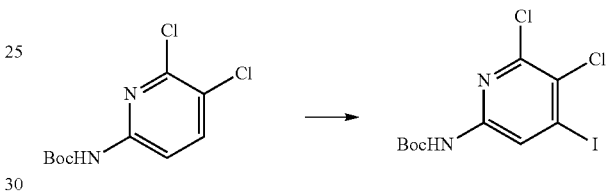

At –78° C. and under nitrogen atmosphere, to a dry 100 mL round bottom flask were slowly added tert-butyl (5,6-dichloropyridin-2-yl)carbamate (5.3 g, 20.14 mmol) and tetrahydrofuran (50 mL), followed by addition of n-butyllithium (44.3 mmol, 2.5M in THF) dropwise. The reaction solution was stirred at –78° C. for 1 hour, followed by slow dropwise addition of a solution of iodine (3.07 g, 24.17 mmol) in tetrahydrofuran (20 mL), and the reaction was continued at –78° C. for 3 hours. After the reaction was completed, H$_2$O (50 mL) was added, followed by extraction with EtOAc (3×80 mL). The organic phases were combined, dried over MgSO$_4$, filtered and concentrated under reduced pressure, and the resulting residue was purified by silica gel chromatography (ethyl acetate/petroleum ether with a gradient of 0 to 5%) to obtain tert-butyl (5,6-dichloro-4-iodopyridin-2-yl)carbamate (4.3 g, yield: 55%).
$^1$H NMR (400 MHz, DMSO-d$_6$) δ 10.44 (s, 1H), 8.36 (s, 1H), 1.46 (s, 9H) ppm; LCMS: m/z 334.1 [M-55]$^+$.

Step 4: methyl 3-((6-((tert-butoxycarbonyl)amino)-2,3-dichloropyridin-4-yl)thio)propionate

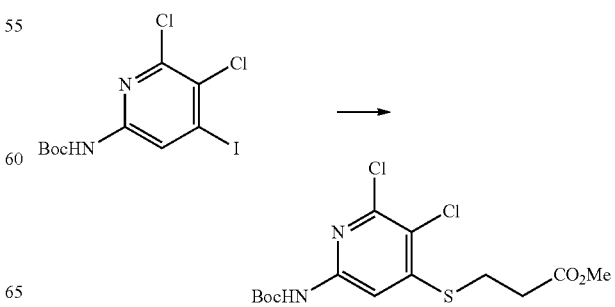

To a dry 100 mL round bottom flask were added tert-butyl (5,6-dichloro-4-iodopyridin-2-yl)carbamate (3.2 g, 8.22 mmol), palladium acetate (92 mg, 0.41 mmol), Xantphos (285 mg, 0.49 mmol), DIPEA (2.12 g, 16.46 mmol) and 1,4-dioxane (30 mL) sequentially. The reaction mixture was stirred at 100° C. for 2 hours, followed by filtration and concentration under reduced pressure, and the resulting residue was purified by silica gel chromatography (ethyl acetate/petroleum ether with a gradient of 0 to 30%) to obtain methyl 3-((6-((tert-butoxycarbonyl)amino)-2,3-dichloropyridin-4-yl)thio)propionate (3 g, yield: 96%).

$^1$H NMR (400 MHz, DMSO-d$_6$) δ 10.25 (s, 1H), 7.73 (s, 1H), 3.64 (s, 3H), 3.26 (t, J=6.9 Hz, 2H), 2.82 (t, J=6.9 Hz, 2H), 1.46 (s, 9H) ppm; LCMS: m/z 326.3[M-55]$^+$.

Step 5: Sodium 6-((tert-butoxycarbonyl)amino)-2,3-dichloropyridine-4-thiolate (F-1A)

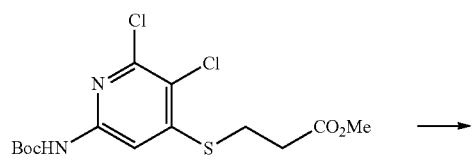

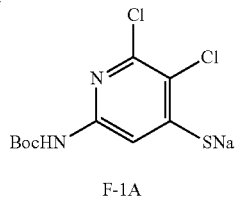

F-1A

To a dry 100 mL round bottom flask were successively added methyl 3-((6-((tert-butoxycarbonyl)amino)-2,3-dichloropyridin-4-yl)thio)propionate and tetrahydrofuran (30 mL). A solution of sodium ethoxide in ethanol (21%, 6 mL) was slowly added dropwise at room temperature, and the reaction solution was stirred at room temperature for 1 hour. After concentration under reduced pressure, dichloromethane (10 mL) was added, and a large amount of brown solid was precipitated out, followed by filtration. The filter cake was washed with dichloromethane, and dried to obtain sodium 6-((tert-butoxycarbonyl)amino)-2,3-dichloropyridine-4-thiolate (F-1A)(2.1 g, yield: 84%).

$^1$H NMR (400 MHz, DMSO-d$_6$) δ 9.05 (s, 1H), 7.61 (s, 1H), 1.41 (s, 9H) ppm; LCMS: m/z 262.2 [M-55]$^+$.

According to the synthesis method of Example 17, the following intermediates F-1B, F-1C, F-1D, F-1E, F-1F, F-1G, F-1H, F-1I, F-1J, F-1K, F-1L, F-1M, F-1N, F-1O, F-1P were obtained by using similar intermediate raw materials.

| Intermediate | Name | Structure | Analysis data |
|---|---|---|---|
| F-1B | sodium 2-amino-3-chloropyridine-4-thiolate | 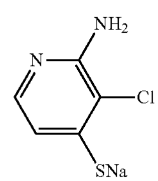 | $^1$H NMR (400 MHz, DMSO-d$_6$) δ 7.06 (d, J = 3.1 Hz, 1H), 6.51 (d, J = 5.2 Hz, 1H) ppm; LCMS: m/z 161.0 [M + H]$^+$. |
| F-1C | sodium 2-amino-5-chloropyridine-4-thiolate | 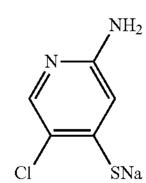 | $^1$H NMR (400 MHz, DMSO-d$_6$) δ 7.88 (s, 1H), 7.49 (d, J = 5.3 Hz, 1H), 7.09 (d, J = 5.3 Hz, 1H) ppm; LCMS: m/z 161.0 [M + H]$^+$. |
| F-1D | sodium 2-chloropyridine-3-thiolate | 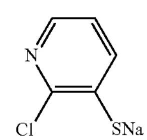 | $^1$H NMR (400 MHz, DMSO-d$_6$) δ 7.57 (dd, J = 7.7, 1.5 Hz, 1H), 7.45 (d, J = 3.5 Hz, 1H), 6.69 (dd, J = 7.6, 4.4 Hz, 1H) ppm; LCMS: m/z 146.0 [M + H]$^+$. |
| F-1E | sodium 2-methylpyridine-3-thiolate | 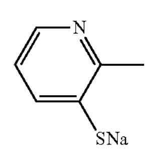 | $^1$H NMR (400 MHz, DMSO-d$_6$) δ 7.59-7.46 (m, 1H), 7.32 (dd, J = 7.7, 1.4 Hz, 1H), 6.53 (dd, J = 7.7, 4.6 Hz, 1H), 2.36 (s, 3H) ppm; LCMS: m/z 126.0 [M + H]$^+$. |

-continued

| Intermediate | Name | Structure | Analysis data |
|---|---|---|---|
| F-1F | sodium quinoline-4-thiolate | 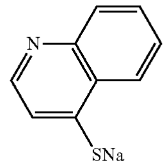 | $^1$H NMR (400 MHz, DMSO-$d_6$) δ 8.79 (d, J = 4.6 Hz, 1H), 8.25 (d, J = 8.0 Hz, 1H), 8.15 (d, J = 8.3 Hz, 1H), 7.74-7.64 (m, 2H), 7.30 (d, J = 4.6 Hz, 1H) ppm; LCMS: m/z 162.0 [M + H]$^+$. |
| F-1G | sodium 2,3-dichloropyridine-4-thiolate | 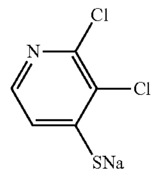 | $^1$H NMR (400 MHz, DMSO-$d_6$) δ 7.31 (d, J = 5.3 Hz, 1H), 7.07 (d, J = 5.3 Hz, 1H) ppm; LCMS: m/z 180.0 [M + H]$^+$. |
| F-1H | sodium 3-chloropyridine-4-thiolate | 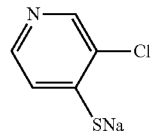 | $^1$H NMR (400 MHz, DMSO-$d_6$) δ 7.88 (s, 1H), 7.49 (d, J = 5.3 Hz, 1H), 7.09 (d, J = 5.3 Hz, 1H) ppm; LCMS: m/z 146.0 [M + H]$^+$. |
| F-1I | sodium benzo[d]thiazole-7-thiolate | 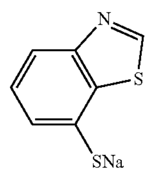 | LCMS: m/z 146.0 [M + H]$^+$. |
| F-1J | sodium 2-(trifluoromethyl)pyridine-3-thiolate | 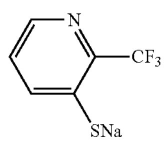 | LCMS: m/z 146.0 [M ' H]$^+$. |
| F-1K | sodium 3-(trifluoromethyl)pyridine-4-thiolate | 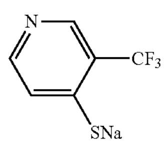 | $^1$HNMR (400 MHz, D$_2$O) δ 8.24 (s, 1H), 7.84 (d, J = 5.6 Hz, 1H), 7.31 (d, J = 5.6 Hz, 1H) ppm; LCMS: m/z 146.0 [M + H]$^+$. |
| F-1L | sodium 6-amino-2-chloropyridine-3-thiolate | 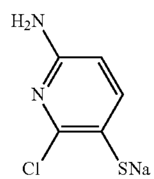 | $^1$H NMR (400 MHz, DMSO-$d_6$) δ 7.29 (d, J = 8.1 Hz, 1H), 6.03 (d, J = 7.8 Hz, 1H), 5.21 (brs, 2H) ppm; LCMS: m/z 160.0 [M + H]$^+$. |
| F-1M | sodium thiazole-2-thiolate | 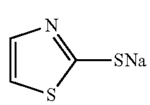 | $^1$H NMR (400 MHz, DMSO-$d_6$) δ 6.95 (d, J = 3.7 Hz, 1H), 6.52 (d, J = 3.7 Hz, 1H) ppm; LCMS: m/z 118.0 [M + H]$^+$. |
| F-1N | sodium 1-methyl-1H-benzo[d]imidazole-4-thiolate | 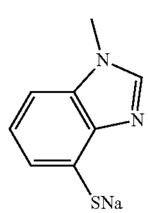 | LCMS: m/z 165.0 [M + H]$^+$. |

-continued

| Intermediate | Name | Structure | Analysis data |
|---|---|---|---|
| F-1O | sodium 2,3-dihydrobenzofuran-4-thiolate | 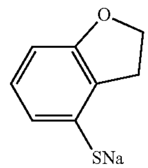 | LCMS: m/z 153.0 [M ' H]⁺. |
| F-1P | sodium 1H-pyrrolo[2,3-b]pyridine-4-thiolate | 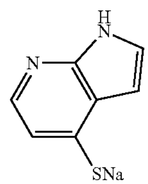 | $^1$H NMR (400 MHz, DMSO-$d_6$) δ 8.21 (d, J = 2.6 Hz, 1H), 7.50 (d, J = 3.5 Hz, 1H), 7.24 (d, J = 5.2 Hz, 1H), 6.38 (d, J = 3.5 Hz, 1H), 3.62 (s, 3H) ppm; LCMS: m/z 165.0 [M + H]⁺. |

Example 18: Preparation of Intermediate: Sodium 3-chloro-2-methylpyridine-4-thiolate (F-1Q)

Step 1: methyl 3-((3-chloro-2-methylpyridin-4-yl)thio)propionate

The intermediate methyl 3-((2,3-dichloropyridin-4-yl)thio)propionate obtained from the synthesis of intermediate F-1G was used in the following reaction.

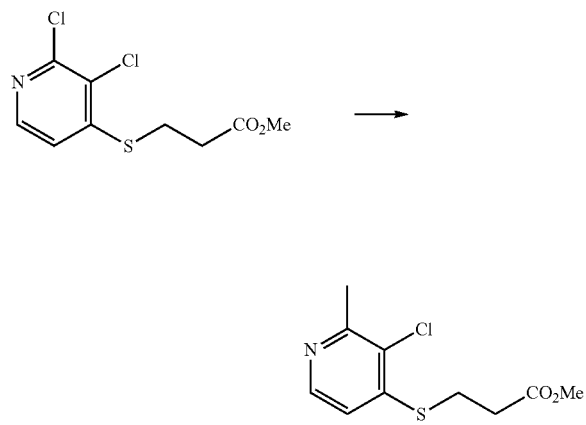

Under nitrogen atmosphere, to a dry 100 mL round bottom flask were added methyl 3-((2,3-dichloropyridin-4-yl)thio)propionate (500 mg, 1.88 mmol), Pd(PPh$_3$)$_4$ (217 mg, 0.188 mmol), trimethylcyclotriboroxane (354 mg, 2.82 mmol), potassium carbonate (389 mg, 2.82 mmol) and 1,4-dioxane (10 mL). The reaction mixture was heated and stirred at 100° C. under nitrogen atmosphere for 6 hours. The residue obtained by filtration and concentration under reduced pressure was purified by silica gel chromatography (ethyl acetate/petroleum ether with a gradient of 0 to 40%) to obtain methyl 3-((3-chloro-2-methylpyridin-4-yl)thio)propionate (320 mg, yield: 69%).

Step 2: sodium 3-chloro-2-methylpyridine-4-thiolate (F-1Q)

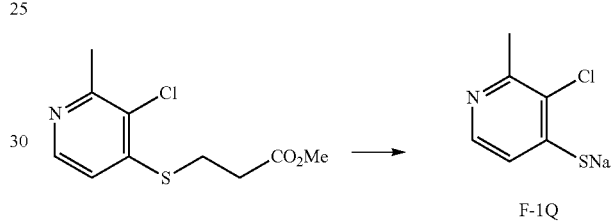

To a dry 100 mL round bottom flask were added methyl 3-((3-chloro-2-methylpyridin-4-yl)thio)propionate (320 mg, 1.30 mmol) and tetrahydrofuran (10 mL) sequentially, and a solution of sodium ethoxide in ethanol (21%, 2 mL) was slowly added dropwise at room temperature, and the reaction solution was stirred at room temperature for 1 hour. The mixture was concentrated under reduced pressure, followed by addition of dichloromethane (10 mL), and a large amount of brown solid was precipitated. The mixture was filtered and the filter cake was washed with dichloromethane, and dried to obtain sodium 3-chloro-2-methylpyridine-4-thiolate F-1Q (200 mg, yield: 85%).

$^1$H NMR (400 MHz, DMSO-$d_6$) δ 7.37 (d, J=4.8 Hz, 1H), 6.97 (d, J=4.8 Hz, 1H), 2.31 (s, 3H) ppm; LCMS: m/z 160.0 [M+H]⁺.

According to the synthesis method of Example 18, the following intermediate F-1R was obtained by using similar intermediate raw materials.

| Intermediate | Name | Structure | Analysis data |
|---|---|---|---|
| F-1R | sodium 3-chloro-2-cyclopropylpyridine-4-thiolate | 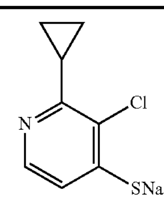 | LCMS: m/z 186.0 [M + H]⁺. |

Example 19: Preparation of Intermediate: Sodium 6-((tert-butoxycarbonyl)amino)-3-chloro-2-methylpyridine-4-thiolate (F-1S)

Step 1: methyl 3-((6-(((tert-butoxycarbonyl)amino)-3-chloro-2-methylpyridin-4-yl)thio)propionate The intermediate methyl 3-((6-(((tert-butoxycarbonyl)amino)-2,3-dichloropyridin-4-yl)thio)propionate obtained from the synthesis of intermediate F-1A was used in the following reaction.

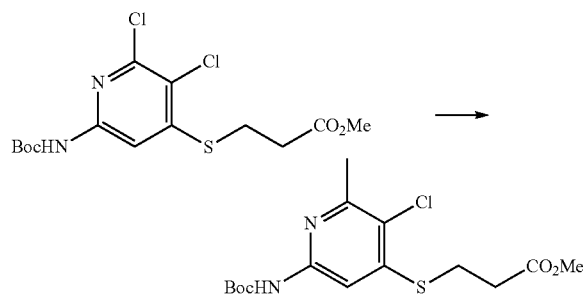

Under nitrogen atmosphere, to a dry 100 mL round bottom flask were successively added methyl 3-((6-((tert-butoxycarbonyl)amino)-2,3-dichloropyridin-4-yl)thio)propionate (600 mg, 1.57 mmol), [1,1'-bis(tert-butylphosphino)ferrocene]palladium dichloride (103 mg, 0.157 mmol), trimethylcyclotriboroxane (301 mg, 2.4 mmol), potassium carbonate (331 mg, 2.4 mmol), 1,4-dioxane (10 mL) and water (1 mL). The reaction mixture was heated and stirred at 100° C. under nitrogen atmosphere for 6 hours. The residue obtained by filtration and concentration under reduced pressure was purified by silica gel chromatography (ethyl acetate/petroleum ether with a gradient of 0 to 40%) to obtain methyl 3-((6-((tert-butoxycarbonyl)amino)-3-chloro-2-methylpyridin-4-yl)thio)propionate (420 mg, yield: 74%).

$^1$H NMR (400 MHz, DMSO-$d_6$) δ 9.90 (s, 1H), 7.64 (s, 1H), 3.64 (s, 3H), 3.21 (t, J=6.9 Hz, 2H), 2.80 (t, J=6.9 Hz, 2H), 1.46 (s, 9H) ppm; LCMS: m/z 361.1 [M+H]$^+$.

Step 2: Sodium 6-((tert-butoxycarbonyl)amino)-3-chloro-2-methylpyridine-4-thiolate (F-1S)

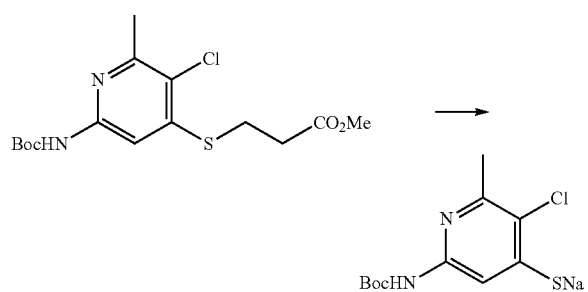

To a dry 100 mL round-bottom flask were added methyl 3-((6-((tert-butoxycarbonyl)amino)-3-chloro-2-methylpyridin-4-yl)thio)propionate (420 mg, 1.17 mmol) and tetrahydrofuran (10 mL) sequentially. A solution of sodium ethoxide in ethanol (21%, 2 mL) was then slowly added dropwise at room temperature, and the reaction solution was stirred at room temperature for 1 hour. The mixture was concentrated under reduced pressure, followed by addition of dichloromethane (10 mL), and a large amount of brown solid was precipitated. The mixture was filtered and the filter cake was washed with dichloromethane, and dried to obtain sodium 6-((tert-butoxycarbonyl)amino)-3-chloro-2-methylpyridine-4-thiolate (F-1S) (320 mg, yield: 92%).

$^1$H NMR (400 MHz, DMSO-$d_6$) δ 9.87 (s, 1H), 7.63 (s, 1H), 3.64 (s, 3H), 1.46 (s, 9H) ppm; LCMS: m/z 275.0 [M+H]$^+$.

Example 20: Preparation of Intermediate: 3-amino-2-chlorobenzenethiol Hydrochloride (F-2A)

Step 1: 2-chloro-3-aminophenyl Tert-Butyl Sulfide

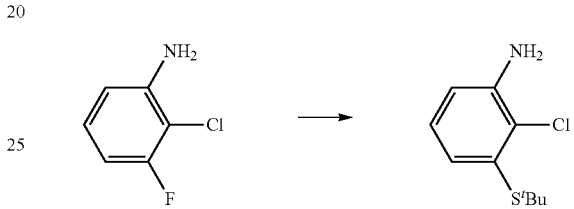

Under nitrogen atmosphere, to a dry 100 mL round bottom flask were added 2-chloro-3-fluoroaniline (5 g, 34.3 mmol) and N-methylpyrrolidone (50 mL) sequentially, followed by 2-methylpropane-2-thiol (8.66 g, 96.04 mmol) and cesium carbonate (22.36 g, 68.6 mmol), and the reaction mixture was heated and stirred at 120° C. for 16 hours. After cooling to room temperature, the reaction solution was diluted with 60 mL of ethyl acetate, washed successively with saturated lithium chloride aqueous solution (30 mL), water (30 mL) and saturated sodium chloride aqueous solution (30 mL), and then dried over anhydrous sodium sulfate, filtered, and concentrated under reduced pressure to obtain 2-chloro-3-aminophenyl tert-butyl sulfide (6.04 g, yield: 82%).

LCMS: m/z 216.1 [M+H]$^+$.

Step 2: 3-amino-2-chlorobenzenethiol Hydrochloride (F-2A)

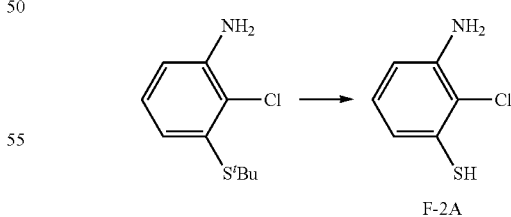

To a dry 100 mL round bottom flask were added 2-chloro-3-aminophenyl tert-butyl sulfide (6.04 g, 28 mmol) and concentrated hydrochloric acid (50 mL), and the reaction mixture was heated and stirred at 45° C. for 8 hours. After cooling to room temperature naturally, the reaction solution was further cooled to 0° C., and a large amount of white solid was precipitated. The mixture was filtered and the filter cake was washed successively with concentrated hydrochloric acid and petroleum ether to obtain 3-amino-2-chlorobenzenethiol hydrochloride F-2A (4.9 g, yield: 90%).

LCMS: m/z 160.0 [M+H]+.

Example 21: Preparation of Compound: 1-(8-((2,3-dichlorophenyl)thio)imidazo[1,2-c]pyrimidin-5-yl)-4-methylpiperidin-4-amine Step 1: Tert-Butyl (1-(8-iodoimidazo[1,2-c]pyrimidin-5-yl)-4-methylpiperidin-4-yl)carbamate

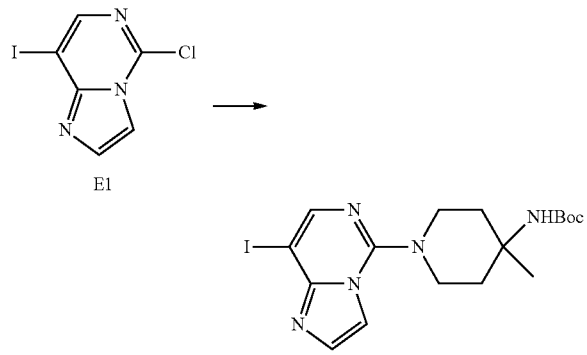

Under nitrogen atmosphere, to a dry 50 mL single-necked flask were added 5-chloro-8-iodoimidazo[1,2-c]pyrimidine (E1) (50 mg, 0.18 mmol), tert-butyl (4-methylpiperidine-4-yl)carbamate (77 mg, 0.36 mmol), DIEA (46 mg, 0.36 mmol) and NMP (5 mL), and then the reaction solution was stirred at 90° C. for 2 hours. After the reaction was completed, the resulting residue was poured into water (10 mL), stirred at room temperature for 5 minutes, and then extracted with ethyl acetate (3×50 mL). The organic phases were combined, dried over MgSO4, filtered and concentrated under reduced pressure. The resulting residue was purified by silica gel chromatography (ethyl acetate/petroleum ether with a gradient of 0 to 80%) to obtain tert-butyl (1-(8-iodoimidazo[1,2-c]pyrimidin-5-yl)-4-methylpiperidin-4-yl) carbamate (70 mg, yield: 43%) as a pale yellow solid.

1H NMR (400 MHz, DMSO-d6) δ 8.02 (s, 1H), 7.89 (d, J=1.5 Hz, 1H), 7.62 (d, J=1.4 Hz, 1H), 3.49 (d, J=13.4 Hz, 2H), 3.21 (ddd, J=13.3, 10.8, 2.6 Hz, 2H), 2.18 (d, J=13.9 Hz, 2H), 1.65 (ddd, J=14.1, 10.7, 3.8 Hz, 2H), 1.40 (s, 9H), 1.28 (s, 3H) ppm; LCMS: m/z 458.1 [M+H]+.

Step 2: Tert-Butyl (1-(8-((2,3-dichlorophenyl)thio)imidazo[1,2-c]pyrimidin-5-yl)-4-methylpiperidin-4-yl) carbamate

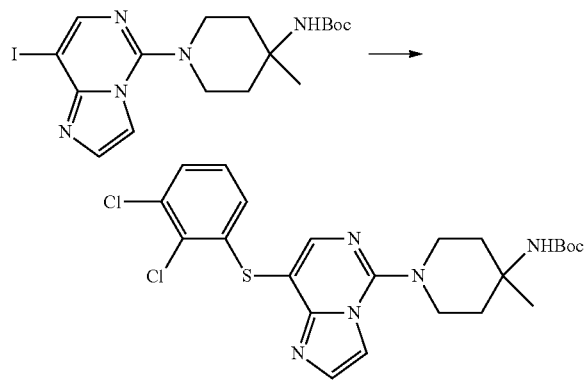

To a dry 50 mL three-necked flask were added tert-butyl (1-(8-iodoimidazo[1,2-c]pyrimidin-5-yl)-4-methylpiperidin-4-yl)carbamate (70 mg, 0.15 mmol), cuprous iodide (3 mg, 0.015 mmol), 1,10-phenanthroline (6 mg, 0.030 mmol), 2,3-dichlorothiophenol (32 mg, 0.18 mmol), potassium phosphate (66 mg, 0.30 mmol) and 5 mL of dioxane sequentially. The mixture was heated for 3 hours under nitrogen atmosphere. After the reaction was completed, saturated NH4Cl solution (10 mL) was added, followed by extraction with ethyl acetate (3×50 mL). The organic phases were combined, dried over Na2SO4, filtered, and the filtrate was concentrated under reduced pressure. The resulting residue was purified by silica gel chromatography (ethyl acetate/petroleum ether with a gradient of 0 to 60%) to obtain tert-butyl (1-(8-((2,3-dichlorophenyl)thio)imidazo[1,2-c]pyrimidin-5-yl)-4-methylpiperidin-4-yl) carbamate (30 mg, yield: 39%) as a pale yellow solid.

LC-MS: m/z 508.1 [M+H]+.

Step 3: 1-(8-((2,3-dichlorophenyl)thio)imidazo[1,2-c]pyrimidin-5-yl)-4-methylpiperidin-4-amine

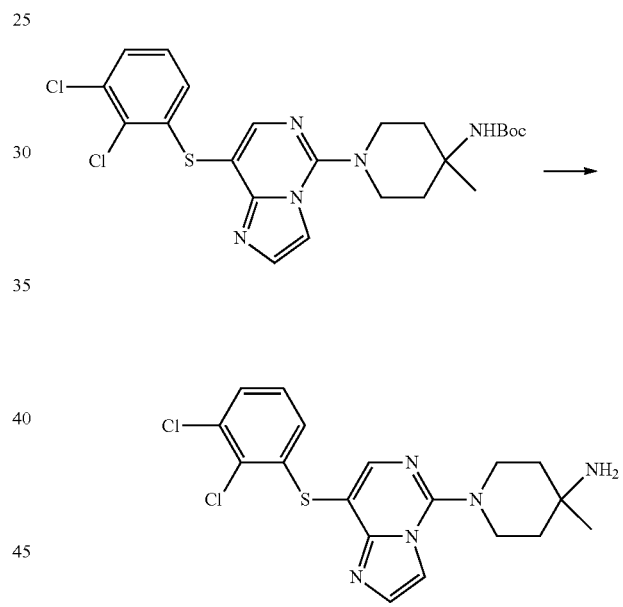

To a dry 50 mL round bottom flask was added a solution of tert-butyl (1-(8-((2,3-dichlorophenyl)thio)imidazo[1,2-c]pyrimidin-5-yl)-4-methylpiperidin-4-yl) carbamate (30 mg, 0.059 mmol) and hydrogen chloride in 1,4-dioxane (7 M, 5 mL), and the mixture was reacted at room temperature for 1 hour. The reaction solution was concentrated under reduced pressure, and the resulting crude product was purified by high-performance liquid chromatography to obtain the product 1-(8-((2,3-dichlorophenyl)thio)imidazo[1,2-c]pyrimidin-5-yl)-4-methylpiperidin-4-amine (15 mg, yield: 62%).

1H NMR (400 MHz, DMSO-d6) δ 8.02 (s, 1H), 7.84 (d, J=1.3 Hz, 1H), 7.55 (d, J=1.2 Hz, 1H), 7.41 (dd, J=8.0, 1.2 Hz, 1H), 7.12 (t, J=8.0 Hz, 1H), 6.69 (dd, J=8.1, 1.2 Hz, 1H), 3.60 (t, J=4.2 Hz, 4H), 1.73-1.60 (m, 4H), 1.19 (s, 3H) ppm; LC-MS: m/z 408.1 [M+H]+.

Using the synthesis method of Example 21, the following compounds were synthesized using commercially available or self-synthesized amines:

Example 22: 8-((2,3-dichlorophenyl)thio)-5-(1,8-diazaspiro[4.5]decan-8-yl)imidazo[1,2-c]pyrimidine

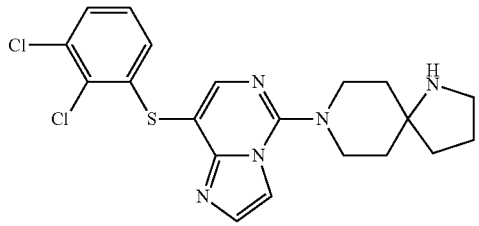 [SMILES: Clc1cccc(Sc2cnc(N3CCC4(CCCN4)CC3)n3ccnc23)c1Cl]

$^1$H NMR (400 MHz, DMSO-$d_6$) δ 8.03 (s, 1H), 7.89 (s, 1H), 7.57 (s, 1H), 7.41 (d, J=8.1 Hz, 1H), 7.12 (t, J=8.0 Hz, 1H), 6.72 (d, J=8.1 Hz, 1H), 3.79 (ddd, J=13.9, 7.1, 3.7 Hz, 2H), 3.49 (ddd, J=12.8, 8.0, 3.4 Hz, 2H), 3.19 (t, J=6.9 Hz, 2H), 2.04 (ddd, J=12.3, 8.1, 3.5 Hz, 2H), 1.93 (dt, J=20.5, 6.5 Hz, 6H) ppm; LC-MS: m/z 434.1 [M+H]$^+$.

Example 23: Preparation of Compound: 8-((2,3-dichlorophenyl)thio)-5-(piperidin-1-yl)imidazo[1,2-c]pyrimidine

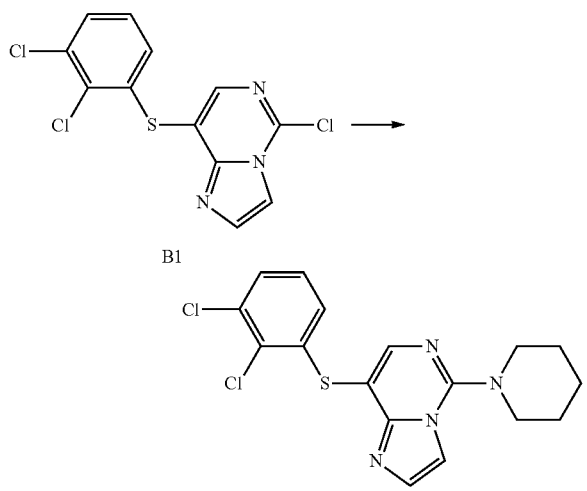

To a dry 50 mL single-necked flask were added 5-chloro-8-((2,3-dichlorophenyl)thio)imidazo[1,2-c]pyrimidine (B1) (50 mg, 0.15 mmol) and piperidine (20 mg, 0.23 mmol), DIEA (39 mg, 0.3 mmol) and NMP (5 mL) sequentially, and then the reaction solution was stirred at 90° C. for 2 hours. After the reaction was completed, the resulting residue was poured into water (100 mL), stirred at room temperature for 5 minutes, and then extracted with ethyl acetate (3×50 mL). The organic phases were combined, dried over MgSO$_4$, filtered and concentrated under reduced pressure. The residue obtained was purified by silica gel chromatography (ethyl acetate/petroleum ether with a gradient of 0 to 80%) and high-performance liquid chromatography to obtain the product tert-butyl ((1-(8-((2,3-dichlorophenyl)thio)imidazo[1,2-c]pyrimidin-5-yl)pyrrolidine-3-yl)methyl)carbamate (20 mg, yield: 35%).
$^1$H NMR (400 MHz, DMSO-$d_6$) δ 8.03 (s, 1H), 7.83 (d, J=1.4 Hz, 1H), 7.55 (d, J=1.4 Hz, 1H), 7.41 (dd, J=8.0, 1.3 Hz, 1H), 7.12 (t, J=8.0 Hz, 1H), 6.69 (dd, J=8.1, 1.3 Hz, 1H), 3.50 (d, J=5.6 Hz, 4H), 1.79-1.63 (m, 6H) ppm; LC-MS: m/z 378.7 [M+H]$^+$.

Using the synthesis method of Example 23, the following compounds were synthesized:

Example 24: 8-((2,3-dichlorophenyl)thio)-5-(3,5-dimethylpiperazin-1-yl)imidazo[1,2-c]pyrimidine

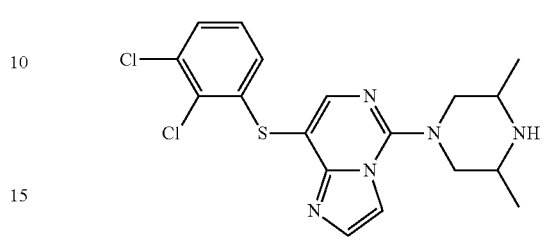

$^1$H NMR (400 MHz, DMSO-$d_6$) δ 8.23 (s, 1H), 8.03 (s, 1H), 7.92 (d, J=1.2 Hz, 1H), 7.55 (d, J=1.2 Hz, 1H), 7.44-7.37 (m, 1H), 7.12 (t, J=8.1 Hz, 1H), 6.69 (dd, J=8.1, 1.1 Hz, 1H), 3.89 (d, J=12.0 Hz, 2H), 3.02 (d, J=6.6 Hz, 2H), 2.72-2.59 (m, 2H), 1.05 (t, J=6.0 Hz, 7H) ppm; LC-MS: m/z 407.7 [M+H]$^+$.

Example 25: 8-((2,3-dichlorophenyl)thio)-5-(4-methylpiperazin-1-yl)imidazo[1,2-c]pyrimidine

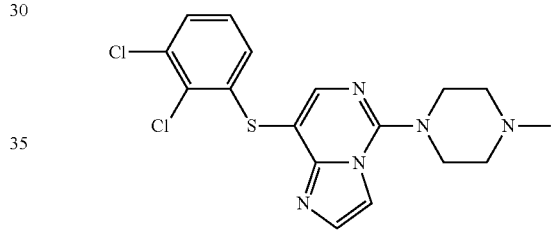

$^1$H NMR (400 MHz, DMSO-$d_6$) δ 8.20 (s, 1H), 8.04 (s, 1H), 7.91 (d, J=1.4 Hz, 1H), 7.57 (d, J=1.4 Hz, 1H), 7.41 (dd, J=8.0, 1.2 Hz, 1H), 7.12 (t, J=8.0 Hz, 1H), 6.70 (dd, J=8.1, 1.2 Hz, 1H), 3.59-3.50 (m, 4H), 2.59-2.53 (m, 4H), 2.27 (s, 3H) ppm; LC-MS: m/z 393.8 [M+H]$^+$.

Example 26: (1-(8-((2,3-dichlorophenyl)thio)imidazo[1,2-c]pyrimidin-5-yl)-4-phenylpiperidin-4-yl)methanamine

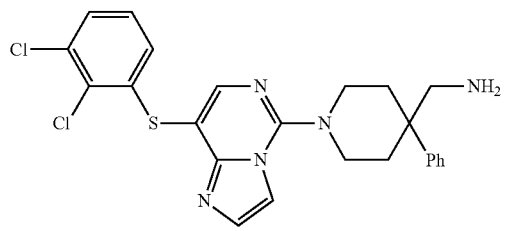 [SMILES: NCC1(c2ccccc2)CCN(c2ncc(Sc3cccc(Cl)c3Cl)c3nccn23)CC1]

$^1$H NMR (400 MHz, DMSO-$d_6$) δ 8.00 (s, 1H), 7.88 (s, 1H), 7.54 (s, 1H), 7.50-7.33 (m, 5H), 7.28 (t, J=6.8 Hz, 1H), 7.10 (t, J=8.0 Hz, 1H), 6.67 (d, J=8.1 Hz, 1H), 3.77 (d, J=12.5 Hz, 2H), 3.31-3.22 (m, 2H), 3.09 (s, 1H), 2.82 (s, 1H), 2.32 (s, 2H), 2.06 (t, J=10.3 Hz, 2H); LC-MS: m/z 484.7 [M+H]$^+$.

Example 27: (R)-8-(8-((2,3-dichlorophenyl)thio) imidazo[1,2-c]pyrimidin-5-yl)-3,3-difluoro-8-azaspiro[4.5]decan-1-amine

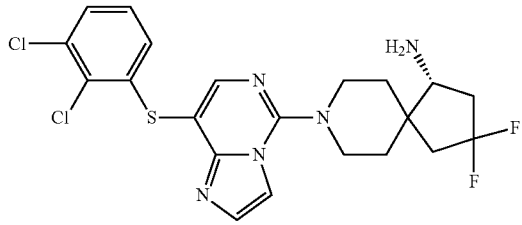 [SMILES: N[C@@H]1CC(F)(F)CC12CCN(c1ncc(Sc3cccc(Cl)c3Cl)c3nccn13)CC2]

¹H NMR (400 MHz, DMSO-d₆) δ 8.03 (s, 1H), 7.81 (d, J=1.5 Hz, 1H), 7.57 (d, J=1.4 Hz, 1H), 7.42 (dd, J=8.0, 1.3 Hz, 1H), 7.12 (t, J=8.1 Hz, 1H), 6.69 (dd, J=8.1, 1.4 Hz, 1H), 3.93 (t, J=14.9 Hz, 2H), 3.31 (d, J=19.3 Hz, 2H), 3.28-3.16 (m, 3H), 2.252.06 (m, 2H), 1.90 (dd, J=32.1, 11.8 Hz, 2H), 1.61-1.45 (m, 2H) ppm; LC-MS: m/z 484.1 [M+H]⁺.

Example 28: (R)-3-(8-((2,3-dichlorophenyl)thio) imidazo[1,2-c]pyrimidin-5-yl)-3-azaspiro[5.5]undecan-7-amine

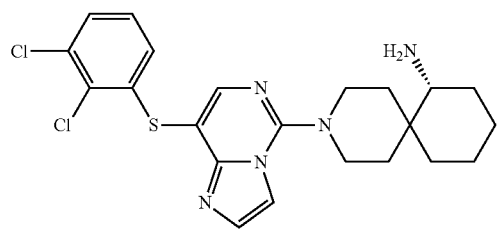 [SMILES: N[C@@H]1CCCCC12CCN(c1ncc(Sc3cccc(Cl)c3Cl)c3nccn13)CC2]

¹H NMR (400 MHz, DMSO-d₆) δ 8.02 (s, 1H), 7.82 (d, J=1.2 Hz, 1H), 7.56 (d, J=1.2 Hz, 1H), 7.41 (dd, J=8.0, 1.2 Hz, 1H), 7.12 (t, J=8.1 Hz, 1H), 6.68 (dd, J=8.1, 1.2 Hz, 1H), 3.80 (d, J=4.8 Hz, 2H), 3.33 (dd, J=29.0, 11.6 Hz, 2H), 2.77 (d, J=5.2 Hz, 1H), 2.04 (dd, J=30.0, 14.7 Hz, 2H), 1.85-1.12 (m, 10H) ppm; LC-MS: m/z 461.7 [M+H]⁺.

Example 29: 1-(8-((2,3-dichlorophenyl)thio)imidazo [1,2-c]pyrimidin-5-yl)-4-ethylpiperidin-4-amine

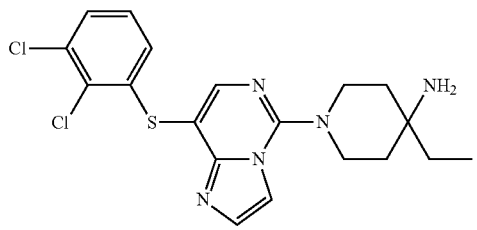 [SMILES: CCC1(N)CCN(c2ncc(Sc3cccc(Cl)c3Cl)c3nccn23)CC1]

¹H NMR (400 MHz, DMSO-d₆) δ 8.03 (s, 1H), 7.88 (d, J=1.5 Hz, 1H), 7.58 (d, J=1.4 Hz, 1H), 7.42 (dd, J=8.0, 1.3 Hz, 1H), 7.12 (t, J=8.1 Hz, 1H), 6.70 (dd, J=8.1, 1.4 Hz, 1H), 3.71-3.64 (m, 4H), 1.90-1.73 (m, 4H), 1.69 (q, J=7.3 Hz, 2H), 0.93 (t, J=7.5 Hz, 3H) ppm; LC-MS: m/z 422.1 [M+H]⁺.

Example 30: 8-(8-((2,3-dichlorophenyl)thio)imidazo [1,2-c]pyrimidin-5-yl)-1-methyl-8-azaspiro[4.5]decan-1-amine

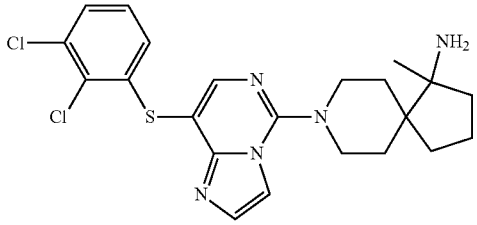 [SMILES: CC1(N)CCCC12CCN(c1ncc(Sc3cccc(Cl)c3Cl)c3nccn13)CC2]

¹H NMR (400 MHz, DMSO-d₆) δ 8.33 (s, 1H), 7.83 (s, 1H), 7.56 (s, 1H), 7.41 (d, J=8.1 Hz, 1H), 7.17-7.08 (m, 1H), 6.69 (d, J=8.2 Hz, 1H), 4.08-3.93 (m, 2H), 3.18-3.04 (m, 2H), 3.04-2.94 (m, 1H), 2.45 (s, 1H), 1.90-1.29 (m, 8H), 0.95 (t, J=6.3 Hz, 3H) ppm; LC-MS: m/z 462.1[M+H]⁺.

Example 31: Preparation of Compound: 1-(8-((2,3-dichlorophenyl)thio)imidazo[1,2-c]pyrimidin-5-yl) pyrrolidin-3-amine Step 1: Tert-Butyl (1-(8-((2,3-dichlorophenyl)thio) imidazo[1,2-c]pyrimidin-5-yl)pyrrolidin-3-yl)carbamate

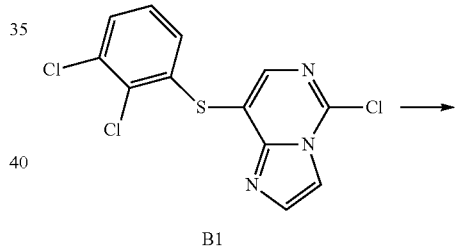

B1

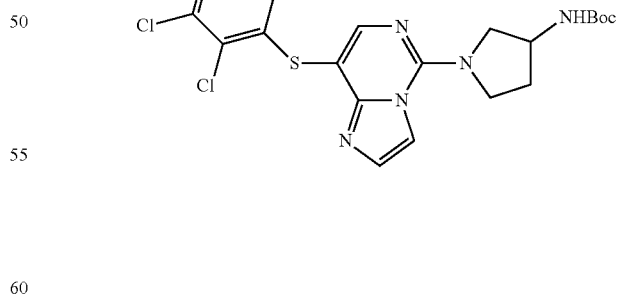

Using the same method as that of Example 23, B1 was substituted by a corresponding amine to obtain tert-butyl (1-(8-((2,3-dichlorophenyl)thio)imidazo[1,2-c]pyrimidin-5-yl)pyrrolidin-3-yl)carbamate.

LC-MS: m/z 424.1[M+H]⁺.

Step 1-(8-((2,3-dichlorophenyl)thio)imidazo[1,2-c]pyrimidin-5-yl)pyrrolidine-3-amine

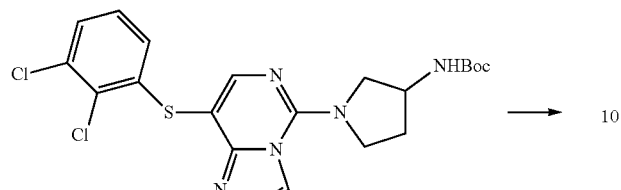

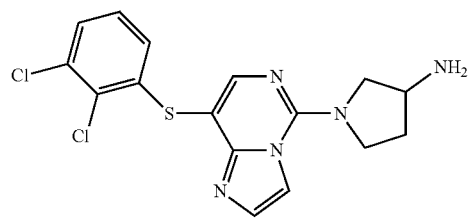

Using the same method as that of Step 3 in Example 21, tert-butyl (1-(8-((2,3-dichlorophenyl)thio)imidazo[1,2-c]pyrimidin-5-yl)pyrrolidine-3-yl)carba mate was subjected to deprotection of the Boc protecting group to obtain compound 1-(8-((2,3-dichlorophenyl)thio)imidazo[1,2-c]pyrimidin-5-yl)pyrrolidine-3-amine.

¹H NMR (400 MHz, DMSO-d₆) δ 8.18 (s, 1H), 7.93 (d, J=1.1 Hz, 1H), 7.46 (s, 1H), 7.40 (d, J=8.0 Hz, 1H), 7.13 (t, J=8.0 Hz, 1H), 6.63 (d, J=8.1 Hz, 1H), 4.14 (d, J=9.3 Hz, 1H), 4.05 (d, J=5.9 Hz, 1H), 3.82 (d, J=11.2 Hz, 3H), 2.24 (d, J=7.3 Hz, 1H), 2.02 (s, 1H) ppm; LC-MS: m/z 379.9 [M+H]⁺.

Using the synthesis method of Example 31, the following compounds were synthesized:

Example 32: 1-(8-((2,3-dichlorophenyl)thio)imidazo[1,2-c]pyrimidin-5-yl)piperidin-4-amine

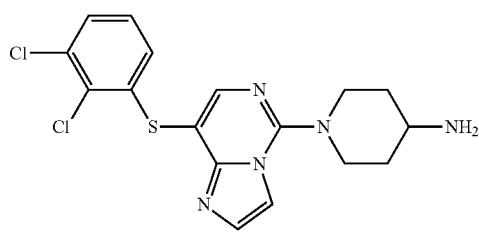 [SMILES: NC1CCN(c2ncc(Sc3cccc(Cl)c3Cl)c3nccn23)CC1]

¹H NMR (400 MHz, DMSO-d₆) δ 8.39 (s, 1H), 8.03 (s, 1H), 7.86 (s, 1H), 7.57 (s, 1H), 7.42 (d, J=7.6 Hz, 1H), 7.12 (t, J=8.0 Hz, 1H), 6.69 (d, J=8.1 Hz, 1H), 4.00 (d, J=13.0 Hz, 2H), 3.13 (d, J=11.5 Hz, 2H), 2.02-1.86 (m, 3H), 1.62 (dd, J=21.0, 9.8 Hz, 2H), 1.23 (s, 1H); LC-MS: m/z 394.7 [M+H]⁺.

Example 33: (1-(8-((2,3-dichlorophenyl)thio)imidazo[1,2-c]pyrimidin-5-yl)pyrrolidin-3-yl)methanamine

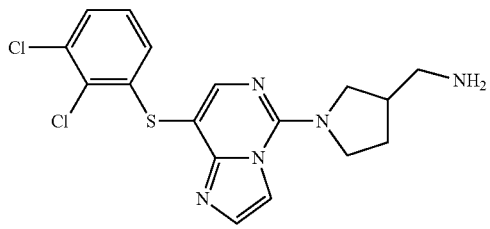 [SMILES: NCC1CCN(c2ncc(Sc3cccc(Cl)c3Cl)c3nccn23)C1]

¹H NMR (400 MHz, DMSO-d₆) δ 8.17 (d, J=1.6 Hz, 1H), 7.91 (s, 1H), 7.45 (d, J=1.5 Hz, 1H), 7.39 (d, J=7.7 Hz, 1H), 7.12 (t, J=8.0 Hz, 1H), 6.63 (d, J=8.1 Hz, 1H), 4.04 (ddd, J=11.5, 8.9, 5.5 Hz, 2H), 3.94-3.86 (m, 1H), 3.72 (dd, J=10.8, 7.6 Hz, 2H), 2.93 (d, J=7.2 Hz, 2H), 2.16 (dq, J=11.9, 6.2 Hz, 1H), 1.79 (dq, J=12.3, 8.3 Hz, 1H) ppm; LC-MS: m/z 394.1 [M+H]⁺.

Example 34: (1-(8-((2,3-dichlorophenyl)thio)imidazo[1,2-c]pyrimidin-5-yl)-4-methylpiperidin-4-yl)methanamine

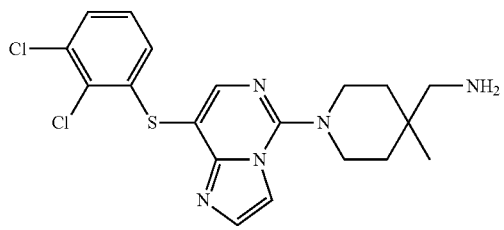 [SMILES: CC1(CN)CCN(c2ncc(Sc3cccc(Cl)c3Cl)c3nccn23)CC1]

¹H NMR (400 MHz, DMSO-d₆) δ 8.03 (s, 1H), 7.83 (d, J=1.5 Hz, 1H), 7.57 (d, J=1.4 Hz, 1H), 7.42 (dd, J=8.0, 1.3 Hz, 1H), 7.12 (t, J=8.1 Hz, 1H), 6.69 (dd, J=8.1, 1.3 Hz, 1H), 3.68 (dt, J=13.7, 4.6 Hz, 2H), 3.44 (td, J=9.6, 4.8 Hz, 2H), 2.76 (s, 2H), 1.70 (ddd, J=13.3, 9.2, 3.7 Hz, 2H), 1.62-1.49 (m, 2H), 1.08 (s, 3H) ppm; LC-MS: m/z 422.1 [M+H]⁺.

Example 35: (1-(8-((2,3-dichlorophenyl)thio)imidazo[1,2-c]pyrimidin-5-yl)piperidin-4-yl)methanamine

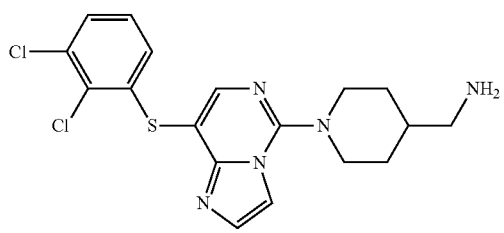 [SMILES: NCC1CCN(c2ncc(Sc3cccc(Cl)c3Cl)c3nccn23)CC1]

¹H NMR (400 MHz, DMSO-d₆) δ 8.30 (s, 1H), 8.03 (s, 1H), 7.83 (s, 1H), 7.57 (s, 1H), 7.42 (d, J=7.7 Hz, 1H), 7.12 (t, J=8.0 Hz, 1H), 6.69 (d, J=8.0 Hz, 1H), 4.05 (d, J=13.2 Hz,

2H), 3.07 (t, J=12.3 Hz, 2H), 2.75 (d, J=5.9 Hz, 2H), 1.88 (d, J=11.8 Hz, 3H), 1.53-1.35 (m, 2H) ppm; LC-MS: m/z 409.8 [M+H]⁺.

Example 36: 2-(1-(8-((2,3-dichlorophenyl)thio)imidazo[1,2-c]pyrimidin-5-yl)piperidin-4-yl)ethan-1-amine

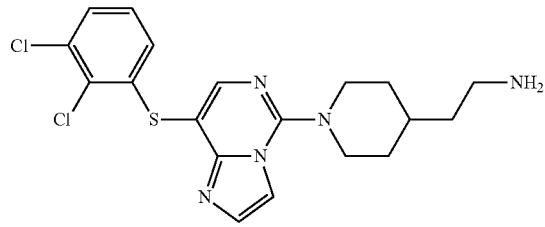 [SMILES: NCCC1CCN(c2ncc(Sc3cccc(Cl)c3Cl)c3nccn23)CC1]

¹H NMR (400 MHz, DMSO-d₆) δ 8.03 (s, 1H), 7.85 (d, J=1.2 Hz, 1H), 7.56 (d, J=1.2 Hz, 1H), 7.41 (dd, J=8.0, 1.2 Hz, 1H), 7.12 (t, J=8.1 Hz, 1H), 6.69 (dd, J=8.1, 1.2 Hz, 1H), 4.02 (d, J=12.9 Hz, 2H), 3.03 (t, J=12.0 Hz, 2H), 2.87-2.78 (m, 2H), 1.82 (d, J=12.5 Hz, 2H), 1.70 (s, 1H), 1.55 (dd, J=14.7, 6.9 Hz, 2H), 1.40 (dd, J=21.6, 11.5 Hz, 2H) ppm; LC-MS: m/z 422.7 [M+H]⁺.

Example 37: Synthesis of Compound: (S)-8-(8-((2,3-dichlorophenyl)thio)imidazo[1,2-c]pyrimidin-5-yl)-2-oxa-8-azaspiro[4.5]decan-4-amine Step 1: (R)—N—((S)-8-(8-((2,3-dichlorophenyl)thio)imidazo[1,2-c]pyrimidin-5-yl)-2-oxa-8-azaspiro[4.5]decan-4-yl)-2-methylpropane-2-sulfinamide

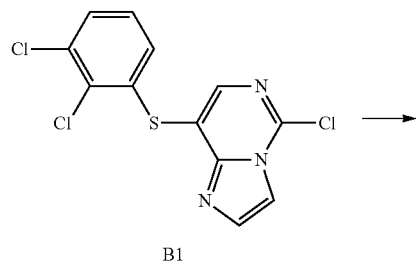

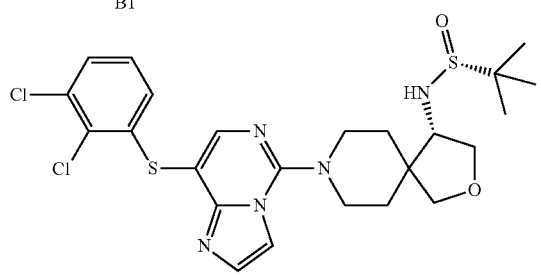

Using the same method as that of Example 23, B1 was substituted by a corresponding amine to obtain (R)—N—((S)-8-(8-((2,3-dichlorophenyl)thio)imidazo[1,2-c]pyrimidin-5-yl)-2-oxa-8-azaspiro[4.5]decan-4-yl)-2-methylpropane-2-sulfinamide.

LC-MS: m/z 554.1 [M+H]⁺.

Step 2: (S)-8-(8-((2,3-dichlorophenyl)thio)imidazo[1,2-c]pyrimidin-5-yl)-2-oxa-8-azaspiro[4.5]decan-4-amine

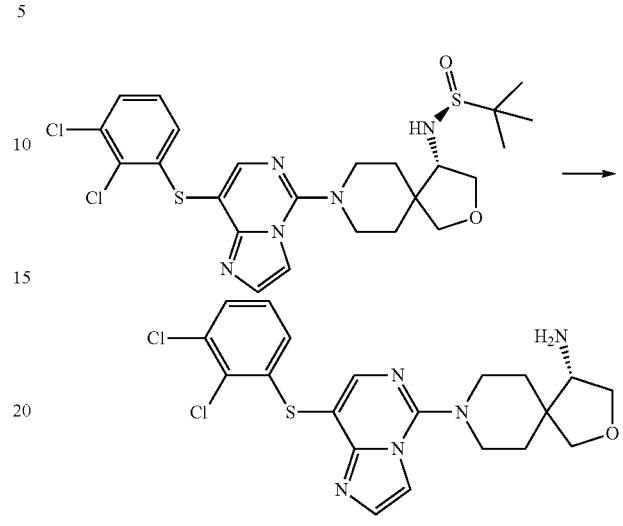

Under nitrogen atmosphere, to a 50 mL single-necked flask were added (R)—N—((S)-8-(8-((2,3-dichlorophenyl)thio)imidazo[1,2-c]pyrimidin-5-yl)-2-oxa-8-azaspiro[4.5]decan-4-yl)-2-methylpropane-2-sulfinamide (70 mg, 0.13 mmol) and methanol (0.5 mL), followed by dropwise addition of a solution of hydrogen chloride in 1,4-dioxane (0.05 mL, 4 M) at room temperature, and the mixture was stirred and reacted at room temperature for 1 hour. After the reaction was completed, the mixture was cooled to room temperature, filtered and concentrated under reduced pressure to obtain a residue, which was purified by high performance liquid chromatography to obtain (S)-8-(8-((2,3-dichlorophenyl)thio)imidazo[1,2-c]pyrimidin-5-yl)-2-oxa-8-azaspiro[4.5]decan-4-amine (10 mg, yield: 17%).

¹H NMR (400 MHz, DMSO-d₆) δ 8.03 (s, 1H), 7.83 (d, J=1.5 Hz, 1H), 7.57 (d, J=1.4 Hz, 1H), 7.42 (dd, J=8.0, 1.4 Hz, 1H), 7.12 (t, J=8.0 Hz, 1H), 6.69 (dd, J=8.1, 1.4 Hz, 1H), 4.00 (dd, J=8.8, 6.4 Hz, 1H), 3.87-3.71 (m, 2H), 3.66 (d, J=8.5 Hz, 1H), 3.29-3.27 (m, 1H), 3.17 (t, J=5.8 Hz, 2H), 1.92-1.76 (m, 2H), 1.57 (dd, J=12.5, 5.8 Hz, 2H), 1.24 (d, J=3.2 Hz, 1H) ppm; LC-MS: m/z 450.1 [M+H]⁺.

According to the synthesis method of Example 37, the following compounds were synthesized:

Example 38: (R)-1-(8-((2,3-dichlorophenyl)thio)imidazo[1,2-c]pyrimidin-5-yl)azepan-4-amine

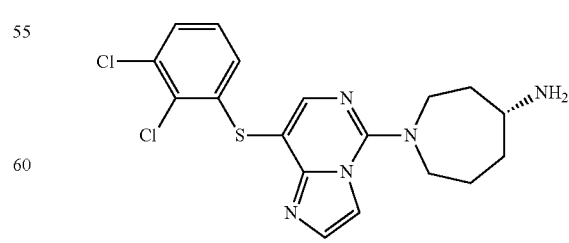

¹H NMR (400 MHz, DMSO-d₆) δ 8.39 (s, 1H), 7.95 (s, 2H), 7.48 (s, 1H), 7.40 (d, J=7.9 Hz, 1H), 7.12 (t, J=8.0 Hz, 1H), 6.66 (d, J=8.0 Hz, 1H), 4.03-3.89 (m, 2H), 3.81-3.61

(m, 2H), 3.20 (s, 1H), 2.15 (s, 1H), 1.95 (d, J=14.1 Hz, 4H), 1.56 (d, J=10.7 Hz, 1H) ppm; LC-MS: m/z 409.8 [M+H]+.

Example 39: (R)-8-(8-((2,3-dichlorophenyl)thio)imidazo[1,2-c]pyrimidin-5-yl)-3,3-dimethyl-1-oxa-8-azaspiro[4.5]decan-4-amine

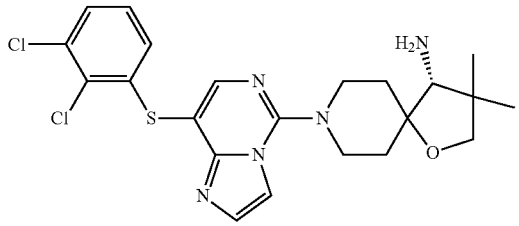 [SMILES: CC1(C)COC2(CCN(c3ncc(Sc4cccc(Cl)c4Cl)c4nccn34)CC2)[C@@H]1N]

¹H NMR (400 MHz, DMSO-d₆) δ 8.18 (s, 1H), 8.03 (s, 1H), 7.84 (s, 1H), 7.56 (s, 1H), 7.41 (d, J=7.9 Hz, 1H), 7.12 (t, J=8.1 Hz, 1H), 6.70 (d, J=8.1 Hz, 1H), 3.94 (t, J=13.7 Hz, 2H), 3.54 (d, J=8.7 Hz, 1H), 3.45 (d, J=8.7 Hz, 1H), 3.32 (d, J=12.2 Hz, 2H), 2.68 (s, 1H), 1.98-1.88 (m, 2H), 1.65 (s, 2H), 1.02 (s, 3H), 0.95 (s, 3H); LC-MS: m/z 479.7 [M+H]+.

Example 40: (S)-8-(8-((2,3-dichlorophenyl)thio)imidazo[1,2-c]pyrimidin-5-yl)-3,3-dimethyl-1-oxa-8-azaspiro[4.5]decan-4-amine

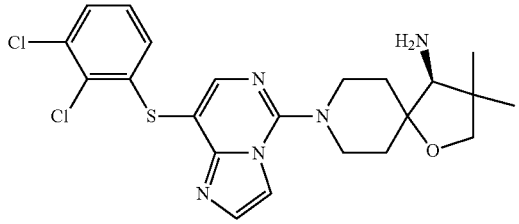 [SMILES: CC1(C)COC2(CCN(c3ncc(Sc4cccc(Cl)c4Cl)c4nccn34)CC2)[C@H]1N]

¹H NMR (400 MHz, DMSO-d₆) δ 8.03 (s, 1H), 7.84 (s, 1H), 7.56 (s, 1H), 7.41 (d, J=7.9 Hz, 1H), 7.12 (t, J=8.0 Hz, 1H), 6.69 (d, J=8.1 Hz, 1H), 3.94 (t, J=14.1 Hz, 2H), 3.54 (d, J=8.7 Hz, 1H), 3.45 (d, J=8.7 Hz, 1H), 3.35-3.25 (m, 2H), 2.69 (s, 1H), 1.98-1.85 (m, 2H), 1.71-1.59 (m, 2H), 1.03 (s, 3H), 0.95 (s, 3H); LC-MS: m/z 479.7 [M+H]+.

Example 41: (1R)-8-(8-((2,3-dichlorophenyl)thio)imidazo[1,2-c]pyrimidin-5-yl)-2-methyl-8-azaspiro[4.5]decan-1-amine

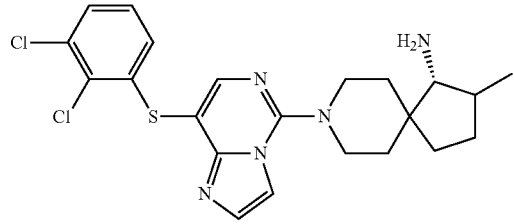 [SMILES: CC1CCC2(CCN(c3ncc(Sc4cccc(Cl)c4Cl)c4nccn34)CC2)[C@@H]1N]

¹H NMR (400 MHz, DMSO-d₆) δ 8.03 (s, 1H), 7.81 (dd, J=7.4, 1.6 Hz, 1H), 7.56 (d, J=1.6 Hz, 1H), 7.41 (dd, J=8.0, 1.4 Hz, 1H), 7.12 (t, J=8.0 Hz, 1H), 6.68 (dd, J=8.1, 1.4 Hz, 1H), 3.95 (d, J=11.9 Hz, 2H), 3.12 (t, J=12.0 Hz, 2H), 2.89 (d, J=5.8 Hz, 1H), 2.08-1.44 (m, 9H), 1.00 (dd, J=31.0, 6.6 Hz, 3H) ppm; LC-MS: m/z 462.1 [M+H]+.

Example 42: (1R)-8-(8-((2,3-dichlorophenyl)thio)imidazo[1,2-c]pyrimidin-5-yl)-3-methyl-8-azaspiro[4.5]decan-1-amine

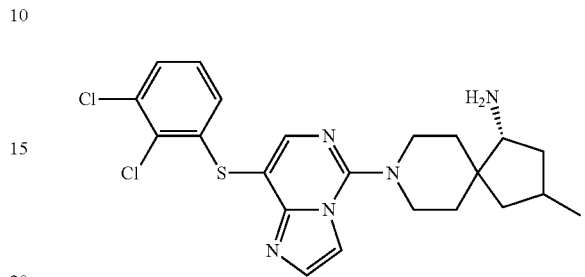

¹H NMR (400 MHz, DMSO-d₆) δ 8.03 (s, 1H), 7.80 (s, 1H), 7.56 (s, 1H), 7.41 (d, J=8.0 Hz, 1H), 7.12 (t, J=8.1 Hz, 1H), 6.69 (d, J=8.1 Hz, 1H), 3.99-3.80 (m, 2H), 3.24-2.98 (m, 3H), 2.27-1.14 (m, 9H), 1.04-0.95 (m, 3H) ppm; LC-MS: m/z 462.1 [M+H]+.

Example 43: (2R,4R)-4-amino-8-(8-((2,3-dichlorophenyl)thio)imidazo[1,2-c]pyrimidin-5-yl)-8-azaspiro[4.5]decan-2-ol

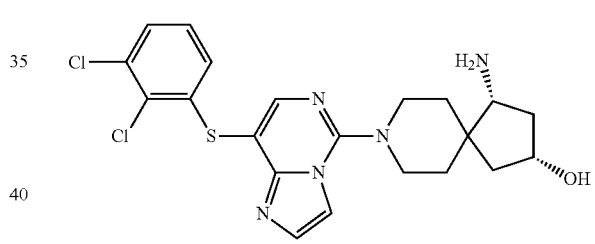

¹H NMR (400 MHz, DMSO-d₆) δ 8.37 (s, 1H), 8.04 (s, 1H), 7.81 (s, 1H), 7.57 (s, 1H), 7.42 (d, J=7.9 Hz, 1H), 7.12 (t, J=8.0 Hz, 1H), 6.68 (d, J=8.0 Hz, 1H), 4.15 (d, J=6.5 Hz, 1H), 3.91 (d, J=14.3 Hz, 2H), 3.22 (s, 2H), 2.93 (t, J=7.3 Hz, 1H), 2.27-2.20 (m, 1H), 1.89-1.66 (m, 5H), 1.54 (dt, J=13.4, 6.7 Hz, 1H), 1.35 (d, J=12.9 Hz, 1H) ppm; LC-MS: m/z 465.7 [M+H]+.

Example 44: (3S,4S)-8-(8-((2,3-dichlorophenyl)thio)imidazo[1,2-c]pyrimidin-5-yl)-3-methyl-2-oxa-8-azaspiro[4.5]decan-4-amine

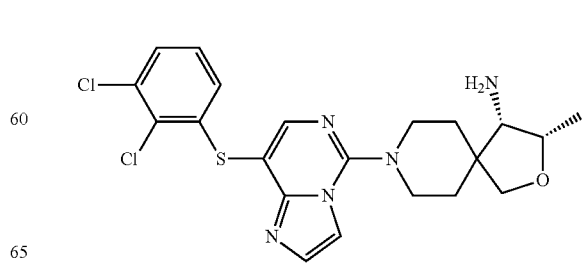

¹H NMR (400 MHz, DMSO-d₆) δ 8.03 (s, 1H), 7.84 (s, 1H), 7.56 (s, 1H), 7.41 (d, J=7.9 Hz, 1H), 7.12 (t, J=8.0 Hz, 1H), 6.69 (d, J=8.0 Hz, 1H), 4.15-4.06 (m, 1H), 3.73 (s, 2H), 3.56 (d, J=8.5 Hz, 1H), 3.42-3.27 (m, 3H), 3.05 (d, J=4.8 Hz, 1H), 1.91 (dt, J=39.6, 9.8 Hz, 2H), 1.67 (dd, J=25.7, 13.7 Hz, 2H), 1.12 (d, J=6.4 Hz, 3H) ppm; LC-MS: m/z 463.7 [M+H]⁺.

Example 45: (R)-8-(8-((2,3-dichlorophenyl)thio) imidazo[1,2-c]pyrimidin-5-yl)-1-oxa-8-azaspiro[4.5] decan-4-amine

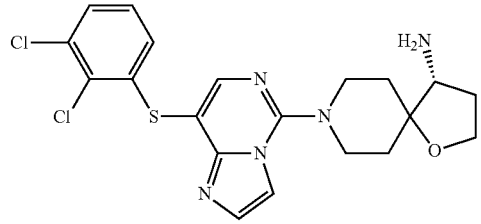

¹H NMR (400 MHz, DMSO-d₆) δ 7.95 (s, 1H), 7.60 (s, 1H), 7.48 (s, 1H), 7.20 (d, J=6.4 Hz, 1H), 6.95 (t, J=6.4 Hz, 1H), 6.70 (d, J=6.4 Hz, 1H), 4.00-3.85 (m, 4H), 3.46 (t, J=8.8 Hz, 1H), 3.20 (t, J=5.2 Hz, 1H), 2.39-2.35 (m, 1H), 1.94-1.89 (m, 2H), 1.80-1.74 (m, 2H), 1.68-1.65 (m, 1H) ppm; LCMS: m/z 450.1 [M+H]⁺.

Example 46: Synthesis of Compound: (R)-8-(8-((2,3-dichlorophenyl)thio)imidazo[1,2-c]pyrimidin-5-yl)-N-methyl-8-azaspiro[4.5]decan-1-amine Step 1: (R)—N—((R)-8-(8-((2,3-dichlorophenyl) thio)imidazo[1,2-c]pyrimidin-5-yl)-8-azaspiro[4.5] decan-1-yl)-2-methylpropane-2-sulfinamide

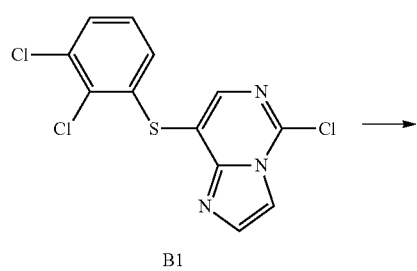

B1

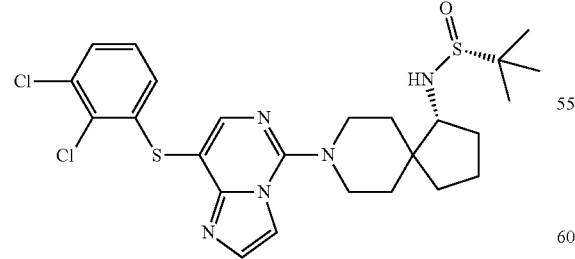

Using the same method as that of Example 23, B1 was substituted by an amine to obtain (R)—N—((R)-8-(8-((2,3-dichlorophenyl)thio)imidazo[1,2-c]pyrimidin-5-yl)-8-azaspiro[4.5]decan-1-yl)-2-methylpropane-2-sulfinamide (70 mg, yield: 80%). LC-MS: m/z 552.1 [M+H]⁺.

Step 2: (R)—N—((R)-8-(8-((2,3-dichlorophenyl) thio)imidazo[1,2-c]pyrimidin-5-yl)-8-azaspiro[4.5] decan-1-yl)-N,2-dimethylpropane-2-sulfinamide

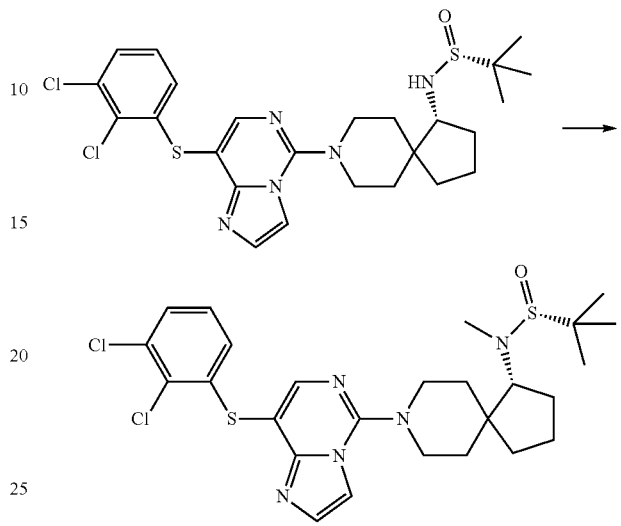

To a dry 50 mL round bottom flask were added (R)—N—((R)-8-(8-((2,3-dichlorophenyl)thio)imidazo[1,2-c]pyrimidin-5-yl)-8-azaspiro[4.5]decan-1-yl)-N,2-dimethylpropane-2-sulfinamide (70 mg, 0.13 mmol) and DMF (5 mL), followed by slow addition of NaH (10.4 mg, 0.26 mmol) at 0° C. The mixture was stirred at 0° C. for 10 minutes, and then CH₃I (28 mg, 0.20 mmol) was slowly added at 0° C., and the resulting mixture was stirred at room temperature for 2 hours. After the reaction was completed, water (10 mL) was added to quench the reaction, followed by extraction with ethyl acetate (3×10 mL). The organic phases were combined, dried over MgSO₄, filtered and concentrated under reduced pressure to obtain a residue, which was then purified by silica gel chromatography (ethyl acetate/petroleum ether with a gradient of 0 to 80%) to obtain (R)—N—((R)-8-(8-((2,3-dichlorophenyl)thio)imidazo[1,2-c]pyrimidin-5-yl)-8-azaspiro[4.5]decan-1-yl)-N,2-dimethylpropane-2-sulfinamide (50 mg, yield: 49%).

LC-MS: m/z 566.1 [M+H]⁺.

Step 3: (R)-8-(8-((2,3-dichlorophenyl)thio)imidazo [1,2-c]pyrimidin-5-yl)-N-methyl-8-azaspiro[4.5] decan-1-amine

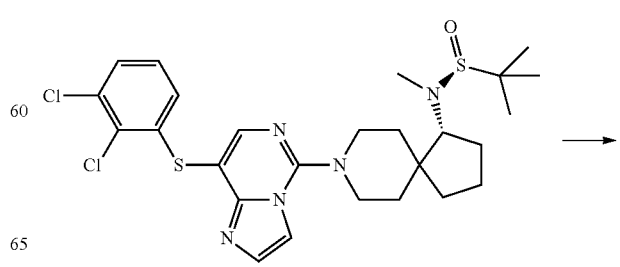

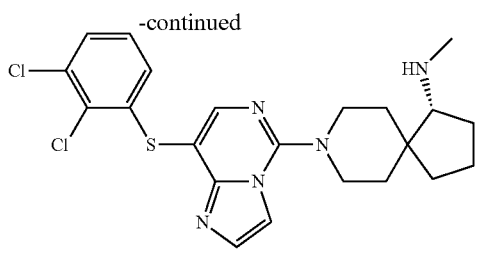

Using the same method as that of Step 2 in Example 37, (R)—N—((R)-8-(8-((2,3-dichlorophenyl)thio)imidazo[1,2-c]pyrimidin-5-yl)-8-azaspiro[4.5]decan-1-yl)-N,2-dimethylpropane-2-sulfinamide was subjected to the removal of the sulfinyl group to obtain (R)-8-(8-((2,3-dichlorophenyl)thio)imidazo[1,2-c]pyrimidin-5-yl)-N-methyl-8-azaspiro [4.5]decan-1-amine.

$^1$H NMR (400 MHz, DMSO-$d_6$) δ 8.30 (s, 1H), 8.03 (s, 1H), 7.82 (s, 1H), 7.55 (s, 1H), 7.41 (d, J=8.0 Hz, 1H), 7.12 (t, J=8.0 Hz, 1H), 6.69 (d, J=8.1 Hz, 1H), 3.87 (d, J=13.2 Hz, 2H), 3.22 (dd, J=22.1, 10.8 Hz, 2H), 2.56 (t, J=7.3 Hz, 1H), 2.35 (s, 3H), 1.89 (ddd, J=33.1, 16.7, 7.8 Hz, 4H), 1.72-1.33 (m, 6H) ppm; LC-MS: m/z 461.7 [M+H]$^+$.

Example 47: (R)-8-(8-((2,3-dichlorophenyl)thio)imidazo[1,2-c]pyrimidin-5-yl)-8-azaspiro[4.5]decan-1-amine Step 1: (R)—N—((R)-8-(8-iodoimidazo[1,2-c]pyrimidin-5-yl)-8-azaspiro[4.5]decan-1-yl)-2-methylpropane-2-sulfinamide

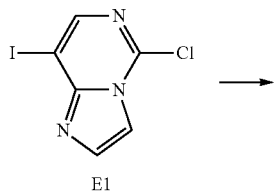

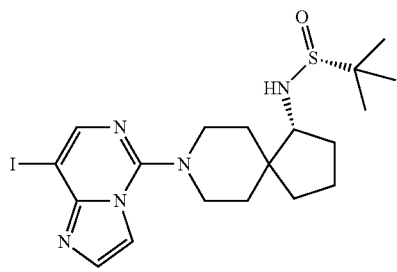

To a dry 50 mL single-necked flask were added 5-chloro-8-iodoimidazo[1,2-c]pyrimidine (E1) (50 mg, 0.18 mmol), (R)-2-methyl-N—((R)-8-azaspiro[4.5]decan-1-yl)propane-2-sulfinamide (C-1A) (93 mg, 0.36 mmol), DIEA (46 mg, 0.36 mmol) and NMP (5 mL), and the reaction mixture was stirred at 90° C. for 2 hours. After the reaction was completed, the obtained residue was poured into water (10 mL), stirred at room temperature for 5 minutes, and then extracted with ethyl acetate (3×20 mL). The combined organic phase was dried over MgSO$_4$, filtered and concentrated under reduced pressure. The resulting residue was purified by silica gel chromatography (ethyl acetate/petroleum ether with a gradient of 0 to 80%) to obtain (R)—N—((R)-8-(8-iodoimidazo[1,2-c]pyrimidin-5-yl)-8-azaspiro[4.5]decan-1-yl)-2-methylpropane-2-sulfinamide as a pale yellow solid (80 mg, yield: 88%).

$^1$H NMR (400 MHz, DMSO-$d_6$) δ 8.02 (s, 1H), 7.79 (d, J=1.4 Hz, 1H), 7.64 (d, J=1.4 Hz, 1H), 4.97 (d, J=8.0 Hz, 1H), 3.77-3.65 (m, 2H), 3.23-3.13 (m, 1H), 3.04 (dd, J=30.0, 11.5 Hz, 2H), 2.03-1.78 (m, 4H), 1.67-1.31 (m, 6H), 1.13 (s, 9H) ppm; LC-MS: m/z 502.1 [M+H]$^+$.

Step 2: (R)—N—((R)-8-(8-((2,3-dichlorophenyl)thio)imidazo[1,2-c]pyrimidin-5-yl)-8-azaspiro[4.5]decan-1-yl)-2-methylpropane-2-sulfinamide To a dry 50 mL three-necked flask were added (R)—N—((R)-8-(8-iodoimidazo[1,2-c]pyrimidin-5-yl)-8-azaspiro[4.5]decan-1-yl)-2-methylpropane-2-sulfinamide (80 mg, 0.16 mmol), cuprous iodide (3 mg, 0.016 mmol), 1,10-phenanthroline (6 mg, 0.032 mmol), 2,3-dichlorothiophenol (34 mg, 0.192 mmol), potassium phosphate (68 mg, 0.32 mmol) and 10 mL of dioxane sequentially. The mixture was heated for 3 hours under nitrogen atmosphere. After the reaction was completed, saturated NH$_4$Cl solution (50 mL) was added, followed by extraction with ethyl acetate (3×20 mL). The organic phases were combined, dried over Na$_2$SO$_4$, filtered, and the filtrate was concentrated under reduced pressure. The resulting residue was purified by silica gel chromatography (methanol/ethyl acetate with a gradient of 0 to 10%) to obtain (R)—N—((R)-8-(8-((2,3-dichlorophenyl)thio)imidazo[1,2-c]pyrimidin-5-yl)-8-azaspiro[4.5]decan-1-yl)-2-methylpropane-2-sulfinamide as a pale yellow solid (60 mg, yield: 68%).

$^1$H NMR (400 MHz, DMSO-$d_6$) δ 8.02 (s, 1H), 7.76 (d, J=1.4 Hz, 1H), 7.56 (d, J=1.4 Hz, 1H), 7.40 (dd, J=8.0, 1.3 Hz, 1H), 7.11 (t, J=8.0 Hz, 1H), 6.68 (dd, J=8.1, 1.3 Hz, 1H), 5.00 (d, J=8.1 Hz, 1H), 3.94 (dd, J=12.8, 3.4 Hz, 2H), 3.26-3.14 (m, 3H), 2.08-1.84 (m, 4H), 1.69-1.36 (m, 6H), 1.14-1.11 (m, 9H) ppm; LC-MS: m/z 552.1 [M+H]$^+$.

Step 3: (R)-8-(8-((2,3-dichlorophenyl)thio)imidazo[1,2-c]pyrimidin-5-yl)-8-azaspiro[4.5]decan-1-amine

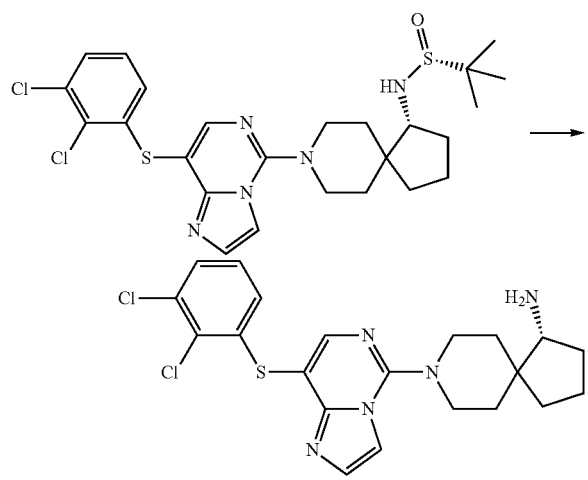

To a dry 50 mL round bottom flask were added (R)—N—((R)-8-(8-((2,3-dichlorophenyl)thio)imidazo[1,2-c]pyrimidin-5-yl)-8-azaspiro[4.5]decan-1-yl)-2-methylpropane-2-sulfinamide (Example 17-2) (60 mg, 0.11 mmol) and a solution of hydrogen chloride in 1,4-dioxane (7 M, 5 mL), and the mixture was reacted at room temperature for 1 hour. The reaction solution was concentrated under reduced pressure, and the resulting crude product was purified by reversed-phase high-performance liquid chromatography to obtain the product (R)-8-(8-((2,3-dichlorophenyl)thio)imidazo[1,2-c]pyrimidin-5-yl)-8-azaspiro[4.5]decan-1-amine (25 mg, yield: 51%).

$^1$H NMR (400 MHz, CD$_3$OD-d$_4$) δ 8.54 (s, 2H), 8.04 (s, 1H), 7.81 (s, 1H), 7.58 (s, 1H), 7.33 (dd, J=8.0, 1.3 Hz, 1H), 7.05 (t, J=8.0 Hz, 1H), 6.68 (dd, J=8.1, 1.3 Hz, 1H), 4.03 (t, J=14.7 Hz, 2H), 3.38 (s, 2H), 2.27 (d, J=5.4 Hz, 1H), 1.97-1.63 (m, 9H) ppm; LC-MS: m/z 448.1 [M+H]$^+$.

According to the synthesis method of Example 47, using commercially available raw materials or self-synthesized intermediates, the following compounds were synthesized:

Example 48: (R)-7-(8-((2,3-dichlorophenyl)thio)imidazo[1,2-c]pyrimidin-5-yl)-7-azaspiro[3.5]nonan-1-amine

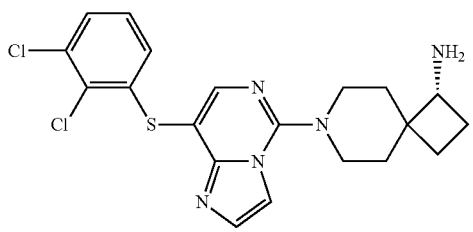 [SMILES: N[C@@H]1CCC12CCN(c1ncc(Sc3cccc(Cl)c3Cl)c3nccn13)CC2]

$^1$H NMR (400 MHz, DMSO-d$_6$) δ 8.34 (s, 1H), 8.02 (s, 1H), 7.82 (d, J=1.6 Hz, 1H), 7.55 (s, 1H), 7.41 (d, J=7.8 Hz, 1H), 7.12 (t, J=8.1 Hz, 1H), 6.69 (d, J=7.9 Hz, 1H), 3.91 (d, J=13.2 Hz, 1H), 3.84-3.73 (m, 1H), 3.18-3.08 (m, 3H), 2.13 (q, J=8.0 Hz, 1H), 1.83 (td, J=10.7, 8.5, 4.2 Hz, 2H), 1.80-1.69 (m, 3H) ppm; LC-MS: m/z 434.1 [M+H]$^+$.

Example 49: 7-(8-((2,3-dichlorophenyl)thio)imidazo[1,2-c]pyrimidin-5-yl)-7-azaspiro[3.5]nonan-2-amine

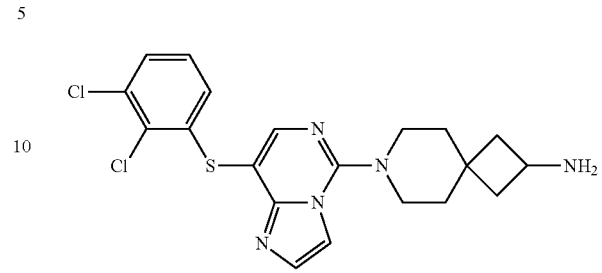

$^1$H NMR (400 MHz, DMSO-d$_6$) δ 8.01 (s, 1H), 7.83 (d, J=1.6 Hz, 1H), 7.56 (d, J=1.5 Hz, 1H), 7.41 (dd, J=8.0, 1.4 Hz, 1H), 7.12 (t, J=8.0 Hz, 1H), 6.69 (dd, J=8.1, 1.4 Hz, 1H), 3.50 (d, J=10.2 Hz, 2H), 3.41 (s, 2H), 2.71-2.64 (m, 1H), 2.36-2.30 (m, 1H), 2.21 (s, 2H), 1.81 (d, J=26.6 Hz, 5H) ppm; LC-MS: m/z 434.1 [M+H]$^+$.

Example 50: (7R)-2-(8-((2,3-dichlorophenyl)thio)imidazo[1,2-c]pyrimidin-5-yl)-2-azaspiro[4.4]nonan-7-ylamine

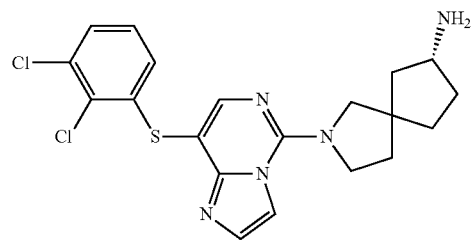 [SMILES: N[C@@H]1CCC2(CCN(c3ncc(Sc4cccc(Cl)c4Cl)c4nccn34)C2)C1]

$^1$H NMR (400 MHz, DMSO-d$_6$) δ 8.36 (brs, 1H), 8.18 (s, 1H), 7.89 (d, J=2.4 Hz, 1H), 7.43 (s, 1H), 7.38 (d, J=6.0 Hz, 1H), 7.11 (t, J=6.4 Hz, 1H), 6.64 (d, J=6.0 Hz, 1H), 3.96-3.74 (m, 4H), 3.53-3.51 (m, 1H), 2.00-1.60 (m, 8H) ppm; LCMS: m/z 434.2 [M+H]$^+$.

Example 51: (R)-8-(8-((6-amino-3-chloro-2-methyl-pyridin-4-yl)thio)imidazo[1,2-c]pyrimidin-5-yl)-3,3-dimethyl-1-oxa-8-azaspiro[4.5]decan-4-amine

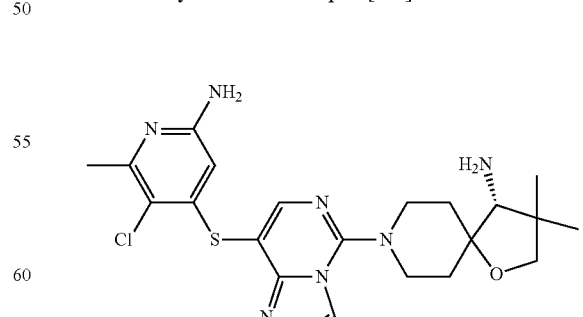

$^1$H NMR (400 MHz, DMSO-d$_6$) δ 8.17 (s, 2H), 8.08 (s, 1H), 7.90 (s, 1H), 7.65 (s, 1H), 5.67 (s, 1H), 4.09-3.93 (m, 2H), 3.61 (dd, J=14.2, 9.1 Hz, 4H), 3.10 (d, J=5.4 Hz, 1H), 2.35 (d, J=15.8 Hz, 3H), 2.03-1.71 (m, 4H), 1.16 (s, 3H), 1.07 (s, 3H) ppm; LCMS: m/z 474.1 [M+H]$^+$.

Example 52: (S)-8-(8-((2,3-dichlorophenyl)thio)imidazo[1,2-c]pyrimidin-5-yl)-8-azaspiro[4.5]decan-1-amine

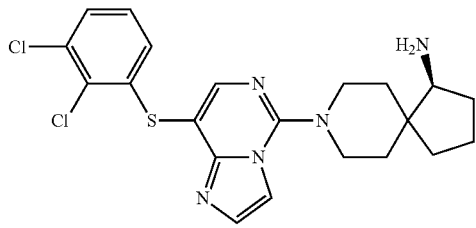 [SMILES: N[C@H]1CCCC12CCN(c1ncc(Sc3cccc(Cl)c3Cl)c3nccn13)CC2]

$^1$H NMR (DMSO-d$_6$) δ 8.43 (s, 1H), 8.02 (s, 1H), 7.79-7.80 (d, 1H), 7.56-7.57 (d, 1H), 7.40-7.42 (d, 1H), 7.11-7.15 (t, 1H), 6.68-6.71 (d, 1H), 3.88 (t, 2H), 3.24 (t, 2H), 3.01 (t, 1H), 1.60-1.90 (m, 5H), 1.30-1.59 (m, 5H) ppm; LC-MS: m/z 448.1 [M+H]$^+$.

Example 53: (R)-8-(8-((2-chlorophenyl)thio)imidazo[1,2-c]pyrimidin-5-yl)-8-azaspiro[4.5]decan-1-amine

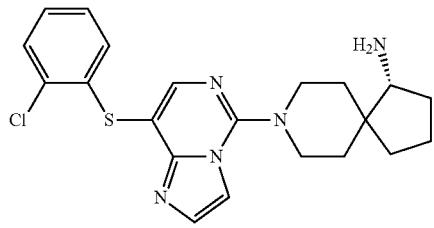

$^1$H NMR (400 MHz, DMSO-d$_6$) δ 7.97 (s, 1H), 7.80 (d, J=1.5 Hz, 1H), 7.57 (d, J=1.4 Hz, 1H), 7.49 (dd, J=7.7, 1.6 Hz, 1H), 7.15 (dtd, J=19.6, 7.4, 1.6 Hz, 2H), 6.76 (dd, J=7.7, 1.7 Hz, 1H), 3.93-3.80 (m, 2H), 3.21 (td, J=11.2, 2.7 Hz, 2H), 3.00 (s, 1H), 2.05-1.75 (m, 4H), 1.75-1.35 (m, 6H) ppm; LCMS: m/z 414.1 [M+H]$^+$.

Example 54: (R)-8-(8-((3-chlorophenyl)thio)imidazo[1,2-c]pyrimidin-5-yl)-8-azaspiro[4.5]decan-1-amine

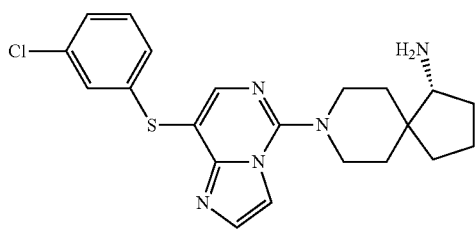 [SMILES: N[C@@H]1CCCC12CCN(c1ncc(Sc3cccc(Cl)c3)c3nccn13)CC2]

$^1$H NMR (CD$_3$OD-d$_4$) δ 7.96 (s, 1H), 7.78 (s, 1H), 7.58 (s, 1H), 7.23-7.27 (m, 3H), 7.14-7.16 (m, 1H), 3.83 (m, 2H), 3.24 (m, 2H), 2.89 (m, 1H), 1.77-1.83 (m, 4H), 1.51-1.62 (m, 2H), 1.354-1.46 (m, 4H) ppm; LCMS: m/z 414.1 [M+H]$^+$.

Example 55: (R)-8-(8-((4-chlorophenyl)thio)imidazo[1,2-c]pyrimidin-5-yl)-8-azaspiro[4.5]decan-1-amine

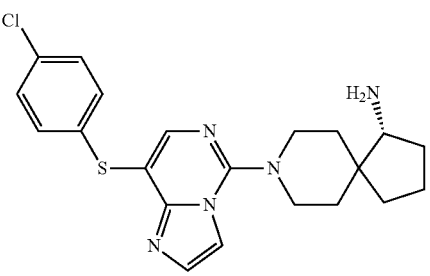 [SMILES: N[C@@H]1CCCC12CCN(c1ncc(Sc3ccc(Cl)cc3)c3nccn13)CC2]

$^1$H NMR (400 MHz, DMSO-d$_6$) δ 7.91 (s, 1H), 7.79-7.75 (m, 1H), 7.58 (d, J=1.2 Hz, 1H), 7.33 (d, J=8.5 Hz, 2H), 7.23 (d, J=8.5 Hz, 2H), 3.91-3.71 (m, 2H), 3.18 (t, J=12.3 Hz, 2H), 3.00 (s, 1H), 2.05-1.66 (m, 5H), 1.64-1.34 (m, 5H) ppm; LCMS: m/z 414.1 [M+H]$^+$.

Example 56: (R)-8-(8-((2,6-dichlorophenyl)thio)imidazo[1,2-c]pyrimidin-5-yl)-8-azaspiro[4.5]decan-1-amine

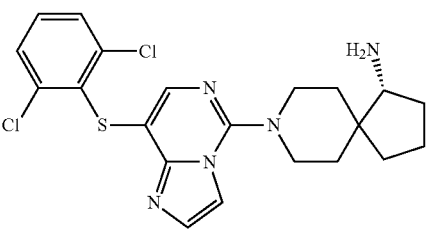 [SMILES: N[C@@H]1CCCC12CCN(c1ncc(Sc3c(Cl)cccc3Cl)c3nccn13)CC2]

$^1$H NMR (400 MHz, DMSO-d$_6$) δ 7.75 (s, 1H), 7.66 (s, 1H), 7.64 (s, 1H), 7.60 (s, 1H), 7.51 (t, J=8.1 Hz, 1H), 7.09 (s, 1H), 3.64 (s, 2H), 3.04 (q, J=12.4 Hz, 2H), 2.74 (t, J=7.2 Hz, 1H), 1.89-1.74 (m, 4H), 1.52 (s, 2H), 1.42-1.24 (m, 4H) ppm; LCMS: m/z 450.0 [M+H]$^+$.

Example 57: (R)-8-(8-((2,4-dichlorophenyl)thio)imidazo[1,2-c]pyrimidin-5-yl)-8-azaspiro[4.5]decan-1-amine

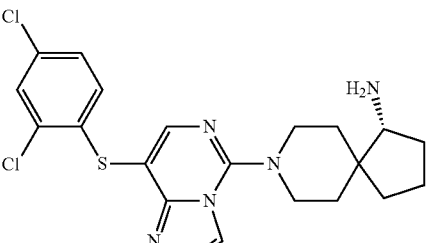

¹H NMR (400 MHz, DMSO-d₆) δ 8.00 (s, 1H), 7.81 (d, J=1.6 Hz, 1H), 7.69 (d, J=2.3 Hz, 1H), 7.56 (d, J=1.4 Hz, 1H), 7.20 (dd, J=8.6, 2.3 Hz, 1H), 6.75 (d, J=8.6 Hz, 1H), 3.94-3.79 (m, 2H), 3.20 (q, J=11.9 Hz, 2H), 2.77 (t, J=7.3 Hz, 1H), 1.90-1.77 (m, 4H), 1.67-1.52 (m, 2H), 1.37 (td, J=27.0, 26.1, 12.9 Hz, 4H) ppm; LCMS: m/z 450.0 [M+H]⁺.

Example 58: (R)-8-(8-((2,5-dichlorophenyl)thio) imidazo[1,2-c]pyrimidin-5-yl)-8-azaspiro[4.5]decan-1-amine

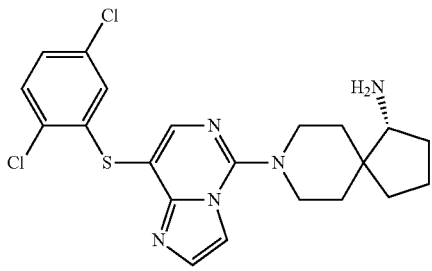 [SMILES: N[C@@H]1CCCC12CCN(c1ncc(Sc3cc(Cl)ccc3Cl)c3nccn13)CC2]

¹H NMR (CD₃OD-d₄) δ 8.02 (s, 1H), 7.82 (s, 1H), 7.52-7.58 (m, 2H), 7.22-7.25 (m, 1H), 6.71 (s, 1H), 3.88-3.89 (m, 2H), 3.22-3.24 (m, 2H), 2.81-2.83 (m, 1H), 1.77-1.83 (m, 4H), 1.51-1.62 (m, 2H), 1.354-1.46 (m, 4H) ppm; LCMS: m/z 450.0 [M+H]⁺.

Example 59: (R)-8-(8-((2-isopropylphenyl)thio) imidazo[1,2-c]pyrimidin-5-yl)-8-azaspiro[4.5]decan-1-amine

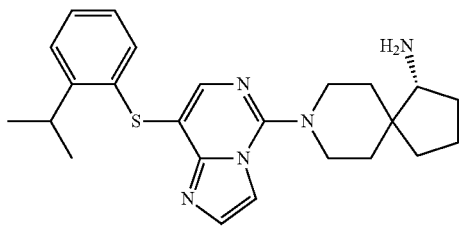 [SMILES: CC(C)c1ccccc1Sc1cnc(N2CCC3(CCC[C@H]3N)CC2)n2ccnc12]

¹H NMR (400 MHz, DMSO-d₆) δ 7.76 (s, 1H), 7.58 (s, 2H), 7.37 (d, J=7.7 Hz, 1H), 7.24 (s, 1H), 7.06 (d, J=6.1 Hz, 2H), 3.73 (s, 2H), 3.52 (s, 1H), 3.11 (d, J=12.8 Hz, 2H), 2.76 (s, 1H), 1.83 (d, J=31.7 Hz, 4H), 1.58 (d, J=42.0 Hz, 2H), 1.36 (s, 4H), 1.24 (d, J=7.0 Hz, 6H) ppm; LCMS: m/z 423.2 [M+H]⁺.

Example 60: (R)-8-(8-((2-methoxyphenyl)thio)imidazo[1,2-c]pyrimidin-5-yl)-8-azaspiro[4.5]decan-1-amine

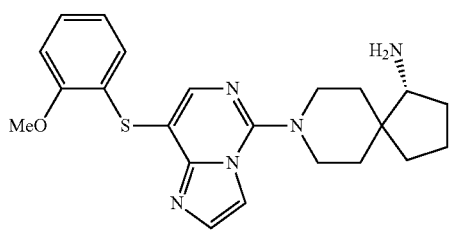 [SMILES: COc1ccccc1Sc1cnc(N2CCC3(CCC[C@H]3N)CC2)n2ccnc12]

¹H NMR (400 MHz, DMSO-d₆) δ 7.77 (s, 1H), 7.73 (s, 1H), 7.58 (s, 1H), 7.19 (t, J=7.9 Hz, 1H), 7.05 (d, J=8.2 Hz, 1H), 6.82-6.69 (m, 2H), 3.87 (s, 3H), 3.77 (d, J=12.4 Hz, 2H), 3.17 (s, 2H), 2.97 (s, 2H), 1.97 (s, 1H), 1.77-1.30 (m, 9H) ppm; LCMS: m/z 410.1 [M+H]⁺.

Example 61: Methyl (R)-2-((5-(1-amino-8-azaspiro[4.5]decan-8-yl)imidazo[1,2-c]pyrimidin-8-yl)thio) benzoate

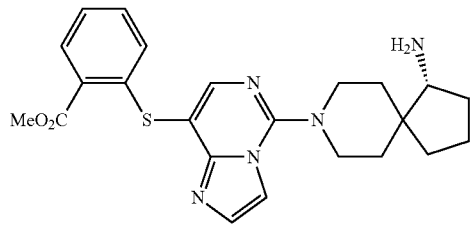

¹H NMR (400 MHz, DMSO-d₆) δ 8.38 (s, 1H), 7.95 (dd, J=7.8, 1.6 Hz, 1H), 7.78 (d, J=1.5 Hz, 1H), 7.53 (d, J=1.4 Hz, 1H), 7.30 (td, J=7.7, 1.6 Hz, 1H), 7.21 (t, J=7.5 Hz, 1H), 6.77 (d, J=8.1 Hz, 1H), 3.91 (s, 3H), 3.85 (d, J=13.4 Hz, 2H), 3.23 (d, J=12.8 Hz, 2H), 2.97 (t, J=7.0 Hz, 1H), 1.97 (d, J=7.0 Hz, 2H), 1.82-1.40 (m, 8H) ppm; LC-MS: m/z 438.1 [M+H]⁺.

Example 62: (R)-8-(8-((4-aminophenyl)thio)imidazo[1,2-c]pyrimidin-5-yl)-8-azaspiro[4.5]decan-1-amine

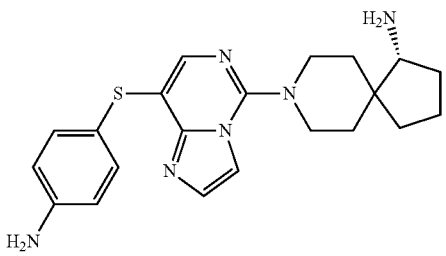 [SMILES: Nc1ccc(Sc2cnc(N3CCC4(CCC[C@H]4N)CC3)n3ccnc23)cc1]

¹H NMR (400 MHz, DMSO-d₆) δ 7.71 (s, 1H), 7.61 (s, 1H), 7.24 (d, J=7.5 Hz, 2H), 7.13 (s, 1H), 6.58 (d, J=7.5 Hz, 2H), 5.48 (s, 2H), 3.60 (s, 2H), 3.17 (s, 2H), 3.04-3.01 (m, 1H), 1.40 (s, 10H) ppm; LC-MS: m/z 396.2 [M+H]⁺.

Example 63: (R)-8-(8-((3-amino-2-chlorophenyl)thio)imidazo[1,2-c]pyrimidin-5-yl)-8-azaspiro[4.5]decan-1-amine

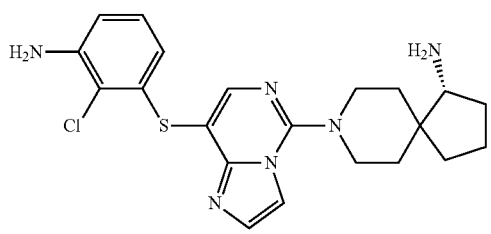 [SMILES: Nc1cccc(Sc2cnc(N3CCC4(CCC[C@H]4N)CC3)n3ccnc23)c1Cl]

¹H NMR (400 MHz, DMSO-d₆) δ 8.31 (s, 2H), 7.85 (s, 1H), 7.78 (s, 1H), 7.58 (s, 1H), 6.80 (t, J=7.9 Hz, 1H), 6.59 (d, J=8.0 Hz, 1H), 5.94 (d, J=7.8 Hz, 1H), 5.50 (s, 2H), 3.84 (t, J=13.1 Hz, 2H), 3.17 (s, 2H), 3.04 (s, 1H), 2.00 (q, J=7.2 Hz, 2H), 1.83-1.37 (m, 10H) ppm; LC-MS: m/z 429.1 [M+H]⁺.

Example 64: (R)-8-(8-((3-(trifluoromethyl)phenyl)thio)imidazo[1,2-c]pyrimidin-5-yl)-8-azaspiro[4.5]decan-1-amine

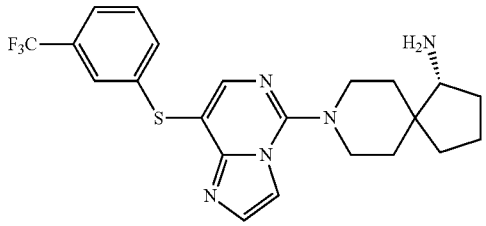 [SMILES: N[C@@H]1CCCC12CCN(c1ncc(Sc3cccc(C(F)(F)F)c3)c3nccn13)CC2]

¹H NMR (400 MHz, DMSO-d₆) δ 8.31 (s, 2H), 8.00 (s, 1H), 7.79 (d, J=1.6 Hz, 1H), 7.59-7.52 (m, 1H), 7.47 (dd, J=16.9, 9.2 Hz, 5H), 3.84 (t, J=13.0 Hz, 2H), 3.22 (d, J=13.1 Hz, 2H), 2.98 (s, 1H), 1.79 (d, J=13.8 Hz, 5H), 1.60-1.36 (m, 5H) ppm; LC-MS: m/z 448.1 [M+H]⁺.

Example 65: (R)—N-(4-((5-(1-amino-8-azaspiro[4.5]decan-8-yl)imidazo[1,2-c]pyrimidin-8-yl)thio)phenyl)acetamide

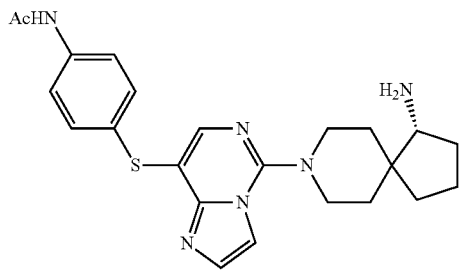 [SMILES: CC(=O)Nc1ccc(Sc2cnc(N3CCC4(CCC[C@H]4N)CC3)n3ccnc23)cc1]

¹H NMR (400 MHz, DMSO-d₆) δ 10.04 (d, J=5.3 Hz, 1H), 8.35 (s, 1H), 7.74 (s, 1H), 7.61 (d, J=13.9 Hz, 2H), 7.54 (d, J=8.5 Hz, 2H), 7.31 (d, J=8.4 Hz, 2H), 3.73 (t, J=12.0 Hz, 2H), 3.12 (s, 2H), 2.97 (s, 1H), 2.02 (s, 3H), 1.96 (s, 1H), 1.74 (dt, J=53.1, 26.6 Hz, 5H), 1.50 (d, J=35.3 Hz, 4H) ppm; LC-MS: m/z 396.2 [M+H]⁺.

Example 66: (R)-5-((5-(1-amino-8-azaspiro[4.5]decan-8-yl)imidazo[1,2-c]pyrimidin-8-yl)thio)-1,3,4-thiadiazol-2-amine

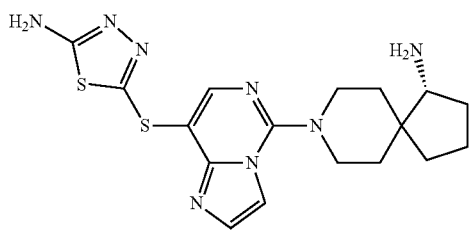 [SMILES: Nc1nnc(Sc2cnc(N3CCC4(CCC[C@H]4N)CC3)n3ccnc23)s1]

¹H NMR (400 MHz, DMSO-d₆) δ 8.33 (s, 1H), 7.96 (s, 1H), 7.81 (d, J=1.5 Hz, 1H), 7.66 (d, J=1.4 Hz, 1H), 7.33 (s, 2H), 3.83 (td, J=11.2, 9.7, 4.9 Hz, 2H), 3.20 (s, 2H), 3.05 (d, J=6.9 Hz, 1H), 1.99 (t, J=6.5 Hz, 1H), 1.86-1.69 (m, 4H), 1.62-1.38 (m, 5H) ppm; LC-MS: m/z 403.1 [M+H]⁺.

Example 67: (R)-8-(8-((1-methyl-1H-imidazol-2-yl)thio)imidazo[1,2-c]pyrimidin-5-yl)-8-azaspiro[4.5]decan-1-amine

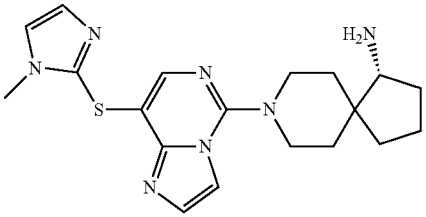 [SMILES: Cn1ccnc1Sc1cnc(N2CCC3(CCC[C@H]3N)CC2)n2ccnc12]

¹H NMR (400 MHz, DMSO-d₆) δ 7.76 (d, J=1.5 Hz, 1H), 7.60 (dd, J=6.8, 1.4 Hz, 1H), 7.39 (d, J=1.1 Hz, 1H), 7.35 (d, J=7.0 Hz, 1H), 7.00 (d, J=1.1 Hz, 1H), 3.80 (d, J=2.6 Hz, 3H), 3.63 (d, J=10.4 Hz, 2H), 3.08 (t, J=12.2 Hz, 2H), 2.73 (t, J=7.3 Hz, 1H), 1.90-1.67 (m, 4H), 1.65-1.51 (m, 2H), 1.50-1.29 (m, 4H) ppm; LC-MS: m/z 384.1 [M+H]⁺.

Example 68: (R)-8-(8-(naphthalen-1-ylthio)imidazo[1,2-c]pyrimidin-5-yl)-8-azaspiro[4.5]decan-1-amine

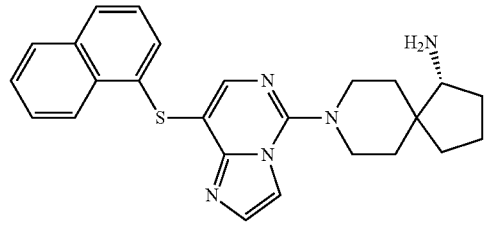 [SMILES: N[C@@H]1CCCC12CCN(c1ncc(Sc3cccc4ccccc34)c3nccn13)CC2]

¹H NMR (CD₃D-d₄) δ 8.35-8.40 (m, 2H), 7.99-8.02 (m, 1H), 7.89-7.91 (m, 1H), 7.76 (m, 1H), 7.57-7.64 (m, 4H), 7.43-7.47 (m, 2H), 3.73 (m, 2H), 3.11 (m, 2H), 2.95 (m, 1H), 1.71-2.05 (m, 4H), 1.35-1.68 (m, 6H) ppm; LC-MS: m/z 430.2 [M+H]⁺.

Example 69: (R)-8-(8-(thiazol-2-ylthio)imidazo[1,2-c]pyrimidin-5-yl)-8-azaspiro[4.5]decan-1-amine

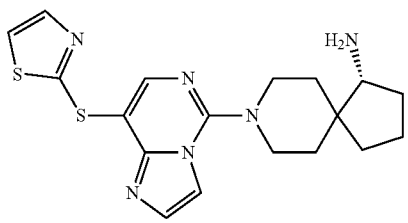 [SMILES: N[C@@H]1CCCC12CCN(c1ncc(Sc3nccs3)c3nccn13)CC2]

¹H NMR (400 MHz, DMSO-d₆) δ 8.35 (s, 1H), 8.11 (s, 1H), 7.82 (s, 1H), 7.69 (d, J=3.3 Hz, 1H), 7.62 (s, 1H), 7.58 (d, J=3.3 Hz, 1H), 3.89 (d, J=4.1 Hz, 2H), 3.25 (t, J=12.2 Hz,

2H), 3.07 (s, 1H), 2.32-2.25 (m, 2H), 2.06-1.69 (m, 5H), 1.65-1.40 (m, 5H) ppm; LC-MS: m/z 387.1 [M+H]+.

Example 70: (R)-8-(8-(oxazol-2-ylthio)imidazo[1,2-c]pyrimidin-5-yl)-8-azaspiro[4.5]decan-1-amine

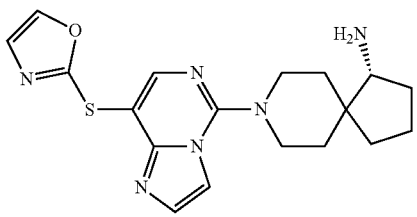 [SMILES: N[C@@H]1CCCC12CCN(c1ncc(Sc3ncco3)c3nccn13)CC2]

¹H NMR (CD₃OD-d₄) δ 8.12 (s, 1H), 8.04 (s, 1H), 7.80 (s, 1H), 7.60 (s, 1H), 7.22 (s, 1H), 3.86 (m, 2H), 3.22 (m, 2H), 2.98 (m, 1H), 1.71-2.05 (m, 4H), 1.35-1.68 (m, 6H) ppm; LC-MS: m/z 371.1 [M+H]+.

Example 71: Synthesis of Compound: (R)—N-(3-((5-(1-amino-8-azaspiro[4.5]decan-8-yl)imidazo[1,2-c]pyrimidin-8-yl)thio)-2-chlorophenyl)acrylamide Step 1: N-(2-chloro-3-((5-((R)-1-(((R)-tert-butylsulfinyl)amino)-8-azaspiro[4.5]decan-8-yl)imidazo[1,2-c]pyrimidin-8-yl)thio)phenyl)acrylamide

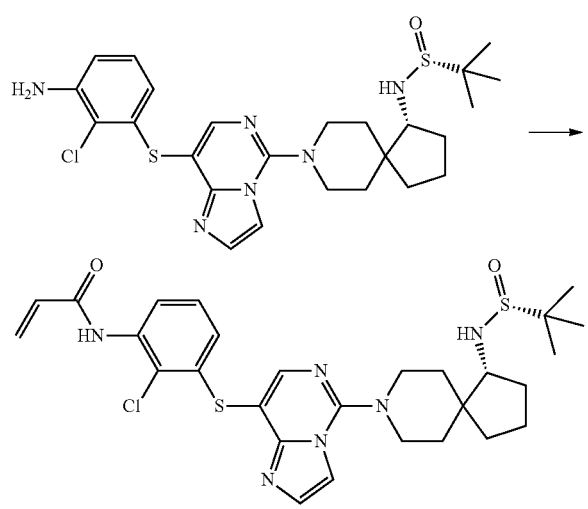

The intermediate (R)—N—((R)-8-(8-((3-amino-2-chlorophenyl)thio)imidazo[1,2-c]pyrimidin-5-yl)-8-azaspiro[4.5]decan-1-yl)-2-methylpropane-2-sulfinamide obtained from the synthesis of Example 63 was used in the following reaction.

To a 100 mL round bottom flask was added (R)—N—((R)-8-(8-((3-amino-2-chlorophenyl)thio)imidazo[1,2-c]pyrimidin-5-yl)-8-azaspiro[4.5]decan-1-yl)-2-methylpropane-2-sulfinamide (60 mg, 0.11 mmol), triethylamine (22 mg, 0.22 mmol) and dichloromethane (5 mL), followed by slow addition of acryloyl chloride (23 mg, 0.22 mmol) to the reaction solution at 0° C. After the addition, the reaction solution was allowed to react at room temperature for 2 hours. After the reaction was completed, 10 mL of water was added to quench the reaction, and then the mixture was extracted with ethyl acetate (3×20 mL). The organic phase was washed with water (20 mL×1) and saturated brine (20 mL×1) sequentially. The organic phase was collected, dried over anhydrous sodium sulfate, filtered, and the filtrate was concentrated under reduced pressure, followed by purification by column chromatography (petroleum ether:ethyl acetate=1:1) to obtain a crude product of N-(2-chloro-3-((5-((R)-1-(((R)-tert-butylsulfinyl)amino)-8-azaspiro[4.5]decan-8-yl)imidazo[1,2-c]pyrimidin-8-yl)thio)phenyl)acrylamide (30 mg, yield: 46%).
LC-MS: m/z 587.2 [M+H]+.

Step 2: (R)—N-(3-((5-(1-amino-8-azaspiro[4.5]decan-8-yl)imidazo[1,2-c]pyrimidin-8-yl)thio)-2-chlorophenyl)acrylamide

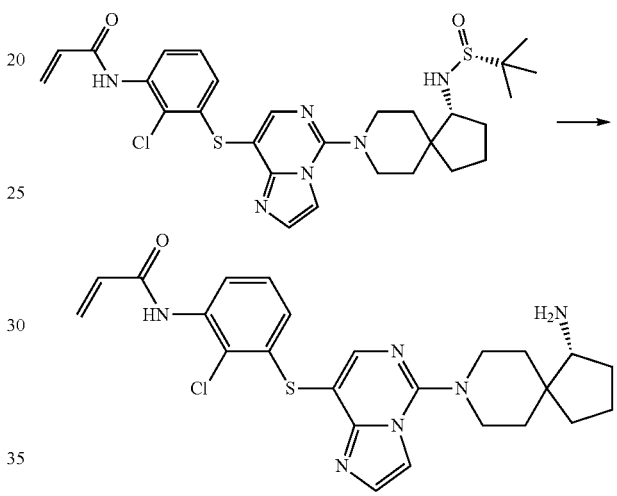

According to the same method as that of Step 2 in Example 37, (R)—N-(3-((5-(1-amino-8-azaspiro[4.5]decan-8-yl)imidazo[1,2-c]pyrimidin-8-yl)thio)-2-chlorophenyl)acrylamide was obtained by the removal of the sulfinyl group.
¹H NMR (400 MHz, DMSO-d₆) δ 9.86 (s, 1H), 7.99 (s, 1H), 7.80 (s, 1H), 7.57 (s, 1H), 7.49 (s, 1H), 7.10 (t, J=8.0 Hz, 1H), 6.72-6.51 (m, 2H), 6.29 (d, J=16.9 Hz, 1H), 5.81 (d, J=10.3 Hz, 1H), 3.87 (dd, J=14.9, 10.9 Hz, 2H), 3.20 (s, 2H), 3.01 (t, J=6.8 Hz, 1H), 2.05-1.34 (m, 10H) ppm; LC-MS: m/z 482.8 [M+H]+.

According to the synthesis method of Example 71, the following compounds were synthesized:

Example 72: (R)—N¹-(3-((5-(1-amino-8-azaspiro[4.5]decan-8-yl)imidazo[1,2-c]pyrimidin-8-yl)thio)

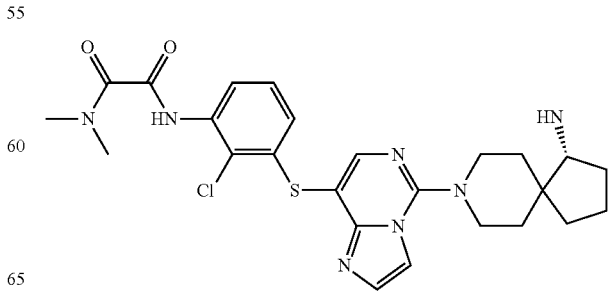

¹H NMR (400 MHz, DMSO-d₆) δ 8.00 (s, 1H), 7.80 (s, 1H), 7.57 (s, 1H), 7.41 (d, J=8.0 Hz, 1H), 7.13 (t, J=8.0 Hz, 1H), 6.62 (d, J=8.2 Hz, 1H), 5.49 (s, 1H), 3.86 (d, J=12.7 Hz, 2H), 3.81 (s, 3H), 3.23 (t, J=12.7 Hz, 2H), 3.11 (s, 3H), 3.02 (d, J=6.8 Hz, 1H), 2.05-1.75 (m, 5H), 1.54 (dd, J=41.2, 13.2 Hz, 5H) ppm; LC-MS: m/z 528.2[M+H]⁺.

Example 73: Synthesis of Compound: (R)—N-(3-((5-(1-amino-8-azaspiro[4.5]decan-8-yl)imidazo[1,2-c]pyrimidin-8-yl)thio)-2-chlorophenyl)-2-hydroxy-4-oxo-4H-pyrido[1,2-a]pyrimidin-3-carboxamide Step 1: ethyl 2-hydroxy-4-oxo-4H-pyrido[1,2-a]pyrimidine-3-carboxylate

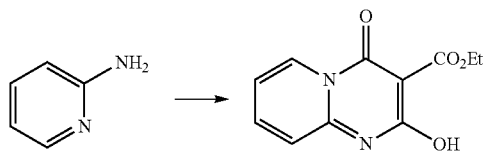

To a solution of pyridine-2-amine (940 mg, 10 mmol) in xylene (10 mL) was added triethyl methanetricarboxylate (4.64 g, 20 mmol) under nitrogen atmosphere. The mixture was stirred at 140° C. for 4 hours. The reaction was monitored by TLC until the raw material was consumed. The reaction mixture was filtered and washed with ethyl acetate to obtain ethyl 2-hydroxy-4-oxo-4H-pyrido[1,2-a]pyrimidine-3-carboxylate (1.95 g, yield: 83%).

¹H NMR (400 MHz, DMSO-d₆) δ 12.47 (s, 1H), 8.93 (dd, J=7.4, 1.5 Hz, 1H), 8.19 (ddd, J=8.6, 7.1, 1.6 Hz, 1H), 7.43-7.34 (m, 2H), 4.15 (q, J=7.1 Hz, 2H), 1.23 (t, J=7.1 Hz, 3H) ppm; LCMS: m/z 235 [M+H]⁺.

Step 2: N-(2-chloro-3-((5-((R)-1-(((R)-tert-butylsulfinyl)amino)-8-azaspiro[4.5]decan-8-yl)imidazo[1,2-c]pyrimidin-8-yl)thio)phenyl)-2-hydroxy-4-oxo-4H-pyrido[1,2-a]pyrimidin-3-carboxamide The intermediate (R)—N—((R)-8-(8-((3-amino-2-chlorophenyl)thio)imidazo[1,2-c]pyrimidin-5-yl)-8-azaspiro[4.5]decan-1-yl)-2-methylpropane-2-sulfinamide obtain from the synthesis of Example 63 was used in the following reaction.

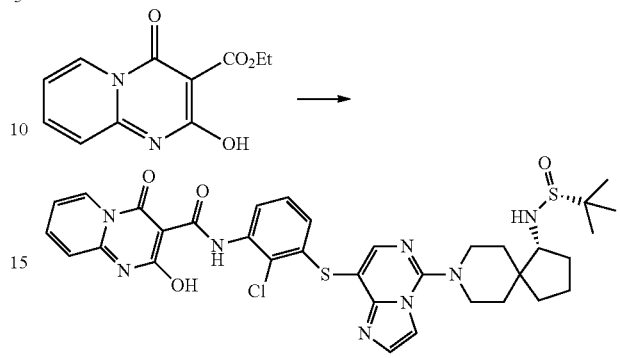

Under nitrogen atmosphere, to a solution of ethyl 2-hydroxy-4-oxo-4H-pyrido[1,2-a]pyrimidine-3-carboxylate (40 mg, 0.169 mmol) in DMF (2 mL) was added (R)—N—((R)-8-(8-((3-amino-2-chlorophenyl)thio)imidazo[1,2-c]pyrimidin-5-yl)-8-azaspiro[4.5]decan-1-yl)-2-methylpropane-2-sulfinamide (60 mg, 0.113 mmol). The mixture was reacted under microwave at 160° C. for 1 hour. After the mixture was cooled to room temperature, the mixture was filtered, diluted with water, extracted with ethyl acetate (20 mL×3), and washed with saturated brine. The organic phases were combined, dried over anhydrous sodium sulfate, filtered and concentrated to obtain N-(2-chloro-3-((5-((R)-1-(((R)-tert-butylsulfinyl)amino)-8-azaspiro[4.5]decan-8-yl)imidazo[1,2-c]pyrimidin-8-yl)thio)phenyl)-2-hydroxy-4-oxo-4H-pyrido[1,2-a]pyrimidin-3-carboxamide (20 mg, yield 21.7%).

LCMS: m/z 721 [M+H]⁺.

Step 3: (R)—N-(3-((5-(1-amino-8-azaspiro[4.5]decan-8-yl)imidazo[1,2-c]pyrimidin-8-yl)thio)-2-chlorophenyl)-2-hydroxy-4-oxo-4H-pyrido[1,2-a]pyrimidin-3-carboxamide

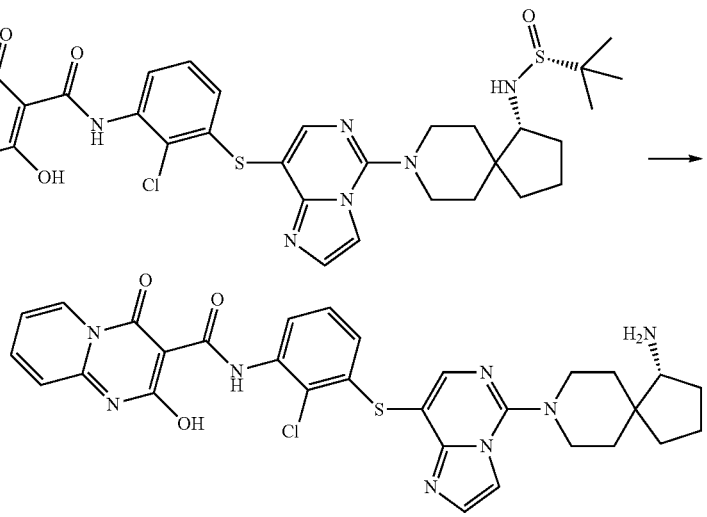

According to the same method as that of Step 2 in Example 37, (R)—N-(3-((5-(1-amino-8-azaspiro[4.5]decan-8-yl)imidazo[1,2-c]pyrimidin-8-yl)thio)-2-chlorophenyl)-2-hydroxy-4-oxo-4H-pyrido[1,2-a]pyrimidine-3-carboxamide was obtained by the removal of the sulfinyl group.

$^1$H NMR (400 MHz, DMSO-$d_6$) δ 8.68 (s, 1H), 8.43 (s, 1H), 7.94 (s, 1H), 7.79 (s, 1H), 7.63 (d, J=34.6 Hz, 2H), 7.03 (d, J=8.2 Hz, 1H), 6.61-6.51 (m, 1H), 6.40 (d, J=8.2 Hz, 1H), 6.00 (d, J=6.9 Hz, 1H), 5.45 (s, 1H), 3.94-3.80 (m, 2H), 3.23 (s, 2H), 3.05 (s, 1H), 2.09-1.34 (m, 10H) ppm; LC-MS: m/z 617.1 [M+H]$^+$.

Example 74: Synthesis of Compound (R)—N-(3-((5-(1-amino-8-azaspiro[4.5]decan-8-yl)imidazo[1,2-c]pyrimidin-8-yl)thio)-2-chlorophenyl)-2-hydroxy-4-oxo-6,7,8,9-tetrahydro-4H-pyrido[1,2-a]pyrimidin-3-carboxamide Step 1: ethyl 2-hydroxy-4-oxo-6,7,8,9-tetrahydro-4H-pyrido[1,2-a]pyrimidine-3-carboxylate

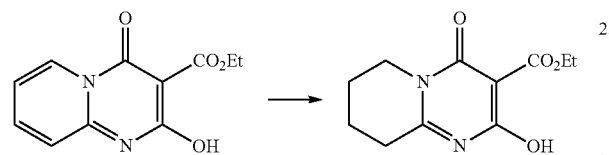

To a 100 mL round bottom flask was added ethyl 2-hydroxy-4-oxo-4H-pyrido[1,2-a]pyrimidine-3-carboxylate (obtained from step 1 of Example 69) (1 g, 4.12 mmol), methanol (25 mL) and 10% Pd/C (862 mg). The mixture was stirred at room temperature under hydrogen atmosphere (hydrogen balloon) for 2.5 hours. The reaction was monitored by TLC until the raw materials were consumed. The reaction mixture was filtered through diatomite and concentrated in vacuum to obtain ethyl 2-hydroxy-4-oxo-6,7,8,9-tetrahydro-4H-pyrido[1,2-a]pyrimidine-3-carboxylate (700 mg, yield: 69.4%).

$^1$H NMR (400 MHz, DMSO-$d_6$) δ 12.39 (s, 1H), 4.09 (q, J=7.1 Hz, 2H), 3.66 (t, J=6.0 Hz, 2H), 2.77 (t, J=6.4 Hz, 2H), 1.88-1.80 (m, 2H), 1.78-1.71 (m, 2H), 1.19 (t, J=7.1 Hz, 3H) ppm; LCMS: m/z [M+H]$^+$.

(R)—N-(3-((5-(1-Amino-8-azaspiro[4.5]decan-8-yl)imidazo[1,2-c]pyrimidin-8-yl)thio)-2-chlorophenyl)-2-hydroxy-4-oxo-6,7,8,9-tetrahydro-4H-pyrido[1,2-a]pyrimidine-3-carboxamide was obtained using the same method as that of Step 2 and Step 3 in Example 73.

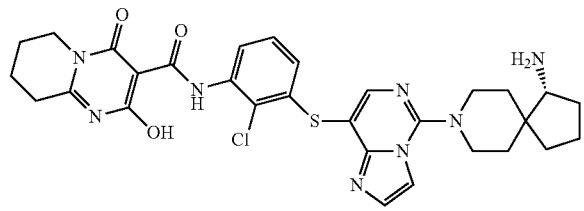 [SMILES: N[C@@H]1CCCC12CCN(c1ncc(Sc3cccc(NC(=O)c4c(O)nc5n(c4=O)CCCC5)c3Cl)c3nccn13)CC2]

$^1$H NMR (400 MHz, DMSO-$d_6$) δ 10.31 (s, 1H), 8.24 (s, 1H), 7.96 (s, 1H), 7.85 (s, 1H), 7.81-7.72 (m, 2H), 7.58 (s, 1H), 3.86 (dd, J=30.5, 16.1 Hz, 4H), 3.29-3.15 (m, 4H), 2.85-2.78 (m, 1H), 2.11-1.61 (m, 14H); LC-MS: m/z 621.1 [M+H]$^+$.

Example 75: Synthesis of (R)-8-(8-(2,3-dichlorophenyl)imidazo[1,2-c]pyrimidin-5-yl)-8-azaspiro[4.5]decan-1-amine Step 1: (R)—N—((R)-8-(8-(2,3-dichlorophenyl)imidazo[1,2-c]pyrimidin-5-yl)-8-azaspiro[4.5]decan-1-yl)-2-methylpropane-2-sulfinamide

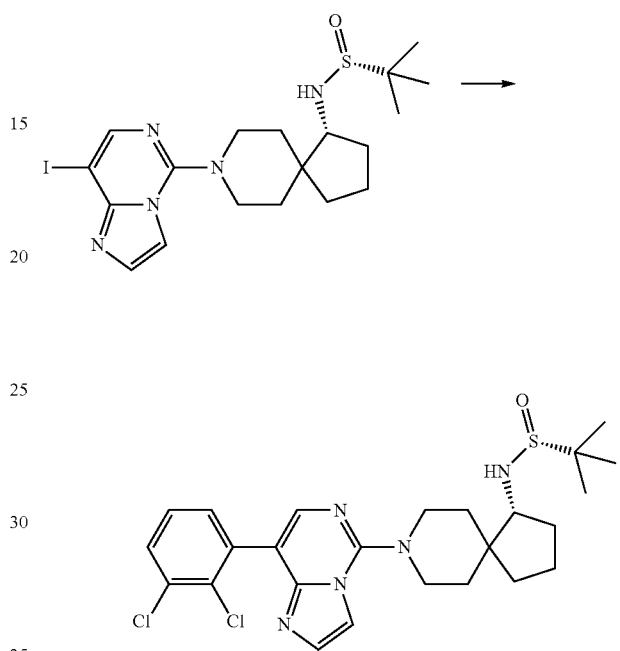

To a 20 mL sealed tube were sequentially added (R)—N—((R)-8-(8-iodoimidazo[1,2-c]pyrimidin-5-yl)-8-azaspiro[4.5]decan-1-yl)-2-methylpropane-2-sulfinamide (60 mg, 0.12 mmol), 1,4-dioxane (2 mL), purified water (0.5 mL), (2,3-dichlorophenyl)boronic acid (50 mg, 0.24 mmol), [1,1'-bis(diphenylphosphino)ferrocene]palladium dichloride (9 mg, 0.012 mmol) and potassium carbonate (50 mg, 0.36 mmol) at room temperature. The reaction system was bubbled with nitrogen for one minute. The sealed tube was heated to 80° C., and the reaction continued for 6 hours. After the reaction was completed, 20 mL of water was added to the reaction solution and extracted with ethyl acetate (50 mL×3). The organic phase was sequentially washed with water (20 mL×1) and saturated saline (20 mL×1). The organic phase was collected, dried over anhydrous sodium sulfate, filtered, and the filtrate was concentrated under reduced pressure, and purified by column chromatography (petroleum ether:ethyl acetate=1:1) to obtain a crude product of (R)—N—((R)-8-(8-(2,3-dichlorophenyl)imidazo[1,2-c]pyrimidin-5-yl)-8-azaspiro[4.5]decan-1-yl)-2-methylpropane-2-sulfinamide (30 mg, yield: 48%) as a pale yellow solid.

LC-MS: m/z 520.1 [M+H]$^+$.

Step 2: (R)-8-(8-(2,3-dichlorophenyl)imidazo[1,2-c]pyrimidin-5-yl)-8-azaspiro[4.5]decan-1-amine

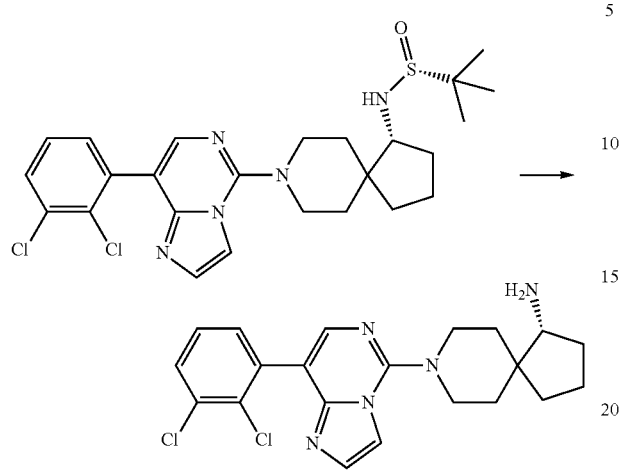

According to the same method as that of Step 2 in Example 37, (R)—N—((R)-8-(8-(2,3-dichlorophenyl)imidazo[1,2-c]pyrimidin-5-yl)-8-azaspiro[4.5]decan-1-yl)-2-methylpropane-2-sulfinamide was subjected to the removal of the sulfinyl group to obtain (R)-8-(8-(2,3-dichlorophenyl)imidazo[1,2-c]pyrimidin-5-yl)-8-azaspiro[4.5]decan-1-amine.

$^1$H NMR (400 MHz, DMSO-d$_6$) δ 8.35 (s, 1H), 7.75 (s, 3H), 7.60 (s, 1H), 7.49 (s, 1H), 3.79 (s, 2H), 3.21-3.12 (m, 2H), 2.93 (s, 1H), 1.82 (s, 5H), 1.46 (s, 7H) ppm; LCMS: m/z 416.1 [M+H]$^+$.

Example 76: Synthesis of Compound: (R)-8-(8-((2-amino-3-chloropyridin-4-yl)thio)imidazo[1,2-c]pyrimidin-5-yl)-8-azaspiro[4.5]decan-1-amine

Step 1: (R)—N—((R)-8-(8-((2-amino-3-chloropyridin-4-yl)thio)imidazo[1,2-c]pyrimidin-5-yl)-8-azaspiro[4.5]decan-1-yl)-2-methylpropane-2-sulfinamide

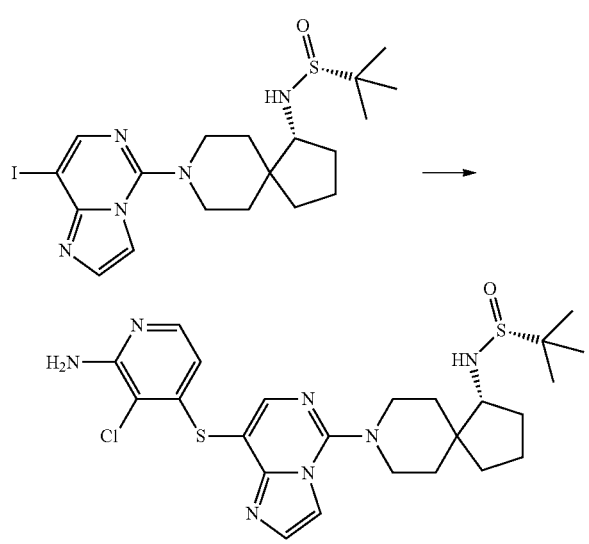

Under nitrogen atmosphere, to a 100 mL single-necked flask were sequentially added the crude (R)—N—((R)-8-(8-iodoimidazo[1,2-c]pyrimidin-5-yl)-8-azaspiro[4.5]decan-1-yl)-2-methylpropane-2-sulfinamide (100 mg, 0.20 mmol), sodium 2-amino-3-chloropyridine-4-thiolate (43 mg, 0.26 mmol), Pd$_2$(dba)$_3$ (20 mg, 0.02 mmol), Xantphos (23 mg, 0.040 mmol), DIPEA (52 mg, 0.40 mmol) and 1,4-dioxane (10 mL). The mixture was heated at 100° C. and stirred for 6 hours under nitrogen atmosphere. After the reaction was completed, the mixture was cooled to room temperature, filtered and concentrated under reduced pressure to obtain a residue, which was purified by silica gel chromatography (ethyl acetate/methanol with a of 0 to 30% gradient) to obtain (R)—N—((R)-8-(8-((2-amino-3-chloropyridin-4-yl)thio)imidazo[1,2-c]pyrimidin-5-yl)-8-azaspiro[4.5]decan-1-yl)-2-methylpropane-2-sulfinamide (40 mg, yield: 37%).
LC-MS: m/z 534.2 [M+H]$^+$.

Step 2: (R)-8-(8-((2-amino-3-chloropyridin-4-yl)thio)imidazo[1,2-c]pyrimidin-5-yl)-8-azaspiro[4.5]decan-1-amine According to the same method as that of Step 2 in Example 37, (R)—N—((R)-8-(8-((2-amino-3-chloropyridin-4-yl)thio)imidazo[1,2-c]pyrimidin-5-yl)-8-azaspiro[4.5]decan-1-yl)-2-methylpropane-2-sulfinamide was subjected to the removal of the sulfinyl group to obtain (R)-8-(8-((2-amino-3-chloropyridin-4-yl)thio)imidazo[1,2-c]pyrimidin-5-yl)-8-azaspiro[4.5]decan-1-amine.

$^1$H NMR (400 MHz, DMSO-d$_6$) δ 8.32 (d, J=6.9 Hz, 1H), 8.02 (s, 1H), 7.81 (s, 1H), 7.58 (d, J=1.4 Hz, 1H), 7.54 (d, J=5.4 Hz, 1H), 6.35 (s, 1H), 5.78 (d, J=5.4 Hz, 1H), 3.89 (t, J=12.5 Hz, 2H), 3.29-3.17 (m, 3H), 3.00 (s, 1H), 1.97 (s, 1H), 1.89-1.33 (m, 6H) ppm; LCMS: m/z 430.1 [M+H]$^+$.

According to the synthesis method of Example 76, the following compounds were synthesized:

Example 77: (R)-8-(8-((3-chloropyridin-4-yl)thio)imidazo[1,2-c]pyrimidin-5-yl)-8-azaspiro[4.5]decan-1-amine

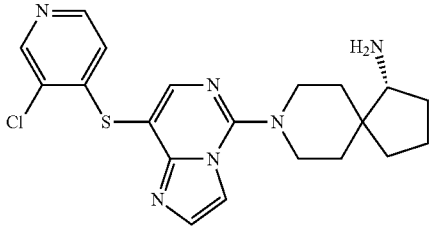 [SMILES: N[C@@H]1CCCC12CCN(c1ncc(Sc3ccncc3Cl)c3nccn13)CC2]

¹H NMR (CD₃OD-d₄) δ 8.54 (s, 1H), 8.35 (s, 1H), 8.15-8.16 (m, 1H), 8.09 (s, 1H), 7.83-7.84 (m, 1H), 7.57-7.58 (m, 1H), 6.67-6.68 (m, 1H), 3.92 (m, 2H), 3.26 (m, 2H), 3.00 (m, 1H), 1.71-2.05 (m, 4H), 1.35-1.68 (m, 6H) ppm; LCMS: m/z 415.1 [M+H]⁺.

Example 78: (R)-8-(8-((3-(trifluoromethyl)pyridin-4-yl)thio)imidazo[1,2-c]pyrimidin-5-yl)-8-azaspiro[4.5]decan-1-amine

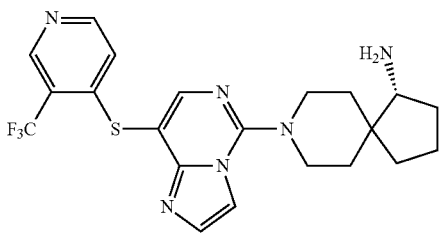 [SMILES: N[C@@H]1CCCC12CCN(c1ncc(Sc3ccncc3C(F)(F)F)c3nccn13)CC2]

¹H NMR (400 MHz, DMSO-d₆) δ 8.82 (s, 1H), 8.41 (d, J=5.5 Hz, 1H), 8.31 (s, 1H), 8.10 (s, 1H), 7.84 (s, 1H), 7.57 (s, 1H), 6.90 (d, J=5.4 Hz, 1H), 3.93 (s, 2H), 3.28-3.20 (m, 2H), 2.94 (s, 1H), 1.90-1.32 (m, 10H); LCMS: m/z 449.1 [M+H]⁺.

Example 79: (3S,4S)-8-(8-((2-amino-5-chloro-pyridin-4-yl)thio)imidazo[1,2-c]pyrimidin-5-yl)-3-methyl-2-oxa-8-azaspiro[4.5]decan-4-amine

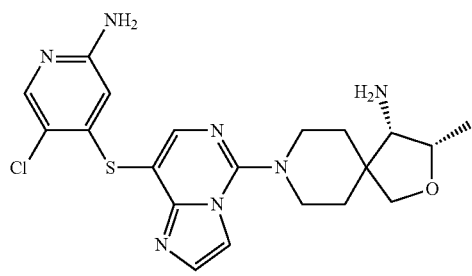 [SMILES: C[C@@H]1OCC2(CCN(c3ncc(Sc4cc(N)ncc4Cl)c4nccn34)CC2)[C@@H]1N]

¹H NMR (400 MHz, DMSO-d₆) δ 8.05 (s, 1H), 7.87 (s, 1H), 7.83 (s, 1H), 7.62 (d, J=1.3 Hz, 1H), 5.91 (s, 2H), 5.65 (s, 1H), 4.13 (d, J=5.2 Hz, 1H), 3.77 (d, J=8.5 Hz, 3H), 3.60 (d, J=8.6 Hz, 1H), 3.40 (s, 1H), 3.14 (s, 1H), 1.81 (dd, J=82.1, 33.6 Hz, 5H), 1.14 (d, J=6.3 Hz, 3H) ppm; LC-MS: m/z 462.1 [M+H]⁺.

Example 80: (3S,4S)-8-(8-((6-amino-3-chloro-2-methyl-pyridin-4-yl)thio)imidazo[1,2-c]pyrimidin-5-yl)-3-methyl-2-oxa-8-azaspiro[4.5]decan-4-amine

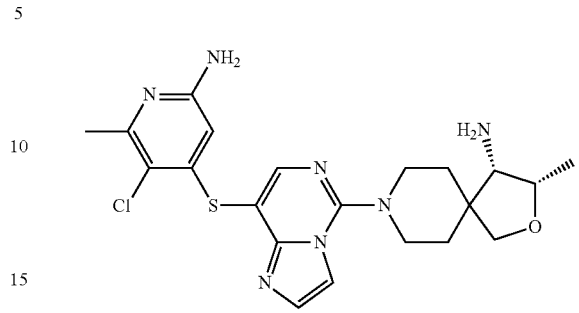

¹H NMR (400 MHz, DMSO-d₆) δ 8.14 (s, 1H), 8.04 (s, 1H), 7.85 (s, 1H), 7.63 (s, 1H), 5.82 (s, 2H), 5.51 (s, 1H), 4.26-4.18 (m, 1H), 3.88 (t, J=13.0 Hz, 3H), 3.70 (d, J=8.9 Hz, 1H), 3.42 (d, J=4.3 Hz, 1H), 3.27 (s, 2H), 2.31 (s, 3H), 1.99 (d, J=10.0 Hz, 2H), 1.80 (d, J=13.5 Hz, 1H), 1.69 (d, J=12.8 Hz, 1H), 1.23 (d, J=6.4 Hz, 3H) ppm; LC-MS: m/z 459.8 [M+H]⁺.

Example 81: (R)-8-(8-((3-chloro-2-cyclopropylpyrimidin-4-yl)thio)imidazo[1,2-c]pyrimidin-5-yl)-8-azaspiro[4.5]decan-1-amine

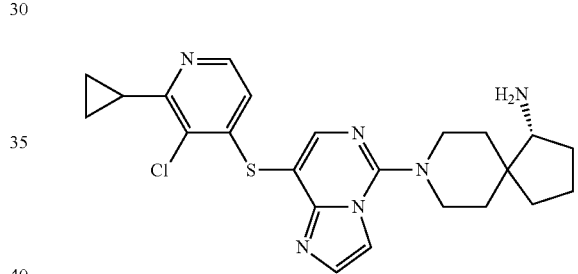

¹H NMR (400 MHz, DMSO-d₆) δ 8.06 (s, 1H), 7.97 (d, J=5.3 Hz, 1H), 7.82 (d, J=1.5 Hz, 1H), 7.57 (d, J=1.4 Hz, 1H), 6.40 (d, J=5.3 Hz, 1H), 3.91 (t, J=13.1 Hz, 2H), 3.25 (t, J=11.7 Hz, 2H), 3.02 (t, J=6.6 Hz, 1H), 2.03-1.65 (m, 5H), 1.67-1.37 (m, 5H), 1.04 (ddt, J=8.0, 5.6, 2.4 Hz, 2H), 0.97 (dq, J=6.9, 4.2, 3.4 Hz, 2H) ppm; LCMS: m/z 455.1 [M+H]⁺.

Example 82: (R)-8-(8-((3-chloro-2-methyl-pyridin-4-yl)thio)imidazo[1,2-c]pyrimidin-5-yl)-8-azaspiro[4.5]decan-1-amine

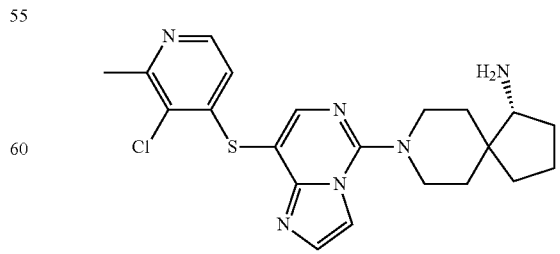

¹H NMR (400 MHz, DMSO-d₆) δ 8.35-8.29 (m, 1H), 8.07 (s, 1H), 8.02 (d, J=5.4 Hz, 1H), 7.83 (s, 1H), 7.57 (d,

J=1.4 Hz, 1H), 6.50 (d, J=5.3 Hz, 1H), 3.91 (t, J=12.9 Hz, 2H), 3.26 (t, J=12.3 Hz, 2H), 3.01 (s, 1H), 2.55 (s, 3H), 2.02-1.77 (m, 4H), 1.75-1.38 (m, 6H) ppm; LCMS: m/z 429.1 [M+H]$^+$.

Example 83: (R)-8-(8-((2-amino-5-chloropyridin-4-yl)thio)imidazo[1,2-c]pyrimidin-5-yl)-8-azaspiro[4.5]decan-1-amine

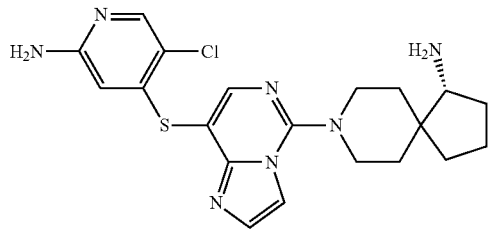 [SMILES: Nc1cc(Sc2cnc(N3CCC4(CCC[C@H]4N)CC3)n3ccnc23)c(Cl)cn1]

$^1$H NMR (CD$_3$OD-d$_4$) δ 8.38 (s, 1H), 8.04 (s, 1H), 7.82-7.84 (m, 2H), 7.61 (m, 1H), 5.93 (s, 2H), 5.66 (m, 1H), 3.87-3.93 (m, 2H), 3.21-3.28 (m, 2H), 2.98 (m, 1H), 1.71-2.05 (m, 4H), 1.35-1.68 (m, 6H) ppm; LCMS: m/z 430.1 [M+H]$^+$.

Example 84: (R)-8-(8-((2,3-dichloropyridin-4-yl)thio)imidazo[1,2-c]pyrimidin-5-yl)-8-azaspiro[4.5]decan-1-amine

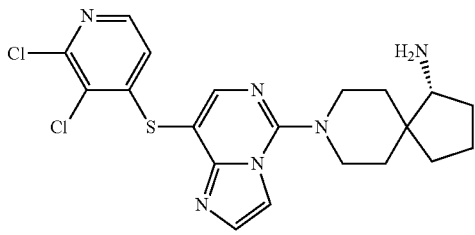 [SMILES: N[C@@H]1CCCC12CCN(c1ncc(Sc3ccnc(Cl)c3Cl)c3nccn13)CC2]

$^1$H NMR (400 MHz, DMSO-d$_6$) δ 8.10 (s, 1H), 8.00 (d, J=5.3 Hz, 1H), 7.83 (d, J=1.5 Hz, 1H), 7.59 (d, J=1.4 Hz, 1H), 6.72 (d, J=5.3 Hz, 1H), 4.03-3.87 (m, 2H), 3.27 (d, J=13.6 Hz, 2H), 3.14 (t, J=6.3 Hz, 1H), 2.05 (q, J=6.4 Hz, 1H), 1.87-1.42 (m, 9H) ppm; LCMS: m/z 449.1 [M+H]$^+$.

Example 85: (R)-8-(8-((2-methylpyridin-3-yl)thio)imidazo[1,2-c]pyrimidin-5-yl)-8-azaspiro[4.5]decan-1-amine

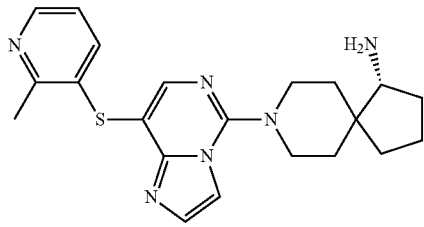 [SMILES: Cc1ncccc1Sc1cnc(N2CCC3(CCC[C@H]3N)CC2)n2ccnc12]

$^1$H NMR (400 MHz, DMSO-d$_6$) δ 8.25 (dd, J=4.7, 1.5 Hz, 1H), 7.89 (s, 1H), 7.79 (d, J=1.4 Hz, 1H), 7.56 (d, J=1.4 Hz, 1H), 7.23 (dd, J=7.9, 1.5 Hz, 1H), 7.06 (dd, J=7.9, 4.7 Hz, 1H), 3.89-3.70 (m, 2H), 3.17 (dd, J=22.2, 10.5 Hz, 2H), 2.80 (t, J=7.2 Hz, 1H), 2.60 (s, 3H), 1.88-1.20 (m, 10H) ppm; LCMS: m/z 395.2 [M+H]$^+$.

Example 86: (R)-8-(8-((2-(trifluoromethyl)pyridin-3-yl)thio)imidazo[1,2-c]pyrimidin-5-yl)-8-azaspiro[4.5]decan-1-amine

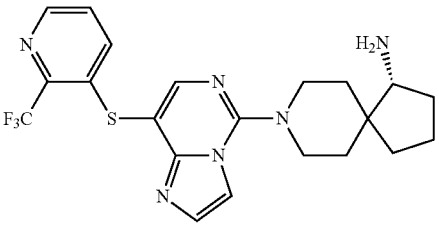 [SMILES: N[C@@H]1CCCC12CCN(c1ncc(Sc3cccnc3C(F)(F)F)c3nccn13)CC2]

$^1$H NMR (400 MHz, DMSO-d$_6$) δ 8.52 (s, 1H), 8.35 (s, 1H), 7.75 (s, 1H), 7.21 (d, J=8.2 Hz, 2H), 6.52 (d, J=8.4 Hz, 2H), 5.39 (s, 2H), 4.69 (s, 2H), 2.87 (s, 1H), 1.93-1.30 (m, 10H) ppm; LCMS: m/z 449.1 [M+H]$^+$.

Example 87: (R)-8-(8-((2-chloropyridin-3-yl)thio)imidazo[1,2-c]pyrimidin-5-yl)-8-azaspiro[4.5]decan-1-amine

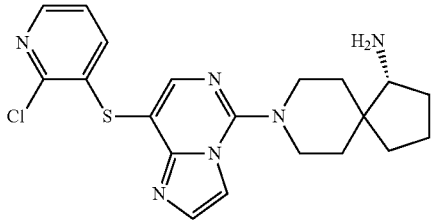

$^1$H NMR (CD$_3$OD-d$_4$) δ 8.38 (s, 1H), 8.16-8.18 (m, 1H), 8.06 (s, 1H), 7.81 (m, 2H), 7.23 (m, 1H), 7.14-7.22 (m, 2H), 3.88 (m, 2H), 3.23 (m, 2H), 2.97 (m, 1H), 1.71-2.05 (m, 4H), 1.35-1.68 (m, 6H) ppm; LCMS: m/z 415.1 [M+H]$^+$.

Example 88: (R)-8-(8-((6-amino-2-chloropyridin-3-yl)thio)imidazo[1,2-c]pyrimidin-5-yl)-8-azaspiro[4.5]decan-1-amine

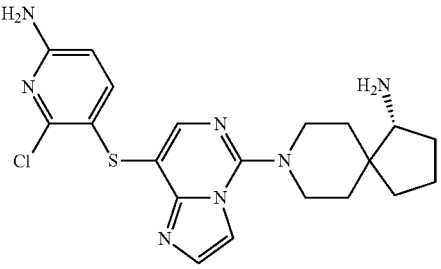

$^1$H NMR (400 MHz, DMSO-d$_6$) δ 8.33 (s, 1H), 7.74 (d, J=1.4 Hz, 1H), 7.61 (d, J=1.4 Hz, 1H), 7.51 (d, J=8.5 Hz, 1H), 7.40 (s, 1H), 6.73 (s, 2H), 6.38 (d, J=8.4 Hz, 1H), 3.68

(d, J=12.5 Hz, 3H), 3.10 (s, 2H), 2.97 (t, J=6.8 Hz, 1H), 2.01-1.31 (m, 10H) ppm. LC-MS: m/z 431.1 [M+H]+.

Example 89: (R)-8-(8-(benzo[d]thiazol-7-ylthio) imidazo[1,2-c]pyrimidin-5-yl)-8-azaspiro[4.5]decan-1-amine

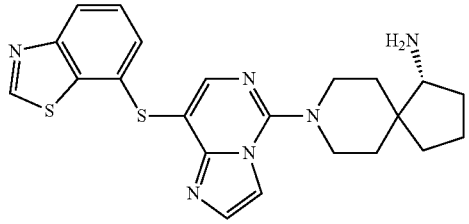

¹HNMR(CD₃OD-d₄) δ 9.43 (m, 1H), 8.35 (s, 3H), 8.00-8.02 (m, 1H), 7.88 (s, 1H), 7.76 (m, 1H), 7.56-7.58 (m, 1H), 7.47-7.51 (m, 1H), 7.38-7.40 (m, 1H), 3.80 (m, 2H), 3.17 (m, 2H), 2.98 (m, 1H), 1.71-2.05 (m, 4H), 1.35-1.68 (m, 6H) ppm; LC-MS: m/z 437.1 [M+H]+.

Example 90: (R)-8-(8-(phenylthio)imidazo[1,2-c] pyrimidin-5-yl)-8-azaspiro[4.5]decan-1-amine

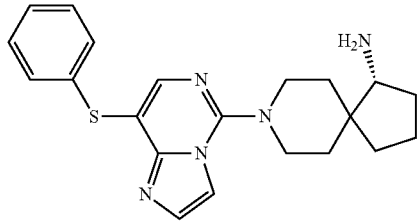 [SMILES: N[C@@H]1CCCC12CCN(c1ncc(Sc3ccccc3)c3nccn13)CC2]

¹H NMR (400 MHz, DMSO-d₆) δ 8.31 (s, 1H), 7.83 (s, 1H), 7.76 (s, 1H), 7.59 (s, 1H), 7.25 (tq, J=14.0, 7.4 Hz, 5H), 3.84-3.70 (m, 2H), 3.16 (d, J=12.4 Hz, 2H), 3.01 (t, J=6.8 Hz, 1H), 1.97 (dd, J=13.2, 7.2 Hz, 1H), 1.86-1.26 (m, 9H) ppm; LCMS: m/z 380.1 [M+H]+.

Example 91: (R)-8-(8-((1-methyl-1H-pyrrolo[2,3-b] pyridin-4-yl)thio)imidazo[1,2-c]pyrimidin-5-yl)-8-azaspiro[4.5]decan-1-amine

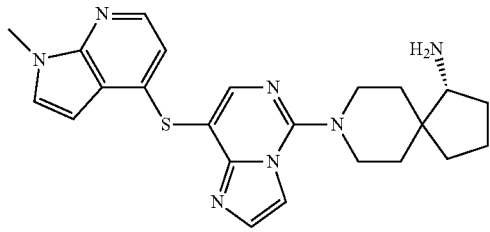 [SMILES: Cn1ccc2c(Sc3cnc(N4CCC5(CCC[C@H]5N)CC4)n4ccnc34)ccnc21]

¹H NMR (400 MHz, DMSO-d₆) δ 8.03 (s, 1H), 7.97 (d, J=5.1 Hz, 1H), 7.80 (s, 1H), 7.61-7.49 (m, 2H), 6.56-6.39 (m, 2H), 3.84 (d, J=22.6 Hz, 5H), 3.22 (t, J=12.5 Hz, 2H), 2.98 (t, J=6.9 Hz, 1H), 2.03-1.33 (m, 10H) ppm; LC-MS: m/z 433.9 [M+H]+.

Example 92: (R)-8-(8-((2,3-dihydrobenzofuran-5-yl) thio)imidazo[1,2-c]pyrimidin-5-yl)-8-azaspiro[4.5] decan-1-amine

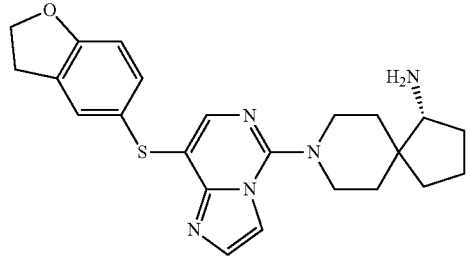 [SMILES: N[C@@H]1CCCC12CCN(c1ncc(Sc3ccc4c(c3)CCO4)c3nccn13)CC2]

¹H NMR (400 MHz, DMSO-d₆) δ 7.72 (s, 1H), 7.62 (s, 1H), 7.46 (s, 1H), 7.39 (s, 1H), 7.27 (d, J=8.2 Hz, 1H), 6.77 (d, J=8.3 Hz, 1H), 4.54 (t, J=8.7 Hz, 2H), 3.69 (t, J=11.9 Hz, 2H), 3.11 (dt, J=29.5, 12.5 Hz, 6H), 1.99 (s, 1H), 1.87-1.36 (m, 9H) ppm; LC-MS: m/z 422.1 [M+H]+.

Example 93: (R)-8-(8-(quinolin-4-ylthio)imidazo[1, 2-c]pyrimidin-5-yl)-8-azaspiro[4.5]decan-1-amine

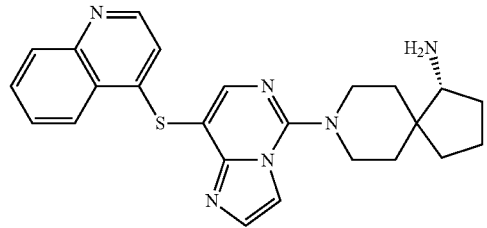 [SMILES: N[C@@H]1CCCC12CCN(c1ncc(Sc3ccnc4ccccc34)c3nccn13)CC2]

¹H NMR (400 MHz, DMSO-d₆) δ 8.52 (d, J=4.8 Hz, 1H), 8.26 (dd, J=8.4, 1.3 Hz, 1H), 8.12 (s, 1H), 8.04 (dd, J=8.5, 1.2 Hz, 1H), 7.89-7.79 (m, 2H), 7.73 (ddd, J=8.2, 6.8, 1.3 Hz, 1H), 7.56 (d, J=1.4 Hz, 1H), 6.82 (d, J=4.8 Hz, 1H), 3.91 (dd, J=15.3, 11.3 Hz, 2H), 3.37-3.16 (m, 2H), 3.05 (t, J=6.5 Hz, 1H), 2.10-1.65 (m, 5H), 1.67-1.38 (m, 5H) ppm; LC-MS: m/z 431.2 [M+H]+.

Example 94: (1R)-8-(8-((2,3-dichloropyridin-4-yl) thio)imidazo[1,2-c]pyrimidin-5-yl)-3-methyl-8-azaspiro[4.5]decan-1-amine

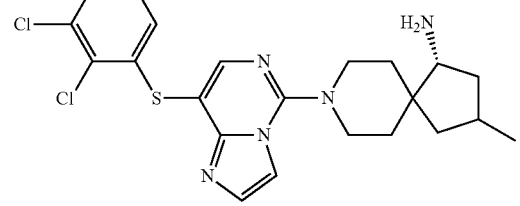

¹H NMR (400 MHz, DMSO-d₆) δ 8.32 (s, 1H), 8.09 (d, J=6.5 Hz, 1H), 8.00 (d, J=5.3 Hz, 1H), 7.84 (s, 1H), 7.57 (s, 1H), 6.71 (d, J=5.3 Hz, 1H), 4.03-3.85 (m, 2H), 3.26-3.15 (m, 2H), 2.98 (d, J=21.9 Hz, 1H), 2.14 (dd, J=25.3, 11.9 Hz, 2H), 1.87 (dd, J=41.5, 14.7 Hz, 3H), 1.43 (dd, J=32.2, 18.7

Hz, 2H), 1.28 (dd, J=18.2, 8.7 Hz, 1H), 1.12 (d, J=12.5 Hz, 1H), 1.05-0.93 (m, 3H) ppm; LC-MS: m/z 462.8 [M+H]⁺.

Example 95: (1R)-8-(8-((2-amino-3-chloropyridin-4-yl)thio)imidazo[1,2-c]pyrimidin-5-yl)-3-methyl-8-azaspiro[4.5]decan-1-amine

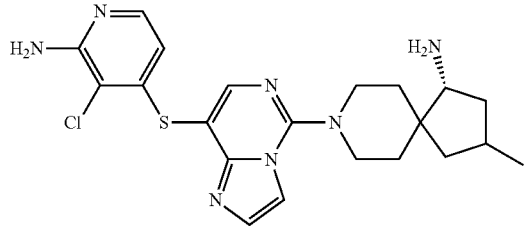

¹H NMR (400 MHz, DMSO-d₆) δ 8.36 (s, 1H), 8.02 (s, 1H), 7.80 (s, 1H), 7.63-7.49 (m, 2H), 6.34 (s, 2H), 5.78 (d, J=5.4 Hz, 1H), 3.98-3.83 (m, 2H), 3.18 (dd, J=27.6, 14.3 Hz, 2H), 3.06-2.94 (m, 1H), 2.23-2.07 (m, 2H), 1.96-1.89 (m, 1H), 1.86-1.67 (m, 2H), 1.51-1.33 (m, 2H), 1.33-1.20 (m, 1H), 1.21-1.09 (m, 1H), 1.08-0.94 (m, 3H) ppm; LC-MS: m/z 443.8 [M+H]⁺.

Example 96: (1R)-8-(8-((6-amino-2,3-dichloropyridin-4-yl)thio)imidazo[1,2-c]pyrimidin-5-yl)-3-methyl-8-azaspiro[4.5]decan-1-amine

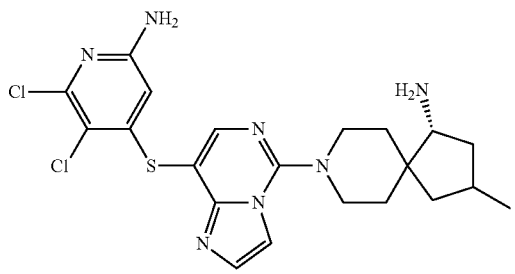 [SMILES: CC1C[C@@H](N)C2(CCN(c3ncc(Sc4cc(N)nc(Cl)c4Cl)c4nccn34)CC2)C1]

¹H NMR (400 MHz, DMSO-d₆) δ 8.33 (s, 1H), 8.06 (s, 1H), 7.84 (s, 1H), 7.61 (s, 1H), 6.33 (s, 2H), 5.62 (s, 1H), 4.00-3.86 (m, 2H), 3.17 (d, J=13.0 Hz, 1H), 3.07-2.95 (m, 1H), 2.25-2.07 (m, 2H), 1.94 (dd, J=12.0, 8.2 Hz, 1H), 1.79 (dd, J=28.2, 13.0 Hz, 2H), 1.45 (dd, J=33.4, 19.7 Hz, 2H), 1.34-1.11 (m, 2H), 1.01 (dd, J=18.3, 10.3 Hz, 3H); LCMS: m/z 447.8 [M+H]⁺.

Example 97: (S)-8-(8-((2,3-dichloropyridin-4-yl)thio)imidazo[1,2-c]pyrimidin-5-yl)-2-oxa-8-azaspiro[4.5]decan-4-amine

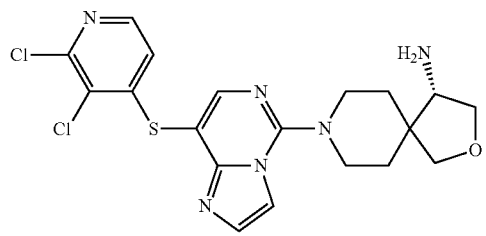 [SMILES: N[C@@H]1COCC12CCN(c1ncc(Sc3ccnc(Cl)c3Cl)c3nccn13)CC2]

¹H NMR (400 MHz, DMSO-d₆) δ 8.19 (s, 1H), 8.10 (s, 1H), 8.00 (d, J=5.3 Hz, 1H), 7.86 (s, 1H), 7.58 (s, 1H), 6.72 (d, J=5.3 Hz, 1H), 4.02 (dd, J=8.8, 6.4 Hz, 1H), 3.85 (dd, J=17.4, 13.7 Hz, 2H), 3.72 (dd, J=21.2, 8.6 Hz, 2H), 3.43 (dd, J=9.0, 4.8 Hz, 2H), 3.25 (dd, J=15.2, 9.6 Hz, 2H), 1.98-1.86 (m, 1H), 1.85-1.73 (m, 1H), 1.61 (s, 2H); LC-MS: m/z 451.7 [M+H]⁺.

Example 98: (S)-8-(8-((2-amino-3-chloropyridin-4-yl)thio)imidazo[1,2-c]pyrimidin-5-yl)-2-oxa-8-azaspiro[4.5]decan-4-amine

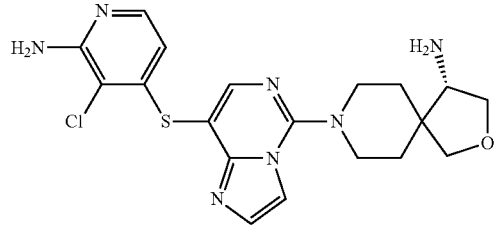 [SMILES: Nc1nccc(Sc2cnc(N3CCC4(CC3)COC[C@H]4N)n3ccnc23)c1Cl]

¹H NMR (400 MHz, DMSO-d₆) δ 8.14 (s, 1H), 8.04 (s, 1H), 7.83 (s, 1H), 7.60 (s, 1H), 7.55 (d, J=5.4 Hz, 1H), 6.35 (s, 2H), 5.78 (d, J=5.4 Hz, 1H), 4.10 (dd, J=9.9, 6.0 Hz, 1H), 3.92-3.76 (m, 4H), 3.69 (dd, J=10.1, 3.1 Hz, 1H), 3.53 (s, 1H), 3.24 (d, J=10.8 Hz, 1H), 1.99-1.83 (m, 2H), 1.73 (d, J=12.0 Hz, 2H), 1.24 (d, J=6.4 Hz, 1H) ppm; LC-MS: m/z 431.8 [M+H]⁺.

Example 99: (3S,4S)-8-(8-((2,3-dichloropyridin-4-yl)thio)imidazo[1,2-c]pyrimidin-5-yl)-3-methyl-2-oxa-8-azaspiro[4.5]decan-4-amine

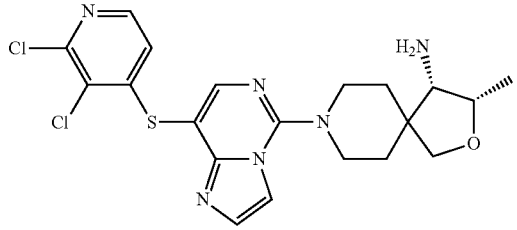 [SMILES: C[C@@H]1OCC2(CCN(c3ncc(Sc4ccnc(Cl)c4Cl)c4nccn34)CC2)[C@@H]1N]

¹H NMR (400 MHz, DMSO-d₆) δ 8.17 (s, 1H), 8.10 (s, 1H), 8.00 (d, J=5.3 Hz, 1H), 7.87 (s, 1H), 7.57 (d, J=1.0 Hz, 1H), 6.72 (d, J=5.3 Hz, 1H), 4.12 (dt, J=12.1, 6.1 Hz, 1H), 3.85-3.67 (m, 3H), 3.57 (d, J=8.5 Hz, 1H), 3.41 (dd, J=26.4, 9.0 Hz, 2H), 3.06 (d, J=4.9 Hz, 1H), 1.99-1.81 (m, 2H), 1.68 (dd, J=27.9, 14.6 Hz, 2H), 1.13 (d, J=6.4 Hz, 3H) ppm; LC-MS: m/z 464.8 [M+H]⁺.

Example 100: (3S,4S)-8-(8-((2-amino-3-chloropyridin-4-yl)thio)imidazo[1,2-c]pyrimidin-5-yl)-3-methyl-2-oxa-8-azaspiro[4.5]decan-4-amine

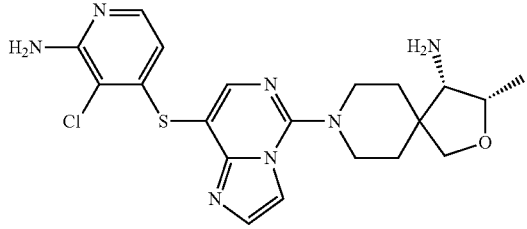 [SMILES: C[C@@H]1OCC2(CCN(c3ncc(Sc4ccnc(N)c4Cl)c4nccn34)CC2)[C@@H]1N]

¹H NMR (400 MHz, DMSO-d₆) δ 8.21 (s, 1H), 8.02 (s, 1H), 7.84 (s, 1H), 7.61-7.50 (m, 2H), 6.34 (s, 2H), 5.79 (d, J=5.4 Hz, 1H), 4.11 (dt, J=12.3, 6.3 Hz, 1H), 3.73 (d, J=8.5 Hz, 3H), 3.56 (d, J=8.5 Hz, 1H), 3.38-3.26 (m, 2H), 3.05 (d, J=4.9 Hz, 1H), 1.99-1.81 (m, 2H), 1.67 (dd, J=26.4, 15.3 Hz, 2H), 1.18-1.02 (m, 3H) ppm; LC-MS: m/z 445.8 [M+H]⁺.

Example 101: 4-((5-(4-amino-4-methylpiperidin-1-yl)imidazo[1,2-c]pyrimidin-8-yl)thio)-3-chloropyridine-2-amine

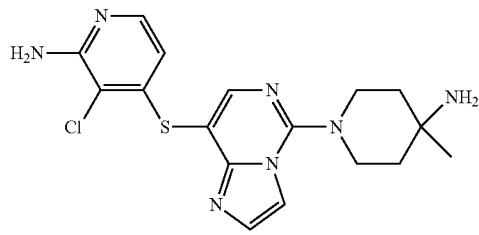 [SMILES: CC1(N)CCN(c2ncc(Sc3ccnc(N)c3Cl)c3nccn23)CC1]

¹H NMR (400 MHz, DMSO-d₆) δ 8.00 (s, 1H), 7.83 (s, 1H), 7.54 (d, J=5.8 Hz, 2H), 6.29 (s, 2H), 5.79 (d, J=5.4 Hz, 1H), 3.60 (d, J=4.3 Hz, 4H), 1.77-1.53 (m, 4H), 1.19 (s, 3H) ppm; LC-MS: m/z 390.1 [M+H]⁺.

Example 102: (R)-8-(8-((6-amino-2,3-dichloropyridin-4-yl)thio)imidazo[1,2-c]pyrimidin-5-yl)-8-azaspiro[4.5]decan-1-amine

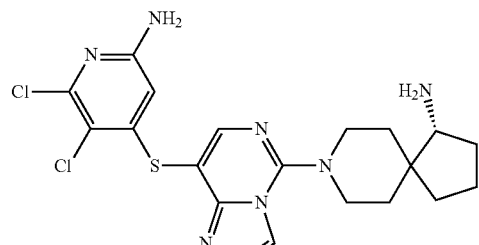

¹H NMR (400 MHz, DMSO-d₆) δ 8.05 (s, 1H), 7.85 (d, J=1.5 Hz, 1H), 7.60 (d, J=1.4 Hz, 1H), 6.32 (s, 2H), 5.62 (s, 1H), 3.90 (dd, J=13.2, 8.5 Hz, 2H), 3.23 (q, J=11.9, 11.0 Hz, 2H), 2.77 (t, J=7.3 Hz, 1H), 1.90-1.77 (m, 4H), 1.67-1.53 (m, 2H), 1.45-1.28 (m, 4H) ppm; LCMS: m/z 466.1 [M+H]⁺.

Example 103: (R)-8-(8-((6-amino-3-chloro-2-methyl-pyridin-4-yl)thio)imidazo[1,2-c]pyrimidin-5-yl)-8-azaspiro[4.5]decan-1-amine

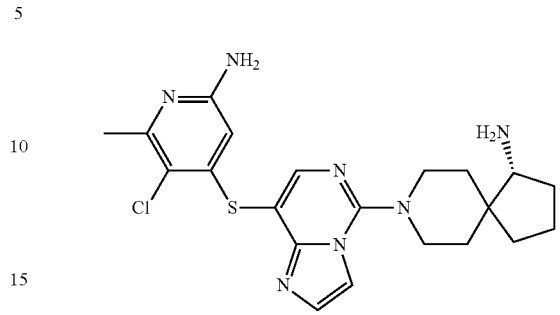

¹H NMR (400 MHz, DMSO-d₆) δ 7.88 (s, 4H), 7.66 (d, J=11.1 Hz, 1H), 5.81 (s, 1H), 3.96 (t, J=13.9 Hz, 2H), 3.37-3.23 (m, 3H), 2.42 (s, 3H), 2.14-2.05 (m, 1H), 1.88-1.46 (m, 9H); LC-MS: m/z 443.8 [M+H]⁺.

Example 104: (S)-8-(8-((6-amino-3-chloro-2-methyl-pyridin-4-yl)thio)imidazo[1,2-c]pyrimidin-5-yl)-2-oxa-8-azaspiro[4.5]decan-4-amine

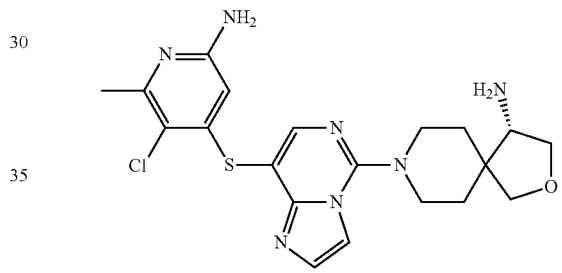

¹H NMR (400 MHz, DMSO-d₆) δ 8.17 (d, J=4.9 Hz, 3H), 7.91 (s, 1H), 7.68 (s, 1H), 5.81 (s, 1H), 4.13 (dd, J=10.4, 5.8 Hz, 1H), 3.90 (d, J=9.0 Hz, 3H), 3.80 (d, J=9.0 Hz, 1H), 3.74 (dd, J=10.3, 2.6 Hz, 1H), 3.63 (s, 1H), 3.40 (dd, J=12.6, 8.6 Hz, 1H), 3.30 (dd, J=12.6, 9.4 Hz, 1H), 2.42 (s, 3H), 1.95-1.81 (m, 2H), 1.75 (d, J=10.3 Hz, 2H); LC-MS: m/z 445.8 [M+H]⁺.

Example 105: (S)-8-(8-((6-amino-2,3-dichloropyridin-4-yl)thio)imidazo[1,2-c]pyrimidin-5-yl)-2-oxa-8-azaspiro[4.5]decan-4-amine

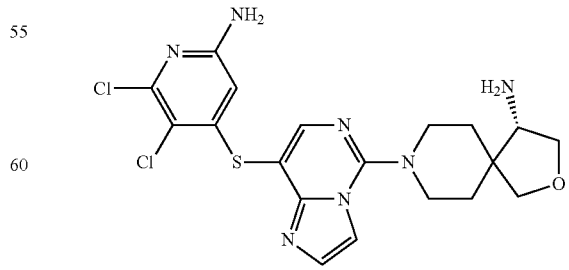

¹H NMR (400 MHz, DMSO-d₆) δ 8.16 (s, 1H), 8.07 (s, 1H), 7.87 (s, 1H), 7.63 (s, 1H), 6.33 (s, 2H), 5.62 (s, 1H), 4.06 (dd, J=9.6, 6.2 Hz, 1H), 3.93-3.74 (m, 4H), 3.56 (dd, J=9.5, 4.0 Hz, 1H), 3.26 (s, 3H), 1.98-1.80 (m, 2H), 1.67 (s, 2H) ppm; LC-MS: m/z 466.6 [M+H]+.

Example 106: (3S,4S)-8-(8-((6-amino-2,3-dichloropyridin-4-yl)thio)imidazo[1,2-c]pyrimidin-5-yl)-3-methyl-2-oxa-8-azaspiro[4.5]decan-4-amine

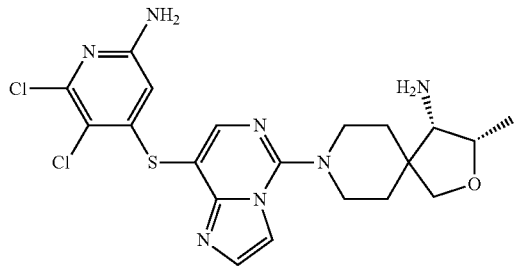 [SMILES: C[C@@H]1OCC2(CCN(c3ncc(Sc4cc(N)nc(Cl)c4Cl)c4nccn34)CC2)[C@@H]1N]

$^{1}$H NMR (400 MHz, DMSO-d$_{6}$) δ 8.18 (s, 3H), 8.08 (s, 1H), 7.87 (s, 1H), 7.65 (s, 1H), 6.35 (s, 2H), 5.64 (s, 1H), 4.31-4.16 (m, 1H), 4.03-3.83 (m, 3H), 3.71 (d, J=9.0 Hz, 1H), 3.46 (s, 1H), 3.24 (d, J=11.2 Hz, 2H), 2.03 (t, J=12.3 Hz, 2H), 1.75 (dd, J=41.2, 13.7 Hz, 2H), 1.24 (d, J=6.5 Hz, 3H); LCMS: m/z 479.7 [M+H]+.

Example 107: (3S,4S)-8-(8-((3-chloro-2-methylpyridin-4-yl)thio)imidazo[1,2-c]pyrimidin-5-yl)-3-methyl-2-oxa-8-azaspiro[4.5]decan-4-amine

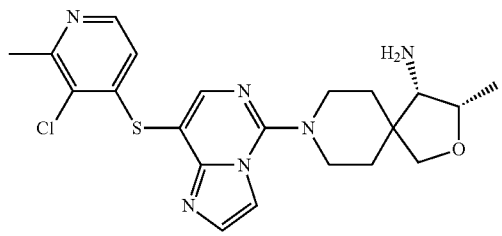

$^{1}$H NMR (400 MHz, DMSO-d$_{6}$) δ 8.06 (s, 1H), 8.01 (d, J=5.3 Hz, 1H), 7.85 (d, J=1.5 Hz, 1H), 7.56 (d, J=1.4 Hz, 1H), 6.50 (d, J=5.3 Hz, 1H), 4.15-4.05 (m, 1H), 3.74-3.66 (m, 5H), 3.45-3.42 (m, 1H), 3.03 (d, J=4.9 Hz, 1H), 2.55 (s, 3H), 2.00-1.60 (m, 4H), 1.12 (d, J=6.4 Hz, 3H) ppm; LC-MS: m/z 445.2 [M+H]+.

Example 108: (S)-8-(8-((6-amino-2,3-dichloropyridin-4-yl)thio)imidazo[1,2-c]pyrimidin-5-yl)-3,3-dimethyl-1-oxa-8-azaspiro[4.5]decan-4-amine

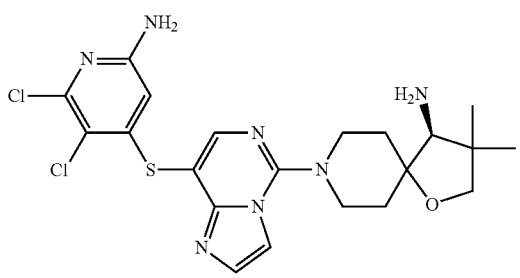 [SMILES: CC1(C)COC2(CCN(c3ncc(Sc4cc(N)nc(Cl)c4Cl)c4nccn34)CC2)[C@H]1N]

$^{1}$H NMR (400 MHz, DMSO-d$_{6}$) δ 8.23 (s, 1H), 8.06 (s, 1H), 7.88 (s, 1H), 7.61 (s, 1H), 6.34 (s, 2H), 5.64 (s, 1H), 3.95 (d, J=14.3 Hz, 2H), 3.55 (s, 1H), 3.44 (s, 1H), 3.31 (d, J=11.5 Hz, 2H), 2.69 (s, 1H), 1.94 (d, J=12.4 Hz, 2H), 1.66 (t, J=11.9 Hz, 2H), 1.06-0.99 (m, 3H), 0.94 (d, J=14.9 Hz, 3H); LC-MS: m/z 493.7 [M+H]+.

Example 109: (R)-8-(8-((6-amino-2,3-dichloropyridin-4-yl)thio)imidazo[1,2-c]pyrimidin-5-yl)-3,3-dimethyl-1-oxa-8-azaspiro[4.5]decan-4-amine

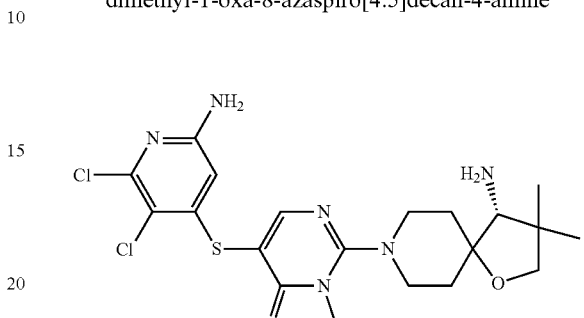

$^{1}$H NMR (400 MHz, DMSO-d$_{6}$) δ 8.15 (s, 2H), 7.89 (s, 1H), 7.64 (s, 1H), 6.33 (s, 1H), 5.63 (s, 1H), 4.03 (s, 2H), 3.59 (d, J=14.4 Hz, 2H), 3.38 (s, 2H), 3.09 (s, 1H), 1.83 (s, 4H), 1.16 (s, 3H), 1.07 (s, 3H); LC-MS: m/z 493.7 [M+H]+.

Example 110: (S)-8-(8-((2-amino-3-chloropyridin-4-yl)thio)imidazo[1,2-c]pyrimidin-5-yl)-3,3-dimethyl-1-oxa-8-azaspiro[4.5]decan-4-amine

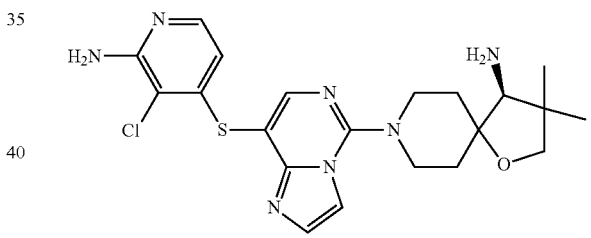

$^{1}$H NMR (400 MHz, DMSO-d$_{6}$) δ 8.16 (s, 1H), 8.02 (s, 1H), 7.84 (s, 1H), 7.61-7.51 (m, 2H), 6.33 (s, 2H), 5.80 (d, J=5.4 Hz, 1H), 4.00-3.88 (m, 2H), 3.55 (d, J=8.7 Hz, 1H), 3.46 (d, J=8.8 Hz, 1H), 3.32-3.27 (m, 2H), 2.73 (s, 1H), 1.98-1.86 (m, 1H), 1.68 (s, 2H), 1.00 (d, J=29.6 Hz, 6H); LC-MS: m/z 459.8 [M+H]+.

Example 111: (R)-8-(8-((2-amino-3-chloropyridin-4-yl)thio)imidazo[1,2-c]pyrimidin-5-yl)-3,3-dimethyl-1-oxa-8-azaspiro[4.5]decan-4-amine

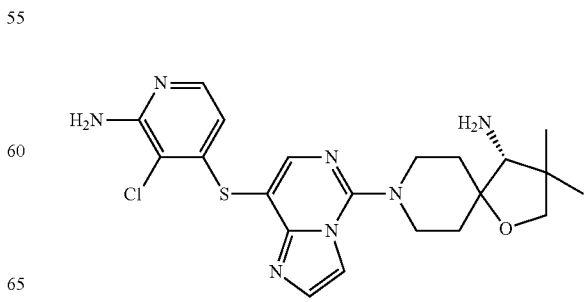

¹H NMR (400 MHz, DMSO-d₆) δ 8.15 (s, 1H), 7.84 (s, 1H), 7.57 (s, 1H), 7.55 (d, J=5.4 Hz, 1H), 6.33 (s, 2H), 5.80 (d, J=5.3 Hz, 1H), 4.01-3.91 (m, 2H), 3.56 (d, J=8.8 Hz, 1H), 3.48 (d, J=8.9 Hz, 1H), 3.32-3.26 (m, 2H), 2.80 (s, 1H), 1.97-1.88 (m, 2H), 1.70 (d, J=12.3 Hz, 2H), 1.06 (s, 3H), 0.99 (s, 3H); LC-MS: m/z 459.8 [M+H]⁺.

Example 112: Synthesis of (R)-8-(8-((3-chloro-2-methoxypyridin-4-yl)thio)imidazo[1,2-c]pyrimidin-5-yl)-8-azaspiro[4.5]decan-1-amine Step 1: methyl ((R)-1-((R)-tert-butylsulfinyl)amino)-8-azaspiro[4.5]decan-8-yl)imidazo[1,2-c]pyrimi dine-8-yl)thio)propionate

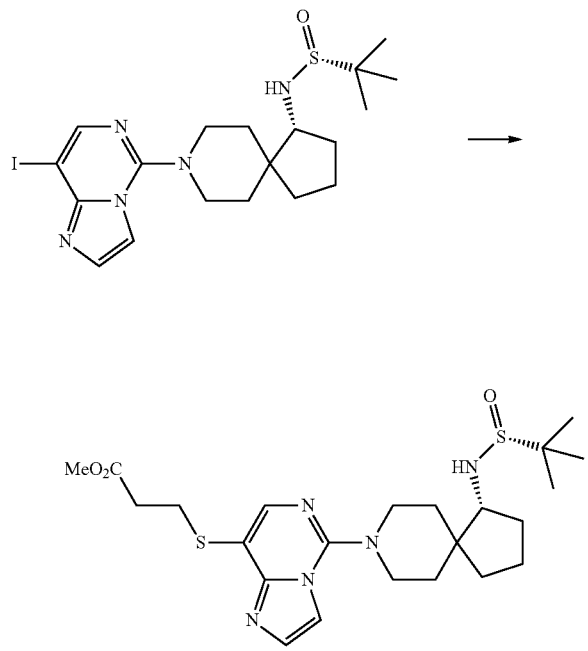 [SMILES: CC(C)(C)[S@@](=O)N[C@@H]1CCCC12CCN(c1ncc(I)c3nccn13)CC2 ; COC(=O)CCSc1cnc(N2CCC3(CCC[C@H]3N[S@](=O)C(C)(C)C)CC2)n2ccnc12]

Under nitrogen atmosphere, to a 100 mL single-necked flask were successively added (R)—N—((R)-8-(8-iodoimidazo[1,2-c]pyrimidin-5-yl)-8-azaspiro[4.5]decan-1-yl)-2-methylpropane-2-sulfinamide (500 mg, 1.0 mmol), methyl mercaptopropionate (132 mg, 1.1 mmol), Pd₂(dba)₃ (46 mg, 0.05 mmol), Xantphos (58 mg, 0.10 mmol), DIPEA (258 mg, 2.0 mmol) and 1,4-dioxane (30 mL). The mixture was heated at 100° C. and stirred for 4 hours under nitrogen atmosphere. After the reaction was completed, the mixture was cooled to room temperature, filtered and concentrated under reduced pressure to obtain a residue, which was purified by silica gel chromatography (ethyl acetate/petroleum ether with a gradient of 0 to 30%) to obtain methyl ((R)-1-((R)-tert-butylsulfinyl)amino)-8-azaspiro[4.5]decan-8-yl)imidazo[1,2-c]pyrimi dine-8-yl)thio)propionate (380 mg, yield: 77%).

LCMS: m/z 494.2 [M+H]⁺.

Step 2: sodium ((R)-1-((R)-1,1-dimethylethylsulfinamido)-8-azaspiro[4.5]decan-8-yl)imidazo[1,2-c]pyrimidin-8-thiolate

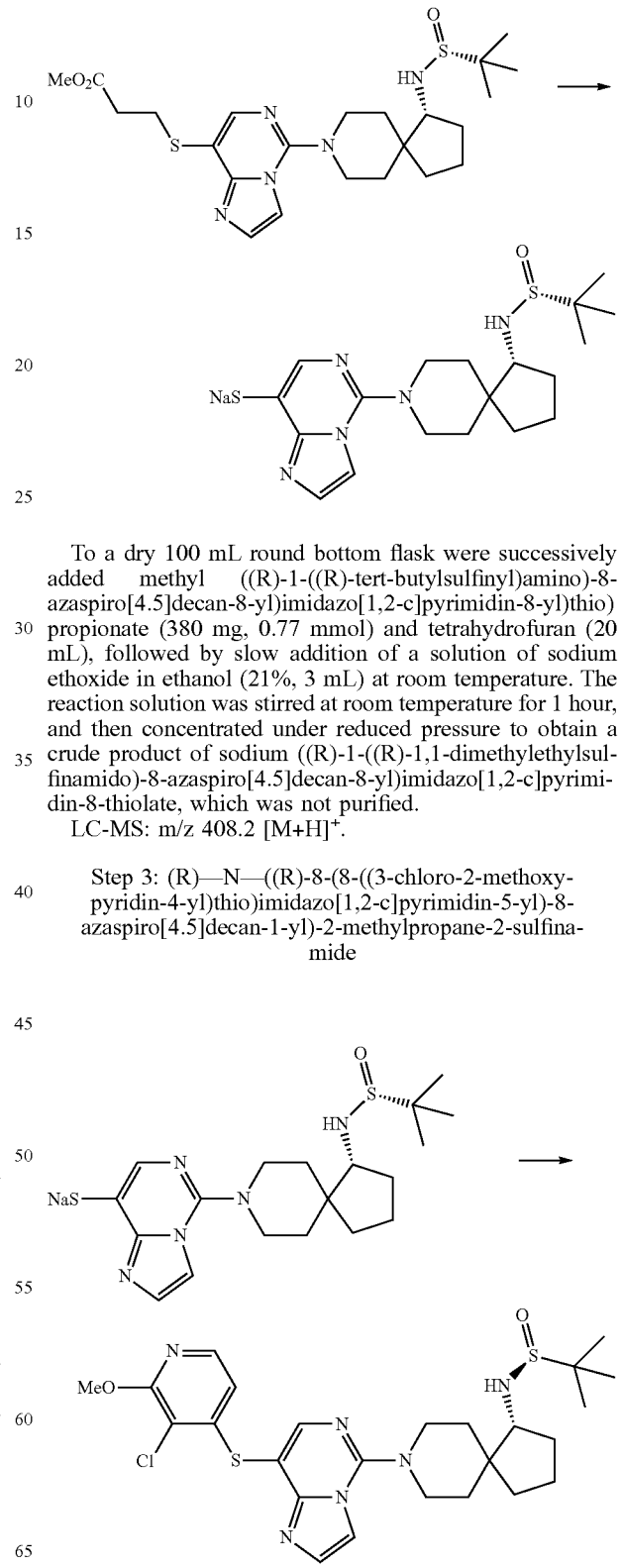

To a dry 100 mL round bottom flask were successively added methyl ((R)-1-((R)-tert-butylsulfinyl)amino)-8-azaspiro[4.5]decan-8-yl)imidazo[1,2-c]pyrimidin-8-yl)thio) propionate (380 mg, 0.77 mmol) and tetrahydrofuran (20 mL), followed by slow addition of a solution of sodium ethoxide in ethanol (21%, 3 mL) at room temperature. The reaction solution was stirred at room temperature for 1 hour, and then concentrated under reduced pressure to obtain a crude product of sodium ((R)-1-((R)-1,1-dimethylethylsulfinamido)-8-azaspiro[4.5]decan-8-yl)imidazo[1,2-c]pyrimidin-8-thiolate, which was not purified.

LC-MS: m/z 408.2 [M+H]⁺.

Step 3: (R)—N—((R)-8-(8-((3-chloro-2-methoxypyridin-4-yl)thio)imidazo[1,2-c]pyrimidin-5-yl)-8-azaspiro[4.5]decan-1-yl)-2-methylpropane-2-sulfinamide Under nitrogen atmosphere, to a 100 mL single-necked flask were added the crude product of sodium ((R)-1-((R)-1,1-dimethylethylsulfinamido)-8-azaspiro[4.5]decan-8-yl)imidazo[1,2-c]pyrimidin-8-thiolate (100 mg, 0.23 mmol), 3-chloro-4-iodo-2-methoxypyridine (71 mg, 0.26 mmol), Pd$_2$(dba)$_3$ (22 mg, 0.024 mmol), Xantphos (28 mg, 0.048 mmol), DIPEA (62 mg, 0.48 mmol) and 1,4-dioxane (10 mL). The reaction solution was heated to 100° C. and stirred for 4 hours under nitrogen atmosphere. After the reaction was completed, the mixture was cooled to room temperature, filtered and concentrated under reduced pressure to obtain a residue, which was purified by silica gel chromatography (ethyl acetate/methanol with a gradient of 0 to 30%) to obtain (R)—N—((R)-8-(8-((3-chloro-2-methoxypyridin-4-yl)thio)imidazo[1,2-c]pyrimidin-5-yl)-8-azaspiro[4.5]decan-1-yl)-2-methylpropane-2-sulfinamide) (51 mg, yield: 40%).

LCMS: m/z 549.2 [M+H]$^+$.

Step 4: (R)-8-(8-((3-chloro-2-methoxypyridin-4-yl)thio)imidazo[1,2-c]pyrimidin-5-yl)-8-azaspiro[4.5]decan-1-amine

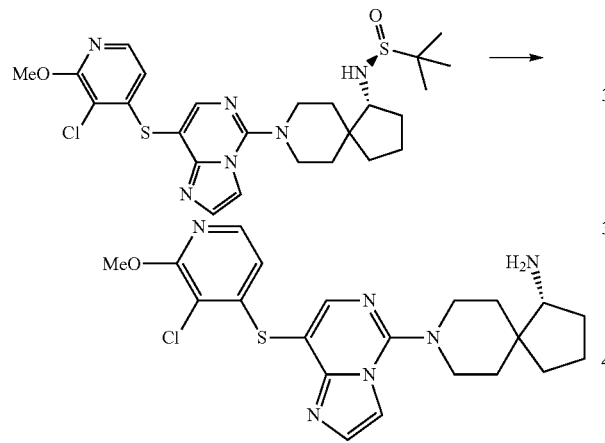

Under nitrogen atmosphere, to a 100 mL single-necked flask were sequentially added (R)—N—((R)-8-(8-((3-chloro-2-methoxypyridin-4-yl)thio)imidazo[1,2-c]pyrimidin-5-yl)-8-azaspiro[4.5]decan-1-yl)-2-methylpropane-2-sulfinamide (40 mg, 0.09 mmol) and methanol (2.3 mL), and a solution of hydrogen chloride in 1,4-dioxane (0.23 mL, 4M) was added dropwise at room temperature. The mixture was stirred at room temperature for 1 hour. After the reaction was completed, the mixture was cooled to room temperature, filtered and concentrated under reduced pressure to obtain a residue, which was purified by high performance liquid chromatography to obtain (R)-8-(8-((3-chloro-2-methoxypyridin-4-yl)thio)imidazo[1,2-c]pyrimidin-5-yl)-8-azaspiro[4.5]decan-1-amine (15 mg, yield: 37%).

$^1$H NMR (400 MHz, DMSO-d$_6$) δ 8.05 (s, 1H), 7.83 (d, J=1.6 Hz, 1H), 7.77 (d, J=5.5 Hz, 1H), 7.56 (d, J=1.5 Hz, 1H), 6.28 (d, J=5.5 Hz, 1H), 3.93 (s, 3H), 3.88 (d, J=9.4 Hz, 2H), 3.23 (d, J=11.6 Hz, 2H), 2.76 (t, J=7.2 Hz, 1H), 1.80 (d, J=11.4 Hz, 4H), 1.66-1.52 (m, 2H), 1.44-1.29 (m, 4H). LCMS: m/z 445.1 [M+H]$^+$.

According to the synthesis method of Example 112, the following compounds were synthesized:

Example 113: Methyl (R)-3-((5-(1-amino-8-azaspiro[4.5]decan-8-yl)imidazo[1,2-c]pyrimidin-8-yl)thio)propionate

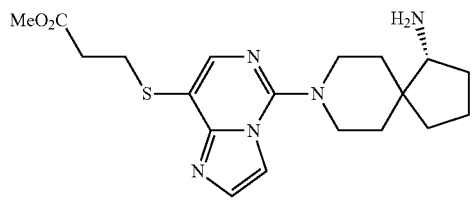 [SMILES: COC(=O)CCSc1cnc(N2CCC3(CCC[C@H]3N)CC2)n2ccnc12]

$^1$H NMR (400 MHz, DMSO-d$_6$) δ 7.73 (d, J=2.7 Hz, 2H), 7.64 (d, J=1.3 Hz, 1H), 3.70 (d, J=4.0 Hz, 2H), 3.56 (s, 3H), 3.26 (t, J=7.0 Hz, 2H), 3.15-3.04 (m, 3H), 2.61 (t, J=7.0 Hz, 2H), 2.05-1.68 (m, 5H), 1.66-1.37 (m, 5H) ppm; LC-MS: m/z 390.1 [M+H]$^+$.

Example 114: (R)-8-(8-((3-chloro-2-fluoropyridin-4-yl)thio)imidazo[1,2-c]pyrimidin-5-yl)-8-azaspiro[4.5]decan-1-amine

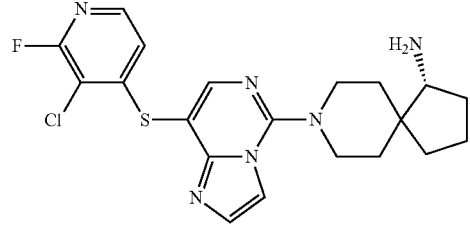 [SMILES: N[C@@H]1CCCC12CCN(c1ncc(Sc3ccnc(F)c3Cl)c3nccn13)CC2]

$^1$H NMR (400 MHz, DMSO-d$_6$) δ 8.10 (s, 1H), 7.86-7.80 (m, 2H), 7.58 (d, J=1.4 Hz, 1H), 6.66 (d, J=5.4 Hz, 1H), 3.95 (d, J=12.7 Hz, 2H), 3.28 (s, 2H), 2.95 (s, 1H), 1.97-1.80 (m, 4H), 1.66 (d, J=32.2 Hz, 2H), 1.56-1.41 (m, 4H) ppm; LCMS: m/z 434.1 [M+H]$^+$.

Example 115: (R)-8-(8-((3-chloro-2-(dimethylamino)pyridin-4-yl)thio)imidazo[1,2-c]pyrimidin-5-yl)-8-azaspiro[4.5]decan-1-amine

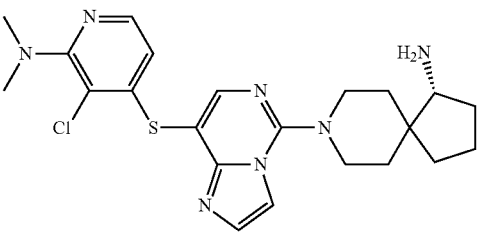 [SMILES: CN(C)c1nccc(Sc2cnc(N3CCC4(CCC[C@H]4N)CC3)n3ccnc23)c1Cl]

$^1$H NMR (400 MHz, DMSO-d$_6$) δ 8.03 (s, 1H), 7.83 (d, J=1.6 Hz, 1H), 7.79 (d, J=5.3 Hz, 1H), 7.56 (d, J=1.4 Hz, 1H), 6.15 (d, J=5.3 Hz, 1H), 3.98-3.79 (m, 2H), 3.23 (d, J=11.6 Hz, 3H), 2.90 (s, 6H), 2.77 (t, J=7.3 Hz, 1H), 1.83-1.74 (m, 7H), 1.69-1.51 (m, 3H), 1.49-1.27 (m, 5H) ppm; LCMS: m/z 458.2 [M+H]$^+$.

Example 116: (R)-4-((5-(1-amino-8-azaspiro[4.5]decan-8-yl)imidazo[1,2-c]pyrimidin-8-yl)thio)indoline-2,3-dione

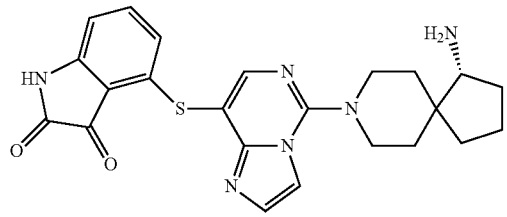 [SMILES: N[C@@H]1CCCC12CCN(c1ncc(Sc3cccc4c3C(=O)C(=O)N4)c3nccn13)CC2]

¹H NMR (400 MHz, DMSO-d₆) δ 8.28 (s, 1H), 8.02 (s, 1H), 7.81 (s, 1H), 7.58 (s, 1H), 7.24 (t, J=8.0 Hz, 1H), 6.58 (d, J=7.7 Hz, 2H), 6.21 (d, J=8.3 Hz, 1H), 3.90 (s, 3H), 3.24 (s, 3H), 2.97 (s, 1H), 1.69 (d, J=93.3 Hz, 9H) ppm; LC-MS: m/z 449.1 [M+H]⁺.

Example 117: Synthesis of Compound: (R)-8-(8-((3-chloropyridazin-4-yl)thio)imidazo[1,2-c]pyrimidin-5-yl)-8-azaspiro[4.5]decan-1-amine Step 1: (R)—N—((R)-8-(8-((3-chloropyridazin-4-yl)thio)imidazo[1,2-c]pyrimidin-5-yl)-8-azaspiro[4.5]decan-1-yl)-2-methylpropane-2-sulfinamide

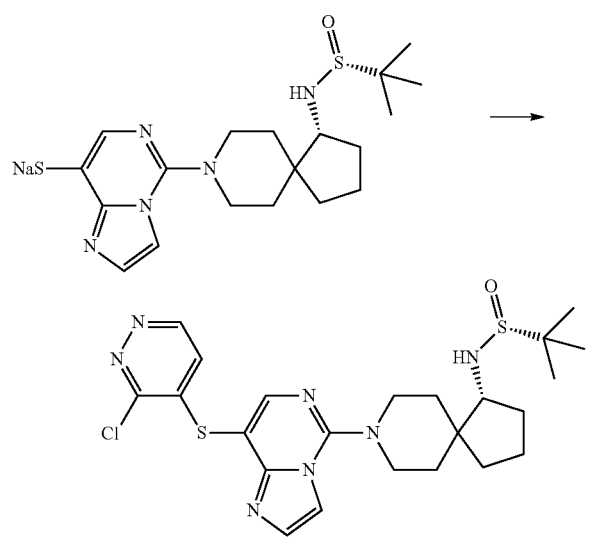

Under nitrogen atmosphere, to a 100 mL single-necked flask were sequentially added the crude product of sodium ((R)-1-((R)-1,1-dimethylethylsulfinamido)-8-azaspiro[4.5]decan-8-yl)imidazo[1,2-c]pyrimidin-8-thiolate (50 mg, 0.12 mmol), 3,4-dichloropyridazine (19 mg, 0.13 mmol) and acetonitrile (3 mL), followed by DIPEA (31 mg, 0.24 mmol), and the reaction solution was heated to 80° C. and stirred for 16 hours. After the reaction solution was cooled, the residue obtained by concentration under reduced pressure was purified by silica gel chromatography (ethyl acetate/methanol with a gradient of 0 to 30%) to obtain (R)—N—((R)-8-(8-((3-chloropyridazin-4-yl)thio)imidazo[1,2-c]pyrimidin-5-yl)-8-azaspiro[4.5]decan-1-yl)-2-methylpropane-2-sulfinamide (10 mg, yield: 16%).

LCMS: m/z 520.2 [M+H]⁺.

Step 2: (R)-8-(8-((3-chloropyridazin-4-yl)thio)imidazo[1,2-c]pyrimidin-5-yl)-8-azaspiro[4.5]decan-1-amine

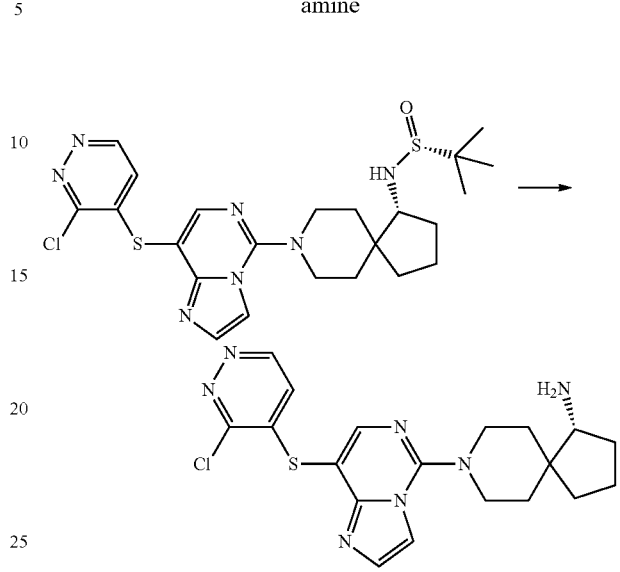

Under nitrogen atmosphere, to a 50 mL single-necked flask were sequentially added (R)—N—((R)-8-(8-((3-chloropyridazin-4-yl)thio)imidazo[1,2-c]pyrimidin-5-yl)-8-azaspiro[4.5]decan-1-yl)-2-methylpropane-2-sulfinamide (10 mg, 0.02 mmol) and methanol (0.5 mL), and a solution of hydrogen chloride in 1,4-dioxane (0.05 mL, 4M) was added dropwise at room temperature. The mixture was stirred at room temperature for 1 hour. After the reaction was completed, the mixture was cooled to room temperature, filtered and concentrated under reduced pressure to obtain a residue, which was then purified by high performance liquid chromatography to obtain (R)-8-(8-((3-chloropyridazin-4-yl)thio)imidazo[1,2-c]pyrimidin-5-yl)-8-azaspiro[4.5]decan-1-amine (2 mg, yield: 24%).

¹H NMR (400 MHz, DMSO-d₆) δ 8.79 (d, J=5.4 Hz, 1H), 8.36 (s, 2H), 8.12 (s, 1H), 7.84 (s, 1H), 7.58 (s, 1H), 7.01 (d, J=5.4 Hz, 1H), 3.88 (d, J=9.4 Hz, 2H), 3.23 (d, J=11.6 Hz, 2H), 2.76 (t, J=7.2 Hz, 1H), 1.70-1.32 (m, 9H); LCMS: m/z 416.1 [M+H]⁺.

According to the synthesis method of Example 117, the following compounds were synthesized:

Example 118: (R)-8-(8-((2-chloropyrimidin-4-yl)thio)imidazo[1,2-c]pyrimidin-5-yl)-8-azaspiro[4.5]decan-1-amine

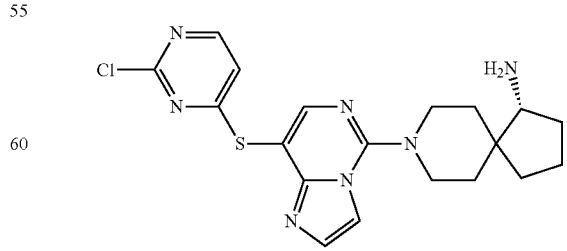

¹H NMR (400 MHz, DMSO-d₆) δ 8.37 (d, J=5.5 Hz, 1H), 8.29 (s, 1H), 8.09 (s, 1H), 7.84 (s, 1H), 7.61 (d, J=1.2 Hz,

1H), 7.06 (d, J=5.5 Hz, 1H), 3.93 (t, J=12.9 Hz, 2H), 3.25 (s, 2H), 3.09 (s, 1H), 2.03 (s, 1H), 1.81 (dd, J=19.3, 13.3 Hz, 4H), 1.65-1.46 (m, 5H) ppm; LCMS: m/z 416.1 [M+H]⁺.

Example 119: Preparation of Compound (R)-8-(8-(pyridin-2-ylthio)imidazo[1,2-c]pyrimidin-5-yl)-8-azaspiro[4.5]decan-1-amine Step 1: (R)-2-methyl-N—(R)-8-(8-(pyridin-2-ylthio)imidazo[1,2-c]pyrimidin-5-yl)-8-azaspiro[4.5]decan-1-yl)propane-2-sulfinamide

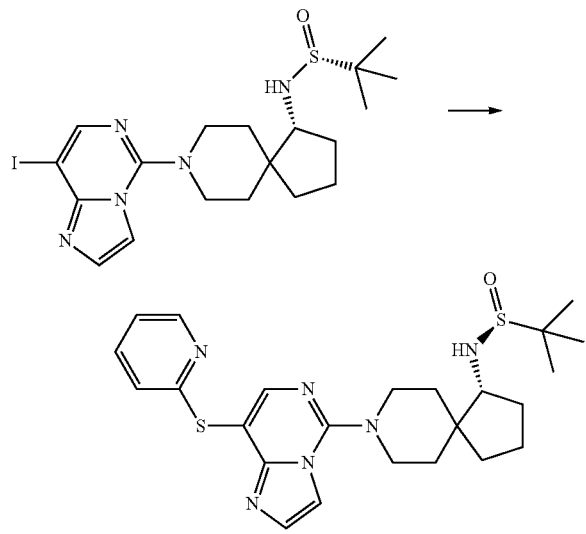

Under nitrogen atmosphere, to a 100 mL single-necked flask were sequentially added (R)—N—((R)-8-(8-iodoimidazo[1,2-c]pyrimidin-5-yl)-8-azaspiro[4.5]decan-1-yl)-2-methylpropane-2-sulfinamide (50 mg, 0.10 mmol), pyridine-2-thiol (13 mg, 0.12 mmol), Cu (OTf)₂ (4 mg, 0.01 mmol), BINAM (3 mg, 0.01 mmol) and 1,4-dioxane (3 mL), followed by cesium carbonate (65 mg, 0.2 mmol). The reaction solution was heated to 100° C. and stirred for 16 hours. After the reaction solution was cooled, the residue obtained by concentration under reduced pressure was purified by silica gel chromatography (ethyl acetate/methanol with a gradient of 0 to 50%) to obtain (R)-2-methyl-N—(R)-8-(8-(pyridin-2-ylthio)imidazo[1,2-c]pyrimidin-5-yl)-8-azaspiro[4.5]decan-1-yl)propane-2-sulfinamide (20 mg, yield: 41%).
LCMS: m/z 485.2 [M+H]⁺.

Step 2: (R)-8-(8-(pyridin-2-ylthio)imidazo[1,2-c]pyrimidin-5-yl)-8-azaspiro[4.5]decan-1-amine

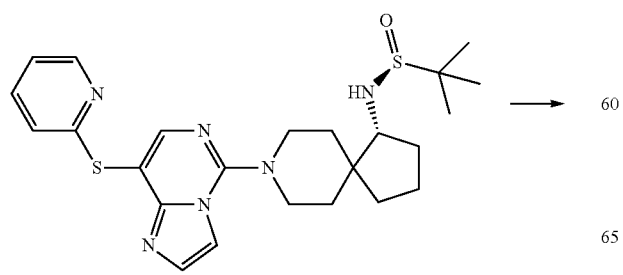

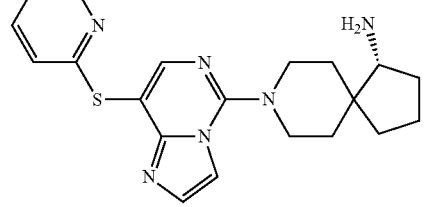

Using the same method as that of Step 2 in Example 37, (R)-2-methyl-N—(R)-8-(8-(pyridin-2-ylthio)imidazo[1,2-c]pyrimidin-5-yl)-8-azaspiro[4.5]decan-1-yl)propane-2-sulfinamide was subjected to the removal of the sulfinyl group to obtain (R)-8-(8-(pyridin-2-ylthio)imidazo[1,2-c]pyrimidin-5-yl)-8-azaspiro[4.5]decan-1-amine.

¹H NMR (400 MHz, DMSO-d₆) δ 8.34 (d, J=3.1 Hz, 2H), 8.02 (s, 1H), 7.78 (s, 1H), 7.63-7.48 (m, 2H), 7.11 (dd, J=7.3, 4.9 Hz, 1H), 6.93 (d, J=8.1 Hz, 1H), 3.86 (t, J=13.0 Hz, 2H), 3.22 (t, J=12.4 Hz, 2H), 3.03 (t, J=6.5 Hz, 1H), 2.04-1.35 (m, 10H) ppm; LCMS: m/z 381.2 [M+H]⁺.

According to the synthesis method of Example 119, the following compounds were synthesized:

Example 120: (R)-8-(8-(pyridazin-3-ylthio)imidazo[1,2-c]pyrimidin-5-yl)-8-azaspiro[4.5]decan-1-amine

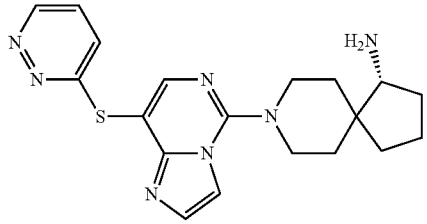 [SMILES: N[C@@H]1CCCC12CCN(c1ncc(Sc3cccnn3)c3nccn13)CC2]

¹H NMR (400 MHz, DMSO-d₆) δ 8.97 (d, J=4.8 Hz, 1H), 8.09 (s, 1H), 7.80 (s, 1H), 7.58 (s, 1H), 7.48 (dd, J=8.9, 4.9 Hz, 1H), 7.33 (d, J=8.8 Hz, 1H), 3.90 (s, 2H), 3.25 (d, J=12.2 Hz, 3H), 3.18 (s, 1H), 1.86-1.46 (m, 9H); LCMS: m/z 382.1 [M+H]⁺.

Example 121: (R)-8-(8-(pyrazin-2-ylthio)imidazo[1,2-c]pyrimidin-5-yl)-8-azaspiro[4.5]decan-1-amine

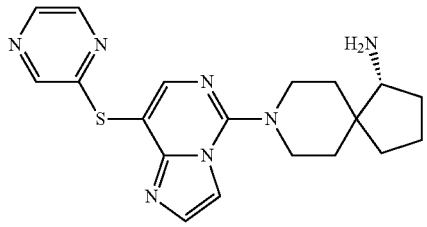 [SMILES: N[C@@H]1CCCC12CCN(c1ncc(Sc3cnccn3)c3nccn13)CC2]

¹H NMR (400 MHz, DMSO-d₆) δ 8.41 (s, 1H), 8.36 (s, 1H), 8.31 (s, 1H), 8.07 (s, 1H), 7.79 (s, 1H), 7.58 (s, 1H), 3.89 (t, J=12.8 Hz, 2H), 3.24 (d, J=12.2 Hz, 2H), 2.06-1.46 (m, 9H); LCMS: m/z 382.1 [M+H]⁺.

Example 122: Preparation of Compound 8-(8-((6-amino-2,3-dichloropyridin-4-yl)thio)imidazo[1,2-c]pyrimidin-5-yl)-1-methyl-8-azaspiro[4.5]decan-1-amine

Step 1: 8-(8-iodoimidazo[1,2-c]pyrimidin-5-yl)-1-methyl-8-azaspiro[4.5]decan-1-amine

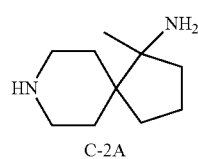

C-2A

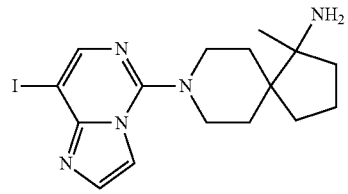

To a solution of 5-chloro-8-iodoimidazo[1,2-c]pyrimidine (56 mg, 0.2 mmol) in anhydrous DMF (10 mL) was added 1-methyl-8-azaspiro[4.5]decan-1-amine (40 mg, 0.24 mmol) at 0° C., followed by diisopropylethylamine (51.6 mg, 0.4 mmol), and the reaction mixture was stirred at 0° C. for 1 hour. After the reaction was completed, the reaction solution was directly used in the next reaction.
LCMS: m/z 412.0 [M+H]⁺.

Step 2: Tert-Butyl (8-(8-iodoimidazo[1,2-c]pyrimidin-5-yl)-1-methyl-8-azaspiro[4.5]decan-1-yl)carbamate

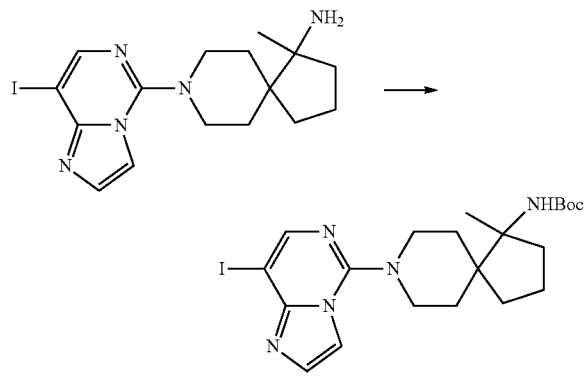

To the solution obtained in the previous step was added (Boc)₂O (87 mg, 0.4 mmol), followed by diisopropylethylamine (51.6 mg, 0.4 mmol), and the reaction solution was stirred at room temperature for 4 hours. After the reaction was completed, water was added to quench the reaction, followed by extraction with ethyl acetate (3×10 mL). The organic phases were combined, dried over anhydrous sodium sulfate, filtered and concentrated under reduced pressure. The resulting residue was purified by silica gel chromatography (ethyl acetate/petroleum ether with a gradient of 0 to 30%) to obtain tert-butyl (8-(8-iodoimidazo[1,2-c]pyrimidin-5-yl)-1-methyl-8-azaspiro[4.5]decan-1-yl)carbamate (15 mg, two-step yield: 7%).
LC-MS: m/z=512.0 [M+H]⁺.

Step 3: Tert-Butyl (8-(8-((6-(((tert-butoxycarbonyl)amino)-2,3-dichloropyridin-4-yl)thio)imidazo[1,2-c]pyrimidin-5-yl)-methyl-8-azaspiro[4.5]decan-1-yl)carbamate

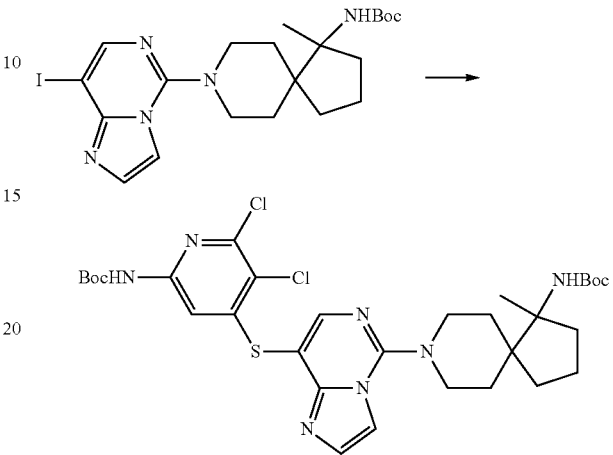

According to the synthesis method of step 1 in Example 76, tert-butyl (8-(8-iodoimidazo[1,2-c]pyrimidin-5-yl)-1-methyl-8-azaspiro[4.5]decan-1-yl)carbamate and sodium 6-((tert-butoxycarbonyl)amino)-2,3-dichloropyridine-4-thiolate were subjected to coupling reaction to obtain tert-butyl (8-(8-((6-((tert-butoxycarbonyl)amino)-2,3-dichloro-pyridin-4-yl)thio)imidazo[1,2-c]pyrimidin-5-yl)-methyl-8-azaspiro[4.5]decan-1-yl)carbamate (4 mg, yield: 15%).
LC-MS: m/z 678.2 [M+H]⁺.

Step 4: 4-((5-(1-amino-1-methyl-8-azaspiro[4.5]decan-8-yl)imidazo[1,2-c]pyrimidin-8-yl)thio)-5,6-dichloropyridin-2-amine

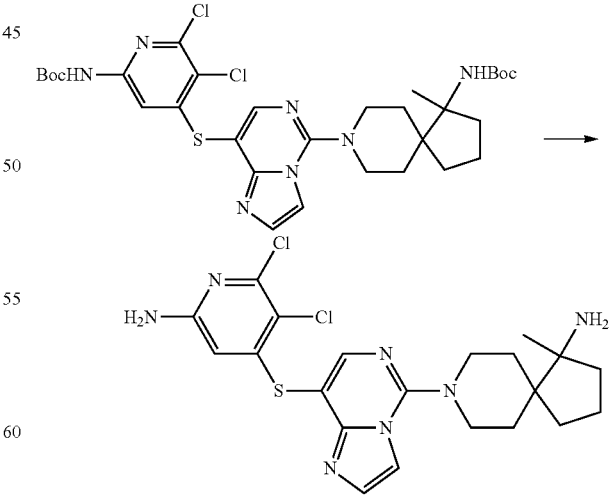

According to the synthesis method of step 3 in Example 21, tert-butyl (8-(8-((6-(((tert-butoxycarbonyl)amino)-2,3-dichloropyridin-4-yl)thio)imidazo[1,2-c]pyrimidin-5-yl)- methyl-8-azaspiro[4.5]decan-1-yl)carbamate was subjected to deprotection of the Boc protecting group to obtain 4-((5-(1-amino-1-methyl-8-azaspiro[4.5]decan-8-yl)imidazo[1,2-c]pyrimidin-8-yl)thio)-5,6-dichloropyridin-2-amine (2 mg, yield: 60%).

¹HNMR (400 MHz, DMSO-d₆) δ 8.10 (s, 1H), 7.87 (s, 1H), 7.64 (s, 1H), 6.42 (s, 2H), 5.63 (s, 1H), 4.06 (s, 2H), 3.18 (t, J=12.4 Hz, 2H), 1.96-1.37 (m, 9H), 1.26 (s, 3H), 0.98-0.84 (m, 1H) ppm; LC-MS: m/z=478.2 [M+H]⁺.

According to the synthesis method of Example 122, the following compounds were synthesized:

Example 123: (R)-8-(8-(((6-amino-3-chloro-2-methyl-pyridin-4-yl)thio)imidazo[1,2-c]pyrimidin-5-yl)-3,3-difluoro-8-azaspiro[4.5]decan-1-amine

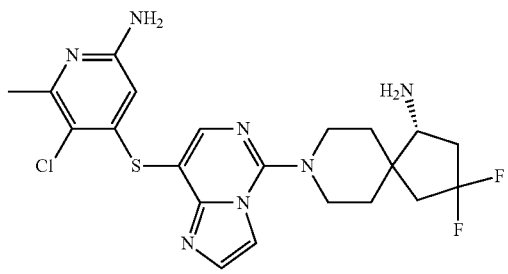 [SMILES: Cc1nc(N)cc(Sc2cnc(N3CCC4(CC3)CC(F)(F)C[C@H]4N)n3ccnc23)c1Cl]

¹H NMR (400 MHz, DMSO-d₆) δ 8.19 (s, 2H), 8.07 (s, 1H), 7.84 (s, 1H), 7.65 (s, 1H), 5.65 (s, 1H), 3.99 (t, J=15.1 Hz, 2H), 3.62-3.55 (m, 3H), 2.74-2.63 (m, 2H), 2.44-2.33 (m, 5H), 2.01 (t, J=11.8 Hz, 1H), 1.85-1.60 (m, 3H) ppm; LC-MS: m/z=480.2 [M+H]⁺.

Example 124: Preparation of Compound (R)-8-(8-((6-amino-2,3-dichloropyridin-4-yl)thio)imidazo[1,2-c]pyrimidin-5-yl)-3,3-difluoro-8-azaspiro[4.5]decan-1-amine Step 1 and Step 2: 5,6-dichloro-4-((5-chloroimidazo[1,2-c]pyrimidin-8-yl)thio)pyridin-2-amine

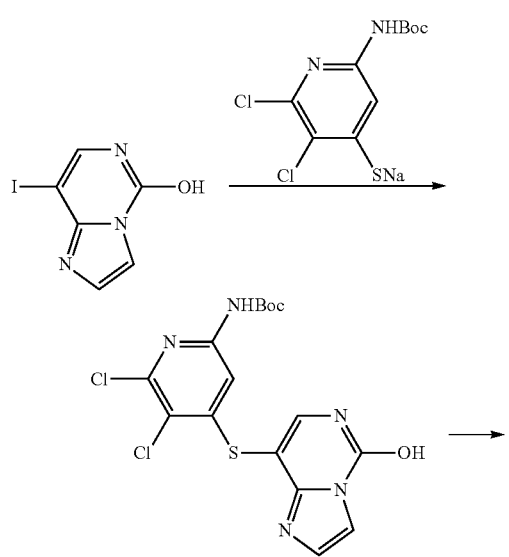

According to the synthesis method of Step 3 and Step 4 in Example 1, 8-iodoimidazo[1,2-c]pyrimidin-5-phenol and sodium 6-((tert-butoxycarbonyl)amino)-2,3-dichloropyridine-4-thiolate were subjected to coupling and halogenation reaction to obtain 5,6-dichloro-4-((5-chloroimidazo[1,2-c]pyrimidin-8-yl)thio)pyridin-2-amine.

LC-MS: m/z 347.9 [M+H]⁺

Step 3: (R)-8-(8-(((6-amino-2,3-dichloropyridin-4-yl)thio)imidazo[1,2-c]pyrimidin-5-yl)-3,3-difluoro-8-azaspiro[4.5]decan-1-amine

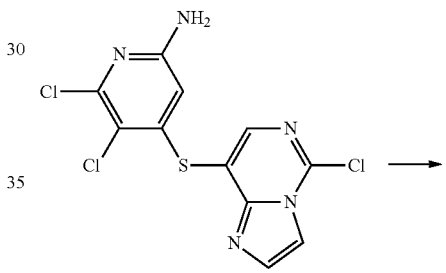

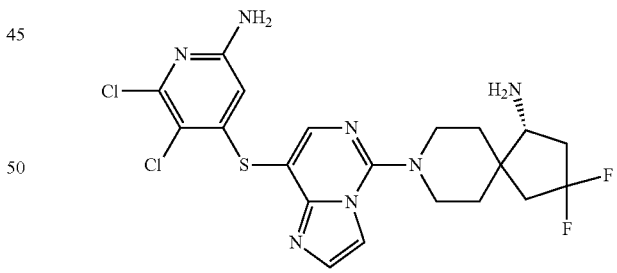

According to the synthesis method of Example 23, 5,6-dichloro-4-((5-chloroimidazo[1,2-c]pyrimidin-8-yl)thio)pyridin-2-amine was substituted by (R)-3,3-difluoro-8-azaspiro[4.5]decan-1-amine to obtain (R)-8-(8-(((6-amino-2,3-dichloropyridin-4-yl)thio)imidazo[1,2-c]pyrimidin-5-yl)-3,3-difluoro-8-azaspiro[4.5]decan-1-amine.

¹H NMR (400 MHz, DMSO-d₆) δ 8.35 (s, 2H), 8.06 (s, 1H), 7.86 (s, 1H), 7.61 (s, 1H), 6.31 (s, 2H), 5.62 (s, 1H), 3.92 (d, J=14.9 Hz, 2H), 3.21 (d, J=12.8 Hz, 3H), 3.07 (t, J=8.1 Hz, 2H), 2.12-1.98 (m, 3H), 1.91 (d, J=12.4 Hz, 2H), 1.47 (t, J=16.6 Hz, 3H) ppm; LC-MS: m/z 501.7 [M+H]⁺.

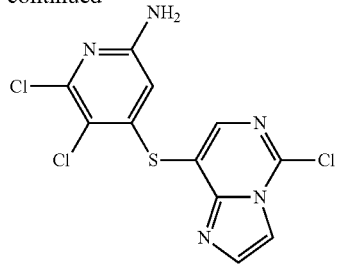

Example 1-2: Preparation of Intermediate: 5-chloro-8-iodo-[1,2,4]triazolo[4,3-c]pyrimidine (E-1)

Step 1: 2-chloro-4-hydrazino-5-iodopyrimidine

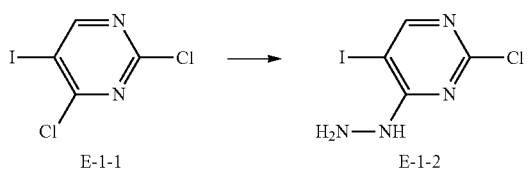 [SMILES: Clc1ncc(I)c(Cl)n1 ; NNc1nc(Cl)ncc1I]

To a dry 100 mL flask were added 2,4-dichloro-5-iodopyrimidine (25 g, 91 mmol) and anhydrous ethanol (20 mL), followed by slow addition of hydrazine hydrate (13.66 g, 272.9 mmol) at 0° C. The mixture was stirred at room temperature for 2 hours, during which a large amount of solid was precipitated. The mixture was filtered and the filter cake was washed with ethanol, and dried in vacuum to obtain 2-chloro-4-hydrazino-5-iodopyrimidine as a brown solid (20 g, yield: 81%).

$^1$H NMR (400 MHz, CDCl$_3$) δ 8.29 (s, 1H), 6.67 (s, 1H), 4.08 (s, 2H) ppm; LC-MS: m/z 271.1 [M+H]$^+$.

Step 2: 5-chloro-8-iodo-[1,2,4]triazolo[4,3-c]pyrimidine

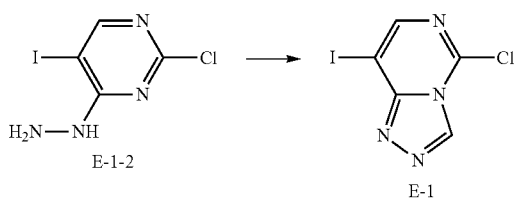 [SMILES: NNc1nc(Cl)ncc1I ; Clc1ncc(I)c2nncn12]

To a dry 50 mL sealed tube were sequentially added 2-chloro-4-hydrazino-5-iodopyrimidine (10 g, 37 mmol) and trimethyl orthoformate (3.92 g, 37 mmol). Under nitrogen atmosphere, the mixture was heated to 80° C. and stirred for 5 hours. After the reaction was completed, the reaction solution was cooled to room temperature. The mixture was slowly poured into saturated sodium bicarbonate solution, and extracted with ethyl acetate (3×100 mL). The organic phases were combined, washed with saturated brine, dried over anhydrous sodium sulfate, filtered and concentrated to obtain the product, which was then isolated by silica gel column chromatography (ethyl acetate: petroleum ether=1:1) to obtain 5-chloro-8-iodo-[1,2,4]triazolo[4,3-c]pyrimidine (5.7 g, yield: 55%).

$^1$H NMR (400 MHz, DMSO-d$_6$) δ 9.69 (s, 1H), 8.28 (s, 1H) ppm; LC-MS: m/z 280.1 [M+H]$^+$.

Example 2-2: Preparation of intermediate: (R)-2-methyl-N—((R)-8-azaspiro[4.5]decan-1-yl)propane-2-sulfinamide (C-1A-2)

Step 1: Tert-Butyl (R)-1-((R)-1,1-dimethylethylsulfinamido)-8-azaspiro[4.5]decane-8-carboxylate

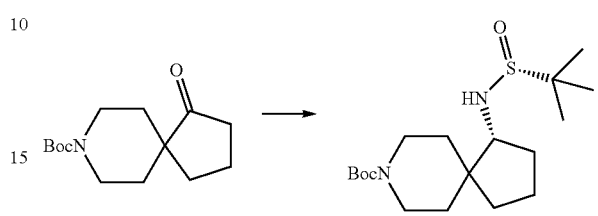

To a 100 mL single-necked flask were sequentially added tert-butyl 1-oxo-8-azaspiro[4.5]decane-8-carboxylate (2.53 g, 10 mmol) and titanium tetraethoxide (6.84 g, 30 mmol) and 50 mL of tetrahydrofuran, and the reaction mixture was stirred under reflux for 4 hours. After the mixture was cooled to room temperature, methanol (10 mL) was added followed by lithium borohydride (0.65 g, 30 mmol). The resulting mixture was stirred at room temperature for 3 hours.

Methanol was slowly added to quench excess borohydride, followed by addition of brine. The resulting mixture was stirred for 15 minutes and then filtered through diatomite. The aqueous mixture was extracted with ethyl acetate (3×50 mL). The organic phases were combined, dried over MgSO$_4$, filtered, and the volatiles were removed under reduced pressure. The resulting residue was purified by silica gel chromatography (ethyl acetate: petroleum ether with a gradient of 0 to 50%) to obtain tert-butyl (R)-1-((R)-1,1-dimethylethylsulfinamido)-8-azaspiro[4.5]decane-8-carboxylate as a white solid (2.86 g, yield: 80%).

LC-MS: m/z 359.1 [M+H]$^+$.

Step 2: (R)-2-methyl-N—((R)-8-azaspiro[4.5]decan-1-yl)propane-2-sulfinamide (C-1A-2)

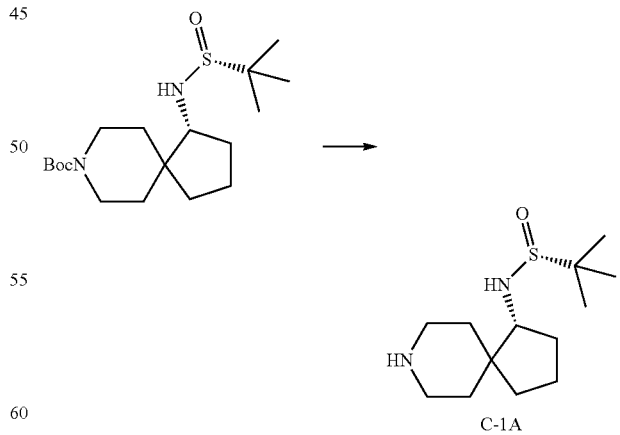

A solution of tert-butyl (R)-1-((R)-1,1-dimethylethylsulfinamido)-8-azaspiro[4.5]decane-8-carboxylate (2.86 g, 8 mmol) and concentrated sulfuric acid (2.0 mL, 32 mmol) in dioxane (50 mL) was stirred at room temperature for 2 hours. Saturated aqueous solution of Na$_2$CO$_3$ was then added until the pH of the mixture reached 11, and the aqueous mixture was extracted with DCM (3×50 mL). The organic phases were combined, washed with brine, dried over Na₂SO₄, filtered, and the volatiles were removed under reduced pressure to obtain (R)-2-methyl-N—((R)-8-azaspiro[4.5]decan-1-yl)propane-2-sulfinamide (C-1A-2) as a white solid (1.86 g, yield: 90%).

¹H NMR (400 MHz, DMSO-d₆) δ 4.82 (d, J=7.5 Hz, 1H), 3.04 (d, J=7.6 Hz, 1H), 2.81 (ddd, J=12.1, 8.0, 4.0 Hz, 2H), 2.60-2.51 (m, 2H), 1.92-1.14 (m, 10H), 1.12 (s, 9H) ppm; LC-MS: m/z 259.1 [M+H]⁺.

According to the synthesis method of Example 2, the following intermediates C-1B-2, C-1C-2, C-1D-2, C-1E-2, C-1F-2, C-1G-2, C-1H-2 were obtained by using similar raw materials.

Example 3-2: Preparation of Intermediate: (R)-2-methyl-N—((S)-2-oxa-8-azaspiro[4.5]decan-4-yl)propane-2-sulfinamide (C-11-2)

Step 1: 1-(tert-butyl) 4-methyl 4-(2-(benzyloxy)-1-hydroxyethyl)piperidine-1,4-dicarboxylate

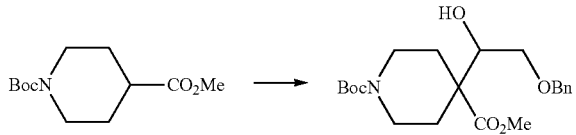

Under nitrogen atmosphere, to a dry 500 mL three-necked flask were sequentially added 1-(tert-butyl) 4-methyl piperidine-1,4-dicarboxylate (45 g, 180 mmol) and tetrahydro-

| No. | Name | Structure | Analysis data |
|---|---|---|---|
| C-1B-2 | (R)-2-methyl-N-((R)-7-aza-spiro[3.5]nonan-1-yl)propane-2-sulfinamide | 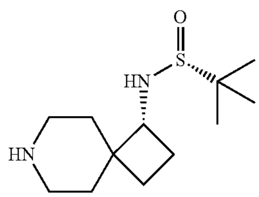 [SMILES: CC(C)(C)[S@@](=O)N[C@@H]1CCC12CCNCC2] | ¹H NMR (400 MHz, CDCl₃) δ 3.56 (t, J = 8.9 Hz, 1H), 3.51-3.20 (m, 2H), 3.18-2.97 (m, 2H), 2.34 (d, J = 10.1 Hz, 1H), 2.06-1.83 (m, 3H), 1.70 (dt, J = 26.3, 12.0 Hz, 3H), 1.52 (t, J = 10.0 Hz, 1H), 1.19 (s, 9H) ppm; LC-MS: m/z 244.1 [M + H]⁺. |
| C-1C-2 | (R)-2-methyl-N-(7-azaspiro[3.5]nonan-2-yl)propane-2-sulfinamide | 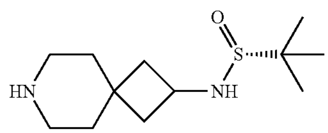 [SMILES: CC(C)(C)[S@@](=O)NC1CC2(CCNCC2)C1] | LC-MS: m/z 244.1 [M + H]⁺ |
| C-1D-2 | (S)-2-methyl-N-((S)-8-azaspiro[4.5]decan-1-yl)propane-2-sulfinamide | 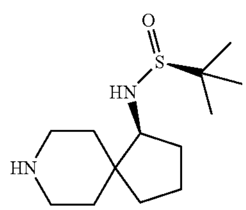 [SMILES: CC(C)(C)[S@](=O)N[C@H]1CCCC12CCNCC2] | LC-MS: m/z 259.1 [M + H]⁺ |
| C-1E-2 | (R)-2-methyl-N-((7R)-2-azaspiro[4.4]nonan-7-yl)propane-2-sulfinamide | 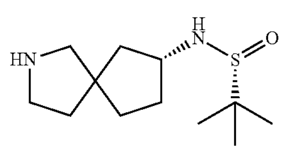 [SMILES: CC(C)(C)[S@@](=O)N[C@@H]1CCC2(CCNC2)C1] | LC-MS: m/z 245.1 [M + H]⁺ |
| C-1F-2 | (R)-2-methyl-N-((R)-3-azaspiro[5.5]undecan-7-yl)propane-2-sulfinamide | 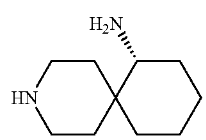 | LC-MS: m/z 169.1 [M + H]⁺ |
| C-1G-2 | (R)-N-((R)-azepan-4-yl)-2-methylpropan-2-sulfinamide | 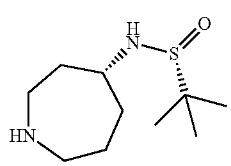 | LC-MS: m/z 219.1 [M + H]⁺ |
| C-1H-2 | (S)-2-methyl-N-((S)-7-azaspiro[3.5]nonan-1-yl)propane-2-sulfinamide | | LC-MS: m/z 245.2 [M + H]⁺ | furan (400 mL). The solution was cooled to −78° C., and LiHMDS (261 mL, 261 mmol) was added dropwise. After the dropwise addition, the mixture was warmed to room temperature, stirred at room temperature for 3 hours, and then cooled to −78° C. again, followed by slow addition of a solution of benzyloxyacetaldehyde (46 g, 300 mmol) in tetrahydrofuran (50 mL). The reaction solution was slowly warmed to room temperature and stirred for 2.5 hours. After the reaction was completed, saturated NH₄Cl solution (200 mL) was added to quench the reaction, followed by extraction with ethyl acetate (3×200 mL). The organic phases were combined, dried over Na₂SO₄, filtered, and the filtrate was concentrated under reduced pressure, and the resulting residue was purified by silica gel chromatography (ethyl acetate/petroleum ether with a gradient of 0 to 50%) to obtain 1-(tert-butyl) 4-methyl 4-(2-(benzyloxy)-1-hydroxyethyl)piperidine-1,4-dicarboxylate (52 g, yield: 73.3%).

$^1$H NMR (400 MHz, CDCl₃) δ 7.36-7.30 (m, 5H), 4.50 (s, 2H), 3.97 (s, 2H), 3.73-3.65 (m, 2H), 3.62 (s, 3H), 3.59-3.48 (m, 3H), 2.88 (d, J=6.2 Hz, 1H), 2.23 (dd, J=13.7, 2.7 Hz, 1H), 2.04-1.88 (m, 2H), 1.74 (d, J=14.7 Hz, 1H), 1.56 (d, J=4.2 Hz, 1H), 1.44 (s, 9H) ppm; LC-MS: m/z 294.1 [M+H]⁺.

Step 2: Tert-Butyl 4-(2-(benzyloxy)-1-hydroxyethyl)-4-(hydroxymethyl)piperidine-1-carboxylate

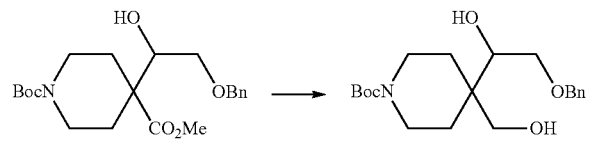

To a dry 500 mL three-necked flask were sequentially added 1-(tert-butyl) 4-methyl 4-(2-(benzyloxy)-1-hydroxyethyl)piperidine-1,4-dicarboxylate (51.4 g, 130 mmol) and tetrahydrofuran (500 mL), and LiBH₄ (11.44 g, 520 mmol) was then added to the solution. The mixture was stirred at room temperature for 6 hours. After the reaction was completed, the reaction was quenched with saturated NaHCO₃ (200 mL), followed by extraction with ethyl acetate (3×200 mL). The organic phases were combined, dried over Na₂SO₄, filtered, the filtrate was concentrated under reduced pressure, and the resulting residue was purified by silica gel chromatography (ethyl acetate/petroleum ether with a gradient of 0 to 50%) to obtain tert-butyl 4-(2-(benzyloxy)-1-hydroxyethyl)-4-(hydroxymethyl)piperidine-1-carboxylate (27 g, yield: 57%).

LC-MS: m/z 266.1 [M+H]⁺.

Step 3: Tert-Butyl 4-(1,2-dihydroxyethyl)-4-(hydroxymethyl)piperidine-1-carboxylate

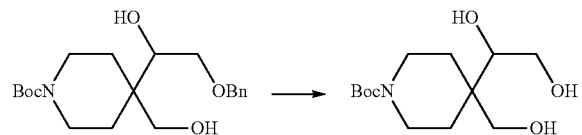 [SMILES: CC(C)(C)OC(=O)N1CCC(CO)(C(O)COCc2ccccc2)CC1 ; CC(C)(C)OC(=O)N1CCC(CO)(C(O)CO)CC1]

To a dry 500 mL single-necked flask were sequentially added tert-butyl 4-(2-(benzyloxy)-1-hydroxyethyl)-4-(hydroxymethyl)piperidine-1-carboxylate (27 g, 74 mmol), methanol (270 mL) and Pd/C (20 g). The flask was purged with hydrogen using a hydrogen balloon three times, and the mixture was stirred at room temperature for 12 hours. The reaction solution was filtered and concentrated to obtain tert-butyl 4-(1,2-dihydroxyethyl)-4-(hydroxymethyl)piperidine-1-carboxylate (18.9 g, yield: 93%).

LC-MS: m/z 176.1 [M+H]⁺.

Step 4: Tert-Butyl 4-hydroxy-2-oxa-8-azaspiro[4.5]decane-8-carboxylate

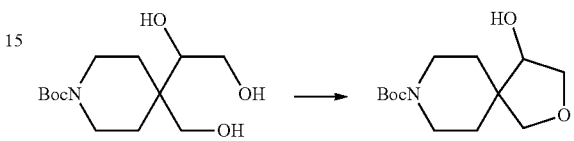

To a dry 500 mL single-necked flask were sequentially added tert-butyl 4-(1,2-dihydroxyethyl)-4-(hydroxymethyl)piperidine-1-carboxylate (18.9 g, 69 mmol), triphenyl phosphine (25.2 g, 86.25 mmol) and tetrahydrofuran (350 mL), and the reaction solution was cooled to 0° C., followed by addition of DEAD (12.46 mL, 86 mmol). The mixture was then warmed to room temperature and stirred for 5 hours. After the reaction was completed, water (200 mL) was added to quench the reaction, followed by extraction with ethyl acetate (3×200 mL). The organic phases were combined and dried over Na₂SO₄, filtered, the filtrate was concentrated under reduced pressure and the resulting residue was purified by silica gel chromatography (methanol/dichloromethane with a gradient of 0 to 2%) to obtain tert-butyl 4-hydroxy-2-oxa-8-azaspiro[4.5]decane-8-carboxylate (13.2 g, yield: 74%).

$^1$H NMR (400 MHz, CDCl₃) δ 4.04 (dd, J=10.0, 4.6 Hz, 1H), 3.98-3.90 (m, 1H), 3.71-3.63 (m, 2H), 3.64-3.49 (m, 3H), 3.20 (dt, J=13.4, 6.3 Hz, 1H), 3.07 (ddd, J=13.2, 9.2, 3.5 Hz, 1H), 1.95 (d, J=5.2 Hz, 1H), 1.74-1.66 (m, 1H), 1.53-1.46 (m, 1H), 1.39 (s, 9H), 1.27-1.11 (m, 1H) ppm; LC-MS: m/z 202.1[M-56+H]⁺.

Step 5: Tert-Butyl 4-oxo-2-oxa-8-azaspiro[4.5]decane-8-carboxylate

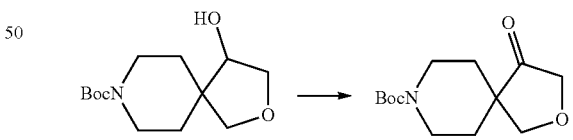

To a dry 500 mL single-necked flask were sequentially added tert-butyl 4-hydroxy-2-oxa-8-azaspiro[4.5]decane-8-carboxylate (13.2 g, 51 mmol), dichloromethane (280 mL) and Dess-Martin oxidant (32.2 g, 76.5 mmol), and the mixture was stirred for 5 hours in an ice bath. After the reaction was completed, a saturated solution (200 mL) of NaHCO₃:Na₂S₂O₃ (1:1) was added, the organic phase was separated, and the aqueous phase was extracted with DCM (3×100 mL). The organic phases were combined, dried over Na₂SO₄ and the filtrate was concentrated under reduced pressure. The resulting residue was purified by silica gel chromatography (ethyl acetate/petroleum ether with a gradient of 0 to 40%) to obtain tert-butyl 4-oxo-2-oxa-8-azaspiro[4.5]decane-8-carboxylate (12 g, yield: 92.1%).

¹H NMR (400 MHz, CDCl₃) δ 4.05 (d, J=13.6 Hz, 4H), 3.87 (d, J=12.9 Hz, 2H), 3.09 (ddd, J=13.5, 9.8, 3.5 Hz, 2H), 1.73 (ddd, J=13.9, 9.8, 4.3 Hz, 2H), 1.53 (d, J=15.1 Hz, 2H), 1.46 (s, 9H) ppm; LC-MS: m/z 200.0 [M-56+H]⁺.

Step 6: Tert-Butyl (S)-4-((R)-1,1-dimethylethylsulfinamido)-2-oxa-8-azaspiro[4.5]decane-8-carboxylate

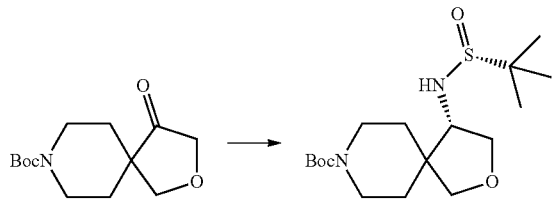 [SMILES: CC(C)(C)OC(=O)N1CCC2(CC1)COCC2=O ; CC(C)(C)OC(=O)N1CCC2(CC1)COC[C@H]2N[S@](=O)C(C)(C)C]

According to the synthesis method of step 1 in Example 2 (intermediate C-1A-2), tert-butyl 4-oxo-2-oxa-8-azaspiro[4.5]decane-8-carboxylate was subjected to reductive amination to obtain tert-butyl (S)-4-((R)-1,1-dimethylethylsulfinamido)-2-oxa-8-azaspiro[4.5]decane-8-carboxylate as a white solid.

¹H NMR (400 MHz, CDCl₃) δ 4.14 (dd, J=9.3, 6.2 Hz, 1H), 3.90 (d, J=13.8 Hz, 2H), 3.77 (s, 2H), 3.70 (dd, J=9.2, 5.3 Hz, 1H), 3.63 (q, J=6.1 Hz, 1H), 3.27 (d, J=6.4 Hz, 1H), 2.90 (t, J=12.4 Hz, 2H), 1.71 (dt, J=16.6, 7.9 Hz, 2H), 1.51 (s, 2H), 1.45 (s, 9H), 1.22 (s, 9H) ppm; LC-MS: m/z 361.1 [M-100]⁺.

Step 7: (R)-2-methyl-N—((S)-2-oxa-8-azaspiro[4.5]decan-4-yl)propane-2-sulfinamide (C-1I-2)

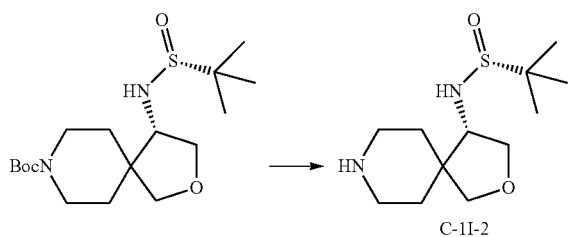 [SMILES: CC(C)(C)OC(=O)N1CCC2(CC1)COC[C@H]2N[S@](=O)C(C)(C)C ; CC(C)(C)[S@@](=O)N[C@@H]1COCC12CCNCC2]

C-1I-2

According to the synthesis method of Step 2 of Example 2 (intermediate C-1A-2), tert-butyl (S)-4-((R)-1-methylethylsulfinamido)-2-oxa-8-azaspiro[4.5]decane-8-carboxylate was subjected to the removal of the Boc protecting group to obtain (R)-2-methyl-N—((S)-2-oxa-8-azaspiro[4.5]decan-4-yl)propane-2-sulfinamide (C-1I-2) as a white solid.

¹H NMR (400 MHz, DMSO-d₆) δ 5.30 (s, 1H), 5.23 (d, J=8.9 Hz, 1H), 3.93 (dd, J=8.6, 7.2 Hz, 1H), 3.69 (d, J=8.6 Hz, 1H), 3.58 (d, J=8.6 Hz, 1H), 3.46 (dd, J=8.5, 7.0 Hz, 2H), 2.89-2.73 (m, 2H), 2.48-2.42 (m, 1H), 1.69-1.50 (m, 2H), 1.39-1.21 (m, 3H), 1.12 (s, 9H) ppm; LC-MS: m/z 261.1 [M+H]⁺.

Example 4-2: Preparation of (R)-2-methyl-N-((3S, 4S)-3-methyl-2-oxa-8-azaspiro[4.5]decan-4-yl)propane-2-sulfinamide (C-1J-2) (same as Example 6-2)

Step 1: ethyl (S)-2-((tert-butyldimethylsilyl)oxy)propionate

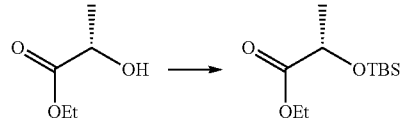

To a solution of ethyl (S)-2-hydroxypropionate (30 g, 254 mmol) in dichloromethane (300 mL) was added imidazole (2.75 g, 304.9 mmol), and the solution was cooled to 0° C. To this solution, tert-butyldimethylsilyl chloride (46.0 g, 304.9 mmol) was added in portions, and the resulting mixture was stirred at room temperature for 16 hours. After the completion of the reaction was confirmed by TLC analysis, the reaction mixture was quenched with water and extracted with dichloromethane (2×100 mL). The organic phases were combined, dried over anhydrous sodium sulfate, filtered and concentrated under reduced pressure to obtain ethyl (S)-2-((tert-butyldimethylsilyl)oxy)propionate as a colorless liquid (50 g, yield 84%).

¹H NMR (400 MHz, CDCl₃) δ 4.32-4.27 (m, 1H), 4.21-4.12 (m, 2H), 1.37 (d, J=6.8 Hz, 3H), 1.27 (d, J=7.2 Hz, 3H), 0.90 (s, 9H), 0.08 (s, 6H) ppm.

Step 2: (S)-2-((tert-butyldimethylsilyl)oxy)propanal

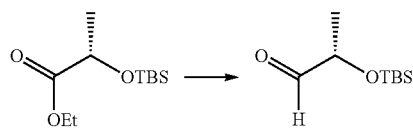

At −78° C., to a solution of ethyl (S)-2-((tert-butyldimethylsilyl)oxy)propionate (25 g, 107.6 mmol) in diethyl ether (500 mL) was slowly added dropwise diisobutylaluminum hydride (1 M in hexane) (129 mL, 129.1 mmol), and the resulting mixture was stirred at −78° C. for 1 hour. After the completion of the reaction was confirmed by TLC analysis, the reaction mixture was slowly warmed to −40° C., and then quenched with a saturated aqueous solution of Rochelle salt (1 L), followed by addition of diethyl ether (500 mL). The resulting mixture was stirred at room temperature for 2 hours, and then extracted with diethyl ether (200 mL). The organic phase was washed with saturated brine (250 mL), dried over Na₂SO₄, filtered and concentrated under reduced pressure to obtain (S)-2-((tert-butyldimethylsilyl)oxy)propanal (19 g, yield: 94%).

¹H NMR (400 MHz, CDCl₃) δ 9.61 (s, 1H), 4.12-4.06 (m, 1H), 1.27 (d, J=6.8 Hz, 3H), 0.91 (s, 9H), 0.10 (s, 6H) ppm.

Step 3: 1-(tert-butyl) 4-ethyl 4-((2S)-2-((tert-butyldimethylsilyl)oxy)-1-hydroxypropyl)piperidine-1,4-dicarboxylate

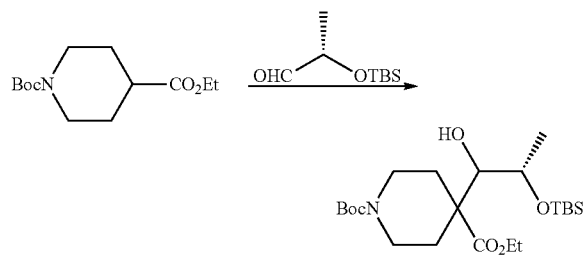

At 0° C., to a stirred solution of 1-(tert-butyl)-4-ethyl piperidine-1,4-dicarboxylate (30 g, 116.6 mmol) in THF (250 mL) was added lithium diisopropylamide (2M in THF) (93.3 mL, 186.6 mmol), and the solution was stirred at 0° C. for 30 minutes, followed by addition of a solution of (S)-2-((tert-butyldimethylsilyl)oxy)propanal (22 g, 116.6 mmol) in THF (50 mL). The resulting reaction mixture was stirred at 0° C. for 1 hour, and then kept at room temperature for 1 hour. After the completion of the reaction was confirmed by TLC analysis, the reaction mixture was quenched with saturated NH$_4$Cl solution and extracted with ethyl acetate (2×250 mL). The organic phases were combined, washed with water (150 mL), and brine (150 mL), dried over anhydrous sodium sulfate, filtered and concentrated under reduced pressure. The crude product was purified by silica gel (60-120 mesh) column chromatography, using 25% ethyl acetate in petroleum ether as eluent to obtain 1-(tert-butyl) 4-ethyl 4-((2S)-2-((tert-butyldimethylsilyl)oxy)-1-hydroxypropyl)piperidine-1,4-dicarboxylate (17 g, yield: 32%) as a light red oil.

$^1$H NMR (400 MHz, CDCl$_3$) δ 4.29-4.09 (m, 2H), 3.96-3.94 (m, 2H), 3.86-3.80 (m, 1H), 3.56-3.54 (m, 1H), 2.86-2.76 (m, 2H), 2.46 (d, J=5.2 Hz, 1H), 2.16-2.13 (m, 1H), 2.13-2.04 (m, 1H), 1.77-1.60 (m, 2H), 1.46 (s, 9H), 1.29-1.24 (m, 3H), 1.12 (d, J=4 Hz, 3H), 0.89 (s, 9H), 0.05 (s, 6H) ppm; LCMS: m/z 346 [M-100]$^+$.

Step 4: Tert-Butyl ((2S)-2-((tert-butyldimethylsilyl)oxy)-1-hydroxypropyl)-4-(hydroxymethyl)piperidine-1-carboxylate

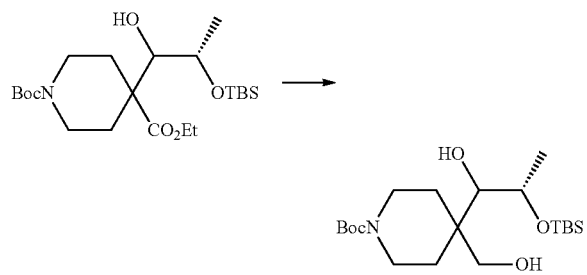

To a stirred solution of 1-(tert-butyl) 4-ethyl 4-((2S)-2-((tert-butyldimethylsilyl)oxy)-1-hydroxypropyl)piperidine-1,4-dicarboxylate (5 g, 11.21 mmol) in THF (50 mL) was added LiBH$_4$ (0.73 g, 33.65 mmol) in portions, and the mixture was stirred at room temperature for 16 hours. After the reaction was completed, the reaction mixture was quenched with saturated NaHCO$_3$ solution at 0° C. and stirred at room temperature for 15 minutes. The precipitated solid was filtered off, and the aqueous phase was extracted with ethyl acetate (2×50 mL). The organic phases were combined, dried over anhydrous sodium sulfate. The crude product obtained by filtration and concentration under reduced pressure was purified by silica gel (100-200 mesh) column chromatography using 25% ethyl acetate in petroleum ether as eluent to obtain tert-butyl ((2S)-2-((tert-butyldimethylsilyl)oxy)-1-hydroxypropyl)-4-(hydroxymethyl)piperidine-1-carboxylate (3 g, yield: 66%).

$^1$H NMR (400 MHz, CDCl$_3$) δ 4.55 (t, J=4.8 Hz, 1H), 4.43 (d, J=6.4 Hz, 1H), 3.52-3.47 (m, 5H), 3.31-3.28 (m, 1H), 3.05-3.01 (m, 2H), 1.58-1.49 (m, 2H), 1.42-1.38 (m, 11H), 1.11 (d, J=6.4 Hz, 3H), 0.85 (m, 9H), 0.04 (s, 6H) ppm; LC-MS: m/z 404.3 [M+H]$^+$.

Step 5: Tert-Butyl 4-((2S)-1,2-dihydroxypropyl)-4-(hydroxymethyl)piperidine-1-carboxylate

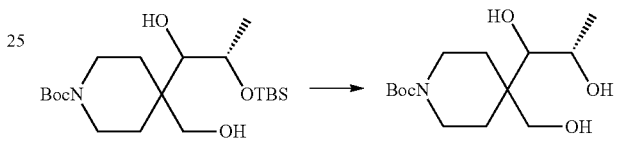

To a solution of tert-butyl ((2S)-2-((tert-butyldimethylsilyl)oxy)-1-hydroxypropyl)-4-(hydroxymethyl)piperidine-1-carboxylate (25 g, 61.93 mmol) in THF (500 mL) was added tetrabutylammonium fluoride (1M in THF) (93 mL, 92.89 mmol), and the resulting reaction mixture was stirred at room temperature for 2 hours. After the completion of the reaction was confirmed by TLC analysis, the reaction mixture was quenched with saturated NaHCO$_3$ solution and extracted with ethyl acetate (2×500 mL). The organic phases were combined and dried over anhydrous sodium sulfate. The crude product obtained by filtration and concentration under reduced pressure was purified by silica gel (60-120 mesh) column chromatography using ethyl acetate in petroleum ether with a gradient of 70-90% as eluent to obtain tert-butyl 4-((2S)-1,2-dihydroxypropyl)-4-(hydroxymethyl) piperidine-1-carboxylate (12 g, yield: 67%) as a colorless liquid.

$^1$H NMR (400 MHz, DMSO-d$_6$) δ 4.72 (t, J=4.8 Hz, 1H), 4.61 (d, J=5.2 Hz, 1H), 4.50 (d, J=7.2 Hz, 1H), 3.72-3.68 (m, 1H), 3.53-3.44 (m, 4H), 3.11-2.98 (m, 3H), 1.68-1.53 (m, 2H), 1.42-1.35 (m, 11H), 1.10 (d, J=6.4 Hz, 3H) ppm; LC-MS: m/z 290.1 [M+H]$^+$.

Step 6: Tert-Butyl (3S)-4-hydroxy-3-methyl-2-oxa-8-azaspiro[4.5]decane-8-carboxylate

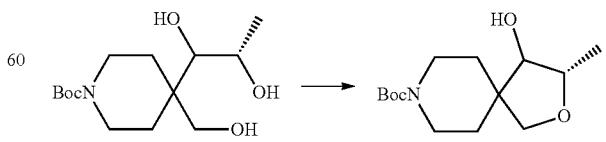

At 0° C., to a stirred suspension of NaH (60% in mineral oil) (1.45 g, 60.5 mmol) in THF (30 mL) was added a solution of tert-butyl 4-((2S)-1,2-dihydroxypropyl)-4-(hydroxymethyl)piperidine-1-carboxylate (5 g, 17.3 mmol) and p-toluenesulfonyl chloride (3.29 g, 17.3 mmol) in THF (20 mL), and the resulting reaction mixture was allowed to react at 0° C. for 3 hours. After the reaction was completed, the reaction mixture was quenched with saturated NH₄Cl solution (250 mL) at −20° C. and extracted with ethyl acetate (2×50 mL). The organic phases were combined, and dried over anhydrous sodium sulfate. The crude product obtained by filtration and concentration under reduced pressure was purified by silica gel (100-200 mesh) column chromatography, using 40% ethyl acetate in petroleum ether as eluent to obtain tert-butyl (3S)-4-hydroxy-3-methyl-2-oxa-8-azaspiro[4.5]decane-8-carboxylate (2.1 g, yield: 44%).

¹H NMR (400 MHz, CDCl₃) δ 3.83-3.62 (m, 5H), 3.43 (d, J=6.0, 1H), 3.07-2.97 (m, 2H), 1.72-1.55 (m, 3H), 1.51-1.42 (m, 11H), 1.33 (d, J=6.4 Hz, 3H) ppm; LC-MS: m/z 172.2 [M-100]⁺.

Step 7: tert-butyl (S)-3-methyl-4-oxo-2-oxa-8-azaspiro[4.5]decane-8-carboxylate

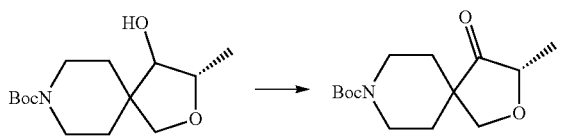 [SMILES: C[C@@H]1OCC2(CCN(C(=O)OC(C)(C)C)CC2)C1O ; C[C@@H]1OCC2(CCN(C(=O)OC(C)(C)C)CC2)C1=O]

Tert-butyl (3S)-4-hydroxy-3-methyl-2-oxa-8-azaspiro[4.5]decane-8-carboxylate (2.1 g, 7.74 mmol) was added to tetrahydrofuran (50 mL), followed by addition of Dess-Martin oxidant (4.26 g, 10.06 mmol), and the mixture was stirred for 1 hour. After the reaction was completed, the solvent was evaporated under reduced pressure. The resulting residue was purified by silica gel (100-200 mesh) column chromatography using 30% ethyl acetate in petroleum ether as eluent, followed by flash chromatography with 0.1% formic acid and acetonitrile as eluent to obtain tert-butyl (S)-3-methyl-4-oxo-2-oxa-8-azaspiro[4.5]decane-8-carboxylate (1.2 g, yield: 57%).

¹H NMR (400 MHz, CDCl₃) δ 4.20 (d, J=9.5 Hz, 1H), 3.94-3.90 (m, 4H), 3.16-3.10 (m, 1H), 3.03-2.97 (m, 1H), 1.81-1.75 (m, 1H), 1.67-1.62 (m, 1H), 1.61-1.57 (m, 1H), 1.42-1.45 (m, 10H), 1.32 (d, J=6.0 Hz, 3H) ppm; LC-MS: m/z 214.1 [M-55]⁺

Step 8: Tert-Butyl (3S,4S)-4-((R)-tert-butylsulfinyl)amino)-3-methyl-2-oxa-8-azaspiro[4.5]decane-8-carboxylate

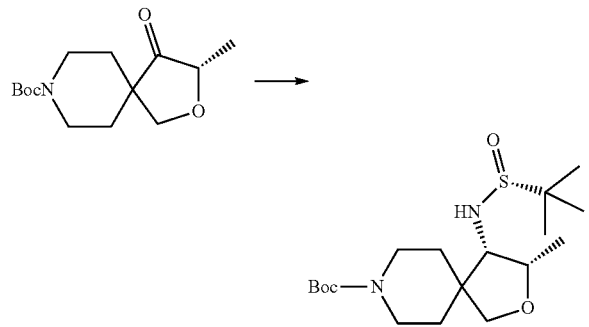

To a stirred solution of tert-butyl (S)-3-methyl-4-oxo-2-oxa-8-azaspiro[4.5]decane-8-carboxylate (1.2 g, 4.46 mmol) in THF (15 mL) were added (R)-2-methylpropane-2-sulfinamide (1.07 g, 8.91 mmol) and titanium tetraethoxide (4.07 g, 17.84 mmol). The resulting reaction mixture was stirred at 90° C. for 20 hours. The reaction mixture was cooled to −4° C., followed by addition of MeOH (2 mL). LiBH₄ (282 mg, 12.99 mmol) was then added thereto in portions and the resulting mixture was stirred at the same temperature for 1 hour. After the reaction was completed, the reaction mixture was quenched with saturated brine at 0° C., stirred at room temperature for 15 minutes, filtered and extracted with ethyl acetate (2×50 mL). The organic phases were combined and dried over anhydrous sodium sulfate. The crude product obtained by filtration and concentration under reduced pressure was purified by flash chromatography using 0.1% formic acid and acetonitrile as eluent to obtain tert-butyl (3S,4S)-4-((R)-tert-butylsulfinyl)amino)-3-methyl-2-oxa-8-azaspiro[4.5]decane-8-carboxylate (1.2 g, yield: 72%).

¹H NMR (400 MHz, CDCl₃) δ 4.20-4.15 (m, 1H), 3.90-3.84 (m, 2H), 3.63-3.59 (m, 1H), 3.49-3.43 (m, 1H), 3.31-3.29 (m, 1H), 2.95-2.81 (m, 2H), 1.90-1.71 (m, 2H), 1.49-1.40 (m, 11H), 1.25 (s, 9H), 1.19 (d, J=6.5 Hz, 3H) ppm; LC-MS: m/z 375.2 [M+H]⁺.

Step 9: (R)-2-methyl-N-((3S,4S)-3-methyl-2-oxa-8-azaspiro[4.5]decan-4-yl)propane-2-sulfinamide (C-1J-2)

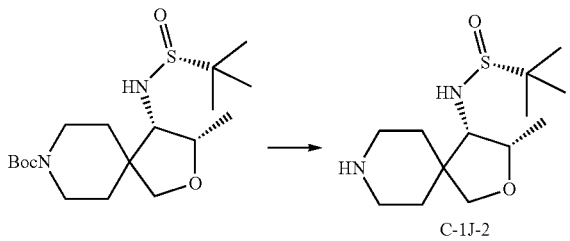 [SMILES: C[C@@H]1OCC2(CCN(C(=O)OC(C)(C)C)CC2)[C@@H]1N[S@](=O)C(C)(C)C ; C[C@@H]1OCC2(CCNCC2)[C@@H]1N[S@](=O)C(C)(C)C]

To a solution of tert-butyl (3S,4S)-4-((R)-tert-butylsulfinyl)amino)-3-methyl-2-oxa-8-azaspiro[4.5]decane-8-carboxylate (1.1 g, 2.936 mmol) in dichloromethane (10 mL) was added trifluoroacetic acid (1.12 mL, 14.68 mmol) dropwise, and the mixture was stirred at room temperature for 6 hours. After of the reaction was completed, the reaction mixture was concentrated under reduced pressure to obtain a crude product, which was purified by chromatography with 0.1% formic acid and acetonitrile to obtain (R)-2-methyl-N-((3S,4S)-3-methyl-2-oxa-8-azaspiro[4.5]decan-4-yl)propane-2-sulfinamide (C-1J-2) (850 mg, yield: 72%).

¹H NMR (400 MHz, DMSO-d₆) δ 8.40 (brs, D₂O Exchangeable, 1H), 8.30 (brs, D₂O Exchangeable, 1H), 5.28 (d, J=12.0 Hz, 1H), 4.13-4.09 (m, 1H), 3.77 (d, J=9.0 Hz, 1H), 3.50-3.45 (m, 2H), 3.29-3.26 (m, 1H), 3.19-3.15 (m, 1H), 2.94-2.85 (m, 2H), 1.87-1.80 (m, 2H), 1.69-1.59 (m, 2H), 1.17 (s, 9H), 1.08 (d, J=6.0 Hz, 3H) ppm; LC-MS: m/z 275.2 [M+H]⁺.

Example 5-2: Preparation of (R)-2-methyl-N-((3R,4S)-3-methyl-2-oxa-8-azaspiro[4.5]decan-4-yl)propane-2-sulfinamide and (R)-2-methyl-N-((3R,4R)-3-methyl-2-oxa-8-azaspiro[4.5]decan-4-yl)propane-2-sulfinamide (C-1K-2)

Step 1: Tert-Butyl (R)-3-methyl-4-oxo-2-oxa-8-azaspiro[4.5]decane-8-carboxylate

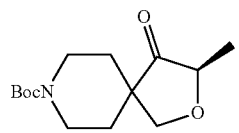 [SMILES: C[C@H]1OCC2(CCN(C(=O)OC(C)(C)C)CC2)C1=O]

According to the method of above Example 4, (R)-2-((tert-butyldimethylsilyl)oxo)propanal was used as raw material to obtain tert-butyl(R)-3-methyl-4-oxo-2-oxa-8-azaspiro[4.5]decane-8-carboxylate

Step 2: tert-butyl (3R,4S)-4-((R)-1,1-dimethylethylsulfinamido)-3-methyl-2-oxa-8-azaspiro[4.5]decane-8-carboxylate and tert-butyl (3R,4R)-4-((R)-1,1-dimethylethylsulfinamido)-3-methyl-2-oxa-8-azaspiro[4.5]decane-8-carboxylate

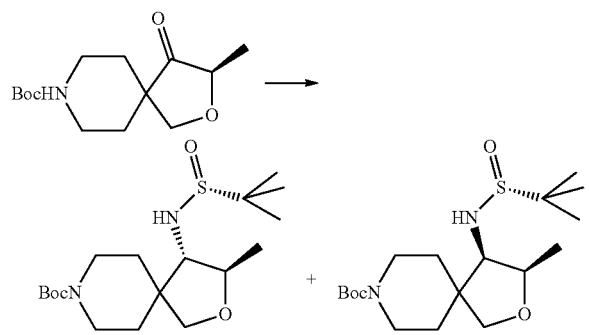

To a stirred solution of tert-butyl (R)-3-methyl-4-oxo-2-oxa-8-azaspiro[4.5]decane-8-carboxylate (0.97 g, 3.71 mmol) in THF (5 mL) were added (R)-2-methylpropane-2-sulfinamide (0.873 g, 7.2 mmol) and titanium tetraethoxide (3.36 mL, 14.74 mmol). The resulting reaction mixture was stirred at 90° C. for 18 hours, and then cooled to −4° C., followed by addition of MeOH (5 mL). LiBH₄ (80 mg, 3.71 mmol) was then added in portions and the resulting mixture was stirred at −4° C. for 1 hour. After the reaction was completed, the reaction mixture was quenched with saturated brine at 0° C. and stirred at room temperature for 15 minutes, followed by filtration and extraction with ethyl acetate (2×50 mL). The organic phases were combined, and dried over anhydrous sodium sulfate. The crude product obtained by filtration and concentration under reduced pressure was purified by flash chromatography using 0.1% formic acid and acetonitrile as eluent to obtain tert-butyl (3R,4S)-4-((R)-1,1-dimethylethylsulfinamido)-3-methyl-2-oxa-8-azaspiro[4.5]decane-8-carboxylate and tert-butyl (3R,4R)-4-((R)-1,1-dimethylethylsulfinamido)-3-methyl-2-oxa-8-azaspiro[4.5]decane-8-carboxylate (0.5 g, yield: 36%).

Step 3: (R)-2-methyl-N-((3R,4S)-3-methyl-2-oxa-8-azaspiro[4.5]decan-4-yl)propane-2-sulfinamide and (R)-2-methyl-N-((3R,4R)-3-methyl-2-oxa-8-azaspiro[4.5]decan-4-yl)propane-2-sulfinamide (C-1K-2)

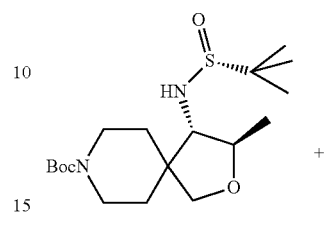

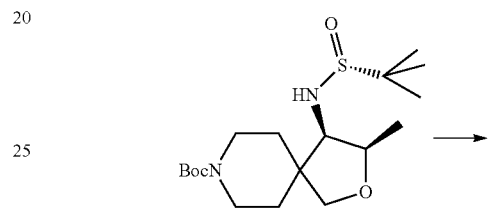

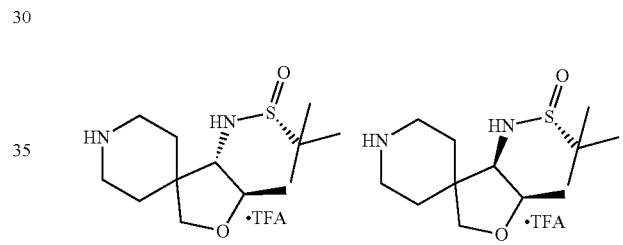

According to the method of step 9 of Example 4-2, a mixture of (R)-2-methyl-N-((3R,4S)-3-methyl-2-oxa-8-azaspiro[4.5]decan-4-yl)propane-2-sulfinamide and (R)-2-methyl-N-((3R,4R)-3-methyl-2-oxa-8-azaspiro[4.5]decan-4-yl)propane-2-sulfinamide was obtained. The crude product was then purified by flash chromatography using 0.1% formic acid and acetonitrile as eluent to obtain (R)-2-methyl-N-((3R,4S)-3-methyl-2-oxa-8-azaspiro[4.5]decan-4-yl)propane-2-sulfinamide (119 g, yield: 24%) and (R)-2-methyl-N-((3R,4R)-3-methyl-2-oxa-8-azaspiro[4.5]decan-4-yl)propane-2-sulfin amide (154 mg, yield: 31%).

(R)-2-methyl-N-((3R,4S)-3-Methyl-2-oxa-8-azaspiro[4.5]decan-4-yl)propane-2-sulfinamide: $^1$H-NMR (400 MHz, DMSO-d$_6$): δ 5.45 (d, D$_2$O Exchangeable, J=11.0 Hz, 1H), 3.78 (d, J=9.0 Hz, 1H), 3.64-3.59 (m, 2H), 3.27-3.25 (m, 1H), 3.17-3.14 (m, 1H), 2.88-2.76 (m, 3H), 1.90-1.85 (m, 1H), 1.82-1.76 (m, 1H), 1.59-1.51 (m, 2H), 1.18-1.17 (m, 12H) ppm; LC-MS: m/z 275.2 [M+H]⁺.

(R)-2-methyl-N-((3R,4R)-3-methyl-2-oxa-8-azaspiro[4.5]decan-4-yl)propane-2-sulfinamide:

$^1$H-NMR (400 MHz, DMSO-d$_6$): δ 5.04 (d, D$_2$O Exchangeable, J=10.5 Hz, 1H), 4.45-4.11 (m, 1H), 3.48 (d, J=8.5 Hz, 1H), 3.50-3.46 (m, 1H), 3.43 (d, J=9.0 Hz, 1H), 3.14-3.12 (m, 1H), 3.04-3.02 (m, 1H), 3.91-3.87 (m, 2H), 1.73-1.68 (m, 2H), 1.62-1.56 (m, 2H), 1.17 (s, 9H), 1.14 (d, J=6.5 Hz, 3H) ppm; LC-MS: m/z 275.2 [M+H]⁺.

Example 6-2: Synthesis of (R)-2-methyl-N-(4-methyl-2-oxa-8-azaspiro[4.5]decan-4-yl)propane-2-sulfinamide (C-1L-2)

Step 1: (R,Z)—N-(8-benzoyl-2-oxa-8-azaspiro[4.5]decan-4-ylidene)-2-methylpropane-2-sulfinamide

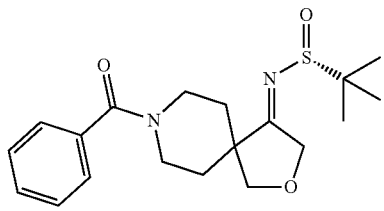 [SMILES: CC(C)(C)[S@@](=O)/N=C1\COCC12CCN(C(=O)c1ccccc1)CC2]

According to the method of Example 3-2, (R,Z)—N-(8-benzoyl-2-oxa-8-azaspiro[4.5]decan-4-ylidene)-2-methylpropane-2-sulfinamide was obtained.

LC-MS: m/z 363.2 [M+H]⁺.

Step 2: (R)—N-(8-benzoyl-4-methyl-2-oxa-8-azaspiro[4.5]decan-4-yl)-2-methylpropane-2-sulfinamide

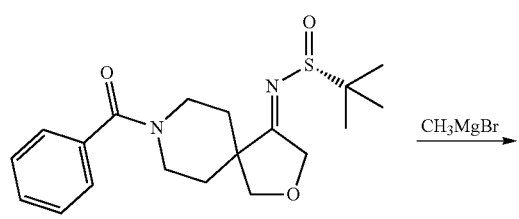

(R,Z)—N-(8-Benzoyl-2-oxa-8-azaspiro[4.5]decan-4-ylidene)-2-methylpropane-2-sulfinamide (200 mg, 0.552 mmol) was dissolved in toluene (5 mL). The solution was cooled to 0° C., and a solution of methylmagnesium bromide (1.1 mL, 3.32 mmol) was then slowly added dropwise thereto. The reaction mixture was then stirred at room temperature for 2.5 hours. The reaction was quenched with saturated ammonium chloride, extracted with ethyl acetate, dried over anhydrous sodium sulfate, and rotary-evaporated under reduced pressure. The crude product was separated with a preparative plate (20% ethyl acetate in petroleum ether) to obtain (R)—N-(8-benzoyl-4-methyl-2-oxa-8-azaspiro[4.5]decan-4-yl)-2-methylpropane-2-sulfinamide (20 mg, yield: 10%).

LC-MS: m/z 379.2 [M+H]⁺.

Step 3: 2-methyl-N—((S)-4-methyl-2-oxa-8-azaspiro[4.5]decan-4-yl)propane-2-sulfinamide (C-1L-2)

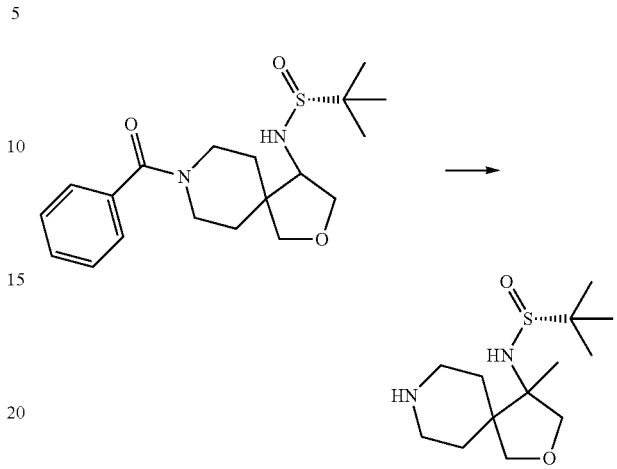

(R)—N-(8-Benzoyl-4-methyl-2-oxa-8-azaspiro[4.5]decan-4-yl)-2-methylpropa ne-2-sulfinamide (100 mg, 0.26 mmol) was dissolved in tetrahydrofuran (5 mL), and cooled to 0° C., followed by slow addition of 4 N NaOH (0.65 mL, 2.6 mmol). The reaction solution was then stirred at room temperature for 2.5 hours. The reaction solution was extracted with ethyl acetate (5×10 mL). The organic phases were combined, dried over MgSO₄, filtered, and the filtrate was concentrated under reduced pressure to obtain 2-methyl-N—((S)-4-methyl-2-oxa-8-azaspiro[4.5]decan-4-yl)propane-2-sulfinamide (50 mg, yield: 70%), which was directly used in the next reaction.

LC-MS: m/z 275.2 [M+H]⁺.

Example 7-2: (R)—N,2-dimethyl-N—((R)-8-azaspiro[4.5]decan-1-yl)propane-2-sulfinamide (C-1M-2)

Step 1: Tert-Butyl (R)-1-((R)—N,2-dimethylpropane-2-ylsulfinamido)-8-azaspiro[4.5]decane-8-carboxylate

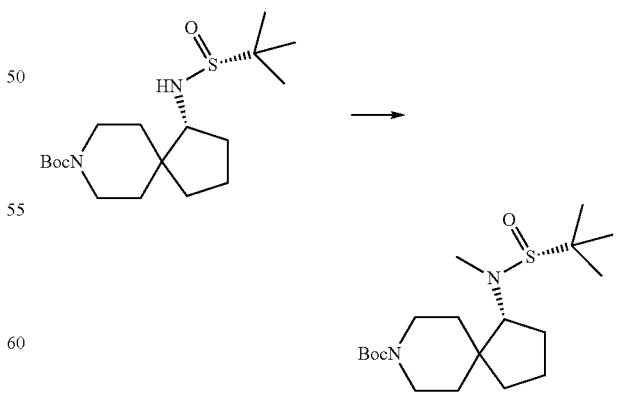

Tert-butyl (R)-1-((R)-1,1-dimethylethylsulfinamido)-8-azaspiro[4.5]decane-8-carboxylate (500 mg, 1.39 mmol) was dissolved in tetrahydrofuran (10 mL) and cooled to 0° C., followed by slow addition of NaH (54 mg, 2.23 mmol).

Iodomethane (396 mg, 2.79 mmol) was then added and the reaction solution was stirred at room temperature overnight. The reaction solution was quenched with water, and then extracted with ethyl acetate (3×10 mL). The organic phases were combined, dried over MgSO₄, filtered, and the filtrate was concentrated under reduced pressure to obtain a crude product. The crude product was separated by a silica gel column (50% ethyl acetate in petroleum ether) to obtain tert-butyl (R)-1-((R)—N,2-dimethylpropane-2-ylsulfinamido)-8-azaspiro[4.5]decane-8-carboxylat e (400 mg, yield: 80%).

LC-MS: m/z 373.2 [M+H]⁺.

Step 2: (R)—N,2-dimethyl-N—((R)-8-azaspiro[4.5]decan-1-yl)propane-2-sulfinamide (C-1M-2)

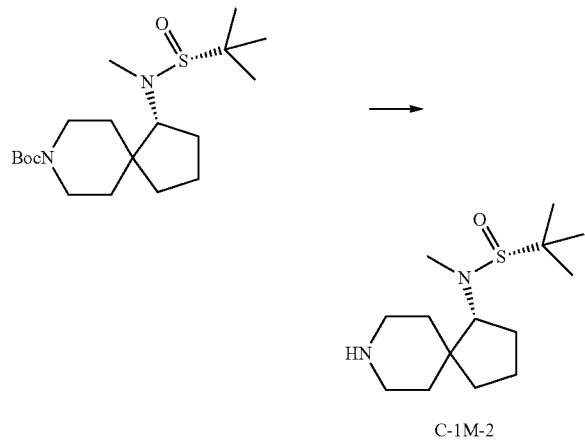

C-1M-2

According to the method of step 9 in Example 4-2, (R)—N,2-dimethyl-N—((R)-8-azaspiro[4.5]decan-1-yl)propane-2-sulfinamide was obtained.

LC-MS: m/z 273.2 [M+H]⁺.

Example 8-2: Preparation of Intermediate: (R)-2-methyl-N-((1R)-3-methyl-8-azaspiro[4.5]decan-1-yl)propane-2-sulfinamide (C-1N-2)

Step 1: Tert-Butyl 4-allyl-4-formylpiperidine-1-carboxylate

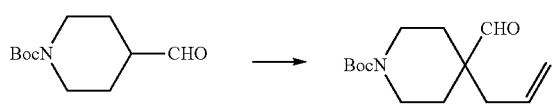

To a dry 1 L flask were sequentially added tert-butyl 4-formylpiperidine-1-carboxylate (35.0 g, 164 mmol), lithium tert-butoxide (15.77 g, 197 mmol) and allyl bromide (11.54 mL, 189 mmol) and DMF (328 mL), and the mixture was stirred at 0° C. for 1 hour. After the reaction was completed, the mixture was poured into a separating funnel charged with saturated aqueous NH₄Cl solution (50%, 500 mL), and extracted with Et₂O (5×50 mL). The organic phases were combined, dried over MgSO₄, filtered, and the filtrate was concentrated under reduced pressure. The resulting residue was purified by silica gel chromatography (ethyl acetate/petroleum ether with a gradient of 0 to 25%) to obtain tert-butyl 4-allyl-4-formylpiperidine-1-carboxylate as a colorless oil (24 g, yield: 48%).

¹H NMR (400 MHz, CDCl₃) δ 9.52 (s, 1H), 5.53-5.76 (m, 1H), 4.96-5.19 (m, 2H), 3.80 (br.s., 2H), 2.97 (t, J=11.49 Hz, 2H), 2.26 (d, J=7.33 Hz, 2H), 1.95 (dt, J=13.71, 3.13 Hz, 2H), 1.38-1.58 (m, 11H) ppm.

Step 2: tert-butyl 4-allyl-4-(1-hydroxyallyl)piperidine-1-carboxylate (C-1N-c-2)

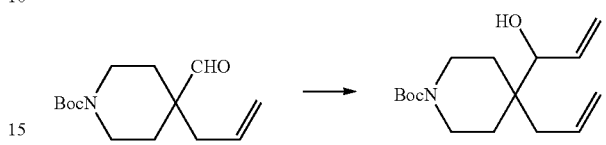

To a 1 L dry three-necked flask were sequentially added tert-butyl 4-allyl-4-formylpiperidine-1-carboxylate (24 g, 95 mmol) and THF (300 mL). The solution was cooled to −78° C., and vinyl magnesium bromide (1 M in THF, 118 mL, 118 mmol) was slowly added dropwise under nitrogen atmosphere. The resulting solution was slowly warmed to room temperature within 1 hour. After the reaction was completed, the mixture was poured into a separating funnel charged with saturated aqueous NH₄Cl solution (250 mL), and extracted with EtOAc (4×50 mL). The organic phases were combined, dried over MgSO₄, filtered, and the filtrate was concentrated under reduced pressure to obtain tert-butyl 4-allyl-4-(1-hydroxyallyl)piperidine-1-carboxylate, which was used in the next step without further purification.

¹H NMR (400 MHz, CDCl₃) δ 6.05-5.83 (m, 2H), 5.32-5.21 (m, 2H), 5.12 (s, 1H), 5.08 (d, J=3.5 Hz, 1H), 4.05-3.97 (m, 1H), 3.71 (s, 2H), 3.12 (ddd, J=13.8, 10.4, 3.6 Hz, 2H), 2.33 (dd, J=14.3, 7.8 Hz, 1H), 2.20 (dd, J=14.3, 7.2 Hz, 1H), 1.60 (q, J=4.3 Hz, 2H), 1.57-1.50 (m, 2H), 1.45 (s, 9H) ppm.

Step 3: Tert-Butyl 4-acryloyl-4-allylpiperidine-1-carboxylate

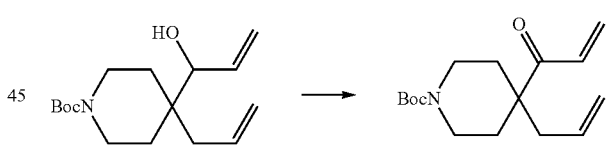

To a dry three-necked flask were sequentially added 4-allyl-4-(1-hydroxyallyl)piperidine-1-carboxylate (26.7 g, 95 mmol), Dess-Martin oxidant (44.3 g, 105 mmol) and anhydrous dichloromethane (380 mL), and the mixture was stirred at room temperature for 1 hour. After the reaction was completed, the mixture was poured into a separating funnel charged with a saturated aqueous solution of NaHCO₃: Na₂SO₃ (1:1, 300 mL), and then extracted with DCM (4×50 mL). The organic phases were combined, dried over MgSO₄, filtered, and the filtrate was concentrated under reduced pressure to obtain a white solid. The white solid was suspended in petroleum ether (250 mL) and sonicated for 20 minutes. The white suspension was filtered through a pad of diatomite and removed under reduced pressure, and the filtrate was concentrated under reduced pressure to obtain tert-butyl 4-acryloyl-4-allylpiperidine-1-carboxylate (25 g, two-step yield: 94%).

¹H NMR (400 MHz, CDCl₃) δ 6.80 (dd, J=16.8, 10.3 Hz, 1H), 6.39 (dd, J=16.8, 1.9 Hz, 1H), 5.70 (dd, J=10.3, 1.9 Hz,

1H), 5.55 (ddt, J=17.5, 10.2, 7.4 Hz, 1H), 5.09-4.98 (m, 2H), 3.77 (s, 2H), 2.94 (s, 2H), 2.31 (d, J=7.4 Hz, 2H), 2.08 (d, J=13.8 Hz, 2H), 1.47-1.41 (m, 11H) ppm.

Step 4: Tert-Butyl 1-oxo-8-azaspiro[4.5]dec-2-ene-8-carboxylate

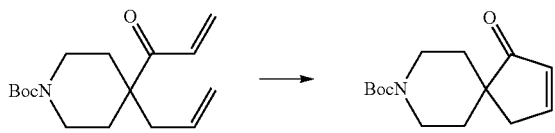 [SMILES: C=CCC1(C(=O)C=C)CCN(C(=O)OC(C)(C)C)CC1 ; CC(C)(C)OC(=O)N1CCC2(CC=CC2=O)CC1]

To a 1 L dry three-necked flask were sequentially added tert-butyl 4-acryloyl-4-allylpiperidine-1-carboxylate (25 g, 89.6 mmol), toluene (degassed, 850 mL) and a solution of Grubbs II Catalyst (2.02 g, 2.38 mmol) in toluene (degassed, 100 mL). The resulting mixture was stirred at 85° C. for 45 minutes under nitrogen atmosphere. After the reaction was completed, the solvent was removed under reduced pressure, and the resulting residue was purified by silica gel chromatography (ethyl acetate/petroleum ether with a gradient of 0-40%) to obtain tert-butyl 1-oxo-8-azaspiro[4.5]dec-2-ene-8-carboxylate (19 g, 83 mmol) as a brown solid. A solution of the compound and DDQ (565 mg, 2.49 mmol) in toluene (540 mL) was stirred at room temperature for 15 minutes. The resulting bright red solution was filtered through a pad of diatomite, followed by addition of activated carbon (100 g), and the resulting suspension was stirred at room temperature for 2 hours. The mixture was filtered through a pad of diatomite and the filtrate was concentrated under reduced pressure. The residue obtained was purified by silica gel chromatography (ethyl acetate/petroleum ether with a gradient of 0-40%) to obtain tert-butyl 1-oxo-8-azaspiro[4.5]dec-2-ene-8-carboxylate (12 g, yield: 53.3%) as a white solid.

Step 5: Tert-Butyl 3-methyl-1-oxo-8-azaspiro[4.5]decane-8-carboxylate

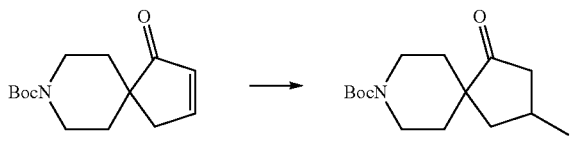 [SMILES: CC(C)(C)OC(=O)N1CCC2(CC=CC2=O)CC1 ; CC1CC(=O)C2(CCN(C(=O)OC(C)(C)C)CC2)C1]

Under nitrogen atmosphere, to a 250 mL dry three-necked flask were sequentially added CuI (3.8 g, 20 mmol) and anhydrous tetrahydrofuran (100 mL). The solution was cooled to −20° C., and MeLi (1.6 M in THF, 25 mL, 40 mmol) was slowly added dropwise to the solution. After the dropwise addition, the reaction solution was allowed to react at −20° C. until the solution was clear. At −20° C., a solution of tert-butyl 1-oxo-8-azaspiro[4.5]dec-2-ene-8-carboxylate (2.51 g, 10 mmol) in tetrahydrofuran (20 mL) was then slowly added dropwise. After the reaction was completed, the mixture was poured into a separating funnel charged with saturated aqueous NH$_4$Cl solution, and extracted with ethyl acetate (3×15 mL). The organic phases were combined, dried over MgSO$_4$, filtered and the filtrate was concentrated under reduced pressure and purified by silica gel chromatography (ethyl acetate/petroleum ether with a gradient of 0 to 50%) to obtain tert-butyl 3-methyl-1-oxo-8-azaspiro[4.5]decane-8-carboxylate (1.6 g, yield: 60%).

$^1$H NMR (400 MHz, CDCl$_3$) δ 3.92 (s, 1H), 3.81 (s, 1H), 3.55 (d, J=5.0 Hz, 1H), 3.13-3.04 (m, 1H), 2.96 (t, J=10.9 Hz, 1H), 2.56-2.46 (m, 1H), 2.31-2.21 (m, 2H), 1.94-1.75 (m, 2H), 1.62-1.49 (m, 1H), 1.45 (s, 9H), 1.41-1.35 (m, 2H), 1.15 (d, J=6.0 Hz, 3H), 0.90 (t, J=6.9 Hz, 3H) ppm.

Step 6 and Step 7: (R)-2-methyl-N-((1R)-3-methyl-8-azaspiro[4.5]decan-1-yl)propane-2-sulfinamide (C-1N-2)

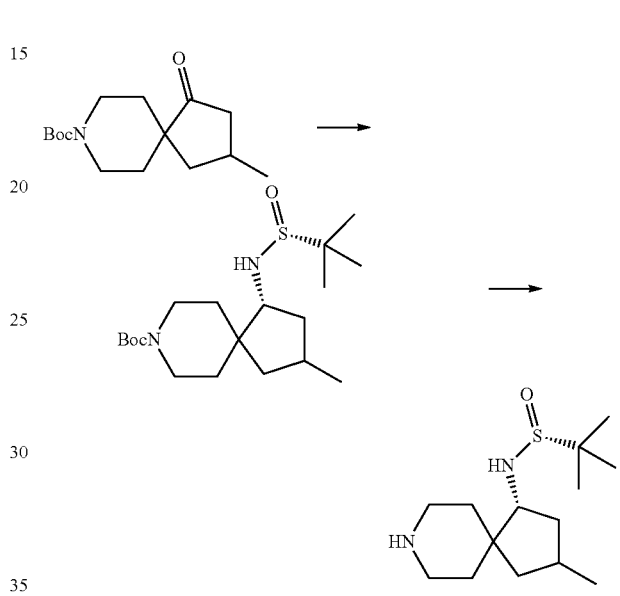

According to the synthesis method of step 8 and step 9 of the intermediate C-1J-2, the ketone intermediate tert-butyl 3-methyl-1-oxo-8-azaspiro[4.5]decane-8-carboxylate was subjected to reductive amination and removal of the Boc protecting group to obtain (R)-2-methyl-N-((1R)-3-methyl-8-azaspiro[4.5]decan-1-yl)propane-2-sulfinamide (C-1N-2).

$^1$H NMR (400 MHz, CDCl$_3$) δ $^1$H NMR (400 MHz, DMSO-d$_6$) δ 3.04-2.95 (m, 1H), 2.75 (s, 2H), 2.62-2.53 (m, 2H), 1.93-1.57 (m, 5H), 1.52-1.27 (m, 13H), 0.96 (d, J=6.5 Hz, 3H) ppm; LCMS: m/z 273 [M+H]$^+$.

Example 9-2: Preparation of Intermediate: Tert-Butyl ((4-methylpiperidin-4-yl)methyl)carbamate (C-4A-2)

Step 1: 1-benzoyl-4-methylpiperidine-4-carbonitrile

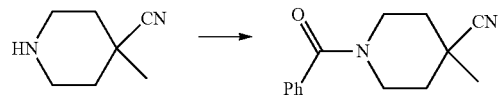

Under nitrogen atmosphere, to a 100 mL dry single-necked flask were sequentially added 4-methylpiperidine-4-carbonitrile (496 mg, 4 mmol), DCM (10 mL) and triethylamine (611 mg, 6 mmol), and benzoyl chloride (670 mg, 4.8 mmol) was then slowly added dropwise at room temperature. The mixture was stirred at room temperature for 1 hour, and the reaction was monitored by TLC until the raw materials were consumed. The reaction solution was quenched with 1N HCl solution, and extracted with dichloromethane (3×20 mL). The organic phases were combined, and dried over Na$_2$SO$_4$. The filtrate was concentrated under reduced pressure and purified by silica gel column chromatography (ethyl acetate/petroleum ether with a gradient of 0 to 40%) to obtain 1-benzoyl-4-methylpiperidine-4-carbonitrile (650 mg, yield: 70.72%).

LC-MS: m/z 229 [M+H]$^+$.

Step 2: Tert-Butyl 1-benzoyl-((4-methylpiperidin-4-yl)methyl)carbamate

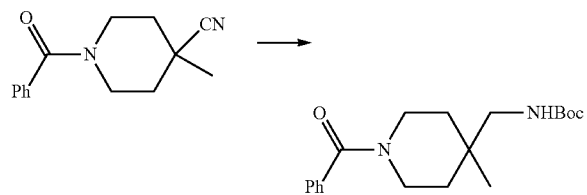

At 0° C. and under nitrogen atmosphere, to a 100 mL dry flask were sequentially added 1-benzoyl-4-methylpiperidine-4-carbonitrile (650 mg, 2.85 mmol), nickel chloride hexahydrate (135 mg, 0.67 mmol), di-tert-butyl dicarbonate (1.86 g, 8.54 mmol) and methanol (12 mL), followed by sodium borohydride (754 mg, 20 mmol). The reaction solution was then stirred at room temperature for 12 hours, and the reaction was monitored by TLC until the raw materials were consumed. After the reaction was completed, the reaction solution was concentrated and extracted with dichloromethane (3×20 mL). The organic phases were combined, and dried over Na$_2$SO$_4$. The filtrate was concentrated under reduced pressure and purified by silica gel column chromatography (ethyl acetate/petroleum ether with a gradient of 0 to 40%) to obtain tert-butyl 1-benzoyl-((4-methylpiperidin-4-yl)methyl)carbamate (620 mg, yield: 65.50%).

LC-MS: m/z 333 [M+H]$^+$.

Step 3: Tert-Butyl ((4-methylpiperidin-4-yl)methyl)carbamate (C-4A-2)

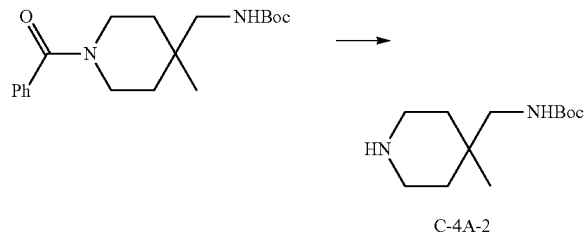

To a 100 mL single-necked flask were sequentially added tert-butyl 1-benzoyl-((4-methylpiperidin-4-yl)methyl)carbamate (620 mg, 1.87 mmol), ethanol (8 mL) and 7N NaOH (2 mL), then the mixture was heated to 90° C. under nitrogen atmosphere and stirred for 8 hours. After the mixture was cooled to room temperature, the mixture was filtered, diluted with water and extracted with ethyl acetate (3×20 mL). The organic phases were combined, and dried over Na$_2$SO$_4$. The filtrate was concentrated under reduced pressure and purified by silica gel column chromatography (ethyl acetate/petroleum ether with a gradient of 0 to 80%) to obtain tert-butyl ((4-methylpiperidin-4-yl)methyl)carbamate (C-4A-2) (300 mg, yield: 70.5%).

$^1$H NMR (400 MHz, DMSO-d$_6$) δ 3.97 (q, J=7.0 Hz, 2H), 2.80 (d, J=6.4 Hz, 2H), 2.65 (d, J=30.3 Hz, 2H), 1.38 (s, 9H), 1.27 (dd, J=16.2, 7.0 Hz, 2H), 1.10 (d, J=12.8 Hz, 2H), 0.81 (s, 3H) ppm; LC-MS: m/z 229 [M+H]$^+$.

Example 10-2: Preparation of Intermediate: Tert-Butyl ((4-phenylpiperidin-4-yl)methyl)carbamate (C-4B-2)

Step 1: Tert-Butyl 4-cyano-4-phenylpiperidine-1-carboxylate

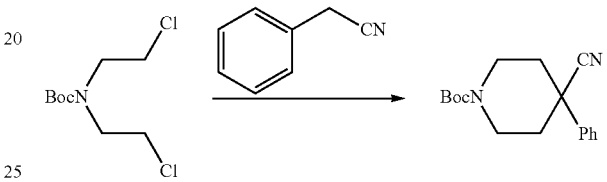

At 0° C., to a solution of tert-butyl (2-chloroethyl)carbamate (2 g, 8.26 mmol) and 2-phenylacetonitrile (968 mg, 8.26 mmol) in anhydrous DMF (20 mL) was added NaH (60% dispersed in mineral oil, 1.6 g, 41.3 mmol) in portions. The reaction mixture was heated at 60° C. for 16 hours. After the reaction was completed, the mixture was quenched with ice water (30 mL), and then extracted (3×50 mL). The organic phases were combined, washed with saturated brine (2×50 mL), then dried over sodium sulfate, filtered and concentrated under reduced pressure. The crude product was purified by silica gel column chromatography (ethyl acetate/petroleum ether with a gradient of 0 to 40%) to obtain tert-butyl 4-cyano-4-phenylpiperidine-1-carboxylate (500 mg, yield: 21%).

LCMS: m/z 187.2 [M-100]$^+$.

Step 2: Tert-Butyl 4-(aminomethyl)-4-phenylpiperidine-1-carboxylate

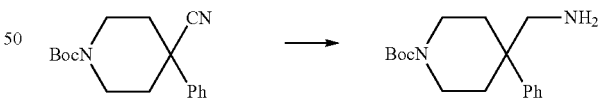

Tert-butyl 4-cyano-4-phenylpiperidine-1-carboxylate (0.5 g, 1.75 mmol) was dissolved in 20 mL of methanol, followed by addition of palladium on carbon (50 mg), and the reaction solution was allowed to react under hydrogen atmosphere for 16 hours. After the reaction was completed, the mixture was filtered and concentrated under reduced pressure to obtain tert-butyl 4-(aminomethyl)-4-phenylpiperidine-1-carboxylate (0.4 g, yield: 80%).

$^1$H NMR (400 MHz, CDCl$_3$) δ 7.38 (t, J=7.6 Hz, 2H), 7.30 (d, J=7.5 Hz, 2H), 7.24 (d, J=7.2 Hz, 1H), 3.75 (d, J=7.8 Hz, 2H), 3.04 (t, J=11.2 Hz, 2H), 2.58 (brs, 2H), 2.21 (d, J=13.9 Hz, 2H), 1.76-1.61 (m, 2H), 1.44 (s, 9H) ppm; LC-MS: m/z 191.0 [M-100]$^+$.

Step 2: (4-phenylpiperidin-4-yl)methanamine (C-4B-2)

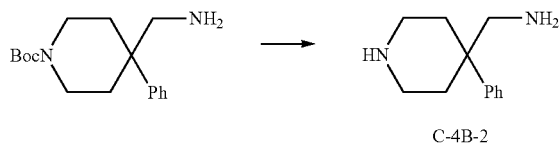 [SMILES: CC(C)(C)OC(=O)N1CCC(CN)(c2ccccc2)CC1 ; NCC1(c2ccccc2)CCNCC1]

C-4B-2

Tert-butyl 4-(aminomethyl)-4-phenylpiperidine-1-carboxylate (0.4 g, 1.37 mmol) was dissolved in 10 mL of methanol, followed by addition of a solution of hydrogen chloride in 1,4-dioxane (4 M, 13.7 mmol) at room temperature. The reaction solution was allowed to react at room temperature for 2 hours. After the reaction was completed, the reaction solution was concentrated under reduced pressure to obtain a crude product of (4-phenylpiperidin-4-yl)methanamine (C-4B-2) (0.25 g, yield: 95%), which was directly used in the next reaction.

LC-MS: m/z 191.2 [M+H]$^+$.

Example 11-2: Preparation of Intermediate: 6-((tert-butoxycarbonyl)amino)-2,3-dichloropyridine-4-thiol (F-1A-2)

Step 1: Tert-Butyl (6-chloropyridin-2-yl)carbamate

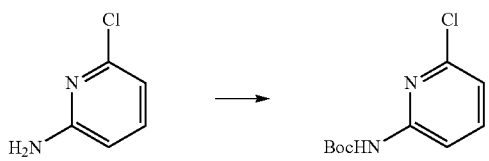 [SMILES: Nc1cccc(Cl)n1 ; CC(C)(C)OC(=O)Nc1cccc(Cl)n1]

Under nitrogen atmosphere, to a dry 250 mL three-necked flask were added 6-chloropyridin-2-amine (8 g, 62.2 mmol) and THF (80 mL), and the mixture was stirred at 0° C. for 10 minutes, followed by addition of NaHDMS (124.4 mL, 1.0 M in THF). The mixture was kept at 0° C., a solution of di-tert-butyl dicarbonate (16.3 g, 74.7 mmol) in tetrahydrofuran (50 mL) was slowly added, and the reaction was continued at 0° C. for 4 hours. After the reaction was completed, H$_2$O (40 mL) was added, followed by extraction with EtOAc (3×100 mL). The organic phases were combined, dried over MgSO$_4$, filtered and concentrated under reduced pressure. The resulting residue was purified by silica gel chromatography (ethyl acetate/petroleum ether with a gradient of 0 to 10%) to obtain tert-butyl (6-chloropyridin-2-yl)carbamate (7 g, yield: 49%).

$^1$H NMR (400 MHz, DMSO-d$_6$) δ 10.04 (s, 1H), 7.79-7.58 (m, 2H), 7.02 (dd, J=5.5, 2.9 Hz, 1H), 1.38 (s, 9H) ppm; LCMS: m/z 288.1 [M+H]$^+$.

Step 2: Tert-Butyl (5,6-dichloropyridin-2-yl)carbamate

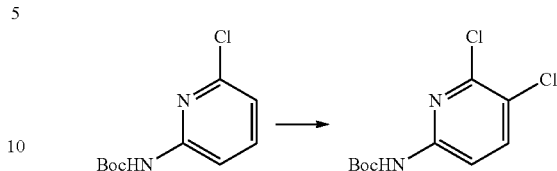

To a dry 100 mL round bottom flask were added tert-butyl (6-chloropyridin-2-yl)carbamate (7 g, 30.6 mmol) and N,N-dimethylformamide (50 mL), and the mixture was stirred at room temperature for 10 minutes, followed by addition of N-chlorosuccinimide (4.50 g, 33.67 mmol). The mixture was allowed to react at 100° C. for 4 hours. After the reaction was completed, the mixture was cooled to room temperature, followed by addition of H$_2$O (50 mL) and extraction with ethyl acetate (3×80 mL), and then washed with saturated aqueous lithium chloride solution (2×40 mL). The organic phase was dried over MgSO$_4$, filtered and concentrated under reduced pressure, and the resulting residue was purified by silica gel chromatography (ethyl acetate/petroleum ether with a gradient of 0 to 5%) to obtain tert-butyl (5,6-dichloropyridin-2-yl)carbamate (5.3 g, yield: 65.8%).

$^1$H NMR (400 MHz, CDCl$_3$) δ 7.86 (d, J=8.7 Hz, 1H), 7.69 (d, J=8.7 Hz, 1H), 7.24 (s, 1H), 1.51 (s, 9H); LCMS: m/z 207.1 [M-55]$^+$.

Step 3: Tert-Butyl (5,6-dichloro-4-iodopyridin-2-yl)carbamate

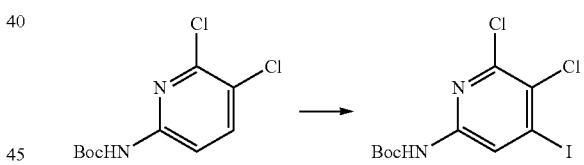

Under nitrogen atmosphere, to a dry 100 mL round bottom flask were added tert-butyl (5,6-dichloropyridin-2-yl)carbamate (5.3 g, 20.14 mmol) and tetrahydrofuran (50 mL). n-Butyllithium (44.3 mmol, 2.5M in THF) was slowly added dropwise at −78° C., and the reaction solution was further stirred at −78° C. for 1 hour. A solution of iodine (3.07 g, 24.17 mmol) in tetrahydrofuran (20 mL) was then slowly added dropwise, and the reaction was continued at −78° C. for 3 hours. After the reaction was completed, H$_2$O (50 mL) was added, followed by extraction with EtOAc (3×80 mL). The organic phases were combined, dried over MgSO$_4$, filtered and concentrated under reduced pressure, and the resulting residue was purified by silica gel chromatography (ethyl acetate/petroleum ether with a gradient of 0 to 5%) to obtain tert-butyl (5,6-dichloro-4-iodopyridin-2-yl)carbamate (4.3 g, yield: 55%).

$^1$H NMR (400 MHz, DMSO-d$_6$) δ 10.44 (s, 1H), 8.36 (s, 1H), 1.46 (s, 9H) ppm; LCMS: m/z 334.1 [M-55]$^+$.

Step 4: methyl 3-((6-((tert-butoxycarbonyl)amino)-2,3-dichloropyridin-4-yl)thio)propionate

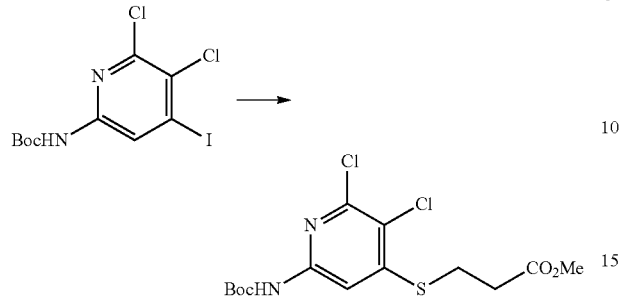

To a dry 100 mL round bottom flask were sequentially added tert-butyl (5,6-dichloro-4-iodopyridin-2-yl)carbamate (3.2 g, 8.22 mmol), palladium acetate (92 mg, 0.41 mmol), Xantphos (285 mg, 0.49 mmol), DIPEA (2.12 g, 16.46 mmol) and 1,4-dioxane (30 mL). The reaction mixture was heated and stirred at 100° C. for 2 hours, then filtered and concentrated under reduced pressure. The resulting residue was purified by silica gel chromatography (ethyl acetate/petroleum ether with a gradient of 0-30%) to obtain methyl 3-((6-((tert-butoxycarbonyl)amino)-2,3-dichloropyridin-4-yl)thio)propionate (3 g, yield: 96%).

$^1$H NMR (400 MHz, DMSO-$d_6$) δ 10.25 (s, 1H), 7.73 (s, 1H), 3.64 (s, 3H), 3.26 (t, J=6.9 Hz, 2H), 2.82 (t, J=6.9 Hz, 2H), 1.46 (s, 9H) ppm; LCMS: m/z 326.3[M-55]$^+$.

Step 5: 6-((tert-butoxycarbonyl)amino)-2,3-dichloropyridine-4-thiol (F-1A-2)

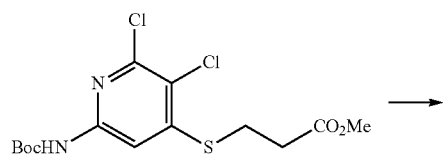

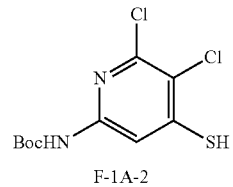
F-1A-2

To a dry 100 mL round bottom flask were sequentially added methyl 3-((6-((tert-butoxycarbonyl)amino)-2,3-dichloropyridin-4-yl)thio)propionate and tetrahydrofuran (30 mL), and a solution of sodium ethoxide in ethanol (21%, 6 mL) was then slowly added dropwise at room temperature. The reaction solution was stirred at room temperature for 1 hour and then concentrated under reduced pressure, followed by addition of dichloromethane (10 mL), and a large amount of brown solid was precipitated. The mixture was filtered, and the filter cake was washed with dichloromethane, and dried to obtain sodium 6-((tert-butoxycarbonyl)amino)-2,3-dichloropyridine-4-thiolate, which was acidified with 1N HCl to pH of 3. The mixture was directly concentrated under reduced pressure, and the obtained crude product of F-1A-2 (2.1 g) was directly used in the next reaction.

$^1$H NMR (400 MHz, DMSO-$d_6$) δ 9.05 (s, 1H), 7.61 (s, 1H), 1.41 (s, 9H) ppm; LCMS: m/z 262.2 [M-55]$^+$.

According to the synthesis method of Example 11-2, the following intermediates F-1B-2, F-1C-2, F-1D-2, F-1E-2, F-1F-2, F-1G-2, F-1H-2, F-1I-2, F-1J-2, F-1K-2 were obtained by using similar intermediate raw materials.

| Intermediate | Name | Structure | Analysis data |
|---|---|---|---|
| F-1B-2 | 2-amino-3-chloropyridine-4-thiol | (pyridine with NH$_2$, Cl, SH) | $^1$H NMR (400 MHz, DMSO-$d_6$) δ 7.06 (d, J = 3.1 Hz, 1H), 6.51 (d, J = 5.2 Hz, 1H) ppm; LCMS: m/z 161.0 [M + H]$^+$. |
| F-1C-2 | 2-amino-5-chloropyridin-4-thiol | (pyridine with NH$_2$, Cl, SH) | $^1$H NMR (400 MHz, DMSO-$d_6$) δ 7.88 (s, 1H), 7.49 (d, J = 5.3 Hz, 1H), 7.09 (d, J = 5.3 Hz, 1H) ppm; LCMS: m/z 161.0 [M + H]$^+$. |
| F-1D-2 | 2-chloropyridine-3-thiol | (pyridine with Cl, SH) | $^1$H NMR (400 MHz, DMSO-$d_6$) δ 7.57 (dd, J = 7.7, 1.5 Hz, 1H), 7.45 (d, J = 3.5 Hz, 1H), 6.69 (dd, J = 7.6, 4.4 Hz, 1H) ppm; LCMS: m/z 146.0 [M + H]$^+$. |

-continued

| Intermediate | Name | Structure | Analysis data |
|---|---|---|---|
| F-1E-2 | 2-methylpyridine-3-thiol | 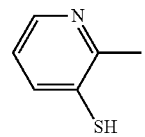 | $^1$H NMR (400 MHz, DMSO-d$_6$) δ 7.59-7.46 (m, 1H), 7.32 (dd, J = 7.7, 1.4 Hz, 1H), 6.53 (dd, J = 7.7, 4.6 Hz, 1H), 2.36 (s, 3H) ppm; LCMS: m/z 126.0 [M + H]$^+$. |
| F-1F-2 | quinoline-4-thiol | 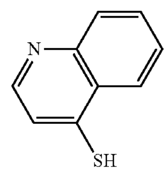 [SMILES: Sc1ccnc2ccccc12] | $^1$H NMR (400 MHz, DMSO-d$_6$) δ 8.79 (d, J = 4.6 Hz, 1H), 8.25 (d, J = 8.0 Hz, 1H), 8.15 (d, J = 8.3 Hz, 1H), 7.74-7.64 (m, 2H), 7.30 (d, J = 4.6 Hz, 1H) ppm; LCMS: m/z 162.0 [M + H]$^+$. |
| F-1G-2 | 2,3-dichloropyridine-4-thiol | 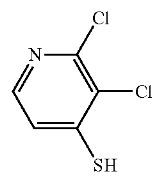 | $^1$H NMR (400 MHz, DMSO-d$_6$) δ 7.31 (d, J = 5.3 Hz, 1H), 7.07 (d, J = 5.3 Hz, 1H) ppm; LCMS: m/z 180.0 [M + H]$^+$. |
| F-1H-2 | 3-chloropyridine-4-thol | 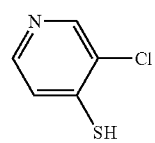 | $^1$H NMR (400 MHz, DMSO-d$_6$) δ 7.88 (s, 1H), 7.49 (d, J = 5.3 Hz, 1H), 7.09 (d, J = 5.3 Hz, 1H) ppm; LCMS: m/z 146.0. |
| F-1I-2 | 2-(trifluoromethyl)pyridin-3-thiol | 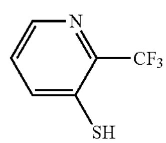 [SMILES: FC(F)(F)c1ncccc1S] | LCMS: m/z 180.0. |
| F-1J-2 | 3-(trifluoromethyl)pyridine-4-thiol | 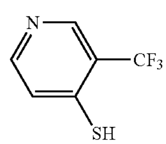 [SMILES: FC(F)(F)c1cnccc1S] | $^1$HNMR (400 MHz, D$_2$O) δ 8.24 (s, 1H), 7.84 (d, J = 5.6 Hz, 1H), 7.31 (d, J = 5.6 Hz, 1H) ppm; LCMS: m/z 146.0. |
| F-1K-2 | 6-amino-2-chloropyridin-3-thiol | 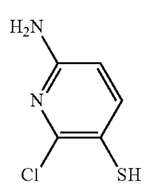 | $^1$H NMR (400 MHz, DMSO-d$_6$) δ 7.29 (d, J = 8.1 Hz, 1H), 6.03 (d, J = 7.8 Hz, 1H), 5.21 (brs, 2H) ppm; LCMS: m/z 160.0. |

Example 12-2: Preparation of Intermediate: 3-chloro-2-methylpyridine-4-thiol (F-1L-2)

Step 1: Methyl 3-((3-chloro-2-methylpyridin-4-yl)thio)propionate

The intermediate methyl 3-((2,3-dichloropyridin-4-yl)thio)propionate obtained from the synthesis of intermediate F-1G-2 was used in the following reaction.

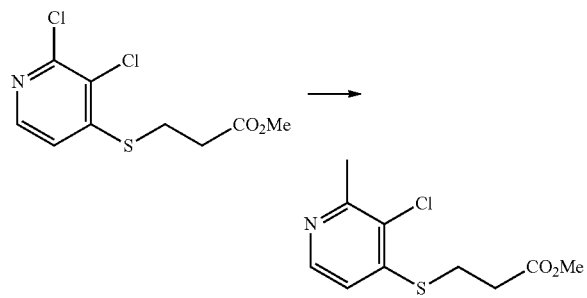

Under nitrogen atmosphere, to a dry 100 mL round bottom flask were successively added methyl 3-((2,3-dichloropyridin-4-yl)thio)propionate (500 mg, 1.88 mmol), Pd(PPh$_3$)$_4$ (217 mg, 0.188 mmol), trimethylcyclotriboroxane (354 mg, 2.82 mmol), potassium carbonate (389 mg, 2.82 mmol) and 1,4-dioxane (10 mL). The reaction mixture was heated and stirred at 100° C. under nitrogen atmosphere for 6 hours. The residue obtained by filtration and concentration under reduced pressure was purified by silica gel chromatography (ethyl acetate/petroleum ether with a gradient of 0 to 40%) to obtain methyl 3-((3-chloro-2-methylpyridin-4-yl)thio)propionate (320 mg, yield: 69%).

Step 2: 3-chloro-2-methylpyridine-4-thiol (F-1L-2)

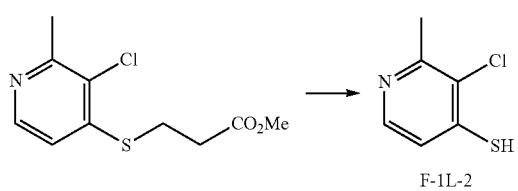

To a dry 100 mL round bottom flask were sequentially added methyl 3-((3-chloro-2-methylpyridin-4-yl)thio)propionate (320 mg, 1.30 mmol) and tetrahydrofuran (10 mL), and a solution of sodium ethoxide in ethanol (21%, 2 mL) was slowly added dropwise at room temperature. The reaction solution was stirred at room temperature for 1 hour, and then concentrated under reduced pressure, followed by addition of dichloromethane (10 mL), and a large amount of brown solid was precipitated. The mixture was filtered, and the filter cake was washed with dichloromethane and dried to obtain sodium 3-chloro-2-methylpyridine-4-thiolate, which was acidified with 1N HCl to pH of 3. The mixture was directly rotary-evaporated to dryness under reduced pressure to obtain a crude product of F-1L-2 (200 mg), which was directly used in the next reaction.

$^1$H NMR (400 MHz, DMSO-d$_6$) δ 7.37 (d, J=4.8 Hz, 1H), 6.97 (d, J=4.8 Hz, 1H), 2.31 (s, 3H) ppm; LCMS: m/z 160.0 [M+H]$^+$.

Example 13-2: Preparation of Intermediate: Sodium 6-((tert-butoxycarbonyl)amino)-3-chloro-2-methylpyridine-4-thiolate (F-1M-2)

Step 1: Methyl 3-((6-((tert-butoxycarbonyl)amino)-3-chloro-2-methylpyridin-4-yl)thio)propionate Methyl 3-((6-((tert-butoxycarbonyl)amino)-2,3-dichloropyridin-4-yl)thio)propionate obtained from the synthesis of intermediate F-1A-2 was used in the following reaction.

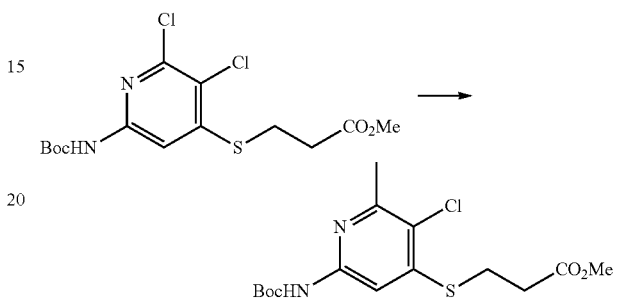

Under nitrogen atmosphere, to a dry 100 mL round bottom flask were added methyl 3-((6-((tert-butoxycarbonyl)amino)-2,3-dichloropyridin-4-yl)thio)propionate (600 mg, 1.57 mmol), [1,1'-bis(tert-butylphosphino)ferrocene] palladium dichloride (103 mg, 0.157 mmol), trimethylcyclotriboroxane (301 mg, 2.4 mmol), potassium carbonate (331 mg, 2.4 mmol), 1,4-dioxane (10 mL) and water (1 mL). The reaction mixture was heated and stirred at 100° C. under nitrogen atmosphere for 6 hours. The residue obtained by filtration and concentration under reduced pressure was purified by silica gel chromatography (ethyl acetate/petroleum ether with a gradient of 0 to 40%) to obtain methyl 3-((6-((tert-butoxycarbonyl)amino)-3-chloro-2-methylpyridin-4-yl)thio)propionate (420 mg, yield: 74%).

$^1$H NMR (400 MHz, DMSO-d$_6$) δ 9.90 (s, 1H), 7.64 (s, 1H), 3.64 (s, 3H), 3.21 (t, J=6.9 Hz, 2H), 2.80 (t, J=6.9 Hz, 2H), 1.46 (s, 9H) ppm; LCMS: m/z 361.1 [M+H]$^+$.

Step 2: sodium 6-((tert-butoxycarbonyl)amino)-3-chloro-2-methylpyridine-4-thiolate (F-1M-2)

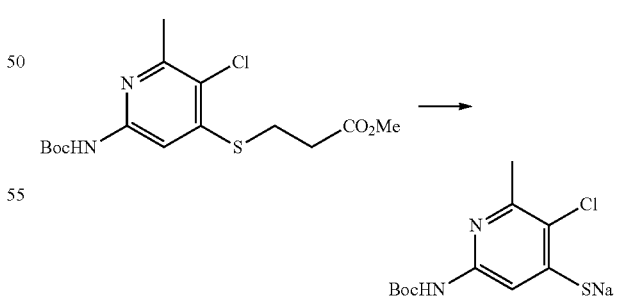

To a dry 100 mL round bottom flask were sequentially added methyl 3-((6-((tert-butoxycarbonyl)amino)-3-chloro-2-methylpyridin-4-yl)thio)propionate (420 mg, 1.17 mmol) and tetrahydrofuran (10 mL), and a solution of sodium ethoxide in ethanol (21%, 2 mL) was then slowly added dropwise at room temperature. The reaction solution was stirred at room temperature for 1 hour, and then concentrated under reduced pressure, followed by addition of dichloromethane (10 mL), and a large amount of brown solid was precipitated. The mixture was filtered, washed with dichloromethane and dried to obtain sodium 6-((tert-butoxycarbonyl)amino)-3-chloro-2-methylpyridine-4-thiolate, which was acidified with 1N HCl to pH of 3. The mixture was directly concentrated under reduced pressure, and the obtained crude product of F-1M-2 (320 mg) was directly used in the next reaction.

$^1$H NMR (400 MHz, DMSO-$d_6$) δ 9.87 (s, 1H), 7.63 (s, 1H), 3.64 (s, 3H), 1.46 (s, 9H) ppm; LCMS: m/z 275.0.

Example 14-2: Preparation of Intermediate: 3-amino-2-chlorobenzenethiol hydrochloride (F-1N-2)

Step 1: 2-chloro-3-aminophenyl Tert-Butyl Sulfide

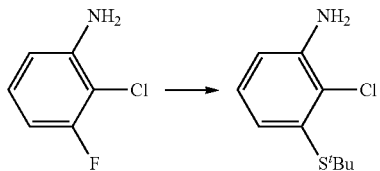

Under nitrogen atmosphere, to a dry 100 mL round bottom flask were sequentially added 2-chloro-3-fluoroaniline (5 g, 34.3 mmol) and N-methylpyrrolidone (50 mL), followed by 2-methylpropane-2-thiol (8.66 g, 96.04 mmol) and cesium carbonate (22.36 g, 68.6 mmol), and the reaction mixture was heated and stirred at 120° C. for 16 hours. After cooling to room temperature, the reaction solution was diluted with 60 mL of ethyl acetate and sequentially washed with saturated lithium chloride aqueous solution (30 mL), water (30 mL) and saturated sodium chloride aqueous solution (30 mL), dried over anhydrous sodium sulfate, filtered, and concentrated under reduced pressure to obtain 2-chloro-3-aminophenyl tert-butyl sulfide (6.04 g, yield: 82%).

LCMS: m/z 216.1 [M+H]$^+$.

Step 2: 3-amino-2-chlorobenzenethiol Hydrochloride (F-1N-2)

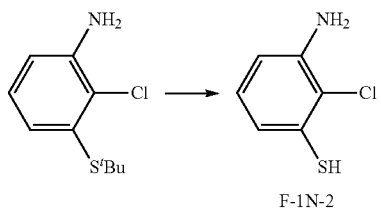

To a dry 100 mL round bottom flask were sequentially added 2-chloro-3-aminophenyl tert-butyl sulfide (6.04 g, 28 mmol) and concentrated hydrochloric acid (50 mL), and the reaction mixture was heated and stirred at 45° C. for 8 hours. After naturally cooling to room temperature, the reaction solution was further cooled to 0° C., during which a large amount of white solid was precipitated. The mixture was filtered, and the filter cake was washed with concentrated hydrochloric acid and petroleum ether to obtain 3-amino-2-chlorobenzenethiol hydrochloride F-1N-2 (4.9 g, yield: 90%).

LCMS: m/z 160.0 [M+H]$^+$.

Example 15-2: Preparation of Compound 1-(8-((2,3-dichlorophenyl)thio)-[1,2,4]triazolo[4,3-c]pyrimidin-5-yl)-4-methylpiperidin-4-amine Step 1: Tert-Butyl (1-(8-iodo-[1,2,4]triazolo[4,3-c]pyrimidin-5-yl)-4-methylpiperidin-4-yl)carbamate

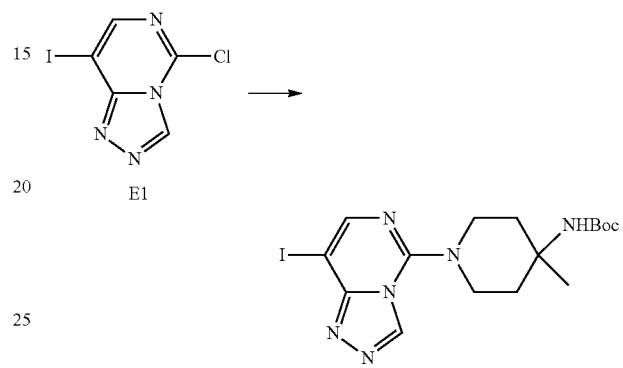

Under nitrogen protection, to a dry 50 mL single-necked flask were added 5-chloro-8-iodo-[1,2,4]triazolo[4,3-c]pyrimidine (E1) (50 mg, 0.18 mmol), tert-butyl (4-methylpiperidin-4-yl)carbamate (77 mg, 0.36 mmol), DIEA (46 mg, 0.36 mmol) and NMP (5 mL), and then the reaction solution was stirred at 90° C. for 2 hours. After the reaction was completed, the obtained residue was poured into water (10 mL), stirred at room temperature for 5 minutes, and then extracted with ethyl acetate (3×50 mL). The organic phases were combined, dried over MgSO$_4$, filtered and concentrated under reduced pressure. The resulting residue was purified by silica gel chromatography (ethyl acetate/petroleum ether with a gradient of 0 to 80%) to obtain tert-butyl (1-(8-iodo-[1,2,4]triazolo[4,3-c]pyrimidin-5-yl)-4-methylpiperidin-4-yl)carbamate as a pale yellow solid (60 mg, yield: 73%).

LCMS: m/z 459.1 [M+H]$^+$.

Step 2: Tert-Butyl (1-(8-((2,3-dichlorophenyl)thio)-[1,2,4]triazolo[4,3-c]pyrimidin-5-yl)-4-methylpiperidin-4-yl)carbamate

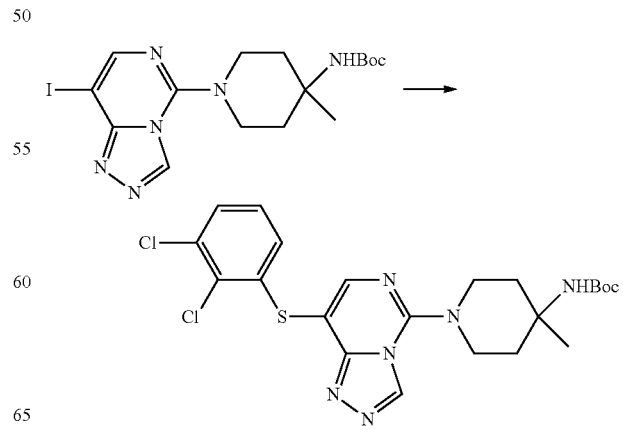

To a dry 50 mL three-necked flask were sequentially added tert-butyl (1-(8-iodo-[1,2,4]triazolo[4,3-c]pyrimidin-5-yl)-4-methylpiperidin-4-yl)carbamate (60 mg, 0.13 mmol), cuprous iodide (3 mg, 0.013 mmol), 1,10-phenanthroline (5 mg, 0.026 mmol), 2,3-dichlorothiophenol (36 mg, 0.2 mmol), potassium phosphate (60 mg, 0.26 mmol) and 5 mL of dioxane. The mixture was heated for 3 hours under nitrogen atmosphere. After the reaction was completed, saturated NH$_4$Cl solution (10 mL) was added, followed by extraction with ethyl acetate (3×50 mL). The organic phases were combined, dried over Na$_2$SO$_4$, filtered, and the filtrate was concentrated under reduced pressure. The resulting residue was purified by silica gel chromatography (ethyl acetate/petroleum ether with a gradient of 0 to 60%) to obtain tert-butyl (1-(8-((2,3-dichlorophenyl)thio)-[1,2,4]triazolo[4,3-c]pyrimidin-5-yl)-4-methylpiperid in-4-yl)carbamate as a pale yellow solid (25 mg, yield: 38%).

LC-MS: m/z 510.1 [M+H]$^+$.

Step 3: 1-(8-((2,3-dichlorophenyl)thio)-[1,2,4]triazolo[4,3-c]pyrimidin-5-yl)-4-methylpiperidin-4-amine

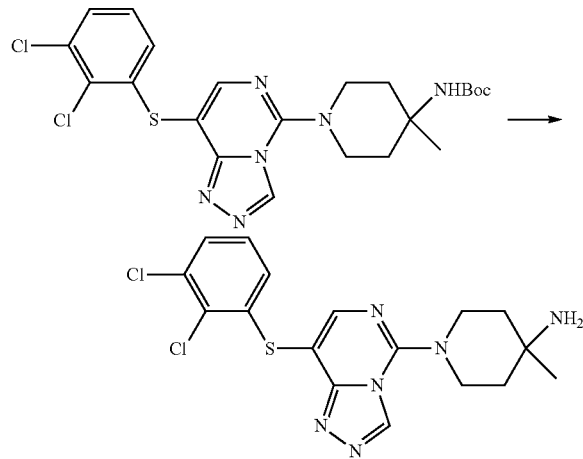

To a dry 50 mL round bottom flask were sequentially added tert-butyl (1-(8-((2,3-dichlorophenyl)thio)-[1,2,4]triazolo[4,3-c]pyrimidin-5-yl)-4-methylpiperid in-4-yl)carbamate (25 mg, 0.049 mmol) and a solution of hydrogen chloride in 1,4-dioxane (7 M, 5 mL), and the mixture was allowed to react at room temperature for 1 hour. After the reaction was completed, saturated NaHCO$_3$ solution (10 mL) was added, followed by extraction with ethyl acetate (3×50 mL). The organic phases were combined, dried over Na$_2$SO$_4$, filtered, and the filtrate was concentrated under reduced pressure. The resulting crude product was purified by high-performance liquid chromatography to obtain the product 1-(8-((2,3-dichlorophenyl)thio)-[1,2,4]triazolo[4,3-c]pyrimidin-5-yl)-4-methylpiperidin-4-amine (10 mg, yield: 49%).

$^1$H NMR (400 MHz, DMSO-d$_6$) δ 9.42 (s, 1H), 8.00 (s, 1H), 7.42 (t, J=8.4 Hz, 1H), 7.14 (t, J=8.0 Hz, 1H), 6.80 (t, J=15.0 Hz, 1H), 3.78 (dd, J=35.6, 5.8 Hz, 4H), 1.75 (s, 4H), 1.26 (s, 3H) ppm; LC-MS: m/z 410.1 [M+H]$^+$.

According to the synthesis method of Example 15-2, the following compounds were synthesized:

Example 16-2: 1-(8-((2,3-dichlorophenyl)thio)-[1,2,4]triazolo[4,3-c]pyrimidin-5-yl)piperidin-4-amine

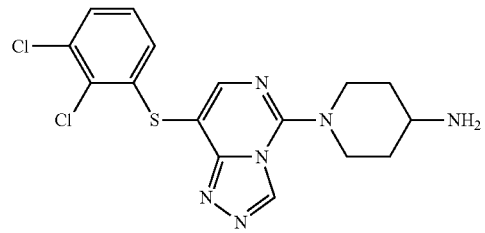 [SMILES: NC1CCN(c2ncc(Sc3cccc(Cl)c3Cl)c3nncn23)CC1]

$^1$H NMR (400 MHz, DMSO-d$_6$) δ 9.45 (s, 1H), 8.31 (s, 1H), 8.02 (s, 1H), 7.44 (d, J=6.9 Hz, 1H), 7.14 (t, J=8.1 Hz, 1H), 6.83 (d, J=8.0 Hz, 1H), 4.18 (d, J=13.5 Hz, 2H), 3.44 (d, J=7.1 Hz, 1H), 3.27 (s, 2H), 1.99 (d, J=10.9 Hz, 2H), 1.68 (d, J=9.9 Hz, 2H) ppm; LC-MS: m/z 395.0 [M+H]$^+$.

Example 17-2: (1-(8-((2,3-dichlorophenyl)thio)-[1,2,4]triazolo[4,3-c]pyrimidin-5-yl)-4-phenylpiperidin-4-yl)methanamine

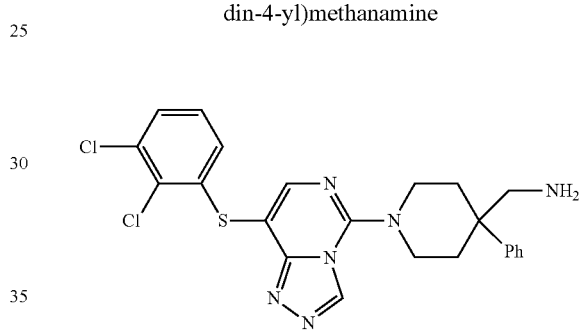

$^1$H NMR (400 MHz, DMSO-d$_6$) δ 9.42 (s, 1H), 7.99 (s, 1H), 7.46 (dt, J=22.1, 7.5 Hz, 5H), 7.33 (t, J=6.8 Hz, 1H), 7.13 (t, J=8.0 Hz, 1H), 6.81 (d, J=8.0 Hz, 1H), 3.97 (d, J=14.4 Hz, 2H), 3.45-3.37 (m, 2H), 2.98 (s, 2H), 2.38 (d, J=14.8 Hz, 2H), 2.06 (t, J=10.4 Hz, 2H) ppm; LC-MS: m/z 485.1 [M+H]$^+$.

Example 18-2: (1-(8-((2,3-dichlorophenyl)thio)-[1,2,4]triazolo[4,3-c]pyrimidin-5-yl)pyrrolidin-3-yl)methanamine

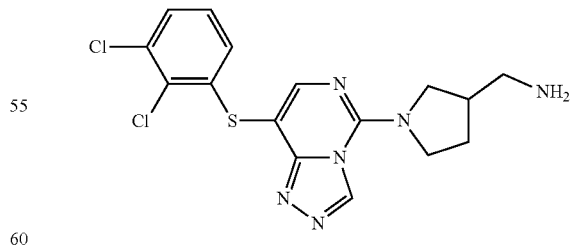

$^1$H NMR (400 MHz, DMSO-d$_6$) δ 9.49 (s, 1H), 7.92 (s, 1H), 7.86 (brs, 2H), 8.42 (d, J=8.0 Hz, 1H), 7.14 (t, J=8.0 Hz, 1H), 6.74 (d, J=8.0 Hz, 1H), 4.16-3.93 (m, 4H), 3.77-3.72 (m, 1H), 3.01-2.97 (m, 1H), 2.66-2.58 (m, 1H), 2.25-2.18 (m, 2H), 1.88-1.76 (m, 1H) ppm; LC-MS: m/z 395.1 [M+H]$^+$.

Example 19-2: (1-(8-((2,3-dichlorophenyl)thio)-[1,2,4]triazolo[4,3-c]pyrimidin-5-yl)-4-methylpiperidin-4-yl)methanamine

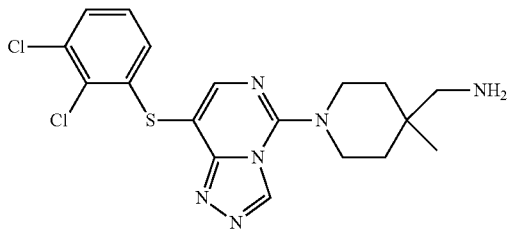 [SMILES: CC1(CN)CCN(c2ncc(Sc3cccc(Cl)c3Cl)c3nncn23)CC1]

¹H NMR (400 MHz, DMSO-d₆) δ 9.38 (s, 1H), 7.98 (s, 1H), 7.43 (dd, J=8.0, 1.3 Hz, 1H), 7.14 (t, J=8.0 Hz, 1H), 6.82 (dd, J=8.1, 1.3 Hz, 1H), 3.92-3.78 (m, 2H), 3.64-3.55 (m, 2H), 2.56 (s, 2H), 1.67 (ddd, J=13.2, 9.4, 3.7 Hz, 2H), 1.53-1.41 (m, 2H), 1.01 (s, 3H) ppm; LC-MS: m/z 423.1 [M+H]⁺.

Example 20-2: 2-(1-(8-((2,3-dichlorophenyl)thio)-[1,2,4]triazolo[4,3-c]pyrimidin-5-yl)piperidin-4-yl)ethan-1-amine

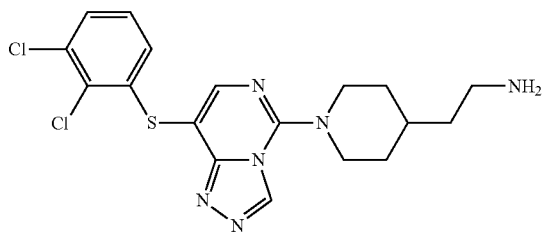 [SMILES: NCCC1CCN(c2ncc(Sc3cccc(Cl)c3Cl)c3nncn23)CC1]

¹H NMR (400 MHz, DMSO-d₆) δ 9.39 (s, 1H), 8.00 (s, 1H), 7.44 (d, J=8.0 Hz, 1H), 7.14 (t, J=8.0 Hz, 1H), 6.83 (d, J=8.1 Hz, 1H), 4.20 (d, J=13.3 Hz, 4H), 3.20 (d, J=12.5 Hz, 2H), 2.83 (t, J=7.7 Hz, 1H), 1.82 (d, J=12.7 Hz, 2H), 1.59-1.49 (m, 2H), 1.39-1.33 (m, 2H), 1.23 (s, 2H) ppm; LC-MS: m/z 424.1 [M+H]⁺.

Example 21-2: 8-((2,3-dichlorophenyl)thio)-5-(3,5-dimethylpiperazin-1-yl)-[1,2,4]triazolo[4,3-c]pyrimidine

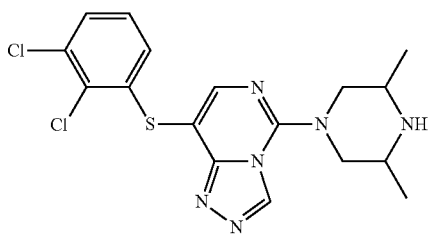 [SMILES: CC1CN(c2ncc(Sc3cccc(Cl)c3Cl)c3nncn23)CC(C)N1]

¹H NMR (400 MHz, DMSO-d₆) δ 9.52 (s, 1H), 8.14 (s, 1H), 8.03 (s, 1H), 7.45 (d, J=7.9 Hz, 1H), 7.14 (t, J=8.1 Hz, 1H), 6.83 (d, J=8.0 Hz, 1H), 4.12 (d, J=12.6 Hz, 2H), 3.23 (s, 2H), 2.94 (s, 2H), 1.15 (d, J=5.9 Hz, 6H) ppm; LC-MS: m/z 410.1 [M+H]⁺.

Example 22-2: 8-(8-((2,3-dichlorophenyl)thio)-[1,2,4]triazolo[4,3-c]pyrimidin-5-yl)-1,8-diazaspiro[4.5]decane

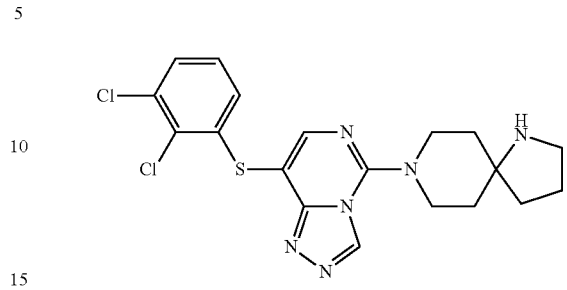

¹H NMR (400 MHz, DMSO-d₆) δ 9.47 (s, 1H), 8.02 (s, 1H), 7.43 (d, J=8.0 Hz, 1H), 7.14 (t, J=8.0 Hz, 1H), 6.85 (d, J=8.1 Hz, 1H), 3.97 (ddd, J=14.1, 6.6, 3.9 Hz, 2H), 3.62 (ddd, J=13.3, 8.9, 3.3 Hz, 2H), 3.30 (t, J=6.7 Hz, 2H), 2.10 (ddd, J=13.1, 8.8, 3.7 Hz, 2H), 2.00 (p, J=6.3 Hz, 6H) ppm; LC-MS: m/z 435.1 [M+H]⁺.

Example 23-2: 4-((5-(4-amino-4-methylpiperidin-1-yl)-[1,2,4]triazolo[4,3-c]pyrimidin-8-yl)thio)-3-chloropyridine-2-amine

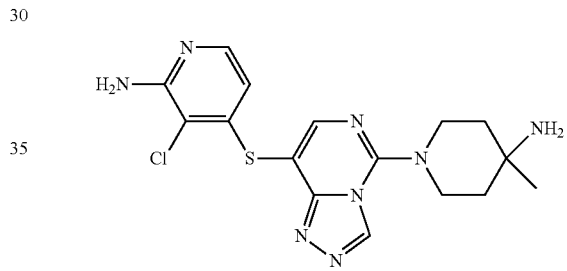

¹H NMR (400 MHz, CD₃OD-d₄) δ 9.24 (s, 1H), 7.94 (s, 1H), 7.42-7.44 (d, J=5.2 Hz, 1H), 5.93-5.94 (d, J=5.6 Hz, 1H), 3.97-4.02 (d, J=14 Hz, 2H), 3.58-3.60 (t, J=10.4 Hz, 2H), 1.92-1.98 (m, 4H), 1.44 (s, 3H) ppm; LC-MS: m/z 391.1[M+H]⁺.

Example 24-2: (R)-8-(8-((2,3-dichlorophenyl)thio)-[1,2,4]triazolo[4,3-c]pyrimidin-5-yl)-8-azaspiro[4.5]decan-1-amine Step 1: (R)—N—((R)-8-(8-iodine-[1,2,4]triazolo[4,3-c]pyrimidin-5-yl)-8-azaspiro[4.5]decan-1-yl)-2-methylpropane-2-sulfinamide

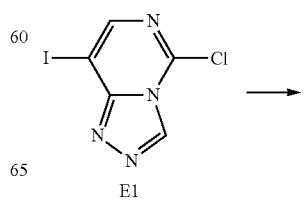

E1

287

-continued

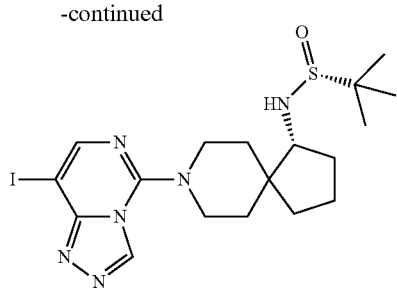

To a dry 50 mL single-necked flask were sequentially added 5-chloro-8-iodo-[1,2,4]triazolo[4,3-c]pyrimidine (E1) (50 mg, 0.18 mmol), (R)-2-methyl-N—((R)-8-azaspiro[4.5]decan-1-yl)propane-2-sulfinamide (C-1A) (93 mg, 0.36 mmol), DIEA (46 mg, 0.36 mmol) and NMP (5 mL), and then the reaction mixture was stirred at 90° C. for 2 hours. After the reaction was completed, the obtained residue was poured into water (10 mL) and stirred at room temperature for 5 minutes, followed by extraction with ethyl acetate (3×20 mL). The organic phases were combined, dried over MgSO₄, filtered and concentrated under reduced pressure. The residue obtained was purified by silica gel chromatography (ethyl acetate/petroleum ether with a gradient of 0 to 80%) to obtain (R)—N—((R)-8-(8-iodo-[1,2,4]triazolo[4,3-c]pyrimidin-5-yl)-8-azaspiro[4.5]decan-1-yl)-2-methylpropane-2-sulfinamide as a pale yellow solid (80 mg, yield: 88%).

LC-MS: m/z 503.1 [M+H]⁺.

Step 2: (R)—N—((R)-8-(8-((2,3-dichlorophenyl)thio)-[1,2,4]triazolo[4,3-c]pyrimidin-5-yl)-8-aza spiro[4.5]decan-1-yl)-2-methylpropane-2-sulfinamide

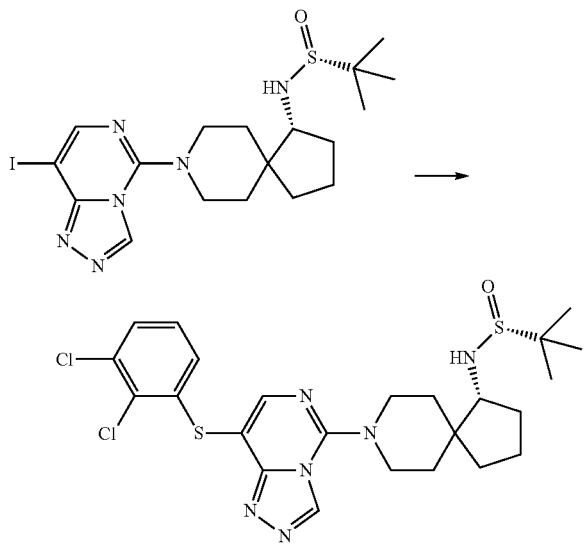

To a dry 50 mL three-necked flask were sequentially added (R)—N—((R)-8-(8-iodo-[1,2,4]triazolo[4,3-c]pyrimidin-5-yl)-8-azaspiro[4.5]decan-1-yl)-2-methylpropane-2-sulfinamide (80 mg, 0.16 mmol), cuprous iodide (3 mg, 0.016 mmol), 1,10-phenanthroline (6 mg, 0.032 mmol), 2,3-dichlorothiophenol (34 mg, 0.192 mmol), potassium phosphate (68 mg, 0.32 mmol) and 10 mL of dioxane, and the mixture was heated for 3 hours under nitrogen atmosphere. After the reaction was completed, saturated NH₄Cl solution (50 mL) was added, followed by extraction with ethyl acetate (3×20 mL). The organic phases were combined, dried over Na₂SO₄, filtered, and the filtrate was concentrated under reduced pressure. The resulting residue was purified by silica gel chromatography (methanol/ethyl acetate with a gradient of 0 to 10%) to obtain (R)—N—((R)-8-(8-((2,3-dichlorophenyl)thio)-[1,2,4]triazolo[4,3-c]pyrimidin-5-yl)-8-aza spiro[4.5]decan-1-yl)-2-methylpropane-2-sulfinamide as a pale yellow solid (60 mg, yield: 68%).

LC-MS: m/z 553.1 [M+H]⁺.

Step 3: (R)-8-(8-((2,3-dichlorophenyl)thio)-[1,2,4]triazolo[4,3-c]pyrimidin-5-yl)-8-azaspiro[4.5]decan-1-amine

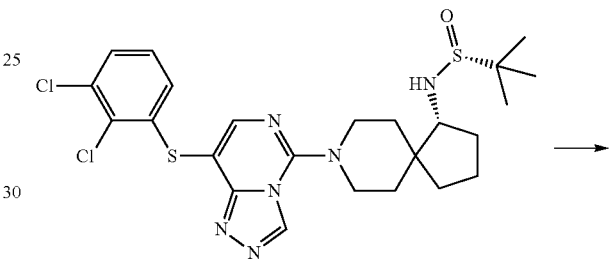

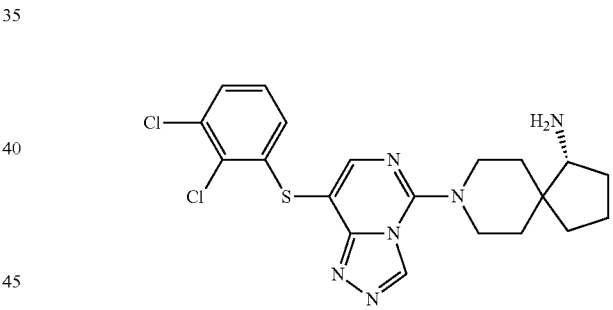

To a dry 50 mL round bottom flask were sequentially added (R)—N—((R)-8-(8-((2,3-dichlorophenyl)thio)-[1,2,4]triazolo[4,3-c]pyrimidin-5-yl)-8-aza spiro[4.5]decan-1-yl)-2-methylpropane-2-sulfinamide (60 mg, 0.11 mmol) and a solution of hydrogen chloride in 1,4-dioxane (7 M, 5 mL), and the reaction solution was allowed to react at room temperature for 1 hour. The reaction solution was evaporated under reduced pressure, and the resulting crude product was purified by reversed-phase high-performance liquid chromatography to obtain the product (R)-8-(8-((2,3-dichlorophenyl)thio)-[1,2,4]triazolo[4,3-c]pyrimidin-5-yl)-8-azaspiro[4.5]decan-1-amine (20 mg, yield: 46%).

¹H NMR (400 MHz, MeOH-d₄) δ 9.15 (s, 1H), 7.90 (s, 1H), 7.23 (d, J=8.0 Hz, J=1.6 Hz, 1H), 6.97 (t, J=8.0 Hz, 1H), 6.74 (d, J=8.0 Hz, J=1.6 Hz, 1H), 4.03-4.11 (m, 2H), 3.32-3.40 (m, 2H), 3.16 (t, J=6.8 Hz, 1H), 2.11-2.14 (m, 1H), 1.51-1.84 (m, 9H) ppm; LC-MS: m/z 451.1 [M+H]⁺.

According to the synthesis method of Example 24-2, the following compounds were synthesized:

Example 25-2: (S)-8-(8-((2,3-dichlorophenyl)thio)-[1,2,4]triazolo[4,3-c]pyrimidin-5-yl)-8-azaspiro[4.5]decan-1-amine

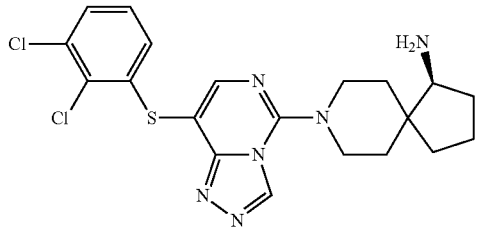 [SMILES: N[C@H]1CCCC12CCN(c1ncc(Sc3cccc(Cl)c3Cl)c3nncn13)CC2]

¹H NMR (400 MHz, MeOD-d₄) δ 9.27 (s, 1H), 8.55 (s, 2H), 8.02 (s, 1H), 7.35 (dd, J=8.0, 1.3 Hz, 1H), 7.08 (t, J=8.1 Hz, 1H), 6.85 (d, J=8.1 Hz, 1H), 4.19 (s, 3H), 3.51-3.48 (m, 2H), 3.21 (s, 1H), 3.15 (s, 1H), 2.31-2.14 (m, 1H), 2.03-1.78 (m, 7H), 1.63 (s, 2H) ppm; LC-MS: m/z 449.1 [M+H]⁺.

Example 26-2: (S)-7-(8-((2,3-dichlorophenyl)thio)-[1,2,4]triazolo[4,3-c]pyrimidin-5-yl)-7-azaspiro[3.5]nonan-1-amine

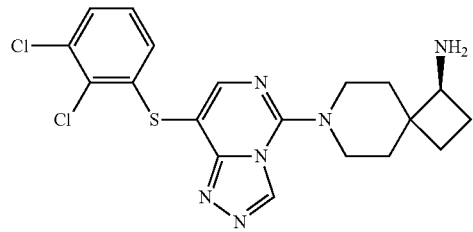 [SMILES: N[C@H]1CCC12CCN(c1ncc(Sc3cccc(Cl)c3Cl)c3nncn13)CC2]

¹H NMR (400 MHz, MeOH-d₄) δ 9.15 (s, 1H), 8.34 (brs, 2H), 7.90 (s, 1H), 7.23 (dd, J=8.0 Hz, J=1.6 Hz, 1H), 6.96 (t, J=8.0 Hz, 1H), 6.74 (dd, J=8.0 Hz, J=1.6 Hz, 1H), 4.11 (d, J=12.0 Hz, 1H), 4.00 (d, J=13.2 Hz, 1H), 3.44-3.40 (m, 1H), 3.35-3.28 (m, 1H), 2.33-2.29 (m, 1H), 2.03-1.95 (m, 2H), 1.91-1.87 (m, 2H), 1.80-1.70 (m, 3H) ppm; LC-MS: m/z 435.1 [M+H]⁺.

Example 27-2: 7-(8-((2,3-dichlorophenyl)thio)-[1,2,4]triazolo[4,3-c]pyrimidin-5-yl)-7-azaspiro[3.5]nonan-2-amine

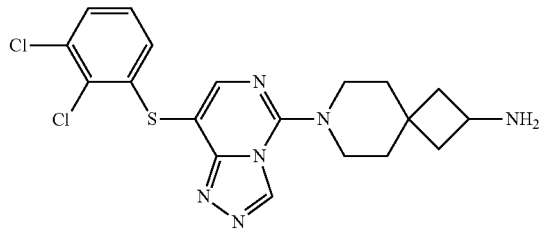 [SMILES: NC1CC2(CCN(c3ncc(Sc4cccc(Cl)c4Cl)c4nncn34)CC2)C1]

¹H NMR (400 MHz, methanol-d₄) δ 9.28 (s, 1H), 8.01 (s, 1H), 7.34 (dd, J=8.0, 1.4 Hz, 1H), 7.08 (t, J=8.0 Hz, 1H), 6.84 (dd, J=8.1, 1.4 Hz, 1H), 3.90-3.83 (m, 2H), 3.76 (t, J=5.7 Hz, 2H), 3.72-3.66 (m, 2H), 2.45 (s, 2H), 2.05 (t, J=10.6 Hz, 2H), 1.95 (t, J=5.7 Hz, 1H), 1.91 (t, J=5.7 Hz, 1H) ppm; LC-MS: m/z 435.1 [M+H]⁺.

Example 28-2: (4R)-2-(8-((2,3-dichlorophenyl)thio)-[1,2,4]triazolo[4,3-c]pyrimidin-5-yl)octahydrocyclopenta[c]pyrrol-4-amine

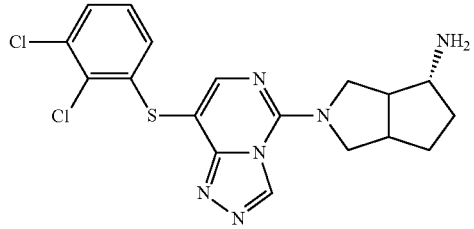 [SMILES: N[C@@H]1CCC2CN(c3ncc(Sc4cccc(Cl)c4Cl)c4nncn34)CC21]

¹H NMR (400 MHz, DMSO-d₆) δ 9.55 (s, 1H), 7.86 (s, 1H), 7.39 (d, J=7.9 Hz, 1H), 7.13 (d, J=8.1 Hz, 1H), 6.73 (d, J=8.1 Hz, 1H), 4.10-4.04 (m, 2H), 3.53 (s, 1H), 3.16 (d, J=4.8 Hz, 1H), 2.79 (s, 1H), 1.86-1.78 (m, 2H), 1.55 (d, J=8.5 Hz, 2H) ppm; LC-MS: m/z 421.1 [M+H]⁺.

Example 29-2: (R)-3-(8-((2,3-dichlorophenyl)thio)-[1,2,4]triazolo[4,3-c]pyrimidin-5-yl)-3-azaspiro[5.5]undecan-7-amine

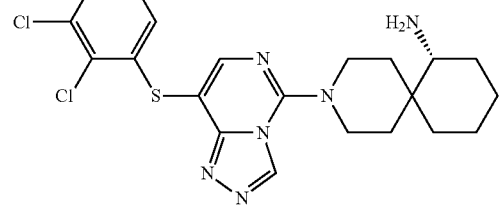

¹H NMR (400 MHz, DMSO-d₆) δ 9.37 (s, 1H), 7.98 (s, 1H), 7.43 (d, J=7.2 Hz, 1H), 7.14 (t, J=8.0 Hz, 1H), 6.81 (d, J=8.1 Hz, 1H), 3.99 (d, J=13.5 Hz, 2H), 3.59-3.51 (m, 2H), 2.82 (d, J=4.6 Hz, 1H), 2.14-1.11 (m, 14H) ppm; LC-MS: m/z 464.1 [M+H]⁺.

Example 30-2: (R)-1-(8-((2,3-dichlorophenyl)thio)-[1,2,4]triazolo[4,3-c]pyrimidin-5-yl)azepan-4-amine

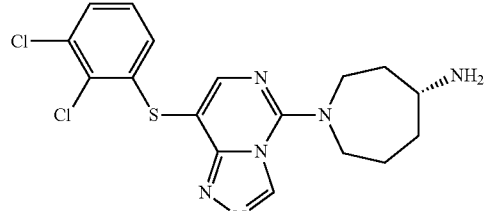

¹H NMR (400 MHz, DMSO-d₆) δ 9.41 (s, 1H), 7.93 (s, 1H), 7.43 (d, J=7.4 Hz, 1H), 7.14 (t, J=8.1 Hz, 1H), 6.77 (d, J=8.0 Hz, 1H), 4.15-3.99 (m, 2H), 3.84 (ddd, J=52.8, 16.3, 7.7 Hz, 2H), 3.21 (s, 31), 2.01 (dd, J=56.3, 34.4 Hz, 51-), 1.65-1.47 (m, 1H) ppm; LC-MS: m/z 410.1 [M+H]⁺.

Example 31-2: (S)-8-(8-((2,3-dichlorophenyl)thio)-[1,2,4]triazolo[4,3-c]pyrimidin-5-yl)-2-oxa-8-azaspiro[4.5]decan-4-amine

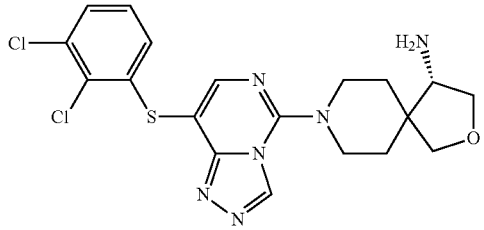 [SMILES: N[C@@H]1COCC12CCN(c1ncc(Sc3cccc(Cl)c3Cl)c3nncn13)CC2]

¹H NMR (400 MHz, DMSO-d₆) δ 9.39 (s, 1H), 8.21 (s, 1H), 8.00 (s, 1H), 7.47-7.39 (m, 1H), 7.14 (t, J=8.0 Hz, 1H), 6.82 (d, J=8.1 Hz, 1H), 4.00 (dd, J=8.8, 6.5 Hz, 2H), 3.73 (d, J=8.5 Hz, 1H), 3.66 (d, J=8.5 Hz, 1H), 3.54-3.46 (m, 2H), 3.39 (dd, J=8.9, 5.0 Hz, 2H), 3.21-3.17 (m, 1H), 1.92-1.75 (m, 2H), 1.64-1.53 (m, 2H) ppm; LC-MS: m/z 450.7 [M+H]⁺.

Example 32-2: (R)-8-(8-((2,3-dichlorophenyl)thio)-[1,2,4]triazolo[4,3-c]pyrimidin-5-yl)-N-methyl-8-azaspiro[4.5]decan-1-amine

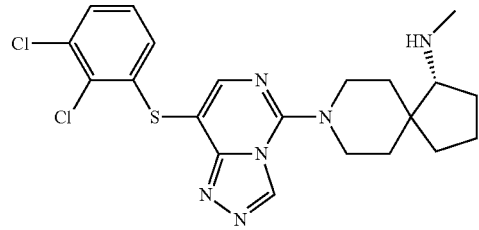 [SMILES: CN[C@@H]1CCCC12CCN(c1ncc(Sc3cccc(Cl)c3Cl)c3nncn13)CC2]

¹H NMR (400 MHz, DMSO-d₆) δ 9.38 (s, 1H), 8.28 (s, 1H), 8.00 (s, 1H), 7.43 (d, J=8.0 Hz, 1H), 7.14 (t, J=8.1 Hz, 1H), 6.82 (d, J=8.0 Hz, 1H), 4.08 (d, J=14.0 Hz, 2H), 2.64 (d, J=21.8 Hz, 1H), 2.37 (s, 3H), 2.06-1.14 (m, 12H) ppm; LC-MS: m/z 463.1 [M+H]⁺.

Example 33-2: (1R)-8-(8-((2,3-dichlorophenyl)thio)-[1,2,4]triazolo[4,3-c]pyrimidin-5-yl)-3-methyl-8-azaspiro[4.5]decan-1-amine

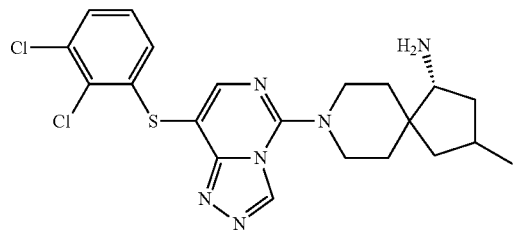 [SMILES: CC1C[C@@H](N)C2(CCN(c3ncc(Sc4cccc(Cl)c4Cl)c4nncn34)CC2)C1]

¹H NMR (400 MHz, DMSO-d₆) δ 9.38 (d, J=3.5 Hz, 1H), 8.37 (s, 1H), 8.00 (d, J=1.0 Hz, 1H), 7.44 (d, J=7.1 Hz, 1H), 7.14 (t, J=8.0 Hz, 1H), 6.81 (dd, J=8.1, 1.1 Hz, 1H), 4.15-4.04 (m, 2H), 3.06-2.93 (m, 2H), 2.15 (dd, J=19.1, 11.5 Hz, 2H), 2.01-1.26 (m, 8H), 1.06-0.99 (m, 3H) ppm; LC-MS: m/z 464.1 [M+H]⁺.

Example 34-2: 8-(8-((2,3-dichlorophenyl)thio)-[1,2,4]triazolo[4,3-c]pyrimidin-5-yl)-4-methyl-2-oxa-8-azaspiro[4.5]decan-4-amine

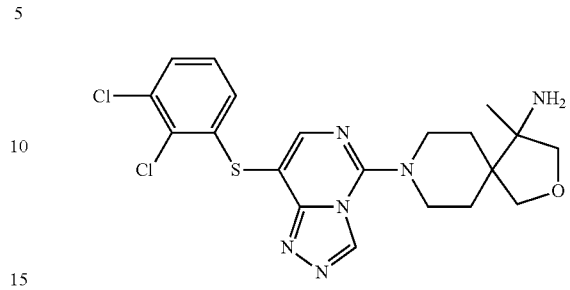

¹H NMR (CD₃OD-d₄) δ 9.31 (s, 1H), 8.49 (s, 1H), 8.02 (s, 1H), 7.34-7.37 (m, 1H), 7.07-7.11 (m, 1H), 6.86-6.88 (m, 1H), 4.19-4.21 (m, 2H), 4.10-4.12 (m, 2H), 3.85-3.94 (m, 2H), 3.37 (m, 1H), 3.18 (m, 1H), 2.04 (m, 2H), 1.80 (m, 2H), 1.38 (s, 3H) ppm; LC-MS: m/z 465.1 [M+H]⁺.

Example 35-2: (3S,4S)-8-(8-((2,3-dichlorophenyl)thio)-[1,2,4]triazolo[4,3-c]pyrimidin-5-yl)-3-methyl-2-oxa-8-azaspiro[4.5]decan-4-amine

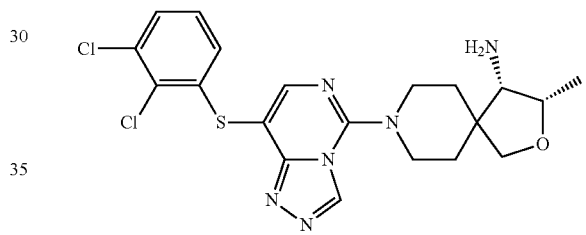

¹H NMR (400 MHz, DMSO-d₆) δ 9.40 (s, 1H), 8.18 (s, 1H), 8.01 (s, 1H), 7.44 (d, J=7.0 Hz, 1H), 7.14 (t, J=8.0 Hz, 1H), 6.82 (d, J=7.2 Hz, 1H), 4.12 (s, 1H), 3.89 (d, J=6.8 Hz, 2H), 3.74 (d, J=8.6 Hz, 1H), 3.59-3.49 (m, 3H), 3.08 (d, J=4.8 Hz, 1H), 1.96-1.81 (m, 2H), 1.73 (s, 2H), 1.13 (d, J=6.4 Hz, 3H) ppm; LC-MS: m/z 466.1 [M+H]⁺.

Example 36-2: (3R,4R)-8-(8-((2,3-dichlorophenyl)thio)-[1,2,4]triazolo[4,3-c]pyrimidine-5-yl)-3-methyl-2-oxa-8-azaspiro[4.5]decan-4-amine

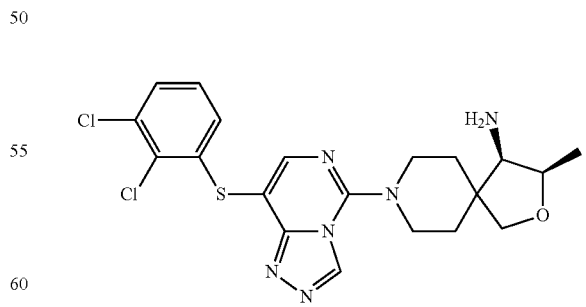

¹H NMR (400 MHz, DMSO-d₆) δ 9.31 (s, 1H), 7.95 (s, 1H), 7.40 (d, J=7.9 Hz, 1H), 7.11 (t, J=8.1 Hz, 1H), 6.78 (d, J=8.0 Hz, 1H), 4.68-4.53 (m, 4H), 3.17-3.08 (m, 1H), 1.89 (s, 2H), 1.71-1.61 (m, 4H), 1.13 (d, J=6.5 Hz, 3H); LC-MS: m/z 465.1 [M+H]⁺.

Example 37-2: 1-(8-(2,3-dichlorophenyl)-[1,2,4]triazolo[4,3-c]pyrimidin-5-yl)-4-methylpiperidin-4-amine Step 1: Tert-Butyl (1-(8-(2,3-dichlorophenyl)-[1,2,4]triazolo[4,3-c]pyrimidin-5-yl)-4-methylpiperidine-4-yl)carbamate

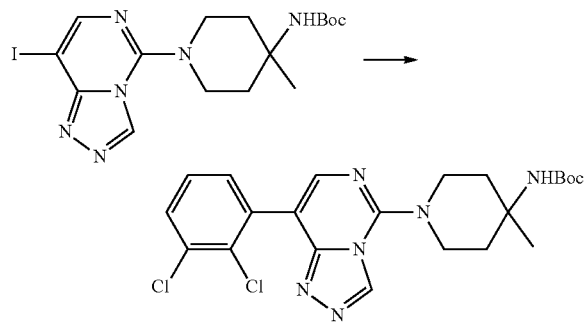

At room temperature, to a 20 mL sealed tube were sequentially added tert-butyl (1-(8-iodo-[1,2,4]triazolo[4,3-c]pyrimidin-5-yl)-4-methylpiperidine-4-yl)carbamate (55 mg, 0.12 mmol) 1,4-dioxane (2 mL), purified water (0.5 mL), (2,3-dichlorophenyl)boronic acid (50 mg, 0.24 mmol), [1,1'-bis(diphenylphosphino)ferrocene]palladium dichloride (9 mg, 0.012 mmol) and potassium carbonate (50 mg, 0.36 mmol). The reaction mixture was bubbled with nitrogen for one minute, and then the sealed tube was heated to 80° C., and the reaction continued for 6 hours. After the reaction was completed, 20 mL of water was added to the reaction solution, followed by extraction with ethyl acetate (50 mL×3). The organic phase was sequentially washed with water (20 mL×1) and saturated saline (20 mL×1). The organic phase was collected, dried over anhydrous sodium sulfate, filtered, and the filtrate was concentrated under reduced pressure to give a residue, which was purified by column chromatography (petroleum ether: ethyl acetate=1:1) to obtain a crude product of tert-butyl (1-(8-(2,3-dichlorophenyl)-[1,2,4]triazolo[4,3-c]pyrimidin-5-yl)-4-methylpiperidine-4-yl)carbamate (33 mg, yield: 57%) as a pale yellow solid.

LC-MS: m/z 477.1 [M+H]$^+$.

Step 2: 1-(8-(2,3-dichlorophenyl)-[1,2,4]triazolo[4,3-c]pyrimidin-5-yl)-4-methylpiperidine-4-amine

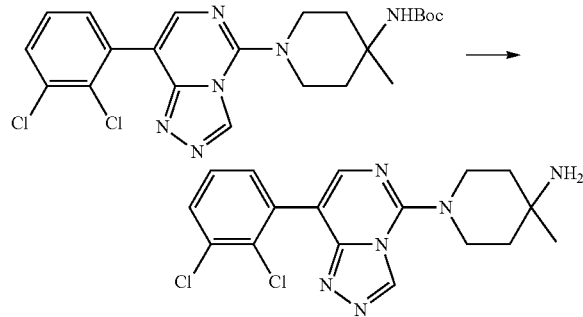

According to the method of step 3 of Example 15-2, tert-butyl (1-(8-(2,3-dichlorophenyl)-[1,2,4]triazolo[4,3-c]pyrimidin-5-yl)-4-methylpiperidin-4-yl)carbamate was subjected to the removal of 1-tert-butoxycarbonyl group to obtain 1-(8-(2,3-dichlorophenyl)-[1,2,4]triazolo[4,3-c]pyrimidin-5-yl)-4-methylpiperidine-4-amine.

$^1$H NMR (400 MHz, DMSO-d$_6$) δ 9.38 (s, 1H), 7.79-7.72 (m, 2H), 7.56-7.46 (m, 2H), 3.68 (t, J=5.3 Hz, 4H), 1.76-1.51 (m, 4H), 1.18 (s, 3H) ppm; LC-MS: m/z 377.1 [M+H]$^+$.

Example 38-2: Synthesis of (R)-8-(8-(2,3-dichlorophenyl)-[1,2,4]triazolo[4,3-c]pyrimidin-5-yl)-8-azaspiro[4.5]decan-1-amine Step 1: (R)—N—((R)-8-(8-(2,3-dichlorophenyl)-[1,2,4]triazolo[4,3-c]pyrimidin-5-yl)-8-azaspiro decan-1-yl)-2-methylpropane-2-sulfinamide

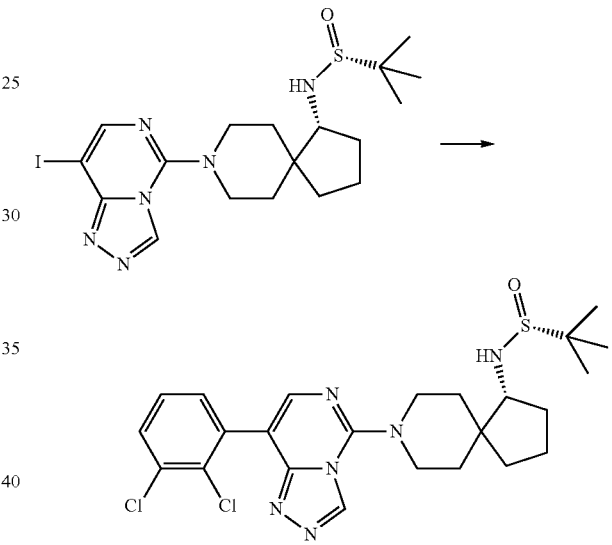

At room temperature, to a 20 mL sealed tube were sequentially added (R)—N—((R)-8-(8-iodo-[1,2,4]triazolo[4,3-c]pyrimidin-5-yl)-8-azaspiro[4.5]decan-1-yl)-2-methylpropane-2-sulfinamide (60 mg, 0.12 mmol), 1,4-dioxane (2 mL), purified water (0.5 mL), (2,3-dichlorophenyl)boronic acid (50 mg, 0.24 mmol), [1,1'-bis(diphenylphosphino)ferrocene]palladium dichloride (9 mg, 0.012 mmol) and potassium carbonate (50 mg, 0.36 mmol). The reaction mixture was bubbled with nitrogen for one minute, and then the sealed tube was heated to 80° C., and the reaction continued for 6 hours. After the reaction was completed, 20 mL of water was added to the reaction solution, followed by extraction with ethyl acetate (50 mL×3). The organic phase was sequentially washed with water (20 mL×1) and saturated saline (20 mL×1). The organic phase was collected, dried over anhydrous sodium sulfate, filtered, and the filtrate was concentrated under reduced pressure to give a residue, which was purified by column chromatography (petroleum ether: ethyl acetate=1:1) to obtain a crude product of (R)—N—((R)-8-(8-(2,3-dichlorophenyl)-[1,2,4]triazolo[4,3-c]pyrimidin-5-yl)-8-azaspiro decan-1-yl)-2-methylpropane-2-sulfinamide (30 mg, yield: 48%) as a pale yellow solid.

LC-MS: m/z 521.1 [M+H]$^+$.

Step 2: (R)-8-(8-(2,3-dichlorophenyl)-[1,2,4]triazolo[4,3-c]pyrimidin-5-yl)-8-azaspiro[4.5]decan-1-amine

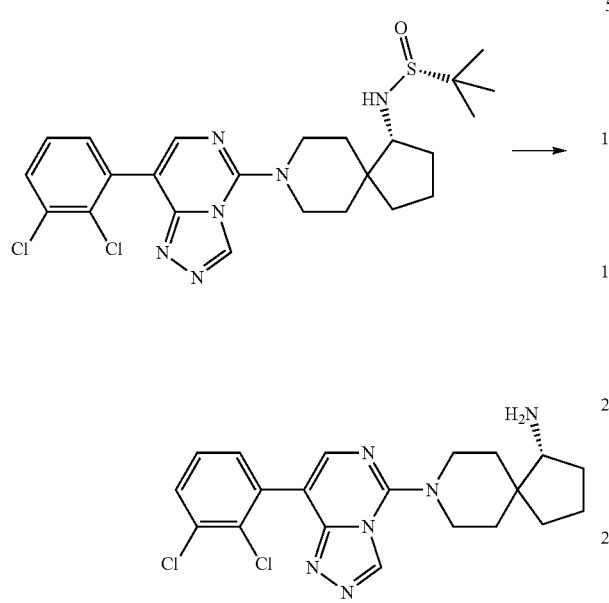

According to the method of step 3 of Example 24-2, (R)—N—((R)-8-(8-(2,3-dichlorophenyl)-[1,2,4]triazolo[4,3-c]pyrimidin-5-yl)-8-azaspiro decan-1-yl)-2-methylpropane-2-sulfinamide was subjected to the removal of the sulfinyl group to obtain (R)-8-(8-(2,3-dichlorophenyl)-[1,2,4]triazolo[4,3-c]pyrimidin-5-yl)-8-azaspiro[4.5]decan-1-amine.

$^1$H NMR (400 MHz, DMSO-$d_6$) δ 9.35 (s, 1H), 7.81-7.71 (m, 2H), 7.58-7.45 (m, 2H), 3.99 (t, J=13.6 Hz, 2H), 3.35 (dd, J=22.9, 10.6 Hz, 2H), 3.06 (t, J=6.2 Hz, 1H), 2.09-1.35 (m, 10H) ppm; LC-MS: m/z 417.1 [M+H]$^+$.

According to the synthesis method of Example 24-2, the following compounds were synthesized:

Example 39-2: methyl (R)-3-((5-(1-amino-8-azaspiro[4.5]decan-8-yl)-[1,2,4]triazolo[4,3-c]pyrimidin-8-yl)thio) propionate

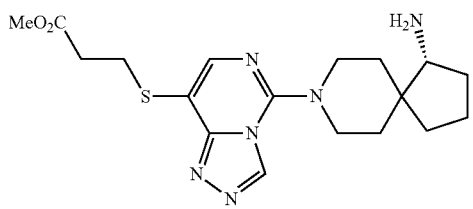 [SMILES: COC(=O)CCSc1cnc(N2CCC3(CCC[C@H]3N)CC2)n2cnnc12]

$^1$H NMR (400 MHz, DMSO-$d_6$) δ 9.32 (s, 1H), 8.34 (s, 1H) 7.71 (s, 1H), 3.88 (t, J=13.3 Hz, 2H), 3.57 (s, 3H), 3.24 (t, J=7.0 Hz, 4H), 3.08 (t, J=6.3 Hz, 1H), 2.68-2.59 (m, 2H), 2.03-1.39 (m, 10H) ppm; LC-MS: m/z 391.1 [M+H]$^+$.

Example 40-2: (R)-8-(8-(phenylthio)-[1,2,4]triazolo[4,3-c]pyrimidin-5-yl)-8-azaspiro[4.5]decan-1-amine

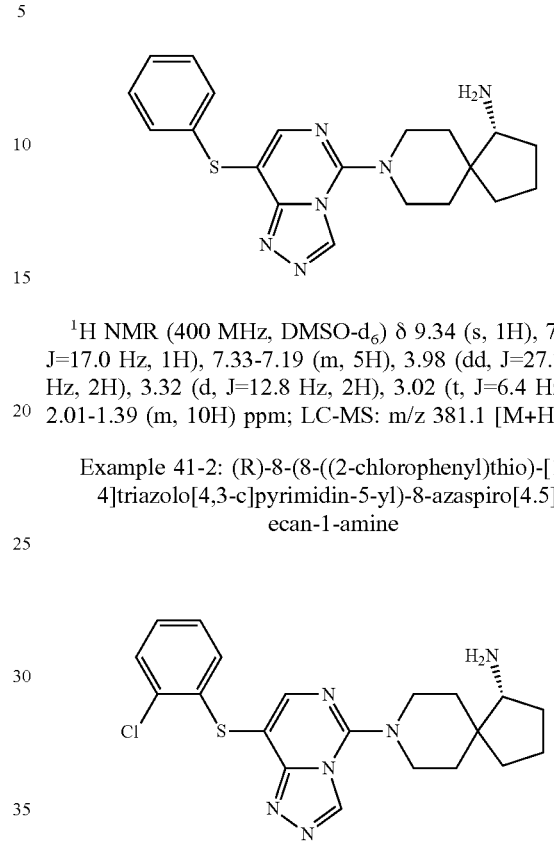

$^1$H NMR (400 MHz, DMSO-$d_6$) δ 9.34 (s, 1H), 7.84 (d, J=17.0 Hz, 1H), 7.33-7.19 (m, 5H), 3.98 (dd, J=27.7, 14.8 Hz, 2H), 3.32 (d, J=12.8 Hz, 2H), 3.02 (t, J=6.4 Hz, 1H), 2.01-1.39 (m, 10H) ppm; LC-MS: m/z 381.1 [M+H]$^+$.

Example 41-2: (R)-8-(8-((2-chlorophenyl)thio)-[1,2,4]triazolo[4,3-c]pyrimidin-5-yl)-8-azaspiro[4.5]decan-1-amine $^1$H NMR (400 MHz, DMSO-$d_6$) δ 9.37 (s, 1H), 7.96 (s, 1H), 7.50 (dd, J=7.7, 1.4 Hz, 1H), 7.16 (dtd, J=21.0, 7.5, 1.5 Hz, 2H), 6.87 (dd, J=7.8, 1.6 Hz, 1H), 4.07 (dd, J=15.4, 11.3 Hz, 2H), 3.39 (dtd, J=13.7, 7.7, 3.1 Hz, 2H), 3.05 (s, 1H), 2.00 (q, J=7.9 Hz, 1H), 1.92-1.36 (m, 9H) ppm; LC-MS: m/z 415.1 [M+H]$^+$.

Example 42-2: (R)-8-(8-((4-chlorophenyl)thio)-[1,2,4]triazolo[4,3-c]pyrimidin-5-yl)-8-azaspiro[4.5]decan-1-amine $^1$H NMR (400 MHz, DMSO-$d_6$) δ 9.34 (s, 1H), 7.92 (s, 1H), 7.34 (d, J=8.6 Hz, 2H), 7.27 (d, J=8.6 Hz, 2H), 4.12-3.92 (m, 2H), 3.35 (tt, J=13.8, 3.4 Hz, 2H), 3.04 (d, J=7.0 Hz, 1H), 1.99 (t, J=5.3 Hz, 1H), 1.92-1.33 (m, 9H) ppm; LC-MS: m/z 415.1 [M+H]$^+$.

Example 43-2: (R)-8-(8-((2,4-dichlorophenyl)thio)-[1,2,4]triazolo[4,3-c]pyrimidin-5-yl)-8-azaspiro[4.5]decan-1-amine

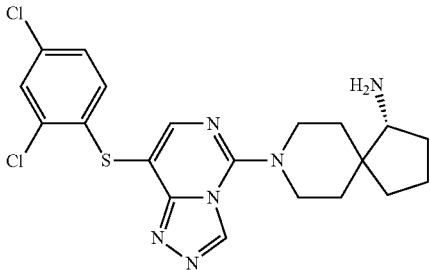 [SMILES: N[C@@H]1CCCC12CCN(c1ncc(Sc3ccc(Cl)cc3Cl)c3nncn13)CC2]

$^1$H NMR (400 MHz, DMSO-d$_6$) δ 9.38 (s, 1H), 7.98 (s, 1H), 7.70 (d, J=2.2 Hz, 1H), 7.20 (dd, J=8.6, 2.3 Hz, 1H), 6.88 (d, J=8.6 Hz, 1H), 4.05 (dd, J=12.3, 6.8 Hz, 2H), 2.76 (t, J=7.3 Hz, 1H), 1.94-1.75 (m, 4H), 1.66-1.53 (m, 2H), 1.45-1.27 (m, 4H) ppm; LC-MS: m/z 449.1 [M+H]$^+$.

Example 44-2: (R)-8-(8-((2,6-dichlorophenyl)thio)-[1,2,4]triazolo[4,3-c]pyrimidin-5-yl)-8-azaspiro[4.5]decan-1-amine

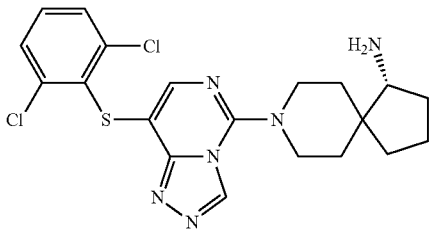 [SMILES: N[C@@H]1CCCC12CCN(c1ncc(Sc3c(Cl)cccc3Cl)c3nncn13)CC2]

$^1$H NMR (400 MHz, DMSO-d$_6$) δ 9.31 (s, 1H), 7.62 (d, J=8.1 Hz, 2H), 7.48 (dd, J=8.7, 7.5 Hz, 1H), 7.34 (s, 1H), 3.82 (s, 2H), 3.21 (td, J=11.7, 11.3, 9.1 Hz, 2H), 2.72 (t, J=7.3 Hz, 1H), 1.85 (ddt, J=11.8, 7.6, 3.9 Hz, 1H), 1.77 (td, J=12.6, 11.4, 7.3 Hz, 3H), 1.64-1.49 (m, 2H), 1.42-1.25 (m, 4H) ppm; LC-MS: m/z 449.1 [M+H]$^+$.

Example 45-2: (R)-8-(8-((2-isopropylphenyl)thio)-[1,2,4]triazolo[4,3-c]pyrimidin-5-yl)-8-azaspiro[4.5]decan-1-amine

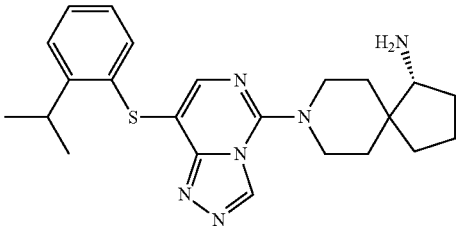 [SMILES: CC(C)c1ccccc1Sc1cnc(N2CCC3(CCC[C@H]3N)CC2)n2cnnc12]

$^1$H NMR (400 MHz, DMSO-d$_6$) δ 9.34 (s, 1H), 7.71 (s, 1H), 7.36 (d, J=7.7 Hz, 1H), 7.22 (ddd, J=8.0, 5.5, 3.1 Hz, 1H), 7.07-7.02 (m, 2H), 3.95 (dd, J=11.9, 6.8 Hz, 2H), 3.57-3.47 (m, 1H), 3.32-3.21 (m, 2H), 2.75 (t, J=7.3 Hz, 1H), 1.89-1.75 (m, 4H), 1.65 1.50 (m, 2H), 1.44-1.29 (m, 4H), 1.27 (d, J=6.8 Hz, 6H) ppm; LC-MS: m/z 423.1 [M+H]$^+$.

Example 46-2: (R)-8-(8-((2-methoxyphenyl)thio)-[1,2,4]triazolo[4,3-c]pyrimidin-5-yl)-8-azaspiro[4.5]decan-1-amine

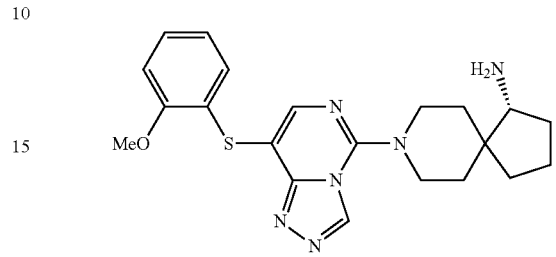

$^1$H NMR (400 MHz, DMSO-d$_6$) δ 9.30 (s, 1H), 7.75 (s, 1H), 7.17 (ddd, J=8.5, 6.1, 2.8 Hz, 1H), 7.03 (d, J=8.2 Hz, 1H), 6.80-6.74 (m, 2H), 3.96 (dd, J=12.5, 8.4 Hz, 4H), 3.86 (s, 3H), 3.35-3.27 (m, 2H), 2.75 (t, J=7.2 Hz, 1H), 1.90-1.76 (m, 2H), 1.65-1.15 (m, 8H) ppm; LC-MS: m/z 411.1 [M+H]$^+$.

Example 47-2: methyl (R)-2-((5-(1-amino-8-azaspiro[4.5]decan-8-yl)-[1,2,4]triazolo[4,3-c]pyrimidin-8-yl)thio) benzoate

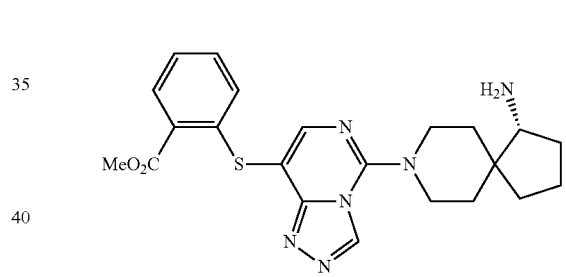

$^1$H NMR (400 MHz, DMSO-d$_6$) δ 9.35 (s, 1H), 7.96 (dd, J=8.2, 5.3 Hz, 2H), 7.33 (t, J=7.7 Hz, 1H), 7.24 (t, J=7.4 Hz, 1H), 6.90 (d, J=8.0 Hz, 1H), 4.04 (dd, J=12.3, 7.8 Hz, 2H), 3.92 (s, 3H), 3.39 (d, J=10.5 Hz, 2H), 2.78 (t, J=7.2 Hz, 1H), 1.89-1.29 (m, 10H); LC-MS: m/z 439.1 [M+H]$^+$.

Example 48-2: (R)—N-(4-((5-(1-amino-8-azaspiro[4.5]decan-8-yl)-[1,2,4]triazolo[4,3-c]pyrimidin-8-yl) thio)phenyl)acetamide

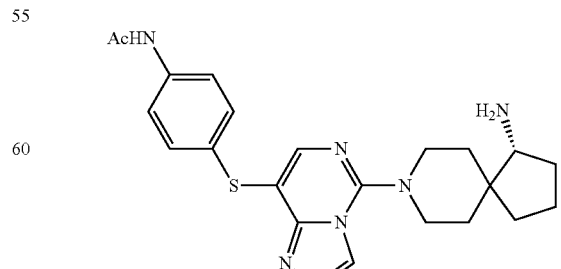

$^1$H NMR (400 MHz, DMSO-d$_6$) δ 10.03 (s, 1H), 9.32 (s, 1H), 8.33 (s, 1H), 7.72 (s, 1H), 7.53 (d, J=8.5 Hz, 2H), 7.31 (d, J=8.5 Hz, 2H), 3.93 (t, J=11.8 Hz, 2H), 3.29 (s, 2H), 2.94 (s, 1H), 2.02 (s, 3H), 1.96 (s, 1H), 1.77 (t, J=11.4 Hz, 3H), 1.67 (s, 1H), 1.57 (d, J=17.2 Hz, 2H), 1.50-1.32 (m, 3H) ppm; LC-MS: m/z 396.2 [M+H]$^+$.

Example 49-2: (R)-8-(8-((4-aminophenyl)thio)-[1,2,4]triazolo[4,3-c]pyrimidin-5-yl)-8-azaspiro[4.5]decan-1-amine

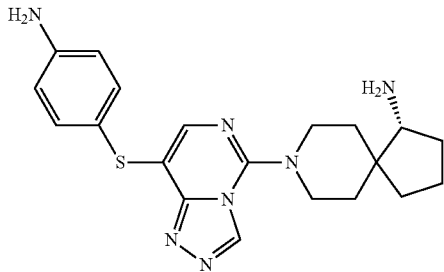 [SMILES: Nc1ccc(Sc2cnc(N3CCC4(CCC[C@H]4N)CC3)n3cnnc23)cc1]

$^1$H NMR (400 MHz, DMSO-d$_6$) δ 9.26 (d, J=15.3 Hz, 1H), 8.37 (s, 1H), 7.23 (dd, J=33.3, 27.4 Hz, 3H), 6.55 (t, J=20.4 Hz, 2H), 3.78 (dd, J=35.2, 22.6 Hz, 4H), 3.26-3.16 (m, 2H), 3.01 (t, J=6.5 Hz, 1H), 1.98 (d, J=10.5 Hz, 1H), 1.89-1.19 (m, 9H) ppm; LC-MS: m/z 396.1 [M+H]$^+$.

Example 50-2: (R)-8-(8-((3-amino-2-chlorophenyl)thio)-[1,2,4]triazolo[4,3-c]pyrimidin-5-yl)-8-azaspiro[4.5]decan-1-amine

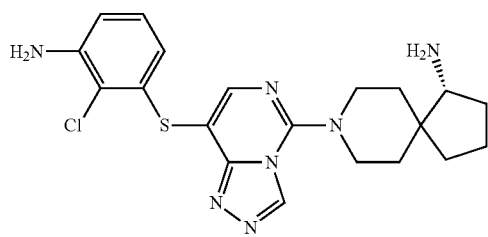 [SMILES: Nc1cccc(Sc2cnc(N3CCC4(CCC[C@H]4N)CC3)n3cnnc23)c1Cl]

$^1$H NMR (400 MHz, DMSO-d$_6$) δ 9.35 (s, 1H), 8.32 (s, 1H), 7.87 (s, 1H), 6.80 (t, J=7.9 Hz, 1H), 6.59 (d, J=7.1 Hz, 1H), 6.01 (d, J=6.9 Hz, 1H), 5.51 (s, 2H), 4.03 (t, J=12.0 Hz, 2H), 3.39 (s, 2H), 2.96 (t, J=6.7 Hz, 1H), 1.96-1.44 (m, 10H) ppm; LC-MS: m/z 430.1 [M+H]$^+$.

Example 51-2: (R)—N-(3-((5-(1-amino-8-azaspiro[4.5]decan-8-yl)-[1,2,4]triazolo[4,3-c]pyrimidin-8-yl) thio)-2-chlorophenyl)acrylamide

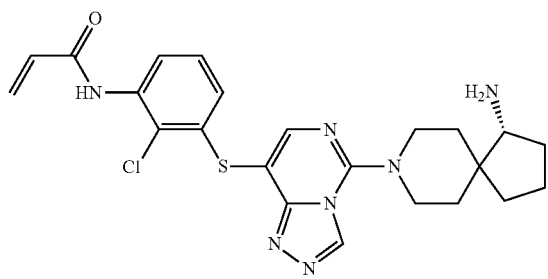 [SMILES: C=CC(=O)Nc1cccc(Sc2cnc(N3CCC4(CCC[C@H]4N)CC3)n3cnnc23)c1Cl]

$^1$H NMR (400 MHz, DMSO-d$_6$) δ 9.86 (s, 1H), 9.38 (s, 1H), 8.34 (s, 1H), 7.97 (s, 1H), 7.53 (d, J=7.7 Hz, 1H), 7.12 (t, J=8.0 Hz, 1H), 6.71-6.59 (m, 2H), 6.29 (dd, J=17.1, 1.8 Hz, 1H), 5.83-5.77 (m, 1H), 4.13-4.03 (m, 2H), 3.53 (s, 2H), 2.94 (s, 1H), 1.92-1.40 (m, 10H) ppm; LC-MS: m/z 484.1 [M+H]$^+$.

Example 52-2: (R)-8-(8-(pyridin-2-ylthio)-[1,2,4]triazolo[4,3-c]pyrimidin-5-yl)-8-azaspiro[4.5]decan-1-amine

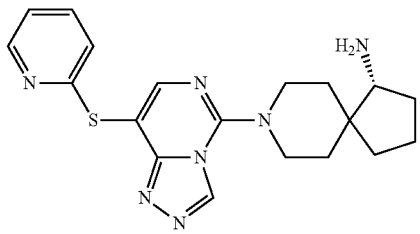 [SMILES: N[C@@H]1CCCC12CCN(c1ncc(Sc3ccccn3)c3nncn13)CC2]

$^1$H NMR (400 MHz, DMSO-d$_6$) δ 9.36 (s, 1H), 8.36 (d, J=4.7 Hz, 1H), 7.96 (s, 1H), 7.59 (t, J=7.7 Hz, 1H), 7.13 (d, J=2.3 Hz, 1H), 7.03 (d, J=8.0 Hz, 1H), 4.10-3.90 (m, 2H), 3.40 (d, J=11.0 Hz, 2H), 2.82 (s, 1H), 1.59 (ddd, J=23.4, 10.6, 4.0 Hz, 10H) ppm; LC-MS: m/z 382.1 [M+H]$^+$.

Example 53-2: (R)-8-(8-((3-chloropyridin-4-yl)thio)-[1,2,4]triazolo[4,3-c]pyrimidin-5-yl)-8-azaspiro[4.5]decan-1-amine

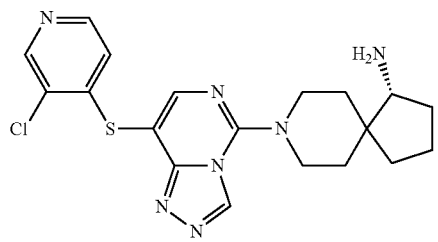 [SMILES: N[C@@H]1CCCC12CCN(c1ncc(Sc3ccncc3Cl)c3nncn13)CC2]

$^1$H NMR (400 MHz, DMSO-d$_6$) δ 9.41 (s, 1H), 8.56 (s, 1H), 8.28 (s, 1H), 8.19 (d, J=5.3 Hz, 1H), 8.04 (s, 1H), 6.84 (d, J=5.3 Hz, 1H), 4.11 (t, J=12.3 Hz, 2H), 3.43 (s, 2H), 3.00 (t, J=6.7 Hz, 1H), 1.99-1.43 (m, 10H) ppm; LC-MS: m/z 416.1 [M+H]$^+$.

Example 54-2: (R)-8-(8-((2,3-dichloropyridin-4-yl)thio)-[1,2,4]triazolo[4,3-c]pyrimidin-5-yl)-8-azaspiro[4.5]decan-1-amine

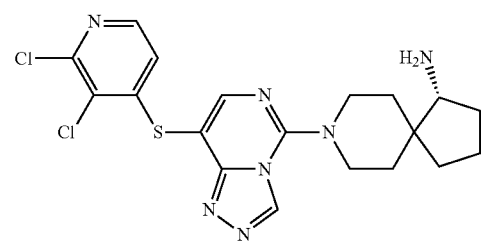 [SMILES: N[C@@H]1CCCC12CCN(c1ncc(Sc3ccnc(Cl)c3Cl)c3nncn13)CC2]

¹HNMR (CD₃OD-d₄) δ 9.42 (s, 1H), 8.34 (s, 1H), 8.03-8.05 (m, 2H), 6.88-6.89 (m, 1H), 4.11-4.12 (m, 2H), 3.44-3.47 (m, 2H), 2.89 (m, 1H), 1.71-2.05 (m, 4H), 1.35-1.68 (m, 6H) ppm; LC-MS: m/z 449.8 [M+H]⁺.

Example 55-2: (R)-8-(8-((3-chloro-2-methylpyridin-4-yl)thio)-[1,2,4]triazolo[4,3-c]pyrimidin-5-yl)-8-azaspiro[4.5]decan-1-amine

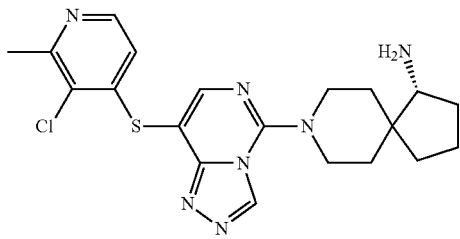 [SMILES: Cc1nccc(Sc2cnc(N3CCC4(CCC[C@H]4N)CC3)n3cnnc23)c1Cl]

¹H NMR (400 MHz, DMSO-d₆) δ 9.41 (s, 1H), 8.31 (s, 1H), 8.05 (d, J=5.4 Hz, 1H), 8.02 (s, 1H), 6.67 (d, J=5.3 Hz, 1H), 4.10 (t, J=12.9 Hz, 2H), 3.46-3.40 (m, 2H), 3.01 (s, 1H), 1.99 (s, 1H), 1.88-1.66 (m, 4H), 1.65-1.39 (m, 5H) ppm; LC-MS: m/z 430.1 [M+H]⁺.

Example 56-2: (R)-8-(8-((3-chloro-2-(dimethylamino)pyridin-4-yl)thio)-[1,2,4]triazolo[4,3-c]pyrimidin-5-yl)-8-azaspiro[4.5]decan-1-amine

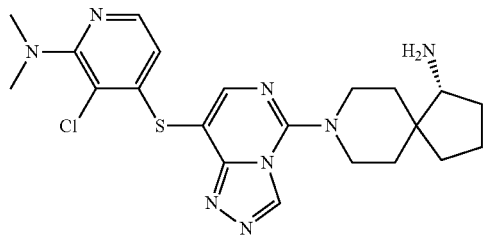 [SMILES: CN(C)c1nccc(Sc2cnc(N3CCC4(CCC[C@H]4N)CC3)n3cnnc23)c1Cl]

¹H NMR (400 MHz, DMSO-d₆) δ 9.38 (s, 1H), 7.98 (d, J=4.2 Hz, 1H), 7.82 (d, J=5.3 Hz, 1H), 6.31 (d, J=5.3 Hz, 1H), 4.16-3.94 (m, 2H), 3.41 (dd, J=15.8, 12.6 Hz, 2H), 2.91 (s, 6H), 2.84 (dd, J=13.1, 5.9 Hz, 1H), 1.90-1.36 (m, 10H) ppm; LC-MS: m/z 459.1 [M+H]⁺.

Example 57-2: (R)-8-(8-((2-amino-5-chloropyridin-4-yl)thio)-[1,2,4]triazolo[4,3-c]pyrimidin-5-yl)-8-azaspiro[4.5]decan-1-amine

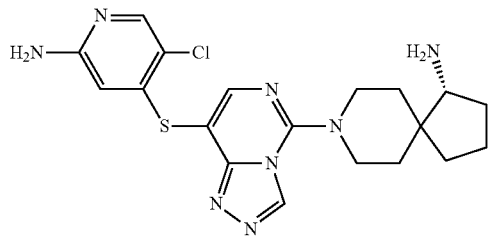 [SMILES: Nc1cc(Sc2cnc(N3CCC4(CCC[C@H]4N)CC3)n3cnnc23)c(Cl)cn1]

¹H NMR (400 MHz, DMSO-d₆) δ 9.45 (s, 1H), 8.37 (s, 1H), 7.99 (s, 1H), 6.56 (s, 1H), 5.78 (s, 2H), 5.59 (s, 1H), 3.98 (s, 2H), 3.72 (s, 1H), 3.63 (d, J=8.3 Hz, 1H), 3.12 (s, 1H), 1.67 (d, J=79.0 Hz, 10H) ppm; LC-MS: m/z 432.1 [M+H]⁺.

Example 58-2: (R)-8-(8-((6-amino-2,3-dichloropyridin-4-yl)thio)-[1,2,4]triazolo[4,3-c]pyrimidin-5-yl)-8-azaspiro[4.5]decan-1-amine

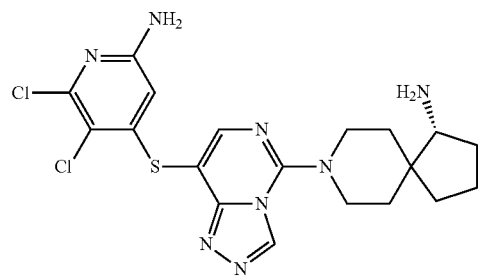 [SMILES: Nc1cc(Sc2cnc(N3CCC4(CCC[C@H]4N)CC3)n3cnnc23)c(Cl)c(Cl)n1]

¹H NMR (400 MHz, DMSO-d₆) δ 9.46 (s, 1H), 8.30 (s, 1H), 8.03 (s, 1H), 6.31 (s, 2H), 5.71 (s, 1H), 4.11 (t, J=12.1 Hz, 2H), 3.44 (d, J=12.4 Hz, 2H), 2.92 (d, J=7.5 Hz, 1H), 1.96-1.77 (m, 4H), 1.70-1.64 (m, 2H), 1.56-1.40 (m, 4H). LC-MS: m/z 465.1 [M+H]⁺.

Example 59-2: (R)-8-(8-((2-methylpyridin-3-yl)thio)-[1,2,4]triazolo[4,3-c]pyrimidin-5-yl)-8-azaspiro decan-1-amine

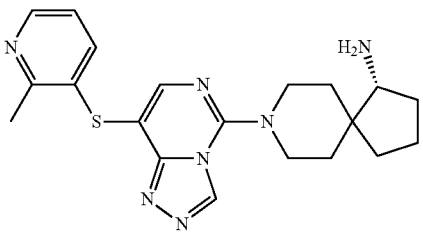 [SMILES: Cc1ncccc1Sc1cnc(N2CCC3(CCC[C@H]3N)CC2)n2cnnc12]

¹H NMR (400 MHz, DMSO-d₆) δ 9.35 (s, 1H), 8.26 (dd, J=4.7, 1.5 Hz, 1H), 7.91 (d, J=3.0 Hz, 1H), 7.31 (dd, J=8.0, 1.4 Hz, 1H), 7.07 (dd, J=7.9, 4.7 Hz, 1H), 4.05-3.94 (m, 2H), 3.30 (s, 3H), 2.80 (t, J=7.3 Hz, 1H), 2.61 (s, 3H), 1.89-1.25 (m, 10H) ppm; LC-MS: m/z 449.8 [M+H]⁺.

Example 60-2: (R)-8-(8-((2-(trifluoromethyl)pyridin-3-yl)thio)-[1,2,4]triazolo[4,3-c]pyrimidin-5-yl)-8-azaspiro[4.5]decan-1-amine

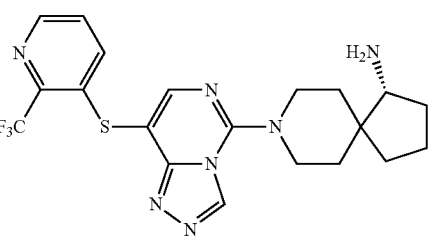

¹H NMR (400 MHz, DMSO-d₆) δ 9.38 (s, 1H), 8.49 (d, J=4.5 Hz, 1H), 8.36 (s, 1H), 8.02 (s, 1H), 7.57 (d, J=8.3 Hz,

1H), 7.46 (dd, J=8.3, 4.5 Hz, 1H), 4.08 (s, 2H), 2.94 (s, 2H), 1.98 (dd, J=14.4, 7.7 Hz, 2H), 1.88-1.64 (m, 4H), 1.52 (d, J 42.8 Hz, 6H) ppm; LC-MS: m/z 450.1 [M+H]⁺.

Example 61-2: (R)-8-(8-(naphthalen-1-ylthio)-[1,2,4]triazolo[4,3-c]pyrimidin-5-yl)-8-azaspiro[4.5]decan-1-amine

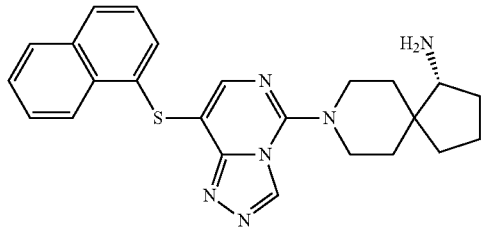 [SMILES: N[C@@H]1CCCC12CCN(c1ncc(Sc3cccc4ccccc34)c3nncn13)CC2]

¹H NMR (400 MHz, DMSO-d₆) δ 9.33 (s, 1H), 8.39 (d, J=8.2 Hz, 1H), 8.27 (d, J=11.7 Hz, 1H), 8.00 (d, J=7.7 Hz, 1H), 7.88 (d, J=7.9 Hz, 1H), 7.73 (s, 1H), 7.69-7.59 (m, 2H), 7.47 (d, J=7.1 Hz, 1H), 7.44-7.38 (m, 1H), 4.03-3.92 (m, 2H), 3.28 (s, 2H), 2.97 (s, 1H), 1.68 (dt, J=107.3, 31.9 Hz, 10H) ppm; LC-MS: m/z 431.2 [M+H]⁺.

Example 62-2: (R)-8-(8-(quinolin-4-ylthio)-[1,2,4]triazolo[4,3-c]pyrimidin-5-yl)-8-azaspiro[4.5]decan-1-amine

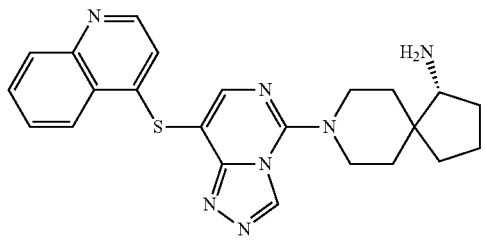 [SMILES: N[C@@H]1CCCC12CCN(c1ncc(Sc3ccnc4ccccc34)c3nncn13)CC2]

¹H NMR (400 MHz, DMSO-d₆) δ 9.40 (s, 1H), 8.54 (d, J=4.7 Hz, 1H), 8.26 (d, J=8.4 Hz, 1H), 8.11-7.99 (m, 2H), 7.85 (t, J=7.6 Hz, 1H), 7.74 (t, J=7.6 Hz, 1H), 6.95 (d, J=4.7 Hz, 1H), 4.19-3.99 (m, 2H), 3.43 (dd, J=17.3, 8.7 Hz, 2H), 2.88 (t, J=7.0 Hz, 1H), 1.94-1.37 (m, 10H) ppm; LC-MS: m/z 432.2 [M+H]⁺.

Example 63-2: (R)-8-(8-((1-methyl-1H-imidazol-2-yl)thio)-[1,2,4]triazolo[4,3-c]pyrimidin-5-yl)-8-azaspiro[4.5]decan-1-amine

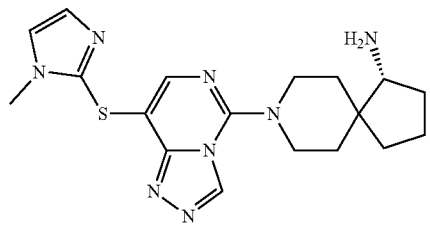 [SMILES: Cn1ccnc1Sc1cnc(N2CCC3(CCC[C@H]3N)CC2)n2cnnc12]

¹H NMR (400 MHz, DMSO-d₆) δ 9.33 (s, 1H), 7.54 (s, 1H), 7.37 (d, J=1.2 Hz, 1H), 6.97 (d, J=1.2 Hz, 1H), 3.85 (d, J=2.4 Hz, 5H), 3.29-3.20 (m, 2H), 2.73 (t, J=7.3 Hz, 1H), 1.87-1.71 (m, 4H), 1.63-1.49 (m, 2H), 1.42-1.25 (m, 4H) ppm; LC-MS: m/z 385.2 [M+H]⁺.

Example 64-2: (1R)-8-(8-((2,3-dichloropyridin-4-yl)thio)-[1,2,4]triazolo[4,3-c]pyrimidin-5-yl)-3-methyl-8-azaspiro[4.5]decan-1-amine

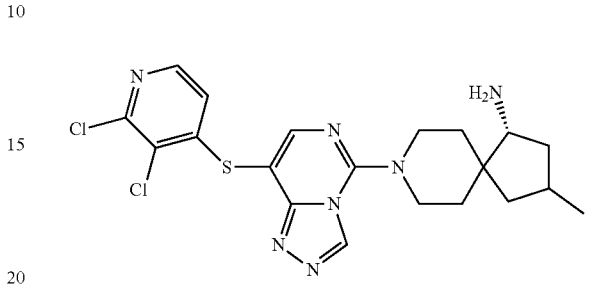

¹H NMR (400 MHz, DMSO-d₆) δ 9.41 (s, 1H), 8.25 (s, 1H), 8.04 (d, J=5.3 Hz, 1H), 8.02 (s, 1H), 6.67 (d, J=5.3 Hz, 1H), 4.02-3.96 (m, 2H), 3.73 (d, J=8.4 Hz, 1H), 3.64 (d, J=8.5 Hz, 1H), 3.52 (d, J=10.0 Hz, 2H), 3.18-3.09 (m, 3H), 2.56 (s, 3H), 1.84 (dd, J=40.8, 9.5 Hz, 2H), 1.57 (d, J=12.5 Hz, 2H) ppm; LC-MS: m/z 434.1 [M+H]⁺.

Example 65-2: (1R)-8-(8-((2-amino-3-chloropyridin-4-yl)thio)-[1,2,4]triazolo[4,3-c]pyrimidin-5-yl)-3-methyl-8-azaspiro[4.5]decan-1-amine

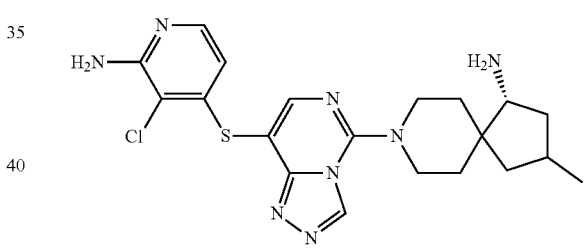

¹H NMR (CD₃OD-d₄) δ 9.37 (s, 1H), 7.98 (s, 1H), 7.57 (s, 1H), 6.36 (m, 2H), 5.93 (m, 1H), 4.16 (m, 2H), 3.44 (m, 2H), 3.10 (m, 1H), 2.42 (m, 1H), 1.31-2.13 (m, 8H), 1.01-1.05 (m, 3H) ppm; LC-MS: m/z 445.1 M+H]⁺.

Example 66-2: (1R)-8-(8-((6-amino-2,3-dichloropyridin-4-yl)thio)-[1,2,4]triazolo[4,3-c]pyrimidin-5-yl)-3-methyl-8-azaspiro[4.5]decan-1-amine

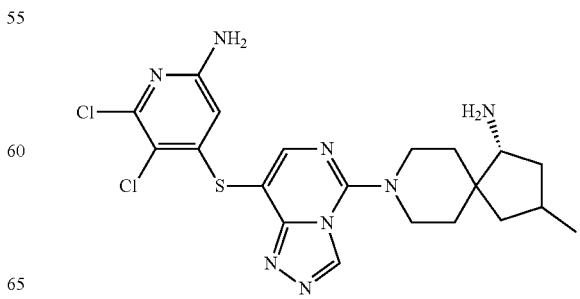

¹H NMR (CD₃OD-d₄) δ 9.45-9.46 (m, 1H), 8.04 (s, 1H), 6.32 (m, 2H), 5.74 (m, 1H), 4.14-4.17 (m, 2H), 3.45 (m, 2H), 3.14 (m, 2H), 1.45-2.41 (m, 8H), 1.02-1.05 (m, 3H) ppm; LC-MS: m/z 479.1 M+H⁺.

Example 67-2: (S)-8-(8-((2,3-dichloropyridin-4-yl)thio)-[1,2,4]triazolo[4,3-c]pyrimidin-5-yl)-2-oxa-8-azaspiro[4.5]decan-4-amine

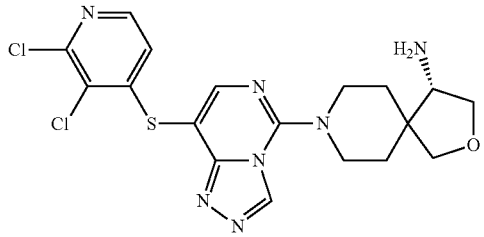 [SMILES: N[C@@H]1COCC12CCN(c1ncc(Sc3ccnc(Cl)c3Cl)c3nncn13)CC2]

¹H NMR (400 MHz, DMSO-d₆) δ 9.43 (s, 1H), 8.08-7.99 (m, 2H), 6.88 (d, J=5.3 Hz, 1H), 4.08-3.95 (m, 3H), 3.75-3.66 (m, 2H), 3.51 (d, J=13.6 Hz, 2H), 3.24-3.15 (m, 2H), 1.93-1.75 (m, 2H), 1.60 (d, J=13.1 Hz, 2H), 1.32 (s, 2H) ppm; LC-MS: m/z 452.1 [M+H]⁺.

Example 68-2: (S)-8-(8-((2-amino-3-chloropyridin-4-yl)thio)-[1,2,4]triazolo[4,3-c]pyrimidin-5-yl)-2-oxa-8-azaspiro[4.5]decan-4-amine

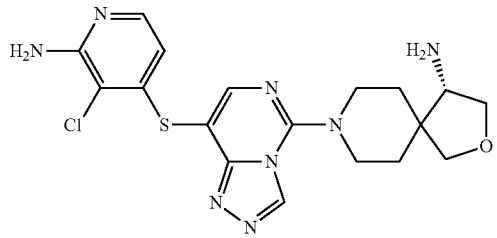 [SMILES: Nc1nccc(Sc2cnc(N3CCC4(CC3)COC[C@H]4N)n3cnnc23)c1Cl]

¹H NMR (400 MHz, DMSO-d₆) δ 9.38 (s, 1H), 8.28 (s, 1H), 7.97 (s, 1H), 7.57 (d, J=5.4 Hz, 1H), 6.34 (s, 2H), 5.95 (d, J=5.4 Hz, 1H), 3.97 (tt, J=13.8, 5.4 Hz, 3H), 3.72 (d, J=8.5 Hz, 1H), 3.64 (d, J=8.4 Hz, 1H), 3.49 (dq, J=10.7, 4.4, 2.9 Hz, 2H), 3.14 (t, J=5.9 Hz, 2H), 1.93-1.74 (m, 2H), 1.57 (dt, J=14.0, 4.3 Hz, 2H) ppm; LC-MS: m/z 433.1 [M+H]⁺.

Example 69-2: (S)-8-(8-((3-chloro-2-methylpyridin-4-yl)thio)-[1,2,4]triazolo[4,3-c]pyrimidin-5-yl)-2-oxa-8-azaspiro[4.5]decan-4-amine

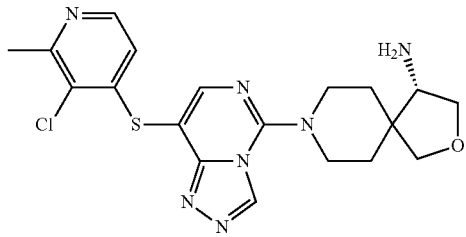 [SMILES: Cc1nccc(Sc2cnc(N3CCC4(CC3)COC[C@H]4N)n3cnnc23)c1Cl]

¹H NMR (400 MHz, DMSO-d₆) δ 9.41 (s, 1H), 8.25 (s, 1H), 8.04 (d, J=5.3 Hz, 1H), 8.02 (s, 1H), 6.67 (d, J=5.3 Hz, 1H), 4.02-3.96 (m, 2H), 3.73 (d, J=8.4 Hz, 1H), 3.64 (d, J=8.5 Hz, 1H), 3.52 (d, J=10.0 Hz, 2H), 3.18-3.09 (m, 3H), 2.56 (s, 3H), 1.84 (dd, J=40.8, 9.5 Hz, 2H), 1.57 (d, J=12.5 Hz, 2H) ppm; LC-MS: m/z 434.1 M+H⁺.

Example 70-2: (S)-8-(8-((6-amino-2,3-dichloropyridin-4-yl)thio)-[1,2,4]triazolo[4,3-c]pyrimidin-5-yl)-2-oxa-8-azaspiro[4.5]decan-4-amine

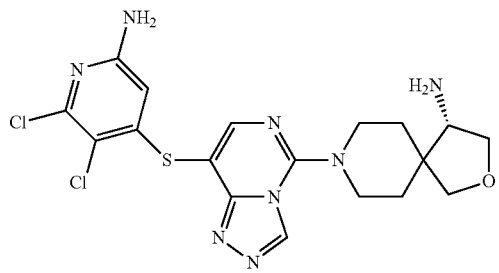 [SMILES: Nc1cc(Sc2cnc(N3CCC4(CC3)COC[C@H]4N)n3cnnc23)c(Cl)c(Cl)n1]

¹H NMR (400 MHz, DMSO-d₆) δ 9.47 (s, 1H), 8.25 (s, 1H), 8.04 (s, 1H), 6.30 (s, 2H), 5.71 (s, 1H), 4.09-3.92 (m, 4H), 3.73 (d, J=8.4 Hz, 1H), 3.65 (d, J=8.4 Hz, 1H), 3.49 (s, 2H), 3.16 (d, J=6.6 Hz, 1H), 1.88 (d, J=10.0 Hz, 2H), 1.59 (s, 2H) ppm; LC-MS: m/z 468 [M+H]⁺.

Example 71-2: (3S,4S)-8-(8-((2,3-dichloropyridin-4-yl)thio)-[1,2,4]triazolo[4,3-c]pyrimidin-5-yl)-3-methyl-2-oxa-8-azaspiro[4.5]decan-4-amine

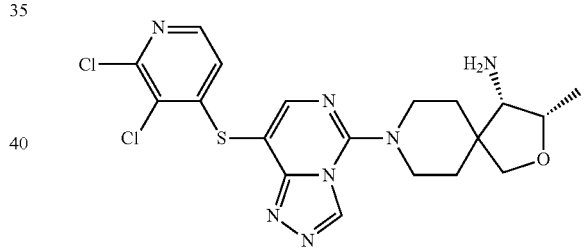

¹H NMR (400 MHz, DMSO-d₆) δ 9.38 (s, 1H), 8.09-7.93 (m, 2H), 6.84 (d, J=5.3 Hz, 1H), 4.10 (q, J=6.1 Hz, 2H), 3.91 (dd, J=13.8, 5.5 Hz, 4H), 3.56 (m, 1H), 2.98 (d, J=5.0 Hz, 1H), 1.98-1.55 (m, 4H), 1.10 (d, J=6.3 Hz, 3H) ppm; LC-MS: m/z 466.1 [M+H]⁺.

Example 72-2: (3S,4S)-8-(8-((3-chloro-2-methylpyridin-4-yl)thio)-[1,2,4]triazolo[4,3-c]pyrimidin-5-yl)-3-methyl-2-oxa-8-azaspiro[4.5]decan-4-amine

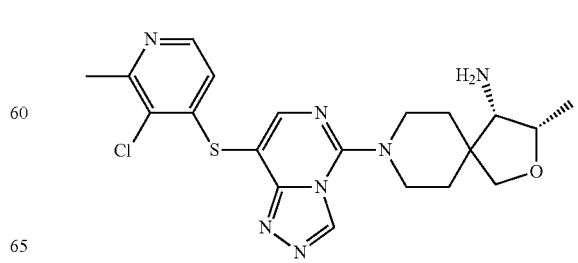

¹H NMR (400 MHz, DMSO-d₆) δ 9.41 (s, 1H), 8.04 (d, J=5.4 Hz, 1H), 8.01 (s, 1H), 6.67 (d, J=5.3 Hz, 1H), 4.12-4.06 (m, 1H), 3.86 (s, 2H), 3.69 (d, J=8.4 Hz, 1H), 3.60 (dd, J=21.1, 9.5 Hz, 2H), 3.52 (d, J=8.5 Hz, 1H), 2.96 (d, J=4.9 Hz, 1H), 2.56 (s, 3H), 1.88 (d, J=48.6 Hz, 2H), 1.64 (s, 2H), 1.08 (dd, J=15.3, 6.5 Hz, 3H) ppm; LC-MS: m/z 446.1 [M+H]⁺.

Example 73-2: (3S,4S)-8-(8-((2-amino-5-chloro-pyridin-4-yl)thio)-[1,2,4]triazolo[4,3-c]pyrimidin-5-y 1)-3-methyl-2-oxa-8-azaspiro[4.5]decan-4-amine

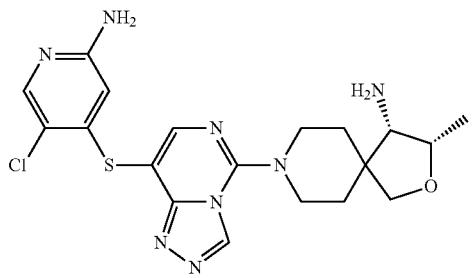 [SMILES: C[C@@H]1OCC2(CCN(c3ncc(Sc4cc(N)ncc4Cl)c4nncn34)CC2)[C@@H]1N]

¹H NMR (400 MHz, DMSO-d₆) δ 9.41 (s, 1H), 7.99 (s, 1H), 7.82 (s, 1H), 5.83 (s, 2H), 5.76 (s, 1H), 4.14 (p, J=6.3 Hz, 2H), 3.96 (ddd, J=15.1, 10.0, 5.1 Hz, 4H), 3.60 (s, 1H), 3.14 (d, J=5.0 Hz, 1H), 1.97-1.62 (m, 4H), 1.13 (t, J=5.9 Hz, 3H) ppm; LC-MS: m/z 447.1 [M+H]⁺.

Example 74-2: (3S,4S)-8-(8-((2-amino-3-chloro-pyridin-4-yl)thio)-[1,2,4]triazolo[4,3-c]pyrimidin-5-y 1)-3-methyl-2-oxa-8-azaspiro[4.5]decan-4-amine

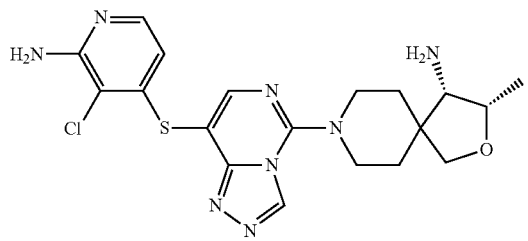 [SMILES: C[C@@H]1OCC2(CCN(c3ncc(Sc4ccnc(N)c4Cl)c4nncn34)CC2)[C@@H]1N]

¹H NMR (CD₃D-d₄) δ 9.39 (s, 1H), 7.97 (s, 1H), 7.57 (s, 1H), 6.35 (m, 2H), 5.95 (m, 1H), 4.09-4.11 (m, 1H), 3.86-3.90 (m, 2H), 3.70-3.72 (m, 1H), 3.54-3.62 (m, 3H), 3.00-3.02 (m, 1H), 1.93-1.95 (m, 1H), 1.80-1.83 (m, 1H), 1.60-1.70 (m, 2H), 1.10-1.12 (m, 3H) ppm; LC-MS: m/z 447.1 [M+H]⁺.

Example 75-2: (3S,4S)-8-(8-((6-amino-2,3-dichloro-pyridin-4-yl)thio)-[1,2,4]triazolo[4,3-c]pyrimidin-5-yl)-3-methyl-2-oxa-8-azaspiro[4.5]decan-4-amine

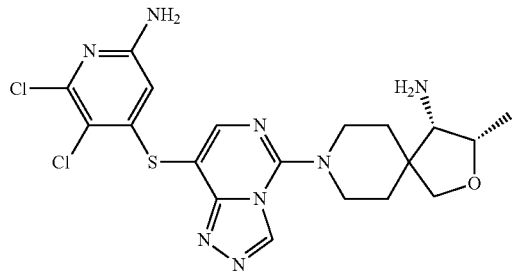 [SMILES: C[C@@H]1OCC2(CCN(c3ncc(Sc4cc(N)nc(Cl)c4Cl)c4nncn34)CC2)[C@@H]1N]

¹H NMR (400 MHz, DMSO-d₆) δ 9.49 (s, 1H), 8.06 (s, 1H), 6.31 (s, 2H), 5.71 (s, 1H), 4.26-4.19 (m, 1H), 4.06 (s, 2H), 3.88 (d, J=9.1 Hz, 1H), 3.71 (d, J=8.8 Hz, 1H), 3.57-3.37 (m, 4H), 1.91 (s, 2H), 1.69 (s, 2H), 1.21 (d, J=6.4 Hz, 3H) ppm; LC-MS: m/z 481.1 [M+H]⁺.

Example 76-2: (3R,4S)-8-(8-((3-chloro-2-methylpyridin-4-yl)thio)-[1,2,4]triazolo[4,3-c]pyrimidin-5-yl)-3-methyl-2-oxa-8-azaspiro[4.5]decan-4-amine

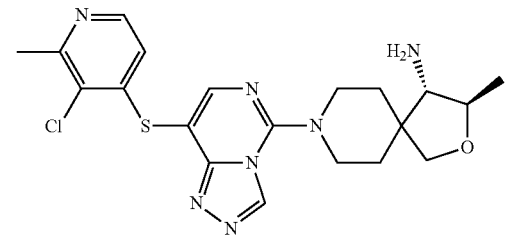

¹H NMR (400 MHz, DMSO-d₆) δ 9.41 (d, J=5.4 Hz, 1H), 8.04 (d, J=5.3 Hz, 1H), 8.01 (s, 1H), 6.67 (d, J=5.2 Hz, 1H), 4.12 (dd, J=33.3, 13.6 Hz, 2H), 3.73 (dd, J=23.6, 8.8 Hz, 2H), 3.39 (dd, J=16.2, 10.4 Hz, 2H), 3.30 (s, 1H), 2.54 (d, J=16.4 Hz, 3H), 2.42 (d, J=8.2 Hz, 1H), 1.93-1.81 (m, 2H), 1.50 (d, J=13.5 Hz, 2H), 1.21 (d, J=6.0 Hz, 3H) ppm; LC-MS: m/z 446.1 [M+H]⁺.

Example 77-2: (3R,4R)-8-(8-((2-amino-3-chloro-pyridin-4-yl)thio)-[1,2,4]triazolo[4,3-c]pyrimidin-5-y 1)-3-methyl-2-oxa-8-azaspiro[4.5]decan-4-amine

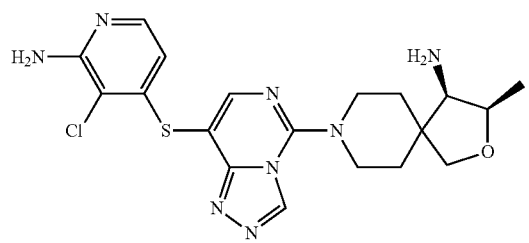 [SMILES: C[C@H]1OCC2(CCN(c3ncc(Sc4ccnc(N)c4Cl)c4nncn34)CC2)[C@H]1N]

¹H NMR (400 MHz, DMSO-d₆) δ 9.35 (s, 1H), 7.95 (s, 1H), 7.55 (d, J=5.4 Hz, 1H), 6.27 (s, 2H), 5.95 (d, J=5.4 Hz,

1H), 4.08 (p, J=6.3 Hz, 2H), 3.85-3.81 (m, 2H), 3.55 (s, 2H), 2.95 (d, J=5.0 Hz, 1H), 1.99-1.56 (m, 5H), 1.09 (d, J=6.4 Hz, 3H) ppm; LC-MS: m/z 447.1 [M+H]⁺.

Example 78-2: 1-(8-((2,3-dichlorophenyl)thio)-[1,2,4]triazolo[1,5-c]pyrimidin-5-yl)-4-methylpiperidin-4-amine

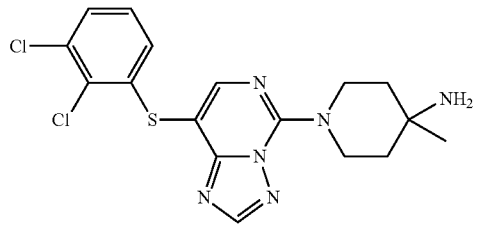 [SMILES: CC1(N)CCN(c2ncc(Sc3cccc(Cl)c3Cl)c3ncnn23)CC1]

¹H NMR (400 MHz, DMSO-d₆) δ 8.48 (s, 1H), 8.23 (s, 1H), 7.40 (dd, J=8.0, 1.2 Hz, 1H), 7.12 (t, J=8.0 Hz, 1H), 6.74 (dd, J=8.1, 1.2 Hz, 1H), 4.54-4.30 (m, 2H), 4.15-3.94 (m, 2H), 1.76-1.48 (m, 4H), 1.18 (s, 3H) ppm; LC-MS: m/z 409.1 [M+H]⁺.

Example 79-2: (R)-1-(8-((2,3-dichlorophenyl)thio)-[1,2,4]triazolo[1,5-c]pyrimidin-5-yl)azepan-4-amine

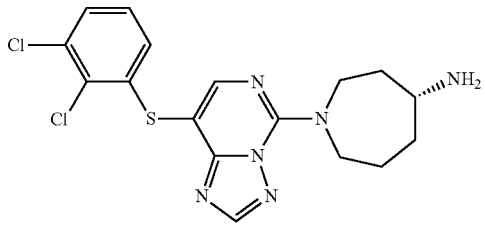 [SMILES: N[C@@H]1CCCN(c2ncc(Sc3cccc(Cl)c3Cl)c3ncnn23)CC1]

¹H NMR (400 MHz, DMSO-d₆) δ 8.47 (s, 1H), 8.21 (s, 1H), 7.41 (d, J=7.5 Hz, 1H), 7.13 (t, J=8.1 Hz, 1H), 6.74 (d, J=7.9 Hz, 1H), 4.15 (dd, J=90.0, 47.9 Hz, 4H), 3.21 (s, 2H), 2.22 (s, 1H), 1.94 (d, J=56.0 Hz, 5H), 1.61 (d, J=12.2 Hz, 1H) ppm; LC-MS: m/z 408.7 [M+H]⁺.

Example 80-2: (R)-3-(8-((2,3-dichlorophenyl)thio)-[1,2,4]triazolo[1,5-c]pyrimidin-5-yl)-3-azaspiro[4.5]undecan-7-amine

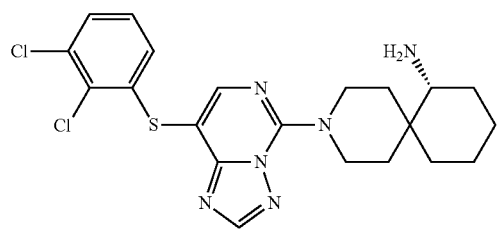 [SMILES: N[C@@H]1CCCCC12CCN(c1ncc(Sc3cccc(Cl)c3Cl)c3ncnn13)CC2]

¹H NMR (400 MHz, DMSO-d₆) δ 8.49 (s, 1H), 8.24 (s, 1H), 7.42 (d, J=7.1 Hz, 1H), 7.12 (t, J=8.0 Hz, 1H), 6.73 (d, J=8.0 Hz, 1H), 4.84 (s, 2H), 3.67-3.53 (m, 2H), 2.89 (d, J=4.3 Hz, 1H), 1.98 (dd, J=24.0, 13.1 Hz, 2H), 1.48 (ddd, J=74.9, 37.6, 6.9 Hz, 12H) ppm; LC-MS: m/z 462.7 [M+H]⁺.

Example 81-2: (3R,4S)-8-(8-((2,3-dichlorophenyl)thio)-[1,2,4]triazolo[1,5-c]pyrimidin-5-yl)-3-methyl-2-oxa-8-azaspiro[4.5]decan-4-amine

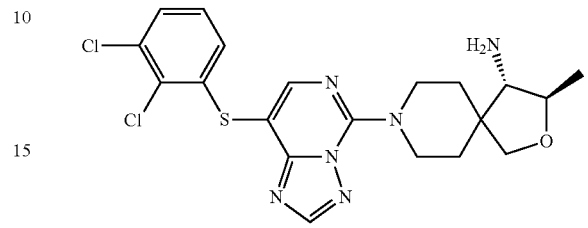

¹H NMR (400 MHz, DMSO-d₆) δ 8.48 (d, J=6.0 Hz, 1H), 8.23 (d, J=6.3 Hz, 1H), 7.41 (d, J=8.0 Hz, 1H), 7.12 (t, J=8.1 Hz, 1H), 6.74 (d, J=8.1 Hz, 1H), 4.95 (dd, J=37.1, 13.4 Hz, 2H), 3.76 (dd, J=26.2, 8.9 Hz, 2H), 3.44 (d, J=7.8 Hz, 1H), 2.42 (d, J=8.1 Hz, 1H), 1.82 (t, J=11.6 Hz, 2H), 1.50 (d, J=13.6 Hz, 2H), 1.28-1.17 (m, 5H) ppm; LC-MS: m/z 465.1 [M+H]⁺.

Example 82-2: (S)-8-(8-((2,3-dichlorophenyl)thio)-[1,2,4]triazolo[1,5-c]pyrimidin-5-yl)-2-oxa-8-azaspiro[4.5]decan-4-amine

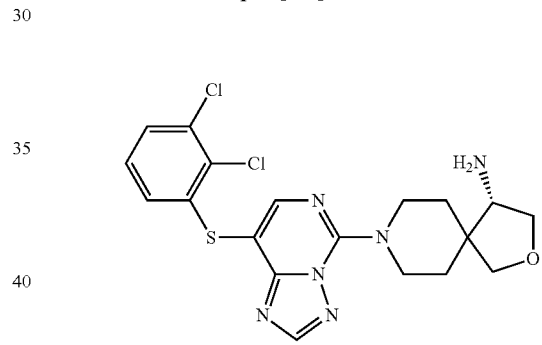

¹H NMR (400 MHz, DMSO-d₆) δ 8.48 (s, 1H), 8.32 (s, 1H), 8.24 (s, 1H), 7.41 (dd, J=8.0, 1.2 Hz, 1H), 7.13 (t, J=8.0 Hz, 1H), 6.72 (dd, J=8.0, J=1.6 Hz, 1H), 4.76 (t, J=16.0 Hz, 2H), 4.06 (dd, J=9.6 Hz, 2.4 Hz, 1H), 3.81 (s, 2H), 3.67-3.54 (m, 3H), 3.35 (t, J=4.8 Hz, 1H), 1.87-1.81 (m, 2H), 1.68-1.65 (m, 2H) ppm; LC-MS: m/z 451.1 [M+H]⁺.

Example 83-2: (3R,4R)-8-(8-((2,3-dichlorophenyl)thio)-[1,2,4]triazolo[1,5-c]pyrimidin-5-yl)-3-methyl-2-oxa-8-azaspiro[4.5]decan-4-amine

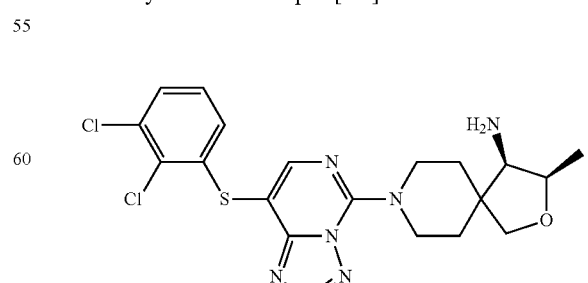

¹H NMR (400 MHz, DMSO-d₆) δ 8.48 (s, 1H), 8.23 (s, 1H), 7.41 (d, J=8.0 Hz, 1H), 7.12 (t, J=8.1 Hz, 1H), 6.74 (d, J=8.1 Hz, 1H), 4.45 (d, J=13.1 Hz, 2H), 4.11-4.05 (m, 2H), 3.96-3.80 (m, 2H), 2.96 (d, J=5.1 Hz, 1H), 2.01-1.93 (m, 2H), 1.78-1.56 (m, 4H), 1.09 (d, J=6.4 Hz, 3H); LC-MS: m/z 465.1 [M+H]⁺.

Example 84-2: (R)-8-(8-(phenylthio)-[1,2,4]triazolo[1,5-c]pyrimidin-5-yl)-8-azaspiro[4.5]decan-1-amine

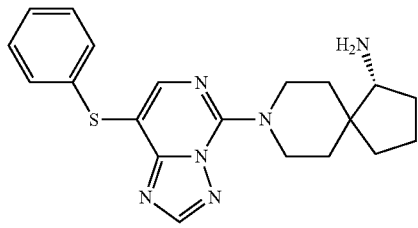

¹H NMR (400 MHz, DMSO-d₆) δ 8.49 (s, 1H), 8.17 (s, 1H), 7.29-7.24 (m, 2H), 7.18 (dd, J=12.1, 7.2 Hz, 3H), 4.86 (t, J=11.7 Hz, 2H), 3.44 (t, J=12.5 Hz, 2H), 3.01 (t, J=6.7 Hz, 1H), 1.97 (dd, J=12.7, 7.3 Hz, 1H), 1.85-1.41 (m, 9H) ppm; LC-MS: m/z 381.2 [M+H]⁺.

Example 85-2: (R)-8-(8-((2-methoxyphenyl)thio)-[1,2,4]triazolo[1,5-c]pyrimidin-5-yl)-8-azaspiro[4.5]decan-1-amine

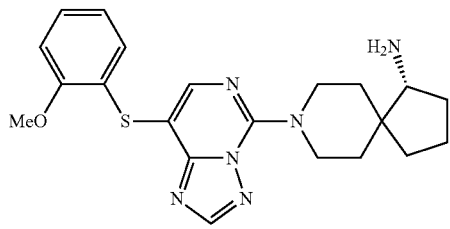 [SMILES: COc1ccccc1Sc1cnc(N2CCC3(CCC[C@H]3N)CC2)n2ncnc12]

¹H NMR (400 MHz, DMSO-d₆) δ 8.48 (s, 1H), 8.34 (s, 1H), 8.10 (s, 1H), 7.14 (t, J=7.8 Hz, 1H), 7.02 (d, J=8.2 Hz, 1H), 6.75 (t, J=7.6 Hz, 1H), 6.64 (d, J=7.7 Hz, 2H), 4.87 (d, J=12.5 Hz, 3H), 3.88 (s, 2H), 2.93 (d, J=7.2 Hz, 1H), 2.02-1.92 (m, 2H), 1.82-1.37 (m, 8H) ppm; LC-MS: m/z 411.1 [M+H]⁺.

Example 86-2: (R)-8-(8-((4-aminophenyl)thio)-[1,2,4]triazolo[1,5-c]pyrimidin-5-yl)-8-azaspiro[4.5]decan-1-amine

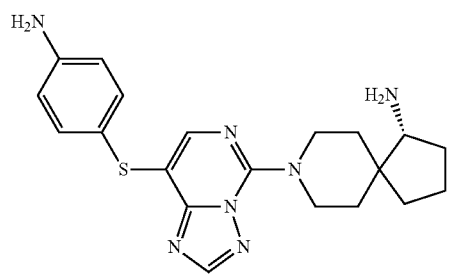 [SMILES: Nc1ccc(Sc2cnc(N3CCC4(CCC[C@H]4N)CC3)n3ncnc23)cc1]

¹H NMR (400 MHz, DMSO-d₆) δ 8.52 (s, 1H), 8.35 (s, 1H), 7.75 (s, 1H), 7.21 (d, J=8.2 Hz, 2H), 6.52 (d, J=8.4 Hz, 2H), 5.39 (s, 2H), 4.69 (s, 2H), 2.87 (s, 1H), 1.93-1.30 (m, 10H) ppm; LC-MS: m/z 396.2 [M+H]⁺.

Example 87-2: (R)-8-(8-((3-(trifluoromethyl)phenyl)thio)-[1,2,4]triazolo[1,5-c]pyrimidin-5-yl)-8-azaspiro[4.5]decan-1-amine

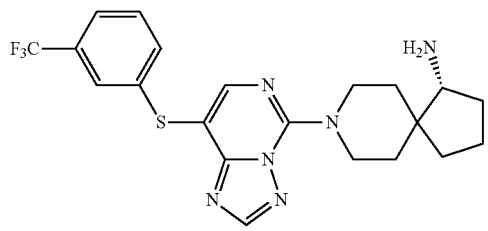 [SMILES: N[C@@H]1CCCC12CCN(c1ncc(Sc3cccc(C(F)(F)F)c3)c3ncnn13)CC2]

¹H NMR (400 MHz, DMSO-d₆) δ 8.47 (d, J=10.2 Hz, 1H), 8.22 (d, J=11.4 Hz, 1H), 7.57 (s, 1H), 7.54-7.36 (m, 3H), 4.97-4.72 (m, 2H), 3.47 (t, J=9.7 Hz, 2H), 2.72 (t, J=7.5 Hz, 1H), 1.83-1.26 (m, 10H); LC-MS: m/z 449.1 [M+H]⁺.

Example 88-2: (R)-8-(8-(pyridin-3-ylthio)-[1,2,4]triazolo[1,5-c]pyrimidin-5-yl)-8-azaspiro[4.5]decan-1-amine

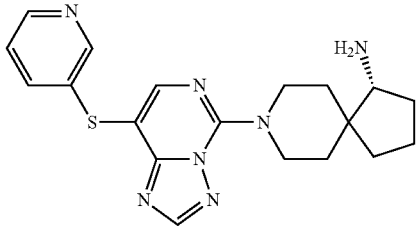 [SMILES: N[C@@H]1CCCC12CCN(c1ncc(Sc3cccnc3)c3ncnn13)CC2]

¹H NMR (400 MHz, DMSO-d₆) δ 8.49 (s, 1H), 8.36 (s, 1H), 8.17 (s, 1H), 7.27 (d, J=7.6 Hz, 2H), 7.23-7.13 (m, 3H), 4.86 (t, J=12.3 Hz, 2H), 3.47 (d, J=2.6 Hz, 2H), 2.96 (t, J=7.0 Hz, 1H), 1.98 (q, J=5.7, 4.2 Hz, 1H), 1.92-1.34 (m, 9H) ppm; LC-MS: m/z 382.2 [M+H]⁺.

Example 89-2: (R)-8-(8-((3-chloropyridin-4-yl)thio)-[1,2,4]triazolo[1,5-c]pyrimidin-5-yl)-8-azaspiro[4.5]decan-1-amine

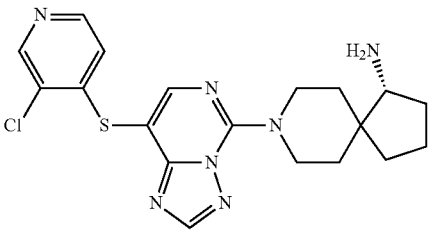

¹H NMR (CD₃D-d₄) δ 8.50-8.54 (m, 2H), 8.37 (s, 1H), 8.26 (m, 1H), 8.16-8.17 (s, 1H), 6.79-6.80 (m, 1H), 4.94 (m,

2H), 3.48-3.53 (m, 2H), 2.91 (m, 1H), 1.71-2.05 (m, 4H), 1.35-1.68 (m, 6H) ppm; LC-MS: m/z 416.1 [M+H]⁺.

Example 90-2: (R)-8-(8-((3-(trifluoromethyl)pyridin-4-yl)thio)-[1,2,4]triazolo[1,5-c]pyrimidin-5-yl)-8-azaspiro[4.5]decan-1-amine

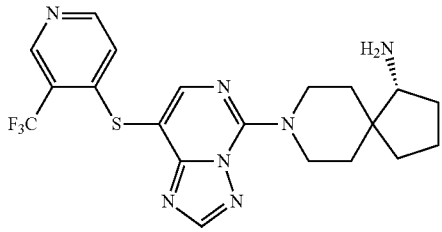 [SMILES: N[C@@H]1CCCC12CCN(c1ncc(Sc3ccncc3C(F)(F)F)c3ncnn13)CC2]

¹H NMR (400 MHz, DMSO-d₆) δ 8.82 (s, 1H), 8.49 (s, 1H), 8.42 (d, J=5.5 Hz, 1H), 8.35 (s, 1H), 8.28 (s, 1H), 7.01 (d, J=5.5 Hz, 1H), 4.96 (s, 2H), 3.51 (t, J=11.8 Hz, 3H), 2.96 (t, J=7.0 Hz, 1H), 2.02-1.35 (m, 10H) ppm; LC-MS: m/z 450.1 [M+H]⁺.

Example 91-2: (R)-8-(8-((2-chloropyridin-3-yl)thio)-[1,2,4]triazolo[1,5-c]pyrimidin-5-yl)-8-azaspiro[4.5]decan-1-amine

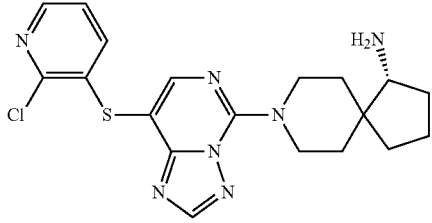

¹H NMR (CD₃OD-d₄) δ 8.49 (m, 1H), 8.36 (s, 1H), 8.26 (m, 1H), 8.16-8.18 (s, 1H), 7.20-7.23 (m, 2H), 4.96-4.94 (m, 2H), 3.50-3.46 (m, 2H), 2.96-2.90 (m, 1H), 1.71-2.05 (m, 4H), 1.35-1.68 (m, 6H) ppm. LC-MS: m/z 416.1 [M+H]⁺.

Example 92-2: (R)-8-(8-((2-methylpyridin-3-yl)thio)-[1,2,4]triazolo[1,5-c]pyrimidin-5-yl)-8-azaspiro decan-1-amine

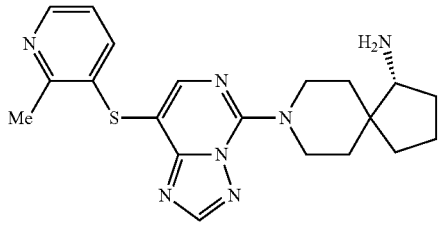 [SMILES: Cc1ncccc1Sc1cnc(N2CCC3(CCC[C@H]3N)CC2)n2ncnc12]

¹H NMR (400 MHz, DMSO-d₆) δ 8.50 (s, 1H), 8.24-8.22 (m, 1H), 8.21 (s, 1H), 7.22 (d, J=8.1 Hz, 1H), 7.04 (dd, J=7.9, 4.5 Hz, 1H), 3.52-3.44 (m, 2H), 3.18-3.10 (m, 3H), 2.59 (s, 3H), 2.04 (s, 1H), 1.86-1.35 (m, 9H) ppm. LC-MS: m/z 396.1 [M+H]⁺.

Example 93-2: (R)-8-(8-((6-amino-2-chloropyridin-3-yl)thio)-[1,2,4]triazolo[1,5-c]pyrimidin-5-yl)-8-azaspiro[4.5]decan-1-amine

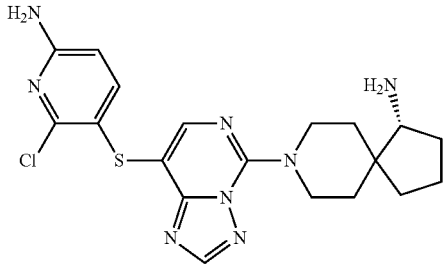 [SMILES: Nc1ccc(Sc2cnc(N3CCC4(CCC[C@H]4N)CC3)n3ncnc23)c(Cl)n1]

¹H NMR (400 MHz, DMSO-d₆) δ 8.52 (s, 1H), 7.98 (s, 1H), 7.40 (d, J=8.5 Hz, 1H), 6.61 (s, 2H), 6.33 (d, J=8.5 Hz, 1H), 4.78 (s, 2H), 3.16 (d, J=5.0 Hz, 1H), 3.04 (s, 1H), 2.67 (s, 2H), 1.82-1.40 (m, 10H) ppm; LC-MS: m/z 431.2 [M+H]⁺.

Example 94-2: (R)-8-(8-((2-amino-3-chloropyridin-4-yl)thio)-[1,2,4]triazolo[1,5-c]pyrimidin-5-yl)-8-azaspiro[4.5]decan-1-amine

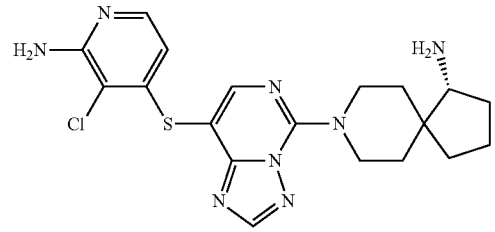 [SMILES: Nc1nccc(Sc2cnc(N3CCC4(CCC[C@H]4N)CC3)n3ncnc23)c1Cl]

¹H NMR (CD₃OD-d₄) δ 8.48 (s, 1H), 8.20 (s, 1H), 7.55 (s, 1H), 6.36 (s, 2H), 5.87 (m, 1H), 4.90 (m, 2H), 3.45-3.48 (m, 2H), 2.74-2.76 (m, 1H), 1.76-1.83 (m, 4H), 1.51-1.63 (m, 2H), 1.35-1.46 (m, 4H) ppm; LC-MS: m/z 431.1 M+H]⁺.

Example 95-2: (R)-8-(8-((6-amino-2,3-dichloropyridin-4-yl)thio)-[1,2,4]triazolo[1,5-c]pyrimidin-5-yl)-8-azaspiro[4.5]decan-1-amine

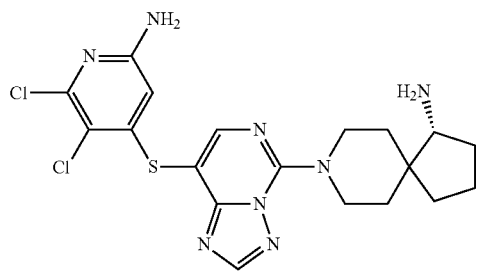 [SMILES: Nc1cc(Sc2cnc(N3CCC4(CCC[C@H]4N)CC3)n3ncnc23)c(Cl)c(Cl)n1]

¹H NMR (400 MHz, CD₃OD-d₄) δ 8.25 (s, 1H), 8.09 (s, 1H), 5.64 (s, 1H), 5.06 (s, 2H), 3.45-3.37 (m, 2H), 2.73 (t, J=7.5 Hz, 1H), 1.97-1.67 (m, 5H), 1.54 (dd, J=11.6, 5.0 Hz, 2H), 1.46-1.31 (m, 3H) ppm; LC-MS: m/z 467.1 M+H]⁺.

Example 96-2: (S)-8-(8-((3-chloro-2-methylpyridin-4-yl)thio)-[1,2,4]triazolo[1,5-c]pyrimidin-5-yl)-2-oxa-8-azaspiro[4.5]decan-4-amine

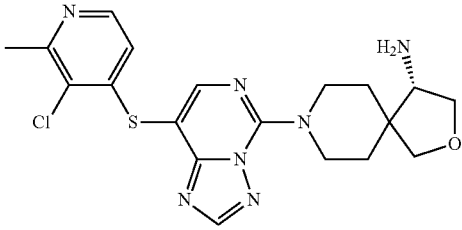 [SMILES: Cc1nccc(Sc2cnc(N3CCC4(CC3)COC[C@H]4N)n3ncnc23)c1Cl]

$^1$H NMR (400 MHz, DMSO-d$_6$) δ 8.50 (s, 1H), 8.24 (d, J=3.4 Hz, 2H), 8.03 (d, J=5.3 Hz, 1H), 6.61 (d, J=5.4 Hz, 1H), 4.02-3.97 (m, 2H), 3.78 (s, 2H), 3.69 (s, 2H), 3.17 (s, 3H), 2.55 (s, 3H), 1.80 (d, J=27.7 Hz, 2H), 1.59 (s, 2H) ppm; LC-MS: m/z 434.1 [M+H]$^+$.

Example 97-2: (3S,4S)-8-(8-((3-chloro-2-methylpyridin-4-yl)thio)-[1,2,4]triazolo[1,5-c]pyrimidin-5-yl)-3-methyl-2-oxa-8-azaspiro[4.5]decan-4-amine

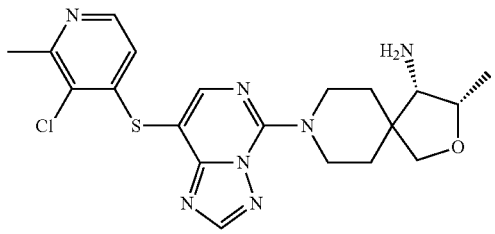

$^1$H NMR (400 MHz, DMSO-d$_6$) δ 8.48 (s, 1H), 8.23 (s, 1H), 8.01 (d, J=5.3 Hz, 1H), 6.59 (d, J=5.4 Hz, 1H), 4.60 (d, J=13.5 Hz, 2H), 4.13 (d, J=5.9 Hz, 1H), 3.75 (dd, J=21.8, 9.9 Hz, 4H), 3.14 (d, J=19.8 Hz, 1H), 2.54 (s, 3H), 1.97-1.60 (m, 4H), 1.13 (d, J=6.4 Hz, 3H) ppm; LC-MS: m/z 446.1 [M+H]$^+$.

Examples 125-127: Pharmacological Related Examples

Example 125: SHP2 Enzyme Activity Inhibition Experiment

Compound powders were dissolved in DMSO to prepare mother liquor.

During the experiment, the stock solutions of the compounds were subjected to 3-fold gradient dilution with DMSO, and 10 different test concentrations of each compound were set. 1 μL of each concentration of the compounds was transferred into the wells of detection plates (Corning, Costar 3915), setting two duplicates for each concentration. The protein used was the activated protein SHP2$^{2E76A}$ with amino acid mutation at position 76 of the protein, and the substrate used was DiFMUP (Invitrogen, E12020). SHP2$^{E76A}$ protein and substrate were diluted with buffer (0.1 M NaAc (pH 7.2), 0.02% Tween 20, 0.1% BSA, 1 mM EDTA, 5 mM DTT) to a concentration of 1.2 nM and 20 M, respectively. 50 L of enzyme solution was added to the detection wells, followed by 50 L of substrate. On the Spectra max i3 (Molecular Devices) instrument, the fluorescence signal was recorded (Ex 358 nm/Em 455 nm) every minute, from which the product accumulation rate was calculated to characterize the enzyme activity. GraphPad Prism 5 was used for nonlinear regression analysis, and the curve of enzyme activity versus compound concentration was fitted by the equation Y=Bottom+(Top-Bottom)/(1+10^((Log IC$_{50}$−X)*HillSlope)) to calculate the IC$_{50}$ value of each compound.

Results

Tables 1.1 and 1.2 below show the IC$_{50}$ values of some compounds of the present disclosure.

The letter "A" refers to IC$_{50}$ less than 100 nM.

The letter "B" refers to IC$_{50}$ ranging from 100 nM to 1000 nM.

The letter "C" refers to IC$_{50}$ ranging from 1000 nM to 10000 nM.

TABLE 1.1

| Compound | IC$_{50}$ |
|---|---|
| 1-(8-((2,3-dichlorophenyl)thio)imidazo[1,2-c]pyrimidin-5-yl)-4-methylpiperidin-4-amine | B |
| 1-(8-((2,3-dichlorophenyl)thio)imidazo[1,2-c]pyrimidin-5-yl)piperidin-4-amine | B |
| (R)-1-(8-((2,3-dichlorophenyl)thio)imidazo[1,2-c]pyrimidin-5-yl)azepan-4-amine | B |
| (1-(8-((2,3-dichlorophenyl)thio)imidazo[1,2-c]pyrimidin-5-yl)pyrrolidin-3-yl)methanamine | B |
| (1-(8-((2,3-dichlorophenyl)thio)imidazo[1,2-c]pyrimidin-5-yl)-4-methylpiperidin-4-yl)methanamine | A |
| (1-(8-((2,3-dichlorophenyl)thio)imidazo[1,2-c]pyrimidin-5-yl)piperidin-4-yl)methanamine | B |
| (R)-7-(8-((2,3-dichlorophenyl)thio)imidazo[1,2-c]pyrimidin-5-yl)-7-azaspiro[3.5]nonan-1-amine | B |
| 7-(8-((2,3-dichlorophenyl)thio)imidazo[1,2-c]pyrimidin-5-yl)-7-azaspiro[3.5]nonan-2-amine | B |
| (S)-8-(8-((2,3-dichlorophenyl)thio)imidazo[1,2-c]pyrimidin-5-yl)-2-oxa-8-azaspiro[4.5]decan-4-amine | A |
| (R)-8-(8-((2,3-dichlorophenyl)thio)imidazo[1,2-c]pyrimidin-5-yl)-1-oxa-8-azaspiro[4.5]decan-4-amine | B |
| (R)-8-(8-((2,3-dichlorophenyl)thio)imidazo[1,2-c]pyrimidin-5-yl)-8-azaspiro[4.5]decan-1-amine | A |
| (1R)-8-(8-((2,3-dichlorophenyl)thio)imidazo[1,2-c]pyrimidin-5-yl)-2-methyl-8-azaspiro[4.5]decan-1-amine | A |
| (1R)-8-(8-((2,3-dichlorophenyl)thio)imidazo[1,2-c]pyrimidin-5-yl)-3-methyl-8-azaspiro[4.5]decan-1-amine | A |

TABLE 1.1-continued

| Compound | IC$_{50}$ |
|---|---|
| (4R)-4-amino-8-(8-((2,3-dichlorophenyl)thio)imidazo[1,2-c]pyrimidin-5-yl)-8-azaspiro[4.5]decan-2-ol | A |
| (3S,4S)-8-(8-((2,3-dichlorophenyl)thio)imidazo[1,2-c]pyrimidin-5-yl)-3-methyl-2-oxa-8-azaspiro[4.5]decan-4-amine | A |
| (3S,4S)-8-(8-((6-amino-2,3-dichloropyridin-4-yl)thio)imidazo[1,2-c]pyrimidin-5-yl)-3-methyl-2-oxa-8-azaspiro[4.5]decan-4-amine | A |
| (R)-8-(8-(2,3-dichlorophenyl)imidazo[1,2-c]pyrimidin-5-yl)-8-azaspiro[4.5]decan-1-amine | B |
| (R)-8-(8-(phenylthio)imidazo[1,2-c]pyrimidin-5-yl)-8-azaspiro[4.5]decan-1-amine | B |
| (R)-8-(8-((2-chlorophenyl)thio)imidazo[1,2-c]pyrimidin-5-yl)-8-azaspiro[4.5]decan-1-amine | A |
| (R)-8-(8-((2,4-dichlorophenyl)thio)imidazo[1,2-c]pyrimidin-5-yl)-8-azaspiro[4.5]decan-1-amine | B |
| (R)-8-(8-((2-isopropylphenyl)thio)imidazo[1,2-c]pyrimidin-5-yl)-8-azaspiro[4.5]decan-1-amine | B |
| (R)-8-(8-((2-methoxyphenyl)thio)imidazo[1,2-c]pyrimidin-5-yl)-8-azaspiro[4.5]decan-1-amine | A |
| (R)-8-(8-((3-amino-2-chlorophenyl)thio)imidazo[1,2-c]pyrimidin-5-yl)-8-azaspiro[4.5]decan-1-amine | B |
| (R)-N-(3-((5-(1-amino-8-azaspiro[4.5]decan-8-yl)imidazo[1,2-c]pyrimidin-8-yl)thio)-2-chlorophenyl)acrylamide | B |
| (R)-8-(8-((2-amino-3-chloropyridin-4-yl)thio)imidazo[1,2-c]pyrimidin-5-yl)-8-azaspiro[4.5]decan-1-amine | A |
| (R)-8-(8-((3-chloropyridin-4-yl)thio)imidazo[1,2-c]pyrimidin-5-yl)-8-azaspiro[4.5]decan-1-amine | B |
| (R)-8-(8-((3-(trifluoromethyl)pyridin-4-yl)thio)imidazo[1,2-c]pyrimidin-5-yl)-8-azaspiro[4.5]decan-1-amine | A |
| (R)-8-(8-((3-chloro-2-fluoropyridin-4-yl)thio)imidazo[1,2-c]pyrimidin-5-yl)-8-azaspiro[4.5]decan-1-amine | A |
| (R)-8-(8-((3-chloro-2-methoxypyridin-4-yl)thio)imidazo[1,2-c]pyrimidin-5-yl)-8-azaspiro[4.5]decan-1-amine | A |
| (R)-8-(8-((3-chloro-2-cyclopropylpyridin-4-yl)thio)imidazo[1,2-c]pyrimidin-5-yl)-8-azaspiro[4.5]decan-1-amine | A |
| (R)-8-(8-((3-chloro-2-methyl-pyridin-4-yl)thio)imidazo[1,2-c]pyrimidin-5-yl)-8-azaspiro[4.5]decan-1-amine | A |
| (R)-8-(8-((3-chloro-2-(dimethylamino)pyridin-4-yl)thio)imidazo[1,2-c]pyrimidin-5-yl)-8-azaspiro[4.5]decan-1-amine | A |
| (R)-8-(8-((2-amino-5-chloropyridin-4-yl)thio)imidazo[1,2-c]pyrimidin-5-yl)-8-azaspiro[4.5]decan-1-amine | A |
| (R)-8-(8-((6-amino-2,3-dichloropyridin-4-yl)thio)imidazo[1,2-c]pyrimidin-5-yl)-8-azaspiro[4.5]decan-1-amine | A |
| (R)-8-(8-((2,3-dichloropyridin-4-yl)thio)imidazo[1,2-c]pyrimidin-5-yl)-8-azaspiro[4.5]decan-1-amine | A |
| (R)-8-(8-((2-methylpyridin-3-yl)thio)imidazo[1,2-c]pyrimidin-5-yl)-8-azaspiro[4.5]decan-1-amine | A |
| (R)-8-(8-((2-(trifluoromethyl)pyridin-3-yl)thio)imidazo[1,2-c]pyrimidin-5-yl)-8-azaspiro[4.5]decan-1-amine | A |
| (R)-8-(8-((2-chloropyridin-3-yl)thio)imidazo[1,2-c]pyrimidin-5-yl)-8-azaspiro[4.5]decan-1-amine | A |
| (R)-8-(8-((6-amino-2-chloropyridin-3-yl)thio)imidazo[1,2-c]pyrimidin-5-yl)-8-azaspiro[4.5]decan-1-amine | A |
| (R)-8-(8-((2-chloropyrimidin-4-yl)thio)imidazo[1,2-c]pyrimidin-5-yl)-8-azaspiro[4.5]decan-1-amine | A |
| (R)-8-(8-((3-chloropyridazin-4-yl)thio)imidazo[1,2-c]pyrimidin-5-yl)-8-azaspiro[4.5]decan-1-amine | B |
| (R)-8-(8-(benzo[d]thiazol-7-ylthio)imidazo[1,2-c]pyrimidin-5-yl)-8-azaspiro[4.5]decan-1-amine | B |
| (R)-8-(8-((1-methyl-1H-pyrrolo[2,3-b]pyridin-4-yl)thio)imidazo[1,2-c]pyrimidin-5-yl)-8-azaspiro[4.5]decan-1-amine | A |
| (R)-8-(8-((2,3-dihydrobenzofuran-5-yl)thio)imidazo[1,2-c]pyrimidin-5-yl)-8-azaspiro[4.5]decan-1-amine | B |
| (R)-8-(8-(naphthalen-1-ylthio)imidazo[1,2-c]pyrimidin-5-yl)-8-azaspiro[4.5]decan-1-amine | A |
| (R)-8-(8-(quinolin-4-ylthio)imidazo[1,2-c]pyrimidin-5-yl)-8-azaspiro[4.5]decan-1-amine | A |
| (R)-4-((5-(1-amino-8-azaspiro[1,2-c]decan-8-yl)imidazo[1,2-c]pyrimidin-8-yl)thio)indoline-2,3-dione | B |
| 4-((5-(4-amino-4-methylpiperidin-1-yl)imidazo[1,2-c]pyrimidin-8-yl)thio)-3-chloropyridin-2-amine | B |
| (1R)-8-(8-((2,3-dichloropyridin-4-yl)thio)imidazo[1,2-c]pyrimidin-5-yl)-3-methyl-8-azaspiro[4.5]decan-1-amine | A |
| (1R)-8-(8-((2-amino-3-chloropyridin-4-yl)thio)imidazo[1,2-c]pyrimidin-5-yl)-3-methyl-8-azaspiro[4.5]decan-1-amine | A |
| (S)-8-(8-((2,3-dichloropyridin-4-yl)thio)imidazo[1,2-c]pyrimidin-5-yl)-2-oxa-8-azaspiro[4.5]decan-4-amine | A |
| (3S,4S)-8-(8-((3-chloro-2-methylpyridin-4-yl)thio)imidazo[1,2-c]pyrimidin-5-yl)-3-methyl-2-oxa-8-azaspiro[4.5]decan-4-amine | A |

TABLE 1.1-continued

| Compound | IC$_{50}$ |
|---|---|
| (S)-8-(8-((6-amino-2,3-dichloropyridin-4-yl)thio)imidazo[1,2-c]pyrimidin-5-yl)-2-oxa-8-azaspiro[4.5]decan-4-amine | A |
| (S)-8-(8-((2-amino-3-chloropyridin-4-yl)thio)imidazo[1,2-c]pyrimidin-5-yl)-2-oxa-8-azaspiro[4.5]decan-4-amine | A |
| (3S,4S)-8-(8-((2,3-dichloropyridin-4-yl)thio)imidazo[1,2-c]pyrimidin-5-yl)-3-methyl-2-oxa-8-azaspiro[4.5]decan-4-amine | A |
| (3S,4S)-8-(8-((2-amino-3-chloropyridin-4-yl)thio)imidazo[1,2-c]pyrimidin-5-yl)-3-methyl-2-oxa-8-azaspiro[4.5]decan-4-amine | A |
| (1-(8-((2,3-dichlorophenyl)thio)imidazo[1,2-c]pyrimidin-5-yl)-4-phenylpiperidin-4-yl)methanamine | B |
| Methyl (R)-2-((5-(1-amino-8-azaspiro[4.5]decan-8-yl)imidazo[1,2-c]pyrimidin-8-yl)thio)benzoate | B |
| (R)-N$^1$-(3-((5-(1-amino-8-azaspiro[4.5]decan-8-yl)imidazo[1,2-c]pyrimidin-8-yl)thio)-2-chlorophenyl)-N$^2$,N$^2$-dimethyloxalamide | B |
| (R)-N-(3-((5-(1-amino-8-azaspiro[4.5]decan-8-yl)imidazo[1,2-c]pyrimidin-8-yl)thio)-2-chlorophenyl)-2-hydroxy-4-oxo-6,7,8,9-tetrahydro-4H-pyrido[1,2-a]pyrimidin-3-carboxamide | B |
| (R)-8-(8-((6-amino-3-chloro-2-methyl-pyridin-4-yl)thio)imidazo[1,2-c]pyrimidin-5-yl)-8-azaspiro[1,2-c]decan-1-amine | A |
| (1R)-8-(8-((6-amino-2,3-dichloropyridin-4-yl)thio)imidazo[1,2-c]pyrimidin-5-yl)-3-methyl-8-azaspiro[4.5]decan-1-amine | A |
| (S)-8-(8-((6-amino-3-chloro-2-methyl-pyridin-4-yl)thio)imidazo[1,2-c]pyrimidin-5-yl)-2-oxa-8-azaspiro[4.5]decan-4-amine | A |
| (3S,4S)-8-(8-((2-amino-5-chloropyridin-4-yl)thio)imidazo[1,2-c]pyrimidin-5-yl)-3-methyl-2-oxa-8-azaspiro[4.5]decan-4-amine | A |
| (3S,4S)-8-(8-((6-amino-3-chloro-2-methyl-pyridin-4-yl)thio)imidazo[1,2-c]pyrimidin-5-yl)-3-methyl-2-oxa-8-azaspiro[4.5]decan-4-amine | A |
| (R)-8-(8-((6-amino-2,3-dichloropyridin-4-yl)thio)imidazo[1,2-c]pyrimidin-5-yl)-3,3-difluoro-8-azaspiro[4.5]decan-1-amine | A |
| (R)-8-(8-((6-amino-3-chloro-2-methyl-pyridin-4-yl)thio)imidazo[1,2-c]pyrimidin-5-yl)-3,3-difluoro-8-azaspiro[4.5]decan-1-amine | A |
| (R)-3-(8-((2,3-dichlorophenyl)thio)imidazo[1,2-c]pyrimidin-5-yl)-3-azaspiro[5.5]undecan-7-amine | B |
| (R)-8-(8-((2,3-dichlorophenyl)thio)imidazo[1,2-c]pyrimidin-5-yl)-3,3-dimethyl-1-oxa-8-azaspiro[4.5]decan-4-amine | B |
| (R)-8-(8-((2,3-dichlorophenyl)thio)imidazo[1,2-c]pyrimidin-5-yl)-3,3-difluoro-8-azaspiro[4.5]decan-1-amine | A |

TABLE 1.2

| Compound | IC$_{50}$ |
|---|---|
| 1-(8-((2,3-dichlorophenyl)thio)-[1,2,4]triazolo[4,3-c]pyrimidin-5-yl)-4-methylpiperidin-4-amine | B |
| 1-(8-((2,3-dichlorophenyl)thio)-[1,2,4]triazolo[4,3-c]pyrimidin-5-yl)piperidin-4-amine | C |
| (1-(8-((2,3-dichlorophenyl)thio)-[1,2,4]triazolo[4,3-c]pyrimidin-5-yl)-4-phenylpiperidin-4-yl)methanamine | A |
| 8-((2,3-dichlorophenyl)thio)-5-(3,5-dimethylpiperazin-1-yl)-[1,2,4]triazolo[4,3-c]pyrimidine | C |
| (R)-1-(8-((2,3-dichlorophenyl)thio)-[1,2,4]triazolo[4,3-c]pyrimidin-5-yl)azepan-4-amine | B |
| (1-(8-((2,3-dichlorophenyl)thio)-[1,2,4]triazolo[4,3-c]pyrimidin-5-yl)pyrrolidin-3-yl)methanamine | B |
| (1-(8-((2,3-dichlorophenyl)thio)-[1,2,4]triazolo[4,3-c]pyrimidin-5-yl)-4-methylpiperidin-4-yl)methanamine | A |
| 2-(1-(8-((2,3-dichlorophenyl)thio)-[1,2,4]triazolo[4,3-c]pyrimidin-5-yl)piperidin-4-yl)ethan-1-amine | C |
| (S)-7-(8-((2,3-dichlorophenyl)thio)-[1,2,4]triazolo[4,3-c]pyrimidin-5-yl)-7-azaspiro[3.5]nonan-1-amine | C |
| 7-(8-((2,3-dichlorophenyl)thio)-[1,2,4]triazolo[4,3-c]pyrimidin-5-yl)-7-azaspiro[3.5]nonan-2-amine | C |
| 8-((2,3-dichlorophenyl)thio)-[1,2,4]triazolo[4,3-c]pyrimidin-5-yl)-1,8-diazaspiro[4.5]decane | C |
| (4R)-2-(8-((2,3-dichlorophenyl)thio)-[1,2,4]triazolo[4,3-c]pyrimidin-5-yl)octahydrocyclopenta[c]pyrrol-4-amine | C |
| (R)-3-(8-((2,3-dichlorophenyl)thio)-[1,2,4]triazolo[4,3-c]pyrimidin-5-yl)-3-azaspiro[5.5]undecan-7-amine | B |
| (S)-8-(8-((2,3-dichlorophenyl)thio)-[1,2,4]triazolo[4,3-c]pyrimidin-5-yl)-2-oxa-8-azaspiro[4.5]decan-4-amine | A |
| (R)-8-(8-((2,3-dichlorophenyl)thio)-[1,2,4]triazolo[4,3-c]pyrimidin-5-yl)-8-azaspiro[4.5]decan-1-amine | A |
| (S)-8-(8-((2,3-dichlorophenyl)thio)-[1,2,4]triazolo[4,3-c]pyrimidin-5-yl)-8-azaspiro[4.5]decan-1-amine | C |
| (R)-8-(8-((2,3-dichlorophenyl)thio)-[1,2,4]triazolo[4,3-c]pyrimidin-5-yl)-N-methyl-8-azaspiro[4.5]decan-1-amine | C |
| (1R)-8-(8-((2,3-dichlorophenyl)thio)-[1,2,4]triazolo[4,3-c]pyrimidin-5-yl)-3-methyl-8-azaspiro[4.5]decan-1-amine | A |
| (3S,4S)-8-(8-((2,3-dichlorophenyl)thio)-[1,2,4]triazolo[4,3-c]pyrimidin-5-yl)-3-methyl-2-oxa-8-azaspiro[4.5]decan-4-amine | A |
| (3R,4R)-8-(8-((2,3-dichlorophenyl)thio)-[1,2,4]triazolo[4,3-c]pyrimidin-5-yl)-3-methyl-2-oxa-8-azaspiro[4.5]decan-4-amine | C |
| 8-(8-((2,3-dichlorophenyl)thio)-[1,2,4]triazolo[4,3-c]pyrimidin-5-yl)-4-methyl-2-oxa-8-azaspiro[4.5]decan-4-amine | C |
| 1-(8-(2,3-dichlorophenyl)-[1,2,4]triazolo[4,3-c]pyrimidin-5-yl)-4-methylpiperidin-4-amine | C |
| (R)-8-(8-(2,3-dichlorophenyl)-[1,2,4]triazolo[4,3-c]pyrimidin-5-yl)-8-azaspiro[4.5]decan-1-amine | C |
| Methyl (R)-3-((5-(1-amino-8-azaspiro[4.5]decan-8-yl)-[1,2,4]triazolo[4,3-c]pyrimidin-8-yl)thio)propionate | C |
| (R)-8-(8-(phenylthio)-[1,2,4]triazolo[4,3-c]pyrimidin-5-yl)-8-azaspiro[4.5]decan-1-amine | C |
| (R)-8-(8-((2-chlorophenyl)thio)-[1,2,4]triazolo[4,3-c]pyrimidin-5-yl)-8-azaspiro[4.5]decan-1-amine | B |
| (R)-8-(8-((4-chlorophenyl)thio)-[1,2,4]triazolo[4,3-c]pyrimidin-5-yl)-8-azaspiro[4.5]decan-1-amine | C |
| (R)-8-(8-((2,4-dichlorophenyl)thio)-[1,2,4]triazolo[4,3-c]pyrimidin-5-yl)-8-azaspiro[4.5]decan-1-amine | B |
| (R)-8-(8-((2,6-dichlorophenyl)thio)-[1,2,4]triazolo[4,3-c]pyrimidin-5-yl)-8-azaspiro[4.5]decan-1-amine | C |
| (R)-8-(8-((2-isopropylphenyl)thio)-[1,2,4]triazolo[4,3-c]pyrimidin-5-yl)-8-azaspiro[4.5]decan-1-amine | B |
| (R)-8-(8-((2-methoxyphenyl)thio)-[1,2,4]triazolo[4,3-c]pyrimidin-5-yl)-8-azaspiro[4.5]decan-1-amine | B |
| Methyl (R)-2-((5-(1-amino-8-azaspiro[4.5]decan-8-yl)-[1,2,4]triazolo[4,3-c]pyrimidin-8-yl)thio)benzoate | C |

TABLE 1.2-continued

| Compound | IC$_{50}$ |
|---|---|
| (R)-8-(8-((4-aminophenyl)thio)-[1,2,4]triazolo[4,3-c]pyrimidin-5-yl)-8-azaspiro[4.5]decan-1-amine | C |
| (R)-8-(8-((3-amino-2-chlorophenyl)thio)-[1,2,4]triazolo[4,3-c]pyrimidin-5-yl)-8-azaspiro[4.5]decan-1-amine | A |
| (R)-N-(3-((5-(1-amino-8-azaspiro[4.5]decan-8-yl)-[1,2,4]triazolo[4,3-c]pyrimidin-8-yl)thio)-2-chlorophenyl)acrylamide | B |
| (R)-N-(4-((5-(1-amino-8-azaspiro[4.5]decan-8-yl)-[1,2,4]triazolo[4,3-c]pyrimidin-8-yl)thio)phenyl)acetamide | C |
| (R)-8-(8-(pyridin-2-ylthio)-[1,2,4]triazolo[4,3-c]pyrimidin-5-yl)-8-azaspiro[4.5]decan-1-amine | C |
| (R)-8-(8-((3-chloropyridin-4-yl)thio)-[1,2,4]triazolo[4,3-c]pyrimidin-5-yl)-8-azaspiro[4.5]decan-1-amine | B |
| (R)-8-(8-((3-chloro-2-methylpyridin-4-yl)thio)-[1,2,4]triazolo[4,3-c]pyrimidin-5-yl)-8-azaspiro[4.5]decan-1-amine | A |
| (R)-8-(8-((3-chloro-2-(dimethylamino)pyridin-4-yl)thio)-[1,2,4]triazolo[4,3-c]pyrimidin-5-yl)-8-azaspiro[4.5]decan-1-amine | B |
| (R)-8-(8-((2-amino-5-chloropyridin-4-yl)thio)-[1,2,4]triazolo[4,3-c]pyrimidin-5-yl)-8-azaspiro[4.5]decan-1-amine | C |
| (R)-8-(8-((6-amino-2,3-dichloropyridin-4-yl)thio)-[1,2,4]triazolo[4,3-c]pyrimidin-5-yl)-8-azaspiro[4.5]decan-1-amine | A |
| (R)-8-(8-((2,3-dichloropyridin-4-yl)thio)-[1,2,4]triazolo[4,3-c]pyrimidin-5-yl)-8-azaspiro[4.5]decan-1-amine | A |
| (R)-8-(8-((2-methylpyridin-3-yl)thio)-[1,2,4]triazolo[4,3-c]pyrimidin-5-yl)-8-azaspiro[4.5]decan-1-amine | B |
| (R)-8-(8-((2-(trifluoromethyl)pyridin-3-yl)thio)-[1,2,4]triazolo[4,3-c]pyrimidin-5-yl)-8-azaspiro[4.5]decan-1-amine | B |
| (R)-8-(8-(naphthalen-1-ylthio)-[1,2,4]triazolo[4,3-c]pyrimidin-5-yl)-8-azaspiro[4.5]decan-1-amine | A |
| (R)-8-(8-(quinolin-4-ylthio)-[1,2,4]triazolo[4,3-c]pyrimidin-5-yl)-8-azaspiro[4.5]decan-1-amine | A |
| (R)-8-(8-((1-methyl-1H-imidazol-2-yl)thio)-[1,2,4]triazolo[4,3-c]pyrimidin-5-yl)-8-azaspiro[4.5]decan-1-amine | C |
| 4-((5-(4-amino-4-methylpiperidin-1-yl)-[1,2,4]triazolo[4,3-c]pyrimidin-8-yl)thio)-3-chloropyridin-2-amine | B |
| (1R)-8-(8-((2,3-dichloropyridin-4-yl)thio)-[1,2,4]triazolo[4,3-c]pyrimidin-5-yl)-3-methyl-8-azaspiro[4.5]decan-1-amine | A |
| (1R)-8-(8-((2-amino-3-chloropyridin-4-yl)thio)-[1,2,4]triazolo[4,3-c]pyrimidin-5-yl)-3-methyl-8-azaspiro[4.5]decan-1-amine | A |
| (1R)-8-(8-((6-amino-2,3-dichloropyridin-4-yl)thio)-[1,2,4]triazolo[4,3-c]pyrimidin-5-yl)-3-methyl-8-azaspiro[4.5]decan-1-amine | A |
| (S)-8-(8-((2,3-dichloropyridin-4-yl)thio)-[1,2,4]triazolo[4,3-c]pyrimidin-5-yl)-2-oxa-8-azaspiro[4.5]decan-4-amine | B |
| (S)-8-(8-(3-chloro-2-methylpyridin-4-yl)thio)-[1,2,4]triazolo[4,3-c]pyrimidin-5-yl)-2-oxa-8-azaspiro[4.5]decan-4-amine | B |
| (S)-8-(8-((6-amino-2,3-dichloropyridin-4-yl)thio)-[1,2,4]triazolo[4,3-c]pyrimidin-5-yl)-2-oxa-8-azaspiro[4.5]decan-4-amine | A |
| (S)-8-(8-((2-amino-3-chloropyridin-4-yl)thio)-[1,2,4]triazolo[4,3-c]pyrimidin-5-yl)-2-oxa-8-azaspiro[4.5]decan-4-amine | B |
| (3S,4S)-8-(8-((2,3-dichloropyridin-4-yl)thio)-[1,2,4]triazolo[4,3-c]pyrimidin-5-yl)-3-methyl-2-oxa-8-azaspiro[4.5]decan-4-amine | A |
| (3S,4S)-8-(8-((3-chloro-2-methylpyridin-4-yl)thio)-[1,2,4]triazolo[4,3-c]pyrimidin-5-yl)-3-methyl-2-oxa-8-azaspiro[4.5]decan-4-amine | A |
| (3S,4S)-8-(8-((2-amino-5-chloropyridin-4-yl)thio)-[1,2,4]triazolo[4,3-c]pyrimidin-5-yl)-3-methyl-2-oxa-8-azaspiro[4.5]decan-4-amine | A |
| (3S,4S)-8-(8-((2-amino-3-chloropyridin-4-yl)thio)-[1,2,4]triazolo[4,3-c]pyrimidin-5-yl)-3-methyl-2-oxa-8-azaspiro[4.5]decan-4-amine | A |
| (3S,4S)-8-(8-((6-amino-2,3-dichloropyridin-4-yl)thio)-[1,2,4]triazolo[4,3-c]pyrimidin-5-yl)-3-methyl-2-oxa-8-azaspiro[4.5]decan-4-amine | A |
| (3R,4S)-8-(8-((3-chloro-2-methylpyridin-4-yl)thio)-[1,2,4]triazolo[4,3-c]pyrimidin-5-yl)-3-methyl-2-oxa-8-azaspiro[4.5]decan-4-amine | A |
| (3R,4R)-8-(8-((2-amino-3-chloropyridin-4-yl)thio)-[1,2,4]triazolo[4,3-c]pyrimidin-5-yl)-3-methyl-2-oxa-8-azaspiro[4.5]decan-4-amine | C |
| 1-(8-((2,3-dichlorophenyl)thio)-[1,2,4]triazolo[1,5-c]pyrimidin-5-yl)-4-methylpiperidin-4-amine | C |
| (R)-8-(8-((6-amino-2-chloropyridin-3-yl)thio)-[1,2,4]triazolo[1,5-c]pyrimidin-5-yl)-8-azaspiro[4.5]decan-1-amine | C |
| (3R,4S)-8-(8-((2,3-dichlorophenyl)thio)-[1,2,4]triazolo[1,5-c]pyrimidin-5-yl)-3-methyl-2-oxa-8-azaspiro[4.5]decan-4-amine | B |
| (R)-8-(8-((3-chloropyridin-4-yl)thio)-[1,2,4]triazolo[1,5-c]pyrimidin-5-yl)-8-azaspiro[4.5]decan-1-amine | C |
| (R)-8-(8-((6-amino-2,3-dichloropyridin-4-yl)thio)-[1,2,4]triazolo[1,5-c]pyrimidin-5-yl)-8-azaspiro[4.5]decan-1-amine | B |
| (R)-8-(8((2-chloropyridin-3-yl)thio)-[1,2,4]triazolo[1,5-c]pyrimidin-5-yl)-8-azaspiro[4.5]decan-1-amine | B |
| (R)-8-(8-(pyridin-3-ylthio)-[1,2,4]triazolo[1,5-c]pyrimidin-5-yl)-8-azaspiro[4.5]decan-1-amine | C |
| (R)-8-(8-((2-methoxyphenyl)thio)-[1,2,4]triazolo[1,5-c]pyrimidin-5-yl)-8-azaspiro[4.5]decan-1-amine | B |
| (R)-8-(8((4-aminophenyl)thio)-[1,2,4]triazolo[1,5-c]pyrimidin-5-yl)-8-azaspiro[4.5]decan-1-amine | C |
| (R)-8-(8-((3-(trifluoromethyl)pyridin-4-yl)thio)-[1,2,4]triazolo[1,5-c]pyrimidin-5-yl)-8-azaspiro[4.5]decan-1-amine | C |
| (R)-8-(8-((2-amino-3-chloropyridin-4-yl)thio)-[1,2,4]triazolo[1,5-c]pyrimidin-5-yl)-8-azaspiro[4.5]decan-1-amine | B |
| (R)-8-(8((2-methylpyridin-3-yl)thio)-[1,2,4]triazolo]1,5-c]pyrimidin-5-yl)-8-azaspiro[4.5]decan-1-amine | C |
| (S)-8-(8-((2,3-dichlorophenyl)thio)-[1,2,4]triazolo[1,5-c]pyrimidin-5-yl)-2-oxa-8-azaspiro[4.5]decan-4-amine | B |
| 3-(8-((2,3-dichlorophenyl)thio)-[1,2,4]triazolo[1,5-c]pyrimidin-5-yl)-3-azaspiro[5.5]undecan-7-amine | B |
| 1-(8-((2,3-dichlorophenyl)thio)-[1,2,4]triazolo[1,5-c]pyrimidin-5-yl)azepan-4-amine | B |
| (R)-8-(8-(phenylthio)-[1,2,4]triazolo[1,5-c]pyrimidin-5-yl)-8-azaspiro[4.5]decan-1-amine | C |
| (3R,4R)-8-(8-((2,3-dichlorophenyl)thio)-[1,2,4]triazolo[1,5-c]pyrimidin-5-yl)-3-methyl-2-oxa-8-azaspiro[4.5]decan-4-amine | C |
| (S)-8-(8-((3-chloro-2-methylpyridin-4-yl)thio)-[1,2,4]triazolo[1,5-c]pyrimidin-5-yl)-2-oxa-8-azaspiro[4.5]decan-4-amine | C |
| (3S,4S)-8-(8-((3-chloro-2-methylpyridin-4-yl)thio)-[1,2,4]triazolo[1,5-c]pyrimidin-5-yl)-3-methyl-2-oxa-8-azaspiro[4.5]decan-4-amine | B |

Example 126: Phosphorylated Protein Kinase (p-ERK) Cell Experiment

The inhibitory activities of the compounds on the phosphorylation level of intracellular protein kinase (ERK) were determined by AlphaLISA method.

Firstly, the cells were treated with the compounds. The compounds to be tested were subjected to 3-fold dilution with 100% DMSO, and a total of 9 different concentration gradients were set. MOLM13 cells were then seeded into 96-well plates at a density of 30,000 cells per well in a volume of 100 L per well. 0.5 L of DMSO or the test compounds with different concentrations was then transferred into each well, setting two duplicates for each concentration, and the final concentration of DMSO was controlled at 0.5%.

Secondly, the cells were lysed. After 2 hours of cell treatment, the medium was removed, and the cells were washed 3 times with phosphate buffered saline. 50 L of freshly prepared lysis buffer was added to each well, and the plates were shaken and kept at room temperature for 10 minutes.

Thirdly, the phosphorylated extracellular signal-regulated kinase (p-ERK) was detected by AlphaLISA@ SureFire® Ultra™ p-ERK 1/2 (Thr202/Tyr204) kit (Perkin Elmer, ALSU-PERK-A10K). 10 L of the above lysate was transferred to a 384-well plate (Perkin Elmer, 6005350), and the phosphorylation level of the extracellular signal-regulated kinase of the sample was detected according to the product instructions. The signal was read using AlphaScreen detector on Spectra max i3 (Molecular Devices). The percentage of inhibition (%) was calculated by the following formula:

Inhibition percentage(%)=(1−p-ERK signal of compound-treated cells/p-ERK signal of DMSO-treated cells)*100

Results

Tables 2.1 and 2.2 below show the IC$_{50}$ values of some compounds of the present disclosure.

The letter "A" refers to IC$_{50}$ less than 100 nM.

The letter "B" refers to IC$_{50}$ ranging from 100 nM to 1000 nM.

The letter "C" refers to IC$_{50}$ ranging from 1000 nM to 10000 nM.

TABLE 2.1

| Compound | IC$_{50}$ |
|---|---|
| (R)-7-(8-((2,3-dichlorophenyl)thio)imidazo[1,2-c]pyrimidin-5-yl)-7-azaspiro[3.5]nonan-1-amine | B |
| (R)-8-(8-((2,3-dichlorophenyl)thio)imidazo[1,2-c]pyrimidin-5-yl)-1-oxa-8-azaspiro[4.5]decan-4-amine | B |
| (R)-8-(8-((2,3-dichlorophenyl)thio)imidazo[1,2-c]pyrimidin-5-yl)-8-azaspiro[4.5]decan-1-amine | B |
| (R)-8-(8-((2-methoxyphenyl)thio)imidazo[1,2-c]pyrimidin-5-yl)-8-azaspiro[4.5]decan-1-amine | B |
| (R)-8-(8-((2-amino-3-chloropyridin-4-yl)thio)imidazo[1,2-c]pyrimidin-5-yl)-8-azaspiro[4.5]decan-1-amine | B |
| (R)-8-(8-((3-chloropyridin-4-yl)thio)imidazo[1,2-c]pyrimidin-5-yl)-8-azaspiro[4.5]decan-1-amine | B |
| (R)-8-(8-((3-chloro-2-methoxypyridin-4-yl)thio)imidazo[1,2-c]pyrimidin-5-yl)-8-azaspiro[4.5]decan-1-amine | B |
| (R)-8-(8-((3-chloro-2-(dimethylamino)pyridin-4-yl)thio)imidazo[1,2-c]pyrimidin-5-yl)-8-azaspiro[4.5]decan-1-amine | B |
| (R)-8-(8-((2-amino-5-chloropyridin-4-yl)thio)imidazo[1,2-c]pyrimidin-5-yl)-8-azaspiro[4.5]decan-1-amine | A |
| (R)-8-(8-((6-amino-2,3-dichloropyridin-4-yl)thio)imidazo[1,2-c]pyrimidin-5-yl)-8-azaspiro[4.5]decan-1-amine | A |
| (R)-8-(8-((2,3-dichloropyridin-4-yl)thio)imidazo[1,2-c]pyrimidin-5-yl)-8-azaspiro[4.5]decan-1-amine | B |
| (R)-8-(8-(2-(trifluoromethyl)pyridin-3-yl)thio)imidazo[1,2-c]pyrimidin-5-yl)-8-azaspiro[4.5]decan-1-amine | B |
| (R)-8-(8((2-chloropyridin-3-yl)thio)imidazo[1,2-c]pyrimidin-5-yl)-8-azaspiro[4.5]decan-1-amine | B |
| (R)-8-(8-(naphthalen-1-ylthio)imidazo[1,2-c]pyrimidin-5-yl)-8-azaspiro[4.5]decan-1-amine | B |
| (R)-8-(8-(quinolin-4-ylthio)imidazo[1,2-c]pyrimidin-5-yl)-8-azaspiro[4.5]decan-1-amine | B |
| (R)-8-(8-((3-chloro-2-fluoropyridin-4-yl)thio)imidazo[1,2-c]pyrimidin-5-yl)-8-azaspiro[4.5]decan-1-amine | B |
| (R)-8-(8-((3-chloro-2-methyl-pyridin-4-yl)thio)imidazo[1,2-c]pyrimidin-5-yl)-8-azaspiro[4.5]decan-1-amine | B |
| (1R)-8-(8-((2,3-dichlorophenyl)thio)imidazo[1,2-c]pyrimidin-5-yl)-2-methyl-8-azaspiro[4.5]decan-1-amine | B |
| (1R)-8-(8-((2,3-dichlorophenyl)thio)imidazo[1,2-c]pyrimidin-5-yl)-3-methyl-8-azaspiro[4.5]decan-1-amine | A |
| (S)-8-(8-((2,3-dichloropyridin-4-yl)thio)imidazo[1,2-c]pyrimidin-5-yl)-2-oxa-8-azaspiro[4.5]decan-4-amine | B |
| (S)-8-(8-((2-amino-3-chloropyridin-4-yl)thio)imidazo[1,2-c]pyrimidin-5-yl)-2-oxa-8-azaspiro[4.5]decan-4-amine | B |
| (R)-8-(8-((1-methyl-1H-pyrrolo[2,3-b]pyridin-4-yl)thio)imidazo[1,2-c]pyrimidin-5-yl)-8-azaspiro[4.5]decan-1-amine | B |
| (R)-8-(8-((3-chloropyridazin-4-yl)thio)imidazo[1,2-c]pyrimidin-5-yl)-8-azaspiro[4.5]decan-1-amine | B |
| (4R)-4-amino-8-(8-((2,3-dichlorophenyl)thio)imidazo[1,2-c]pyrimidin-5-yl)-8-azaspiro[4.5]decan-2-ol | A |
| (3S,4S)-8-(8-((2-amino-3-chloropyridin-4-yl)thio)imidazo[1,2-c]pyrimidin-5-yl)-3-methyl-2-oxa-8-azaspiro[4.5]decan-4-amine | B |
| (3S,4S)-8-(8-((2,3-dichlorophenyl)thio)imidazo[1,2-c]pyrimidin-5-yl)-3-methyl-2-oxa-8-azaspiro[4.5]decan-4-amine | A |
| (S)-8-(8-((6-amino-2,3-dichloropyridin-4-yl)thio)imidazo[1,2-c]pyrimidin-5-yl)-2-oxa-8-azaspiro[4.5]decan-4-amine | A |
| (3S,4S)-8-(8-((3-chloro-2-methylpyridin-4-yl)thio)imidazo[1,2-c]pyrimidin-5-yl)-3-methyl-2-oxa-8-azaspiro[4.5]decan-4-amine | A |
| (R)-N-(3-((5-(1-amino-8-azaspiro[4.5]decan-8-yl)imidazo[1,2-c]pyrimidin-8-yl)thio)-2-chlorophenyl)acrylamide | B |
| (3S,4S)-8-(8-((2,3-dichlorophenyl)thio)imidazo[1,2-c]pyrimidin-5-yl)-3-methyl-2-oxa-8-azaspiro[4.5]decan-4-amine | B |
| (3S,4S)-8-(8-((6-amino-2,3-dichloropyridin-4-yl)thio)imidazo[1,2-c]pyrimidin-5-yl)-3-methyl-2-oxa-8-azaspiro[4.5]decan-4-amine | A |
| (1R)-8-(8-((2,3-dichloropyridin-4-yl)thio)imidazo[1,2-c]pyrimidin-5-yl)-3-methyl-8-azaspiro[4.5]decan-1-amine | A |
| (1R)-8-(8-((2-amino-3-chloropyridin-4-yl)thio)imidazo[1,2-c]pyrimidin-5-yl)-3-methyl-8-azaspiro[4.5]decan-1-amine | A |
| (R)-8-(8-((3-(trifluoromethyl)pyridin-4-yl)thio)imidazo[1,2-c]pyrimidin-5-yl)-8-azaspiro[4.5]decan-1-amine | B |
| (R)-8-(8-((2,3-dichlorophenyl)thio)imidazo[1,2-c]pyrimidin-5-yl)-3,3-difluoro-8-azaspiro[4.5]decan-1-amine | B |
| (R)-8-(8-((6-amino-2,3-dichloropyridin-4-yl)thio)imidazo[1,2-c]pyrimidin-5-yl)-3,3-difluoro-8-azaspiro[4.5]decan-1-amine | A |
| (R)-8-(8-((6-amino-3-chloro-2-methyl-pyridin-4-yl)thio)imidazo[1,2-c]pyrimidin-5-yl)-8-azaspiro[4.5]decan-1-amine | A |
| (S)-8-(8-((6-amino-3-chloro-2-methyl-pyridin-4-yl)thio)imidazo[1,2-c]pyrimidin-5-yl)-2-oxa-8-azaspiro[4.5]decan-4-amine | B |
| (3S,4S)-8-(8-((2-amino-5-chloro-pyridin-4-yl)thio)imidazo[1,2-c]pyrimidin-5-yl)-3-methyl-2-oxa-8-azaspiro[4.5]decan-4-amine | A |
| (3S,4S)-8-(8-((6-amino-3-chloro-2-methyl-pyridin-4-yl)thio)imidazo[1,2-c]pyrimidin-5-yl)-3-methyl-2-oxa-8-azaspiro[4.5]decan-4-amine | A |
| (R)-N-(3-((5-(1-amino-8-azaspiro[4.5]decan-8-yl)imidazo[1,2-c]pyrimidin-8-yl)hio)-2-chlorophenyl)-2-hydroxy-4-oxo-6,7,8,9-tetrahydro-4H-pyrido[1,2-a]pyrimidin-3-carboxamide | A |
| (R)-8-(8-((6-amino-3-chloro-2-methyl-pyridin-4-yl)thio)imidazo[1,2-c]pyrimidin-5-yl)-3,3-difluoro-8-azaspiro[4.5]decan-1-amine | A |

TABLE 2.2

| Compound name | IC$_{50}$ |
|---|---|
| 1-(8-((2,3-dichlorophenyl)thio)-[1,2,4]triazolo[4,3-c]pyrimidin-5-yl)-4-methylpiperidin-4-amine | C |
| (1-(8-((2,3-dichlorophenyl)thio)-[1,2,4]triazolo[4,3-c]pyrimidin-5-yl)pyrrolidin-3-yl)methanamine | C |
| (1-(8-((2,3-dichlorophenyl)thio)-[1,2,4]triazolo[4,3-c]pyrimidin-5-yl)-4-methylpiperidin-4-yl)methanamine | B |
| (R)-3-(8-((2,3-dichlorophenyl)thio)-[1,2,4]triazolo[4,3-c]pyrimidin-5-yl)-3-azaspiro[5.5]undecan-7-amine | C |
| (S)-8-(8-((2,3-dichlorophenyl)thio)-[1,2,4]triazolo[4,3-c]pyrimidin-5-yl)-2-oxa-8-azaspiro[4.5]decan-4-amine | B |
| (1R)-8-(8-(((2,3-dichlorophenyl)thio)-[1,2,4]triazolo[4,3-c]pyrimidin-5-yl)-3-methyl-8-azaspiro[4.5]decan-1-amine | A |
| (3S,4S)-8-(8-((2,3-dichlorophenyl)thio)-[1,2,4]triazolo[4,3-c]pyrimidin-5-yl)-3-methyl-2-oxa-8-azaspiro[4.5]decan-4-amine | B |
| (R)-8-(8-((2-chlorophenyl)thio)-[1,2,4]triazolo[4,3-c]pyrimidin-5-yl)-8-azaspiro[4.5]decan-1-amine | B |
| (R)-8-(8-((3-amino-2-chlorophenyl)thio)-[1,2,4]triazolo[4,3-c]pyrimidin-5-yl)-8-azaspiro[4.5]decan-1-amine | B |
| (R)-N-(3-((5-(1-amino-8-azaspiro[4.5]decan-8-yl)-[1,2,4]triazolo[4,3-c]pyrimidin-8-yl)thio)-2-chlorophenyl)acrylamide | C |
| (R)-8-(8-((3-chloropyridin-4-yl)thio)-[1,2,4]triazolo[4,3-c]pyrimidin-5-yl)-8-azaspiro[4.5]decan-1-amine | B |
| (R)-8-(8-((3-chloro-2-methylpyridin-4-yl)thio)-[1,2,4]triazolo[4,3-c]pyrimidin-5-yl)-8-azaspiro[4.5]decan-1-amine | B |
| (R)-8-(8-((6-amino-2,3-dichloropyridin-4-yl)thio)-[1,2,4]triazolo[4,3-c]pyrimidin-5-yl)-8-azaspiro[4.5]decan-1-amine | B |
| (R)-8-(8-((2,3-dichloropyridin-4-yl)thio)-[1,2,4]triazolo[4,3-c]pyrimidin-5-yl)-8-azaspiro[4.5]decan-1-amine | C |
| (R)-8-(8-((2-(trifluoromethyl)pyridin-3-yl)thio)-[1,2,4]triazolo[4,3-c]pyrimidin-5-yl)-8-azaspiro[4.5]decan-1-amine | C |
| 4-((5-(4-amino-4-methylpiperidin-1-yl)-[1,2,4]triazolo[4,3-c]pyrimidin-8-yl)thio)-3-chloropyridin-2-amine | C |
| (1R)-8-(8-((6-amino-2,3-dichloropyridin-4-yl)thio)-[1,2,4]triazolo[4,3-c]pyrimidin-5-yl)-3-methyl-8-azaspiro[4.5]decan-1-amine | A |
| (S)-8-(8-((2-amino-3-chloropyridin-4-yl)thio)-[1,2,4]triazolo[4,3-c]pyrimidin-5-yl)-2-oxa-8-azaspiro[4.5]decan-4-amine | B |
| (3S,4S)-8-(8-((3-chloro-2-methylpyridin-4-yl)thio)-[1,2,4]triazolo[4,3-c]pyrimidin-5-yl)-3-methyl-2-oxa-8-azaspiro[4.5]decan-4-amine | B |
| (R)-8-(8-((2-amino-3-chloropyridin-4-yl)thio)-[1,2,4]triazolo[1,5-c]pyrimidin-5-yl)-8-azaspiro[4.5]decan-1-amine | C |
| (R)-8-(8-((6-amino-2,3-dichloropyridin-4-yl)thio)-[1,2,4]triazolo[1,5-c]pyrimidin-5-yl)-8-azaspiro[4.5]decan-1-amine | B |
| (S)-8-(8-((2,3-dichlorophenyl)thio)-[1,2,4]triazolo[1,5-c]pyrimidin-5-yl)-2-oxa-8-azaspiro[4.5]decan-4-amine | C |

Example 127: MOLM-13 Cell Proliferation Experiment

MOLM-13 cells suspended in medium (RPMI-1640, containing 10% FBS and 1% Penicillin-Streptomycin, Gibco) were seeded on 384-well plates at 800 cells (40 μL/well). The cells were immediately treated with the test compounds at concentration of 50, 16.67, 5.56, 1.85, 0.617, 0.206, 0.069, 0.023, 0.0076 P M. After 3 days, 5 L of CellTiter-Glo reagent (Promega, ZG7572) was added to each well, and the plates were kept at room temperature in the dark for 10 minutes. The fluorescence signal was detected by Spectra max i3 (Molecular Devices). The relative growth rate of the treated cells was compared with that of DMSO control.

Results

Tables 3.1 and 3.2 below show the $IC_{50}$ values of some compounds of the present disclosure.

The letter "A" refers to $IC_{50}$ less than 100 nM.

The letter "B" refers to $IC_{50}$ ranging from 100 nM to 1000 nM.

The letter "C" refers to $IC_{50}$ ranging from 1000 nM to 10000 nM.

TABLE 3.1

| Compound name | $IC_{50}$ |
| --- | --- |
| 1-(8-((2,3-dichlorophenyl)thio)imidazo[1,2-c]pyrimidin-5-yl)-4-methylpiperidin-4-amine | B |
| (1-(8-((2,3-dichlorophenyl)thio)imidazo[1,2-c]pyrimidin-5-yl)-4-methylpiperidin-4-yl)methanamine | B |
| (R)-7-(8-((2,3-dichlorophenyl)thio)imidazo[1,2-c]pyrimidin-5-yl)-7-azaspiro[3.5]nonan-1-amine | B |
| (S)-8-(8-((2,3-dichlorophenyl)thio)imidazo[1,2-c]pyrimidin-5-yl)-2-oxa-8-azaspiro[4.5]decan-4-amine | B |
| (R)-8-(8-((2,3-dichlorophenyl)thio)imidazo[1,2-c]pyrimidin-5-yl)-8-azaspiro[4.5]decan-1-amine | B |
| (1R)-8-(8-((2,3-dichlorophenyl)thio)imidazo[1,2-c]pyrimidin-5-yl)-2-methyl-8-azaspiro[4.5]decan-1-amine | B |
| (1R)-8-(8-((2,3-dichlorophenyl)thio)imidazo[1,2-c]pyrimidin-5-yl)-3-methyl-8-azaspiro[4.5]decan-1-amine | B |
| (4R)-4-amino-8-(8-((2,3-dichlorophenyl)thio)imidazo[1,2-c]pyrimidin-5-yl)-8-azaspiro[4.5]decan-2-ol | A |
| (3S,4S)-8-(8-((2,3-dichlorophenyl)thio)imidazo[1,2-c]pyrimidin-5-yl)-3-methyl-2-oxa-8-azaspiro[4.5]decan-4-amine | A |
| (3S,4S)-8-(8-((6-amino-3-chloro-2-methyl-pyridin-4-yl)thio)imidazo[1,2-c]pyrimidin-5-yl)-3-methyl-2-oxa-8-azaspiro[4.5]decan-4-amine | A |
| (3S,4S)-8-(8-((6-amino-2,3-dichloropyridin-4-yl)thio)imidazo[1,2-c]pyrimidin-5-yl)-3-methyl-2-oxa-8-azaspiro[4.5]decan-4-amine | A |
| (R)-8-(8-(phenylthio)imidazo[1,2-c]pyrimidin-5-yl)-8-azaspiro[4.5]decan-1-amine | B |
| (R)-8-(8-((2-methoxyphenyl)thio)imidazo[1,2-c]pyrimidin-5-yl)-8-azaspiro[4.5]decan-1-amine | B |
| (R)-8-(8-((3-amino-2-chlorophenyl)thio)imidazo[1,2-c]pyrimidin-5-yl)-8-azaspiro[4.5]decan-1-amine | B |
| (R)-N-(3-((5-(1-amino-8-azaspiro[4.5]decan-8-yl)imidazo[1,2-c]pyrimidin-8-yl)thio)-2-chlorophenyl)acrylamide | B |
| (R)-8-(8-((2-amino-3-chloropyridin-4-yl)thio)imidazo[1,2-c]pyrimidin-5-yl)-8-azaspiro[4.5]decan-1-amine | B |
| (R)-8-(8-((3-chloropyridin-4-yl)thio)imidazo[1,2-c]pyrimidin-5-yl)-8-azaspiro[4.5]decan-1-amine | B |
| (R)-8-(8-((3-(trifluoromethyl)pyridin-4-yl)thio)imidazo[1,2-c]pyrimidin-5-yl)-8-azaspiro[4.5]decan-1-amine | B |
| (R)-8-(8-((3-chloro-2-fluoropyridin-4-yl)thio)imidazo[1,2-c]pyrimidin-5-yl)-8-azaspiro[4.5]decan-1-amine | B |
| (R)-8-(8-((3-chloro-2-methoxypyridin-4-yl)thio)imidazo[1,2-c]pyrimidin-5-yl)-8-azaspiro[4.5]decan-1-amine | B |
| (R)-8-(8-((3-chloro-2-cyclopropylpyridin-4-yl)thio)imidazo[1,2-c]pyrimidin-5-yl)-8-azaspiro[4.5]decan-1-amine | B |
| (R)-8-(8-((3-chloro-2-methyl-pyridin-4-yl)thio)imidazo[1,2-c]pyrimidin-5-yl)-8-azaspiro[4.5]decan-1-amine | A |
| (R)-8-(8-((3-chloro-2-(dimethylamino)pyridin-4-yl)thio)imidazo[1,2-c]pyrimidin-5-yl)-8-azaspiro[4.5]decan-1-amine | B |
| (R)-8-(8-((2-amino-5-chloropyridin-4-yl)thio)imidazo[1,2-c]pyrimidin-5-yl)-8-azaspiro[4.5]decan-1-amine | A |
| (R)-8-(8-((6-amino-2,3-dichloropyridin-4-yl)thio)imidazo[1,2-c]pyrimidin-5-yl)-8-azaspiro[4.5]decan-1-amine | A |
| (R)-8-(8-((2,3-dichloropyridin-4-yl)thio)imidazo[1,2-c]pyrimidin-5-yl)-8-azaspiro[4.5]decan-1-amine | A |
| (R)-8-(8((2-methylpyridin-3-yl)thio)imidazo[1,2-c]pyrimidin-5-yl)-8-azaspiro[4.5]decan-1-amine | B |
| (R)-8-(8-((2-(trifluoromethyl)pyridin-3-yl)thio)imidazo[1,2-c]pyrimidin-5-yl)-8-azaspiro[4.5]decan-1-amine | B |
| (R)-8-(8((2-chloropyridin-3-yl)thio)imidazo[1,2-c]pyrimidin-5-yl)-8-azaspiro[4.5]decan-1-amine | B |
| (R)-8-(8-((3-chloropyridazin-4-yl)thio)imidazo[1,2-c]pyrimidin-5-yl)-8-azaspiro[4.5]decan-1-amine | B |
| (R)-8-(8-((1-methyl-1H-pyrrolo[2,3-b]pyridin-4-yl)thio)imidazo[1,2-c]pyrimidin-5-yl)-8-azaspiro[4.5]decan-1-amine | B |

TABLE 3.1-continued

| Compound name | $IC_{50}$ |
| --- | --- |
| (R)-8-(8-(naphthalen-1-ylthio)imidazo[1,2-c]pyrimidin-5-yl)-8-azaspiro[4.5]decan-1-amine | B |
| (R)-8-(8-(quinolin-4-ylthio)imidazo[1,2-c]pyrimidin-5-yl)-8-azaspiro[4.5]decan-1-amine | A |
| (1R)-8-(8-((2,3-dichloropyridin-4-yl)thio)imidazo[1,2-c]pyrimidin-5-yl)-3-methyl-8-azaspiro[4.5]decan-1-amine | A |
| (3S,4S)-8-(8-((3-chloro-2-methylpyridin-4-yl)thio)imidazo[1,2-c]pyrimidin-5-yl)-3-methyl-2-oxa-8-azaspiro[4.5]decan-4-amine | A |
| (1R)-8-(8-((2-amino-3-chloropyridin-4-yl)thio)imidazo[1,2-c]pyrimidin-5-yl)-3-methyl-8-azaspiro[4.5]decan-1-amine | A |
| (S)-8-(8-((2,3-dichloropyridin-4-yl)thio)imidazo[1,2-c]pyrimidin-5-yl)-2-oxa-8-azaspiro[4.5]decan-4-amine | B |
| (S)-8-(8-((6-amino-2,3-dichloropyridin-4-yl)thio)imidazo[1,2-c]pyrimidin-5-yl)-2-oxa-8-azaspiro[4.5]decan-4-amine | A |
| (S)-8-(8-((2-amino-3-chloropyridin-4-yl)thio)imidazo[1,2-c]pyrimidin-5-yl)-2-oxa-8-azaspiro[4.5]decan-4-amine | B |
| (3S,4S)-8-(8-((2,3-dichloropyridin-4-yl)thio)imidazo[1,2-c]pyrimidin-5-yl)-3-methyl-2-oxa-8-azaspiro[4.5]decan-4-amine | A |
| (3S,4S)-8-(8-((2-amino-3-chloropyridin-4-yl)thio)imidazo[1,2-c]pyrimidin-5-yl)-3-methyl-2-oxa-8-azaspiro[4.5]decan-4-amine | A |
| (1R)-8-(8-((6-amino-2,3-dichloropyridin-4-yl)thio)imidazo[1,2-c]pyrimidin-5-yl)-3-methyl-8-azaspiro[4.5]decan-1-amine | A |
| (R)-8-(8-((2,3-dichlorophenyl)thio)imidazo[1,2-c]pyrimidin-5-yl)-3,3-difluoro-8-azaspiro[4.5]decan-1-amine | B |
| Methyl (R)-2-((5-(1-amino-8-azaspiro[4.5]decan-8-yl)imidazo[1,2-c]pyrimidin-8-yl)thio)benzoate | B |
| (R)-8-(8-((6-amino-2,3-dichloropyridin-4-yl)thio)imidazo[1,2-c]pyrimidin-5-yl)-3,3-difluoro-8-azaspiro[4.5]decan-1-amine | B |
| (S)-8-(8-((6-amino-3-chloro-2-methyl-pyridin-4-yl)thio)imidazo[1,2-c]pyrimidin-5-yl)-2-oxa-8-azaspiro[4.5]decan-4-amine | B |
| (3S,4S)-8-(8-((6-amino-3-chloro-2-methyl-pyridin-4-yl)thio)imidazo[1,2-c]pyrimidin-5-yl)-3-methyl-2-oxa-8-azaspiro[4.5]decan-4-amine | B |
| (S)-8-(8-((6-amino-3-chloro-2-methyl-pyridin-4-yl)thio)imidazo[1,2-c]pyrimidin-5-yl)-2-oxa-8-azaspiro[4.5]decan-4-amine | A |
| (R)-N1-(3-((5-(1-amino-8-azaspiro[4.5]decan-8-yl)imidazo[1,2-c]pyrimidin-8-yl)thio)-2-chlorophenyl)-N2,N2-dimethyloxalamide | B |
| (R)-N-(3-((5-(1-amino-8-azaspiro[4.5]decan-8-yl)imidazo[1,2-c]pyrimidin-8-yl)thio)-2-chlorophenyl)-2-hydroxy-4-oxo-6,7,8,9-tetrahydro-4H-pyrido[1,2-a]pyrimidin-3-carboxamide | B |

TABLE 3.2

| Compound name | $IC_{50}$ |
| --- | --- |
| 1-(8-((2,3-dichlorophenyl)thio)-[1,2,4]triazolo[4,3-c]pyrimidin-5-yl)-4-methylpiperidin-4-amine | C |
| (1-(8-((2,3-dichlorophenyl)thio)-[1,2,4]triazolo[4,3-c]pyrimidin-5-yl)-4-phenylpiperidin-4-yl)methanamine | B |
| (R)-1-(8-((2,3-dichlorophenyl)thio)-[1,2,4]triazolo[4,3-c]pyrimidin-5-yl)azepan-4-amine | C |
| (1-(8-((2,3-dichlorophenyl)thio)-[1,2,4]triazolo[4,3-c]pyrimidin-5-yl)pyrrolidin-3-yl)methanamine | C |
| (1-(8-((2,3-dichlorophenyl)thio)-[1,2,4]triazolo[4,3-c]pyrimidin-5-yl)-4-methylpiperidin-4-yl)methanamine | C |
| (R)-3-(8-((2,3-dichlorophenyl)thio)-[1,2,4]triazolo[4,3-c]pyrimidin-5-yl)-3-azaspiro[5.5]undecan-7-amine | C |
| (S)-8-(8-((2,3-dichlorophenyl)thio)-[1,2,4]triazolo[4,3-c]pyrimidin-5-yl)-2-oxa-8-azaspiro[4.5]decan-4-amine | B |
| (R)-8-(8-((2,3-dichlorophenyl)thio)-[1,2,4]triazolo[4,3-c]pyrimidin-5-yl)-8-azaspiro[4.5]decan-1-amine | B |
| (1R)-8-(8-((2,3-dichlorophenyl)thio)-[1,2,4]triazolo[4,3-c]pyrimidin-5-yl)-3-methyl-8-azaspiro[4.5]decan-1-amine | A |
| (3S,4S)-8-(8-((2,3-dichlorophenyl)thio)-[1,2,4]triazolo[4,3-c]pyrimidin-5-yl)-3-methyl-2-oxa-8-azaspiro[4.5]decan-4-amine | B |
| (R)-8-(8-((2-chlorophenyl)thio)-[1,2,4]triazolo[4,3-c]pyrimidin-5-yl)-8-azaspiro[4.5]decan-1-amine | B |
| (R)-8-(8-((2,4-dichlorophenyl)thio)-[1,2,4]triazolo[4,3-c]pyrimidin-5-yl)-8-azaspiro[4.5]decan-1-amine | C |
| (R)-8-(8-((2-isopropylphenyl)thio)-[1,2,4]triazolo[4,3-c]pyrimidin-5-yl)-8-azaspiro[4.5]decan-1-amine | C |
| (R)-8-(8-((2-methoxyphenyl)thio)-[1,2,4]triazolo[4,3-c]pyrimidin-5-yl)-8-azaspiro[4.5]decan-1-amine | B |
| (R)-8-(8-((3-amino-2-chlorophenyl)thio)-[1,2,4]triazolo[4,3-c]pyrimidin-5-yl)-8-azaspiro[4.5]decan-1-amine | B |
| (R)-N-(3-((5-(1-amino-8-azaspiro[4.5]decan-8-yl)-[1,2,4]triazolo[4,3-c]pyrimidin-8-yl)thio)-2-chlorophenyl)acrylamide | B |

TABLE 3.2-continued

| Compound name | IC$_{50}$ |
|---|---|
| (R)-8-(8-((3-chloropyridin-4-yl)thio)-[1,2,4]triazolo[4,3-c]pyrimidin-5-yl)-8-azaspiro[4.5]decan-1-amine | B |
| (R)-8-(8-((3-chloro-2-methylpyridin-4-yl)thio)-[1,2,4]triazolo[4,3-c]pyrimidin-5-yl)-8-azaspiro[4.5]decan-1-amine | B |
| (R)-8-(8-((6-amino-2,3-dichloropyridin-4-yl)thio)-[1,2,4]triazolo[4,3-c]pyrimidin-5-yl)-8-azaspiro[4.5]decan-1-amine | B |
| (R)-8-(8-((2,3-dichloropyridin-4-yl)thio)-[1,2,4]triazolo[4,3-c]pyrimidin-5-yl)-8-azaspiro[4.5]decan-1-amine | B |
| (R)-8-(8(2-methylpyridin-3-yl)thio)-[1,2,4]triazolo[4,3-c]pyrimidin-5-yl)-8-azaspiro[4.5]decan-1-amine | C |
| (R)-8-(8-((2-(trifluoromethyl)pyridin-3-yl)thio)-[1,2,4]triazolo[4,3-c]pyrimidin-5-yl)-8-azaspiro[4.5]decan-1-amine | B |
| (R)-8-(8-(naphthalen-1-ylthio)-[1,2,4]triazolo[4,3-c]pyrimidin-5-yl)-8-azaspiro[4.5]decan-1-amine | B |
| 4-((5-(4-amino-4-methylpiperidin-1-yl)-[1,2,4]triazolo[4,3-c]pyrimidin-8-yl)thio)-3-chloropyridin-2-amine | C |
| (1R)-8-(8-((2,3-dichloropyridin-4-yl)thio)-[1,2,4]triazolo[4,3-c]pyrimidin-5-yl)-3-methyl-8-azaspiro[4.5]decan-1-amine | B |
| (1R)-8-(8-((2-amino-3-chloropyridin-4-yl)thio)-[1,2,4]triazolo[4,3-c]pyrimidin-5-yl)-3-methyl-8-azaspiro[4.5]decan-1-amine | B |
| (1R)-8-(8-((6-amino-2,3-dichloropyridin-4-yl)thio)-[1,2,4]triazolo[4,3-c]pyrimidin-5-yl)-3-methyl-8-azaspiro[4.5]decan-1-amine | A |
| (S)-8-(8-((2,3-dichloropyridin-4-yl)thio)-[1,2,4]triazolo[4,3-c]pyrimidin-5-yl)-2-oxa-8-azaspiro[4.5]decan-4-amine | B |
| (S)-8-(8-((3-chloro-2-methylpyridin-4-yl)thio)-[1,2,4]triazolo[4,3-c]pyrimidin-5-yl)-2-oxa-8-azaspiro[4.5]decan-4-amine | B |
| (S)-8-(8-((6-amino-2,3-dichloropyridin-4-yl)thio)-[1,2,4]triazolo[4,3-c]pyrimidin-5-yl)-2-oxa-8-azaspiro[4.5]decan-4-amine | C |
| (S)-8-(8-((2-amino-3-chloropyridin-4-yl)thio)-[1,2,4]triazolo[4,3-c]pyrimidin-5-yl)-2-oxa-8-azaspiro[4.5]decan-4-amine | C |
| (3S,4S)-8-(8-((2-amino-5-chloropyridin-4-yl)thio)-[1,2,4]triazolo[4,3-c]pyrimidin-5-yl)-3-methyl-2-oxa-8-azaspiro[4.5]decan-4-amine | C |
| (3S,4S)-8-(8-((2-amino-3-chloropyridin-4-yl)thio)-[1,2,4]triazolo[4,3-c]pyrimidin-5-yl)-3-methyl-2-oxa-8-azaspiro[4.5]decan-4-amine | B |
| (3S,4S)-8-(8-((6-amino-2,3-dichloropyridin-4-yl)thio)-[1,2,4]triazolo[4,3-c]pyrimidin-5-yl)-3-methyl-2-oxa-8-azaspiro[4.5]decan-4-amine | B |
| (R)-8-(8-((2-amino-3-chloropyridin-4-yl)thio)-[1,2,4]triazolo[1,5-c]pyrimidin-5-yl)-8-azaspiro[4.5]decan-1-amine | B |
| (R)-8-(8-((3-chloropyridin-4-yl)thio)-[1,2,4]triazolo[1,5-c]pyrimidin-5-yl)-8-azaspiro[4.5]decan-1-amine | C |
| (R)-8-(8-((6-amino-2,3-dichloropyridin-4-yl)thio)-[1,2,4]triazolo[1,5-c]pyrimidin-5-yl)-8-azaspiro[4.5]decan-1-amine | B |
| (R)-8-(8((2-chloropyridin-3-yl)thio)-[1,2,4]triazolo[1,5-c]pyrimidin-5-yl)-8-azaspiro[4.5]decan-1-amine | C |
| (R)-8-(8((2-methoxyphenyl)thio)-[1,2,4]triazolo[1,5-c]pyrimidin-5-yl)-8-azaspiro[4.5]decan-1-amine | C |
| (S)-8-(8-((2,3-dichlorophenyl)thio)-[1,2,4]triazolo[1,5-c]pyrimidin-5-yl)-2-oxa-8-azaspiro[4.5]decan-4-amine | B |
| 3-(8-((2,3-dichlorophenyl)thio)-[1,2,4]triazolo[1,5-c]pyrimidin-5-yl)-3-azaspiro[5.5]undecan-7-amine | C |
| 1-(8-((2,3-dichlorophenyl)thio)-[1,2,4]triazolo[1,5-c]pyrimidin-5-yl)azepan-4-amine | C |
| (3S,4S)-8-(8-((3-chloro-2-methylpyridin-4-yl)thio)-[1,2,4]triazolo[1,5-c]pyrimidin-5-yl)-3-methyl-2-oxa-8-azaspiro[4.5]decan-4-amine | C |

The applicant has tested the compound SHP099 (6-(4-amino-4-methylpiperidin-1-yl)-3-(2,3-dichlorophenyl)pyrazin-2-amine) disclosed in WO2015/107493A1 or literature (Nature 2016, 535, 148-152) according to the same test method as the SHP2 enzyme activity inhibition experiment described in Example 125, the phosphorylated protein kinase (p-ERK) cell experiment described in Example 126 and the MOLM-13 cell proliferation experiment described in Example 127. Table 4 below lists the comparative experimental data between the compounds obtained in some examples of the present disclosure and SHP099. After comparison, it is found that the pyrimidine-fused compounds of the present disclosure have more superior activities.

TABLE 4

| Compound name | SHP2 enzyme activity IC$_{50}$ (μm) | p-ERK IC$_{50}$ (μm) | MOLM-13 cell proliferation IC$_{50}$ (μm) |
|---|---|---|---|
| SHP099: | | | |
| 6-(4-amino-4-methylpiperidin-1-yl)-3-(2,3-dichlorophenyl)pyrazin-2-amine) | 0.33 | 2.07 | 1.37 |
| (R)-8-(8-((2-amino-3-chloropyridin-4-yl)thio)imidazo[1,2-c]pyrimidin-5-yl)-8-azaspiro[4.5]decan-1-amine | 0.02 | 0.41 | 0.27 |
| (R)-8-(8-((2,3-dichloropyridin-4-yl)thio)imidazo[1,2-c]pyrimidin-5-yl)-8-azaspiro[4.5]decan-1-amine | 0.057 | 0.159 | 0.042 |
| (R)-8-(8-((2-methoxyphenyl)thio)imidazo[1,2-c]pyrimidin-5-yl)-8-azaspiro[4.5]decan-1-amine | 0.083 | 0.469 | 0.210 |
| (3S,4S)-8-(8-((6-amino-3-chloro-2-methyl-pyridin-4-yl)thio)imidazo[1,2-c]pyrimidin-5-yl)-3-methyl-2-oxa-8-azaspiro[4.5]decan-4-amine | 0.016 | 0.043 | 0.042 |
| (R)-8-(8-((2-amino-5-chloropyridin-4-yl)thio)imidazo[1,2-c]pyrimidin-5-yl)-8-azaspiro[4.5]decan-1-amine | 0.025 | 0.032 | 0.043 |
| (R)-8-(8-(naphthalen-1-ylthio)imidazo[1,2-c]pyrimidin-5-yl)-8-azaspiro[4.5]decan-1-amine | 0.028 | 0.49 | 0.15 |
| (R)-8-(8-(quinolin-4-ylthio)imidazo[1,2-c]pyrimidin-5-yl)-8-azaspiro[4.5]decan-1-amine | 0.02 | 0.031 | 0.099 |
| (R)-8-(8-((3-chloro-2-methyl-pyridin-4-yl)thio)imidazo[1,2-c]pyrimidin-5-yl)-8-azaspiro[4.5]decan-1-amine | 0.04 | 0.18 | 0.058 |
| (1R)-8-(8-((2,3-dichlorophenyl)thio)imidazo[1,2-c]pyrimidin-5-yl)-3-methyl-8-azaspiro[4.5]decan-1-amine | 0.011 | 0.053 | 0.14 |
| (4R)-4-amino-8-(8-((2,3-dichlorophenyl)thio)imidazo[1,2-c]pyrimidin-5-yl)-8-azaspiro[4.5]decan-2-ol | 0.009 | 0.028 | 0.042 |
| (1R)-8-(8-((2-amino-3-chloropyridin-4-yl)thio)imidazo[1,2-c]pyrimidin-5-yl)-3-methyl-8-azaspiro[4.5]decan-1-amine | 0.032 | 0.059 | 0.054 |
| (3S,4S)-8-(8-((2,3-dichloropyridin-4-yl)thio)imidazo[1,2-c]pyrimidin-5-yl)-3-methyl-2-oxa-8-azaspiro[4.5]decan-4-amine | 0.005 | 0.035 | 0.038 |

TABLE 4-continued

| Compound name | SHP2 enzyme activity IC$_{50}$ (µm) | p-ERK IC$_{50}$ (µm) | MOLM-13 cell proliferation IC$_{50}$ (µm) |
| --- | --- | --- | --- |
| (3S,4S)-8-(8-((2-amino-3-chloropyridin-4-yl)thio)imidazo[1,2-c]pyrimidin-5-yl)-3-methyl-2-oxa-8-azaspiro[4.5]decan-4-amine | 0.02 | 0.15 | 0.076 |
| (S)-8-(8-((6-amino-2,3-dichloropyridin-4-yl)thio)imidazo[1,2-c]pyrimidin-5-yl)-2-oxa-8-azaspiro[4.5]decan-4-amine | 0.009 | 0.028 | 0.054 |
| (3S,4S)-8-(8-((2,3-dichlorophenyl)thio)imidazo[1,2-c]pyrimidin-5-yl)-3-methyl-2-oxa-8-azaspiro[4.5]decan-4-amine | 0.008 | 0.103 | 0.068 |
| (3S,4S)-8-(8-((6-amino-2,3-dichloropyridin-4-yl)thio)imidazo[1,2-c]pyrimidin-5-yl)-3-methyl-2-oxa-8-azaspiro[4.5]decan-4-amine | 0.01 | 0.047 | 0.05 |
| (1R)-8-(8-((2,3-dichloropyridin-4-yl)thio)imidazo[1,2-c]pyrimidin-5-yl)-3-methyl-8-azaspiro[4.5]decan-1-amine | 0.008 | 0.034 | 0.028 |
| (R)-8-(8-((6-amino-2,3-dichloropyridin-4-yl)thio)imidazo[1,2-c]pyrimidin-5-yl)-3,3-difluoro-8-azaspiro[4.5]decan-1-amine | 0.035 | 0.062 | 0.15 |
| (R)-8-(8-((6-amino-3-chloro-2-methyl-pyridin-4-yl)thio)imidazo[1,2-c]pyrimidin-5-yl)-8-azaspiro[4.5]decan-1-amine | 0.017 | 0.037 | 0.21 |
| (S)-8-(8-((6-amino-3-chloro-2-methyl-pyridin-4-yl)thio)imidazo[1,2-c]pyrimidin-5-yl)-2-oxa-8-azaspiro[4.5]decan-4-amine | 0.034 | 0.16 | 0.34 |
| (3S,4S)-8-(8-((2-amino-5-chloro-pyridin-4-yl)thio)imidazo[1,2-c]pyrimidin-5-yl)-3-methyl-2-oxa-8-azaspiro[4.5]decan-4-amine | 0.021 | 0.094 | 0.18 |
| (3S,4S)-8-(8-((3-chloro-2-methylpyridin-4-yl)thio)imidazo[1,2-c]pyrimidin-5-yl)-3-methyl-2-oxa-8-azaspiro[4.5]decan-4-amine | 0.015 | 0.019 | 0.050 |
| (3S,4S)-8-(8-((6-amino-3-chloro-2-methyl-pyridin-4-yl)thio)imidazo[1,2-c]pyrimidin-5-yl)-3-methyl-2-oxa-8-azaspiro[4.5]decan-4-amine | 0.016 | 0.043 | 0.042 |
| (R)-8-(8-((6-amino-3-chloro-2-methyl-pyridin-4-yl)thio)imidazo[1,2-c]pyrimidin-5-yl)-3,3-difluoro-8-azaspiro[4.5]decan-1-amine | 0.026 | 0.097 | 0.15 |
| (R)-8-(8-((6-amino-2,3-dichloropyridin-4-yl)thio)imidazo[1,2-c]pyrimidin-5-yl)-8-azaspiro[4.5]decan-1-amine | 0.012 | 0.009 | 0.016 |
| (1-(8-((2,3-dichlorophenyl)thio)-[1,2,4]triazolo[4,3-c]pyrimidin-5-yl)-4-methylpiperidin-4-yl)methanamine | 0.04 | 0.17 | 1.355 |
| (S)-8-(8-((2,3-dichlorophenyl)thio)-[1,2,4]triazolo[4,3-c]pyrimidin-5-yl)-2-oxa-8-azaspiro[4.5]decan-4-amine | 0.02 | 0.168 | 0.892 |
| (1R)-8-(8-((2,3-dichlorophenyl)thio)-[1,2,4]triazolo[4,3-c]pyrimidin-5-yl)-3-methyl-8-azaspiro[4.5]decan-1-amine | 0.004 | 0.064 | 0.059 |
| (3S,4S)-8-(8-((2,3-dichlorophenyl)thio)-[1,2,4]triazolo[4,3-c]pyrimidin-5-yl)-3-methyl-2-oxa-8-azaspiro[4.5]decan-4-amine | 0.003 | 0.195 | 0.158 |
| (R)-8-(8-((2-chlorophenyl)thio)-[1,2,4]triazolo[4,3-c]pyrimidin-5-yl)-8-azaspiro[4.5]decan-1-amine | 0.140 | 0.548 | 0.485 |
| (R)-8-(8-((3-amino-2-chlorophenyl)thio)-[1,2,4]triazolo[4,3-c]pyrimidin-5-yl)-8-azaspiro[4.5]decan-1-amine | 0.025 | 0.245 | 0.389 |
| (R)-8-(8-((3-chloropyridin-4-yl)thio)-[1,2,4]triazolo[4,3-c]pyrimidin-5-yl)-8-azaspiro[4.5]decan-1-amine | 0.1 | 0.357 | 0.324 |
| (R)-8-(8-((3-chloro-2-methylpyridin-4-yl)thio)-[1,2,4]triazolo[4,3-c]pyrimidin-5-yl)-8-azaspiro[4.5]decan-1-amine | 0.027 | 0.177 | 0.232 |
| (R)-8-(8-((6-amino-2,3-dichloropyridin-4-yl)thio)-[1,2,4]triazolo[4,3-c]pyrimidin-5-yl)-8-azaspiro[4.5]decan-1-amine | 0.02 | 0.750 | 0.303 |
| (1R)-8-(8-((6-amino-2,3-dichloropyridin-4-yl)thio)-[1,2,4]triazolo[4,3-c]pyrimidin-5-yl)-3-methyl-8-azaspiro[4.5]decan-1-amine | 0.002 | 0.047 | 0.017 |
| (3S,4S)-8-(8-((2,3-dichloropyridin-4-yl)thio)-[1,2,4]triazolo[4,3-c]pyrimidin-5-yl)-3-methyl-2-oxa-8-azaspiro[4.5]decan-4-amine | 0.005 | 0.161 | 0.133 |
| (3S,4S)-8-(8-((3-chloro-2-methylpyridin-4-yl)thio)-[1,2,4]triazolo[4,3-c]pyrimidin-5-yl)-3-methyl-2-oxa-8-azaspiro[4.5]decan-4-amine | 0.017 | 0.369 | 0.277 |
| (3S,4S)-8-(8-((2-amino-3-chloropyridin-4-yl)thio)-[1,2,4]triazolo[4,3-c]pyrimidin-5-yl)-3-methyl-2-oxa-8-azaspiro[4.5]decan-4-amine | 0.013 | 0.335 | 0.102 |

The above examples are preferred embodiments of the present disclosure, but the embodiments of the present disclosure are not limited by the above examples.

Any other changes, modifications, substitutions, combinations, and simplifications made without departing from the spirit and principles of the present disclosure shall be equivalent alternatives, and shall be included in the protection scope of the present invention.

What is claimed is:

1. A compound selected from the group consisting of

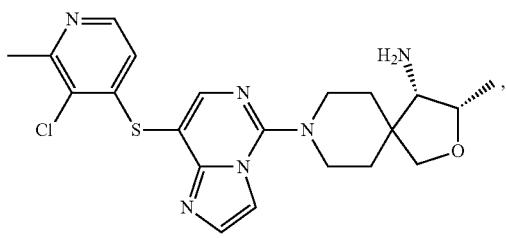

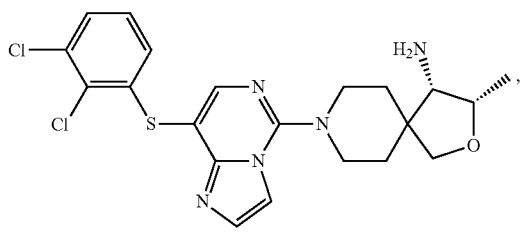

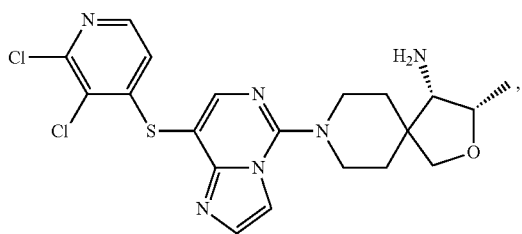

and

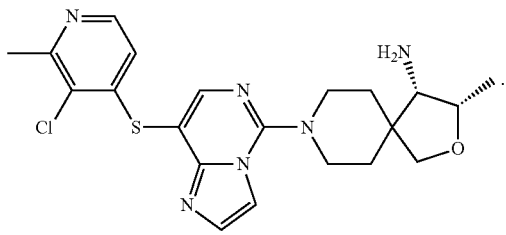

or a pharmaceutically acceptable salt thereof.

2. The compound or pharmaceutically acceptable salt thereof as defined in claim 1, wherein the compound is

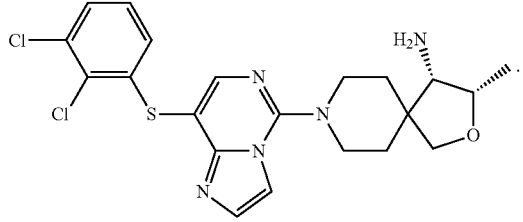 [SMILES: C[C@@H]1OCC2(CCN(c3ncc(Sc4cccc(Cl)c4Cl)c4nccn34)CC2)[C@@H]1N]

3. The compound or pharmaceutically acceptable salt thereof as defined in claim 1, wherein the compound is

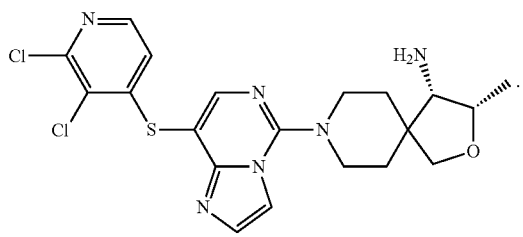 [SMILES: C[C@@H]1OCC2(CCN(c3ncc(Sc4ccnc(Cl)c4Cl)c4nccn34)CC2)[C@@H]1N]

4. The compound or pharmaceutically acceptable salt thereof as defined in claim 1, wherein the compound is

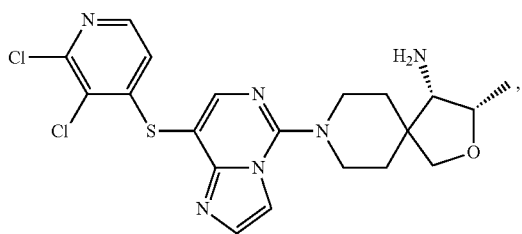

5. A pharmaceutical composition, comprising the compound or pharmaceutically acceptable salt thereof as defined in claim 1, and a pharmaceutically acceptable excipient.

6. A method for the treatment of a disease or condition associated with abnormal activity of SHP2 in a subject in need thereof, comprising administering the compound or the pharmaceutically acceptable salt thereof as defined in claim 1 to the subject, wherein the disease or condition is selected from Noonan syndrome, Leopard syndrome, juvenile myelomonocytic leukemia, neuroblastoma, melanoma, acute myeloid leukemia, breast cancer, esophageal cancer, lung cancer, colon cancer, head cancer, neuroblastoma, head and neck squamous cell carcinoma, gastric cancer, anaplastic large cell lymphoma and glioblastoma.

7. A pharmaceutical preparation, comprising the compound or pharmaceutically acceptable salt thereof as defined in claim 1.

8. The pharmaceutical preparation as defined in claim 7, wherein the pharmaceutical preparation is adapted for oral administration, sublingual administration, subcutaneous injection, intravenous injection, intramuscular injection, intrasternal injection, nasal administration, local topical administration or rectal administration;
and/or, the pharmaceutical preparation is adapted to be administered once or multiple times a day.

9. A combination product comprising
(i) the compound or pharmaceutically acceptable salt thereof as defined in claim 1; and
(ii) another medicament,
wherein the another medicament is selected from anticancer medicaments, tumor immune medicaments, antiallergic medicaments, antiemetic medicaments, analgesics, and cell protection medicaments.

10. A method for treatment of a disease or condition associated with abnormal activity of SHP2 in a subject in need thereof, comprising administering the pharmaceutical composition thereof as defined in claim 5 to the subject, wherein the disease or condition is selected from Noonan syndrome, Leopard syndrome, juvenile myelomonocytic leukemia, neuroblastoma, melanoma, acute myeloid leukemia, breast cancer, esophageal cancer, lung cancer, colon cancer, head cancer, neuroblastoma, head and neck squamous cell carcinoma, gastric cancer, anaplastic large cell lymphoma and glioblastoma.

11. A method for the treatment of a disease or condition associated with abnormal activity of SHP2 in a subject in need thereof, comprising administering the pharmaceutical composition thereof as defined in claim 7 to the subject, wherein the disease or condition is selected from Noonan syndrome, Leopard syndrome, juvenile myelomonocytic leukemia, neuroblastoma, melanoma, acute myeloid leukemia, breast cancer, esophageal cancer, lung cancer, colon cancer, head cancer, neuroblastoma, head and neck squamous cell carcinoma, gastric cancer, anaplastic large cell lymphoma and glioblastoma.

12. A method for the treatment of a disease or condition associated with abnormal activity of SHP2 in a subject in need thereof, comprising administering the pharmaceutical composition thereof as defined in claim 9 to the subject, wherein the disease or condition is selected from Noonan syndrome, Leopard syndrome, juvenile myelomonocytic leukemia, neuroblastoma, melanoma, acute myeloid leukemia, breast cancer, esophageal cancer, lung cancer, colon cancer, head cancer, neuroblastoma, head and neck squamous cell carcinoma, gastric cancer, anaplastic large cell lymphoma and glioblastoma.

* * * * *